(12) United States Patent
Lundegaard et al.

(10) Patent No.: US 11,013,781 B2
(45) Date of Patent: May 25, 2021

(54) PEPTIDE COMBINATIONS AND USES THEREOF FOR TREATING GRASS ALLERGY

(71) Applicants: ALK-Abelló A/S, Hørsholm (DK); La Jolla Institute for Allergy And Immunology, La Jolla, CA (US)

(72) Inventors: Claus Lundegaard, Søborg (DK); Shashank Gupta, Copenhagen (DK); Bjoern Peters, La Jolla, CA (US); Susanne Sønderkær, Ølstykke (DK); Jens Brimnes, Søborg (DK); Peter Adler Würtzen, Vedbæk (DK); Helene Henmar, Kokkedal (DK); Thomas Christian Mygind, Bagsværd (DK); Lise Lund Mærkedahl, Fredensborg (DK); Alessandro Sette, La Jolla, CA (US)

(73) Assignees: ALK-ABELLÓ AS, Hørsholm (DK); LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 94 days.

(21) Appl. No.: 15/739,440

(22) PCT Filed: Jul. 1, 2016

(86) PCT No.: PCT/US2016/040773
§ 371 (c)(1),
(2) Date: Dec. 22, 2017

(87) PCT Pub. No.: WO2017/004561
PCT Pub. Date: Jan. 5, 2017

(65) Prior Publication Data
US 2018/0207228 A1    Jul. 26, 2018

Related U.S. Application Data

(60) Provisional application No. 62/187,630, filed on Jul. 1, 2015.

(51) Int. Cl.
| | | |
|---|---|---|
| *A61K 38/10* | (2006.01) | |
| *C07K 7/08* | (2006.01) | |
| *A61K 39/36* | (2006.01) | |
| *A61P 27/14* | (2006.01) | |
| *A61P 11/02* | (2006.01) | |
| *A61K 39/39* | (2006.01) | |

(52) U.S. Cl.
CPC .............. *A61K 38/10* (2013.01); *A61K 39/36* (2013.01); *A61K 39/39* (2013.01); *A61P 11/02* (2018.01); *A61P 27/14* (2018.01); *C07K 7/08* (2013.01)

(58) Field of Classification Search
None
See application file for complete search history.

(56) References Cited

U.S. PATENT DOCUMENTS

| | | | |
|---|---|---|---|
| 5,480,972 A | 1/1996 | Avjioglu et al. | |
| 5,691,167 A | 11/1997 | Avjioglu et al. | |
| 5,710,126 A | 1/1998 | Griffith et al. | |
| 5,721,119 A | 2/1998 | Singh et al. | |
| 5,736,149 A | 4/1998 | Avjioglu et al. | |
| 5,736,362 A | 4/1998 | Singh et al. | |
| 5,840,316 A | 11/1998 | Singh et al. | |
| 5,869,333 A | 2/1999 | Singh et al. | |
| 6,008,340 A | 12/1999 | Ball et al. | |
| 6,197,313 B1 | 3/2001 | Singh et al. | |
| 6,214,358 B1 | 4/2001 | Singh et al. | |
| 6,239,269 B1 | 5/2001 | Singh et al. | |
| 6,265,566 B1 | 7/2001 | Singh et al. | |
| 6,277,383 B1 | 8/2001 | Singh et al. | |
| 6,441,157 B1 | 8/2002 | Singh et al. | |
| 6,451,324 B1 | 9/2002 | Singh et al. | |
| 6,559,120 B2 | 5/2003 | Ball et al. | |
| 7,112,333 B1 | 9/2006 | Griffith et al. | |
| 7,148,019 B2 | 12/2006 | Ball et al. | |
| 7,514,083 B1 | 4/2009 | Singh et al. | |
| 8,753,644 B2 * | 6/2014 | Hafner .................. | A61K 38/10 424/185.1 |

FOREIGN PATENT DOCUMENTS

| | | |
|---|---|---|
| JP | 2007-244216 A | 9/2007 |
| WO | WO 94/21675 A2 | 9/1994 |
| WO | WO 95/06728 A2 | 3/1995 |
| WO | WO 03/024998 A1 | 3/2003 |

(Continued)

OTHER PUBLICATIONS

Altschul, S., et al., "Basic Local Alignment Search Tool," *J. Mol. Biol.*, 1990, vol. 215, pp. 403-410.

Bostick, D., et anon, "A new topological method to measure protein structure similarity," *Biochemical and Biophysical Research Communications*, 2003, vol. 304, pp. 320-325.

Greenbaum, J.,et al, "Functional classification of class II human leukocyte antigen (HLA) molecules reveals seven different supertypes and a surprising degree of repertoire sharing across supertypes," *Immunogenetics*, 2011, vol. 63, pp. 325-335.

Henmar, H., et al., "Allergenicity, immunogenicity and dose-relationship of three intact allergen vaccines and four allergoid vaccines for subcutaneoUS-grass pollen immunotherapy," *Clinical & Experimental Immunology*, 2008, vol. 153, pp. 316-323.

(Continued)

*Primary Examiner* — Lianko G Garyu
(74) *Attorney, Agent, or Firm* — Womble Bond Dickinson (US) LLP

(57) ABSTRACT

The invention relates to combinations of peptides derived from a portion of an amino sequence of a grass pollen allergen, e.g. the allergens Phl p 1, Phl p 2, Phl p 3, Phl p 4 and/or Phl p 5, or a peptide variant thereof. Such peptides comprise at least one T cell epitope mid a high number of patients in a worldwide population will have HLA Class II alleles with the potential to bind the peptides of the peptide combinations. The invention also relates to the use of such peptide combinations in relieving an immune response caused by grass pollen species.

9 Claims, 29 Drawing Sheets

Figure 1A:
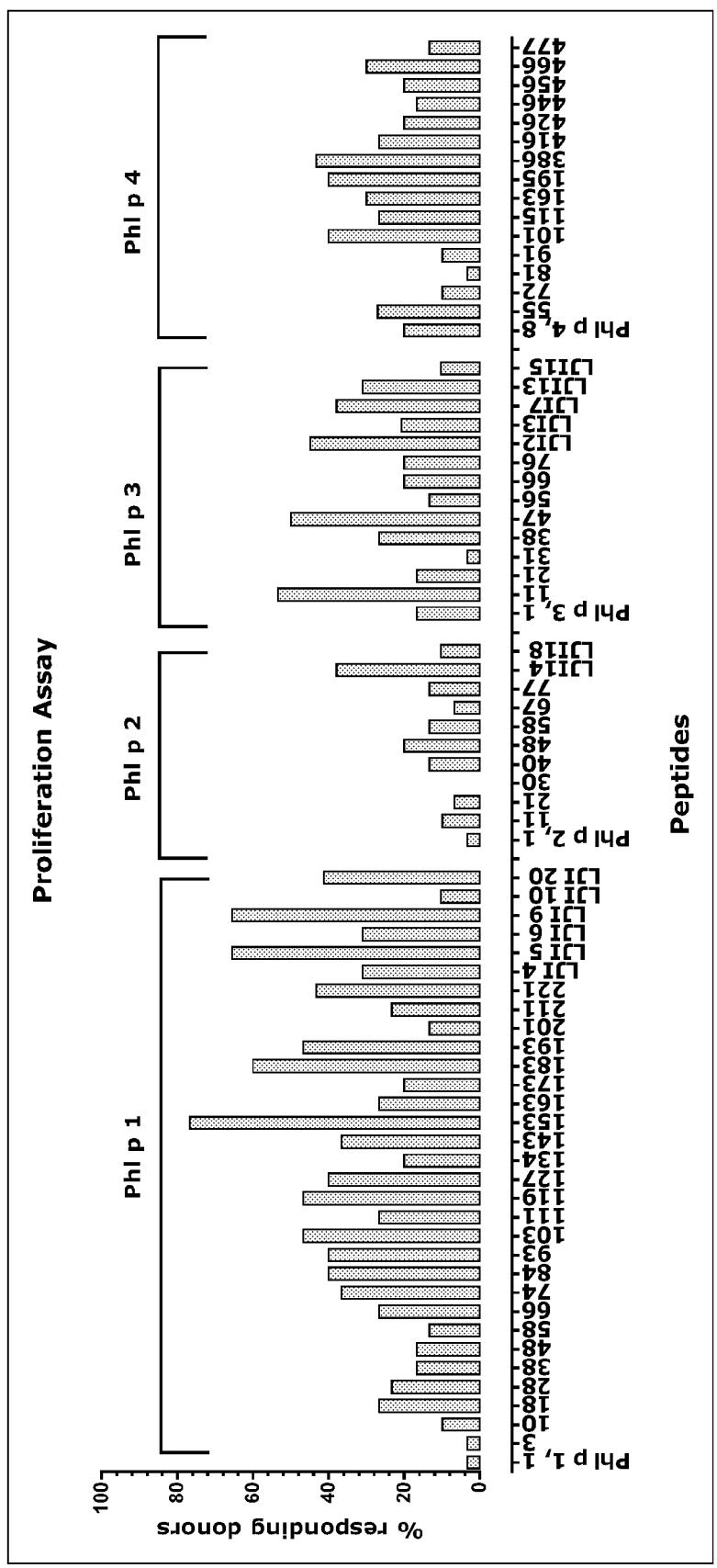

Specification includes a Sequence Listing.

(56) References Cited

FOREIGN PATENT DOCUMENTS

| WO | WO 03/082924 A1 | 10/2003 |
|---|---|---|
| WO | WO 2005/049107 A2 | 6/2005 |
| WO | WO 2006/054280 A2 | 5/2006 |
| WO | WO 2007/031080 A1 | 3/2007 |
| WO | WO 2007/066341 A2 | 6/2007 |
| WO | WO 2007/140505 A2 | 12/2007 |
| WO | WO 2010/089554 A1 | 8/2010 |
| WO | WO 2011/029869 A1 | 3/2011 |
| WO | WO 2011/106645 A1 | 9/2011 |
| WO | WO 2012/049310 A1 | 4/2012 |
| WO | WO 2013/092605 A1 | 6/2013 |
| WO | WO 2013/104901 A2 | 7/2013 |
| WO | WO 2013/119853 A1 | 8/2013 |
| WO | WO 2014/064543 A1 | 5/2014 |
| WO | WO 2014/188429 A1 | 11/2014 |
| WO | WO 2015/100360 A1 | 7/2015 |
| WO | WO 2017/055235 A1 | 4/2017 |

OTHER PUBLICATIONS

Karosiene, E., et al., "NetMHCIIpan-3.0, a common pan-specific MHC class II prediction method including all three human MHC class II isotypes, HLA-DR, HLA-DP and HLA-DQ," *Immunogenetics*, 2013, vol. 65, pp. 711-724.

McKinney, D., et al., "A strategy to determine HLA class II restriction broadly covering the DR, DP, and DQ allelic variants most commonly expressed in the general population," *Immunogenetics*, 2013, vol. 65, pp. 357-370.

Moldaver, D., et anon, "Immunotherapy with peptides," *Allergy*, 2011, vol. 66, pp. 784-791.

Murugan, N., et anon, "Prediction of MHC Class II binding peptides basd on an iterative learning model," *Immunome Research*, 2005, vol. 1(6), pp. 1-10.

Needleman, S., et anon, "A General Method Appliable to the Search for Similarities in the Amino Acid Sequence of Two Proteins," *J. Mol. Biol.*, 1970, vol. 48, pp. 443-453.

Paul, S., et al., "Development and validation of a broad scheme for prediction of HLA class II restricted T cell epitopes," *Journal of Immunological Methods*, 2015, vol. 422, pp. 28-34.

Pearson, William R., "Flexible Sequence Similarity Searching with the FASTA3 Program Package," *Bioinformatics Methods and Protocols. Methods in Molecular Biology*, 2000, Misener S., Krawetz S.A. (eds), Humana Press, Inc., vol. 132.

Pearson, W., et anon, "Improved tools for biological sequence comparison," *Proc. Natl. Acad. Sci. US-A*, 1988, vol. 85, pp. 2444-2448.

Sidney, J., et al., "Measurement of MHC/Peptide Interactions by Gel Filtration or Monoclonal Antibody Capture," *Current Protocols in Immunology*, 2013, Supplement 100, pp. 18.3.1-18.3.36.

Sidney, J., et al., "Measurement of MHC/Peptide Interactions by Gel Filtration," *Current Protocols in Immunology*, 1998, Supplement 31, pp. 18.3.1-18.3.19.

Sidney, J., et al., "Quantitative peptide binding motifs for 19 human and moUS-e MHC class I molecules derived US-ing positional scanning combinatorial peptide libraries," *Immunome Research*, 2008, vol. 4(2), pp. 1-14.

Sidney, J., et al., "Divergent Motifs but Overlapping Binding Repertoires of Six HLA-DQ Molecules Frequently Expressed in the Worldwide Human Population," *The Journal of Immunology*, 2010, vol. 185, pp. 4189-4198.

Sidney, J., et al., "Five HLA-DP molecules Frequently Expressed in the Worldwide Human Population Share a Common HLA Supertypic Binding Specificity," *The Journal of Immunology*, 2010, vol. 184, pp. 2492-2503.

Smith, et anon, "Comparison of Biosesquences," *Advances In Applied Mathematics*, 1981, vol. 2, pp. 482-489.

Smith, et anon, "Identification of Common Molecular Subsequences," *J. Mol. Bio.*, 1981, vol. 147, pp. 195-197.

Verhoef, A., et al., "T Cell Epitope Immunotherapy Induces a $CD4^+$T Cell Population with Regulatory Activity," *PLOS Medicine*, 2005, vol. 2(3), pp. 0253-0261.

Banerjee, S., et al., "Conversion of Der p 23, a New Major House Dust Mite Allergen, into a Hypoallergenic Vaccine," *The Journal of Immunology*, 2014, vol. 192, pp. 4867-4875.

Cooper, B., et al., "Relative, Label-free Protein Quantitation: Spectral Counting Error Statistics from Nine Replicate MudPIT Samples," *J Am Soc Mass Spectrom*, 2010, vol. 21, pp. 1534-1546.

Goodman, R., et al., "Criteria used to categorise proteins as allergens for inclusion in allergenonline.org: a curated database for risk assessment," *Clinical and Transitional Allergy*, 2014, vol. 4(Suppl 2), p. 12.

Haqqani, A., et al., "Chapter 16—Quantitative Protein Profiling by Mass Spectrometry Using Isotope-Coded Affinity Tags," *Methods Mol. Biol.*, 2008, vol. 439, pp. 241-256.

Henmar, H., et al., "Allergenicity, immunogenicity and dose-relationship of three intact allergen vaccines and four allergoid vaccines for subcutaneous grass pollen immunotherapy," *Clinical and Experimental Immunology*, 2008, vol. 153, pp. 316-323.

Ishihama, Y., et al., "Exponentially Modified Protein Abundance Index (emPAI) for Extimation of Absolute Protein Amount in Proteomics by the Number of Sequenced Peptides per Protein," *Molecular & Cellular Proteomics*, 2005, vol. 4, pp. 1265-1272.

Jeong, K., et al., "Immunoglobulin E Reactivity of Recombinant Allergen Tyr p 13 from *Tyrophagus palrescentiae* Homologous to Fatty Acid Binding Protein," *Clinical And Diagnostic Laboratory Immunology*, 2005, vol. 12(5), pp. 581-585.

NCBI, Accession No. XP_005494816, 2015, pp. 1-2.

NCBI, Accession No. XP_012788259, 2015, pp. 1-2.

Rider, S., et al., "Draft genome of the scabies mite," *Parasites & Vectors*, 2015, vol. 8(585), pp. 1-14.

Tang, V., et al., Identification and Characterization of a Group of Polymorphic, Single Domain Peptidoglycan Hydrolases of the N1pC/P60 Superfamily in Dust Mites, *The FASEB Journal*, 2015, vol. 29(1, Supplement 720.2), pp. 1-2.

Trauger, S., et al., "Peptide and protein analysis with mass spectrometry," *Spectroscopy*, 2002, vol. 16, pp. 15-28.

UNIPROT, Accession No. Q09JE3, 2006, pp. 1-2.

UNIPROT, Accession No. A2I463, 2007, 1 page.

UNIPROT, Accession No. T2B4F3, 2013, 1 page.

UNIPROT, Accession No. A0A132AL66, 2016, 1 page.

Wells, W., et al., "Comparative Study of Three Proteomic Quantitative Methods, DIGE, cICAT, and iTRAQ, Using 2D Gel- or LC-MALDI TOF/TOF," *Journal of Proteome Research*, 2006, vol. 5, pp. 651-658.

* cited by examiner

Dose Response of Peptides, Proliferation

Dose Response of Peptides, Proliferation

SEQUENCE LISTING

```
<160> NUMBER OF SEQ ID NOS: 349

<210> SEQ ID NO 1
<211> LENGTH: 20
<212> TYPE: PRT
<213> ORGANISM: Phleum Pratense

<400> SEQUENCE: 1

Trp Leu Asp Ala Lys Ser Thr Trp Tyr Gly Lys Pro Thr Gly Ala Gly
1               5                   10                  15

Pro Lys Asp Asn
            20

<210> SEQ ID NO 2
<211> LENGTH: 20
<212> TYPE: PRT
<213> ORGANISM: Artificial sequence
<220> FEATURE:
<223> OTHER INFORMATION: Modified sequence

<400> SEQUENCE: 2

Gly Arg Gly Ser Gly Ser Ser Phe Glu Ile Lys Ser Thr Lys Pro Glu
1               5                   10                  15

Ala Ser Ser Gly
            20

<210> SEQ ID NO 3
<211> LENGTH: 20
<212> TYPE: PRT
<213> ORGANISM: Artificial sequence
<220> FEATURE:
```

<223> OTHER INFORMATION: Modified sequence

<400> SEQUENCE: 3

Glu Ile Lys Ser Thr Lys Pro Glu Ala Ser Ser Gly Glu Pro Val Val
1               5                   10                  15

Val His Ile Thr
            20

<210> SEQ ID NO 4
<211> LENGTH: 20
<212> TYPE: PRT
<213> ORGANISM: Phleum Pratense

<400> SEQUENCE: 4

Thr Asp Asp Asn Glu Glu Pro Ile Ala Pro Tyr His Phe Asp Leu Ser
1               5                   10                  15

Gly His Ala Phe
            20

<210> SEQ ID NO 5
<211> LENGTH: 20
<212> TYPE: PRT
<213> ORGANISM: Phleum Pratense

<400> SEQUENCE: 5

Tyr His Phe Asp Leu Ser Gly His Ala Phe Gly Ala Met Ala Lys Lys
1               5                   10                  15

Gly Asp Glu Gln
            20

<210> SEQ ID NO 6
<211> LENGTH: 20
<212> TYPE: PRT
<213> ORGANISM: Phleum Pratense

<400> SEQUENCE: 6

Gly Asp Glu Gln Lys Leu Arg Ser Ala Gly Glu Leu Glu Leu Gln Phe
1               5                   10                  15

Arg Arg Val Lys
            20

<210> SEQ ID NO 7
<211> LENGTH: 20
<212> TYPE: PRT
<213> ORGANISM: Artificial sequence
<220> FEATURE:
<223> OTHER INFORMATION: Modified sequence

<400> SEQUENCE: 7

Ala Gly Glu Leu Glu Leu Gln Phe Arg Arg Val Lys Ser Lys Tyr Pro
1               5                   10                  15

Glu Gly Thr Lys
            20

<210> SEQ ID NO 8
<211> LENGTH: 20
<212> TYPE: PRT
<213> ORGANISM: Phleum Pratense

<400> SEQUENCE: 8

Lys Gly Ser Asn Pro Asn Tyr Leu Ala Leu Leu Val Lys Tyr Val Asn
1               5                   10                  15

```
Gly Asp Gly Asp
         20

<210> SEQ ID NO 9
<211> LENGTH: 20
<212> TYPE: PRT
<213> ORGANISM: Phleum Pratense

<400> SEQUENCE: 9

Leu Val Lys Tyr Val Asn Gly Asp Gly Val Val Ala Val Asp Ile
1               5                   10                  15

Lys Glu Lys Gly
         20

<210> SEQ ID NO 10
<211> LENGTH: 20
<212> TYPE: PRT
<213> ORGANISM: Phleum Pratense

<400> SEQUENCE: 10

Lys Asp Lys Trp Ile Glu Leu Lys Glu Ser Trp Gly Ala Ile Trp Arg
1               5                   10                  15

Ile Asp Thr Pro
         20

<210> SEQ ID NO 11
<211> LENGTH: 20
<212> TYPE: PRT
<213> ORGANISM: Phleum Pratense

<400> SEQUENCE: 11

Trp Gly Ala Ile Trp Arg Ile Asp Thr Pro Asp Lys Leu Thr Gly Pro
1               5                   10                  15

Phe Thr Val Arg
         20

<210> SEQ ID NO 12
<211> LENGTH: 20
<212> TYPE: PRT
<213> ORGANISM: Phleum Pratense

<400> SEQUENCE: 12

Val Arg Tyr Thr Thr Glu Gly Gly Thr Lys Thr Glu Ala Glu Asp Val
1               5                   10                  15

Ile Pro Glu Gly
         20

<210> SEQ ID NO 13
<211> LENGTH: 20
<212> TYPE: PRT
<213> ORGANISM: Phleum Pratense

<400> SEQUENCE: 13

Thr Glu Ala Glu Asp Val Ile Pro Glu Gly Trp Lys Ala Asp Thr Ser
1               5                   10                  15

Tyr Glu Ser Lys
         20

<210> SEQ ID NO 14
<211> LENGTH: 20
<212> TYPE: PRT
<213> ORGANISM: Phleum Pratense
```

```
<400> SEQUENCE: 14

Ile Pro Lys Val Pro Pro Gly Pro Asn Ile Thr Ala Thr Tyr Gly Asp
1               5                   10                  15

Lys Trp Leu Asp
            20

<210> SEQ ID NO 15
<211> LENGTH: 20
<212> TYPE: PRT
<213> ORGANISM: Phleum Pratense

<400> SEQUENCE: 15

Lys Val Pro Pro Gly Pro Asn Ile Thr Ala Thr Tyr Gly Asp Lys Trp
1               5                   10                  15

Leu Asp Ala Lys
            20

<210> SEQ ID NO 16
<211> LENGTH: 20
<212> TYPE: PRT
<213> ORGANISM: Phleum Pratense

<400> SEQUENCE: 16

Ile Thr Ala Thr Tyr Gly Asp Lys Trp Leu Asp Ala Lys Ser Thr Trp
1               5                   10                  15

Tyr Gly Lys Pro
            20

<210> SEQ ID NO 17
<211> LENGTH: 20
<212> TYPE: PRT
<213> ORGANISM: Artificial sequence
<220> FEATURE:
<223> OTHER INFORMATION: Modified sequence

<400> SEQUENCE: 17

Lys Pro Thr Gly Ala Gly Pro Lys Asp Asn Gly Gly Ala Ser Gly Tyr
1               5                   10                  15

Lys Asp Val Asp
            20

<210> SEQ ID NO 18
<211> LENGTH: 20
<212> TYPE: PRT
<213> ORGANISM: Artificial sequence
<220> FEATURE:
<223> OTHER INFORMATION: Modified sequence

<400> SEQUENCE: 18

Gly Gly Ala Ser Gly Tyr Lys Asp Val Asp Lys Pro Pro Phe Ser Gly
1               5                   10                  15

Met Thr Gly Ser
            20

<210> SEQ ID NO 19
<211> LENGTH: 20
<212> TYPE: PRT
<213> ORGANISM: Artificial sequence
<220> FEATURE:
<223> OTHER INFORMATION: Modified sequence

<400> SEQUENCE: 19

Lys Pro Pro Phe Ser Gly Met Thr Gly Ser Gly Asn Thr Pro Ile Phe
```

```
1               5                   10                  15

Lys Ser Gly Arg
            20

<210> SEQ ID NO 20
<211> LENGTH: 20
<212> TYPE: PRT
<213> ORGANISM: Artificial sequence
<220> FEATURE:
<223> OTHER INFORMATION: Modified sequence

<400> SEQUENCE: 20

Gly Asn Thr Pro Ile Phe Lys Ser Gly Arg Gly Ser Gly Ser Ser Phe
1               5                   10                  15

Glu Ile Lys Ser
            20

<210> SEQ ID NO 21
<211> LENGTH: 20
<212> TYPE: PRT
<213> ORGANISM: Phleum Pratense

<400> SEQUENCE: 21

Ser Gly Glu Pro Val Val Val His Ile Thr Asp Asp Asn Glu Glu Pro
1               5                   10                  15

Ile Ala Pro Tyr
            20

<210> SEQ ID NO 22
<211> LENGTH: 20
<212> TYPE: PRT
<213> ORGANISM: Phleum Pratense

<400> SEQUENCE: 22

Ala Phe Gly Ala Met Ala Lys Lys Gly Asp Glu Gln Lys Leu Arg Ser
1               5                   10                  15

Ala Gly Glu Leu
            20

<210> SEQ ID NO 23
<211> LENGTH: 20
<212> TYPE: PRT
<213> ORGANISM: Artificial sequence
<220> FEATURE:
<223> OTHER INFORMATION: Modified sequence

<400> SEQUENCE: 23

Phe Arg Arg Val Lys Ser Lys Tyr Pro Glu Gly Thr Lys Val Thr Phe
1               5                   10                  15

His Val Glu Lys
            20

<210> SEQ ID NO 24
<211> LENGTH: 20
<212> TYPE: PRT
<213> ORGANISM: Phleum Pratense

<400> SEQUENCE: 24

Glu Gly Thr Lys Val Thr Phe His Val Glu Lys Gly Ser Asn Pro Asn
1               5                   10                  15

Tyr Leu Ala Leu
            20
```

```
<210> SEQ ID NO 25
<211> LENGTH: 20
<212> TYPE: PRT
<213> ORGANISM: Phleum Pratense

<400> SEQUENCE: 25

Val Val Ala Val Asp Ile Lys Glu Lys Gly Lys Asp Lys Trp Ile Glu
1               5                   10                  15

Leu Lys Glu Ser
            20

<210> SEQ ID NO 26
<211> LENGTH: 20
<212> TYPE: PRT
<213> ORGANISM: Phleum Pratense

<400> SEQUENCE: 26

Thr Pro Asp Lys Leu Thr Gly Pro Phe Thr Val Arg Tyr Thr Thr Glu
1               5                   10                  15

Gly Gly Thr Lys
            20

<210> SEQ ID NO 27
<211> LENGTH: 20
<212> TYPE: PRT
<213> ORGANISM: Phleum Pratense

<400> SEQUENCE: 27

Glu Trp Val Ala Met Thr Lys Gly Glu Gly Val Trp Thr Phe Asp
1               5                   10                  15

Ser Glu Glu Pro
            20

<210> SEQ ID NO 28
<211> LENGTH: 20
<212> TYPE: PRT
<213> ORGANISM: Phleum Pratense

<400> SEQUENCE: 28

Glu Gly Gly Val Trp Thr Phe Asp Ser Glu Glu Pro Leu Gln Gly Pro
1               5                   10                  15

Phe Asn Phe Arg
            20

<210> SEQ ID NO 29
<211> LENGTH: 20
<212> TYPE: PRT
<213> ORGANISM: Phleum Pratense

<400> SEQUENCE: 29

Glu Pro Leu Gln Gly Pro Phe Asn Phe Arg Phe Leu Thr Glu Lys Gly
1               5                   10                  15

Met Lys Asn Val
            20

<210> SEQ ID NO 30
<211> LENGTH: 20
<212> TYPE: PRT
<213> ORGANISM: Phleum Pratense

<400> SEQUENCE: 30

Val Pro Lys Val Thr Phe Thr Val Glu Lys Gly Ser Asn Glu Lys His
```

```
                1               5                  10                 15

Leu Ala Val Leu
            20

<210> SEQ ID NO 31
<211> LENGTH: 20
<212> TYPE: PRT
<213> ORGANISM: Phleum Pratense

<400> SEQUENCE: 31

Gly Ser Asn Glu Lys His Leu Ala Val Leu Val Lys Tyr Glu Gly Asp
1               5                   10                  15

Thr Met Ala Glu
            20

<210> SEQ ID NO 32
<211> LENGTH: 20
<212> TYPE: PRT
<213> ORGANISM: Phleum Pratense

<400> SEQUENCE: 32

Val Lys Tyr Glu Gly Asp Thr Met Ala Glu Val Glu Leu Arg Glu His
1               5                   10                  15

Gly Ser Asp Glu
            20

<210> SEQ ID NO 33
<211> LENGTH: 20
<212> TYPE: PRT
<213> ORGANISM: Phleum Pratense

<400> SEQUENCE: 33

Glu Val Glu Leu Arg Glu His Gly Ser Asp Glu Trp Val Ala Met Thr
1               5                   10                  15

Lys Gly Glu Gly
            20

<210> SEQ ID NO 34
<211> LENGTH: 20
<212> TYPE: PRT
<213> ORGANISM: Phleum Pratense

<400> SEQUENCE: 34

Arg Phe Leu Thr Glu Lys Gly Met Lys Asn Val Phe Asp Asp Val Val
1               5                   10                  15

Pro Glu Lys Tyr
            20

<210> SEQ ID NO 35
<211> LENGTH: 20
<212> TYPE: PRT
<213> ORGANISM: Phleum Pratense

<400> SEQUENCE: 35

Val Phe Asp Asp Val Val Pro Glu Lys Tyr Thr Ile Gly Ala Thr Tyr
1               5                   10                  15

Ala Pro Glu Glu
            20

<210> SEQ ID NO 36
<211> LENGTH: 20
<212> TYPE: PRT
```

```
<213> ORGANISM: Phleum Pratense

<400> SEQUENCE: 36

Gly Ser Asp Pro Lys Lys Leu Val Leu Asn Ile Lys Tyr Thr Arg Pro
1               5                   10                  15

Gly Asp Ser Leu
            20

<210> SEQ ID NO 37
<211> LENGTH: 20
<212> TYPE: PRT
<213> ORGANISM: Phleum Pratense

<400> SEQUENCE: 37

His Gly Ser Glu Glu Trp Glu Pro Leu Thr Lys Lys Gly Asn Val Trp
1               5                   10                  15

Glu Val Lys Ser
            20

<210> SEQ ID NO 38
<211> LENGTH: 20
<212> TYPE: PRT
<213> ORGANISM: Phleum Pratense

<400> SEQUENCE: 38

Thr Lys Lys Gly Asn Val Trp Glu Val Lys Ser Ser Lys Pro Leu Val
1               5                   10                  15

Gly Pro Phe Asn
            20

<210> SEQ ID NO 39
<211> LENGTH: 20
<212> TYPE: PRT
<213> ORGANISM: Phleum Pratense

<400> SEQUENCE: 39

Lys Ser Ser Lys Pro Leu Val Gly Pro Phe Asn Phe Arg Phe Met Ser
1               5                   10                  15

Lys Gly Gly Met
            20

<210> SEQ ID NO 40
<211> LENGTH: 20
<212> TYPE: PRT
<213> ORGANISM: Phleum Pratense

<400> SEQUENCE: 40

Asn Phe Arg Phe Met Ser Lys Gly Gly Met Arg Asn Val Phe Asp Glu
1               5                   10                  15

Val Ile Pro Thr
            20

<210> SEQ ID NO 41
<211> LENGTH: 20
<212> TYPE: PRT
<213> ORGANISM: Phleum Pratense

<400> SEQUENCE: 41

Ala Val Gln Val Thr Phe Thr Val Gln Lys Gly Ser Asp Pro Lys Lys
1               5                   10                  15

Leu Val Leu Asn
            20
```

```
<210> SEQ ID NO 42
<211> LENGTH: 20
<212> TYPE: PRT
<213> ORGANISM: Phleum Pratense

<400> SEQUENCE: 42

Ile Lys Tyr Thr Arg Pro Gly Asp Ser Leu Ala Glu Val Glu Leu Arg
1               5                   10                  15

Gln His Gly Ser
            20

<210> SEQ ID NO 43
<211> LENGTH: 20
<212> TYPE: PRT
<213> ORGANISM: Phleum Pratense

<400> SEQUENCE: 43

Ala Glu Val Glu Leu Arg Gln His Gly Ser Glu Glu Trp Glu Pro Leu
1               5                   10                  15

Thr Lys Lys Gly
            20

<210> SEQ ID NO 44
<211> LENGTH: 20
<212> TYPE: PRT
<213> ORGANISM: Phleum Pratense

<400> SEQUENCE: 44

Arg Asn Val Phe Asp Glu Val Ile Pro Thr Ala Phe Lys Ile Gly Lys
1               5                   10                  15

Thr Tyr Thr Pro
            20

<210> SEQ ID NO 45
<211> LENGTH: 20
<212> TYPE: PRT
<213> ORGANISM: Artificial sequence
<220> FEATURE:
<223> OTHER INFORMATION: Modified sequence

<400> SEQUENCE: 45

Lys Glu Asp Phe Leu Gly Ser Leu Val Lys Glu Ile Pro Pro Arg Leu
1               5                   10                  15

Leu Tyr Ala Lys
            20

<210> SEQ ID NO 46
<211> LENGTH: 20
<212> TYPE: PRT
<213> ORGANISM: Artificial sequence
<220> FEATURE:
<223> OTHER INFORMATION: Modified sequence

<400> SEQUENCE: 46

Tyr Ile Ile Thr Pro Thr Asn Val Ser His Ile Gln Ser Ala Val Val
1               5                   10                  15

Ser Gly Arg Arg
            20

<210> SEQ ID NO 47
<211> LENGTH: 20
<212> TYPE: PRT
```

<213> ORGANISM: Phleum Pratense

<400> SEQUENCE: 47

Phe Ala Val Val Asp Leu Asn Lys Met Arg Ala Val Trp Val Asp Gly
1               5                   10                  15

Lys Ala Arg Thr
            20

<210> SEQ ID NO 48
<211> LENGTH: 20
<212> TYPE: PRT
<213> ORGANISM: Phleum Pratense

<400> SEQUENCE: 48

Gly Phe Gly Met Leu Leu Arg Lys Tyr Gly Ile Ala Ala Glu Asn Val
1               5                   10                  15

Ile Asp Val Lys
            20

<210> SEQ ID NO 49
<211> LENGTH: 20
<212> TYPE: PRT
<213> ORGANISM: Phleum Pratense

<400> SEQUENCE: 49

Ser Met Gly Asp Asp His Phe Trp Ala Val Arg Gly Gly Gly Gly Glu
1               5                   10                  15

Ser Phe Gly Ile
            20

<210> SEQ ID NO 50
<211> LENGTH: 20
<212> TYPE: PRT
<213> ORGANISM: Phleum Pratense

<400> SEQUENCE: 50

Thr Pro Phe Pro His Arg Lys Gly Val Leu Phe Asn Ile Gln Tyr Val
1               5                   10                  15

Asn Tyr Trp Phe
            20

<210> SEQ ID NO 51
<211> LENGTH: 20
<212> TYPE: PRT
<213> ORGANISM: Phleum Pratense

<400> SEQUENCE: 51

Gly Arg Arg His Ser Val Arg Ile Arg Val Arg Ser Gly Gly His Asp
1               5                   10                  15

Tyr Glu Gly Leu
            20

<210> SEQ ID NO 52
<211> LENGTH: 20
<212> TYPE: PRT
<213> ORGANISM: Phleum Pratense

<400> SEQUENCE: 52

Val Arg Ser Gly Gly His Asp Tyr Glu Gly Leu Ser Tyr Arg Ser Leu
1               5                   10                  15

Gln Pro Glu Thr
            20

<210> SEQ ID NO 53
<211> LENGTH: 20
<212> TYPE: PRT
<213> ORGANISM: Phleum Pratense

<400> SEQUENCE: 53

Leu Ser Tyr Arg Ser Leu Gln Pro Glu Thr Phe Ala Val Val Asp Leu
1               5                   10                  15

Asn Lys Met Arg
            20

<210> SEQ ID NO 54
<211> LENGTH: 20
<212> TYPE: PRT
<213> ORGANISM: Phleum Pratense

<400> SEQUENCE: 54

Asp Gly Lys Ala Arg Thr Ala Trp Val Asp Ser Gly Ala Gln Leu Gly
1               5                   10                  15

Glu Leu Tyr Tyr
            20

<210> SEQ ID NO 55
<211> LENGTH: 20
<212> TYPE: PRT
<213> ORGANISM: Phleum Pratense

<400> SEQUENCE: 55

Trp Ser Lys Asp Ile Tyr Asn Tyr Met Glu Pro Tyr Val Ser Lys Asn
1               5                   10                  15

Pro Arg Gln Ala
            20

<210> SEQ ID NO 56
<211> LENGTH: 20
<212> TYPE: PRT
<213> ORGANISM: Phleum Pratense

<400> SEQUENCE: 56

Pro Tyr Val Ser Lys Asn Pro Arg Gln Ala Tyr Ala Asn Tyr Arg Asp
1               5                   10                  15

Ile Asp Leu Gly
            20

<210> SEQ ID NO 57
<211> LENGTH: 20
<212> TYPE: PRT
<213> ORGANISM: Phleum Pratense

<400> SEQUENCE: 57

Arg Asn Glu Val Val Asn Asp Val Ser Thr Tyr Ala Ser Gly Lys Val
1               5                   10                  15

Trp Gly Gln Lys
            20

<210> SEQ ID NO 58
<211> LENGTH: 20
<212> TYPE: PRT
<213> ORGANISM: Phleum Pratense

<400> SEQUENCE: 58

```
Tyr Ala Ser Gly Lys Val Trp Gly Gln Lys Tyr Phe Lys Gly Asn Phe
1               5                   10                  15

Glu Arg Leu Ala
            20

<210> SEQ ID NO 59
<211> LENGTH: 20
<212> TYPE: PRT
<213> ORGANISM: Phleum Pratense

<400> SEQUENCE: 59

Tyr Phe Lys Gly Asn Phe Glu Arg Leu Ala Ile Thr Lys Gly Lys Val
1               5                   10                  15

Asp Pro Thr Asp
            20

<210> SEQ ID NO 60
<211> LENGTH: 20
<212> TYPE: PRT
<213> ORGANISM: Phleum Pratense

<400> SEQUENCE: 60

Thr Lys Gly Lys Val Asp Pro Thr Asp Tyr Phe Arg Asn Glu Gln Ser
1               5                   10                  15

Ile Pro Pro Leu
            20

<210> SEQ ID NO 61
<211> LENGTH: 20
<212> TYPE: PRT
<213> ORGANISM: Phleum Pratense

<400> SEQUENCE: 61

Ala Gly Tyr Thr Pro Ala Ala Pro Ala Gly Ala Glu Pro Ala Gly Lys
1               5                   10                  15

Ala Thr Thr Glu
            20

<210> SEQ ID NO 62
<211> LENGTH: 20
<212> TYPE: PRT
<213> ORGANISM: Phleum Pratense

<400> SEQUENCE: 62

Glu Gln Lys Leu Ile Glu Lys Ile Asn Ala Gly Phe Lys Ala Ala Leu
1               5                   10                  15

Ala Ala Ala Ala
            20

<210> SEQ ID NO 63
<211> LENGTH: 20
<212> TYPE: PRT
<213> ORGANISM: Phleum Pratense

<400> SEQUENCE: 63

Gly Phe Lys Ala Ala Leu Ala Ala Ala Ala Gly Val Pro Pro Ala Asp
1               5                   10                  15

Lys Tyr Arg Thr
            20

<210> SEQ ID NO 64
<211> LENGTH: 20
```

```
<212> TYPE: PRT
<213> ORGANISM: Phleum Pratense

<400> SEQUENCE: 64

Asp Lys Tyr Arg Thr Phe Val Ala Thr Phe Gly Ala Ala Ser Asn Lys
1               5                   10                  15

Ala Phe Ala Glu
            20

<210> SEQ ID NO 65
<211> LENGTH: 20
<212> TYPE: PRT
<213> ORGANISM: Phleum Pratense

<400> SEQUENCE: 65

Thr Ser Lys Leu Asp Ala Ala Tyr Lys Leu Ala Tyr Lys Thr Ala Glu
1               5                   10                  15

Gly Ala Thr Pro
            20

<210> SEQ ID NO 66
<211> LENGTH: 20
<212> TYPE: PRT
<213> ORGANISM: Phleum Pratense

<400> SEQUENCE: 66

Glu Ala Lys Tyr Asp Ala Tyr Val Ala Thr Leu Ser Glu Ala Leu Arg
1               5                   10                  15

Ile Ile Ala Gly
            20

<210> SEQ ID NO 67
<211> LENGTH: 20
<212> TYPE: PRT
<213> ORGANISM: Phleum Pratense

<400> SEQUENCE: 67

Val Ala Thr Leu Ser Glu Ala Leu Arg Ile Ile Ala Gly Thr Leu Glu
1               5                   10                  15

Val His Ala Val
            20

<210> SEQ ID NO 68
<211> LENGTH: 20
<212> TYPE: PRT
<213> ORGANISM: Phleum Pratense

<400> SEQUENCE: 68

Ile Glu Lys Val Asp Ala Ala Phe Lys Val Ala Ala Thr Ala Ala Asn
1               5                   10                  15

Ala Ala Pro Ala
            20

<210> SEQ ID NO 69
<211> LENGTH: 20
<212> TYPE: PRT
<213> ORGANISM: Phleum Pratense

<400> SEQUENCE: 69

Lys Val Ala Ala Thr Ala Ala Asn Ala Ala Pro Ala Asn Asp Lys Phe
1               5                   10                  15

Thr Val Phe Glu
```

<210> SEQ ID NO 70
<211> LENGTH: 20
<212> TYPE: PRT
<213> ORGANISM: Phleum Pratense

<400> SEQUENCE: 70

Pro Ala Asn Asp Lys Phe Thr Val Phe Glu Ala Ala Phe Asn Asn Ala
1               5                   10                  15

Ile Lys Ala Ser
            20

<210> SEQ ID NO 71
<211> LENGTH: 20
<212> TYPE: PRT
<213> ORGANISM: Phleum Pratense

<400> SEQUENCE: 71

Ser Thr Gly Gly Ala Tyr Glu Ser Tyr Lys Phe Ile Pro Ala Leu Glu
1               5                   10                  15

Ala Ala Val Lys
            20

<210> SEQ ID NO 72
<211> LENGTH: 20
<212> TYPE: PRT
<213> ORGANISM: Phleum Pratense

<400> SEQUENCE: 72

Lys Phe Ile Pro Ala Leu Glu Ala Ala Val Lys Gln Ala Tyr Ala Ala
1               5                   10                  15

Thr Val Ala Thr
            20

<210> SEQ ID NO 73
<211> LENGTH: 20
<212> TYPE: PRT
<213> ORGANISM: Phleum Pratense

<400> SEQUENCE: 73

Ala Pro Glu Val Lys Tyr Thr Val Phe Glu Thr Ala Leu Lys Lys Ala
1               5                   10                  15

Ile Thr Ala Met
            20

<210> SEQ ID NO 74
<211> LENGTH: 20
<212> TYPE: PRT
<213> ORGANISM: Phleum Pratense

<400> SEQUENCE: 74

Ala Glu Pro Ala Gly Lys Ala Thr Thr Glu Glu Gln Lys Leu Ile Glu
1               5                   10                  15

Lys Ile Asn Ala
            20

<210> SEQ ID NO 75
<211> LENGTH: 20
<212> TYPE: PRT
<213> ORGANISM: Phleum Pratense

<400> SEQUENCE: 75

Ala Ala Gly Val Pro Pro Ala Asp Lys Tyr Arg Thr Phe Val Ala Thr
1               5                   10                  15

Phe Gly Ala Ala
            20

<210> SEQ ID NO 76
<211> LENGTH: 20
<212> TYPE: PRT
<213> ORGANISM: Phleum Pratense

<400> SEQUENCE: 76

Gly Ala Ala Ser Asn Lys Ala Phe Ala Glu Gly Leu Ser Gly Glu Pro
1               5                   10                  15

Lys Gly Ala Ala
            20

<210> SEQ ID NO 77
<211> LENGTH: 20
<212> TYPE: PRT
<213> ORGANISM: Phleum Pratense

<400> SEQUENCE: 77

Ala Glu Gly Leu Ser Gly Glu Pro Lys Gly Ala Ala Glu Ser Ser Ser
1               5                   10                  15

Lys Ala Ala Leu
            20

<210> SEQ ID NO 78
<211> LENGTH: 20
<212> TYPE: PRT
<213> ORGANISM: Phleum Pratense

<400> SEQUENCE: 78

Ala Ala Glu Ser Ser Ser Lys Ala Ala Leu Thr Ser Lys Leu Asp Ala
1               5                   10                  15

Ala Tyr Lys Leu
            20

<210> SEQ ID NO 79
<211> LENGTH: 20
<212> TYPE: PRT
<213> ORGANISM: Phleum Pratense

<400> SEQUENCE: 79

Ala Tyr Lys Thr Ala Glu Gly Ala Thr Pro Glu Ala Lys Tyr Asp Ala
1               5                   10                  15

Tyr Val Ala Thr
            20

<210> SEQ ID NO 80
<211> LENGTH: 20
<212> TYPE: PRT
<213> ORGANISM: Phleum Pratense

<400> SEQUENCE: 80

Arg Ile Ile Ala Gly Thr Leu Glu Val His Ala Val Lys Pro Ala Ala
1               5                   10                  15

Glu Glu Val Lys
            20

<210> SEQ ID NO 81

```
<211> LENGTH: 20
<212> TYPE: PRT
<213> ORGANISM: Phleum Pratense

<400> SEQUENCE: 81

Ala Val Lys Pro Ala Ala Glu Glu Val Lys Val Ile Pro Ala Gly Glu
1               5                   10                  15

Leu Gln Val Ile
            20

<210> SEQ ID NO 82
<211> LENGTH: 20
<212> TYPE: PRT
<213> ORGANISM: Phleum Pratense

<400> SEQUENCE: 82

Val Ile Pro Ala Gly Glu Leu Gln Val Ile Glu Lys Val Asp Ala Ala
1               5                   10                  15

Phe Lys Val Ala
            20

<210> SEQ ID NO 83
<211> LENGTH: 20
<212> TYPE: PRT
<213> ORGANISM: Phleum Pratense

<400> SEQUENCE: 83

Glu Ala Ala Phe Asn Asn Ala Ile Lys Ala Ser Thr Gly Gly Ala Tyr
1               5                   10                  15

Glu Ser Tyr Lys
            20

<210> SEQ ID NO 84
<211> LENGTH: 20
<212> TYPE: PRT
<213> ORGANISM: Phleum Pratense

<400> SEQUENCE: 84

Lys Gln Ala Tyr Ala Ala Thr Val Ala Thr Ala Pro Glu Val Lys Tyr
1               5                   10                  15

Thr Val Phe Glu
            20

<210> SEQ ID NO 85
<211> LENGTH: 20
<212> TYPE: PRT
<213> ORGANISM: Phleum Pratense

<400> SEQUENCE: 85

Thr Ala Leu Lys Lys Ala Ile Thr Ala Met Ser Glu Ala Gln Lys Ala
1               5                   10                  15

Ala Lys Pro Ala
            20

<210> SEQ ID NO 86
<211> LENGTH: 20
<212> TYPE: PRT
<213> ORGANISM: Phleum Pratense

<400> SEQUENCE: 86

Ala Met Ser Glu Ala Gln Lys Ala Ala Lys Pro Ala Ala Ala Ala Thr
1               5                   10                  15
```

```
Ala Thr Ala Thr
            20

<210> SEQ ID NO 87
<211> LENGTH: 20
<212> TYPE: PRT
<213> ORGANISM: Phleum Pratense

<400> SEQUENCE: 87

Lys Pro Ala Ala Ala Ala Thr Ala Thr Ala Thr Ser Ala Val Gly Ala
1               5                   10                  15

Ala Thr Gly Ala
            20

<210> SEQ ID NO 88
<211> LENGTH: 20
<212> TYPE: PRT
<213> ORGANISM: Phleum Pratense

<400> SEQUENCE: 88

Thr Ser Ala Val Gly Ala Ala Thr Gly Ala Ala Thr Ala Ala Thr Gly
1               5                   10                  15

Gly Tyr Lys Val
            20

<210> SEQ ID NO 89
<211> LENGTH: 20
<212> TYPE: PRT
<213> ORGANISM: Cynodon dactylon

<400> SEQUENCE: 89

Ala Ile Gly Asp Lys Pro Gly Pro Asn Ile Thr Ala Thr Tyr Gly Ser
1               5                   10                  15

Lys Trp Leu Glu
            20

<210> SEQ ID NO 90
<211> LENGTH: 20
<212> TYPE: PRT
<213> ORGANISM: Cynodon dactylon

<400> SEQUENCE: 90

Thr Ala Thr Tyr Gly Ser Lys Trp Leu Glu Ala Arg Ala Thr Phe Tyr
1               5                   10                  15

Gly Ser Asn Pro
            20

<210> SEQ ID NO 91
<211> LENGTH: 20
<212> TYPE: PRT
<213> ORGANISM: Cynodon dactylon

<400> SEQUENCE: 91

Ala Arg Ala Thr Phe Tyr Gly Ser Asn Pro Arg Gly Ala Ala Pro Asp
1               5                   10                  15

Asp His Gly Gly
            20

<210> SEQ ID NO 92
<211> LENGTH: 20
<212> TYPE: PRT
<213> ORGANISM: Artificial sequence
<220> FEATURE:
```

<223> OTHER INFORMATION: Modified sequence

<400> SEQUENCE: 92

Arg Gly Ala Ala Pro Asp Asp His Gly Gly Ala Ser Gly Tyr Lys Asp
1               5                   10                  15

Val Asp Lys Pro
            20

<210> SEQ ID NO 93
<211> LENGTH: 20
<212> TYPE: PRT
<213> ORGANISM: Artificial sequence
<220> FEATURE:
<223> OTHER INFORMATION: Modified sequence

<400> SEQUENCE: 93

Ala Ser Gly Tyr Lys Asp Val Asp Lys Pro Pro Phe Asp Gly Met Thr
1               5                   10                  15

Ala Ser Gly Asn
            20

<210> SEQ ID NO 94
<211> LENGTH: 20
<212> TYPE: PRT
<213> ORGANISM: Artificial sequence
<220> FEATURE:
<223> OTHER INFORMATION: Modified sequence

<400> SEQUENCE: 94

Pro Phe Asp Gly Met Thr Ala Ser Gly Asn Glu Pro Ile Phe Lys Asp
1               5                   10                  15

Gly Leu Gly Ser
            20

<210> SEQ ID NO 95
<211> LENGTH: 20
<212> TYPE: PRT
<213> ORGANISM: Artificial sequence
<220> FEATURE:
<223> OTHER INFORMATION: Modified sequence

<400> SEQUENCE: 95

Glu Pro Ile Phe Lys Asp Gly Leu Gly Ser Arg Ala Ser Tyr Glu Ile
1               5                   10                  15

Lys Ser Lys Glu
            20

<210> SEQ ID NO 96
<211> LENGTH: 20
<212> TYPE: PRT
<213> ORGANISM: Artificial sequence
<220> FEATURE:
<223> OTHER INFORMATION: Modified sequence

<400> SEQUENCE: 96

Arg Ala Ser Tyr Glu Ile Lys Ser Lys Glu Pro Val Glu Ser Ser Gly
1               5                   10                  15

Glu Pro Val Leu
            20

<210> SEQ ID NO 97
<211> LENGTH: 20
<212> TYPE: PRT
<213> ORGANISM: Artificial sequence -continued

```
<220> FEATURE:
<223> OTHER INFORMATION: Modified sequence

<400> SEQUENCE: 97

Pro Val Glu Ser Ser Gly Glu Pro Val Leu Val Lys Ile Thr Asp Lys
1               5                   10                  15

Asn Tyr Glu His
            20

<210> SEQ ID NO 98
<211> LENGTH: 20
<212> TYPE: PRT
<213> ORGANISM: Cynodon dactylon

<400> SEQUENCE: 98

Val Lys Ile Thr Asp Lys Asn Tyr Glu His Ile Ala Ala Tyr His Phe
1               5                   10                  15

Asp Leu Ser Gly
            20

<210> SEQ ID NO 99
<211> LENGTH: 20
<212> TYPE: PRT
<213> ORGANISM: Cynodon dactylon

<400> SEQUENCE: 99

Ile Ala Ala Tyr His Phe Asp Leu Ser Gly Lys Ala Phe Gly Ala Met
1               5                   10                  15

Ala Lys Lys Gly
            20

<210> SEQ ID NO 100
<211> LENGTH: 20
<212> TYPE: PRT
<213> ORGANISM: Cynodon dactylon

<400> SEQUENCE: 100

Gly Lys Ala Phe Gly Ala Met Ala Lys Lys Gly Gln Glu Asp Lys Leu
1               5                   10                  15

Arg Lys Ala Gly
            20

<210> SEQ ID NO 101
<211> LENGTH: 20
<212> TYPE: PRT
<213> ORGANISM: Cynodon dactylon

<400> SEQUENCE: 101

Gly Gln Glu Asp Lys Leu Arg Lys Ala Gly Glu Leu Thr Leu Gln Phe
1               5                   10                  15

Arg Arg Val Lys
            20

<210> SEQ ID NO 102
<211> LENGTH: 20
<212> TYPE: PRT
<213> ORGANISM: Artificial sequence
<220> FEATURE:
<223> OTHER INFORMATION: Modified sequence

<400> SEQUENCE: 102

Glu Leu Thr Leu Gln Phe Arg Arg Val Lys Ser Lys Tyr Pro Ser Gly
1               5                   10                  15
```

```
Thr Lys Ile Thr
            20

<210> SEQ ID NO 103
<211> LENGTH: 20
<212> TYPE: PRT
<213> ORGANISM: Artificial sequence
<220> FEATURE:
<223> OTHER INFORMATION: Modified sequence

<400> SEQUENCE: 103

Ser Lys Tyr Pro Ser Gly Thr Lys Ile Thr Phe His Ile Glu Lys Gly
1               5                  10                  15

Ser Asn Asp His
            20

<210> SEQ ID NO 104
<211> LENGTH: 20
<212> TYPE: PRT
<213> ORGANISM: Cynodon dactylon

<400> SEQUENCE: 104

Phe His Ile Glu Lys Gly Ser Asn Asp His Tyr Leu Ala Leu Leu Val
1               5                  10                  15

Lys Tyr Ala Ala
            20

<210> SEQ ID NO 105
<211> LENGTH: 20
<212> TYPE: PRT
<213> ORGANISM: Cynodon dactylon

<400> SEQUENCE: 105

Tyr Leu Ala Leu Leu Val Lys Tyr Ala Ala Gly Asp Gly Asn Ile Val
1               5                  10                  15

Ala Val Asp Ile
            20

<210> SEQ ID NO 106
<211> LENGTH: 20
<212> TYPE: PRT
<213> ORGANISM: Cynodon dactylon

<400> SEQUENCE: 106

Gly Asp Gly Asn Ile Val Ala Val Asp Ile Lys Pro Arg Asp Ser Asp
1               5                  10                  15

Glu Phe Ile Pro
            20

<210> SEQ ID NO 107
<211> LENGTH: 20
<212> TYPE: PRT
<213> ORGANISM: Cynodon dactylon

<400> SEQUENCE: 107

Lys Pro Arg Asp Ser Asp Glu Phe Ile Pro Met Lys Ser Ser Trp Gly
1               5                  10                  15

Ala Ile Trp Arg
            20

<210> SEQ ID NO 108
<211> LENGTH: 20
```

```
<212> TYPE: PRT
<213> ORGANISM: Cynodon dactylon

<400> SEQUENCE: 108

Pro Met Lys Ser Ser Trp Gly Ala Ile Trp Arg Ile Asp Pro Lys Lys
 1               5                  10                  15

Pro Leu Lys Gly
         20

<210> SEQ ID NO 109
<211> LENGTH: 20
<212> TYPE: PRT
<213> ORGANISM: Cynodon dactylon

<400> SEQUENCE: 109

Trp Arg Ile Asp Pro Lys Lys Pro Leu Lys Gly Pro Phe Ser Ile Arg
 1               5                  10                  15

Leu Thr Ser Glu
         20

<210> SEQ ID NO 110
<211> LENGTH: 20
<212> TYPE: PRT
<213> ORGANISM: Cynodon dactylon

<400> SEQUENCE: 110

Gly Pro Phe Ser Ile Arg Leu Thr Ser Glu Gly Gly Ala His Leu Val
 1               5                  10                  15

Gln Asp Asp Val
         20

<210> SEQ ID NO 111
<211> LENGTH: 20
<212> TYPE: PRT
<213> ORGANISM: Cynodon dactylon

<400> SEQUENCE: 111

Glu Gly Gly Ala His Leu Val Gln Asp Asp Val Ile Pro Ala Asn Trp
 1               5                  10                  15

Lys Pro Asp Thr
         20

<210> SEQ ID NO 112
<211> LENGTH: 20
<212> TYPE: PRT
<213> ORGANISM: Cynodon dactylon

<400> SEQUENCE: 112

Asp Asp Val Ile Pro Ala Asn Trp Lys Pro Asp Thr Val Tyr Thr Ser
 1               5                  10                  15

Lys Leu Gln Phe
         20

<210> SEQ ID NO 113
<211> LENGTH: 15
<212> TYPE: PRT
<213> ORGANISM: Phleum Pratense

<400> SEQUENCE: 113

Ala Phe Lys Val Ala Ala Thr Ala Ala Asn Ala Ala Pro Ala Asn
 1               5                  10                  15
```

```
<210> SEQ ID NO 114
<211> LENGTH: 15
<212> TYPE: PRT
<213> ORGANISM: Artificial sequence
<220> FEATURE:
<223> OTHER INFORMATION: Modified sequence

<400> SEQUENCE: 114

Ile Asn Val Gly Phe Lys Ala Ala Val Ala Ala Ala Ala Gly Val
1               5                   10                  15

<210> SEQ ID NO 115
<211> LENGTH: 15
<212> TYPE: PRT
<213> ORGANISM: Phleum Pratense

<400> SEQUENCE: 115

Asn Val Trp Glu Val Lys Ser Ser Lys Pro Leu Val Gly Pro Phe
1               5                   10                  15

<210> SEQ ID NO 116
<211> LENGTH: 15
<212> TYPE: PRT
<213> ORGANISM: Phleum Pratense

<400> SEQUENCE: 116

Asn Phe Arg Phe Met Ser Lys Gly Gly Met Arg Asn Val Phe Asp
1               5                   10                  15

<210> SEQ ID NO 117
<211> LENGTH: 15
<212> TYPE: PRT
<213> ORGANISM: Artificial sequence
<220> FEATURE:
<223> OTHER INFORMATION: Modified sequence

<400> SEQUENCE: 117

Ser Gly Ile Ala Phe Gly Ser Met Ala Lys Lys Gly Asp Glu Gln
1               5                   10                  15

<210> SEQ ID NO 118
<211> LENGTH: 15
<212> TYPE: PRT
<213> ORGANISM: Artificial sequence
<220> FEATURE:
<223> OTHER INFORMATION: Modified sequence

<400> SEQUENCE: 118

Gly Glu Leu Glu Leu Gln Phe Arg Arg Val Lys Ser Lys Tyr Pro
1               5                   10                  15

<210> SEQ ID NO 119
<211> LENGTH: 15
<212> TYPE: PRT
<213> ORGANISM: Phleum Pratense

<400> SEQUENCE: 119

Ser Thr Trp Tyr Gly Lys Pro Thr Gly Ala Gly Pro Lys Asp Asn
1               5                   10                  15

<210> SEQ ID NO 120
<211> LENGTH: 15
<212> TYPE: PRT
<213> ORGANISM: Phleum Pratense

<400> SEQUENCE: 120
```

```
Glu Glu Trp Glu Pro Leu Thr Lys Lys Gly Asn Val Trp Glu Val
1               5                   10                  15

<210> SEQ ID NO 121
<211> LENGTH: 15
<212> TYPE: PRT
<213> ORGANISM: Phleum Pratense

<400> SEQUENCE: 121

Asn Tyr Leu Ala Leu Leu Val Lys Tyr Val Asn Gly Asp Gly Asp
1               5                   10                  15

<210> SEQ ID NO 122
<211> LENGTH: 15
<212> TYPE: PRT
<213> ORGANISM: Artificial sequence
<220> FEATURE:
<223> OTHER INFORMATION: Modified sequence

<400> SEQUENCE: 122

Lys Pro Pro Phe Ser Gly Met Thr Gly Ser Gly Asn Thr Pro Ile
1               5                   10                  15

<210> SEQ ID NO 123
<211> LENGTH: 15
<212> TYPE: PRT
<213> ORGANISM: Lollium Perenne

<400> SEQUENCE: 123

Leu Ile Glu Lys Ile Asn Ala Gly Phe Lys Ala Ala Val Ala Ala
1               5                   10                  15

<210> SEQ ID NO 124
<211> LENGTH: 15
<212> TYPE: PRT
<213> ORGANISM: Lollium Perenne

<400> SEQUENCE: 124

Asn Ala Gly Phe Lys Ala Ala Val Ala Ala Ala Val Val Pro
1               5                   10                  15

<210> SEQ ID NO 125
<211> LENGTH: 15
<212> TYPE: PRT
<213> ORGANISM: Lollium Perenne

<400> SEQUENCE: 125

Ser Asp Ala Lys Thr Leu Val Leu Asn Ile Lys Tyr Thr Arg Pro
1               5                   10                  15

<210> SEQ ID NO 126
<211> LENGTH: 15
<212> TYPE: PRT
<213> ORGANISM: Lollium Perenne

<400> SEQUENCE: 126

Met Arg Asn Val Phe Asp Asp Val Pro Ala Asp Phe Lys Val
1               5                   10                  15

<210> SEQ ID NO 127
<211> LENGTH: 15
<212> TYPE: PRT
<213> ORGANISM: Lollium Perenne

<400> SEQUENCE: 127
```

-continued

```
Asn Val Phe Asp Glu Val Ile Pro Thr Ala Phe Thr Val Gly Lys
1               5                   10                  15

<210> SEQ ID NO 128
<211> LENGTH: 15
<212> TYPE: PRT
<213> ORGANISM: Lollium Perenne

<400> SEQUENCE: 128

Asp Ala Tyr Val Ala Thr Leu Thr Glu Ala Leu Arg Val Ile Ala
1               5                   10                  15

<210> SEQ ID NO 129
<211> LENGTH: 15
<212> TYPE: PRT
<213> ORGANISM: Lollium Perenne

<400> SEQUENCE: 129

Ala Phe Lys Ile Ala Ala Thr Ala Ala Asn Ala Ala Pro Thr Asn
1               5                   10                  15

<210> SEQ ID NO 130
<211> LENGTH: 15
<212> TYPE: PRT
<213> ORGANISM: Lollium Perenne

<400> SEQUENCE: 130

Asp Gly Val Trp Glu Ile Lys Ser Asp Lys Pro Leu Lys Gly Pro
1               5                   10                  15

<210> SEQ ID NO 131
<211> LENGTH: 15
<212> TYPE: PRT
<213> ORGANISM: Poa pratensis

<400> SEQUENCE: 131

Asp Ile Asn Val Gly Phe Lys Ala Ala Val Ala Ala Ala Ala Gly
1               5                   10                  15

<210> SEQ ID NO 132
<211> LENGTH: 15
<212> TYPE: PRT
<213> ORGANISM: Poa pratensis

<400> SEQUENCE: 132

Glu Pro Ile Ala Ala Tyr His Phe Asp Leu Ser Gly Lys Ala Phe
1               5                   10                  15

<210> SEQ ID NO 133
<211> LENGTH: 15
<212> TYPE: PRT
<213> ORGANISM: Poa pratensis

<400> SEQUENCE: 133

Phe Lys Ala Ala Val Ala Ala Ala Gly Ala Pro Pro Ala Asp
1               5                   10                  15

<210> SEQ ID NO 134
<211> LENGTH: 20
<212> TYPE: PRT
<213> ORGANISM: Artificial sequence
<220> FEATURE:
<223> OTHER INFORMATION: Modified sequence

<400> SEQUENCE: 134
```

Gly Arg Gly Ser Gly Ser Ser Phe Glu Ile Lys Ser Thr Lys Pro Glu
1               5                   10                  15

Ser Ser Ser Gly
            20

<210> SEQ ID NO 135
<211> LENGTH: 20
<212> TYPE: PRT
<213> ORGANISM: Artificial sequence
<220> FEATURE:
<223> OTHER INFORMATION: Modified sequence

<400> SEQUENCE: 135

Glu Ile Lys Ser Thr Lys Pro Glu Ser Ser Ser Gly Glu Ala Val Thr
1               5                   10                  15

Val Thr Ile Thr
            20

<210> SEQ ID NO 136
<211> LENGTH: 20
<212> TYPE: PRT
<213> ORGANISM: Lollium Perenne

<400> SEQUENCE: 136

Tyr His Phe Asp Leu Ser Gly His Ala Phe Gly Ser Met Ala Lys Lys
1               5                   10                  15

Gly Glu Glu Gln
            20

<210> SEQ ID NO 137
<211> LENGTH: 20
<212> TYPE: PRT
<213> ORGANISM: Artificial sequence
<220> FEATURE:
<223> OTHER INFORMATION: Modified sequence

<400> SEQUENCE: 137

Gly Glu Glu Gln Asn Val Arg Ser Ala Gly Glu Leu Glu Leu Gln Phe
1               5                   10                  15

Arg Arg Val Lys
            20

<210> SEQ ID NO 138
<211> LENGTH: 20
<212> TYPE: PRT
<213> ORGANISM: Artificial sequence
<220> FEATURE:
<223> OTHER INFORMATION: Modified sequence

<400> SEQUENCE: 138

Ala Gly Glu Leu Glu Leu Gln Phe Arg Arg Val Lys Ser Lys Tyr Pro
1               5                   10                  15

Asp Asp Thr Lys
            20

<210> SEQ ID NO 139
<211> LENGTH: 20
<212> TYPE: PRT
<213> ORGANISM: Lollium Perenne

<400> SEQUENCE: 139

Lys Ala Ser Asn Pro Asn Tyr Leu Ala Ile Leu Val Lys Tyr Val Asp
1               5                   10                  15

-continued

Gly Asp Gly Asp
        20

<210> SEQ ID NO 140
<211> LENGTH: 20
<212> TYPE: PRT
<213> ORGANISM: Lollium Perenne

<400> SEQUENCE: 140

Leu Val Lys Tyr Val Asp Gly Asp Gly Asp Val Val Ala Val Asp Ile
1               5                   10                  15

Lys Glu Lys Gly
        20

<210> SEQ ID NO 141
<211> LENGTH: 20
<212> TYPE: PRT
<213> ORGANISM: Lollium Perenne

<400> SEQUENCE: 141

Lys Asp Lys Trp Ile Glu Leu Lys Glu Ser Trp Gly Ala Val Trp Arg
1               5                   10                  15

Ile Asp Thr Pro
        20

<210> SEQ ID NO 142
<211> LENGTH: 20
<212> TYPE: PRT
<213> ORGANISM: Lollium Perenne

<400> SEQUENCE: 142

Trp Gly Ala Val Trp Arg Ile Asp Thr Pro Asp Lys Leu Thr Gly Pro
1               5                   10                  15

Phe Thr Val Arg
        20

<210> SEQ ID NO 143
<211> LENGTH: 20
<212> TYPE: PRT
<213> ORGANISM: Artificial sequence
<220> FEATURE:
<223> OTHER INFORMATION: Modified sequence

<400> SEQUENCE: 143

Val Arg Tyr Thr Thr Glu Gly Gly Thr Lys Ser Glu Phe Glu Asp Val
1               5                   10                  15

Ile Pro Glu Gly
        20

<210> SEQ ID NO 144
<211> LENGTH: 20
<212> TYPE: PRT
<213> ORGANISM: Artificial sequence
<220> FEATURE:
<223> OTHER INFORMATION: Modified sequence

<400> SEQUENCE: 144

Ser Glu Phe Glu Asp Val Ile Pro Glu Gly Trp Lys Ala Asp Thr Ser
1               5                   10                  15

Tyr Ser Ala Lys
        20

<210> SEQ ID NO 145

<211> LENGTH: 20
<212> TYPE: PRT
<213> ORGANISM: Cynodon dactylon

<400> SEQUENCE: 145

Trp Leu Glu Ala Arg Ala Thr Phe Tyr Gly Ser Asn Pro Arg Gly Ala
1               5                   10                  15

Ala Pro Asp Asp
            20

<210> SEQ ID NO 146
<211> LENGTH: 20
<212> TYPE: PRT
<213> ORGANISM: Artificial sequence
<220> FEATURE:
<223> OTHER INFORMATION: Modified sequence

<400> SEQUENCE: 146

Gly Leu Gly Ser Arg Ala Ser Tyr Glu Ile Lys Ser Lys Glu Pro Val
1               5                   10                  15

Glu Ser Ser Gly
            20

<210> SEQ ID NO 147
<211> LENGTH: 20
<212> TYPE: PRT
<213> ORGANISM: Artificial sequence
<220> FEATURE:
<223> OTHER INFORMATION: Modified sequence

<400> SEQUENCE: 147

Glu Ile Lys Ser Lys Glu Pro Val Glu Ser Ser Gly Glu Pro Val Leu
1               5                   10                  15

Val Lys Ile Thr
            20

<210> SEQ ID NO 148
<211> LENGTH: 20
<212> TYPE: PRT
<213> ORGANISM: Cynodon dactylon

<400> SEQUENCE: 148

Thr Asp Lys Asn Tyr Glu His Ile Ala Ala Tyr His Phe Asp Leu Ser
1               5                   10                  15

Gly Lys Ala Phe
            20

<210> SEQ ID NO 149
<211> LENGTH: 20
<212> TYPE: PRT
<213> ORGANISM: Cynodon dactylon

<400> SEQUENCE: 149

Tyr His Phe Asp Leu Ser Gly Lys Ala Phe Gly Ala Met Ala Lys Lys
1               5                   10                  15

Gly Gln Glu Asp
            20

<210> SEQ ID NO 150
<211> LENGTH: 20
<212> TYPE: PRT
<213> ORGANISM: Cynodon dactylon

<400> SEQUENCE: 150

Gly Gln Glu Asp Lys Leu Arg Lys Ala Gly Glu Leu Thr Leu Gln Phe
1               5                   10                  15

Arg Arg Val Lys
            20

<210> SEQ ID NO 151
<211> LENGTH: 20
<212> TYPE: PRT
<213> ORGANISM: Artificial sequence
<220> FEATURE:
<223> OTHER INFORMATION: Modified sequence

<400> SEQUENCE: 151

Ala Gly Glu Leu Thr Leu Gln Phe Arg Arg Val Lys Ser Lys Tyr Pro
1               5                   10                  15

Ser Gly Thr Lys
            20

<210> SEQ ID NO 152
<211> LENGTH: 20
<212> TYPE: PRT
<213> ORGANISM: Cynodon dactylon

<400> SEQUENCE: 152

Lys Gly Ser Asn Asp His Tyr Leu Ala Leu Leu Val Lys Tyr Ala Ala
1               5                   10                  15

Gly Asp Gly Asn
            20

<210> SEQ ID NO 153
<211> LENGTH: 20
<212> TYPE: PRT
<213> ORGANISM: Cynodon dactylon

<400> SEQUENCE: 153

Leu Val Lys Tyr Ala Ala Gly Asp Gly Asn Ile Val Ala Val Asp Ile
1               5                   10                  15

Lys Pro Arg Asp
            20

<210> SEQ ID NO 154
<211> LENGTH: 20
<212> TYPE: PRT
<213> ORGANISM: Cynodon dactylon

<400> SEQUENCE: 154

Ser Asp Glu Phe Ile Pro Met Lys Ser Ser Trp Gly Ala Ile Trp Arg
1               5                   10                  15

Ile Asp Pro Lys
            20

<210> SEQ ID NO 155
<211> LENGTH: 20
<212> TYPE: PRT
<213> ORGANISM: Cynodon dactylon

<400> SEQUENCE: 155

Trp Gly Ala Ile Trp Arg Ile Asp Pro Lys Lys Pro Leu Lys Gly Pro
1               5                   10                  15

Phe Ser Ile Arg
            20

```
<210> SEQ ID NO 156
<211> LENGTH: 20
<212> TYPE: PRT
<213> ORGANISM: Cynodon dactylon

<400> SEQUENCE: 156

Ile Arg Leu Thr Ser Glu Gly Gly Ala His Leu Val Gln Asp Val
1               5                   10                  15

Ile Pro Ala Asn
            20

<210> SEQ ID NO 157
<211> LENGTH: 20
<212> TYPE: PRT
<213> ORGANISM: Cynodon dactylon

<400> SEQUENCE: 157

Leu Val Gln Asp Asp Val Ile Pro Ala Asn Trp Lys Pro Asp Thr Val
1               5                   10                  15

Tyr Thr Ser Lys
            20

<210> SEQ ID NO 158
<211> LENGTH: 20
<212> TYPE: PRT
<213> ORGANISM: Lollium Perenne

<400> SEQUENCE: 158

Glu Trp Leu Ala Leu Lys Lys Asn Gly Asp Gly Val Trp Glu Ile Lys
1               5                   10                  15

Ser Asp Lys Pro
            20

<210> SEQ ID NO 159
<211> LENGTH: 20
<212> TYPE: PRT
<213> ORGANISM: Lollium Perenne

<400> SEQUENCE: 159

Gly Asp Gly Val Trp Glu Ile Lys Ser Asp Lys Pro Leu Lys Gly Pro
1               5                   10                  15

Phe Asn Phe Arg
            20

<210> SEQ ID NO 160
<211> LENGTH: 20
<212> TYPE: PRT
<213> ORGANISM: Lollium Perenne

<400> SEQUENCE: 160

Lys Pro Leu Lys Gly Pro Phe Asn Phe Arg Phe Val Ser Glu Lys Gly
1               5                   10                  15

Met Arg Asn Val
            20

<210> SEQ ID NO 161
<211> LENGTH: 20
<212> TYPE: PRT
<213> ORGANISM: Lollium Perenne

<400> SEQUENCE: 161

Gly Ser Asp Ala Lys Thr Leu Val Leu Asn Ile Lys Tyr Thr Arg Pro
```

```
1               5                   10                  15

Gly Asp Thr Leu
            20

<210> SEQ ID NO 162
<211> LENGTH: 20
<212> TYPE: PRT
<213> ORGANISM: Lollium Perenne

<400> SEQUENCE: 162

His Gly Ser Glu Glu Trp Glu Pro Met Thr Lys Lys Gly Asn Leu Trp
1               5                   10                  15

Glu Val Lys Ser
            20

<210> SEQ ID NO 163
<211> LENGTH: 20
<212> TYPE: PRT
<213> ORGANISM: Lollium Perenne

<400> SEQUENCE: 163

Thr Lys Lys Gly Asn Leu Trp Glu Val Lys Ser Ala Lys Pro Leu Thr
1               5                   10                  15

Gly Pro Met Asn
            20

<210> SEQ ID NO 164
<211> LENGTH: 20
<212> TYPE: PRT
<213> ORGANISM: Lollium Perenne

<400> SEQUENCE: 164

Lys Ser Ala Lys Pro Leu Thr Gly Pro Met Asn Phe Arg Phe Leu Ser
1               5                   10                  15

Lys Gly Gly Met
            20

<210> SEQ ID NO 165
<211> LENGTH: 20
<212> TYPE: PRT
<213> ORGANISM: Lollium Perenne

<400> SEQUENCE: 165

Asn Phe Arg Phe Leu Ser Lys Gly Gly Met Lys Asn Val Phe Asp Glu
1               5                   10                  15

Val Ile Pro Thr
            20

<210> SEQ ID NO 166
<211> LENGTH: 20
<212> TYPE: PRT
<213> ORGANISM: Artificial sequence
<220> FEATURE:
<223> OTHER INFORMATION: Modified sequence

<400> SEQUENCE: 166

Phe Ala Val Val Asp Leu Asn Gln Met Arg Ala Val Leu Val Asp Gly
1               5                   10                  15

Lys Ala Arg Thr
            20

<210> SEQ ID NO 167
```

```
<211> LENGTH: 20
<212> TYPE: PRT
<213> ORGANISM: Artificial sequence
<220> FEATURE:
<223> OTHER INFORMATION: Modified sequence

<400> SEQUENCE: 167

Gln Val Glu Arg Asp Phe Leu Thr Ser Leu Thr Lys Asp Ile Pro Pro
1               5                   10                  15

Arg Gln Leu Tyr
            20

<210> SEQ ID NO 168
<211> LENGTH: 20
<212> TYPE: PRT
<213> ORGANISM: Artificial sequence
<220> FEATURE:
<223> OTHER INFORMATION: Modified sequence

<400> SEQUENCE: 168

Tyr Ile Ile Thr Pro Thr Asn Ala Ser His Ile Gln Ala Ala Val Val
1               5                   10                  15

Ser Gly Arg Arg
            20

<210> SEQ ID NO 169
<211> LENGTH: 20
<212> TYPE: PRT
<213> ORGANISM: Cynodon dactylon

<400> SEQUENCE: 169

Phe Ala Val Val Asp Met Asn Lys Met Arg Ala Val Ser Ile Asp Gly
1               5                   10                  15

Lys Ala Ala Thr
            20

<210> SEQ ID NO 170
<211> LENGTH: 20
<212> TYPE: PRT
<213> ORGANISM: Cynodon dactylon

<400> SEQUENCE: 170

Gly Phe Gly Met Leu Leu Arg Lys Tyr Gly Thr Ala Ala Asp Asn Val
1               5                   10                  15

Ile Asp Ala Lys
            20

<210> SEQ ID NO 171
<211> LENGTH: 20
<212> TYPE: PRT
<213> ORGANISM: Cynodon dactylon

<400> SEQUENCE: 171

Ala Met Gly Glu Asp His Phe Trp Ala Ile Arg Gly Gly Gly Gly Glu
1               5                   10                  15

Ser Phe Gly Ile
            20

<210> SEQ ID NO 172
<211> LENGTH: 20
<212> TYPE: PRT
<213> ORGANISM: Cynodon dactylon

<400> SEQUENCE: 172
```

```
Thr Pro Phe Pro Arg Arg Ser Gly Val Leu Phe Asn Ile Gln Tyr Val
1               5                   10                  15

Val Tyr Trp Phe
            20

<210> SEQ ID NO 173
<211> LENGTH: 20
<212> TYPE: PRT
<213> ORGANISM: Lollium Perenne

<400> SEQUENCE: 173

Thr Ala Ala Thr Pro Ala Thr Pro Ala Thr Pro Ala Thr Pro Ala Ala
1               5                   10                  15

Val Pro Ser Gly
            20

<210> SEQ ID NO 174
<211> LENGTH: 20
<212> TYPE: PRT
<213> ORGANISM: Lollium Perenne

<400> SEQUENCE: 174

Glu Gln Lys Leu Ile Glu Lys Ile Asn Ala Gly Phe Lys Ala Ala Val
1               5                   10                  15

Ala Ala Ala Ala
            20

<210> SEQ ID NO 175
<211> LENGTH: 20
<212> TYPE: PRT
<213> ORGANISM: Lollium Perenne

<400> SEQUENCE: 175

Gly Phe Lys Ala Ala Val Ala Ala Ala Val Val Pro Pro Ala Asp
1               5                   10                  15

Lys Tyr Lys Thr
            20

<210> SEQ ID NO 176
<211> LENGTH: 20
<212> TYPE: PRT
<213> ORGANISM: Lollium Perenne

<400> SEQUENCE: 176

Asp Lys Tyr Lys Thr Phe Val Glu Thr Phe Gly Thr Phe Ala Thr Asn Lys
1               5                   10                  15

Ala Phe Val Glu
            20

<210> SEQ ID NO 177
<211> LENGTH: 20
<212> TYPE: PRT
<213> ORGANISM: Lollium Perenne

<400> SEQUENCE: 177

Thr Ser Lys Leu Asp Ala Ala Leu Lys Leu Ala Tyr Glu Ala Ala Gln
1               5                   10                  15

Gly Ala Thr Pro
            20

<210> SEQ ID NO 178
```

```
<211> LENGTH: 20
<212> TYPE: PRT
<213> ORGANISM: Lollium Perenne

<400> SEQUENCE: 178

Glu Ala Lys Tyr Asp Ala Tyr Val Ala Thr Leu Thr Glu Ala Leu Arg
1               5                   10                  15

Val Ile Ala Gly
            20

<210> SEQ ID NO 179
<211> LENGTH: 20
<212> TYPE: PRT
<213> ORGANISM: Lollium Perenne

<400> SEQUENCE: 179

Val Ala Thr Leu Thr Glu Ala Leu Arg Val Ile Ala Gly Thr Leu Glu
1               5                   10                  15

Val His Ala Val
            20

<210> SEQ ID NO 180
<211> LENGTH: 20
<212> TYPE: PRT
<213> ORGANISM: Lollium Perenne

<400> SEQUENCE: 180

Ile Asp Lys Val Asp Ala Ala Tyr Arg Thr Ala Ala Thr Ala Ala Asn
1               5                   10                  15

Ala Ala Pro Ala
            20

<210> SEQ ID NO 181
<211> LENGTH: 20
<212> TYPE: PRT
<213> ORGANISM: Lollium Perenne

<400> SEQUENCE: 181

Arg Thr Ala Ala Thr Ala Ala Asn Ala Ala Pro Ala Asn Asp Lys Phe
1               5                   10                  15

Thr Val Phe Glu
            20

<210> SEQ ID NO 182
<211> LENGTH: 20
<212> TYPE: PRT
<213> ORGANISM: Lollium Perenne

<400> SEQUENCE: 182

Pro Ala Asn Asp Lys Phe Thr Val Phe Glu Asn Thr Phe Asn Asn Ala
1               5                   10                  15

Ile Lys Val Ser
            20

<210> SEQ ID NO 183
<211> LENGTH: 20
<212> TYPE: PRT
<213> ORGANISM: Lollium Perenne

<400> SEQUENCE: 183

Ser Leu Gly Ala Ala Tyr Asp Ser Tyr Lys Phe Ile Pro Thr Leu Val
1               5                   10                  15
```

Ala Ala Val Lys
            20

<210> SEQ ID NO 184
<211> LENGTH: 20
<212> TYPE: PRT
<213> ORGANISM: Lollium Perenne

<400> SEQUENCE: 184

Lys Phe Ile Pro Thr Leu Val Ala Ala Val Lys Gln Ala Tyr Ala Ala
1               5                   10                  15

Lys Gln Ala Thr
            20

<210> SEQ ID NO 185
<211> LENGTH: 20
<212> TYPE: PRT
<213> ORGANISM: Lollium Perenne

<400> SEQUENCE: 185

Ala Pro Glu Val Lys Tyr Thr Val Ser Glu Thr Ala Leu Lys Lys Ala
1               5                   10                  15

Val Thr Ala Met
            20

<210> SEQ ID NO 186
<211> LENGTH: 15
<212> TYPE: PRT
<213> ORGANISM: Lollium Perenne

<400> SEQUENCE: 186

Ala Tyr Arg Thr Ala Ala Thr Ala Ala Asn Ala Ala Pro Ala Asn
1               5                   10                  15

<210> SEQ ID NO 187
<211> LENGTH: 15
<212> TYPE: PRT
<213> ORGANISM: Lollium Perenne

<400> SEQUENCE: 187

Ile Asn Ala Gly Phe Lys Ala Ala Leu Ala Ala Ala Ala Gly Val
1               5                   10                  15

<210> SEQ ID NO 188
<211> LENGTH: 20
<212> TYPE: PRT
<213> ORGANISM: Phalaris aquatica

<400> SEQUENCE: 188

Pro Thr Pro Arg Thr Pro Pro Leu Leu Pro Pro Pro Arg Ala Arg Asp
1               5                   10                  15

Lys Ala Thr Leu
            20

<210> SEQ ID NO 189
<211> LENGTH: 20
<212> TYPE: PRT
<213> ORGANISM: Phalaris aquatica

<400> SEQUENCE: 189

Ala Ser Arg Arg Pro Trp Trp Ala Ser Val Pro Pro Ala Asp Lys Phe
1               5                   10                  15

Lys Thr Phe Ala

<210> SEQ ID NO 190
<211> LENGTH: 20
<212> TYPE: PRT
<213> ORGANISM: Phalaris aquatica

<400> SEQUENCE: 190

Lys Ala Lys Leu Asp Ala Ala Tyr Arg Val Ala Tyr Glu Ala Ala Glu
1               5                   10                  15

Gly Ser Thr Pro
            20

<210> SEQ ID NO 191
<211> LENGTH: 20
<212> TYPE: PRT
<213> ORGANISM: Phalaris aquatica

<400> SEQUENCE: 191

Glu Ala Lys Tyr Asp Ala Phe Ile Ala Ala Leu Thr Glu Ala Leu Arg
1               5                   10                  15

Val Ile Ala Gly
            20

<210> SEQ ID NO 192
<211> LENGTH: 20
<212> TYPE: PRT
<213> ORGANISM: Phalaris aquatica

<400> SEQUENCE: 192

Ile Ala Ala Leu Thr Glu Ala Leu Arg Val Ile Ala Gly Ala Phe Glu
1               5                   10                  15

Val His Ala Val
            20

<210> SEQ ID NO 193
<211> LENGTH: 20
<212> TYPE: PRT
<213> ORGANISM: Phalaris aquatica

<400> SEQUENCE: 193

Val Asp Lys Ile Asp Ala Ala Phe Lys Ile Ala Ala Thr Ala Ala Asn
1               5                   10                  15

Ser Ala Pro Ala
            20

<210> SEQ ID NO 194
<211> LENGTH: 20
<212> TYPE: PRT
<213> ORGANISM: Phalaris aquatica

<400> SEQUENCE: 194

Lys Ile Ala Ala Thr Ala Ala Asn Ser Ala Pro Ala Asn Asp Lys Phe
1               5                   10                  15

Thr Val Phe Glu
            20

<210> SEQ ID NO 195
<211> LENGTH: 20
<212> TYPE: PRT
<213> ORGANISM: Phalaris aquatica

<400> SEQUENCE: 195

-continued

```
Pro Ala Asn Asp Lys Phe Thr Val Phe Glu Gly Ala Phe Asn Lys Ala
1               5                   10                  15

Ile Lys Glu Ser
            20

<210> SEQ ID NO 196
<211> LENGTH: 20
<212> TYPE: PRT
<213> ORGANISM: Phalaris aquatica

<400> SEQUENCE: 196

Ser Thr Ala Gly Ala Tyr Glu Thr Tyr Lys Phe Ile Pro Ser Leu Glu
1               5                   10                  15

Ala Ala Val Lys
            20

<210> SEQ ID NO 197
<211> LENGTH: 20
<212> TYPE: PRT
<213> ORGANISM: Phalaris aquatica

<400> SEQUENCE: 197

Lys Phe Ile Pro Ser Leu Glu Ala Ala Val Lys Gln Ala Tyr Gly Ala
1               5                   10                  15

Thr Val Ala Arg
            20

<210> SEQ ID NO 198
<211> LENGTH: 20
<212> TYPE: PRT
<213> ORGANISM: Phalaris aquatica

<400> SEQUENCE: 198

Ala Pro Glu Val Lys Tyr Ala Val Phe Glu Ala Gly Leu Thr Lys Ala
1               5                   10                  15

Ile Thr Ala Met
            20

<210> SEQ ID NO 199
<211> LENGTH: 15
<212> TYPE: PRT
<213> ORGANISM: Phalaris aquatica

<400> SEQUENCE: 199

Ala Phe Lys Ile Ala Ala Thr Ala Ala Asn Ser Ala Pro Ala Asn
1               5                   10                  15

<210> SEQ ID NO 200
<211> LENGTH: 15
<212> TYPE: PRT
<213> ORGANISM: Phalaris aquatica

<400> SEQUENCE: 200

Ile Asn Ala Ala Ser Arg Arg Pro Trp Trp Ala Ser Val Pro Pro
1               5                   10                  15

<210> SEQ ID NO 201
<211> LENGTH: 20
<212> TYPE: PRT
<213> ORGANISM: Artificial sequence
<220> FEATURE:
<223> OTHER INFORMATION: Modified sequence
<220> FEATURE:
```

```
<221> NAME/KEY: MOD_RES
<222> LOCATION: (20)..(20)
<223> OTHER INFORMATION: AMIDATION

<400> SEQUENCE: 201

Lys Gly Ser Asn Pro Asn Tyr Leu Ala Leu Leu Val Lys Tyr Val Asn
1               5                   10                  15

Gly Asp Gly Asp
            20

<210> SEQ ID NO 202
<211> LENGTH: 22
<212> TYPE: PRT
<213> ORGANISM: Artificial sequence
<220> FEATURE:
<223> OTHER INFORMATION: Modified sequence

<400> SEQUENCE: 202

Arg Lys Gly Ser Asn Pro Asn Tyr Leu Ala Leu Leu Val Lys Tyr Val
1               5                   10                  15

Asn Gly Asp Gly Asp Arg
            20

<210> SEQ ID NO 203
<211> LENGTH: 22
<212> TYPE: PRT
<213> ORGANISM: Phleum Pratense

<400> SEQUENCE: 203

Lys Gly Lys Asp Lys Trp Ile Glu Leu Lys Glu Ser Trp Gly Ala Ile
1               5                   10                  15

Trp Arg Ile Asp Thr Pro
            20

<210> SEQ ID NO 204
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 204

Lys Gly Lys Asp Lys Trp Ile Glu Leu Lys Glu Ser Trp Gly Ala Ile
1               5                   10                  15

Trp Arg Ile Asp Thr Pro
            20

<210> SEQ ID NO 205
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION

<400> SEQUENCE: 205

Glu Ala Lys Tyr Asp Ala Tyr Val Ala Thr Leu Ser Glu Ala Leu Arg
1               5                   10                  15
```

Ile Ile Ala Gly
          20

<210> SEQ ID NO 206
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 206

Arg Glu Ala Lys Tyr Asp Ala Tyr Val Ala Thr Leu Ser Glu Ala Leu
1               5                   10                  15

Arg Ile Ile Ala Gly Arg
          20

<210> SEQ ID NO 207
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 207

Ala Pro Glu Val Lys Tyr Thr Val Phe Glu Thr Ala Leu Lys Lys Ala
1               5                   10                  15

Ile Thr Ala Met
          20

<210> SEQ ID NO 208
<211> LENGTH: 22
<212> TYPE: PRT
<213> ORGANISM: Artificial sequence
<220> FEATURE:
<223> OTHER INFORMATION: Modified sequence

<400> SEQUENCE: 208

Arg Ala Pro Glu Val Lys Tyr Thr Val Phe Glu Thr Ala Leu Lys Lys
1               5                   10                  15

Ala Ile Thr Ala Met Arg
          20

<210> SEQ ID NO 209
<211> LENGTH: 19
<212> TYPE: PRT
<213> ORGANISM: Phleum Pratense

<400> SEQUENCE: 209

Ala Pro Glu Val Lys Tyr Thr Val Phe Glu Thr Ala Leu Lys Lys Ala
1               5                   10                  15

Ile Thr Ala

<210> SEQ ID NO 210
<211> LENGTH: 19
<212> TYPE: PRT
<213> ORGANISM: Artificial sequence
<220> FEATURE:
<223> OTHER INFORMATION: Modified sequence

```
<220> FEATURE:
<221> NAME/KEY: MOD_RES
<222> LOCATION: (19)..(19)
<223> OTHER INFORMATION: AMIDATION

<400> SEQUENCE: 210

Ala Pro Glu Val Lys Tyr Thr Val Phe Glu Thr Ala Leu Lys Lys Ala
1               5                   10                  15

Ile Thr Ala

<210> SEQ ID NO 211
<211> LENGTH: 21
<212> TYPE: PRT
<213> ORGANISM: Artificial sequence
<220> FEATURE:
<223> OTHER INFORMATION: Modified sequence

<400> SEQUENCE: 211

Arg Ala Pro Glu Val Lys Tyr Thr Val Phe Glu Thr Ala Leu Lys Lys
1               5                   10                  15

Ala Ile Thr Ala Arg
            20

<210> SEQ ID NO 212
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION

<400> SEQUENCE: 212

Ala Gly Glu Leu Glu Leu Gln Phe Arg Arg Val Lys Ser Lys Tyr Pro
1               5                   10                  15

Glu Gly Thr Lys
            20

<210> SEQ ID NO 213
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 213

Ala Gly Glu Leu Glu Leu Gln Phe Arg Arg Val Lys Ser Lys Tyr Pro
1               5                   10                  15

Glu Gly Thr Lys
            20

<210> SEQ ID NO 214
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (20)..(20)
<223> OTHER INFORMATION: AMIDATION

<400> SEQUENCE: 214

Ala Gly Glu Leu Glu Leu Gln Phe Arg Arg Val Lys Ser Lys Tyr Pro
1               5                   10                  15

Glu Gly Thr Lys
            20

<210> SEQ ID NO 215
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION

<400> SEQUENCE: 215

Trp Gly Ala Ile Trp Arg Ile Asp Thr Pro Asp Lys Leu Thr Gly Pro
1               5                   10                  15

Phe Thr Val Arg
            20

<210> SEQ ID NO 216
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 216

Trp Gly Ala Ile Trp Arg Ile Asp Thr Pro Asp Lys Leu Thr Gly Pro
1               5                   10                  15

Phe Thr Val Arg
            20

<210> SEQ ID NO 217
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 217

Trp Gly Ala Ile Trp Arg Ile Asp Thr Pro Asp Lys Leu Thr Gly Pro
1               5                   10                  15

Phe Thr Val Arg
            20

<210> SEQ ID NO 218
```

```
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION

<400> SEQUENCE: 218

Ser Thr Gly Gly Ala Tyr Glu Ser Tyr Lys Phe Ile Pro Ala Leu Glu
1               5                   10                  15

Ala Ala Val Lys
            20

<210> SEQ ID NO 219
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 219

Ser Thr Gly Gly Ala Tyr Glu Ser Tyr Lys Phe Ile Pro Ala Leu Glu
1               5                   10                  15

Ala Ala Val Lys
            20

<210> SEQ ID NO 220
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 220

Ser Thr Gly Gly Ala Tyr Glu Ser Tyr Lys Phe Ile Pro Ala Leu Glu
1               5                   10                  15

Ala Ala Val Lys
            20

<210> SEQ ID NO 221
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (21)..(21)
<223> OTHER INFORMATION: AMIDATION

<400> SEQUENCE: 221

Arg Trp Gly Ala Ile Trp Arg Ile Asp Thr Pro Asp Lys Leu Thr Gly
1               5                   10                  15
```

```
Pro Phe Thr Val Arg
            20

<210> SEQ ID NO 222
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 222

Ile Glu Lys Val Asp Ala Ala Phe Lys Val Ala Ala Thr Ala Ala Asn
1               5                   10                  15

Ala Ala Pro Ala
            20

<210> SEQ ID NO 223
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (21)..(21)
<223> OTHER INFORMATION: AMIDATION

<400> SEQUENCE: 223

Ile Glu Lys Val Asp Ala Ala Phe Lys Val Ala Ala Thr Ala Ala Asn
1               5                   10                  15

Ala Ala Pro Ala Arg
            20

<210> SEQ ID NO 224
<211> LENGTH: 22
<212> TYPE: PRT
<213> ORGANISM: Phleum Pratense

<400> SEQUENCE: 224

Lys Ala Ser Thr Gly Gly Ala Tyr Glu Ser Tyr Lys Phe Ile Pro Ala
1               5                   10                  15

Leu Glu Ala Ala Val Lys
            20

<210> SEQ ID NO 225
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 225

Lys Ala Ser Thr Gly Gly Ala Tyr Glu Ser Tyr Lys Phe Ile Pro Ala
1               5                   10                  15

Leu Glu Ala Ala Val Lys
            20

<210> SEQ ID NO 226
```

```
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 226

Lys Phe Ile Pro Ala Leu Glu Ala Ala Val Lys Gln Ala Tyr Ala Ala
 1               5                  10                  15

Thr Val Ala Thr
            20

<210> SEQ ID NO 227
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (21)..(21)
<223> OTHER INFORMATION: AMIDATION

<400> SEQUENCE: 227

Lys Phe Ile Pro Ala Leu Glu Ala Ala Val Lys Gln Ala Tyr Ala Ala
 1               5                  10                  15

Thr Val Ala Thr Arg
            20

<210> SEQ ID NO 228
<211> LENGTH: 15
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (15)..(15)
<223> OTHER INFORMATION: AMIDATION

<400> SEQUENCE: 228

Ala Phe Lys Val Ala Ala Thr Ala Ala Asn Ala Ala Pro Ala Asn
 1               5                  10                  15

<210> SEQ ID NO 229
<211> LENGTH: 16
<212> TYPE: PRT
<213> ORGANISM: Artificial sequence
<220> FEATURE:
<223> OTHER INFORMATION: Modified sequence

<400> SEQUENCE: 229

Ala Phe Lys Val Ala Ala Thr Ala Ala Asn Ala Ala Pro Ala Asn Arg
 1               5                  10                  15

<210> SEQ ID NO 230
<211> LENGTH: 19
<212> TYPE: PRT
<213> ORGANISM: Phleum Pratense

<400> SEQUENCE: 230

Pro Leu Gln Gly Pro Phe Asn Phe Arg Phe Leu Thr Glu Lys Gly Met
 1               5                  10                  15
```

Lys Asn Val

<210> SEQ ID NO 231
<211> LENGTH: 20
<212> TYPE: PRT
<213> ORGANISM: Artificial sequence
<220> FEATURE:
<223> OTHER INFORMATION: Modified sequence

<400> SEQUENCE: 231

Lys Gly Ser Asn Pro Asn Tyr Leu Ala Leu Leu Val Lys Tyr Val Gln
1               5                   10                  15

Gly Glu Gly Asp
            20

<210> SEQ ID NO 232
<211> LENGTH: 20
<212> TYPE: PRT
<213> ORGANISM: Phleum Pratense

<400> SEQUENCE: 232

Ala Tyr Glu Ser Tyr Lys Phe Ile Pro Ala Leu Glu Ala Ala Val Lys
1               5                   10                  15

Gln Ala Tyr Ala
            20

<210> SEQ ID NO 233
<211> LENGTH: 21
<212> TYPE: PRT
<213> ORGANISM: Phleum Pratense

<400> SEQUENCE: 233

Ile Glu Lys Val Asp Ala Ala Phe Lys Val Ala Ala Thr Ala Ala Asn
1               5                   10                  15

Ala Ala Pro Ala Asn
            20

<210> SEQ ID NO 234
<211> LENGTH: 15
<212> TYPE: PRT
<213> ORGANISM: Cynodon dactylon

<400> SEQUENCE: 234

Ser Gly Lys Ala Phe Gly Ala Met Ala Lys Lys Gly Gln Glu Asp
1               5                   10                  15

<210> SEQ ID NO 235
<211> LENGTH: 10
<212> TYPE: PRT
<213> ORGANISM: Cynodon dactylon

<400> SEQUENCE: 235

Phe Ile Pro Met Lys Ser Ser Trp Gly Ala
1               5                   10

<210> SEQ ID NO 236
<211> LENGTH: 17
<212> TYPE: PRT
<213> ORGANISM: Cynodon dactylon

<400> SEQUENCE: 236

Lys Ser Ser Trp Gly Ala Ile Trp Arg Ile Asp Pro Lys Lys Pro Leu
1               5                   10                  15

Lys

<210> SEQ ID NO 237
<211> LENGTH: 14
<212> TYPE: PRT
<213> ORGANISM: Lollium Perenne

<400> SEQUENCE: 237

Lys Tyr Asp Ala Tyr Val Ala Thr Leu Thr Glu Ala Leu Arg
1               5                   10

<210> SEQ ID NO 238
<211> LENGTH: 18
<212> TYPE: PRT
<213> ORGANISM: Lollium Perenne

<400> SEQUENCE: 238

Lys Phe Ile Pro Thr Leu Val Ala Ala Val Lys Gln Ala Tyr Ala Ala
1               5                   10                  15

Lys Gln

<210> SEQ ID NO 239
<211> LENGTH: 13
<212> TYPE: PRT
<213> ORGANISM: Lollium Perenne

<400> SEQUENCE: 239

Leu Lys Lys Ala Val Thr Ala Met Ser Glu Ala Glu Lys
1               5                   10

<210> SEQ ID NO 240
<211> LENGTH: 17
<212> TYPE: PRT
<213> ORGANISM: Lollium Perenne

<400> SEQUENCE: 240

Pro Glu Val Lys Tyr Ala Val Phe Glu Ala Ala Leu Thr Lys Ala Ile
1               5                   10                  15

Thr

<210> SEQ ID NO 241
<211> LENGTH: 15
<212> TYPE: PRT
<213> ORGANISM: Artificial sequence
<220> FEATURE:
<223> OTHER INFORMATION: Modified sequence

<400> SEQUENCE: 241

Lys Ile Pro Ala Gly Glu Leu Gln Ile Ile Asp Lys Ile Asp Ala
1               5                   10                  15

<210> SEQ ID NO 242
<211> LENGTH: 18
<212> TYPE: PRT
<213> ORGANISM: Artificial sequence
<220> FEATURE:
<223> OTHER INFORMATION: Modified sequence

<400> SEQUENCE: 242

Lys Pro Glu Val Lys Tyr Ala Val Phe Glu Ala Ala Leu Thr Lys Ala
1               5                   10                  15

Ile Thr

-continued

```
<210> SEQ ID NO 243
<211> LENGTH: 19
<212> TYPE: PRT
<213> ORGANISM: Artificial sequence
<220> FEATURE:
<223> OTHER INFORMATION: Modified sequence

<400> SEQUENCE: 243

Lys Lys Pro Glu Val Lys Tyr Ala Val Phe Glu Ala Ala Leu Thr Lys
1               5                   10                  15

Ala Ile Thr

<210> SEQ ID NO 244
<211> LENGTH: 16
<212> TYPE: PRT
<213> ORGANISM: Artificial sequence
<220> FEATURE:
<223> OTHER INFORMATION: Modified sequence

<400> SEQUENCE: 244

Lys Lys Ile Pro Ala Gly Glu Leu Gln Ile Ile Asp Lys Ile Asp Ala
1               5                   10                  15

<210> SEQ ID NO 245
<211> LENGTH: 17
<212> TYPE: PRT
<213> ORGANISM: Artificial sequence
<220> FEATURE:
<223> OTHER INFORMATION: Modified sequence

<400> SEQUENCE: 245

Lys Lys Ile Pro Ala Gly Glu Leu Gln Ile Ile Asp Lys Ile Asp Ala
1               5                   10                  15

Lys

<210> SEQ ID NO 246
<211> LENGTH: 20
<212> TYPE: PRT
<213> ORGANISM: Cynodon dactylon

<400> SEQUENCE: 246

Thr Asp Lys Asn Tyr Glu His Ile Ala Ala Tyr His Phe Asp Leu Ser
1               5                   10                  15

Gly Lys Ala Phe
            20

<210> SEQ ID NO 247
<211> LENGTH: 20
<212> TYPE: PRT
<213> ORGANISM: Paspalum notatum

<400> SEQUENCE: 247

Thr Asp Met Asn Tyr Glu Pro Ile Ala Pro Tyr His Phe Asp Leu Ser
1               5                   10                  15

Gly Lys Ala Phe
            20

<210> SEQ ID NO 248
<211> LENGTH: 20
<212> TYPE: PRT
<213> ORGANISM: Poa pratensis

<400> SEQUENCE: 248

Thr Asp Asp Asn Glu Glu Pro Ile Ala Ala Tyr His Phe Asp Leu Ser
```

```
1               5                   10                  15

Gly Lys Ala Phe
         20

<210> SEQ ID NO 249
<211> LENGTH: 20
<212> TYPE: PRT
<213> ORGANISM: Sorghum halepense

<400> SEQUENCE: 249

Thr Asp Met Asn Tyr Glu Gln Ile Ala Ala Tyr His Phe Asp Leu Ala
1               5                   10                  15

Gly Thr Ala Phe
         20

<210> SEQ ID NO 250
<211> LENGTH: 20
<212> TYPE: PRT
<213> ORGANISM: Artificial sequence
<220> FEATURE:
<223> OTHER INFORMATION: Modified sequence

<400> SEQUENCE: 250

Tyr His Phe Asp Leu Ser Gly Lys Ala Phe Gly Ala Met Ala Lys Lys
1               5                   10                  15

Gly Glu Glu Asp
         20

<210> SEQ ID NO 251
<211> LENGTH: 20
<212> TYPE: PRT
<213> ORGANISM: Dactylis glomerata

<400> SEQUENCE: 251

Tyr His Phe Asp Leu Ser Gly His Ala Phe Gly Ser Met Ala Lys Lys
1               5                   10                  15

Gly Glu Glu Gln
         20

<210> SEQ ID NO 252
<211> LENGTH: 20
<212> TYPE: PRT
<213> ORGANISM: Phalaris aquatica

<400> SEQUENCE: 252

Tyr His Phe Asp Leu Ser Gly His Ala Phe Gly Ser Met Ala Lys Lys
1               5                   10                  15

Gly Glu Glu Glu
         20

<210> SEQ ID NO 253
<211> LENGTH: 20
<212> TYPE: PRT
<213> ORGANISM: Poa pratensis

<400> SEQUENCE: 253

Tyr His Phe Asp Leu Ser Gly Lys Ala Phe Gly Ala Met Ala Lys Lys
1               5                   10                  15

Gly Glu Glu Gln
         20

<210> SEQ ID NO 254
```

```
<211> LENGTH: 20
<212> TYPE: PRT
<213> ORGANISM: Sorghum halepense

<400> SEQUENCE: 254

Tyr His Phe Asp Leu Ala Gly Thr Ala Phe Gly Ala Met Ala Lys Lys
1               5                   10                  15

Gly Glu Glu Glu
            20

<210> SEQ ID NO 255
<211> LENGTH: 20
<212> TYPE: PRT
<213> ORGANISM: Artificial sequence
<220> FEATURE:
<223> OTHER INFORMATION: Modified sequence

<400> SEQUENCE: 255

Gly Glu Glu Asp Lys Leu Arg Lys Ala Gly Glu Leu Met Leu Gln Phe
1               5                   10                  15

Arg Arg Val Lys
            20

<210> SEQ ID NO 256
<211> LENGTH: 20
<212> TYPE: PRT
<213> ORGANISM: Dactylis glomerata

<400> SEQUENCE: 256

Gly Glu Glu Gln Lys Leu Arg Ser Ala Gly Glu Leu Glu Leu Gln Phe
1               5                   10                  15

Arg Arg Val Lys
            20

<210> SEQ ID NO 257
<211> LENGTH: 20
<212> TYPE: PRT
<213> ORGANISM: Paspalum notatum

<400> SEQUENCE: 257

Gly Leu Asn Asp Lys Leu Arg His Tyr Gly Ile Phe Asp Leu Glu Phe
1               5                   10                  15

Arg Arg Val Arg
            20

<210> SEQ ID NO 258
<211> LENGTH: 20
<212> TYPE: PRT
<213> ORGANISM: Phalaris aquatica

<400> SEQUENCE: 258

Gly Glu Glu Glu Asn Val Arg Gly Ala Gly Glu Leu Glu Leu Gln Phe
1               5                   10                  15

Arg Arg Val Lys
            20

<210> SEQ ID NO 259
<211> LENGTH: 20
<212> TYPE: PRT
<213> ORGANISM: Poa pratensis

<400> SEQUENCE: 259

Gly Glu Glu Gln Lys Leu Arg Ser Ala Gly Glu Leu Glu Leu Lys Phe
```

```
                1               5                   10                  15

Arg Arg Val Lys
            20

<210> SEQ ID NO 260
<211> LENGTH: 20
<212> TYPE: PRT
<213> ORGANISM: Sorghum halepense

<400> SEQUENCE: 260

Gly Glu Glu Glu Lys Leu Arg Lys Ala Gly Ile Ile Asp Met Lys Phe
1               5                   10                  15

Arg Arg Val Lys
            20

<210> SEQ ID NO 261
<211> LENGTH: 20
<212> TYPE: PRT
<213> ORGANISM: Artificial sequence
<220> FEATURE:
<223> OTHER INFORMATION: Modified sequence

<400> SEQUENCE: 261

Ala Gly Glu Leu Thr Leu Gln Phe Arg Arg Val Lys Ser Lys Tyr Pro
1               5                   10                  15

Ser Gly Thr Lys
            20

<210> SEQ ID NO 262
<211> LENGTH: 20
<212> TYPE: PRT
<213> ORGANISM: Artificial sequence
<220> FEATURE:
<223> OTHER INFORMATION: Modified sequence

<400> SEQUENCE: 262

Ala Gly Glu Leu Glu Leu Gln Phe Arg Arg Val Lys Ser Lys Tyr Pro
1               5                   10                  15

Glu Gly Thr Lys
            20

<210> SEQ ID NO 263
<211> LENGTH: 20
<212> TYPE: PRT
<213> ORGANISM: Artificial sequence
<220> FEATURE:
<223> OTHER INFORMATION: Modified sequence

<400> SEQUENCE: 263

Ala Gly Glu Leu Glu Leu Gln Phe Arg Arg Val Lys Ser Lys Tyr Pro
1               5                   10                  15

Asp Gly Thr Lys
            20

<210> SEQ ID NO 264
<211> LENGTH: 20
<212> TYPE: PRT
<213> ORGANISM: Artificial sequence
<220> FEATURE:
<223> OTHER INFORMATION: Modified sequence

<400> SEQUENCE: 264

Tyr Gly Ile Phe Asp Leu Glu Phe Arg Arg Val Arg Ser Lys Tyr Gln
1               5                   10                  15
```

Gly Gly Gln Lys
        20

<210> SEQ ID NO 265
<211> LENGTH: 20
<212> TYPE: PRT
<213> ORGANISM: Artificial sequence
<220> FEATURE:
<223> OTHER INFORMATION: Modified sequence

<400> SEQUENCE: 265

Ala Gly Glu Leu Glu Leu Lys Phe Arg Arg Val Lys Ser Glu Tyr Pro
1               5                   10                  15

Glu Gly Thr Lys
        20

<210> SEQ ID NO 266
<211> LENGTH: 20
<212> TYPE: PRT
<213> ORGANISM: Artificial sequence
<220> FEATURE:
<223> OTHER INFORMATION: Modified sequence

<400> SEQUENCE: 266

Lys Gly Ser Asn Pro Asn Tyr Leu Ala Leu Leu Val Lys Tyr Ala Ala
1               5                   10                  15

Gly Asp Gly Asn
        20

<210> SEQ ID NO 267
<211> LENGTH: 20
<212> TYPE: PRT
<213> ORGANISM: Dactylis glomerata

<400> SEQUENCE: 267

Lys Gly Ser Asn Pro Asn Tyr Leu Ala Leu Leu Val Lys Tyr Val Asp
1               5                   10                  15

Gly Asp Gly Asp
        20

<210> SEQ ID NO 268
<211> LENGTH: 20
<212> TYPE: PRT
<213> ORGANISM: Festuca pratensis

<400> SEQUENCE: 268

Lys Gly Ser Asn Pro Asn Tyr Leu Ala Ile Leu Val Lys Tyr Val Asp
1               5                   10                  15

Gly Asp Gly Asp
        20

<210> SEQ ID NO 269
<211> LENGTH: 20
<212> TYPE: PRT
<213> ORGANISM: Lollium Perenne

<400> SEQUENCE: 269

Lys Ala Ser Asn Pro Asn Tyr Leu Ala Ile Leu Val Lys Tyr Val Asp
1               5                   10                  15

Gly Asp Gly Asp
        20

```
<210> SEQ ID NO 270
<211> LENGTH: 20
<212> TYPE: PRT
<213> ORGANISM: Paspalum notatum

<400> SEQUENCE: 270

Lys Gly Ser Asn Pro Asn Tyr Leu Ala Met Leu Val Lys Phe Val Ala
1               5                   10                  15

Asp Asp Gly Asp
            20

<210> SEQ ID NO 271
<211> LENGTH: 20
<212> TYPE: PRT
<213> ORGANISM: Poa pratensis

<400> SEQUENCE: 271

Lys Gly Ser Asn Pro Asn Tyr Leu Ala Leu Leu Val Lys Tyr Val Thr
1               5                   10                  15

Gly Asp Gly Asp
            20

<210> SEQ ID NO 272
<211> LENGTH: 20
<212> TYPE: PRT
<213> ORGANISM: Artificial sequence
<220> FEATURE:
<223> OTHER INFORMATION: Modified sequence

<400> SEQUENCE: 272

Trp Gly Ala Ile Trp Arg Ile Asp Pro Pro Lys Pro Leu Lys Gly Pro
1               5                   10                  15

Phe Thr Ile Arg
            20

<210> SEQ ID NO 273
<211> LENGTH: 20
<212> TYPE: PRT
<213> ORGANISM: Dactylis glomerata

<400> SEQUENCE: 273

Trp Gly Ala Ile Trp Arg Val Asp Thr Pro Asp Lys Leu Thr Gly Pro
1               5                   10                  15

Phe Thr Val Arg
            20

<210> SEQ ID NO 274
<211> LENGTH: 20
<212> TYPE: PRT
<213> ORGANISM: Festuca pratensis

<400> SEQUENCE: 274

Trp Gly Ala Val Trp Arg Ile Asp Thr Pro Asp Lys Leu Thr Gly Pro
1               5                   10                  15

Phe Thr Val Arg
            20

<210> SEQ ID NO 275
<211> LENGTH: 20
<212> TYPE: PRT
<213> ORGANISM: Paspalum notatum

<400> SEQUENCE: 275
```

Trp Gly Ala Ile Trp Arg Met Asp Thr Pro Lys Ala Leu Val Pro Pro
1               5                   10                  15

Phe Ser Ile Arg
            20

<210> SEQ ID NO 276
<211> LENGTH: 20
<212> TYPE: PRT
<213> ORGANISM: Poa pratensis

<400> SEQUENCE: 276

Trp Gly Ser Ile Trp Arg Val Asp Thr Pro Asp Lys Leu Thr Gly Pro
1               5                   10                  15

Phe Thr Val Arg
            20

<210> SEQ ID NO 277
<211> LENGTH: 20
<212> TYPE: PRT
<213> ORGANISM: Sorghum halepense

<400> SEQUENCE: 277

Trp Gly Ala Ile Trp Arg Lys Asp Ser Asp Lys Pro Ile Lys Phe Pro
1               5                   10                  15

Val Thr Val Gln
            20

<210> SEQ ID NO 278
<211> LENGTH: 20
<212> TYPE: PRT
<213> ORGANISM: Dactylis glomerata

<400> SEQUENCE: 278

Gly Ser Asp Pro Lys Lys Leu Val Leu Asp Ile Lys Tyr Thr Arg Pro
1               5                   10                  15

Gly Asp Thr Leu
            20

<210> SEQ ID NO 279
<211> LENGTH: 20
<212> TYPE: PRT
<213> ORGANISM: Lollium Perenne

<400> SEQUENCE: 279

Gly Ser Asp Ala Lys Thr Leu Val Leu Asn Ile Lys Tyr Thr Arg Pro
1               5                   10                  15

Gly Asp Thr Leu
            20

<210> SEQ ID NO 280
<211> LENGTH: 20
<212> TYPE: PRT
<213> ORGANISM: Artificial sequence
<220> FEATURE:
<223> OTHER INFORMATION: Modified sequence

<400> SEQUENCE: 280

Glu Arg Asp Phe Leu Thr Ser Leu Thr Lys Asp Ile Pro Pro Arg Gln
1               5                   10                  15

Leu Tyr Ala Lys
            20

```
<210> SEQ ID NO 281
<211> LENGTH: 20
<212> TYPE: PRT
<213> ORGANISM: Dactylis glomerata

<400> SEQUENCE: 281

Val Asp Lys Ile Asp Ala Ala Tyr Lys Ile Ala Ala Thr Ala Ala Asn
1               5                   10                  15

Ala Ala Pro Ala
            20

<210> SEQ ID NO 282
<211> LENGTH: 20
<212> TYPE: PRT
<213> ORGANISM: Lollium Perenne

<400> SEQUENCE: 282

Val Asp Lys Ile Asp Ala Ala Phe Lys Ile Ala Ala Thr Ala Ala Asn
1               5                   10                  15

Ala Ala Pro Thr
            20

<210> SEQ ID NO 283
<211> LENGTH: 20
<212> TYPE: PRT
<213> ORGANISM: Phalaris aquatica

<400> SEQUENCE: 283

Val Asp Lys Ile Asp Ala Ala Phe Lys Ile Ala Ala Thr Ala Ala Asn
1               5                   10                  15

Ser Ala Pro Ala
            20

<210> SEQ ID NO 284
<211> LENGTH: 20
<212> TYPE: PRT
<213> ORGANISM: Artificial sequence
<220> FEATURE:
<223> OTHER INFORMATION: Modified sequence

<400> SEQUENCE: 284

Ile Asp Lys Val Asp Ala Ala Phe Lys Val Ala Ala Thr Ala Ala Asn
1               5                   10                  15

Ala Ala Pro Ala
            20

<210> SEQ ID NO 285
<211> LENGTH: 20
<212> TYPE: PRT
<213> ORGANISM: Dactylis glomerata

<400> SEQUENCE: 285

Lys Ile Ala Ala Thr Ala Ala Asn Ala Ala Pro Ala Asn Asp Lys Phe
1               5                   10                  15

Thr Val Phe Glu
            20

<210> SEQ ID NO 286
<211> LENGTH: 20
<212> TYPE: PRT
<213> ORGANISM: Lollium Perenne

<400> SEQUENCE: 286
```

```
Lys Ile Ala Ala Thr Ala Ala Asn Ala Ala Pro Thr Asn Asp Lys Phe
1               5                   10                  15

Thr Val Phe Glu
            20

<210> SEQ ID NO 287
<211> LENGTH: 20
<212> TYPE: PRT
<213> ORGANISM: Phalaris aquatica

<400> SEQUENCE: 287

Lys Ile Ala Ala Thr Ala Ala Asn Ser Ala Pro Ala Asn Asp Lys Phe
1               5                   10                  15

Thr Val Phe Glu
            20

<210> SEQ ID NO 288
<211> LENGTH: 20
<212> TYPE: PRT
<213> ORGANISM: Dactylis glomerata

<400> SEQUENCE: 288

Ser Thr Gly Gly Ala Tyr Glu Ser Tyr Lys Phe Ile Pro Thr Leu Glu
1               5                   10                  15

Ala Ala Val Lys
            20

<210> SEQ ID NO 289
<211> LENGTH: 20
<212> TYPE: PRT
<213> ORGANISM: Artificial sequence
<220> FEATURE:
<223> OTHER INFORMATION: Modified sequence

<400> SEQUENCE: 289

Ser Thr Gly Gly Ala Tyr Glu Thr Tyr Lys Phe Ile Pro Ser Leu Glu
1               5                   10                  15

Ala Ala Val Lys
            20

<210> SEQ ID NO 290
<211> LENGTH: 20
<212> TYPE: PRT
<213> ORGANISM: Phalaris aquatica

<400> SEQUENCE: 290

Ser Thr Ala Gly Ala Tyr Glu Thr Tyr Lys Phe Ile Pro Ser Leu Glu
1               5                   10                  15

Ala Ala Val Lys
            20

<210> SEQ ID NO 291
<211> LENGTH: 20
<212> TYPE: PRT
<213> ORGANISM: Artificial sequence
<220> FEATURE:
<223> OTHER INFORMATION: Modified sequence

<400> SEQUENCE: 291

Ser Thr Gly Gly Ala Tyr Gln Ser Tyr Lys Phe Ile Pro Ala Leu Glu
1               5                   10                  15

Ala Ala Val Lys
            20
```

<210> SEQ ID NO 292
<211> LENGTH: 20
<212> TYPE: PRT
<213> ORGANISM: Dactylis glomerata

<400> SEQUENCE: 292

Lys Phe Ile Pro Thr Leu Glu Ala Ala Val Lys Gln Ala Tyr Ala Ala
1               5                   10                  15

Thr Val Ala Ala
            20

<210> SEQ ID NO 293
<211> LENGTH: 20
<212> TYPE: PRT
<213> ORGANISM: Lollium Perenne

<400> SEQUENCE: 293

Lys Phe Ile Pro Ser Leu Glu Ala Ala Val Lys Gln Ala Tyr Ala Ala
1               5                   10                  15

Thr Val Ala Ala
            20

<210> SEQ ID NO 294
<211> LENGTH: 20
<212> TYPE: PRT
<213> ORGANISM: Phalaris aquatica

<400> SEQUENCE: 294

Lys Phe Ile Pro Ser Leu Glu Ala Ala Val Lys Gln Ala Tyr Gly Ala
1               5                   10                  15

Thr Val Ala Arg
            20

<210> SEQ ID NO 295
<211> LENGTH: 20
<212> TYPE: PRT
<213> ORGANISM: Artificial sequence
<220> FEATURE:
<223> OTHER INFORMATION: Modified sequence

<400> SEQUENCE: 295

Lys Phe Ile Pro Ala Leu Glu Ala Ala Val Lys Gln Ser Tyr Ala Ala
1               5                   10                  15

Thr Val Ala Thr
            20

<210> SEQ ID NO 296
<211> LENGTH: 20
<212> TYPE: PRT
<213> ORGANISM: Dactylis glomerata

<400> SEQUENCE: 296

Ala Pro Glu Val Lys Tyr Ala Val Phe Glu Ala Ala Leu Thr Lys Ala
1               5                   10                  15

Ile Thr Ala Met
            20

<210> SEQ ID NO 297
<211> LENGTH: 20
<212> TYPE: PRT
<213> ORGANISM: Lollium Perenne

```
<400> SEQUENCE: 297

Ala Pro Glu Val Lys Tyr Thr Val Ser Glu Thr Ala Leu Lys Lys Ala
1               5                   10                  15

Val Thr Ala Met
            20

<210> SEQ ID NO 298
<211> LENGTH: 20
<212> TYPE: PRT
<213> ORGANISM: Artificial sequence
<220> FEATURE:
<223> OTHER INFORMATION: Modified sequence

<400> SEQUENCE: 298

Ala Pro Glu Val Lys Tyr Ala Val Phe Glu Thr Ala Leu Lys Lys Ala
1               5                   10                  15

Ile Ser Ala Met
            20

<210> SEQ ID NO 299
<211> LENGTH: 20
<212> TYPE: PRT
<213> ORGANISM: Artificial sequence
<220> FEATURE:
<223> OTHER INFORMATION: Modified sequence

<400> SEQUENCE: 299

Ala Pro Ala Val Lys Tyr Thr Val Phe Glu Thr Ala Leu Lys Lys Ala
1               5                   10                  15

Ile Thr Ala Met
            20

<210> SEQ ID NO 300
<211> LENGTH: 20
<212> TYPE: PRT
<213> ORGANISM: Dactylis glomerata

<400> SEQUENCE: 300

Ala Tyr Glu Ser Tyr Lys Phe Ile Pro Thr Leu Glu Ala Ala Val Lys
1               5                   10                  15

Gln Ala Tyr Ala
            20

<210> SEQ ID NO 301
<211> LENGTH: 20
<212> TYPE: PRT
<213> ORGANISM: Lollium Perenne

<400> SEQUENCE: 301

Ala Tyr Glu Thr Tyr Lys Phe Ile Pro Ser Leu Glu Ala Ala Val Lys
1               5                   10                  15

Gln Ala Tyr Ala
            20

<210> SEQ ID NO 302
<211> LENGTH: 20
<212> TYPE: PRT
<213> ORGANISM: Phalaris aquatica

<400> SEQUENCE: 302

Ala Tyr Glu Thr Tyr Lys Phe Ile Pro Ser Leu Glu Ala Ala Val Lys
1               5                   10                  15
```

Gln Ala Tyr Gly
            20

<210> SEQ ID NO 303
<211> LENGTH: 20
<212> TYPE: PRT
<213> ORGANISM: Artificial sequence
<220> FEATURE:
<223> OTHER INFORMATION: Modified sequence

<400> SEQUENCE: 303

Ala Tyr Gln Ser Tyr Lys Phe Ile Pro Ala Leu Glu Ala Ala Val Lys
1               5                   10                  15

Gln Ser Tyr Ala
            20

<210> SEQ ID NO 304
<211> LENGTH: 21
<212> TYPE: PRT
<213> ORGANISM: Dactylis glomerata

<400> SEQUENCE: 304

Val Asp Lys Ile Asp Ala Ala Tyr Lys Ile Ala Ala Thr Ala Ala Asn
1               5                   10                  15

Ala Ala Pro Ala Asn
            20

<210> SEQ ID NO 305
<211> LENGTH: 21
<212> TYPE: PRT
<213> ORGANISM: Lollium Perenne

<400> SEQUENCE: 305

Val Asp Lys Ile Asp Ala Ala Phe Lys Ile Ala Ala Thr Ala Ala Asn
1               5                   10                  15

Ala Ala Pro Thr Asn
            20

<210> SEQ ID NO 306
<211> LENGTH: 21
<212> TYPE: PRT
<213> ORGANISM: Phalaris aquatica

<400> SEQUENCE: 306

Val Asp Lys Ile Asp Ala Ala Phe Lys Ile Ala Ala Thr Ala Ala Asn
1               5                   10                  15

Ser Ala Pro Ala Asn
            20

<210> SEQ ID NO 307
<211> LENGTH: 21
<212> TYPE: PRT
<213> ORGANISM: Artificial sequence
<220> FEATURE:
<223> OTHER INFORMATION: Modified sequence

<400> SEQUENCE: 307

Ile Asp Lys Val Asp Ala Ala Phe Lys Val Ala Ala Thr Ala Ala Asn
1               5                   10                  15

Ala Ala Pro Ala Asn
            20

<210> SEQ ID NO 308

```
<211> LENGTH: 23
<212> TYPE: PRT
<213> ORGANISM: Artificial sequence
<220> FEATURE:
<223> OTHER INFORMATION: Modified sequence

<400> SEQUENCE: 308

Arg Lys Ala Ser Thr Gly Gly Ala Tyr Glu Ser Tyr Lys Phe Ile Pro
1               5                   10                  15

Ala Leu Glu Ala Ala Val Lys
            20

<210> SEQ ID NO 309
<211> LENGTH: 23
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (23)..(23)
<223> OTHER INFORMATION: AMIDATION

<400> SEQUENCE: 309

Arg Lys Ala Ser Thr Gly Gly Ala Tyr Glu Ser Tyr Lys Phe Ile Pro
1               5                   10                  15

Ala Leu Glu Ala Ala Val Lys
            20

<210> SEQ ID NO 310
<211> LENGTH: 21
<212> TYPE: PRT
<213> ORGANISM: Artificial sequence
<220> FEATURE:
<223> OTHER INFORMATION: Modified sequence

<400> SEQUENCE: 310

Arg Ala Pro Glu Val Lys Tyr Thr Val Phe Glu Thr Ala Leu Lys Lys
1               5                   10                  15

Ala Ile Thr Ala Met
            20

<210> SEQ ID NO 311
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (21)..(21)
<223> OTHER INFORMATION: AMIDATION

<400> SEQUENCE: 311

Arg Ala Pro Glu Val Lys Tyr Thr Val Phe Glu Thr Ala Leu Lys Lys
1               5                   10                  15

Ala Ile Thr Ala Met
            20

<210> SEQ ID NO 312
<211> LENGTH: 22
<212> TYPE: PRT
<213> ORGANISM: Artificial sequence
<220> FEATURE:
<223> OTHER INFORMATION: Modified sequence

<400> SEQUENCE: 312
```

```
Arg Ala Pro Glu Val Lys Tyr Thr Val Phe Glu Thr Ala Leu Lys Lys
1               5                   10                  15

Ala Ile Thr Ala Met Arg
            20

<210> SEQ ID NO 313
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 313

Arg Ala Pro Glu Val Lys Tyr Thr Val Phe Glu Thr Ala Leu Lys Lys
1               5                   10                  15

Ala Ile Thr Ala Met Arg
            20

<210> SEQ ID NO 314
<211> LENGTH: 21
<212> TYPE: PRT
<213> ORGANISM: Artificial sequence
<220> FEATURE:
<223> OTHER INFORMATION: Modified sequence

<400> SEQUENCE: 314

Arg Lys Gly Ser Asn Pro Asn Tyr Leu Ala Leu Leu Val Lys Tyr Val
1               5                   10                  15

Asn Gly Asp Gly Asp
            20

<210> SEQ ID NO 315
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 315

Arg Lys Gly Ser Asn Pro Asn Tyr Leu Ala Leu Leu Val Lys Tyr Val
1               5                   10                  15

Asn Gly Asp Gly Asp Arg
            20

<210> SEQ ID NO 316
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (1)..(1)
<223> OTHER INFORMATION: ACETYLATION

<400> SEQUENCE: 316

Glu Lys Gly Ser Asn Pro Asn Tyr Leu Ala Leu Leu Val Lys Tyr Val
1               5                   10                  15
```

Asn Gly Asp Gly Asp
        20

<210> SEQ ID NO 317
<211> LENGTH: 21
<212> TYPE: PRT
<213> ORGANISM: Artificial sequence
<220> FEATURE:
<223> OTHER INFORMATION: Modified sequence

<400> SEQUENCE: 317

Arg Trp Gly Ala Ile Trp Arg Ile Asp Thr Pro Asp Lys Leu Thr Gly
1               5                   10                  15

Pro Phe Thr Val Arg
        20

<210> SEQ ID NO 318
<211> LENGTH: 22
<212> TYPE: PRT
<213> ORGANISM: Artificial sequence
<220> FEATURE:
<223> OTHER INFORMATION: Modified sequence

<400> SEQUENCE: 318

Arg Trp Gly Ala Ile Trp Arg Ile Asp Thr Pro Asp Lys Leu Thr Gly
1               5                   10                  15

Pro Phe Thr Val Arg Arg
        20

<210> SEQ ID NO 319
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 319

Arg Trp Gly Ala Ile Trp Arg Ile Asp Thr Pro Asp Lys Leu Thr Gly
1               5                   10                  15

Pro Phe Thr Val Arg Arg
        20

<210> SEQ ID NO 320
<211> LENGTH: 21
<212> TYPE: PRT
<213> ORGANISM: Phleum Pratense

<400> SEQUENCE: 320

Lys Gly Ser Asp Pro Lys Lys Leu Val Leu Asn Ile Lys Tyr Thr Arg
1               5                   10                  15

Pro Gly Asp Ser Leu
        20

<210> SEQ ID NO 321
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES

```
<222> LOCATION: (20)..(20)
<223> OTHER INFORMATION: AMIDATION

<400> SEQUENCE: 321

Gly Ser Asp Pro Lys Lys Leu Val Leu Asn Ile Lys Tyr Thr Arg Pro
1               5                   10                  15
Gly Asp Ser Leu
            20

<210> SEQ ID NO 322
<211> LENGTH: 21
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (21)..(21)
<223> OTHER INFORMATION: AMIDATION

<400> SEQUENCE: 322

Lys Gly Ser Asp Pro Lys Lys Leu Val Leu Asn Ile Lys Tyr Thr Arg
1               5                   10                  15
Pro Gly Asp Ser Leu
            20

<210> SEQ ID NO 323
<211> LENGTH: 22
<212> TYPE: PRT
<213> ORGANISM: Artificial sequence
<220> FEATURE:
<223> OTHER INFORMATION: Modified sequence

<400> SEQUENCE: 323

Arg Glu Ala Lys Tyr Asp Ala Tyr Val Ala Thr Leu Ser Glu Ala Leu
1               5                   10                  15
Arg Ile Ile Ala Gly Arg
            20

<210> SEQ ID NO 324
<211> LENGTH: 21
<212> TYPE: PRT
<213> ORGANISM: Artificial sequence
<220> FEATURE:
<223> OTHER INFORMATION: Modified sequence

<400> SEQUENCE: 324

Arg Ile Glu Lys Val Asp Ala Ala Phe Lys Val Ala Ala Thr Ala Ala
1               5                   10                  15
Asn Ala Ala Pro Ala
            20

<210> SEQ ID NO 325
<211> LENGTH: 22
<212> TYPE: PRT
<213> ORGANISM: Artificial sequence
<220> FEATURE:
<223> OTHER INFORMATION: Modified sequence

<400> SEQUENCE: 325

Arg Ile Glu Lys Val Asp Ala Ala Phe Lys Val Ala Ala Thr Ala Ala
1               5                   10                  15
Asn Ala Ala Pro Ala Arg
            20
```

```
<210> SEQ ID NO 326
<211> LENGTH: 22
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (22)..(22)
<223> OTHER INFORMATION: AMIDATION

<400> SEQUENCE: 326

Arg Ile Glu Lys Val Asp Ala Ala Phe Lys Val Ala Ala Thr Ala Ala
1               5                   10                  15

Asn Ala Ala Pro Ala Arg
            20

<210> SEQ ID NO 327
<211> LENGTH: 20
<212> TYPE: PRT
<213> ORGANISM: Artificial sequence
<220> FEATURE:
<223> OTHER INFORMATION: Modified sequence
<220> FEATURE:
<221> NAME/KEY: MOD_RES
<222> LOCATION: (20)..(20)
<223> OTHER INFORMATION: AMIDATION

<400> SEQUENCE: 327

Lys Asp Lys Trp Ile Glu Leu Lys Glu Ser Trp Gly Ala Ile Trp Arg
1               5                   10                  15

Ile Asp Thr Pro
            20

<210> SEQ ID NO 328
<211> LENGTH: 240
<212> TYPE: PRT
<213> ORGANISM: Phleum Pratense

<400> SEQUENCE: 328

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val Val His Ile Thr Asp Asp Asn
                85                  90                  95

Glu Glu Pro Ile Ala Pro Tyr His Phe Asp Leu Ser Gly His Ala Phe
            100                 105                 110

Gly Ala Met Ala Lys Lys Gly Asp Glu Gln Lys Leu Arg Ser Ala Gly
        115                 120                 125

Glu Leu Glu Leu Gln Phe Arg Arg Val Lys Cys Lys Tyr Pro Glu Gly
    130                 135                 140

Thr Lys Val Thr Phe His Val Glu Lys Gly Ser Asn Pro Asn Tyr Leu
145                 150                 155                 160

Ala Leu Leu Val Lys Tyr Val Asn Gly Asp Gly Asp Val Val Ala Val
```

165                 170                 175
Asp Ile Lys Glu Lys Gly Lys Asp Lys Trp Ile Glu Leu Lys Glu Ser
                180                 185                 190

Trp Gly Ala Ile Trp Arg Ile Asp Thr Pro Asp Lys Leu Thr Gly Pro
            195                 200                 205

Phe Thr Val Arg Tyr Thr Thr Glu Gly Gly Thr Lys Thr Glu Ala Glu
210                 215                 220

Asp Val Ile Pro Glu Gly Trp Lys Ala Asp Thr Ser Tyr Glu Ser Lys
225                 230                 235                 240

<210> SEQ ID NO 329
<211> LENGTH: 96
<212> TYPE: PRT
<213> ORGANISM: Phleum Pratense

<400> SEQUENCE: 329

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
                20                  25                  30

Leu Arg Glu His Gly Ser Asp Glu Trp Val Ala Met Thr Lys Gly Glu
            35                  40                  45

Gly Gly Val Trp Thr Phe Asp Ser Glu Glu Pro Leu Gln Gly Pro Phe
        50                  55                  60

Asn Phe Arg Phe Leu Thr Glu Lys Gly Met Lys Asn Val Phe Asp Asp
65                  70                  75                  80

Val Val Pro Glu Lys Tyr Thr Ile Gly Ala Thr Tyr Ala Pro Glu Glu
                85                  90                  95

<210> SEQ ID NO 330
<211> LENGTH: 97
<212> TYPE: PRT
<213> ORGANISM: Phleum Pratense

<400> SEQUENCE: 330

Ala Val Gln Val Thr Phe Thr Val Gln Lys Gly Ser Asp Pro Lys Lys
1               5                   10                  15

Leu Val Leu Asn Ile Lys Tyr Thr Arg Pro Gly Asp Ser Leu Ala Glu
                20                  25                  30

Val Glu Leu Arg Gln His Gly Ser Glu Glu Trp Glu Pro Leu Thr Lys
            35                  40                  45

Lys Gly Asn Val Trp Glu Val Lys Ser Ser Lys Pro Leu Val Gly Pro
        50                  55                  60

Phe Asn Phe Arg Phe Met Ser Lys Gly Gly Met Arg Asn Val Phe Asp
65                  70                  75                  80

Glu Val Ile Pro Thr Ala Phe Lys Ile Gly Lys Thr Tyr Thr Pro Glu
                85                  90                  95

Glu

<210> SEQ ID NO 331
<211> LENGTH: 500
<212> TYPE: PRT
<213> ORGANISM: Phleum Pratense

<400> SEQUENCE: 331

Tyr Phe Pro Pro Ala Ala Lys Glu Asp Phe Leu Gly Cys Leu Val
1               5                   10                  15

```
Lys Glu Ile Pro Pro Arg Leu Leu Tyr Ala Lys Ser Ser Pro Ala Tyr
             20                  25                  30
Pro Ser Val Leu Gly Gln Thr Ile Arg Asn Ser Arg Trp Ser Ser Pro
             35                  40                  45
Asp Asn Val Lys Pro Leu Tyr Ile Ile Thr Pro Thr Asn Val Ser His
         50                  55                  60
Ile Gln Ser Ala Val Val Cys Gly Arg Arg His Ser Val Arg Ile Arg
65                  70                  75                  80
Val Arg Ser Gly Gly His Asp Tyr Glu Gly Leu Ser Tyr Arg Ser Leu
                 85                  90                  95
Gln Pro Glu Thr Phe Ala Val Val Asp Leu Asn Lys Met Arg Ala Val
             100                 105                 110
Trp Val Asp Gly Lys Ala Arg Thr Ala Trp Val Asp Ser Gly Ala Gln
             115                 120                 125
Leu Gly Glu Leu Tyr Tyr Ala Ile Tyr Lys Ala Ser Pro Thr Leu Ala
             130                 135                 140
Phe Pro Ala Gly Val Cys Pro Thr Ile Gly Val Gly Gly Asn Phe Ala
145                 150                 155                 160
Gly Gly Gly Phe Gly Met Leu Leu Arg Lys Tyr Gly Ile Ala Ala Glu
                 165                 170                 175
Asn Val Ile Asp Val Lys Leu Val Asp Ala Asn Gly Lys Leu His Asp
             180                 185                 190
Lys Lys Ser Met Gly Asp Asp His Phe Trp Ala Val Arg Gly Gly Gly
             195                 200                 205
Gly Glu Ser Phe Gly Ile Val Val Ala Trp Gln Val Lys Leu Leu Pro
             210                 215                 220
Val Pro Pro Thr Val Thr Ile Phe Lys Ile Ser Lys Thr Val Ser Glu
225                 230                 235                 240
Gly Ala Val Asp Ile Ile Asn Lys Trp Gln Val Val Ala Pro Gln Leu
                 245                 250                 255
Pro Ala Asp Leu Met Ile Arg Ile Ile Ala Gln Gly Pro Lys Ala Thr
             260                 265                 270
Phe Glu Ala Met Tyr Leu Gly Thr Cys Lys Thr Leu Thr Pro Leu Met
             275                 280                 285
Ser Ser Lys Phe Pro Glu Leu Gly Met Asn Pro Ser His Cys Asn Glu
             290                 295                 300
Met Ser Trp Ile Gln Ser Ile Pro Phe Val His Leu Gly His Arg Asp
305                 310                 315                 320
Ala Leu Glu Asp Asp Leu Leu Asn Arg Asn Asn Ser Phe Lys Pro Phe
                 325                 330                 335
Ala Glu Tyr Lys Ser Asp Tyr Val Tyr Gln Pro Phe Pro Lys Thr Val
             340                 345                 350
Trp Glu Gln Ile Leu Asn Thr Trp Leu Val Lys Pro Gly Ala Gly Ile
             355                 360                 365
Met Ile Phe Asp Pro Tyr Gly Ala Thr Ile Ser Ala Thr Pro Glu Ser
             370                 375                 380
Ala Thr Pro Phe Pro His Arg Lys Gly Val Leu Phe Asn Ile Gln Tyr
385                 390                 395                 400
Val Asn Tyr Trp Phe Ala Pro Gly Ala Ala Ala Pro Leu Ser Trp
                 405                 410                 415
Ser Lys Asp Ile Tyr Asn Tyr Met Glu Pro Tyr Val Ser Lys Asn Pro
             420                 425                 430
Arg Gln Ala Tyr Ala Asn Tyr Arg Asp Ile Asp Leu Gly Arg Asn Glu
```

```
                435                 440                 445
Val Val Asn Asp Val Ser Thr Tyr Ala Ser Gly Lys Val Trp Gly Gln
    450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 332
<211> LENGTH: 270
<212> TYPE: PRT
<213> ORGANISM: Phleum Pratense

<400> SEQUENCE: 332

Ala Gly Tyr Thr Pro Ala Ala Pro Ala Gly Ala Glu Pro Ala Gly Lys
1               5                   10                  15

Ala Thr Thr Glu Glu Gln Lys Leu Ile Glu Lys Ile Asn Ala Gly Phe
                20                  25                  30

Lys Ala Ala Leu Ala Ala Ala Gly Val Pro Pro Ala Asp Lys Tyr
            35                  40                  45

Arg Thr Phe Val Ala Thr Phe Gly Ala Ala Ser Asn Lys Ala Phe Ala
    50                  55                  60

Glu Gly Leu Ser Gly Glu Pro Lys Gly Ala Ala Glu Ser Ser Ser Lys
65                  70                  75                  80

Ala Ala Leu Thr Ser Lys Leu Asp Ala Ala Tyr Lys Leu Ala Tyr Lys
                85                  90                  95

Thr Ala Glu Gly Ala Thr Pro Glu Ala Lys Tyr Asp Ala Tyr Val Ala
            100                 105                 110

Thr Leu Ser Glu Ala Leu Arg Ile Ile Ala Gly Thr Leu Glu Val His
        115                 120                 125

Ala Val Lys Pro Ala Ala Glu Glu Val Lys Val Ile Pro Ala Gly Glu
    130                 135                 140

Leu Gln Val Ile Glu Lys Val Asp Ala Ala Phe Lys Val Ala Ala Thr
145                 150                 155                 160

Ala Ala Asn Ala Ala Pro Ala Asn Asp Lys Phe Thr Val Phe Glu Ala
                165                 170                 175

Ala Phe Asn Asn Ala Ile Lys Ala Ser Thr Gly Gly Ala Tyr Glu Ser
            180                 185                 190

Tyr Lys Phe Ile Pro Ala Leu Glu Ala Ala Val Lys Gln Ala Tyr Ala
        195                 200                 205

Ala Thr Val Ala Thr Ala Pro Glu Val Lys Tyr Thr Val Phe Glu Thr
    210                 215                 220

Ala Leu Lys Lys Ala Ile Thr Ala Met Ser Glu Ala Gln Lys Ala Ala
225                 230                 235                 240

Lys Pro Ala Ala Ala Ala Thr Ala Thr Ala Thr Ser Ala Val Gly Ala
                245                 250                 255

Ala Thr Gly Ala Ala Thr Ala Ala Thr Gly Gly Tyr Lys Val
            260                 265                 270

<210> SEQ ID NO 333
<211> LENGTH: 246
<212> TYPE: PRT
<213> ORGANISM: Cynodon dactylon
```

<400> SEQUENCE: 333

Ala Ile Gly Asp Lys Pro Gly Pro Asn Ile Thr Ala Thr Tyr Gly Ser
1               5                   10                  15

Lys Trp Leu Glu Ala Arg Ala Thr Phe Tyr Gly Ser Asn Pro Arg Gly
            20                  25                  30

Ala Ala Pro Asp Asp His Gly Gly Ala Cys Gly Tyr Lys Asp Val Asp
        35                  40                  45

Lys Pro Pro Phe Asp Gly Met Thr Ala Cys Gly Asn Glu Pro Ile Phe
    50                  55                  60

Lys Asp Gly Leu Gly Cys Arg Ala Cys Tyr Glu Ile Lys Cys Lys Glu
65                  70                  75                  80

Pro Val Glu Cys Ser Gly Glu Pro Val Leu Val Lys Ile Thr Asp Lys
                85                  90                  95

Asn Tyr Glu His Ile Ala Ala Tyr His Phe Asp Leu Ser Gly Lys Ala
            100                 105                 110

Phe Gly Ala Met Ala Lys Lys Gly Gln Glu Asp Lys Leu Arg Lys Ala
        115                 120                 125

Gly Glu Leu Thr Leu Gln Phe Arg Arg Val Lys Cys Lys Tyr Pro Ser
130                 135                 140

Gly Thr Lys Ile Thr Phe His Ile Glu Lys Gly Ser Asn Asp His Tyr
145                 150                 155                 160

Leu Ala Leu Leu Val Lys Tyr Ala Ala Gly Asp Gly Asn Ile Val Ala
                165                 170                 175

Val Asp Ile Lys Pro Arg Asp Ser Asp Glu Phe Ile Pro Met Lys Ser
            180                 185                 190

Ser Trp Gly Ala Ile Trp Arg Ile Asp Pro Lys Lys Pro Leu Lys Gly
        195                 200                 205

Pro Phe Ser Ile Arg Leu Thr Ser Glu Gly Gly Ala His Leu Val Gln
    210                 215                 220

Asp Asp Val Ile Pro Ala Asn Trp Lys Pro Asp Thr Val Tyr Thr Ser
225                 230                 235                 240

Lys Leu Gln Phe Gly Ala
                245

<210> SEQ ID NO 334
<211> LENGTH: 522
<212> TYPE: PRT
<213> ORGANISM: Cynodon dactylon

<400> SEQUENCE: 334

Met Ala Arg Ser Arg Ala Phe Ala Phe Ala Leu Leu Ile Cys Ala Val
1               5                   10                  15

Ala Ala Ser Cys His Val Ala Leu Ser Ala Pro Pro Tyr Ala Lys
            20                  25                  30

Gln Val Glu Arg Asp Phe Leu Thr Cys Leu Thr Lys Asp Ile Pro Pro
        35                  40                  45

Arg Gln Leu Tyr Ala Lys Ser Ser Pro Ala Tyr Ala Ser Val Trp Ser
    50                  55                  60

Ser Thr Val Arg Asn Ile Lys Phe Leu Ser Asp Lys Thr Val Lys Pro
65                  70                  75                  80

Leu Tyr Ile Ile Thr Pro Thr Asn Ala Ser His Ile Gln Ala Ala Val
                85                  90                  95

Val Cys Gly Arg Arg His Gly Met Arg Ile Arg Val Arg Ser Gly Gly
            100                 105                 110

-continued

His Asp Tyr Glu Gly Leu Ser Tyr Arg Ser Glu Lys Pro Glu Pro Phe
        115                 120                 125

Ala Val Val Asp Met Asn Lys Met Arg Ala Val Ser Ile Asp Gly Lys
130                 135                 140

Ala Ala Thr Ala Trp Val Asp Ser Gly Ala Gln Leu Gly Asp Leu Tyr
145                 150                 155                 160

Tyr Gly Ile Ala Lys Ala Ser Pro Lys Leu Gly Phe Pro Ala Gly Val
                165                 170                 175

Cys Thr Thr Ile Gly Val Gly His Phe Ser Gly Gly Phe Gly
                180                 185                 190

Met Leu Leu Arg Lys Tyr Gly Thr Ala Ala Asp Asn Val Ile Asp Ala
                195                 200                 205

Lys Val Val Asp Ala Gln Gly Arg Leu Leu Asp Arg Lys Ala Met Gly
                210                 215                 220

Glu Asp His Phe Trp Ala Ile Arg Gly Gly Gly Glu Ser Phe Gly
225                 230                 235                 240

Ile Val Ala Ser Trp Gln Val Lys Leu Leu Pro Val Pro Pro Lys Val
                245                 250                 255

Thr Val Phe Gln Val His Lys Gly Ile Lys Glu Gly Ala Ile Asp Leu
                260                 265                 270

Val Thr Lys Trp Gln Thr Val Ala Pro Ala Leu Pro Asp Asp Leu Met
                275                 280                 285

Ile Arg Ile Met Ala Met Gly Gln Gly Ala Met Phe Glu Ala Leu Tyr
                290                 295                 300

Leu Gly Thr Cys Lys Asp Leu Val Leu Leu Met Thr Ala Arg Phe Pro
305                 310                 315                 320

Glu Leu Gly Met Asn Ala Thr His Cys Lys Glu Met Thr Trp Ile Glu
                325                 330                 335

Ser Val Pro Tyr Ile Pro Met Gly Pro Lys Gly Thr Val Arg Asp Leu
                340                 345                 350

Leu Asn Arg Thr Ser Asn Ile Lys Ala Phe Gly Lys Tyr Lys Ser Asp
                355                 360                 365

Tyr Val Leu Glu Pro Ile Pro Lys Ser Asp Trp Glu Lys Ile Phe Thr
370                 375                 380

Trp Leu Val Lys Pro Gly Ala Gly Val Met Ile Met Asp Pro Tyr Gly
385                 390                 395                 400

Gly Gly Ile Ala Ser Val Pro Glu Ser Ala Thr Pro Phe Pro Arg Arg
                405                 410                 415

Ser Gly Val Leu Phe Asn Ile Gln Tyr Val Val Tyr Trp Phe Gly Glu
                420                 425                 430

Gly Ala Ala Ala Leu Pro Thr Gln Trp Thr Arg Asp Ile Tyr Asp Phe
                435                 440                 445

Met Thr Pro Tyr Val Ser Lys Asn Pro Arg Gln Ala Tyr Val Asn Tyr
                450                 455                 460

Arg Asp Leu Asp Leu Gly Val Asn Gln Val Val Gly Asn Val Ser Thr
465                 470                 475                 480

Tyr Ala Ser Gly Lys Val Trp Gly Glu Lys Tyr Phe Lys Gly Asn Phe
                485                 490                 495

Glu Arg Leu Ala Arg Thr Lys Gly Lys Ile Asp Pro Glu Asp Tyr Phe
                500                 505                 510

Arg Asn Glu Gln Ser Ile Pro Pro Leu Leu
                515                 520

```
<210> SEQ ID NO 335
<211> LENGTH: 264
<212> TYPE: PRT
<213> ORGANISM: Dactylis glomerata

<400> SEQUENCE: 335
```

| Met | Ala | Ser | Ser | Ser | Ser | Val | Leu | Leu | Val | Ala | Leu | Phe | Ala |
|---|---|---|---|---|---|---|---|---|---|---|---|---|---|
| 1 | | | | 5 | | | | | 10 | | | | 15 |

| Val | Phe | Leu | Gly | Ser | Ala | His | Gly | Ile | Pro | Lys | Val | Pro | Gly | Pro |
|---|---|---|---|---|---|---|---|---|---|---|---|---|---|---|
| | | | 20 | | | | | 25 | | | | 30 | | |

| Asn | Ile | Thr | Ala | Thr | Tyr | Gly | Asp | Lys | Trp | Leu | Asp | Ala | Lys | Ser | Thr |
|---|---|---|---|---|---|---|---|---|---|---|---|---|---|---|---|
| | | | 35 | | | | | 40 | | | | | 45 | | |

| Trp | Tyr | Gly | Lys | Pro | Thr | Gly | Ala | Gly | Pro | Lys | Asp | Asn | Gly | Gly | Ala |
|---|---|---|---|---|---|---|---|---|---|---|---|---|---|---|---|
| | 50 | | | | | 55 | | | | | 60 | | | | |

| Cys | Gly | Tyr | Lys | Asp | Val | Asp | Lys | Ala | Pro | Phe | Asn | Gly | Met | Thr | Gly |
|---|---|---|---|---|---|---|---|---|---|---|---|---|---|---|---|
| 65 | | | | | 70 | | | | | 75 | | | | | 80 |

| Cys | Gly | Asn | Thr | Pro | Ile | Phe | Lys | Asp | Gly | Arg | Gly | Cys | Gly | Ser | Cys |
|---|---|---|---|---|---|---|---|---|---|---|---|---|---|---|---|
| | | | | 85 | | | | | 90 | | | | | 95 | |

| Phe | Glu | Ile | Lys | Cys | Thr | Lys | Pro | Glu | Ser | Cys | Ser | Gly | Glu | Ala | Val |
|---|---|---|---|---|---|---|---|---|---|---|---|---|---|---|---|
| | | | | 100 | | | | | 105 | | | | | 110 | |

| Thr | Val | His | Ile | Thr | Asp | Asp | Asn | Glu | Glu | Pro | Ile | Ala | Pro | Tyr | His |
|---|---|---|---|---|---|---|---|---|---|---|---|---|---|---|---|
| | | | | 115 | | | | | 120 | | | | | 125 | |

| Phe | Asp | Leu | Ser | Gly | His | Ala | Phe | Gly | Ser | Met | Ala | Lys | Lys | Gly | Glu |
|---|---|---|---|---|---|---|---|---|---|---|---|---|---|---|---|
| | 130 | | | | | 135 | | | | | 140 | | | | |

| Glu | Gln | Lys | Leu | Arg | Ser | Ala | Gly | Glu | Leu | Glu | Leu | Gln | Phe | Arg | Arg |
|---|---|---|---|---|---|---|---|---|---|---|---|---|---|---|---|
| 145 | | | | | 150 | | | | | 155 | | | | | 160 |

| Val | Lys | Cys | Lys | Tyr | Pro | Glu | Gly | Thr | Lys | Val | Thr | Phe | His | Val | Glu |
|---|---|---|---|---|---|---|---|---|---|---|---|---|---|---|---|
| | | | | 165 | | | | | 170 | | | | | 175 | |

| Lys | Gly | Ser | Asn | Pro | Asn | Tyr | Leu | Ala | Leu | Leu | Val | Lys | Tyr | Val | Asp |
|---|---|---|---|---|---|---|---|---|---|---|---|---|---|---|---|
| | | | 180 | | | | | 185 | | | | | 190 | | |

| Gly | Asp | Gly | Asp | Val | Val | Ala | Val | Asp | Ile | Lys | Glu | Lys | Gly | Lys | Asp |
|---|---|---|---|---|---|---|---|---|---|---|---|---|---|---|---|
| | | 195 | | | | | 200 | | | | | 205 | | | |

| Lys | Trp | Ile | Ala | Leu | Lys | Glu | Ser | Trp | Gly | Ala | Ile | Trp | Arg | Val | Asp |
|---|---|---|---|---|---|---|---|---|---|---|---|---|---|---|---|
| 210 | | | | | 215 | | | | | 220 | | | | | |

| Thr | Pro | Asp | Lys | Leu | Thr | Gly | Pro | Phe | Thr | Val | Arg | Tyr | Thr | Thr | Glu |
|---|---|---|---|---|---|---|---|---|---|---|---|---|---|---|---|
| 225 | | | | | 230 | | | | | 235 | | | | | 240 |

| Gly | Gly | Thr | Lys | Ser | Glu | Val | Glu | Asp | Val | Ile | Pro | Glu | Gly | Trp | Lys |
|---|---|---|---|---|---|---|---|---|---|---|---|---|---|---|---|
| | | | | 245 | | | | | 250 | | | | | 255 | |

| Ala | Asp | Thr | Ser | Tyr | Glu | Ala | Lys |
|---|---|---|---|---|---|---|---|
| | | | 260 | | | | |

```
<210> SEQ ID NO 336
<211> LENGTH: 96
<212> TYPE: PRT
<213> ORGANISM: Dactylis glomerata

<400> SEQUENCE: 336
```

| Val | Lys | Val | Thr | Phe | Lys | Val | Glu | Lys | Gly | Ser | Asp | Pro | Lys | Lys | Leu |
|---|---|---|---|---|---|---|---|---|---|---|---|---|---|---|---|
| 1 | | | | 5 | | | | | 10 | | | | | 15 | |

| Val | Leu | Asp | Ile | Lys | Tyr | Thr | Arg | Pro | Gly | Asp | Thr | Leu | Ala | Glu | Val |
|---|---|---|---|---|---|---|---|---|---|---|---|---|---|---|---|
| | | | 20 | | | | | 25 | | | | | 30 | | |

| Glu | Leu | Arg | Gln | His | Gly | Ser | Glu | Trp | Pro | Leu | Thr | Lys | Lys |
|---|---|---|---|---|---|---|---|---|---|---|---|---|---|
| | | | 35 | | | | | 40 | | | | | 45 |

| Gly | Asn | Leu | Trp | Glu | Val | Lys | Ser | Ser | Lys | Pro | Leu | Thr | Gly | Pro | Phe |
|---|---|---|---|---|---|---|---|---|---|---|---|---|---|---|---|
| | 50 | | | | | 55 | | | | | 60 | | | | |

| Asn | Phe | Arg | Phe | Met | Ser | Lys | Gly | Gly | Met | Arg | Asn | Val | Phe | Asp | Glu |

```
                65                  70                  75                  80
Val Ile Pro Thr Ala Phe Lys Ile Gly Thr Thr Tyr Thr Pro Glu Glu
                    85                  90                  95

<210> SEQ ID NO 337
<211> LENGTH: 265
<212> TYPE: PRT
<213> ORGANISM: Dactylis glomerata

<400> SEQUENCE: 337

Ala Asp Ala Gly Tyr Thr Pro Ala Ala Ala Thr Pro Ala Thr Ala
1               5                   10                  15

Gly Gly Lys Ala Met Thr Glu Glu Gln Thr Leu Ile Glu Asp Val Asn
                20                  25                  30

Ala Gly Phe Lys Ala Ala Val Ala Ala Ser Ser Ala Pro Pro Ala
            35                  40                  45

Asp Lys Phe Lys Thr Phe Glu Ala Thr Phe Thr Ala Ala Cys Lys Ala
        50                  55                  60

Asn Ile Ala Ala Ala Thr Lys Val Pro Leu Phe Val Ala Lys Leu
65                  70                  75                  80

Asp Ala Ala Tyr Ala Val Ala Tyr Lys Thr Ala Thr Gly Pro Thr Pro
                85                  90                  95

Glu Ala Lys Tyr Asp Ala Phe Val Ala Ala Leu Thr Glu Ala Leu Arg
            100                 105                 110

Val Ile Ala Gly Ala Leu Glu Val His Ala Val Lys Pro Ala Ala Glu
        115                 120                 125

Glu Val Pro Ala Ala Lys Ile Pro Ala Gly Glu Leu Gln Ile Val Asp
    130                 135                 140

Lys Ile Asp Ala Ala Tyr Lys Ile Ala Ala Thr Ala Ala Asn Ala Ala
145                 150                 155                 160

Pro Ala Asn Asp Lys Phe Thr Val Phe Glu Gly Ala Phe Asn Lys Ala
                165                 170                 175

Ile Lys Glu Ser Thr Gly Gly Ala Tyr Glu Ser Tyr Lys Phe Ile Pro
            180                 185                 190

Thr Leu Glu Ala Ala Val Lys Gln Ala Tyr Ala Ala Thr Val Ala Ala
        195                 200                 205

Ala Pro Glu Val Lys Tyr Ala Val Phe Glu Ala Ala Leu Thr Lys Ala
    210                 215                 220

Ile Thr Ala Met Ser Glu Ala Gln Lys Val Ala Thr Pro Ala Ala Val
225                 230                 235                 240

Ala Thr Gly Ala Ala Thr Ala Ala Ala Ser Ala Ala Thr Gly Ala Ala
                245                 250                 255

Thr Ala Ala Ala Gly Gly Tyr Lys Val
            260                 265

<210> SEQ ID NO 338
<211> LENGTH: 263
<212> TYPE: PRT
<213> ORGANISM: Festuca pratensis

<400> SEQUENCE: 338

Met Ala Ser Ser Ser Val Leu Leu Val Val Ala Leu Phe Ala Val
1               5                   10                  15

Phe Leu Gly Ser Ala His Gly Ile Ala Lys Val Pro Pro Gly Pro Asn
                20                  25                  30

Ile Thr Ala Glu Tyr Gly Asp Lys Trp Leu Asp Ala Lys Ser Thr Trp
```

-continued

```
                35                  40                  45
Tyr Gly Lys Pro Thr Gly Ala Gly Pro Lys Asp Asn Gly Gly Ala Cys
 50                  55                  60

Gly Tyr Lys Asp Val Asp Lys Ala Pro Phe Asn Gly Met Thr Gly Cys
 65                  70                  75                  80

Gly Asn Thr Ala Ile Phe Lys Asp Gly Arg Gly Cys Gly Ser Cys Phe
                 85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
            115                 120                 125

Asp Leu Ser Gly His Ala Phe Gly Ser Met Ala Lys Lys Gly Glu Glu
        130                 135                 140

Gln Lys Leu Arg Ser Ala Gly Glu Leu Glu Leu Gln Phe Arg Arg Val
145                 150                 155                 160

Lys Cys Lys Tyr Pro Asp Gly Thr Lys Pro Thr Phe His Val Glu Lys
                165                 170                 175

Gly Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
210                 215                 220

Pro Asp Lys Leu Thr Gly Pro Phe Thr Val Arg Tyr Thr Thr Glu Gly
225                 230                 235                 240

Gly Thr Lys Ser Glu Val Glu Val Ile Pro Glu Gly Trp Lys Ala
                245                 250                 255

Asp Thr Ser Tyr Ser Ala Lys
            260

<210> SEQ ID NO 339
<211> LENGTH: 263
<212> TYPE: PRT
<213> ORGANISM: Lollium Perenne

<400> SEQUENCE: 339

Met Ala Ser Ser Ser Val Leu Leu Val Val Ala Leu Phe Ala Val
  1               5                  10                  15

Phe Leu Gly Ser Ala His Gly Ile Ala Lys Val Pro Pro Gly Pro Asn
                 20                  25                  30

Ile Thr Ala Glu Tyr Gly Asp Lys Trp Leu Asp Ala Lys Ser Thr Trp
             35                  40                  45

Tyr Gly Lys Pro Thr Gly Ala Gly Pro Lys Asp Asn Gly Gly Ala Cys
 50                  55                  60

Gly Tyr Lys Asp Val Asp Lys Ala Pro Phe Asn Gly Met Thr Gly Cys
 65                  70                  75                  80

Gly Asn Thr Pro Ile Phe Lys Asp Gly Arg Gly Cys Gly Ser Cys Phe
                 85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
            115                 120                 125

Asp Leu Ser Gly His Ala Phe Gly Ser Met Ala Lys Lys Gly Glu Glu
        130                 135                 140
```

```
Gln Lys Leu Arg Ser Ala Gly Glu Leu Glu Leu Gln Phe Arg Arg Val
145                 150                 155                 160

Lys Cys Lys Tyr Pro Asp Gly Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Val Glu Asp Val Ile Pro Glu Gly Trp Lys Ala
                245                 250                 255

Asp Thr Ser Tyr Ser Ala Lys
                260

<210> SEQ ID NO 340
<211> LENGTH: 97
<212> TYPE: PRT
<213> ORGANISM: Lollium Perenne

<400> SEQUENCE: 340

Ala Ala Pro Val Glu Phe Thr Val Glu Lys Gly Ser Asp Glu Lys Asn
1               5                   10                  15

Leu Ala Leu Ser Ile Lys Tyr Asn Lys Glu Gly Asp Ser Met Ala Glu
            20                  25                  30

Val Glu Leu Lys Glu His Gly Ser Asn Glu Trp Leu Ala Leu Lys Lys
        35                  40                  45

Asn Gly Asp Gly Val Trp Glu Ile Lys Ser Asp Lys Pro Leu Lys Gly
    50                  55                  60

Pro Phe Asn Phe Arg Phe Val Ser Glu Lys Gly Met Arg Asn Val Phe
65                  70                  75                  80

Asp Asp Val Val Pro Ala Asp Phe Lys Val Gly Thr Thr Tyr Lys Pro
                85                  90                  95

Glu

<210> SEQ ID NO 341
<211> LENGTH: 97
<212> TYPE: PRT
<213> ORGANISM: Lollium Perenne

<400> SEQUENCE: 341

Thr Lys Val Asp Leu Thr Val Glu Lys Gly Ser Asp Ala Lys Thr Leu
1               5                   10                  15

Val Leu Asn Ile Lys Tyr Thr Arg Pro Gly Asp Thr Leu Ala Glu Val
            20                  25                  30

Glu Leu Arg Gln His Gly Ser Glu Glu Trp Pro Met Thr Lys Lys
        35                  40                  45

Gly Asn Leu Trp Glu Val Lys Ser Ala Lys Pro Leu Thr Gly Pro Met
    50                  55                  60

Asn Phe Arg Phe Leu Ser Lys Gly Gly Met Lys Asn Val Phe Asp Glu
65                  70                  75                  80

Val Ile Pro Thr Ala Phe Thr Val Gly Lys Thr Tyr Thr Pro Glu Tyr
                85                  90                  95

Asn
```

<210> SEQ ID NO 342
<211> LENGTH: 307
<212> TYPE: PRT
<213> ORGANISM: Lollium Perenne

<400> SEQUENCE: 342

Met Ala Val Gln Lys Tyr Thr Val Ala Leu Phe Leu Ala Val Ala Leu
1               5                   10                  15

Val Ala Gly Pro Ala Ala Ser Tyr Ala Asp Ala Gly Tyr Thr Pro
            20                  25                  30

Ala Ala Ala Ala Thr Pro Ala Thr Pro Ala Ala Thr Pro Ala Ala Ala
                35                  40                  45

Gly Gly Lys Ala Thr Thr Asp Glu Gln Lys Leu Leu Glu Asp Val Asn
50                  55                  60

Ala Gly Phe Lys Ala Ala Val Ala Ala Ala Asn Ala Pro Pro Ala
65                  70                  75                  80

Asp Lys Phe Lys Ile Phe Glu Ala Phe Ser Glu Ser Ser Lys Gly
                85                  90                  95

Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Glu Ala Thr Pro Glu
        115                 120                 125

Ala Lys Tyr Asp Ala Phe Val Thr Ala Leu Thr Glu Ala Leu Arg Val
    130                 135                 140

Ile Ala Gly Ala Leu Glu Val His Ala Val Lys Pro Ala Thr Glu Glu
145                 150                 155                 160

Val Leu Ala Ala Lys Ile Pro Thr Gly Glu Leu Gln Ile Val Asp Lys
                165                 170                 175

Ile Asp Ala Ala Phe Lys Ile Ala Ala Thr Ala Ala Asn Ala Ala Pro
            180                 185                 190

Thr Asn Asp Lys Phe Thr Val Phe Glu Ser Ala Phe Asn Lys Ala Leu
        195                 200                 205

Asn Glu Cys Thr Gly Gly Ala Tyr Glu Thr Tyr Lys Phe Ile Pro Ser
210                 215                 220

Leu Glu Ala Ala Val Lys Gln Ala Tyr Ala Ala Thr Val Ala Ala Ala
225                 230                 235                 240

Pro Glu Val Lys Tyr Ala Val Phe Glu Ala Ala Leu Thr Lys Ala Ile
                245                 250                 255

Thr Ala Met Thr Gln Ala Gln Lys Ala Gly Lys Pro Ala Ala Ala Ala
            260                 265                 270

Ala Thr Ala Ala Ala Thr Val Ala Thr Ala Ala Thr Ala Ala Ala
        275                 280                 285

Val Leu Pro Pro Pro Leu Leu Val Gln Ser Leu Ile Ser Leu Leu
    290                 295                 300

Ile Tyr Tyr
305

<210> SEQ ID NO 343
<211> LENGTH: 339
<212> TYPE: PRT
<213> ORGANISM: Lollium Perenne

<400> SEQUENCE: 343

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
              20                  25                  30

Ala Thr Pro Ala Thr Pro Ala Ala Pro Ala Thr Ala Thr Pro Ala
         35                  40                  45

Thr Pro Ala Thr Pro Ala Thr Pro Ala Ala Val Pro Ser Gly Lys Ala
 50                  55                  60

Thr Thr Glu Glu Gln Lys Leu Ile Glu Lys Ile Asn Ala Gly Phe Lys
 65                  70                  75                  80

Ala Ala Val Ala Ala Ala Ala Val Val Pro Pro Ala Asp Lys Tyr Lys
                 85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
                115                 120                 125

Lys Leu Asp Ala Ala Leu Lys Leu Ala Tyr Glu Ala Ala Gln Gly Ala
130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
                180                 185                 190

Ile Asp Lys Val Asp Ala Ala Tyr Arg Thr Ala Ala Thr Ala Ala Asn
                195                 200                 205

Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240

Ile Pro Thr Leu Val Ala Val Lys Gln Ala Tyr Ala Ala Lys Gln
                245                 250                 255

Ala Thr Ala Pro Glu Val Lys Tyr Thr Val Ser Glu Thr Ala Leu Lys
                260                 265                 270

Lys Ala Val Thr Ala Met Ser Glu Ala Glu Lys Glu Ala Thr Pro Ala
                275                 280                 285

Ala Ala Ala Thr Ala Thr Pro Thr Pro Ala Ala Thr Ala Thr Ala
290                 295                 300

Thr Pro Ala Ala Ala Tyr Ala Thr Ala Thr Pro Ala Ala Ala Thr Ala
305                 310                 315                 320

Thr Ala Thr Pro Ala Ala Thr Ala Thr Pro Ala Ala Ala Gly Gly
                325                 330                 335

Tyr Lys Val

<210> SEQ ID NO 344
<211> LENGTH: 265
<212> TYPE: PRT
<213> ORGANISM: Paspalum notatum

<400> SEQUENCE: 344

Met Gly Ser Leu Ala Lys Ile Val Ala Val Ala Val Leu Ala Ala
 1               5                  10                  15

Leu Val Ala Gly Gly Ser Cys Gly Pro Pro Lys Val Pro Pro Gly Pro
                 20                  25                  30

Asn Ile Thr Thr Asn Tyr Asn Gly Lys Trp Leu Pro Ala Lys Ala Thr
                 35                  40                  45

```
Trp Tyr Gly Gln Pro Asn Gly Ala Gly Pro Asp Asp Asn Gly Gly Ala
    50                  55                  60

Cys Gly Ile Lys Asn Val Asn Leu Pro Pro Tyr Asn Gly Phe Thr Ala
65                  70                  75                  80

Cys Gly Asn Pro Pro Ile Phe Lys Asp Gly Lys Gly Cys Gly Ser Cys
                85                  90                  95

Tyr Glu Ile Arg Cys Asn Lys Pro Glu Cys Ser Gly Gln Pro Val Thr
            100                 105                 110

Val Phe Ile Thr Asp Met Asn Tyr Glu Pro Ile Ala Pro Tyr His Phe
        115                 120                 125

Asp Leu Ser Gly Lys Ala Phe Gly Ala Met Ala Lys Pro Gly Leu Asn
    130                 135                 140

Asp Lys Leu Arg His Tyr Gly Ile Phe Asp Leu Glu Phe Arg Arg Val
145                 150                 155                 160

Arg Cys Lys Tyr Gln Gly Gly Gln Lys Ile Val Phe His Val Glu Lys
                165                 170                 175

Gly Ser Asn Pro Asn Tyr Leu Ala Met Leu Val Lys Phe Val Ala Asp
            180                 185                 190

Asp Gly Asp Ile Val Leu Met Glu Leu Lys Glu Lys Ser Ser Asp Trp
        195                 200                 205

Lys Pro Met Lys Leu Ser Trp Gly Ala Ile Trp Arg Met Asp Thr Pro
    210                 215                 220

Lys Ala Leu Val Pro Pro Phe Ser Ile Arg Leu Thr Ser Glu Ser Gly
225                 230                 235                 240

Lys Lys Val Ile Ala Gln Asp Val Ile Pro Val Asn Trp Lys Pro Asp
                245                 250                 255

Thr Val Tyr Asn Ser Asn Val Gln Phe
            260                 265

<210> SEQ ID NO 345
<211> LENGTH: 269
<212> TYPE: PRT
<213> ORGANISM: Phalaris aquatica

<400> SEQUENCE: 345

Met Met Lys Met Val Cys Ser Ser Ser Ser Ser Leu Leu Val Val
1               5                   10                  15

Ala Ala Leu Leu Ala Val Phe Val Gly Ser Ala Gln Gly Ile Ala Lys
            20                  25                  30

Val Pro Pro Gly Pro Asn Ile Thr Ala Glu Tyr Gly Asp Lys Trp Leu
        35                  40                  45

Asp Ala Lys Ser Thr Trp Tyr Gly Lys Pro Thr Gly Ala Gly Pro Lys
    50                  55                  60

Asp Asn Gly Gly Ala Cys Gly Tyr Lys Asp Val Asp Lys Ala Pro Phe
65                  70                  75                  80

Asn Gly Met Thr Gly Cys Gly Asn Thr Pro Ile Phe Lys Asp Gly Arg
                85                  90                  95

Gly Cys Gly Ser Cys Phe Glu Leu Lys Cys Ser Lys Pro Glu Ser Cys
            100                 105                 110

Ser Gly Glu Pro Ile Thr Val His Ile Thr Asp Asp Asn Glu Glu Pro
        115                 120                 125

Ile Ala Pro Tyr His Phe Asp Leu Ser Gly His Ala Phe Gly Ser Met
    130                 135                 140

Ala Lys Lys Gly Glu Glu Glu Asn Val Arg Gly Ala Gly Glu Leu Glu
```

```
145                 150                 155                 160
Leu Gln Phe Arg Arg Val Lys Cys Lys Tyr Pro Asp Gly Thr Lys Pro
                165                 170                 175

Thr Phe His Val Glu Lys Gly Ser Asn Pro Asn Tyr Leu Ala Leu Leu
            180                 185                 190

Val Lys Tyr Val Asp Gly Asp Gly Asp Val Val Ala Val Asp Ile Lys
        195                 200                 205

Glu Lys Gly Lys Asp Lys Trp Ile Glu Leu Lys Glu Ser Trp Gly Ala
    210                 215                 220

Ile Trp Arg Ile Asp Thr Pro Asp Lys Leu Thr Gly Pro Phe Thr Val
225                 230                 235                 240

Arg Tyr Thr Thr Glu Gly Gly Thr Lys Ala Glu Phe Glu Asp Val Ile
                245                 250                 255

Pro Glu Gly Trp Lys Ala Asp Thr His Asp Ala Ser Lys
            260                 265

<210> SEQ ID NO 346
<211> LENGTH: 320
<212> TYPE: PRT
<213> ORGANISM: Phalaris aquatica

<400> SEQUENCE: 346

Met Ala Val Gln Lys Tyr Thr Met Ala Leu Phe Leu Ala Val Ala Leu
1               5                   10                  15

Val Ala Gly Pro Ala Ala Pro Thr Pro Pro Thr Pro Arg Thr Pro Pro
            20                  25                  30

Leu Leu Pro Pro Pro Arg Ala Arg Asp Lys Ala Thr Leu Thr Ser Arg
        35                  40                  45

Ser Val Glu Asp Ile Asn Ala Ala Ser Arg Arg Pro Trp Trp Ala Ser
    50                  55                  60

Val Pro Pro Ala Asp Lys Phe Lys Thr Phe Ala Asp His Val Leu Cys
65                  70                  75                  80

Val Pro Asn Ala Asp Val Thr Ser Ala Ala Thr Lys Ala Pro Gln Leu
                85                  90                  95

Lys Ala Lys Leu Asp Ala Ala Tyr Arg Val Ala Tyr Glu Ala Ala Glu
            100                 105                 110

Gly Ser Thr Pro Glu Ala Lys Tyr Asp Ala Phe Ile Ala Ala Leu Thr
        115                 120                 125

Glu Ala Leu Arg Val Ile Ala Gly Ala Phe Glu Val His Ala Val Lys
    130                 135                 140

Pro Ala Thr Glu Glu Val Val Ala Asp Pro Val Gly Glu Leu Gln Ile
145                 150                 155                 160

Val Asp Lys Ile Asp Ala Ala Phe Lys Ile Ala Ala Thr Ala Ala Asn
                165                 170                 175

Ser Ala Pro Ala Asn Asp Lys Phe Thr Val Phe Glu Gly Ala Phe Asn
            180                 185                 190

Lys Ala Ile Lys Glu Ser Thr Ala Gly Ala Tyr Glu Thr Tyr Lys Phe
        195                 200                 205

Ile Pro Ser Leu Glu Ala Ala Val Lys Gln Ala Tyr Gly Ala Thr Val
    210                 215                 220

Ala Arg Ala Pro Glu Val Lys Tyr Ala Val Phe Glu Ala Gly Leu Thr
225                 230                 235                 240

Lys Ala Ile Thr Ala Met Ser Glu Ala Gln Lys Val Ala Lys Pro Pro
                245                 250                 255
```

```
Leu Ser Pro Gln Pro Pro Gln Val Leu Pro Leu Ala Ala Gly Gly Ala
            260                 265                 270

Ala Thr Val Ala Ala Ser Asp Val Arg Val Cys Arg Ser His Gly
        275                 280                 285

Thr Leu Gln Asp Ala Cys Leu Leu Arg Cys Arg Gly Gly Cys Gln Pro
    290                 295                 300

Val Val Trp Arg Gly Gly Ser His Arg Ala Arg Gly Gly Tyr Lys Val
305                 310                 315                 320
```

<210> SEQ ID NO 347
<211> LENGTH: 263
<212> TYPE: PRT
<213> ORGANISM: Poa pratensis

<400> SEQUENCE: 347

```
Met Ala Ser Ser Ser Val Leu Leu Val Val Ala Leu Phe Ala Val
1               5                   10                  15

Phe Leu Gly Thr Ala His Gly Ile Ala Lys Val Pro Pro Gly Pro Asn
            20                  25                  30

Ile Thr Ala Thr Tyr Gly Asp Lys Trp Leu Asp Ala Lys Ser Thr Trp
        35                  40                  45

Tyr Gly Lys Pro Thr Gly Ala Gly Pro Lys Asp Asn Gly Gly Ala Cys
50                  55                  60

Gly Tyr Lys Asp Val Asp Lys Ala Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ser Cys Ser Gly Glu Pro Val Leu
            100                 105                 110

Val His Ile Thr Asp Asp Asn Glu Glu Pro Ile Ala Ala Tyr His Phe
        115                 120                 125

Asp Leu Ser Gly Lys Ala Phe Gly Ala Met Ala Lys Lys Gly Glu Glu
    130                 135                 140

Gln Lys Leu Arg Ser Ala Gly Glu Leu Glu Leu Lys Phe Arg Arg Val
145                 150                 155                 160

Lys Cys Glu Tyr Pro Glu Gly Thr Lys Val Thr Phe His Val Glu Lys
                165                 170                 175

Gly Ser Asn Pro Asn Tyr Leu Ala Leu Leu Val Lys Tyr Val Thr Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ser Ile Trp Arg Val Asp Thr
    210                 215                 220

Pro Asp Lys Leu Thr Gly Pro Phe Thr Val Arg Tyr Thr Thr Glu Gly
225                 230                 235                 240

Gly Thr Lys Gly Glu Ala Glu Asp Val Ile Pro Glu Gly Trp Lys Ala
                245                 250                 255

Asp Thr Ala Tyr Ala Ser Lys
            260
```

<210> SEQ ID NO 348
<211> LENGTH: 303
<212> TYPE: PRT
<213> ORGANISM: Poa pratensis

<400> SEQUENCE: 348

Met Ala Val Gln Lys Tyr Thr Val Ala Leu Phe Leu Thr Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Ala Ala Gly Ala Ala Gly Lys Ile Thr Pro Thr
        35                  40                  45

Gln Glu Gln Lys Leu Met Glu Asp Ile Asn Val Gly Phe Lys Ala Ala
50                  55                  60

Val Ala Ala Ala Gly Ala Pro Pro Ala Asp Lys Phe Lys Thr Phe
65              70                  75                  80

Gln Ala Ala Phe Ser Ala Ser Val Glu Ala Ser Ala Ala Lys Leu Asn
                85                  90                  95

Ala Ala Gln Ala Pro Gly Phe Val Ser His Val Ala Ala Thr Ser Asp
            100                 105                 110

Ala Thr Tyr Lys Ala Ala Val Gly Ala Thr Pro Glu Ala Lys Phe Asp
        115                 120                 125

Ser Phe Val Ala Ala Phe Thr Glu Ala Leu Arg Ile Ile Ala Gly Val
    130                 135                 140

Leu Lys Val His Ala Val Lys Pro Ile Thr Glu Glu Thr Gly Ala Ala
145                 150                 155                 160

Lys Ile Pro Ala Gly Glu Gln Gln Ile Ile Asp Lys Ile Asp Ala Ala
                165                 170                 175

Phe Lys Val Ala Ala Thr Ala Ala Asn Ala Ala Pro Ala Asn Asp Lys
            180                 185                 190

Phe Thr Val Phe Glu Ala Ala Phe Asn Asn Ala Ile Lys Glu Ser Thr
        195                 200                 205

Gly Gly Ala Tyr Asp Thr Tyr Lys Ser Ile Pro Ser Leu Glu Ala Ala
    210                 215                 220

Val Lys Gln Ala Tyr Ala Ala Thr Ile Ala Ala Pro Glu Val Lys
225                 230                 235                 240

Phe Ala Val Phe Lys Ala Ala Leu Thr Lys Ala Ile Thr Ala Met Ala
            245                 250                 255

Glu Val Gln Lys Val Ser Lys Pro Val Ala Gly Ala Ala Thr Val Ala
        260                 265                 270

Ala Gly Ala Ala Thr Ala Ala Thr Gly Ala Ala Thr Gly Ala Ala Gly
    275                 280                 285

Ala Ala Thr Gly Ala Ala Thr Val Ser Ala Gly Gly Tyr Lys Val
        290                 295                 300

<210> SEQ ID NO 349
<211> LENGTH: 532
<212> TYPE: PRT
<213> ORGANISM: Sorghum halepense

<400> SEQUENCE: 349

Met Gly Val Asn Met Met Ser Trp Ser Met Gln Val Ala Leu Val Val
1               5                   10                  15

Ala Leu Ala Phe Leu Val Gly Gly Ala Trp Cys Gly Pro Pro Lys Val
            20                  25                  30

Ala Pro Gly Lys Asn Ile Thr Ala Thr Tyr Gly Ser Asp Trp Leu Glu
        35                  40                  45

Ala Lys Ala Thr Trp Tyr Gly Lys Pro Thr Gly Ala Gly Pro Asp Asp
    50                  55                  60

Asn Gly Gly Ala Cys Gly Tyr Lys Asp Val Asn Lys Ala Pro Phe Asn
65                  70                  75                  80

```
Ser Met Gly Ala Cys Gly Asn Leu Pro Ile Phe Lys Asp Gly Leu Gly
                85                  90                  95
Cys Gly Ser Cys Phe Glu Ile Lys Cys Asp Lys Pro Ala Glu Cys Ser
            100                 105                 110
Gly Glu Ala Val Val His Ile Thr Asp Met Asn Tyr Glu Gln Ile
        115                 120                 125
Ala Ala Tyr His Phe Asp Leu Ala Gly Thr Ala Phe Gly Ala Met Ala
    130                 135                 140
Lys Gly Glu Glu Glu Lys Leu Arg Lys Ala Gly Ile Ile Asp Met
145                 150                 155                 160
Lys Phe Arg Arg Val Lys Cys Lys Tyr Gly Glu Lys Val Thr Phe His
                165                 170                 175
Val Glu Lys Gly Ser Asn Pro Asn Tyr Leu Ala Leu Leu Val Lys Tyr
            180                 185                 190
Val Asp Gly Asp Gly Asp Val Gly Val Asp Ile Lys Glu Lys Gly
        195                 200                 205
Gly Asp Ala Tyr Gln Pro Leu Lys His Ser Trp Gly Ala Ile Trp Arg
    210                 215                 220
Lys Asp Ser Asp Lys Pro Ile Lys Phe Pro Val Thr Val Gln Ile Thr
225                 230                 235                 240
Thr Glu Gly Gly Thr Lys Thr Ala Tyr Glu Asp Val Ile Pro Glu Gly
                245                 250                 255
Trp Lys Ala Asp Thr Thr Tyr Thr Ala Lys Met Gly Val Asn Met Met
            260                 265                 270
Ser Trp Ser Met Gln Val Ala Leu Val Val Ala Leu Ala Phe Leu Val
        275                 280                 285
Gly Gly Ala Trp Cys Gly Pro Pro Lys Val Ala Pro Gly Lys Asn Ile
    290                 295                 300
Thr Ala Thr Tyr Gly Ser Asp Trp Leu Glu Ala Lys Ala Thr Trp Tyr
305                 310                 315                 320
Gly Lys Pro Thr Gly Ala Gly Pro Asp Asp Asn Gly Ala Cys Gly
                325                 330                 335
Tyr Lys Asp Val Asn Lys Ala Pro Phe Asn Ser Met Gly Ala Cys Gly
            340                 345                 350
Asn Leu Pro Ile Phe Lys Asp Gly Leu Gly Cys Gly Ser Cys Phe Glu
        355                 360                 365
Ile Lys Cys Asp Lys Pro Ala Glu Cys Ser Gly Glu Ala Val Val Val
    370                 375                 380
His Ile Thr Asp Met Asn Tyr Glu Gln Ile Ala Ala Tyr His Phe Asp
385                 390                 395                 400
Leu Ala Gly Thr Ala Phe Gly Ala Met Ala Lys Lys Gly Glu Glu Glu
                405                 410                 415
Lys Leu Arg Lys Ala Gly Ile Ile Asp Met Lys Phe Arg Arg Val Lys
            420                 425                 430
Cys Lys Tyr Gly Glu Lys Val Thr Phe His Val Glu Lys Gly Ser Asn
        435                 440                 445
Pro Asn Tyr Leu Ala Leu Leu Val Lys Tyr Val Asp Gly Asp Gly Asp
    450                 455                 460
Val Val Gly Val Asp Ile Lys Glu Lys Gly Gly Asp Ala Tyr Gln Pro
465                 470                 475                 480
Leu Lys His Ser Trp Gly Ala Ile Trp Arg Lys Asp Ser Asp Lys Pro
                485                 490                 495
```

```
Ile Lys Phe Pro Val Thr Val Gln Ile Thr Thr Glu Gly Gly Thr Lys
            500                 505                 510

Thr Ala Tyr Glu Asp Val Ile Pro Glu Gly Trp Lys Ala Asp Thr Thr
            515                 520                 525

Tyr Thr Ala Lys
    530
```

PEPTIDE COMBINATIONS AND USES THEREOF FOR TREATING GRASS ALLERGY

CROSS-REFERENCE TO RELATED APPLICATIONS

This application is a national stage filing under 35 U.S.C. 371 of PCT/US2016/040773 filed Jul. 1, 2016, which International Application was published by the International Bureau in English on Jan. 5, 2017, and claims priority from U.S. Provisional Application No. 62/187,630, filed Jul. 1, 2015, which applications are hereby incorporated by reference in their entirety in this application.

FIELD OF THE INVENTION

The present invention relates to compositions comprising peptides derived from grass pollen allergens and methods of using such compositions for modulating an immune response, for treating a subject for an allergic response and/or for inducing or promoting immunological tolerance in a subject, as well as use of such compositions in diagnostic methods and kits comprising such compositions.

BACKGROUND OF THE INVENTION

Allergy to grass affects populations in many parts of the world. The most common grass species are e.g. Rye grass (Lolium perenne), Timothy grass (Phleum pratense), Bermuda grass (Cynodon dactylon), Velvet grass (Holcus lanatus), Orchard grass (Dactylis glomerata), Canary grass (Phalaris aquatica), Bahia grass (Paspalum notatum) and Meadow grass/Kentucky bluegrass (Poa pratensis), which all have been shown to contain the major allergen of group 1 (Lol p 1, Phl p 1, Cyn d 1, Hol l 1, Dac g 1, Pha a 1, Pas n 1 and Poa p 1). Most of the grasses (except Bermuda grass) have been shown to also contain the major allergen of group 5 (Lol p 5, Phl p 5, Hol l 5, Dac g 5, Pha a 5, and Poa p 5). Most grasses also contain allergens from the minor allergen groups 2/3 and 4. Some grass species are very similar, which gives rise to a high degree of immunological cross reactivity at a level of T cell recognition, but also more distant grass species can lead to high cross reactivity.

Allergen-specific immunotherapy (AIT) is the only disease modifying therapy that is effective for the treatment of IgE mediated allergies thereby leading to induction of long term immunological and clinical tolerance. Currently, grass allergen specific products based on whole, intact or modified allergens are typically administered for the treatment of grass allergy. Typically, such products are administered by subcutaneous injection or by the sublingual route to a subject over an extended period of time, frequently months or years and are now appreciated to induce a state of immunological and clinical "tolerance" in the subject. The mechanism of action is thought to involve induction of IgG inhibitory antibodies, suppression of mast cell/basophil reactivity, suppression of T cell responses, the promotion of T cell anergy, and/or clonal deletion, and in the long term results is a reduction in allergic responses of the patient.

Unfortunately, allergen-specific immunotherapy bears the risk of inducing IgE-mediated adverse events including serious anaphylactic responses. Therefore, this therapy is not as widely offered to allergic subjects as its beneficial effect actually justifies. In recent years, it has been suggested to treat allergy using smaller fragments (peptides) of the primary amino acid sequence of allergens (e.g. of the major allergens), that contain one or more epitope(s) recognized by T cells involved in the allergic reaction. This concept has been termed peptide immunotherapy (PIT), in which, repeated doses of the peptide is administered, typically by intradermal injection, to a subject (Moldaver and Larche 2011).

More specifically on the molecular level, peptides are bound by Human Leucocyte Antigen (HLA)MHC (Major histocompatibility Complex) class II molecules (referred to as HLA at gene level) on the surface of Antigen Presenting Cells (APC) which present the peptides for CD4+ T cell surveillance. This peptide-HLA MHC complex is then recognized by specific T cell receptors on the cell surface of T cells that upon interaction, and the complex bearing APCs become activated, leading to the activation of T cells. A major difference of peptide-based immunotherapy versus therapies based on full-length allergens is that this interaction is hypothesized to occur without a concomitant "danger signal" being elicited. This is thought to drive the T cell response in a more tolerogenic direction. It has also been hypothesized that this interaction leads to less activation of the APC compared to whole proteins and thus having the potential to drive the T cell response in a more tolerogenic direction.

Peptide-based immunotherapy (PIT) represents a potentially attractive alternative to allergen extracts, with a more favourable safety profile and a significantly shorter treatment regimen than existing therapies. In contrast to therapies based on intact allergens, PIT solely addresses the T cell compartment of the immune system without engaging existing antibody responses because of the lack of antibody epitopes due to the smaller size of peptides compared to allergens. Consequently, no IgE-mediated adverse events are expected with peptide therapy. Peptide immunotherapy is today in clinical development and does seem to have a favourable safety profile over the whole-allergen based vaccines.

A shortcoming of using the T cell epitope-containing peptides is, however, associated with the restriction of each peptide to only bind a subset of the naturally occurring MHC Class II molecules within the human population. A mix of several peptides covering different HLA Class II alleles is therefore mandatory to generate an immunotherapy allergy treatment acting broadly on a population level. As this antigen repertoire of MHC Class II alleles varies from one individual to another and from one ethnic population to another, it is challenging to provide peptide-based immunotherapies that can be offered to allergic subjects of any geographic region in the world unless numerous peptides are included in the vaccine. Taken into consideration the enormous costs and risks in the clinical development of new vaccines and the increasing demands from regulatory bodies to meet high standards for toxicity testing, dose justification, safety and efficacy trials, it is desirable to provide peptide vaccines containing as few peptides as possible, but at the same time to be able to treat the majority of grass allergic subjects in a worldwide population with a single immunotherapy product as is presently the case with extract based immunotherapy products. Such a product should comprise as a first requirement a combination of peptides that are able to bind the worldwide MHC Class II allele repertoire, and the resulting peptide-MHC complexes should as a second requirement be recognized by the T cells of the subject so as to induce tolerogenic immunological reactions. Research has shown that a single peptide matching the MHC molecule in a mouse model is sufficient to elicit an immunogenic response (or to induce a tolerogenic response) (Cambell et al, 2009). On the other hand, other studies in mice indicate that peptide immunotherapy using one peptide alone did not reduce the severity of allergic airway inflammation, but that it is required that the mice are treated with at least two peptides that match the MHC molecules of the mice being treated (Mackenzie K J et al 2013)".

International patent applications WO 1994/21675, WO 1995/06728, WO 2003/024998, WO 2003/082924 and WO2010/089554, WO 2011/106645, and U.S. Pat. Nos. 5,721,119, 5,736,362, 5,840,316, 5,869,333, 5,965,368, 6,197,313, 6,239,269, 6,265,566, 6,277,383, 6,451,324, 6,008,340, 6,559,120, 7,148,019, 6,214,358, 6,441,157, 7,514,083, 5,480,972, 5,691,167, 5,736,149, 5,710,126, 7,112,333 all relate to peptides of grass allergens and their use in treating grass allergy. However, a very limited amount of work regarding combinations of grass peptides has been conducted.

It is an object of claims of the present invention to provide improved grass peptide combinations for modulating an immune response, for treating a subject for an allergic response and/or for inducing or promoting immunological tolerance in a subject, and for use in diagnostic methods and kits comprising such grass peptide combinations. It is another object of the invention to provide peptide combinations exhibiting very good HLA Class II coverage in a worldwide population and being immunologically potent in a worldwide population. It is another object of the invention to provide peptide combinations having good cross reactivity to other grass species. It is another object of the invention to provide peptide combinations of only 3, 4, 5, 6 or 7 grass peptides yet obtaining at least 70%, and more preferably around 90-100% donor coverage in a donor cohort representative of a worldwide population. Another object of the invention is to provide peptide combinations which are so immunologically potent that even at very low doses of peptides, the percentage of responding donors can be retained at a very high level in a donor cohort representative of a worldwide population. Another object of the invention is to provide peptide combinations which have minor risk of inducing IgE-mediated adverse events. An additional object of the invention is to provide peptide combinations of peptides which have a sufficient solubility profile for being formulated in a pharmaceutical product, preferably which have acceptable estimated in vivo stability.

SUMMARY OF THE INVENTION

It has been found by the present inventors that it is possible to assemble peptide combinations comprising or consisting of a few peptides, such as three, four, five or six peptides, which cover a high fraction of the HLA Class II allele repertoire of a worldwide population and which also produce a T cell response in a high fraction of a donor population allergic to one or more grass species.

The invention provides a number of compositions comprising peptide combinations having a high worldwide HLA Class II allele coverage and high T cell reactivity. In an embodiment disclosed herein, the inventors of the present invention have found that a peptide composition comprising at least four peptides produce a T cell response in a high fraction of grass pollen allergic donors selected to represent a diverse set of HLA class II molecules (see Example 24). In an embodiment disclosed herein, peptides of the compositions are found to be soluble in various buffers at different pH (see Example 18). Further in an embodiment as disclosed herein, the inventors have found that the same mixes have high cross-reactivity to homologue peptides derived from allergens in other grass species (see Example 21). Finally, in an embodiment disclosed herein, the inventors have found that mixes of the present invention are able to provide a high T cell reactivity of PBMCs derived from donors allergic to grass pollen even in low concentrations (see Example 23). The inventors have further found that a number of peptides of the present invention result in a high yield and purity when produced using a standard peptide synthesis set-up (see Example 19). At the same time, the inventors have found that a number of peptides of the present invention have a favourable stability when incubated with human serum (see Example 20).

In an embodiment disclosed herein, the inventors of the present invention have found that a peptide mix comprising at least four peptides produce a T cell response in a surprisingly high fraction of grass pollen allergic donors selected to represent a diverse set of HLA class II molecules. Further in an embodiment disclosed herein, peptides of mixes of the present invention are found to be soluble in various buffers at different pH. In a further embodiment disclosed herein, mixes of the present invention are selected in order to maximize the cross-reactivity to homologue peptides derived from allergens in other grass species. Finally, in an embodiment disclosed herein, a number of mixes of the present invention have been selected based on the results of dose response studies, in order to provide a high T cell reactivity even in low concentrations.

Accordingly, the present invention relates to a composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof;

or wherein one or more of said first, second, third and fourth peptide(s) independently are selected from the group consisting of peptides a) to e):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence SEQ ID NO: 69 (236), or a variant thereof;
d) a peptide having the amino acid sequence SEQ ID NO: 36 (217), or a variant thereof; and
e) a peptide having the amino acid sequence of SEQ ID NO: 232 (285), or a variant thereof;

with the proviso that the group consisting of the first through fourth peptides does not comprise more than one peptide of each of the peptides a) to d), and does not comprise more than two peptides of peptides e).

More specifically, the present invention in one embodiment relates to a composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof.

In one embodiment, the composition according to the present invention, further comprises a fifth peptide selected from the group consisting of peptides having the amino acid sequence of SEQ ID NOs: 1 to 327, such as any one or more of the peptides mentioned in Tables 1 to 9 and Table 34; and wherein said fifth peptide is not identical to any one of said respective first, second, third, fourth peptide in the composition.

In a more specific embodiment, the composition according to the present invention further comprises a fifth peptide selected from the group consisting of peptides a) to h):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
f) a peptide having the amino acid sequence of SEQ ID NO: 4 (204), or a variant thereof;
g) a peptide having the amino acid sequence of SEQ ID NO: 11 (211), or a variant thereof;
h) a peptide having the amino acid sequence of SEQ ID NO: 45 (222), or a variant thereof;
wherein said fifth peptide is not identical to any one of said respective first, second, third and fourth peptides in the composition. In another more specific embodiment, the composition according to the present invention, further comprises a fifth peptide selected from the group consisting of peptides f) to h).

In one embodiment, the composition according to the invention further comprises a sixth peptide selected from the group consisting of peptides having the amino acid sequence of SEQ ID NOs: 1 to 327 as mentioned herein, such as any one of the peptides mentioned in Tables 1 to 9 and Table 34; wherein said sixth peptide is not identical to any one of said first, second, third, fourth or fifth peptides in the composition.

In a more specific embodiment, the composition according to the invention further comprises a sixth peptide selected from the group consisting of peptides a) to h):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
f) a peptide having the amino acid sequence of SEQ ID NO: 4 (204), or a variant thereof;
g) a peptide having the amino acid sequence of SEQ ID NO: 11 (211), or a variant thereof;
h) a peptide having the amino acid sequence of SEQ ID NO: 45 (222), or a variant thereof;
wherein said sixth peptide is not identical to any one of said first, second, third, fourth or fifth peptides in the composition.

In an even more specific embodiment, the composition according to the invention further comprises a fifth peptide having the amino acid sequence of SEQ ID NO: 4 (204), or a variant thereof; and a sixth peptide having the amino acid sequence of SEQ ID NO: 45 (222), or a variant thereof. In another more specific embodiment, the composition according to the invention further comprises a fifth peptide having the amino acid sequence of SEQ ID NO: 11 (211), or a variant thereof; and a sixth peptide having the amino acid sequence of SEQ ID NO: 45 (222), or a variant thereof.

In one aspect of the present invention, the compositions comprising peptides as defined herein are pharmaceutical compositions. In one embodiment the pharmaceutical composition comprises a pharmaceutically acceptable carrier, excipient and/or adjuvant. In a further embodiment, the pharmaceutical composition is formulated as a vaccine for parenteral administration.

Another aspect of the invention provides a kit comprising a compartment and instructions, wherein the compartment comprises the composition of the invention and wherein the instructions are for use in treating allergy to grass.

An aspect of the invention provides a method for relieving or reducing (e.g. treating) an immune response being triggered by a grass pollen allergen of a grass species in a subject in need thereof, said method comprising administering to said subject a therapeutically effective amount of the composition of the invention.

Another aspect of the invention provides a method for relieving one or more symptoms of an immune response being triggered by a grass pollen allergen of a grass species in a subject in need thereof, said method comprising administering to said subject a therapeutically effective amount of the composition of the invention.

Another aspect of the invention provides a method for inducing (developing) immunological tolerance against a grass pollen allergen of a grass species in a subject in need thereof, said method comprising administering to said subject a therapeutically effective amount of the composition of the invention.

In one aspect of the invention, compositions as defined herein are for use in a method of treatment further defined herein, such as e.g. a composition as defined herein for use in relieving an immune response triggered by an allergen of a grass species in a subject in need thereof; for use in relieving one or more symptoms of an immune response triggered by an allergen of a grass species in a subject in need thereof; and/or for inducing immunological tolerance against an allergen of a grass species in a subject in need thereof.

In another aspect of the invention, compositions as defined herein are for the preparation of a medicament for use in a method of treatment as defined herein.

In still further aspects, the invention relates to a kit comprising a compartment and instructions, wherein the compartment comprises a composition described herein and wherein the instructions are for use in treating allergy to grass, such as Timothy grass or rye grass.

In still further aspects, the invention relates to a method of determining whether T cells of a subject in need of treatment recognize a composition as defined herein, comprising contacting T cells obtained from the subject with said composition or a single peptide thereof and detecting whether the T cells are stimulated by said composition or single peptide. Thus such an aspect of the invention provides an in-vitro method for determining whether T cells and/or peripheral blood mononuclear cells recognize a composition as defined herein, comprising contacting cells obtained from a subject with said composition or a single peptide thereof, and detecting whether said cells are stimulated by the composition or single peptide, optionally wherein said subject is in need of treatment.

A final aspect of the invention provides a diagnostic kit comprising a composition of the invention as defined herein.

The invention further provides methods of assembling combinations of peptides from a set of T cell epitope containing peptides. Accordingly, such peptide combinations may be assembled by first providing a set of T cell epitope containing peptides (for example as disclosed in Example 3), then estimating the HLA Class II allele coverage of each individual T cell epitope containing-peptide (for example as disclosed in Example 4), then assembling peptides covering diverse HLA alleles to cover the HLA Class II allele repertoire of a worldwide population (for example as disclosed in Example 6) and then verifying in a qualified donor population (for example as disclosed in Example 2) that the suggested peptide combinations are able to produce a T cell response in a high fraction of the population (for example as described in Example 7). The same method may be used to assemble peptide combinations aimed to target a subpopulation in which case the peptide combination should cover the HLA Class II alleles present in that subpopulation and produce a T cell response in a high fraction of the subpopulation.

Thus, there is herein provided a combination of peptides (herein also named "peptide combination" or "peptide mix") for use as an "allergy vaccine" in the treatment of allergy to grass, which combination is suitable for addressing the immune system of the majority of the world population. The peptides selected for the herein disclosed peptide combinations derive from one or more of the grass allergens Phl p 1, Phl p 2, Phl p 3, Phl p 4 and Phl p 5, and are shown to produce a T cell response in many donors and to have a satisfactorily high worldwide HLA Class II coverage. In one embodiment, peptides of a peptide combination as disclosed herein primarily are distinct peptides derived from different regions of the grass allergens, or optionally wherein the amino acid residues of one distinct peptide overlap with few amino acid residues of another distinct peptide such as overlapping with less than 13, such as less than 12, 11, 10 or 9 amino acid residues. In another embodiment of the invention, peptides of a peptide combination as disclosed herein primarily are distinct peptides derived from different regions of the grass allergens, or the amino acid residues of one distinct peptide overlap with few amino acid residues of another distinct peptide such as overlapping with less than 17, such as less than 16, such as less than 15, such as less than 14, such as leas than 13, such as less than 12, 11, 10 or 9 amino acid residues. In a preferable embodiment of the invention, when the peptides in a composition of the invention overlap, the overlapping peptides are either a) predicted to bind different HLA class II alleles, and/or b) demonstrated in in vitro HLA class II binding assays to bind to different HLA class II alleles and/or c) demonstrated to elicit a T cell response in a differing set of donors, as measured using stimulation of PBMCs derived from grass pollen allergic donors. Table 15 reports peptides shown to produce a T cell response in a high fraction of the donor population ("selected high responder peptides"). Tables 54 to 57 report a further selection of peptide mixes shown to produce a T cell response in a high fraction of a donor population of grass pollen allergic individuals.

LEGENDS TO THE FIGURES

Figure 1B:
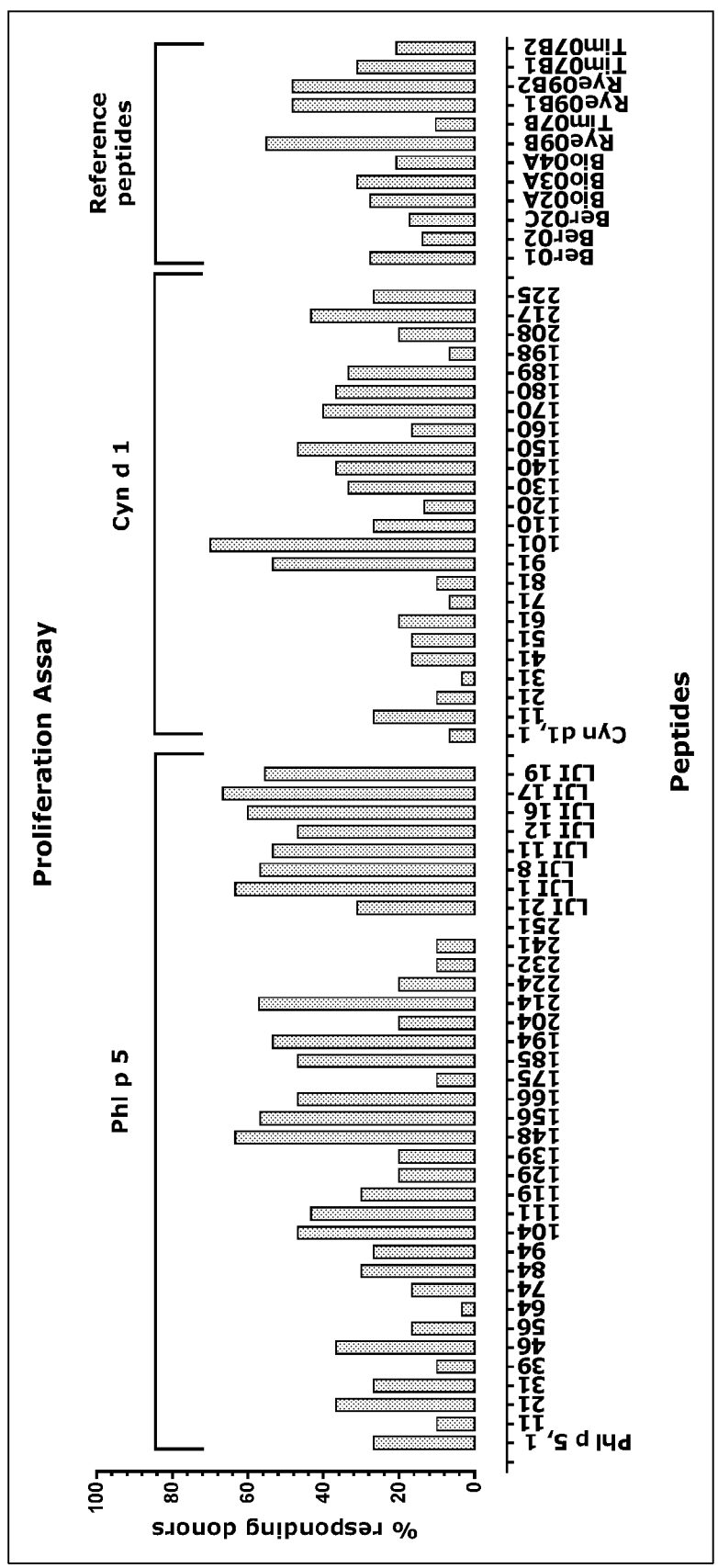

FIGS. 1a & 1b: Illustrates the percentage of grass allergic donor derived T cell lines responding to the peptides in an in-vitro T cell proliferation assay on being exposed to the *Phleum pratense* derived peptides FIGS. 2a & 2b: Demonstrates the percentage of grass allergic donor derived T cell lines responding to the peptides in an in-vitro IL-5 release Fluorospot assay on being exposed to the *Phleum pratense* derived peptides FIGS. 3a & 3b: Shows the percentage of grass allergic donor derived T cell lines responding to the peptides in an in-vitro IL-5 release Fluorospot assay on being exposed to the *Phleum pratense* derived peptides FIG. 4a: Shows the comparison of the 20-mer peptides to corresponding 15-mer peptides with respect to the T cell proliferation FIG. 4b: Shows the comparison of the 20-mer peptides to corresponding 15-mer peptides with respect to the IL-5 ELISpot FIG. 5a: Shows the percentage of grass allergic donor derived T cell lines (TCL-01 DK-2) responding to the peptide in an in-vitro IL-5 release Fluorospot assay on being exposed to the combinations FIG. 5b: Shows the percentage of grass allergic donor derived T cell lines (TCL-02 DK-2) responding to the peptide-combinations in an in-vitro T cell proliferation assay on being exposed to the combinations FIG. 6: Shows the percentage of grass allergic donor derived T cell lines (TCL-03 DK-1) responding to the peptide-combinations in an in-vitro T cell proliferation assay on being exposed to the combinations FIG. 7a: Shows the percentage of grass allergic donor derived T cell lines (TCL-03DK1+DK2) responding to the peptide-combinations in an in-vitro T cell proliferation assay on being exposed to the combinations at Zug/ml FIG. 7b: Shows the percentage of grass allergic donor derived T cell lines (TCL-03DK1+DK2) responding to the peptide-mixes in an in-vitro T cell proliferation assay on being exposed to the titrated amounts of peptide combinations FIG. 8a: Shows the percentage of grass allergic donor derived T cell lines responding to either *Phleum* peptides or homologue peptides in an in-vitro T cell proliferation assay on being exposed to either Phl p 1 (*Phleum pratense* 1) peptides or corresponding homologue peptides from Lp1 (*Lolium perenne* 1) or Cd 1 (*Cynodon dactylon* 1). The *Phleum* peptides are named by referencing its corresponding starting position in the respective full length allergen mentioned in Example 1. The corresponding homologues are referred to either as Lp 1 or Cd 1.

Figure 8A:
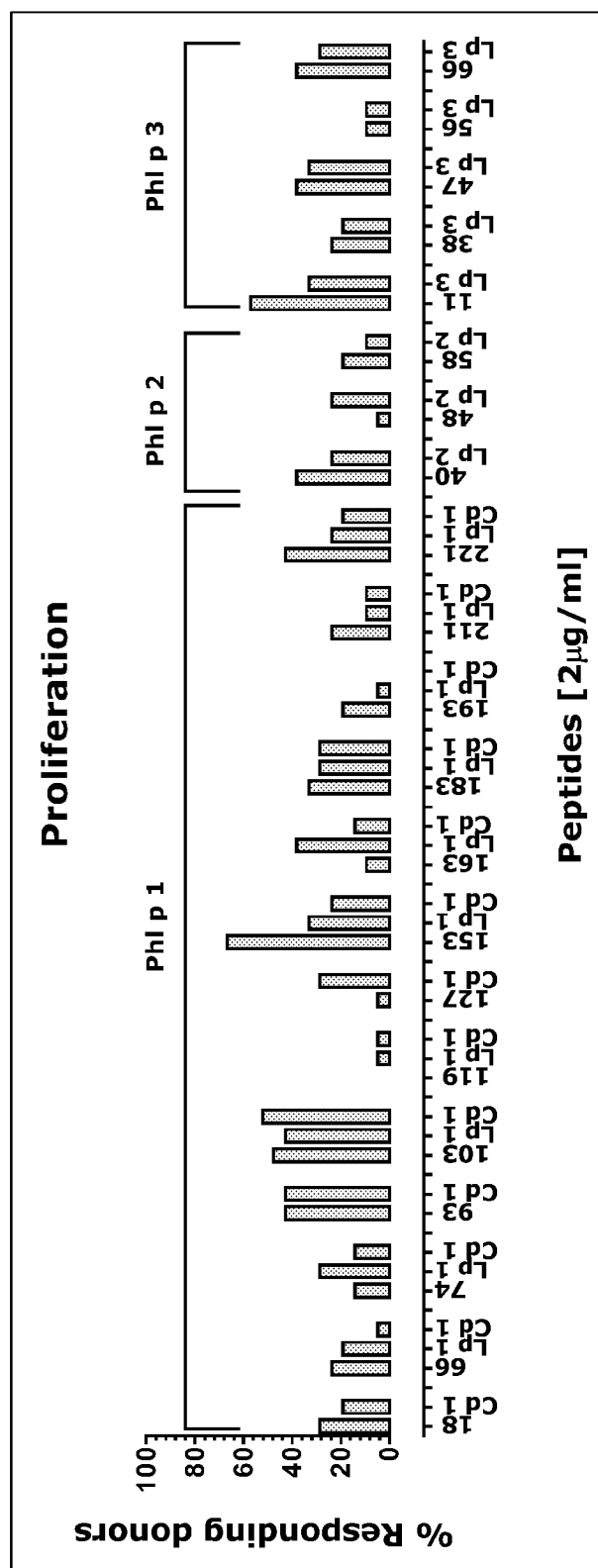
Figure 8B:
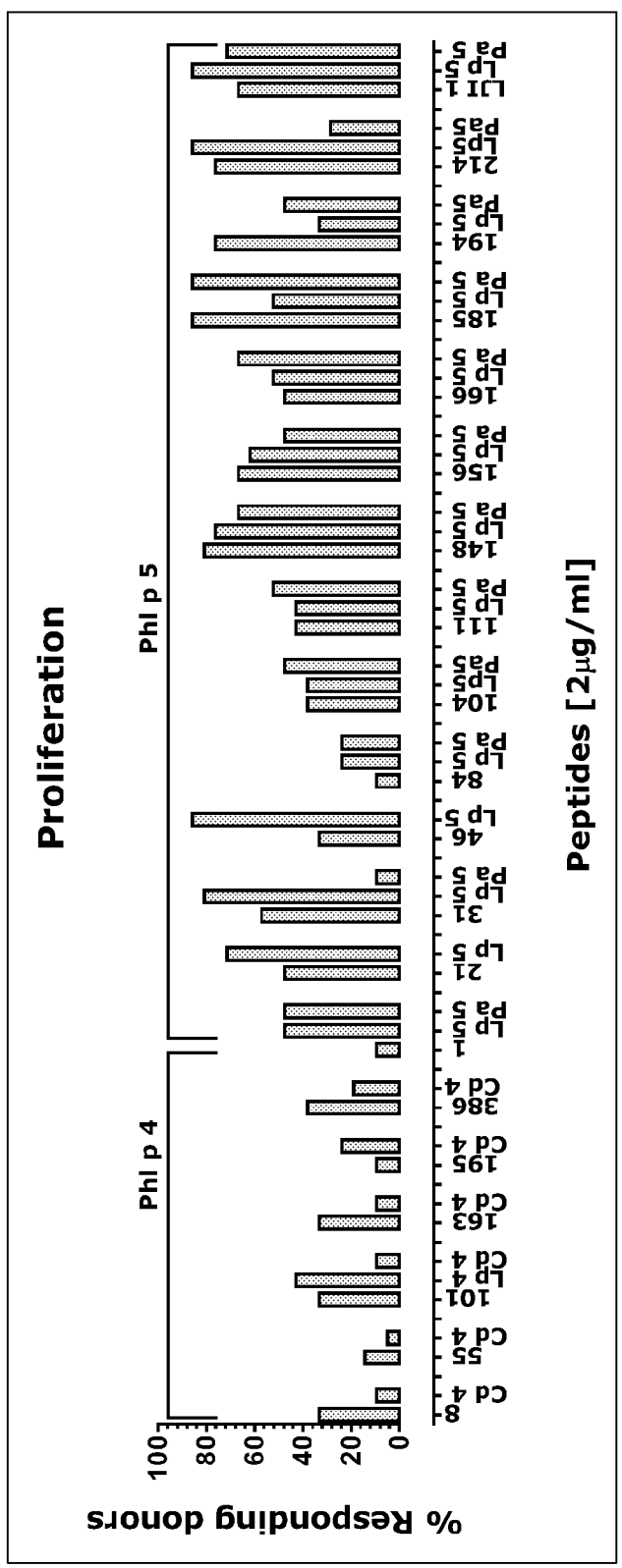

FIG. 8b: Shows the percentage of grass allergic donor derived T cell lines responding to either native or homologue peptides in an in-vitro T cell proliferation assay on being exposed to either Phl p 4 peptides or corresponding homologue peptides from Cd 4 (*Cynodon dactylon* 4), Lp5 (*Lolium perenne* 5); and on being exposed to either Phl p 5 peptides or corresponding homologue peptides from Lp5 (*Lolium perenne* 5), and Pa 5 (*Phalaris aquatica* 5). The *Phleum* peptides are named by referencing its corresponding starting position in the respective full length allergen mentioned in Example 1. The corresponding homologues are referred to either as Cd 4, LP 4, LP 5 or Pa 5.

Figure 9:
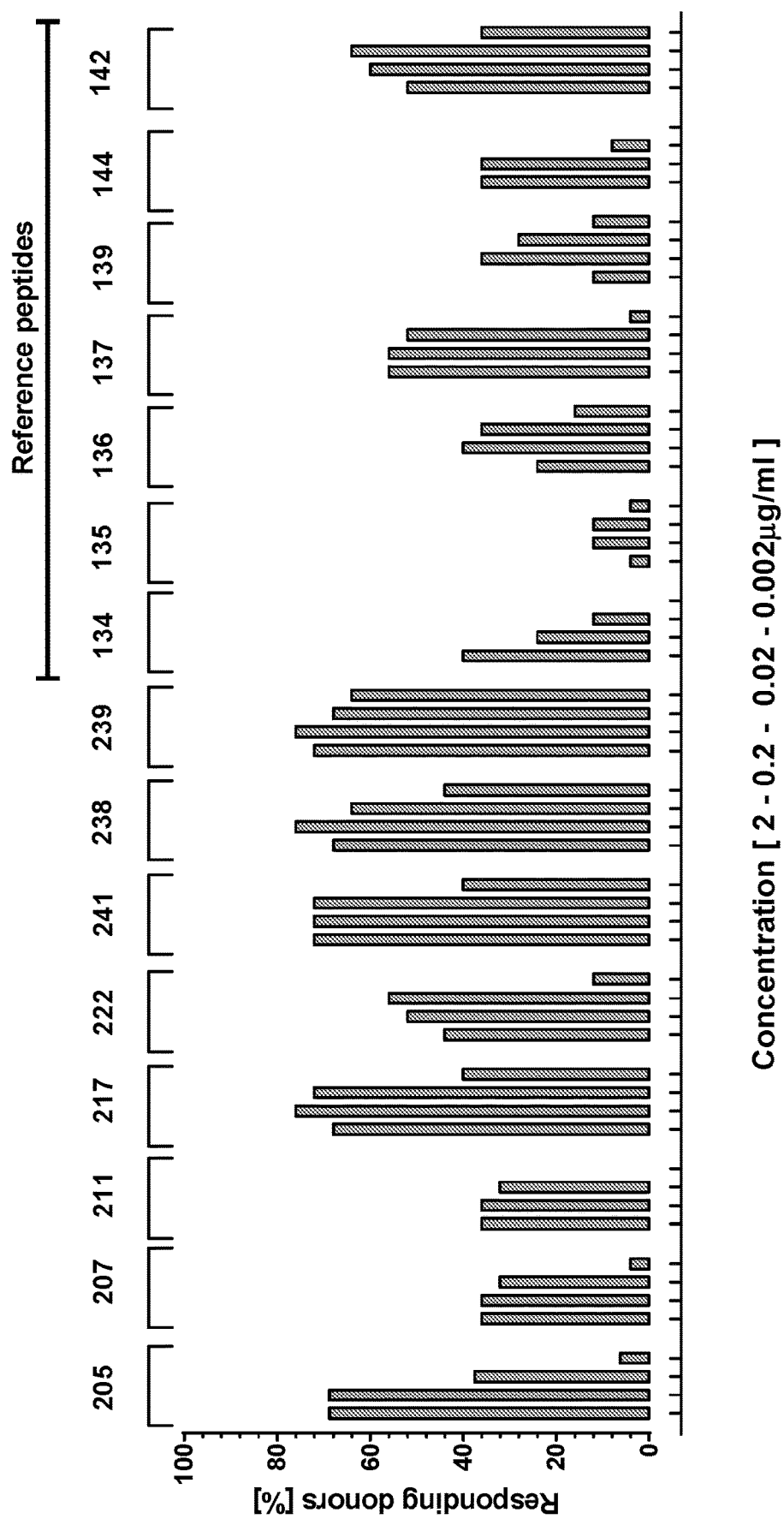

FIG. 9: Shows the percentage of grass allergic donor derived T cell lines (TCL-03DK1+DK2) responding to the peptide-mixes in a in-vitro T cell proliferation assay on being exposed to the titrated amounts of peptide-mixes.

Figure 10A:
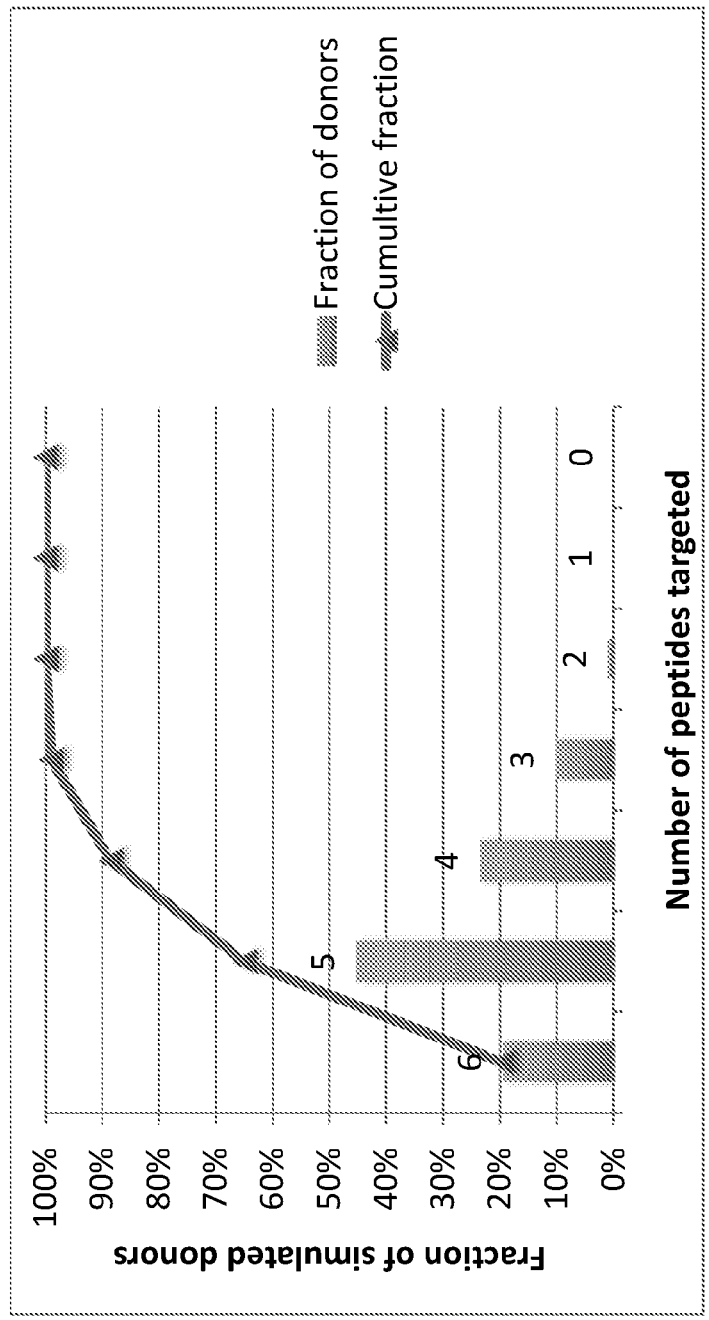

FIG. 10a: Shows predicted valence visualized in a diagram for peptide combination 2610 showing how large a fraction of the in silico donors have one or more HLAs that is predicted to bind to 0, 1, 2, 3, 4, 5 and 6 peptides in the mix. Also the cumulative curve is visualized.

Figure 10B:
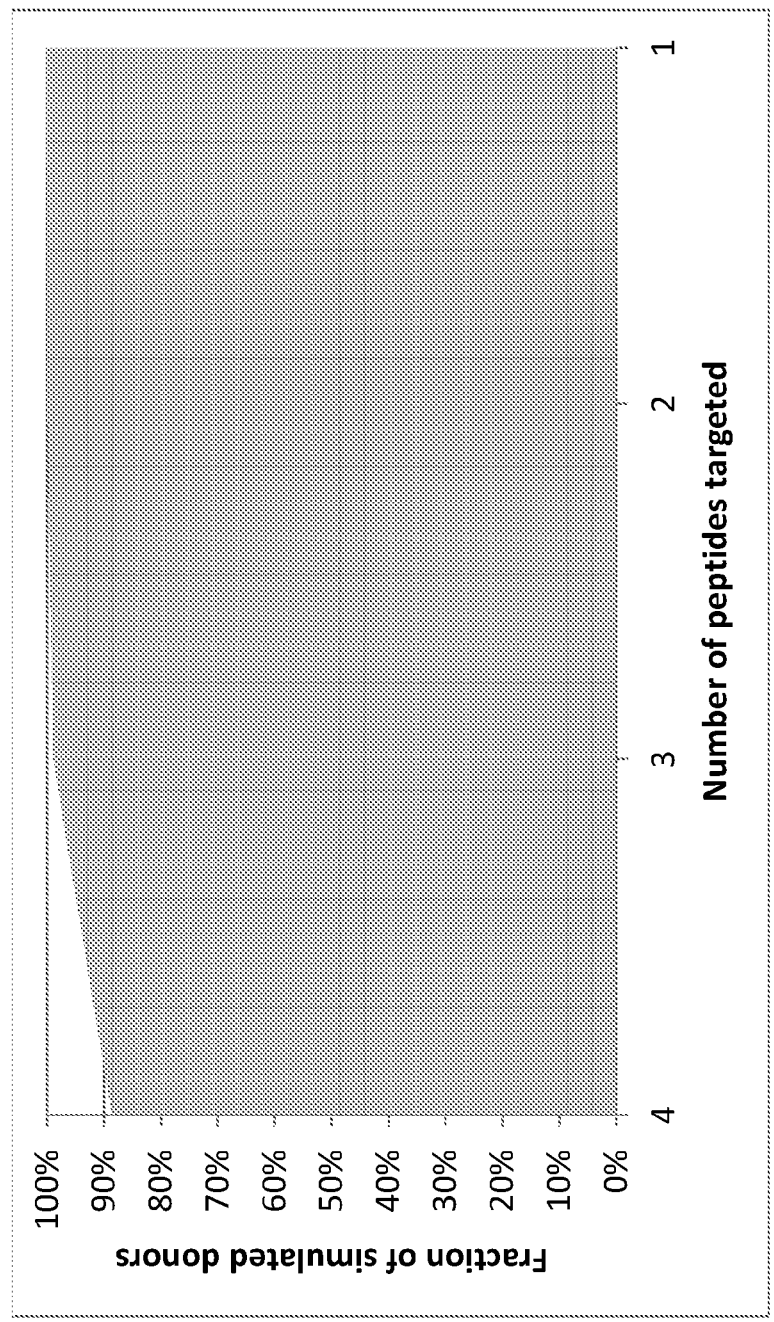

FIG. 10b: Shows predicted valence expressed as Area Under the Curve (AUC) for peptide combination 2610. The part of the cumulative curve of FIG. 10a between 4 and 1 peptides were evaluated and the area under this curve was then defined as the predicted valence AUC.

Figure 11:
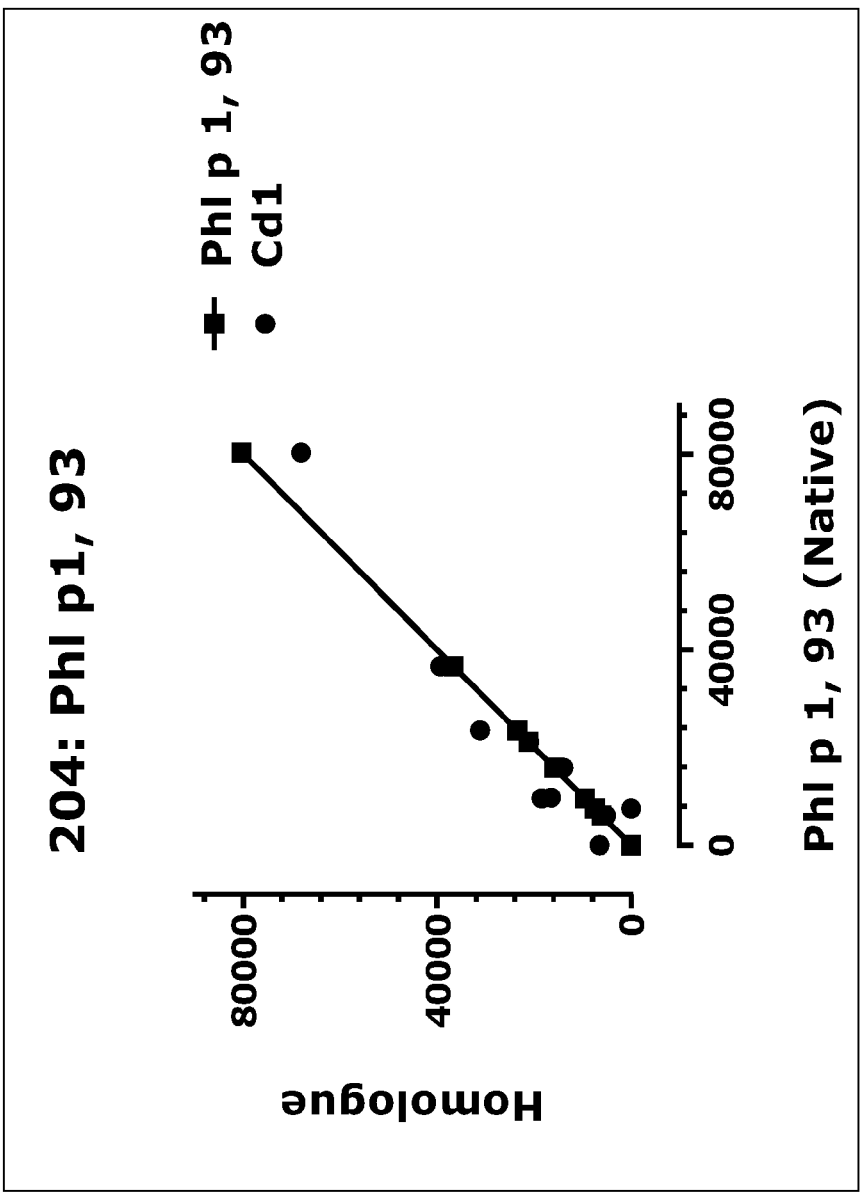

FIG. 11: Cross reactivity of peptide 204 as described in Example 9.

Figure 12:
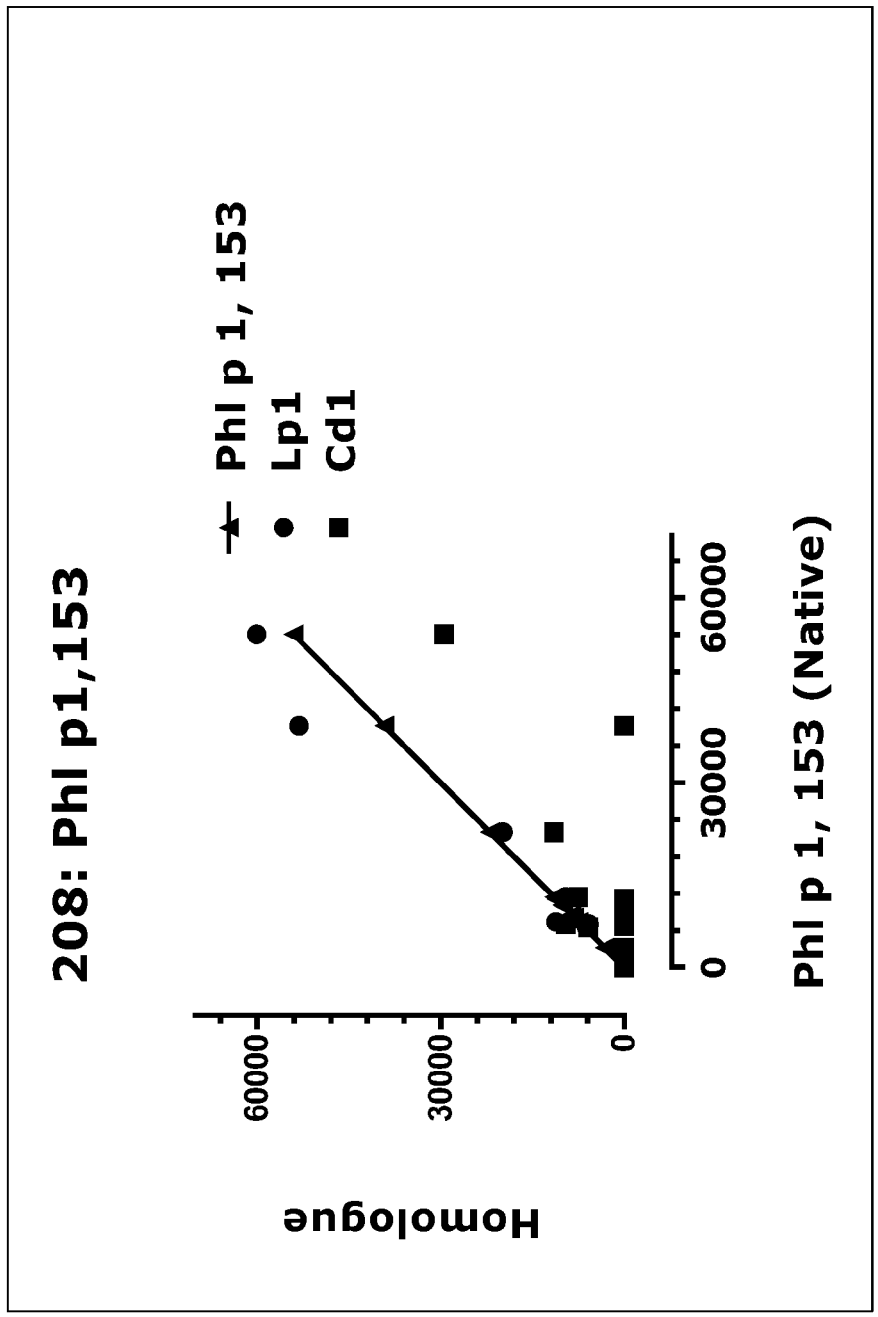

FIG. 12: Cross reactivity of peptide 208 as described in Example 9.

Figure 13:
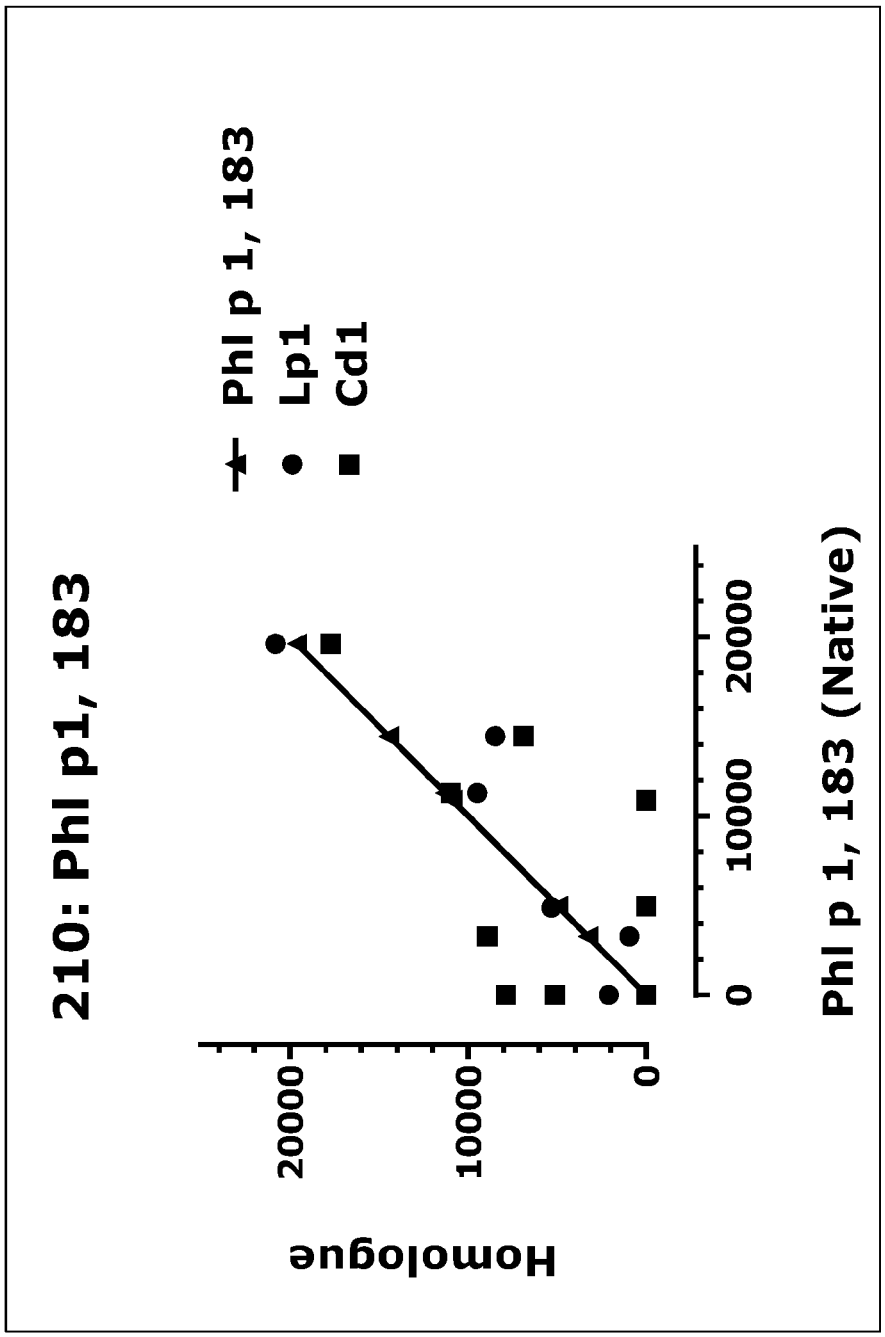

FIG. 13: Cross reactivity of peptide 210 as described in Example 9.

Figure 14:
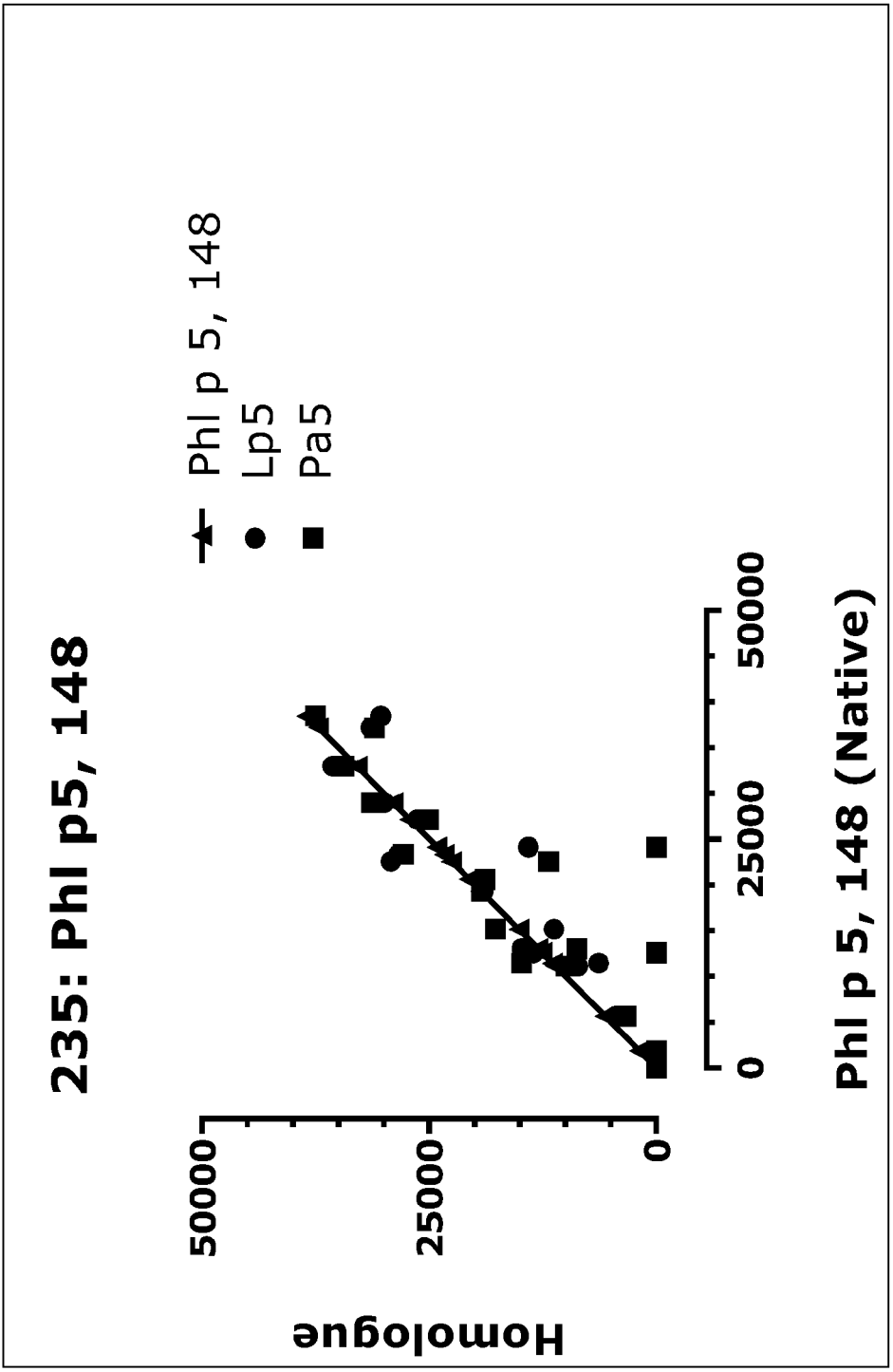

FIG. 14: Cross reactivity of peptide 235 as described in Example 9.

Figure 15:
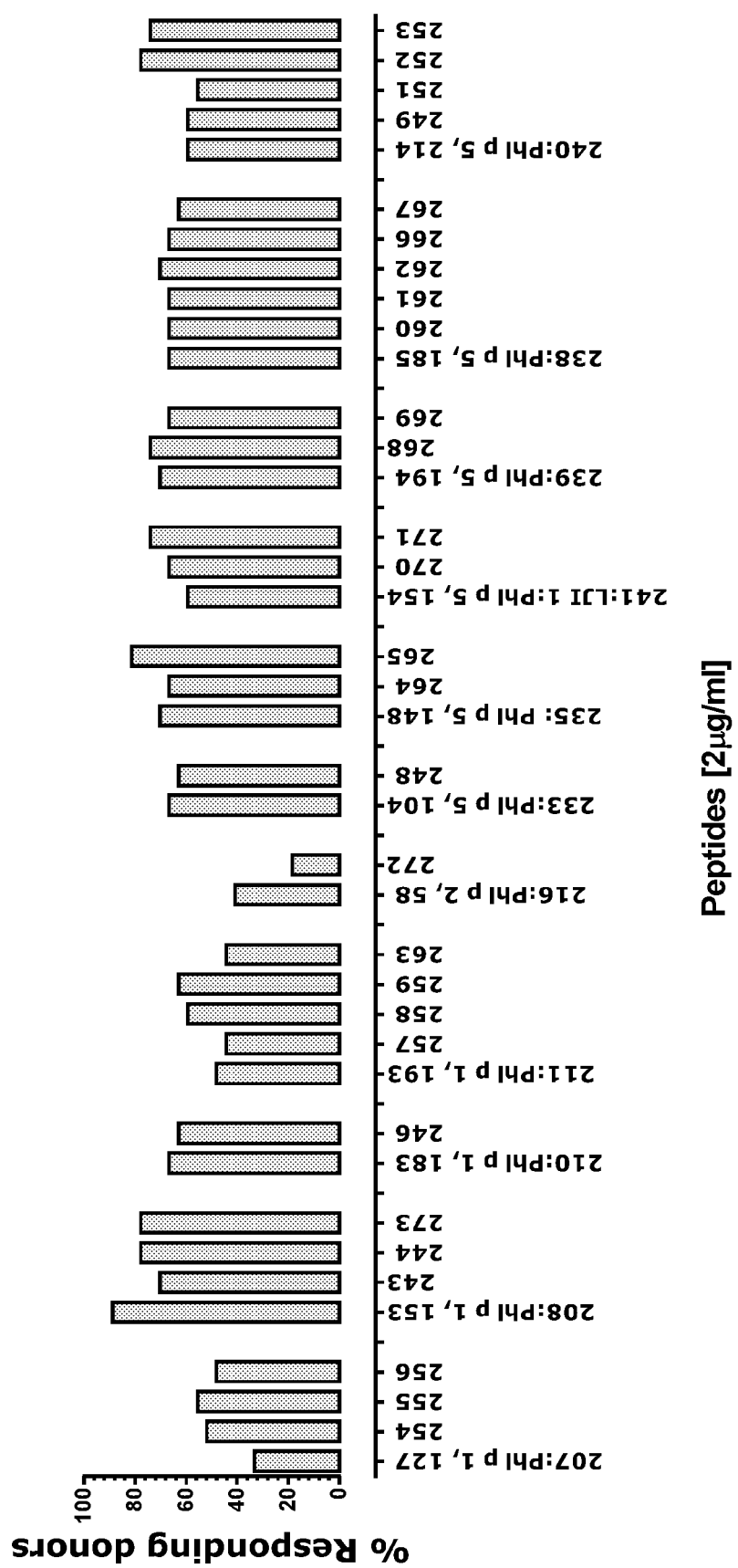

FIG. 15: T cell reactivity towards modified peptides. The figure depicts the % of donors responding to the individual modified peptides and their parent peptides. The data have been grouped according to allergen group and amino acid number of the parent peptide. The characteristics of the individual peptides are listed in Table 34. On the X-axis, modified peptides are denoted by their peptide name listed in Table 34.

Figure 16:
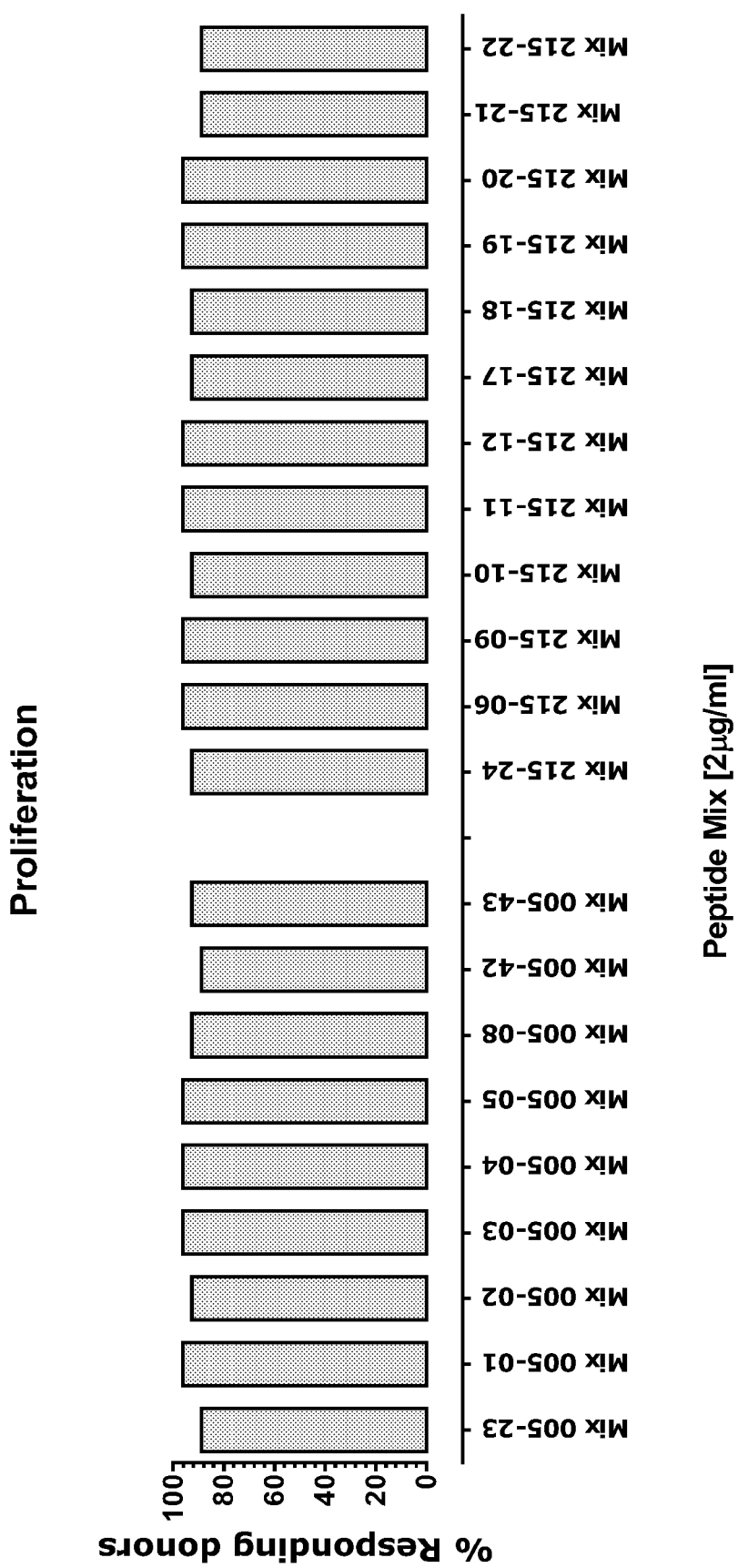

FIG. 16: T cell reactivity of some peptide combinations in which one or more parent peptides have been replaced with modified versions of the parent peptide (variants). The figure depicts the % of donors responding to the individual peptide combinations not containing modified peptides (mix 005-23 and mix 215-24) and the peptide combinations where one or more peptides have been replaced by modified forms of the same peptides (variants). The parent peptide(s) which have been replaced and the modified peptide(s) which they were replaced with can be found in Examples 15-17, see for example Table 37.

Figure 17:
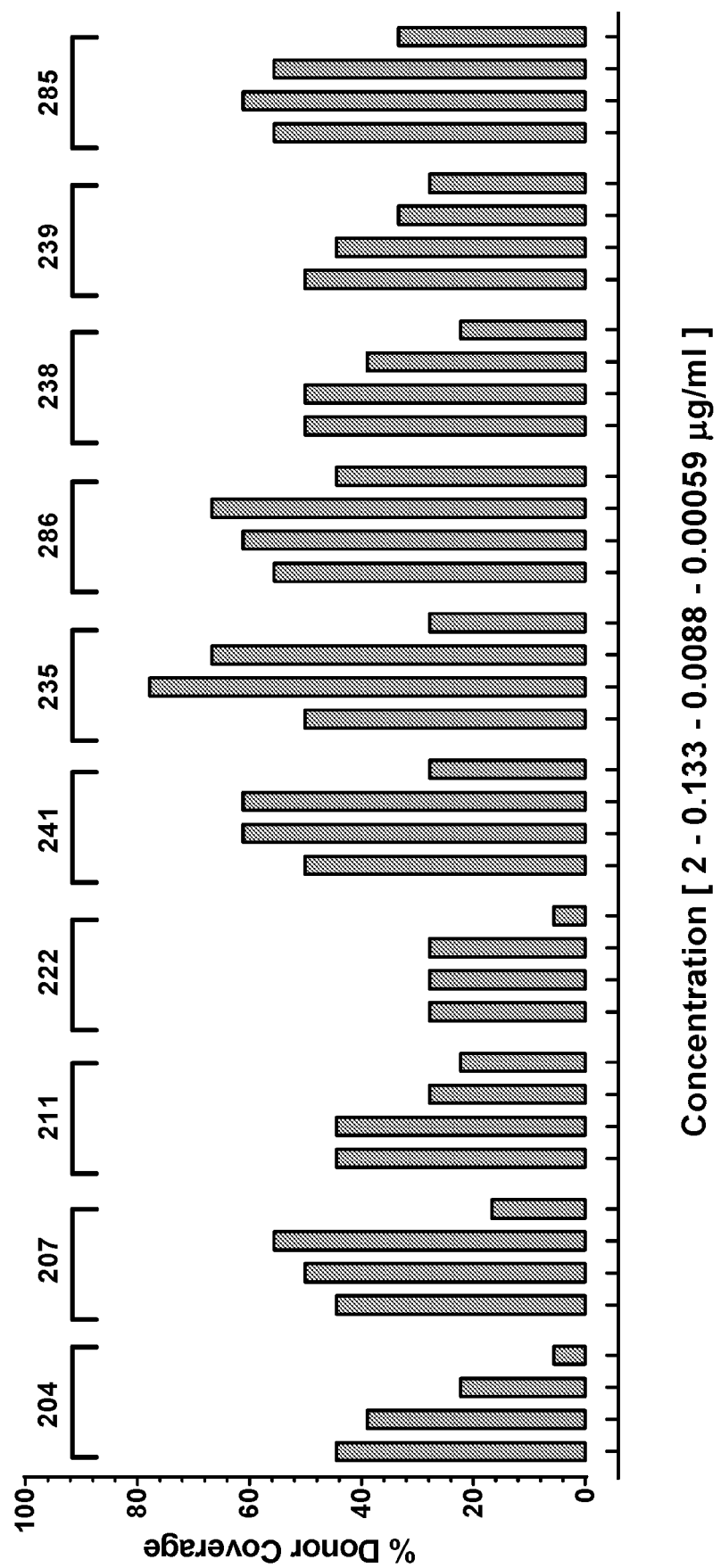

FIG. 17: Dose response data of selected single peptides including peptides 207, 238, 239 and 241. For each peptide name written on top the figure, the ticks on the x-axis correspond to concentrations 2, 0.133, 0.0088 and 0.00059 µg/ml, respectively. The dose response is shown as the percentage of donor coverage (i.e. the percentage of responding donors) as measured in T cell proliferation assays.

Figure 18:
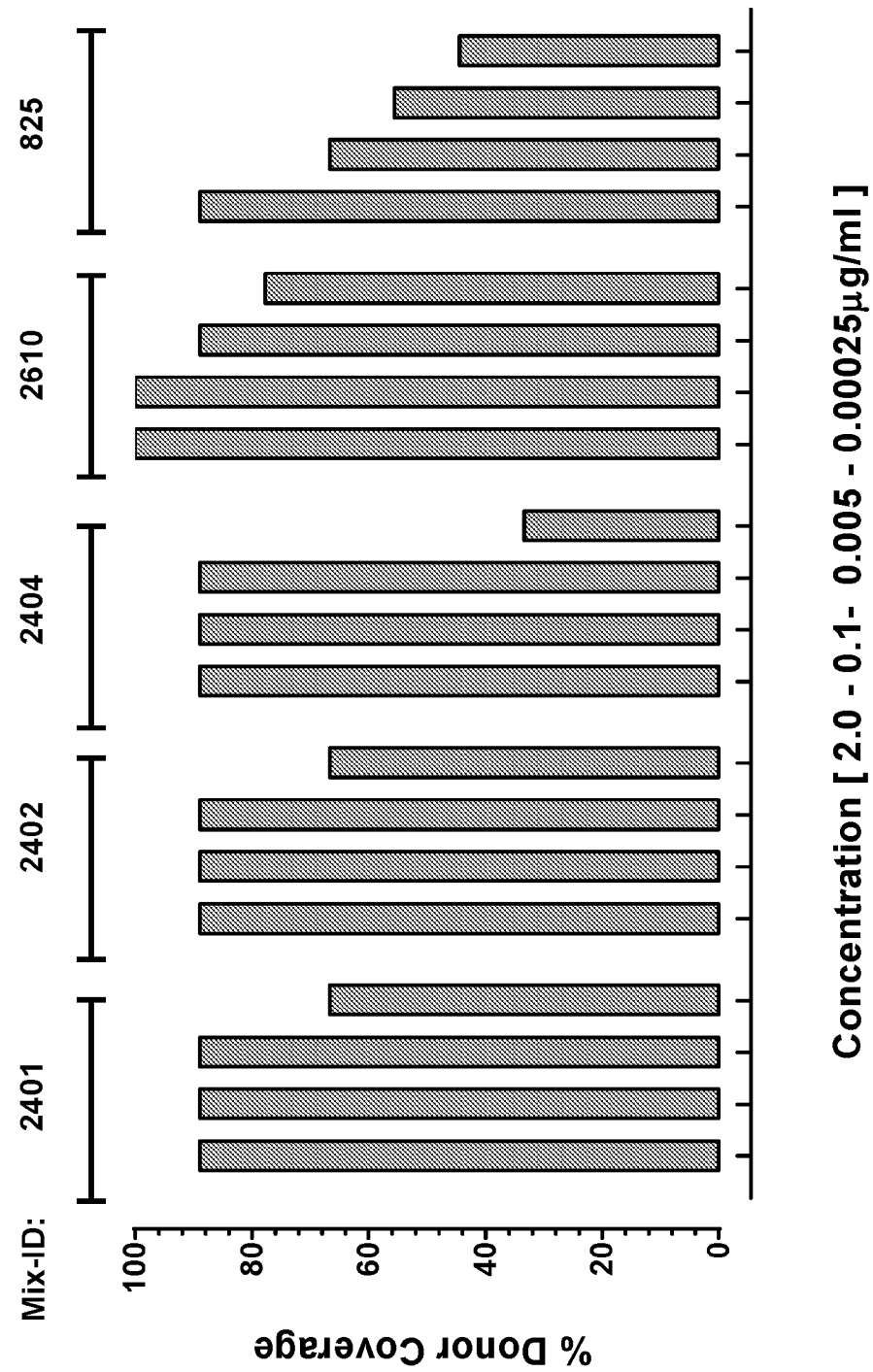

FIG. 18: Dose response data of selected peptide mixes comprising peptides of peptide names 207, 238, 239 and 241. For each peptide mix written on top the figure, the ticks on the x-axis correspond to concentrations 2, 0.1, 0.005 and 0.00025 µg/ml, respectively. The dose response is shown as the percentage of donor coverage (i.e. the percentage of responding donors) as measured in T cell proliferation assays.

Figure 19:
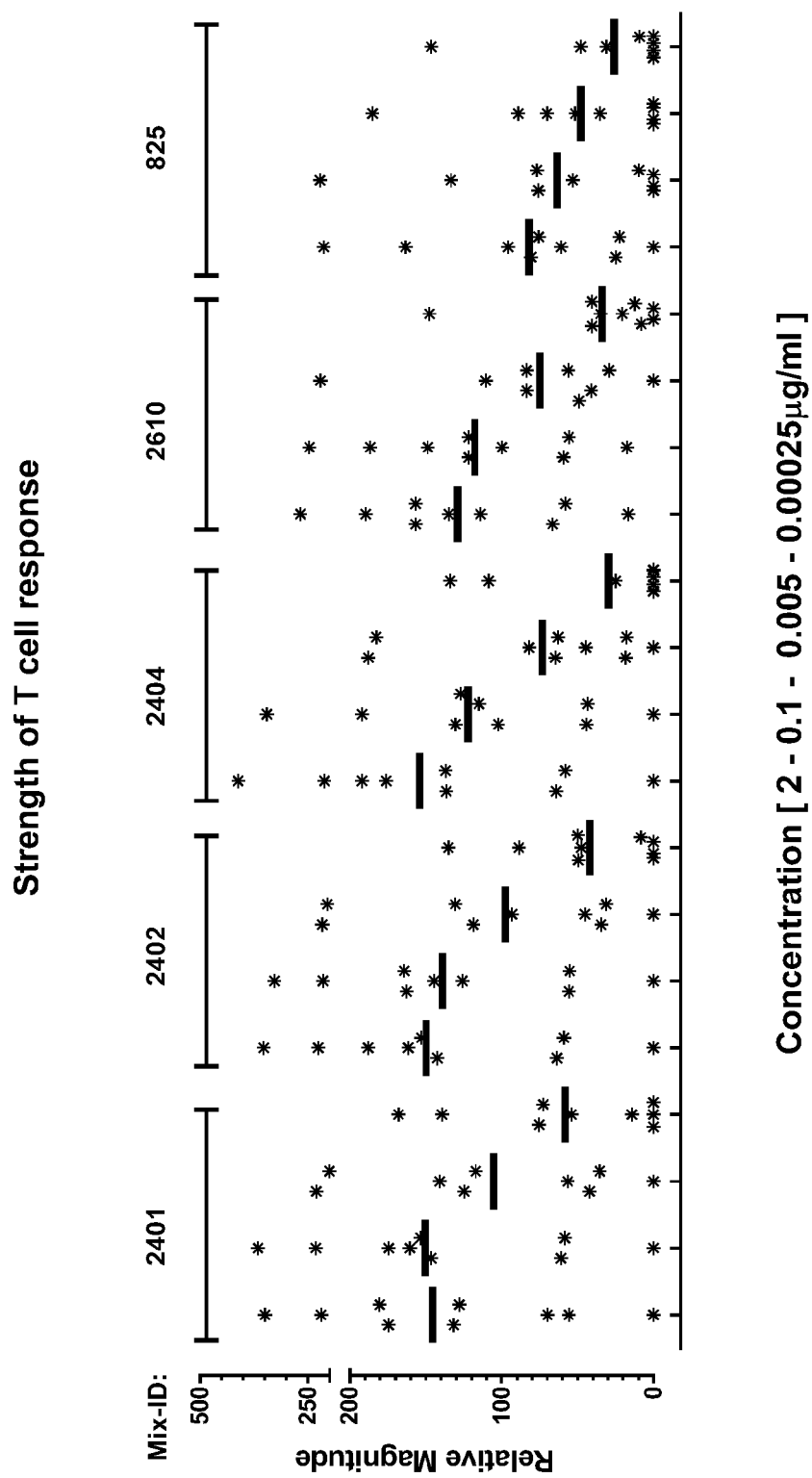

FIG. 19: Dose response data on selected peptide mixes shown as the relative magnitude of the T cell response for individual donors. The data correspond to the data presented in FIG. 18. The relative magnitude of the T cell response measured in proliferation studies as compared to the magnitude of the response to Phl p 1 or Phl p 5 is shown in asterisks. The average relative magnitude calculated for all donors is shown in horizontal black bars. For each peptide name written on top the figure, the ticks on the x-axis correspond to concentrations 2, 0.1, 0.005 and 0.00025 µg/ml, respectively.

Figure 20:
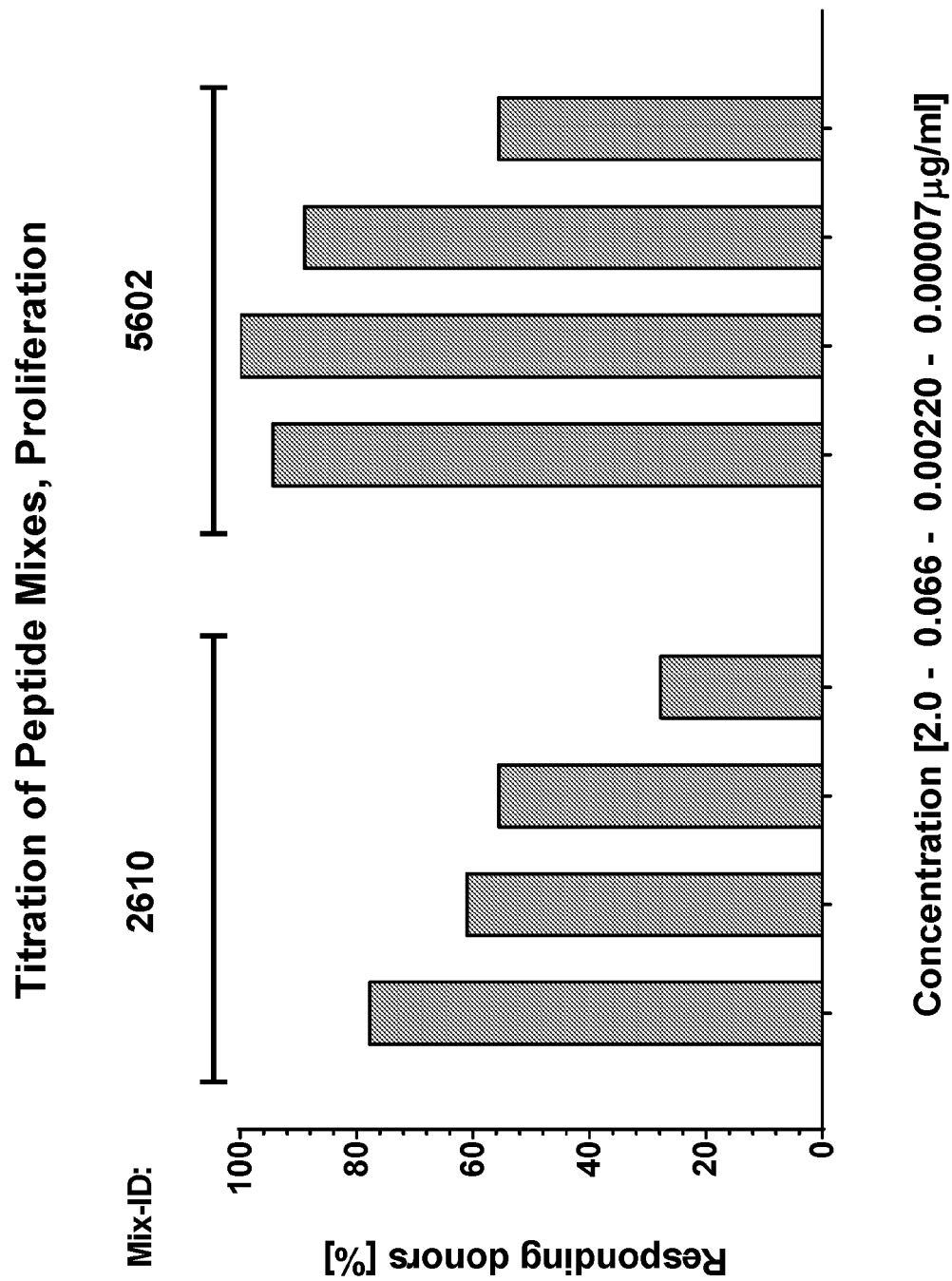

FIG. 20: Dose response data on selected peptide mixes 2610 and 5610 (each comprising peptides 207, 238, 239 and 241). The dose response data are shown as percentage of responding donors (i.e. the donor coverage) based on the T cell response for individual donors as measured in a proliferation study. For each peptide name written on top the figure, the ticks on the x-axis correspond to concentrations 2, 0.066, 0.00220 and 0.00007 µg/ml, respectively.

Figure 21:
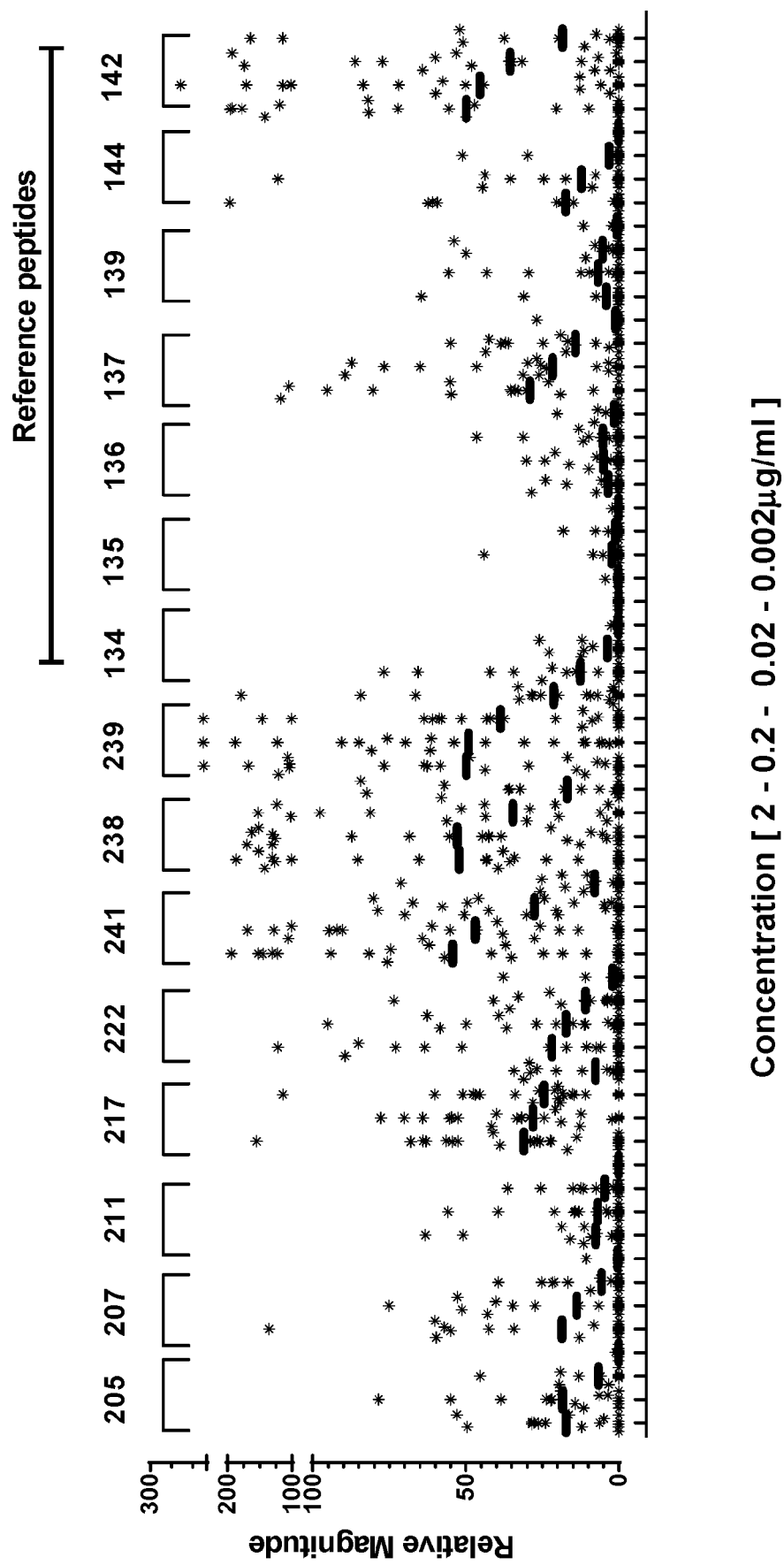

FIG. 21: Dose response data on selected peptides shown as the relative magnitude of the T cell response for individual donors. The data correspond to the data presented in FIG. 9. The relative magnitude of the T cell response measured in proliferation studies is shown in asterisks. The average relative magnitude calculated for all donors is shown in horizontal black bars. For each peptide name written on top the figure, the ticks on the x-axis correspond to concentrations 2, 0.2, 0.02 and 0.002 µg/ml, respectively.

DETAILED DISCLOSURE OF THE INVENTION

Definitions

The term "peptide" as used herein denotes an individual (e.g. isolated) amino acid molecule having a sequence length of about 12 to 30 amino acid residues. It may be even as short as 9 amino acids and also somewhat longer than 30 amino acids. In a preferred embodiment, a peptide has a sequence length of about 12 to 30 amino acids. A peptide as referred to herein may be a linear peptide. A peptide as used herein may be a parent peptide or a variant thereof and for example salts of these.

The term "parent peptide" as used herein denotes an individually identified peptide, with a region containing at least one T cell epitope that herein is found to elicit an in-vitro T cell response in a high fraction of the donor population and to have broad HLA Class II coverage.

For example, the individual peptides having an amino acid sequence of SEQ ID NO: 64 (231), SEQ ID NO: 73 (240), SEQ ID NO: 233 (286), SEQ ID NO: 232 (285), SEQ ID NO: 66 (233), SEQ ID NO: 61 (228), SEQ ID NO: 62 (229), SEQ ID NO: 63 (230), SEQ ID NO: 65 (232), SEQ ID NO: 67 (234), SEQ ID NO: 70 (237), SEQ ID NO: 7 (207), SEQ ID NO: 8 (208), SEQ ID NO: 11 (211), SEQ ID NO: 1 (201), SEQ ID NO: 3 (203), SEQ ID NO: 4 (204), SEQ ID NO: 5 (205), SEQ ID NO: 9 (209), SEQ ID NO: 10 (210), SEQ ID NO: 12 (212), SEQ ID NO: 13 (213), SEQ ID NO: 28 (215), SEQ ID NO: 29 (216), SEQ ID NO: 36 (217), SEQ ID NO: 38 (219), SEQ ID NO: 39 (220), SEQ ID NO: 40 (221), SEQ ID NO: 45 (222), SEQ ID NO: 46 (223), SEQ ID NO: 47 (224), SEQ ID NO: 48 (225), SEQ ID NO: 49 (226), and SEQ ID NO: 50 (227), are considered parent peptides. As shown herein, an individual peptide derived from the same region of the allergen as the parent peptide and which overlaps with at least 11 contiguous amino acid residues of the parent peptide is expected to produce a T cell response in a high fraction of the same donors as the parent peptide.

In one embodiment of the invention parent peptides are selected from the group of peptides having the sequences of SEQ ID NOs: 1 to 200, 202-203, 205, 208, 211, 224, 229-308, 310, 312, 314, 320, 323-325.

In another embodiment of the invention parent peptides are selected from the group of peptides having the sequences of SEQ ID NOs: 1 to 200.

In one embodiment of the invention, parent peptides are selected from the group of peptides having the amino acid sequences of SEQ ID NOs: 4, 5, 6, 7, 11, 36, 45, 69, 71, 72, 113 and 232.

In one embodiment of the invention, parent peptides are selected from the group of peptides having the amino acid sequences of SEQ ID NOs: 4, 5, 6, 7, 11, 36, 45, 69, 71, 72 and 113.

In one embodiment of the invention parent peptides are selected from the group of peptides having the sequences of SEQ ID NOs: 4, 7, 45, 71, 72 and 113.

In one embodiment of the invention parent peptides are selected from the group of peptides having the sequences of SEQ ID NOs: 11, 7, 45, 71, 72 and 113.

In one embodiment of the invention parent peptides are selected from the group of peptides having the sequences of SEQ ID NOs: 7, 71, 72 and 113.

Thus, the term "a group of peptides" or "peptide group" is meant to denote a collection of individual peptides derived from the same region of an allergen and which have at least about 11-13 contiguous amino acids overlapping with the amino acid sequence of a parent peptide defined herein, optionally with 1, 2, or 3 modifications (e.g. substitutions or deletions of amino acid residues within the 11-13 contiguous amino acids—such as the serine for cysteine substitution). A group of peptides therefore contains one or more parent peptides defined herein and modifications (or variants) of said parent peptides. Example 1 contains examples of parent peptides and Example 14 contains examples of modifications (or variants) of some parent peptides of the invention.

As used herein an "epitope" refers to a region or part of an antigen, such as a peptide disclosed herein, that elicits an immune response when administered to a subject. An epitope may be a T cell epitope, i.e., an epitope that elicits, stimulates, induces, promotes, increases or enhances a T cell activity, function or response. For example a Th2 cell epitope. Any peptide or combination of peptides of interest can be analyzed to determine whether they include at least one T cell epitope using any number of assays (e.g. T cell proliferation assays, lymphokine secretion assays, T cell non-responsiveness studies, etc.).

The term "allergen" refers to an antigen which elicits, induces, stimulates, or enhances an immune response by a cell of the immune system of an exposed animal (e.g., human). An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in predisposed subjects. An allergen is an allergenic protein.

A "region" of an allergen is to be understood as a stretch of contiguous amino acids in the allergen. When one peptide is derived from the same region of an allergen as another peptide, it is to be understood as both peptides aligning to the same region of that allergen.

If no other meaning is given specifically the term "T cell response" refers to an interleukine or a proliferation response by a T cell. It may be determined as explained in Example 3. It may in some instances be referred to simply as a "response" to a peptide.

The term "allergic response" is intended to refer to the hypersensitive immune reaction to a normally inocuous environmental substance known as an allergen. The most common mechanism of allergic reactions is the binding of IgE to the surface of mast cells, which causes asthma, hay fever and other common allergic reactions The term "subject" or "individual" is intended to refer to a mammal, in particular to a human being or a person, but the individual may also be an animal, such as a cat, dog, horse.

The term "cross reactive" or "cross reactivity" is in general the ability of a T cell receptor (of an individual) to recognize different antigenic (poly-)peptides. Herein the cross reactivity is focused on the ability of a T cell line to respond to a peptide of an allergen which is considered to be a homologue to an allergen used to establish the given T cell line. Specifically, T cell lines established on *Phleum pratense* allergens are used to test peptides derived from allergens of other grasses considered to be homologues of the *Phleum pratense* allergens. A peptide eliciting a T cell response in such a T cell line is considered to cross react with a peptide of *Phleum pratense*. The term "donor coverage" is to be understood as the percentage of donors in a donor population which respond to a given peptide or peptide combination such as determined in Examples 3 and 7. Herein the donor population is preferably one which represents a worldwide donor population, but it could also be a subgroup.

The human leukocyte antigen (HLA) system is the locus of genes that encode for proteins on the cell surface that present the antigen to T cells and are termed as MHC (Major histocompatibility complex) at protein level. The HLA term has been commonly used in the patent which should in general be understood as MHC class II molecules.

HLA alleles are referred to herein using mostly a simpler notation, such as DRB1_0101 or DPA10102-DPB10101, respectively instead of the official HLA nomenclature, as presented at the web site "HLA Nomenclature"<url:http://hla.alleles.org/>. The amino acid sequence of an expressed HLA allele can be identified as HLA-X*YY:ZZ where X denotes a specific locus, e.g. the DRB1 locus. YY is a two digit number referring to the allele group, formerly defined by the serotype. ZZ is a two or three digit number (herein always two digits) defining the specific HLA protein. Thus a specific beta chain may be referred to as e.g., HLA-DRB1*01:01, and a specific alpha-beta chain pair may be denoted as HLA-DPA1*02:01-HLA-DPB1*01:01. In the terminology used herein, that same specific alpha-beta chain pair may alternatively be denoted as HLA-DPA10201-HLA-DPB10101.

"Donor response valency (or valence)" is a calculation of the average number of peptides in a peptide combination that a subject is able to respond to. The donor response valency is calculated from experimental single peptide T cell reactivity in a donor cohort having an HLA repertoire representing the population group to be targeted. Herein, it is calculated as described in Example 12 or Example 24.

"Predicted peptide binding valency (or valence)" is a calculation of the average number of peptides in a peptide combination that a subject will be able to bind. The predicted peptide binding valency is calculated from predicted binding data from a virtual cohort having an HLA repertoire representing the population group to be targeted. Herein it is calculated as described in Example 12 or Example 24.

"Relative donor response valency (or valence)" or "relative predicted peptide binding valency (or valence)" for a peptide in a peptide combination is to be understood as a valency divided by the total number of peptides in a peptide combination. Such relative valencies will be higher if all or most peptides included in the peptide combination have higher donor coverage than if some of the peptides included do not contribute much donor coverage in the donor population. A high relative valency reflects high efficiency in the final product.

"pI" refers to the isoelectric point of a peptide or of a polypeptide. It may be calculated theoretically using programmes readily available on the internet or it may be determined experimentally according to known methods. Herein the pI's used are theoretically determined unless it is mentioned to be experimentally determined.

The "pI range of the peptides of the composition" refers to the the span between the highest and the lowest pI of all peptides of a composition (peptide combination).

Composition Comprising Peptides of the Invention

In an embodiment disclosed herein, the inventors of the present invention have found that a peptide composition comprising at least four peptides to produce a T cell response in a surprisingly high fraction of grass pollen allergic donors selected to represent a diverse set of HLA class II molecules (see Example 24). In a further embodiment disclosed herein, at the same time, peptides of the compositions of the present invention are found to be soluble in various buffers at different pH (see Example 18). In a further embodiment disclosed herein, the inventors have found that the same mixes have surprisingly high cross-reactivity to homologue peptides derived from allergens in other grass species (see Example 21). Finally, in yet a further embodiment disclosed herein, the inventors have found that mixes of the present invention are able to provide a surprisingly high T cell reactivity of PBMCs derived from donors allergic to grass pollen even in low concentrations (see Example 23). The inventors have further found that a number of peptides of the present invention result in a high yield and purity when produced using a standard peptide synthesis set-up (see Example 19). At the same time, the inventors have found that a number of peptides of the present invention have a surprisingly favourable stability when incubated with human serum (see Example 20).

The following embodiments describe the compositions of the invention:

Embodiment 1. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof;
or wherein one or more of said respective first, second, third and fourth peptide(s) independently are selected from the group consisting of peptides a) to e):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence SEQ ID NO: 69 (236), or a variant thereof;
d) a peptide having the amino acid sequence SEQ ID NO: 36 (217), or a variant thereof; and
e) a peptide having the amino acid sequence of SEQ ID NO: 232 (285), or a variant thereof;
with the proviso that the group consisting of the first through fourth peptides does not comprise more than one peptide of each of the peptides a) to d), and does not comprise more than two peptides of peptides e).

Embodiment 2. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof;
or wherein one or more of said first, second, third and fourth peptide(s) independently are selected from the group consisting of peptides a) to e):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence SEQ ID NO: 69 (236), or a variant thereof;
d) a peptide having the amino acid sequence SEQ ID NO: 36 (217), or a variant thereof; and
e) a peptide having the amino acid sequence of SEQ ID NO: 232 (285), or a variant thereof;
with the proviso that the group consisting of the first through fourth peptides does not comprise more than one peptide of each of the peptides a) to d), and does not comprise more than two peptides of peptides e),
and wherein a variant of any one of said respective first, second, third, fourth peptide and peptides a) to e) is selected from the group consisting of:
I) a peptide consisting of 20 amino acid residues in length having at least 80% sequence identity over at least 14 contiguous amino acid residues with the sequence of any one of said respective said first, second, third peptide and peptides a) to e);
II) a peptide consisting of 15 amino acid residues in length having at least 80% sequence identity over at least 14 contiguous amino acid residues with any one of the sequence of said fourth peptide of SEQ ID NO:113;
III) a longer peptide of up to 30 amino acid residues in length and having at least 80% sequence identity over at least 14 contiguous amino acids with the sequence of any one of said respective first, second, third peptide and peptides a) to e);
IV) a shorter peptide consisting of 13 to 14 amino acids and having at least 80%, sequence identity over at least 13 contiguous amino acids with the sequence of said fourth peptide of SEQ ID NO:113;
V) a shorter peptide consisting of consisting of 15 to 19 amino acids and having at least 80% sequence identity over at least 14 contiguous amino acids of any one of said respective first, second, third peptide and peptides a) to e).

Embodiment 3. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof;
or wherein one or more of said first, second, third and fourth peptide(s) independently are selected from the group consisting of peptides a):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence SEQ ID NO: 69 (236), or a variant thereof;
d) a peptide having the amino acid sequence SEQ ID NO: 36 (217), or a variant thereof; and e) a peptide having the amino acid sequence of SEQ ID NO: 232 (285), or a variant thereof;

with the proviso that the group consisting of the first through fourth peptides does not comprise more than one peptide of each of the peptides a) to d), and does not comprise more than two peptides of peptides e), and wherein a variant of any one of said first, second, third, fourth peptide and peptides a) to e) is selected from the group consisting of:

I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues of the sequence of any one of said respective first, second and third peptide and peptides a) to e);

II) a peptide consisting of 15 amino acid residues in length having at least 80%, such as 85%, 90%, 95%, 97%, 98% or 99% sequence identity over at least 14, such as 15 contiguous amino acid residues of the sequence of said fourth peptide having the amino acid sequence of SEQ ID NO:113;

III) a peptide consisting of 20 amino acid residues in length and comprising a fragment of at least 14, such as 15, such as 16, such as 17, such as 18, such as 19, such as 20 contiguous amino acids derived from any one of said respective first, second and third peptide and peptides a) to e) with 1, 2 or 3 amino acid substitutions;

IV) a peptide consisting of 15 amino acid residues in length and comprising a fragment of at least 14, such as 15 contiguous amino acids derived from said fourth peptide having the amino acid sequence of SEQ ID NO:113 with 1, 2 or 3 amino acid substitutions;

V) a longer peptide of up to 30, such as 20 to 25, or such as 26 to 30 amino acid residues in length comprising the amino acid sequence of any one of said respective first, second and third peptide and peptides a) to e);

VI) a longer peptide of up to 30, such as 16 to 20, or such as 21 to 30 amino acid residues in length comprising the amino acid sequence of said fourth peptide having the amino acid sequence of SEQ ID NO:113;

VII) a longer peptide of up to 30, such as 20 to 25, or such as 26 to 30 amino acid residues in length comprising at least 14, such as at least 15 contiguous amino acid residues of the sequence of any one of said respective first, second and third peptide and peptides a) to e);

VIII) a longer peptide of up to 30, such as 16 to 20, or such as 21 to 25, or such as 26 to 30 amino acid residues in length comprising at least 14, such as at least 15 contiguous amino acid residues of the amino acid sequence of said fourth peptide having the amino acid sequence of SEQ ID NO:113;

IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids of any one of said respective first, second and third peptide and peptides a) to e);

X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15, contiguous amino acids of said fourth peptide having the amino acid sequence of SEQ ID NO:113;

XI) a longer peptide of up to 30, such as 20 to 25, or such as 26 to 30 amino acid residues in length; said longer peptide comprising a fragment of 14, or 15 contiguous amino acids derived from of any one of said respective first, second and third peptide and peptides a) to e) with 1, 2 or 3 amino acid substitutions;

XII) a longer peptide of up to 30, such as 16 to 20, such as 21 to 25, or such as 26 to 30 amino acid residues in length; said longer peptide comprising a fragment of 14, or 15 contiguous amino acids derived from said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence having the amino acid sequence of SEQ ID NO:113, XIV) a shorter peptide consisting of 15 to 19 contiguous amino acids of the sequence of any one of said respective first, second and third peptide and peptides a) to e);

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids of said fourth peptide having the amino acid sequence having the amino acid sequence of SEQ ID NO:113;

XVI) a shorter peptide consisting of consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second and third peptide and peptides a) to e);

XVII) a shorter peptide consisting of 13 to 14 amino acid residues derived from 13 to 14 contiguous amino acids of the sequence of said fourth peptide of SEQ ID NO:113 with 1, 2, or 3 amino acid substitutions, XVIII) a shorter peptide consisting of 15 to 19 amino acids derived from 15 to 19 contiguous amino acids of the sequence of any one of said first, second, third peptide and peptides a) to e) with 1, 2, or 3 amino acid substitutions.

Embodiment 4. A composition comprising four peptides of non-identical amino acid sequences, said composition comprising:

1) a first peptide having the amino acid sequence of SEQ ID NO: 7 (207);
2) a second peptide having the amino acid sequence of SEQ ID NO: 71 (238);
3) a third peptide having the amino acid sequence of SEQ ID NO: 72 (239); and
4) a fourth peptide having the amino acid sequence of SEQ ID NO: 113 (241);

or wherein one or more of said first, second, third and fourth peptide(s) independently are selected from the group consisting of peptides a) to e):

a) a peptide having the amino acid sequence of SEQ ID NO: 5 (205);
b) a peptide having the amino acid sequence of SEQ ID NO: 6 (206);
c) a peptide having the amino acid sequence SEQ ID NO: 69 (236);
d) a peptide having the amino acid sequence SEQ ID NO: 36 (217); and
e) a peptide having the amino acid sequence of SEQ ID NO: 232 (285);

with the proviso that the group consisting of the first through fourth peptides does not comprise more than one peptide of each of the peptides a) to e.

Embodiment 5. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof.

Embodiment 6. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof; and
wherein a variant of any one of said first, second, third and fourth peptides is selected from the group consisting of:
I) a peptide consisting of 20 amino acid residues in length having at least 80% sequence identity over at least 14 contiguous amino acid residues with the sequence of any one of said respective first, second and third peptide;
II) a peptide consisting of 15 amino acid residues in length having at least 80% sequence identity over at least 14 contiguous amino acid residues with the sequence of said fourth peptide of SEQ ID NO:113;
III) a longer peptide of up to 30 amino acid residues in length and having at least 80% sequence identity over at least 14 contiguous amino acids with the sequence of any one of said respective first, second and third peptide;
IV) a shorter peptide consisting of 13 to 14 amino acids and having at least 80%, sequence identity over at least 13 contiguous amino acids with the sequence of said fourth peptide of SEQ ID NO:113;
V) a shorter peptide consisting of consisting of 15 to 19 amino acids and having at least 80% sequence identity over at least 14 contiguous amino acids with the sequence of any one of said respective first, second and third peptide.

Embodiment 7. A composition comprising four peptides of non-identical amino acid sequences, said composition comprising:
1) a first peptide having the amino acid sequence of SEQ ID NO: 7 (207), or a variant thereof;
2) a second peptide having the amino acid sequence of SEQ ID NO: 71 (238), or a variant thereof;
3) a third peptide having the amino acid sequence of SEQ ID NO: 72 (239), or a variant thereof; and
4) a fourth peptide having the amino acid sequence of SEQ ID NO: 113 (241), or a variant thereof; and
wherein a variant of any one of said first, second, third and fourth peptides is selected from the group consisting of:
I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues of the sequence of any one of said respective first, second and third peptide;
II) a peptide consisting of 15 amino acid residues in length having at least 80%, such as 85%, 90%, 95%, 97%, 98% or 99% sequence identity over at least 14, such as 15 contiguous amino acid residues of the sequence of said fourth peptide having the amino acid sequence of SEQ ID NO:113;
III) a peptide consisting of 20 amino acid residues in length and comprising a fragment of at least 14, such as 15, such as 16, such as 17, such as 18, such as 19, such as 20 contiguous amino acids derived from the sequence of any one of said respective first, second and third peptide with 1, 2 or 3 amino acid substitutions;
IV) a peptide consisting of 15 amino acid residues in length and comprising a fragment of at least 14, such as 15 contiguous amino acids derived from said fourth peptide having the amino acid sequence of SEQ ID NO:113 with 1, 2 or 3 amino acid substitutions;
V) a longer peptide of up to 30, such as 20 to 25, or such as 26 to 30 amino acid residues in length comprising the amino acid sequence of any one of said respective first, second, third and fourth peptide;
VI) a longer peptide of up to 30, such as 16 to 20, or such as 21 to 30 amino acid residues in length comprising the amino acid sequence of said fourth peptide having the amino acid sequence of SEQ ID NO:113;
VII) a longer peptide of up to 30, such as 20 to 25, or such as 26 to 30 amino acid residues in length comprising at least 14, such as at least 15 contiguous amino acid residues of the sequence of any one of said respective first, second, third and fourth peptide;
VIII) a longer peptide of up to 30, such as 16 to 20, or such as 21 to 25, or such as 26 to 30 amino acid residues in length comprising at least 14, such as at least 15 contiguous amino acid residues of the amino acid sequence of said fourth peptide having the amino acid sequence of SEQ ID NO:113;
IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of any one of said respective first, second, third and fourth peptides;
X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15 contiguous amino acids with the sequence of said fourth peptide having the amino acid sequence of SEQ ID NO:113;
XI) a longer peptide of up to 30, such as 20 to 25, or such as 26 to 30 amino acid residues in length; said longer peptide comprising a fragment of 14, or 15 contiguous amino acids derived from the sequence of any one of said respective first, second, third and fourth peptides with 1, 2 or 3 amino acid substitutions;
XII) a longer peptide of up to 30, such as 16 to 20, such as 21 to 25, or such as 26 to 30 amino acid residues in length; said longer peptide comprising a fragment of 14, or 15 contiguous amino acids derived from the sequence of said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence having the amino acid sequence of SEQ ID NO:113, XIV) a shorter peptide consisting of 15 to 19 contiguous amino acids of the sequence of any one of said respective first, second, third and fourth peptide;

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids with the sequence of said fourth peptide having the sequence of SEQ ID NO:113;

XVI) a shorter peptide consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second, third and fourth peptide;

XVII) a shorter peptide consisting of 13 to 14 amino acid residues derived from 13 to 14 contiguous amino acids of the sequence of said fourth peptide of SEQ ID NO:113 with 1, 2, or 3 amino acid substitutions, XVIII) a shorter peptide consisting of 15 to 19 amino acids derived from 15 to 19 contiguous amino acids of the sequence of any one of said respective first, second, third and fourth peptide with 1, 2, or 3 amino acid substitutions.

Embodiment 8. A composition comprising four peptides of non-identical amino acid sequences, said composition comprising:
1) a first peptide having the amino acid sequence of SEQ ID NO: 7 (207);
2) a second peptide having the amino acid sequence of SEQ ID NO: 71 (238);
3) a third peptide having the amino acid sequence of SEQ ID NO: 72 (239); and
4) a fourth peptide having the amino acid sequence of SEQ ID NO: 113 (241).

Embodiment 9. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 4 (204), or a variant thereof; and
6) a sixth peptide has the amino acid sequence of SEQ ID NO: 45 (222), or a variant thereof.

Embodiment 10. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 4 (204), or a variant thereof; and
6) a sixth peptide has the amino acid sequence of SEQ ID NO: 45 (222), or a variant thereof and wherein the variant of any one of said first, second, third, fourth, fifth and sixth peptide is selected from the group consisting of:
I) a peptide consisting of 20 amino acid residues in length having at least 80% sequence identity over at least 14 contiguous amino acid residues with the sequence of any one of said respective first, second, third, fifth and sixth peptide;
II) a peptide consisting of 15 amino acid residues in length having at least 80% sequence identity over at least 14 contiguous amino acid residues with the sequence of said fourth peptide of SEQ ID NO:113;
III) a longer peptide of up to 30 amino acid residues in length and having at least 80% sequence identity over at least 14 contiguous amino acids with the sequence of any one of said respective first, second, third, fourth, fifth and sixth peptide;
IV) a shorter peptide consisting of 13 to 14 amino acids and having at least 80%, sequence identity over at least 13 contiguous amino acids with the sequence of said fourth peptide of SEQ ID NO:113;
V) a shorter peptide consisting of consisting of 15 to 19 amino acids and having at least 80% sequence identity over at least 14 contiguous amino acids with the sequence of any one of said respective first, second, third, fifth and sixth peptides.

Embodiment 11. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 4 (204), or a variant thereof; and
6) a sixth peptide has the amino acid sequence of SEQ ID NO: 45 (222), or a variant thereof;

and wherein the variant of any one of said first, second, third, fourth, fifth and sixth peptide is selected from the group consisting of:
I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues with the sequence of any one of said respective first, second, third, fifth and sixth peptide;
II) a peptide consisting of 15 amino acid residues in length having at least 80%, such as 85%, 90%, 95%, 97%, 98% or 99% sequence identity over at least 14, such as 15 contiguous amino acid residues of the sequence with the sequence of said fourth peptide having the amino acid sequence of SEQ ID NO:113;
III) a peptide consisting of 20 amino acid residues in length and comprising a fragment of at least 14, such as 15, such as 16, such as 17, such as 18, such as 19, such as 20 contiguous amino acids derived from the sequence of any one of said first, second, third, fifth and sixth peptide with 1, 2 or 3 amino acid substitutions;

IV) a peptide consisting of 15 amino acid residues in length and comprising a fragment of at least 14, such as 15 contiguous amino acids derived from the sequence of said fourth peptide having the amino acid sequence of SEQ ID NO: 113 with 1, 2 or 3 amino acid substitutions;

V) a longer peptide of up to 30, such as 20 to 25, or such as 26 to 30 amino acid residues in length comprising the amino acid sequence of one of said respective first, second, third, fourth, fifth and sixth peptide;

VI) a longer peptide of up to 30, such as 16 to 20, or such as 21 to 30 amino acid residues in length comprising the amino acid sequence of said fourth peptide having the amino acid sequence of SEQ ID NO:113;

VII) a longer peptide of up to 30, such as 20 to 25, or such as 26 to 30 amino acid residues in length comprising at least 14, such as at least 15 contiguous amino acid residues of the sequence of any one of said respective first, second, third, fourth, fifth and sixth peptide;

VIII) a longer peptide of up to 30, such as 16 to 20, or such as 21 to 25, or such as 26 to 30 amino acid residues in length comprising at least 14, such as at least 15 contiguous amino acid residues with the amino acid sequence of said fourth peptide having the amino acid sequence of SEQ ID NO:113;

IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of any one of said respective first, second, third, fourth, fifth and sixth peptide;

X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of said fourth peptide having the amino acid sequence of SEQ ID NO:113;

XI) a longer peptide of up to 30, such as 20 to 25, or such as 26 to 30 amino acid residues in length; said longer peptide comprising a fragment of 14, or 15 contiguous amino acids derived from the sequence of any one of said respective first, second, third, fourth, fifth and sixth peptide with 1, 2 or 3 amino acid substitutions;

XII) a longer peptide of up to 30, such as 16 to 20, such as 21 to 25, or such as 26 to 30 amino acid residues in length; said longer peptide comprising a fragment of 14, or 15 contiguous amino acids derived from the sequence of said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence of SEQ ID NO:113, XIV) a shorter peptide consisting of 15 to 19 contiguous amino acids of the sequence of any one of said respective first, second, third, fourth, fifth and sixth peptide;

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids with the sequence of said fourth peptide having the amino acid sequence of SEQ ID NO:113;

XVI) a shorter peptide consisting of consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second, third, fourth, fifth and sixth peptide;

XVII) a shorter peptide consisting of 13 to 14 amino acid residues derived from 13 to 14 contiguous amino acids of the sequence of said fourth peptide of SEQ ID NO:113 with 1, 2, or 3 amino acid substitutions; and XVIII) a shorter peptide consisting of 15 to 19 amino acids derived from 15 to 19 contiguous amino acids of the sequence of any one of said respective first, second, third, fourth, fifth and sixth peptides with 1, 2, or 3 amino acid substitutions.

Embodiment 12. A composition according to the present invention wherein the peptides in the composition comprise, or consist of, of six non-identical peptides, wherein
1) a first peptide has the amino acid sequence of SEQ ID NO: 7 (207);
2) a second peptide has the amino acid sequence of SEQ ID NO: 71 (238);
3) a third peptide has the amino acid sequence of SEQ ID NO:72 (239);
4) a fourth peptide has the amino acid sequence of SEQ ID NO: 113 (241);
5) a fifth peptide has the amino acid sequence of SEQ ID NO: 4 (204); and
6) a sixth peptide has the amino acid sequence of SEQ ID NO: 45 (222).

Embodiment 13. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof.

Embodiment 14. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof
and wherein the variant of any one of said first, second, third, fourth, fifth, sixth peptides is selected from the group consisting of:
I) a peptide consisting of 20 amino acid residues in length having at least 80% sequence identity over at least 14 contiguous amino acid residues with the sequence of any one of said respective first, second, third, fifth and sixth peptide;

II) a peptide consisting of 15 amino acid residues in length having at least 80% sequence identity over at least 14 contiguous amino acid residues with the sequence of said fourth peptide of SEQ ID NO:113;

III) a longer peptide of up to 30 amino acid residues in length and having at least 80% sequence identity over at least 14 contiguous amino acids with the sequence of any one of said respective first, second, third, fourth, fifth and sixth peptide;

IV) a shorter peptide consisting of 13 to 14 amino acids and having at least 80% sequence identity over at least 13 contiguous amino acids with the sequence of said fourth peptide of SEQ ID NO:113;

V) a shorter peptide consisting of consisting of 15 to 19 amino acids and having at least 80% sequence identity over at least 14 contiguous amino acids with the sequence of any one of said respective first, second, third, fifth and sixth peptides.

Embodiment 15. A composition according to the present invention wherein the peptides in the composition comprise, or consist of, of six non-identical peptides, wherein 1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof;

and wherein the variant of any one of said first, second, third, fourth, fifth and sixth peptide is selected from the group consisting of:

I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues of the sequence of any one of said respective first, second, third, fifth and sixth peptide;

II) a peptide consisting of 15 amino acid residues in length having at least 80%, such as 85%, 90%, 95%, 97%, 98% or 99% sequence identity over at least 14, such as 15 contiguous amino acid residues of the sequence of said fourth peptide having the amino acid sequence of SEQ ID NO:113;

III) a peptide consisting of 20 amino acid residues in length and comprising a fragment of at least 14, such as 15, such as 16, such as 17, such as 18, such as 19, such as 20 contiguous amino acids derived from the sequence of any one of said first, second, third, fifth and sixth peptide with 1, 2 or 3 amino acid substitutions;

IV) a peptide consisting of 15 amino acid residues in length and comprising a fragment of at least 14, such as 15 contiguous amino acids derived from said fourth peptide having the amino acid sequence of SEQ ID NO:113 with 1, 2 or 3 amino acid substitutions;

V) a longer peptide of up to 30, such as 20 to 25, or such as 26 to 30 amino acid residues in length comprising the amino acid sequence of one of said respective first, second, third, fourth, fifth and sixth peptide;

VI) a longer peptide of up to 30, such as 16 to 20, or such as 21 to 30 amino acid residues in length comprising the amino acid sequence of said fourth peptide having the amino acid sequence of SEQ ID NO:113;

VII) a longer peptide of up to 30, such as 20 to 25, or such as 26 to 30 amino acid residues in length comprising at least 14, such as at least 15 contiguous amino acid residues of the sequence of any one of said respective first, second, third, fourth, fifth and sixth peptide;

VIII) a longer peptide of up to 30, such as 16 to 20, or such as 21 to 25, or such as 26 to 30 amino acid residues in length comprising at least 14, such as at least 15 contiguous amino acid residues of the amino acid sequence of said fourth peptide having the amino acid sequence of SEQ ID NO:113;

IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of any one of said respective first, second, third, fourth, fifth and sixth peptide;

X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15, contiguous amino acids of said fourth peptide having the amino acid sequence of SEQ ID NO:113;

XI) a longer peptide of up to 30, such as 20 to 25, or such as 26 to 30 amino acid residues in length; said longer peptide comprising a fragment of 14, or 15 contiguous amino acids derived from the sequence of any one of said respective first, second, third, fourth, fifth and sixth peptide with 1, 2 or 3 amino acid substitutions;

XII) a longer peptide of up to 30, such as 16 to 20, such as 21 to 25, or such as 26 to 30 amino acid residues in length; said longer peptide comprising a fragment of 14, or 15 contiguous amino acids derived from said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence of SEQ ID NO:113, XIV) a shorter peptide consisting of 15 to 19 contiguous amino acids of the sequence of any one of said respective first, second, third, fourth, fifth and sixth peptide;

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids with the sequence of said fourth peptide having the amino acid sequence of SEQ ID NO:113;

XVI) a shorter peptide consisting of consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second, third, fourth, fifth and sixth peptide;

XVII) a shorter peptide consisting of 13 to 14 amino acid residues derived from 13 to 14 contiguous amino acids of the sequence of said fourth peptide of SEQ ID NO:113 with 1, 2, or 3 amino acid substitutions; and XVIII) a shorter peptide consisting of 15 to 19 amino acids derived from 15 to 19 contiguous amino acids of the sequence of any one of said respective first, second, third, fourth, fifth and sixth peptides with 1, 2, or 3 amino acid substitutions.

Embodiment 16. A composition according to the present invention wherein the peptides in the composition comprise, or consist of, of six non-identical peptides, wherein
1) a first peptide has the amino acid sequence of SEQ ID NO: 7 (207);
2) a second peptide has the amino acid sequence of SEQ ID NO: 71 (238);
3) a third peptide has the amino acid sequence of SEQ ID NO:72 (239);
4) a fourth peptide has the amino acid sequence of SEQ ID NO: 113 (241);
5) a fifth peptide has the amino acid sequence of SEQ ID NO: 4 (204); and
6) a sixth peptide has the amino acid sequence of SEQ ID NO: 45 (222).

Embodiment 17. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof.

Embodiment 18. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof;
and wherein the variant of any one of said respective first, second, third, fourth, fifth and sixth peptide is selected from the group consisting of:
I) a peptide consisting of 20 amino acid residues in length having at least 80% sequence identity over at least 14 contiguous amino acid residues with the sequence of any one of said respective first, second, third, fifth and sixth peptide;
II) a peptide consisting of 15 amino acid residues in length having at least 80% sequence identity over at least 14 contiguous amino acid residues with the sequence of said fourth peptide of SEQ ID NO:113;
III) a longer peptide of up to 30 amino acid residues in length and having at least 80% sequence identity over at least 14 contiguous amino acids with the sequence of any one of said respective first, second, third, fourth, fifth and sixth peptide;
IV) a shorter peptide consisting of 13 to 14 amino acids and having at least 80%, sequence identity over at least 13 contiguous amino acids with the sequence of said fourth peptide of SEQ ID NO:113;
V) a shorter peptide consisting of consisting of 15 to 19 amino acids and having at least 80% sequence identity over at least 14 contiguous amino acids with the sequence of any one of said respective first, second, third, fifth and sixth peptides.

Embodiment 19. A composition according to the present invention wherein the peptides in the composition comprise, or consist of, of six non-identical peptides, wherein
1) a first peptide has the amino acid sequence of SEQ ID NO: 7 (207), or a variant thereof;
2) a second peptide has the amino acid sequence of SEQ ID NO: 71 (238), or a variant thereof;
3) a third peptide has the amino acid sequence of SEQ ID NO:72 (239), or a variant thereof;
4) a fourth peptide has the amino acid sequence of SEQ ID NO: 113 (241), or a variant thereof;
5) a fifth peptide has the amino acid sequence of SEQ ID NO: 11 (211), or a variant thereof; and
6) a sixth peptide has the amino acid sequence of SEQ ID NO: 45 (222), or a variant thereof;
and wherein the variant of any one of said first, second, third, fourth, fifth and sixth peptide is selected from the group consisting of:
I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues of the sequence of any one of said respective first, second, third, fifth and sixth peptide;
II) a peptide consisting of 15 amino acid residues in length having at least 80%, such as 85%, 90%, 95%, 97%, 98% or 99% sequence identity over at least 14, such as 15 contiguous amino acid residues of the sequence of said fourth peptide having the amino acid sequence of SEQ ID NO:113;
III) a peptide consisting of 20 amino acid residues in length and comprising a fragment of at least 14, such as 15, such as 16, such as 17, such as 18, such as 19, such as 20 contiguous amino acids derived from the sequence of any one of said first, second, third, fifth and sixth peptide with 1, 2 or 3 amino acid substitutions;
IV) a peptide consisting of 15 amino acid residues in length and comprising a fragment of at least 14, such as 15 contiguous amino acids derived from said fourth peptide having the amino acid sequence of SEQ ID NO:113 with 1, 2 or 3 amino acid substitutions;
V) a longer peptide of up to 30, such as 20 to 25, or such as 26 to 30 amino acid residues in length comprising the amino acid sequence of one of said respective first, second, third, fourth, fifth and sixth peptide;
VI) a longer peptide of up to 30, such as 16 to 20, or such as 21 to 30 amino acid residues in length comprising the amino acid sequence of said fourth peptide having the amino acid sequence of SEQ ID NO:113;
VII) a longer peptide of up to 30, such as 20 to 25, or such as 26 to 30 amino acid residues in length comprising at least 14, such as at least 15 contiguous amino acid residues of the sequence of any one of said respective first, second, third, fourth, fifth and sixth peptide;
VIII) a longer peptide of up to 30, such as 16 to 20, or such as 21 to 25, or such as 26 to 30 amino acid residues in length comprising at least 14, such as at least 15 contiguous amino acid residues of the amino acid sequence of said fourth peptide having the amino acid sequence of SEQ ID NO:113;

IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of any one of said respective first, second, third, fourth, fifth and sixth peptide;

X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15, contiguous amino acids of said fourth peptide having the amino acid sequence of SEQ ID NO:113;

XI) a longer peptide of up to 30, such as 20 to 25, or such as 26 to 30 amino acid residues in length; said longer peptide comprising a fragment of 14, or 15 contiguous amino acids derived from the sequence of any one of said respective first, second, third, fourth, fifth and sixth peptide with 1, 2 or 3 amino acid substitutions;

XII) a longer peptide of up to 30, such as 16 to 20, such as 21 to 25, or such as 26 to 30 amino acid residues in length; said longer peptide comprising a fragment of 14, or 15 contiguous amino acids derived from said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence of SEQ ID NO:113, XIV) a shorter peptide consisting of 15 to 19 contiguous amino acids of the sequence of any one of said respective first, second, third, fourth, fifth and sixth peptide;

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids with the sequence of said fourth peptide having the amino acid sequence of SEQ ID NO:113;

XVI) a shorter peptide consisting of consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second, third, fourth, fifth and sixth peptide;

XVII) a shorter peptide consisting of 13 to 14 amino acid residues derived from 13 to 14 contiguous amino acids of the sequence of said fourth peptide of SEQ ID NO:113 with 1, 2, or 3 amino acid substitutions; and XVIII) a shorter peptide consisting of 15 to 19 amino acids derived from 15 to 19 contiguous amino acids of the sequence of any one of said respective first, second, third, fourth, fifth and sixth peptides with 1, 2, or 3 amino acid substitutions.

Embodiment 20. A composition according to the present invention wherein the peptides in the composition comprise, or consist of, of six non-identical peptides, wherein
1) a first peptide has the amino acid sequence of SEQ ID NO: 7 (207);
2) a second peptide has the amino acid sequence of SEQ ID NO: 71 (238);
3) a third peptide has the amino acid sequence of SEQ ID NO:72 (239);
4) a fourth peptide has the amino acid sequence of SEQ ID NO: 113 (241);
5) a fifth peptide has the amino acid sequence of SEQ ID NO: 11 (211); and
6) a sixth peptide has the amino acid sequence of SEQ ID NO: 45 (222).

Embodiment 21. The composition according to any one of the preceding embodiments, further comprising a fifth peptide selected from the group of peptides having the amino acid sequence of SEQ ID NOs: 1 to 327 or a variant thereof, for example such as any one or more of the peptides mentioned in Tables 1 to 9 and Table 34; and wherein said fifth peptide is not identical to any one of said respective first, second, third and fourth peptide in the composition.

Embodiment 22. The composition according to any one of the preceding embodiments, further comprising a fifth peptide selected from the group consisting of peptides a) to h):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
f) a peptide having the amino acid sequence of SEQ ID NO: 4 (204), or a variant thereof;
g) a peptide having the amino acid sequence of SEQ ID NO: 11 (211), or a variant thereof;
h) a peptide having the amino acid sequence of SEQ ID NO: 45 (222), or a variant thereof;
wherein said fifth peptide is not identical to any one of said respective first, second, third and fourth peptides in the composition.

Embodiment 23. The composition according to any one of the preceding embodiments, further comprising a fifth peptide selected from the group consisting of peptides a) to h):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
f) a peptide having the amino acid sequence of SEQ ID NO: 4 (204), or a variant thereof;
g) a peptide having the amino acid sequence of SEQ ID NO: 11 (211), or a variant thereof;
h) a peptide having the amino acid sequence of SEQ ID NO: 45 (222), or a variant thereof;
wherein said fifth peptide is not identical to any one of said respective first, second, third and fourth peptides in the composition;
and wherein a variant of any one of said first, second, third, fourth peptide and peptide a) to h) is selected from the group consisting of:
I) a peptide consisting of 20 amino acid residues in length having at least 80% sequence identity over at least 14 contiguous amino acid residues with the sequence of any one of said respective first, second, third peptide and peptide a) to h);

II) a peptide consisting of 15 amino acid residues in length having at least 80% sequence identity over at least 14 contiguous amino acid residues with the sequence of said fourth peptide having the amino acid sequence of SEQ ID NO: 113;

III) a longer peptide of up to 30 amino acid residues in length and having at least 80% sequence identity over at least 14 contiguous amino acids with the sequence of any one of said respective first, second, third, fourth peptide and peptide a) to h);

IV) a shorter peptide consisting of 13 to 14 amino acids and having at least 80% sequence identity over at least 13 contiguous amino acids with the sequence of said fourth peptide having the amino acid sequence of SEQ ID NO:113;

V) a shorter peptide consisting of consisting of 15 to 19 amino acids and having at least 80% sequence identity over at least 14 contiguous amino acids with the sequence of any one of said respective first, second, third peptide and peptide a) to h).

Embodiment 24. The composition according to any one of the preceding embodiments, further comprising a fifth peptide selected from the group consisting of peptides a) to f):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
f) a peptide having the amino acid sequence of SEQ ID NO: 4 (204), or a variant thereof;
wherein said fifth peptide is not identical to any one of said respective first, second, third and fourth peptides in the composition.

Embodiment 25. The composition according to any one of the preceding embodiments, further comprising a fifth peptide selected from the group consisting of peptides a), c) and f):
a) a peptide having the amino acid sequence of SEQ ID NO: 5 (205), or a variant thereof;
c) a peptide having the amino acid sequence of SEQ ID NO: 69 (236), or a variant thereof;
f) a peptide having the amino acid sequence of SEQ ID NO: 4 (204), or a variant thereof;
wherein said fifth peptide is not identical to any one of said respective first, second, third and fourth peptides in the composition.

Embodiment 26. The composition according to any one of the preceding embodiments, further comprising a fifth peptide selected from the group consisting of peptides a) to e) and h):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
h) a peptide having the amino acid sequence of SEQ ID NO: 45 (222), or a variant thereof;
wherein said fifth peptide is not identical to any one of said respective first, second, third and fourth peptides in the composition.

Embodiment 27. The composition according to any one of the preceding embodiments, further comprising a fifth peptide selected from the group consisting of peptides c), d) and h):
c) a peptide having the amino acid sequence of SEQ ID NO: 69 (236), or a variant thereof;
d) a peptide having the amino acid sequence of SEQ ID NO: 36 (217), or a variant thereof;
h) a peptide having the amino acid sequence of SEQ ID NO: 45 (222), or a variant thereof;
wherein said fifth peptide is not identical to any one of said respective first, second, third and fourth peptides in the composition.

Embodiment 28. The composition according to any one of the preceding embodiments, further comprising a fifth selected from the group consisting of peptides a) to e) and g):
a) a peptide having the amino acid sequence of SEQ ID NO: 5 (205), or a variant thereof;
b) a peptide having the amino acid sequence of SEQ ID NO: 6 (206), or a variant thereof;
c) a peptide having the amino acid sequence of SEQ ID NO: 69 (236), or a variant thereof;
d) a peptide having the amino acid sequence of SEQ ID NO: 36 (217), or a variant thereof;
e) a peptide having the amino acid sequence of SEQ ID NO: 232 (285), or a variant thereof;
g) a peptide having the amino acid sequence of SEQ ID NO: 11 (211), or a variant thereof;
wherein said fifth peptide is not identical to any one of said respective first, second, third and fourth peptides in the composition.

Embodiment 29. The composition according to any one of the preceding embodiments, further comprising a fifth peptide selected from the group consisting of peptides f) to h):
f) a peptide having the amino acid sequence of SEQ ID NO: 4 (204), or a variant thereof;
g) a peptide having the amino acid sequence of SEQ ID NO: 11 (211), or a variant thereof;
h) a peptide having the amino acid sequence of SEQ ID NO: 45 (222), or a variant thereof;
wherein said fifth peptide is not identical to any one of said respective first, second, third and fourth peptides in the composition.

Embodiment 30. The composition according to any one of the preceding embodiments, further comprising a fifth peptide selected from the group consisting of peptides f) and h):
f) a peptide having the amino acid sequence of SEQ ID NO: 4 (204), or a variant thereof;
h) a peptide having the amino acid sequence of SEQ ID NO: 45 (222), or a variant thereof;
wherein said fifth peptide is not identical to any one of said respective first, second, third and fourth peptides in the composition.

Embodiment 31. The composition according to any one of the preceding embodiments, further comprising a fifth peptide selected from the group consisting of peptides g) and h):

g) a peptide having the amino acid sequence of SEQ ID NO: 11 (211), or a variant thereof;

h) a peptide having the amino acid sequence of SEQ ID NO: 45 (222), or a variant thereof;

wherein said fifth peptide is not identical to any one of said respective first, second, third and fourth peptides in the composition.

Embodiment 32. The composition according to any one of the preceding embodiments, further comprising a fifth peptide having the amino acid sequence of SEQ ID NO: 4 (204), or a variant thereof; wherein said fifth peptide is not identical to any one of said respective first, second, third and fourth peptides in the composition.

Embodiment 33. The composition according to any one of the preceding embodiments, further comprising a fifth peptide having the amino acid sequence of SEQ ID NO: 45 (222), or a variant thereof; wherein said fifth peptide is not identical to any one of said respective first, second, third and fourth peptides in the composition.

Embodiment 34. The composition according to any one of the preceding embodiments, further comprising a fifth peptide having the amino acid sequence of SEQ ID NO: 11 (211), or a variant thereof; wherein said fifth peptide is not identical to any one of said respective first, second, third and fourth peptides in the composition.

Embodiment 35. The composition according to any one of the preceding embodiments, further comprising a fifth peptide having the amino acid sequence of SEQ ID NO: 69 (236), or a variant thereof; wherein said fifth peptide is not identical to any one of said respective first, second, third and fourth peptides in the composition.

Embodiment 36. The composition according to any one of the preceding embodiments, further comprising a fifth peptide having the amino acid sequence of SEQ ID NO: 36 (217), or a variant thereof; wherein said fifth peptide is not identical to any one of said respective first, second, third and fourth peptides in the composition.

Embodiment 37. The composition according to any one of the preceding embodiments, further comprising a sixth peptide selected from the groups consisting of peptides having the amino acid sequence of SEQ ID NOs: 1 to 327 as mentioned herein, such as any one of the peptides mentioned in Tables 1 to 9 and Table 34; wherein said sixth peptide is not identical to any one of said respective first, second, third, fourth or fifth peptides in the composition.

Embodiment 38. The composition according to any one of the preceding embodiments, further comprising a sixth peptide selected from the group consisting of peptides a) to h):

a) a peptide having the amino acid sequence of SEQ ID NO: 5 (205), or a variant thereof;

b) a peptide having the amino acid sequence of SEQ ID NO: 6 (206), or a variant thereof;

c) a peptide having the amino acid sequence of SEQ ID NO: 69 (236), or a variant thereof;

d) a peptide having the amino acid sequence of SEQ ID NO: 36 (217), or a variant thereof;

e) a peptide having the amino acid sequence of SEQ ID NO: 232 (285), or a variant thereof;

f) a peptide having the amino acid sequence of SEQ ID NO: 4 (204), or a variant thereof;

g) a peptide having the amino acid sequence of SEQ ID NO: 11 (211), or a variant thereof;

h) a peptide having the amino acid sequence of SEQ ID NO: 45 (222), or a variant thereof;

wherein said sixth peptide is not identical to any one of said respective first, second, third, fourth or fifth peptides in the composition.

Embodiment 39. The composition according to any one of the preceding embodiments, further comprising a sixth peptide selected from the group consisting of peptides f) to h):

f) a peptide having the amino acid sequence of SEQ ID NO: 4 (204), or a variant thereof;

g) a peptide having the amino acid sequence of SEQ ID NO: 11 (211), or a variant thereof;

h) a peptide having the amino acid sequence of SEQ ID NO: 45 (222), or a variant thereof;

wherein said sixth peptide is not identical to any one of said respective first, second, third, fourth or fifth peptides in the composition.

Embodiment 40. The composition according to any one of the preceding embodiments, further comprising a sixth peptide selected from the group consisting of peptides a), c) and f):

a) a peptide having the amino acid sequence of SEQ ID NO: 5 (205), or a variant thereof;

c) a peptide having the amino acid sequence of SEQ ID NO: 69 (236), or a variant thereof;

f) a peptide having the amino acid sequence of SEQ ID NO: 4 (204), or a variant thereof;

wherein said sixth peptide is not identical to any one of said respective first, second, third, fourth or fifth peptides in the composition.

Embodiment 41. The composition according to any one of the preceding embodiments, further comprising a sixth peptide selected from the group consisting of peptides c), d) and h):

c) a peptide having the amino acid sequence of SEQ ID NO: 69 (236), or a variant thereof;

d) a peptide having the amino acid sequence of SEQ ID NO: 36 (217), or a variant thereof;

h) a peptide having the amino acid sequence of SEQ ID NO: 45 (222), or a variant thereof;

wherein said sixth peptide is not identical to any one of said respective first, second, third, fourth or fifth peptides in the composition.

Embodiment 42. The composition according to any one of Embodiment 1 to Embodiment 39, further comprising a sixth peptide selected from the group consisting of peptides g) and h):

g) a peptide having the amino acid sequence of SEQ ID NO: 11 (211), or a variant thereof;

h) a peptide having the amino acid sequence of SEQ ID NO: 45 (222), or a variant thereof;

wherein said sixth peptide is not identical to any one of said respective first, second, third, fourth or fifth peptides in the composition.

Embodiment 43. The composition according to any one of the preceding embodiments, further comprising a fifth peptide having the amino acid sequence of SEQ ID NO: 4 (204), or a variant thereof; and a sixth peptide having the amino acid sequence of SEQ ID NO: 45 (222), or a variant thereof.

Embodiment 44. The composition according to any one of the preceding embodiments, further comprising a fifth peptide having the amino acid sequence of SEQ ID NO: 11 (211), or a variant thereof; and a sixth peptide having the amino acid sequence of SEQ ID NO: 45 (222), or a variant thereof.

Embodiment 45. The composition according to any one of the preceding embodiments, wherein one or more of said first, second, third or fourth peptides are independently selected from the group consisting of peptides b), c), and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof.

Embodiment 46. The composition according to any one of the preceding embodiments, wherein said first and/or fourth peptide is selected from the group consisting of peptides b) and c):
  b) a peptide having the amino acid sequence of SEQ ID NO: 6 (206), or a variant thereof;
  c) a peptide having the amino acid sequence of SEQ ID NO: 69 (236), or a variant thereof;
  and wherein one of said second or third peptides are selected from the group consisting of peptides e):
  e) a peptide having the amino acid sequence of SEQ ID NO: 232 (285), or a variant thereof.

Embodiment 47. The composition according to any one of the preceding embodiments, wherein said first peptide is SEQ ID NO: 7 (207) or a variant thereof; or is selected from any one of the peptides a) to e):
  a) a peptide having the amino acid sequence of SEQ ID NO: 5 (205), or a variant thereof;
  b) a peptide having the amino acid sequence of SEQ ID NO: 6 (206), or a variant thereof;
  c) a peptide having the amino acid sequence of SEQ ID NO: 69 (236), or a variant thereof;
  d) a peptide having the amino acid sequence of SEQ ID NO: 36 (217), or a variant thereof;
  e) a peptide having the amino acid sequence of SEQ ID NO: 232 (285), or a variant thereof; and,
  wherein said second peptide has the amino acid sequence of SEQ ID NO: 71 (238), or a variant thereof; and
  wherein said third peptide has the amino acid sequence of SEQ ID NO:72 (239), or a variant thereof; and
  wherein said fourth peptide has the amino acid sequence of SEQ ID NO:113 (241), or a variant thereof.

Embodiment 48. The composition according to any one of the preceding embodiments, wherein said first peptide is SEQ ID NO: 7 (207) or a variant thereof; or is selected from any one of the peptides b) and c):
  b) SEQ ID NO: 6 (206), or a variant thereof;
  c) SEQ ID NO: 69 (236), or a variant thereof; and,
  wherein said second peptide has the amino acid sequence of SEQ ID NO: 71 (238), or a variant thereof; and
  wherein said third peptide has the amino acid sequence of SEQ ID NO:72 (239), or a variant thereof; and
  wherein said fourth peptide has the amino acid sequence of SEQ ID NO:113 (241), or a variant thereof.

Embodiment 49. The composition according to any one of the preceding embodiments, wherein said second peptide has the amino acid sequence of SEQ ID NO: 71 (238) or a variant thereof; or is selected from any one of the peptides a) to e):
  a) a peptide having the amino acid sequence of SEQ ID NO: 5 (205), or a variant thereof;
  b) a peptide having the amino acid sequence of SEQ ID NO: 6 (206), or a variant thereof;
  c) a peptide having the amino acid sequence of SEQ ID NO: 69 (236), or a variant thereof;
  d) a peptide having the amino acid sequence of SEQ ID NO: 36 (217), or a variant thereof;
  e) a peptide having the amino acid sequence of SEQ ID NO: 232 (285), or a variant thereof; and,
  wherein said first peptide has the amino acid sequence of SEQ ID NO: 7 (207), or a variant thereof; and
  wherein said third peptide has the amino acid sequence of SEQ ID NO:72 (239), or a variant thereof; and
  wherein said fourth peptide has the amino acid sequence of SEQ ID NO:113 (241), or a variant thereof.

Embodiment 50. The composition according to any one of the preceding embodiments, wherein said second peptide has the amino acid sequence of SEQ ID NO: 71 (238) or a variant thereof; or is selected from any one of the peptides b), c) and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof; and,
  wherein said first peptide has the amino acid sequence of SEQ ID NO: 7 (207), or a variant thereof; and
  wherein said third peptide has the amino acid sequence of SEQ ID NO:72 (239), or a variant thereof; and
  wherein said fourth peptide has the amino acid sequence of SEQ ID NO:113 (241), or a variant thereof.

Embodiment 51. The composition according to any one of the preceding embodiments, wherein said third peptide has the amino acid sequence of SEQ ID NO: 72 (239) or a variant thereof; or is selected from any one of the peptides a) to e):
  a) a peptide having the amino acid sequence of SEQ ID NO: 5 (205), or a variant thereof;
  b) a peptide having the amino acid sequence of SEQ ID NO: 6 (206), or a variant thereof;
  c) a peptide having the amino acid sequence of SEQ ID NO: 69 (236), or a variant thereof;
  d) a peptide having the amino acid sequence of SEQ ID NO: 36 (217), or a variant thereof;
  e) a peptide having the amino acid sequence of SEQ ID NO: 232 (285), or a variant thereof; and,
  wherein said first peptide has the amino acid sequence of SEQ ID NO: 7 (207), or a variant thereof; and
  wherein said second peptide has the amino acid sequence of SEQ ID NO:71 (238), or a variant thereof; and
  wherein said fourth peptide has the amino acid sequence of SEQ ID NO:113 (241), or a variant thereof.

Embodiment 52. The composition according to any one of the preceding embodiments, wherein said third peptide has the amino acid sequence of SEQ ID NO: 72 (239) or a variant thereof; or is selected from any one of the peptides b), c) and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof; and,
  wherein said first peptide has the amino acid sequence of SEQ ID NO: 7 (207), or a variant thereof; and
  wherein said second peptide has the amino acid sequence of SEQ ID NO:71 (238), or a variant thereof; and
  wherein said fourth peptide has the amino acid sequence of SEQ ID NO:113 (241), or a variant thereof.

Embodiment 53. The composition according to any one of the preceding embodiments, wherein said fourth peptide has the amino acid sequence of SEQ ID NO: 113 (241) or a variant thereof; or is selected from any one of the peptides a) to e):
  a) a peptide having the amino acid sequence of SEQ ID NO: 5 (205), or a variant thereof;
  b) a peptide having the amino acid sequence of SEQ ID NO: 6 (206), or a variant thereof;
  c) a peptide having the amino acid sequence of SEQ ID NO: 69 (236), or a variant thereof;
  d) a peptide having the amino acid sequence of SEQ ID NO: 36 (217), or a variant thereof;
  e) a peptide having the amino acid sequence of SEQ ID NO: 232 (285), or a variant thereof; and,
  wherein said first peptide has the amino acid sequence of SEQ ID NO: 7 (207), or a variant thereof; and
  wherein said second peptide has the amino acid sequence of SEQ ID NO:71 (238), or a variant thereof; and
  wherein said third peptide has the amino acid sequence of SEQ ID NO:72 (239), or a variant thereof.

Embodiment 54. The composition according to any one of the preceding embodiments, wherein said fourth peptide has the amino acid sequence of SEQ ID NO: 113 (241) or a variant thereof; or is selected from any one of the peptides b) and c):
  b) a peptide having the amino acid sequence of SEQ ID NO: 6 (206), or a variant thereof;
  c) a peptide having the amino acid sequence of SEQ ID NO: 69 (236), or a variant thereof; and,
  wherein said first peptide has the amino acid sequence of SEQ ID NO: 7 (207), or a variant thereof; and
  wherein said second peptide has the amino acid sequence of SEQ ID NO:71 (238), or a variant thereof; and
  wherein said third peptide has the amino acid sequence of SEQ ID NO:72 (239), or a variant thereof.

Embodiment 55. The composition according to any one of the preceding embodiments, wherein said first, second, third, fourth, fifth or sixth peptide has the amino acid sequence of SEQ ID NO: 5 (205), or a variant thereof.

Embodiment 56. The composition according to any one of the preceding embodiments, wherein said first, second, third or fourth, fifth or sixth peptide has the amino acid sequence of SEQ ID NO: 6 (206), or a variant thereof.

Embodiment 57. The composition according to any one of the preceding embodiments, wherein said first, second, third or fourth, fifth or sixth peptide has the amino acid sequence of SEQ ID NO: 69 (236), or a variant thereof.

Embodiment 58. The composition according to any one of the preceding embodiments, wherein said first, second, third or fourth, fifth or sixth peptide has the amino acid sequence of SEQ ID NO: 36 (217), or a variant thereof.

Embodiment 59. The composition according to any one of the preceding embodiments, wherein said first, second, third or fourth, fifth or sixth peptide has the amino acid sequence of SEQ ID NO: 232 (285), or a variant thereof.

Embodiment 60. The composition according to any one of the preceding embodiments, wherein the peptides in the composition comprise, or consist of, four non-identical peptides, wherein
  1) said first peptide has the amino acid sequence of SEQ ID NO: 7 (207), or a variant thereof;
  2) said second peptide has the amino acid sequence of SEQ ID NO: 71 (238), or a variant thereof;
  3) said third peptide has the amino acid sequence of SEQ ID NO:72 (239), or a variant thereof; and
  4) said fourth peptide has the amino acid sequence of SEQ ID NO:113 (241), or a variant thereof.

Embodiment 61. The composition according to any one of the preceding embodiments, wherein the peptides in the composition comprise, or consist of, five non-identical peptides, said composition comprising:
  1) a first peptide having the amino acid sequence of SEQ ID NO: 7 (207), or a variant thereof;
  2) a second peptide having the amino acid sequence of SEQ ID NO: 71 (238), or a variant thereof;
  3) a third peptide having the amino acid sequence of SEQ ID NO: 72 (239), or a variant thereof; and
  4) a fourth peptide having the amino acid sequence of SEQ ID NO: 113 (241), or a variant thereof;
  or wherein one or more of said first, second, third or fourth peptides are selected independently from the peptides b), c) and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof; and
  wherein said fifth peptide has the amino acid sequence of SEQ ID NO:4 (204), or a variant thereof, or is selected from the group consisting of peptides a) and c):
  a) a peptide having the amino acid sequence of SEQ ID NO: 5 (205), or a variant thereof;
  c) a peptide having the amino acid sequence of SEQ ID NO: 69 (236), or a variant thereof.

Embodiment 62. The composition according to any one of the preceding embodiments, wherein the peptides in the composition comprise, or consist of, five non-identical peptides, wherein
  1) said first peptide has the amino acid sequence of SEQ ID NO: 7 (207), or a variant thereof;
  2) said second peptide has the amino acid sequence of SEQ ID NO: 71 (238), or a variant thereof;
  3) said third peptide has the amino acid sequence of SEQ ID NO:72 (239), or a variant thereof;
  4) said fourth peptide has the amino acid sequence of SEQ ID NO:113 (241), or a variant thereof; and
  5) said fifth peptide has the amino acid sequence of SEQ ID NO:4 (204), or a variant thereof.

Embodiment 63. The composition according to any one of the preceding embodiments, wherein the peptides in the composition comprise, or consist of, five non-identical peptides, said composition comprising:
  1) a first peptide having the amino acid sequence of SEQ ID NO: 7 (207), or a variant thereof;
  2) a second peptide having the amino acid sequence of SEQ ID NO: 71 (238), or a variant thereof;
  3) a third peptide having the amino acid sequence of SEQ ID NO: 72 (239), or a variant thereof; and
  4) a fourth peptide having the amino acid sequence of SEQ ID NO: 113 (241), or a variant thereof;
  or wherein one or more of said first, second, third or fourth peptides are independently selected from the group consisting of peptides b), c), and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof;

and wherein said fifth peptide has the amino acid sequence of SEQ ID NO:45 (222), or a variant thereof, or is selected from the group consisting of peptides c) and d):
  c) a peptide having the amino acid sequence of SEQ ID NO: 69 (236), or a variant thereof;
  d) a peptide having the amino acid sequence of SEQ ID NO: 36 (217), or a variant thereof.

Embodiment 64. The composition according to any one of the preceding embodiments, wherein the peptides in the composition comprise, or consist of, of five non-identical peptides, wherein
  1) a first peptide has the amino acid sequence of SEQ ID NO: 7 (207), or a variant thereof;
  2) a second peptide has the amino acid sequence of SEQ ID NO: 71 (238), or a variant thereof;
  3) a third peptide has the amino acid sequence of SEQ ID NO:72 (239), or a variant thereof;
  4) a fourth peptide has the amino acid sequence of SEQ ID NO: 113 (241), or a variant thereof; and
  5) a fifth peptide has the amino acid sequence of SEQ ID NO:45 (222), or a variant thereof.

Embodiment 65. The composition according to any one of the preceding embodiments, wherein the peptides in the composition comprise, or consist of, six non-identical peptides, said composition comprising:
  1) a first peptide having the amino acid sequence of SEQ ID NO: 7 (207), or a variant thereof;
  2) a second peptide having the amino acid sequence of SEQ ID NO: 71 (238), or a variant thereof;
  3) a third peptide having the amino acid sequence of SEQ ID NO: 72 (239), or a variant thereof; and
  4) a fourth peptide having the amino acid sequence of SEQ ID NO: 113 (241), or a variant thereof;
  or wherein one or more of said first, second, third or fourth peptides are selected independently from the peptides b), c) and e):
  b) a peptide having the amino acid sequence of SEQ ID NO: 6 (206), or a variant thereof;
  c) a peptide having the amino acid sequence of SEQ ID NO: 69 (236), or a variant thereof;
  e) a peptide having the amino acid sequence of SEQ ID NO: 232 (285), or a variant thereof;
  and wherein
  5) a fifth peptide has the amino acid sequence of SEQ ID NO:4 (204), or a variant thereof, or is selected from the group consisting of peptides a) and c):
  a) a peptide having the amino acid sequence of SEQ ID NO: 5 (205), or a variant thereof;
  c) a peptide having the amino acid sequence of SEQ ID NO: 69 (236), or a variant thereof;
  and wherein
  6) a sixth peptide has the amino acid sequence of SEQ ID NO:45 (222), or a variant thereof, or is selected from the group consisting of peptides c) and d):
  c) a peptide having the amino acid sequence of SEQ ID NO: 69 (236), or a variant thereof;
  d) a peptide having the amino acid sequence of SEQ ID NO: 36 (217), or a variant thereof.

Embodiment 66. The composition according to any one of the preceding embodiments, wherein the peptides in the composition comprise, or consist of, of six non-identical peptides, wherein
  1) a first peptide has the amino acid sequence of SEQ ID NO: 7 (207), or a variant thereof;
  2) a second peptide has the amino acid sequence of SEQ ID NO: 71 (238), or a variant thereof;
  3) a third peptide has the amino acid sequence of SEQ ID NO:72 (239), or a variant thereof;
  4) a fourth peptide has the amino acid sequence of SEQ ID NO: 113 (241), or a variant thereof;
  5) a fifth peptide has the amino acid sequence of SEQ ID NO: 4 (204), or a variant thereof; and
  6) a sixth peptide has the amino acid sequence of SEQ ID NO: 45 (222), or a variant thereof.

Embodiment 67. The composition according to any one of the preceding embodiments, wherein the peptides in the composition comprise, or consist of, six non-identical peptides, wherein
  1) said first peptide has the amino acid sequence of SEQ ID NO: 7 (207), or a variant thereof;
  2) said second peptide has the amino acid sequence of SEQ ID NO: 71 (238), or a variant thereof;
  3) said third peptide has the amino acid sequence of SEQ ID NO:72 (239), or a variant thereof;
  4) said fourth peptide has the amino acid sequence of SEQ ID NO: 113 (241), or a variant thereof;
  5) said fifth peptide has the amino acid sequence of SEQ ID NO: 11 (211), or a variant thereof; and
  6) said sixth peptide has the amino acid sequence of SEQ ID NO: 45 (222), or a variant thereof.

Embodiment 68. The composition according to any one of the preceding embodiments, wherein the variant of any one of said respective first, second, third, fourth, fifth and sixth peptide and peptides a) to e) as defined in Embodiment 1 is selected from the group consisting of:
  I) a peptide consisting of 20 amino acid residues in length having at least 80%, such as 85%, 90%, 95%, 97%, 98% or 99% sequence identity over at least 14, such as at least 15, such as at least 16, such as at least 17, such as at least 18, such as at least 19, such as 20 contiguous amino acid residues with the sequence of any one of said respective first, second, third, fifth, sixth peptide and peptides a) to e);
  II) a peptide consisting of 15 amino acid residues in length having at least 80%, such as 85%, 90%, 95%, 97%, 98% or 99% sequence identity over at least 14, such as 15 contiguous amino acid residues with the sequence of said fourth peptide having the amino acid sequence of SEQ ID NO:113;
  III) a peptide consisting of 20 amino acid residues in length and comprising a fragment of at least 14, such as 15, such as 16, such as 17, such as 18, such as 19, such as 20 contiguous amino acids derived from the sequence of any one of said respective first, second, third, fifth, sixth peptide and peptides a) to e) as defined in any one of the preceding embodiments with 1, 2 or 3 amino acid substitutions;
  IV) a peptide consisting of 15 amino acid residues in length and comprising a fragment of at least 14, such as 15 contiguous amino acids derived from the sequence of said fourth peptide having the amino acid sequence of SEQ ID NO:113 with 1, 2 or 3 amino acid substitutions;
  V) a longer peptide of up to 30, such as 20 to 25, or such as 26 to 30 amino acid residues in length comprising the amino acid sequence of any one of respective said first, second, third, fourth, fifth, sixth peptide and peptides a) to e) as defined in any one of the preceding embodiments;
  VI) a longer peptide of up to 30, such as 16 to 20, or such as 21 to 30 amino acid residues in length comprising the amino acid sequence of said fourth peptide having the amino acid sequence of SEQ ID NO:113;

VII) a longer peptide of up to 30, such as 20 to 25, or such as 26 to 30 amino acid residues in length comprising at least 14, such as at least 15 contiguous amino acid residues of the sequence of any one of said respective first, second, third, fourth, fifth, sixth peptide and peptides a) to e) as defined in any one of the preceding embodiments;

VIII) a longer peptide of up to 30, such as 16 to 20, or such as 21 to 25, or such as 26 to 30 amino acid residues in length comprising at least 14, such as at least 15 contiguous amino acid residues of the amino acid sequence of said fourth peptide having the amino acid sequence of SEQ ID NO:113;

IX) a longer peptide of up to 30, such as 20 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of any one of said respective first, second, third, fourth, fifth, sixth peptide and peptides a) to e) as defined in any one of the preceding embodiments;

X) a longer peptide of up to 30, such as 16 to 20, or such as 21 to 25, or such as 26 to 30 amino acid residues in length and having at least 80%, such as at least 85%, 90%, 95%, 97%, 98% or 99% sequence identity over at least 14, such as at least 15, contiguous amino acids with the sequence of said fourth peptide having the amino acid sequence of SEQ ID NO:113;

XI) a longer peptide of up to 30, such as 20 to 25, or such as 26 to 30 amino acid residues in length; said longer peptide comprising a fragment of 14, or 15 contiguous amino acids derived from of any one of said respective first, second, third, fourth, fifth, sixth peptide and peptides a) to e) as defined in any one of the preceding embodiments with 1, 2 or 3 amino acid substitutions;

XII) a longer peptide of up to 30, such as 16 to 20, such as 21 to 25, or such as 26 to 30 amino acid residues in length; said longer peptide comprising a fragment of 14, or 15 contiguous amino acids derived from the sequence of said fourth peptide having the amino acid sequence of SEQ ID NO:113 with 1, 2 or 3 amino acid substitutions;

XIII) a shorter peptide consisting of 13 to 14 contiguous amino acids of the sequence of said fourth peptide having the amino acid sequence of SEQ ID NO:113;

XIV) a shorter peptide consisting of 15 to 19 contiguous amino acids of the sequence of any one of said first, second, third, fourth, fifth, sixth peptide and peptides a) to e) as defined in any one of the preceding embodiments;

XV) a shorter peptide consisting of 13 to 14 contiguous amino acids and having at least 80%, such as at least 85%, 90%, 95%, 97%, 98% or 99% sequence identity over at least 13, such as at least 14 contiguous amino acids with the sequence of said fourth peptide having the amino acid sequence of SEQ ID NO:113;

XVI) a shorter peptide consisting of consisting of 15 to 19 amino acids and having at least 80%, such as at least 85%, 90%, 95%, 97%, 98% or 99% sequence identity over at least 14, such as at least 15, such as at least 16, such as at least 17, such as at least 18, such as at least 19 contiguous amino acids with the sequence of any one of said respective first, second, third, fourth, fifth, sixth peptide and peptides a) to e) as defined in any one of the preceding embodiments;

XVII) a shorter peptide consisting of 13 to 14 amino acid residues derived from 13 to 14 contiguous amino acids of the sequence of said fourth peptide having the amino acid sequence of SEQ ID NO:113 with 1, 2, or 3 amino acid substitutions, XVIII) a shorter peptide consisting of 15 to 19 amino acids derived from 15 to 19 contiguous amino acids of the sequence of any one of said respective first, second, third, fourth, fifth, sixth peptide and peptides a) to h) as defined in any one of the preceding embodiments with 1, 2, or 3 amino acid substitutions.

Embodiment 69. The composition according to Embodiment 68, wherein the amino acid sequence flanking the N-terminal of said contiguous amino acids is derived from the amino acid sequence flanking the N-terminal of said contiguous amino acids when aligned with more than 60% sequence identity to a native allergen sequence of SEQ ID NOs: 328 to 349 with 0, 1, 2 or 3 substitutions, such as a native allergen sequence of SEQ ID NOs: 328 to 332 with 0, 1, 2 or 3 substitutions.

Embodiment 70. The composition according to any one of Embodiment 68 and Embodiment 69, wherein the amino acid sequence flanking the C-terminal of said contiguous amino acids is derived from the amino acid sequence flanking the C-terminal of said contiguous amino acids when aligned with more than 60% sequence identity to a native allergen sequence of SEQ ID NOs: 328 to 349 with 0, 1, 2 or 3 substitutions, such as a native allergen sequence of SEQ ID NOs: 328 to 332 with 0, 1, 2 or 3 substitutions.

Embodiment 71. The composition according to any one of embodiments 68 and 70, wherein the amino acid sequence flanking the N-terminal of said contiguous amino acids is derived from the amino acid sequence flanking the N-terminal of said contiguous amino acids when aligned with more than 60% sequence identity to an isoform of an allergen of *Phleum pratense* with 0, 1, 2 or 3 substitutions.

Embodiment 72. The composition according to any one of embodiments 68, 69 and 71, wherein the amino acid sequence flanking the C-terminal of said contiguous amino acids is derived from the amino acid sequence flanking the C-terminal of said contiguous amino acids when aligned with more than 60% sequence identity to an isoform of an allergen of *Phleum pratense* with 0, 1, 2 or 3 substitutions.

Embodiment 73. The composition according to any one of embodiments 68, 70 and 72, wherein the amino acid sequence flanking the N-terminal of said contiguous amino acids is derived from the amino acid sequence flanking the N-terminal of said contiguous amino acids when aligned with more than 60% sequence identity to an allergen of another species of grass, wherein said allergen is selected from the allergens having the amino acid sequence selected from SEQ ID NOs: 333 to 349.

Embodiment 74. The composition according to any one of embodiments 68, 69, 71 and 73, wherein the amino acid sequence flanking the C-terminal of said contiguous amino acids is derived from the amino acid sequence flanking the C-terminal of said contiguous amino acids when aligned with more than 60% sequence identity to an allergen of another species of grass, wherein said allergen is selected from the allergens having the amino acid sequence selected from SEQ ID NOs: 333 to 349.

Embodiment 75. The composition according to any one of embodiments 69 to 74, wherein the amino acid sequence flanking the N-terminal of said contiguous amino acids is identical to the amino acid sequence flanking the N-terminal of said contiguous amino acids when aligned.

Embodiment 76. The composition according to any one of embodiments 69 to 75, wherein the amino acid sequence flanking the C-terminal of said contiguous amino acids is identical to the amino acid sequence flanking the C-terminal of said contiguous amino acids when aligned.

Embodiment 77. The composition according to any one of embodiments 69 to 76, wherein a variant of I), IX) and/or XVI) has at least 80%, such as at least 85%, 90%, 95%, 97%, 98% or 99% sequence identity over at least 16, such as 16 to 19, such as at least 17, such as at least 18, or such as at least 19 contiguous amino acids contiguous amino acids with the sequence of any one of said respective first, second, third, fifth and sixth peptide and peptides a) to e) as defined in any one of the preceding embodiments.

Embodiment 78. The composition according to any one of embodiments 69 to 77, wherein a variant of I) and/or IX) has at least 80%, such as at least 85%, 90%, 95%, 97%, 98% or 99% sequence identity over at least 16 to 20, such as 18 to 20 contiguous amino acids with the sequence of any one of said respective first, second, third, fifth and sixth peptide and peptides a) to e) as defined in any one of the preceding embodiments.

Embodiment 79. The composition according to any one of embodiments 69 to 78, wherein a variant of I) and/or IX) has at least 80%, such as at least 85%, 90%, 95%, 97%, 98% or 99% sequence identity over 20 contiguous amino acids with the sequence of any one of said respective first, second, third, fifth, sixth peptide and peptides a) to e) as defined in any one of the preceding embodiments.

Embodiment 80. The composition according to any one of Embodiment 68 to Embodiment 79, wherein a variant of I) and/or IX) has at least 90%, 95%, or 99% sequence identity over at least 16 to 20, such as 16 to 18, or such as 19 to 20 contiguous amino acids of any one of said first, second, third, fifth, sixth peptide and peptides a) to e) as defined in any one of the preceding embodiments.

Embodiment 81. The composition according to any one of Embodiment 68 to Embodiment 80, wherein a variant of 1) and/or IX) has at least 95% sequence identity over 20 contiguous amino acids of any one of said first, second, third, fifth, sixth peptide and peptides a) to e) as defined in any one of the preceding embodiments.

Embodiment 82. The composition according to any one of Embodiment 68 to Embodiment 81, wherein a variant of II) and/or X) has at least 85%, 90%, 95%, or 99% sequence identity over 15 contiguous amino acids of said fourth peptide having the amino acid sequence having the amino acid sequence of SEQ ID NO:113.

Embodiment 83. The composition according to any one of Embodiment 68 to Embodiment 82, wherein a variant of II) and/or X) has at least 90% sequence identity over at least 15 contiguous amino acids of said fourth peptide having the amino acid sequence having the amino acid sequence of SEQ ID NO:113.

Embodiment 84. The composition according to any one of Embodiment 68 to Embodiment 83, wherein a variant of III), IV), XI), XII), XVII) and/or XVIII) has 1 to 2 substitutions.

Embodiment 85. The composition according to any one of embodiments Embodiment 68 to Embodiment 84, wherein a variant is selected from variants of I), II), IX), X), XV) and XVI).

Embodiment 86. The composition according to any one of Embodiment 68 to Embodiment 85, wherein a variant is selected from variants of I), II), IX), X), XV) and XVI), and wherein a variant of II) and X) has at least 90% sequence identity over at least 15 contiguous amino acids of said fourth peptide of SEQ ID NO:113; and wherein a variant of XV) has at least 90% sequence identity over at least 14 contiguous amino acids of said fourth peptide of SEQ ID NO:113, and wherein a variant of I), IX) has at least 95% sequence identity over 20 contiguous amino acids of any one of said first, second, third, fifth, sixth peptide and peptides a) to e) as defined in any one of the preceding embodiments; and wherein a variant of XVI) has at least 95% sequence identity over 19 contiguous amino acids of any one of said first, second, third, fifth, sixth peptide and peptides a) to e) as defined in any one of the preceding embodiments.

Embodiment 87. The composition according to any one of Embodiment 68 to Embodiment 86, wherein a variant is selected from variants of III), IV), XI), XII), XVII) and XVIII).

Embodiment 88. The composition according to any one of embodiments Embodiment 68 to Embodiment 87, wherein a variant is selected from variants of III), IV), XI), XII), XVII) and XVIII), and each variant has 1 to 2 substitutions.

Embodiment 89. The composition according to any one of Embodiment 68 to Embodiment 88, wherein a variant is selected from variants of V), VI), XIII) and XIV).

Embodiment 90. The composition according to any one of the preceding embodiments, wherein 0, 1, 2, 3 or 4 lysine (K) amino acid residues; and/or 0, 1, 2, 3 or 4 arginine amino acid residues (R); and/or 0, 1, 2, 3 or 4 glutamic amino acid residues (E); and/or 0, 1, 2, 3 or 4 aspartic acid amino acid residues (D) are added to the N- or C-terminus of said first, second, third, fourth, fifth, sixth peptide, or any one of peptides a) to h) as defined in any one of the preceding embodiments, or variants thereof.

Embodiment 91. The composition according to any one of the preceding embodiments, wherein 0, 1, 2, 3 or 4 lysine (K) amino acid residues are added to the N- or C-terminus of said first, second, third, fourth, fifth, sixth peptide, or any one of peptides a) to e) as defined in any one of the preceding embodiments, or variants thereof.

Embodiment 92. The composition according to any one of the preceding embodiments, wherein one or more additional amino acid residues are added to the N- or C-terminus of said first, second, third, fourth, fifth, sixth peptide, or any one of peptides a) to e) as defined in any one of the preceding embodiments, peptide or variants thereof; and wherein said one or more additional amino acids is the same amino acid residue or amino acid sequence flanking the N- and/or C-terminal ends of said first, second, third, fourth, fifth, sixth and/or any one of peptides a) to e) as defined in any one of the preceding embodiments, when said peptide is aligned with the native allergen sequence it is derived from, or with another grass pollen allergen from the same grass pollen allergen group.

Embodiment 93. The composition according to any one of the preceding embodiments, wherein the variant comprises a deletion of a hydrophobic residue up to three amino acids from the N- or C-terminus of said first, second, third, fourth, fifth, sixth and/or any one of peptides a) to e) as defined in any one of the preceding embodiments; and/or a deletion of any two consecutive amino acids comprising the amino acid sequence aspartate-glycine (DG) that are up to four amino acids from the N- or C-terminus of said first, second, third, fourth, fifth, sixth and/or any one of peptides a) to e) as defined in any one of the preceding embodiments.

Embodiment 94. The composition according to any one of the preceding embodiments, wherein a peptide of the composition contains at least one T cell epitope, optionally a Th-2 cell epitope.

Embodiment 95. The composition according to any one of the preceding embodiments, wherein a variant of the first, second, third, fourth, fifth, sixth peptide and any one of peptides a) to e) as defined in embodiment 1 binds to at least 70%, such as at least 80%, 85%, 90% or 95%, of the group of HLA Class II alleles that said a variant of the first, second, third, fourth, fifth, sixth peptide and peptides a) to e) as defined in any one of the preceding embodiments, respectively, binds to when determined under the same in vitro or in silico test conditions.

Embodiment 96. The composition according to any one of the preceding embodiments, wherein a variant of the first, second, third, fourth, fifth, sixth peptide and any one of peptides a) to e) as defined in embodiment 1 binds to at least 70%, such as at least 80%, 85%, 90% or 95% of the group of HLA Class II alleles listed in any of Table 10, Table 11 and Table 28a that said first, second, third, fourth, fifth, sixth peptide and peptides a) to e) as defined in any one of the preceding embodiments, respectively, binds to when determined under the same in vitro and/or in silico test conditions.

Embodiment 97. The composition according to any one of the preceding embodiments, wherein a variant of the first, second, third, fourth, fifth, sixth peptide and any one of peptides a) to e) as defined in embodiment 1 binds to at least 70%, such as at least 80%, 85%, 90% or 95% of the group of HLA Class II alleles listed in Table 10 that said first, second, third, fourth, fifth, sixth peptide and peptides a) to e) as defined in any one of the preceding embodiments, respectively, binds to when determined under the same in vitro and/or in silico test conditions.

Embodiment 98. The composition according to any one of the preceding embodiments, wherein a variant of the first, second, third, fourth, fifth, sixth peptide and any one of peptides a) to e) as defined in embodiment 1 binds to at least 70%, such as at least 80%, 85%, 90% or 95% of the group of HLA Class II alleles listed in Table 28a that said first, second, third, fourth, fifth, sixth peptide and peptides a) to e) as defined in any one of the preceding embodiments, respectively, binds to when determined under the same in vitro or in silico test conditions.

Embodiment 99. The composition according to any one of the preceding embodiments, wherein the variant of the first, second, third, fourth, fifth, sixth peptide and any one of peptides a) to e) as defined in embodiment 1 is predicted to bind to at least 70%, such as at least 80%, 85%, 90% or 95%, of the group of HLA Class II alleles listed in any of Table 10 and Table 11 that said first, second, third, fourth, fifth, sixth peptide and peptides a) to e) as defined in any one of the preceding embodiments, respectively, is predicted to bind to using the same test conditions.

Embodiment 100. The composition according to any one of the preceding embodiments, wherein the variant of the first, second, third, fourth, fifth, sixth peptide and any one of peptides a) to e) as defined in embodiment 1 stimulate cytokine IL-5 production of allergen specific T cells or peripheral blood mononuclear cells obtained from a subject suffering from grass pollen allergy under the same in vitro test conditions as said first, second, third, fourth, fifth, sixth peptide and any one of peptides a) to e) as as defined in any one of the preceding embodiments, respectively.

Embodiment 101. The composition according to any one of the preceding embodiments, wherein the variant of the first, second, third, fourth, fifth, sixth peptide and any one of peptides a) to e) as defined in embodiment 1 stimulate a proliferation of allergen specific T cells or peripheral blood mononuclear cells obtained from a subject suffering from grass pollen allergy under the same in vitro test conditions as said first, second, third, fourth, fifth, sixth peptide and any one of peptides a) to e) as defined in any one of the preceding embodiments, respectively.

Embodiment 102. The composition according to any one of the preceding embodiments, wherein a variant of the peptide having the amino acid sequence of SEQ ID NO: 7 (207) is selected from the group consisting of peptides having the amino acid sequences of SEQ ID NO: 117 (117), SEQ ID NO: 138 (305), SEQ ID NO: 151 (318), SEQ ID NO: 262 (382), SEQ ID NO: 263 (383), SEQ ID NO: 265 (385), SEQ ID NO: 212 (254), SEQ ID NO: 213 (255) and SEQ ID NO: 214 (256).

Embodiment 103. The composition according to any one of the preceding embodiments, wherein a variant of the peptide having the amino acid sequence of SEQ ID NO: 7 (207) is selected from the group consisting of peptides having the amino acid sequences of SEQ ID NO: 117 (117), SEQ ID NO: 262 (382), SEQ ID NO: 263 (383) and SEQ ID NO: 265 (385).

Embodiment 104. The composition according to any one of the preceding embodiments, wherein a variant of the peptide having the amino acid sequence of SEQ ID NO: 71 (238) is selected from the group consisting of peptides having the amino acid sequences of SEQ ID NO: 183 (350), SEQ ID NO: 288 (404), SEQ ID NO: 289 (405), SEQ ID NO: 290 (363), SEQ ID NO: 291 (406), SEQ ID NO: 232 (285), SEQ ID NO: 300 (413), SEQ ID NO: 301 (414), SEQ ID NO: 302 (415), SEQ ID NO: 303 (416), SEQ ID NO: 218 (260), SEQ ID NO: 219 (261) and SEQ ID NO: 220 (262).

Embodiment 105. The composition according to any one of the preceding embodiments, wherein a variant of the peptide having the amino acid sequence of SEQ ID NO: 71 (238) is selected from the group consisting of peptides having the amino acid sequences of SEQ ID NO: 288 (404), SEQ ID NO: 289 (405), SEQ ID NO: 290 (363) and SEQ ID NO: 291 (406).

Embodiment 106. The composition according to any one of the preceding embodiments, wherein a variant of the peptide having the amino acid sequence of SEQ ID NO: 72 (239) is selected from the group consisting of peptides having the amino acid sequences of SEQ ID NO: 232 (285), SEQ ID NO: 300 (413), SEQ ID NO: 301 (414), SEQ ID NO: 302 (415), SEQ ID NO: 303 (416), SEQ ID NO: 184 (351), SEQ ID NO: 226 (268), SEQ ID NO: 227 (269), SEQ ID NO: 238 (138), SEQ ID NO: 292 (407), SEQ ID NO: 293 (408), SEQ ID NO: 294 (364) and SEQ ID NO: 295 (409).

Embodiment 107. The composition according to any one of the preceding embodiments, wherein a variant of the peptide having the amino acid sequence of SEQ ID NO: 72 (239) is selected from the group consisting of peptides having the amino acid sequences of SEQ ID NO: 292 (407), SEQ ID NO: 293 (408), SEQ ID NO: 294 (364) and SEQ ID NO: 295 (409).

Embodiment 108. The composition according to any one of the preceding embodiments, wherein a variant of the peptide having the amino acid sequence of SEQ ID NO: 113 (241) is selected from the group consisting of peptides having the amino acid sequences of SEQ ID NO:

281 (399), SEQ ID NO: 282 (400), SEQ ID NO: 283 (360), SEQ ID NO: 68 (235), SEQ ID NO: 180 (347), SEQ ID NO: 233 (286), SEQ ID NO: 307 (420), SEQ ID NO: 284 (401), SEQ ID NO: 129 (129), SEQ ID NO: 186 (353), SEQ ID NO: 199 (366), SEQ ID NO: 228 (270) and SEQ ID NO: 271 (229).

Embodiment 109. The composition according to any one of the preceding embodiments, wherein a variant of the peptide having the amino acid sequence of SEQ ID NO: 113 (241) is selected from the group consisting of peptides having the amino acid sequences of SEQ ID NO: 186 (353) and SEQ ID NO: 199 (366).

Embodiment 110. The composition according to any one of the preceding embodiments, wherein a variant of the peptide having the amino acid sequence of SEQ ID NO: 4 (204) is selected from the group consisting of peptides having the amino acid sequences SEQ ID NO: 148 (315), SEQ ID NO: 247 (368), SEQ ID NO: 248 (369), SEQ ID NO: 249 (370) and SEQ ID NO: 132 (132).

Embodiment 111. The composition according to any one of the preceding embodiments, wherein a variant of the peptide having the amino acid sequence of SEQ ID NO: 4 (204) is selected from the group consisting of peptides having the amino acid sequences of SEQ ID NO: 247 (368), SEQ ID NO: 248 (369) and SEQ ID NO: 249 (370).

Embodiment 112. The composition according to any one of the preceding embodiments, wherein a variant of the peptide having the amino acid sequence of SEQ ID NO: 45 (222) is the peptide having the amino acid sequence of SEQ ID NO: 280.

Embodiment 113. The composition according to any one of the preceding embodiments, wherein a variant of the peptide having the amino acid sequence of SEQ ID NO: 11 (211) is selected from the group consisting of peptides having the amino acid sequences of SEQ ID NO: 272 (391), SEQ ID NO: 273 (392), SEQ ID NO: 274 (393), SEQ ID NO: 275 (394), SEQ ID NO: 276 (395) and SEQ ID NO: 277 (396).

Embodiment 114. The composition according to any one of the preceding embodiments, wherein a variant of the peptide having the amino acid sequence of SEQ ID NO: 11 (211) is selected from the group consisting of peptides having the amino acid sequences of SEQ ID NO: 272 (391), SEQ ID NO: 273 (392), SEQ ID NO: 274 (393), SEQ ID NO: 275 (394), SEQ ID NO: 276 (395) and SEQ ID NO: 277 (396).

Embodiment 115. The composition according to any one of the preceding embodiments, wherein a variant of the peptide having the amino acid sequence of SEQ ID NO: 11 (211) is selected from the group consisting of peptides having the amino acid sequences of SEQ ID NO: 273 (392), SEQ ID NO: 274 (393), SEQ ID NO: 275 (394) and SEQ ID NO: 276 (395).

Embodiment 116. The composition according to any one of the preceding embodiments, wherein a variant of the peptide having the amino acid sequence of SEQ ID NO: 5 (205) is selected from the group consisting of peptides having the amino acid sequences of SEQ ID NO: 99 (37), SEQ ID NO: 136 (303), SEQ ID NO: 149 (316), SEQ ID NO: 250 (371), SEQ ID NO: 251 (372), SEQ ID NO: 252 (373), SEQ ID NO: 253 (374), SEQ ID NO: 254 (375), SEQ ID NO: 117 (116) and SEQ ID NO: 234 (134).

Embodiment 117. The composition according to any one of the preceding embodiments, wherein a variant of the peptide having the amino acid sequence of SEQ ID NO: 5 (205) is selected from the group consisting of peptides having the amino acid sequences of SEQ ID NO: 250 (371), SEQ ID NO: 251 (372), SEQ ID NO: 252 (373), SEQ ID NO: 253 (374) and SEQ ID NO: 254 (375).

Embodiment 118. The composition according to any one of the preceding embodiments, wherein a variant of the peptide having the amino acid sequence of SEQ ID NO: 5 (205) is selected from the group consisting of peptides having the amino acid sequences of SEQ ID NO: 251 (372), SEQ ID NO: 252 (373) and SEQ ID NO: 254 (375).

Embodiment 119. The composition according to any one of the preceding embodiments, wherein a variant of the peptide having the amino acid sequence of SEQ ID NO: 6 (206) is selected from the group consisting of peptides having the amino acid sequences of SEQ ID NO: 137 (304), SEQ ID NO: 150 (317), SEQ ID NO: 255 (376), SEQ ID NO: 256 (377), SEQ ID NO: 257 (378), SEQ ID NO: 258 (379), SEQ ID NO: 259 (380), SEQ ID NO: 260 (381) and SEQ ID NO: 101 (39).

Embodiment 120. The composition according to any one of the preceding embodiments, wherein a variant of the peptide having the amino acid sequence of SEQ ID NO: 6 (206) is selected from the group consisting of peptides having the amino acid sequences of SEQ ID NO: 256 (377) and SEQ ID NO: 258 (379).

Embodiment 121. The composition according to any one of the preceding embodiments, wherein a variant of the peptide having the amino acid sequence of SEQ ID NO: 36 (217) is selected from the group consisting of peptides having the amino acid sequences of SEQ ID NO: 161 (328) and SEQ ID NO: 278 (397).

Embodiment 122. The composition according to any one of the preceding embodiments, wherein a variant of the peptide having the amino acid sequence of SEQ ID NO: 69 (236) is selected from the group consisting of peptides having the amino acid sequences of SEQ ID NO: 181 (348), SEQ ID NO: 194 (361), SEQ ID NO: 285 (402), SEQ ID NO: 286 (403) and SEQ ID NO: 287 (361).

Embodiment 123. The composition according to any one of the preceding embodiments, wherein a variant of the peptide having the amino acid sequence of SEQ ID NO: 69 (236) is selected from the group consisting of peptides having the amino acid sequences of SEQ ID NO: 285 (402), SEQ ID NO: 286 (403) and SEQ ID NO: 287 (361).

Embodiment 124. The composition according to any one of the preceding embodiments, wherein a variant of the peptide having the amino acid sequence of SEQ ID NO: 232 (285) is selected from the group consisting of peptides having the amino acid sequences of SEQ ID NO: 183 (350), SEQ ID NO: 288 (404), SEQ ID NO: 289 (405), SEQ ID NO: 290 (363), SEQ ID NO: 291 (406), SEQ ID NO: 232 (285), SEQ ID NO: 300 (413), SEQ ID NO: 301 (414), SEQ ID NO: 302 (415), SEQ ID NO: 303 (416), SEQ ID NO: 218 (260), SEQ ID NO: 219 (261), SEQ ID NO: 220 (262), SEQ ID NO: 232 (285), SEQ ID NO: 300 (413), SEQ ID NO: 301 (414), SEQ ID NO: 302 (415), SEQ ID NO: 303 (416), SEQ ID NO: 184 (351), SEQ ID NO: 226 (268), SEQ ID NO: 227 (269), SEQ ID NO: 238 (138), SEQ ID NO: 292 (407), SEQ ID NO: 293 (408), SEQ ID NO: 294 (364) and SEQ ID NO: 295 (409).

Embodiment 125. The composition according to any one of the preceding embodiments, wherein a variant of the peptide having the amino acid sequence of SEQ ID NO: 232 (285) is selected from the group consisting of peptides having the amino acid sequences of SEQ ID NO: 300 (413), SEQ ID NO: 301 (414), SEQ ID NO: 302 (415) and SEQ ID NO: 303 (416).

Embodiment 126. The composition according to any one of the preceding embodiments, wherein a variant peptide is derived by substituting one or more serine residues in the amino acid sequence of said first, second, third, fourth, fifth, sixth and/or any one of peptides a) to e) as defined in embodiment 1, with a cysteine amino acid.

Embodiment 127. The composition according to any one of the preceding embodiments, wherein the variant thereof is a peptide derivative.

Embodiment 128. The composition according to Embodiment 127, wherein the peptide derivative is amidated at the C-terminal end.

Embodiment 129. The composition according to Embodiment 127, wherein the derivative comprises (a) N-terminal acetylation; (b) C-terminal amidation; (c) one or more hydrogens on the side chain amines of an arginine and/or a lysine residue replaced with a methylene group; (d) glycosylated residues and/or (e) phosphorylated residues.

Embodiment 130. The composition according to any one of the preceding embodiments, wherein said first, second, third, fourth, fifth, sixth and/or any one of peptides a) to e) as defined in any one of the preceding embodiments, or the variant thereof, is a salt.

Embodiment 131. The composition according to embodiment Embodiment 130, wherein the salt is an acetate salt.

Embodiment 132. The composition according to any one of the preceding embodiments, wherein the peptides are obtained synthetically or by recombinant expression.

Embodiment 133. The composition according to any one of the preceding embodiments, wherein the peptides are freeze-dried.

Embodiment 134. The composition according to any one of the preceding embodiments, wherein each peptide in the composition is present in a molar concentration of 1 to 1000 µM, preferably 1-100 µM and more preferred in 1-10 µM.

Embodiment 135. The composition according to any one of the preceding embodiments, wherein each peptide in the composition is present in a soluble form in a molar concentration of 1 to 1000 µM preferably 1-100 µM and more preferred in 1-10 µM.

Embodiment 136. The composition according to any one of the preceding embodiments, wherein each peptide in the composition is present in equimolar concentrations or in substantially equimolar concentrations.

Embodiment 137. The composition according to any one of embodiments 1 to Embodiment 136, wherein the composition is a pharmaceutical composition.

Embodiment 138. The pharmaceutical composition according to Embodiment 137, further comprising a pharmaceutically acceptable carrier, excipient and/or adjuvant, optionally sterile.

Embodiment 139. The pharmaceutical composition according to any one of Embodiment 137 and Embodiment 138 formulated as a vaccine for parenteral administration.

Embodiment 140. The pharmaceutical composition according to any one of Embodiment 137 to Embodiment 139, wherein the pharmaceutical composition is a powder.

Embodiment 141. The pharmaceutical composition according to any one of Embodiment 137 to Embodiment 140, wherein the composition is formulated to be re-dissolved before use Embodiment 142. The pharmaceutical composition according to any one of Embodiment 137 to Embodiment 141, wherein the composition is isotonic.

Embodiment 143. A kit comprising a compartment and instructions, wherein the compartment comprises the composition according to any one of embodiments 1 to Embodiment 142 and wherein the instructions are for use in treating allergy to grass.

Embodiment 144. The kit according to embodiment 143, wherein the kit further comprises packaging material comprising corrugated fiber, glass, plastic, foil, ampules, vials, blister pack, preloaded syringes or tubes, optionally that maintains sterility of the components.

Embodiment 145. The kit according to any one of embodiments 143 and Embodiment 144, wherein the kit further comprises labels or inserts comprising printed matter or computer readable medium optionally including identifying components, dose amounts, clinical pharmacology, instructions for the clinician or for a subject using one or more of the kit components, prophylactic or therapeutic benefits, adverse side effects or manufacturer information.

Embodiment 146. A method for relieving or reducing (e.g. treating) an immune response being triggered by a grass pollen allergen of a grass species in a subject in need thereof, said method comprising administering to said subject a therapeutically effective amount of the composition according to any one of embodiment 1 to Embodiment 142.

Embodiment 147. A method for relieving one or more symptoms of an immune response being triggered by a grass pollen allergen of a grass species in a subject in need thereof, said method comprising administering to said subject a therapeutically effective amount of the composition according to any one of embodiment 1 to Embodiment 142.

Embodiment 148. A method for inducing (developing) immunological tolerance against a grass pollen allergen of a grass species in a subject in need thereof, said method comprising administering to said subject a therapeutically effective amount of the composition according to any one of embodiment 1 to Embodiment 142.

Embodiment 149. The method according to any one of embodiments 146 to 148, wherein the method comprises relieving one or more symptom(s) associated with allergic rhinitis, allergic conjunctivitis, allergic asthma and/or allergic eczema (e.g. atopic dermatitis).

Embodiment 150. The method according to Embodiment 149, wherein the one or more symptom(s) are symptoms associated with allergic rhinitis.

Embodiment 151. The method according to embodiment Embodiment 150, wherein the method comprises reducing the intensity of itchy nose; reducing the number of sneezes within a given period (e.g. daily, weekly, monthly); reducing the intensity of blocked nose (congestion); reducing the amount of nasal fluid; reducing the eosinophilic count in nasal fluid; reducing specific IgE antibody level (titer) in nasal fluid or in serum; and/or reducing basophil histamine release of blood.

Embodiment 152. The method according to Embodiment 149, wherein the one or more symptom(s) are symptoms associated with allergic conjunctivitis.

Embodiment 153. The method according to Embodiment 152, wherein the method comprises reducing the intensity of itchy eyes, redness in the white of the eyes and/or watery eyes; reducing the eosinophilic count in conjunctival tissue scrapings; reducing specific IgE antibody level (titer) in conjunctival tissue scrapings or in serum and/or reducing basophil histamine release of blood.

Embodiment 154. The method according to Embodiment 149, wherein the one or more symptom(s) are symptoms associated with allergic asthma.

Embodiment 155. The method according to Embodiment 154, wherein the method comprises reducing the intensity and/or number of coughs within a given period (e.g. daily, weekly, monthly); reducing the intensity of wheezes; improving being short of breath; improving lung function; reducing specific IgE antibody level (titer) in lung fluid or in serum and/or reducing basophil histamine release of blood.

Embodiment 156. The method according to embodiment Embodiment 149, wherein the one or more symptom(s) are symptoms associated with atopic dermatitis.

Embodiment 157. The method according to embodiment Embodiment 156, wherein the method comprises reducing itch intensity of the skin; reducing eczema score and/or reducing number of (peripheral) blood eosinophils.

Embodiment 158. The method according to any one of embodiments 146 to Embodiment 157, wherein the method comprises reducing the subject's need for concomitant treatment with corticosteroids or H1 antihistamines to reduce, relieve or suppress one or more symptoms of the immune response.

Embodiment 159. The method according to any one of embodiment 146 to Embodiment 158, wherein the grass allergy is clinically presented as atopic dermatitis, urticaria, contact dermatitis, allergic conjunctivitis, allergic rhinitis, allergic asthma, anaphylaxis, and/or hay fever.

Embodiment 160. The method according to any one of embodiment 146 to Embodiment 159, wherein the method decreases, reduces, suppresses or inhibits atopic dermatitis, urticaria, contact dermatitis, allergic conjunctivitis, allergic rhinitis, allergic asthma, anaphylaxis, and/or hay fever.

Embodiment 161. The method according to any one of embodiment 146 to Embodiment 160, wherein the method comprises inducing or increasing an IgG antibody response in the subject to an allergen of a grass pollen species.

Embodiment 162. The method according to any one of embodiment 146 to Embodiment 161, wherein the method comprises decreasing an IgE antibody response in the subject to an allergen of a grass pollen species.

Embodiment 163. The method according to any one of embodiment 146 to Embodiment 162, wherein the method comprises decreasing a T cell response in the subject to an allergen of a grass pollen species.

Embodiment 164. The method according to any one of embodiment 146 to Embodiment 163, wherein the method comprises increasing the level of the regulatory transcription factor Foxp3 in the subject.

Embodiment 165. The method according to any one of embodiment 146 to Embodiment 164, wherein the subject is sensitized to an allergen of a grass pollen species (e.g. has specific IgE antibodies against an allergen of a grass pollen species and/or has a T cell response against an allergen of a grass pollen species).

Embodiment 166. The method according to any one of embodiment 146 to Embodiment 165, wherein the grass pollen species is from one or more grasses of the species *Phleum pratense* (Timothy grass), *Cynodon dactylon* (Bermuda grass), *Lolium perenne* (Rye grass), *Sorghum halepense* (Johnson grass) and *Phalaris aquatica* (Canary grass).

Embodiment 167. The method according to any one of embodiment 146 to Embodiment 166, wherein the allergen of a grass pollen species is a group 1 allergen, a group 2 allergen, a group 3 allergen, a group 4 allergen or a group 5 allergen.

Embodiment 168. The method according to any one of embodiment 146 to Embodiment 167, wherein the allergen of a grass pollen species is Phl p 1, Phl p 2, Phl p3, Phl p 4, or Phl p 5.

Embodiment 169. The method according to any one of embodiment 146 to Embodiment 168, wherein the allergen of a grass pollen species is Phl p 1, Phl p 4, or Phl p 5.

Embodiment 170. The method according to any one of embodiment 146 to Embodiment 169, wherein the allergen of a grass pollen species is Phl p 1.0102, Phl p 2.0101, Phl p 3.0102, Phl p 4.varQ2I6V7 or Phl p 5.0109.

Embodiment 171. The method according to any one of embodiment 146 to Embodiment 170, wherein the treatment comprises repeated administration of the composition in weekly, bi-weekly, monthly or quarterly intervals.

Embodiment 172. The method according to any one of embodiment 146 to Embodiment 171, wherein the treatment is by immunotherapy.

Embodiment 173. The method according to any one of embodiment 146 to Embodiment 172, wherein a single dose of each single peptide of the composition is in the range of 1 to 1000 nanomoles.

Embodiment 174. The method according to any one of embodiment 146 to Embodiment 173, wherein the administration comprises administering a volume of about 50 to 150 microliters of the composition (e.g. by intradermal administration).

Embodiment 175. The method according to any one of embodiment 146 to Embodiment 174, wherein the administration is subcutaneous, intradermal, epicutaneous, rectal, topical, sublingual, oral, buccal, intranasal, respiratory or intralymphatic administration routes.

Embodiment 176. The method according to any one of embodiment 146 to Embodiment 175, wherein the administration is by any route selected from subcutaneous, intradermal, epicutaneous administration routes.

Embodiment 177. The method according to any one of embodiment 146 to Embodiment 176, wherein the subject is a mammal, such as a human, a pet, such as a dog or a cat, or a domestic animal, such as a horse.

Embodiment 178. A composition according to any one of Embodiment 1 to Embodiment 142 for use in a method according to any one of Embodiment 146 to Embodiment 177.

Embodiment 179. Use of a composition according to any one of Embodiment 1 to Embodiment 142 for the preparation of a medicament for use in a method according to any one of Embodiment 146 to Embodiment 177.

Embodiment 180. An in-vitro method for determining whether T cells and/or peripheral blood mononuclear cells recognize a composition as defined in any of Embodiment 1 to Embodiment 142, comprising contacting cells obtained from a subject with said composition or a single peptide thereof, and detecting whether said cells are stimulated by the composition or single peptide, optionally wherein said subject is in need of treatment.

Embodiment 181. The method of Embodiment 180 carried out to determine whether a subject has, or is at risk of developing, an allergy to a grass pollen allergen.

Embodiment 182. A diagnostic kit comprising a composition according to any one of Embodiment 1 to Embodiment 142.

Embodiment 183. A kit comprising a composition according to any one of embodiments 1 to 142 for use in a method according to any one of embodiments 146 to 177.

Modified Peptides

A parent peptide as described herein may be modified as described herein. Such peptides are referred to as variant peptides. Some modifications correspond to naturally occurring variations of the original allergens, such as in isoforms (within species or intra species) or in homologous allergens in other grass species (inter species). Other modifications are non-natural modifications of the parent peptide.

A parent peptide as described herein may contain one or more modifications, which optionally may result in greater or less activity or function, for example in the ability to elicit, stimulate or induce an in vitro immune response (e.g. T cell proliferation or T cell cytokine production); in the ability to bind HLA Class II alleles; in the ability to induce or enhance immunological tolerance to a relevant antigen, e.g. a grass allergen, such as group 1, 2, 3, 4 or 5 allergen; or in the ability to dissolve in solvents e.g. in an aqueous solution, or in the ability to resist oxidation.

Variants

A variant, which is also termed a "variant peptide" or "modified peptide" herein, is a peptide, which is derived from but not identical to a parent peptide as defined herein. A variant may for instance include one or more deletions of amino acid residues from the N- and/or C-terminal end of the parent peptide as defined herein one or more additions of amino acid residues to the N- and/or C-terminal of the parent peptide as defined herein and/or one or more amino acid substitutions, additions or deletions within the amino acid sequence of the parent peptide as defined herein. One type of variant is a "derivative", where chemical modifications are introduced, for instance in the side-chains of one of more of the amino acid residues of the parent peptide's amino acid sequence (thus effectively resulting in a peptide that includes an amino acid residue substitution relative to the parent peptide as defined herein). A derivative can also include a chemical modification that involves the N-terminal amino group and/or the C-terminal COOH group. Derivatives are described in more detail herein. It is important to note that some derivatives of the parent peptides as defined herein, are those that could be obtained by substituting an amino acid residue with another naturally occurring amino acid residue, whereas other derivatives involve chemical modifications that result in the provision of peptides that could not be encoded by a nucleic acid sequence.

Typically, a longer variant of the parent peptide as defined herein may be up to 60 amino acids in length, for example up to 55, 50, 45, 40, 35, 30, 28, 25, 24, or 22 amino acids in length. More typically, a longer variant peptide is up to about 30 amino acids in length, such as up to 25 amino acids in length. The longer variant may comprise the amino acid sequence of a parent peptide disclosed herein, or an amino acid sequence having at least 65% identity or similarity over the length of the amino acid sequence of the parent peptide as defined herein, or a fragment thereof, such as over at least 12 contiguous amino acids, for example over at least 13, 14, 15, 16, 17, 18, 19, 20 contiguous amino acids of the parent peptide as defined herein. Typically, the longer variant comprises an amino acid sequence having at least 70%, 75%, 80%, 85%, 90%, 95%, 97%, 98% or 99% identity or similarity over the length of the amino acid sequence of the parent peptide as defined herein, or over at least 12 contiguous amino acids, for example over at least 13, 14, 15, 16, 17, 18, 19 or 20 contiguous amino acids of the parent peptide as defined herein. Therefore, in some embodiments, a variant of the parent peptide as defined herein is a longer peptide up to 30 amino acid residues in length that comprises one or more additional amino acid residues at the N- and/or C-terminal end of the parent peptide as defined herein, or comprises an amino acid sequence having at least 80%, such as at least 85%, 90% or 95% identity or similarity over at least 14 contiguous amino acids of the parent peptide as defined herein, such as over at least 15, 16, 17, 18 contiguous amino acids of the parent peptide as defined herein.

A variant of the parent peptide may also include a fragment of a parent peptide as defined herein disclosed herein. A fragment of the parent peptide can have one or more amino acids less than the parent peptide as defined herein, either comprising deletions from within the amino acid sequence of the parent peptide as defined herein and/or amino acid deletions from the N- and/or C-terminus of the parent peptide as defined herein. Typically, a fragment will have a length of at least 12 amino acids, for example at least 13, 14, 15, 16 or 17 amino acids, and will have at least 65% identity or similarity over the length of the fragment, or over the length of at least 12 contiguous amino acids, when aligned with the parent peptide as defined herein. In some embodiments, the percentage identity or similarity is at least 70%, 75%, 80%, 85%, 90% or 95% over the length of the fragment, or over at least 12, 13, 14 or 15 contiguous amino acids of the parent peptide as defined herein. Therefore, in some embodiments, a variant thereof may be a shorter peptide comprising an amino acid sequence having at least 80%, such as at least 85%, 90% or 95% identity or similarity over at least 14 contiguous amino acids of the parent peptide as defined herein, such as over at least 15, 16, 17, 18 contiguous amino acids of the parent peptide.

As mentioned, a variant of a parent peptide as defined herein may comprise additional amino acids or may consist of a fragment of the parent peptide as defined herein. Thus, a variant of a parent peptide as defined herein may consist of 12-30 amino acids, for example 13-30, 14-30, 15-30, 16-30, 12-28, 13-28, 14-28, 15-28, 16-28, 13-26, 14-26, 15-26, 16-26, 13-25, 14-25, 15-25, 15-25, 13-24, 14-24, 15-24, 16-24, 3-22, 14-22, 15-22, 16-22, 13-20, 14-20, 15-20, 16-20 amino acids, such as particularly 12, 13, 14, 15, 16, 17, 18, 19, 20, 21, 22, 23, 24, 25, 26, 27, 28, 29 or 30 amino acids.

Moreover, a variant of a parent peptide as defined herein may comprise an amino acid sequence having at least 65% sequence identity or similarity over at least 14 contiguous amino acids with the sequence of the parent peptide as defined herein, optionally wherein the percent sequence identity or similarity is at least 70% 80%, 85%, 90% or 95% over at least 15 contiguous amino acids with the sequence of a parent peptide as defined herein, such as over at least 16, 17, 18 or 20 contiguous amino acids of the parent peptide sequence.

In some embodiments, the variant of the parent peptides as defined herein consists of 14-30 amino acids residues and comprises an amino acid sequence having at least 80% sequence identity or similarity over at least 14 contiguous amino acids of the parent peptide as defined herein. In other embodiments, the variant consists of 15-30 amino acids residues and comprises an amino acid sequence having at least 80% sequence identity or similarity over at least 15 contiguous amino acids of the parent peptide as defined herein. For example, the percent identity or similarity may be at least 85%, such as at least 90% or 95% over at least 14 contiguous amino acids, for example over at least 15, 16, 17, or 18 contiguous amino acids of the parent sequence as defined herein. Thus, in such embodiments, the variant consists of 14-30 amino acid residues, such as 15-30 amino acid residues, wherein one, two or three amino acid residues within at least 14, such as at least 15, 16, 17 or 18 contiguous amino acids of the parent peptide as defined herein are substituted.

In particular embodiments, the variant is a peptide consisting of 17-30 amino acids and comprises an amino acid sequence having at least 80%, such as at least 85%, 90% or 95% identity or similarity over at least 14 or 15 contiguous amino acids of the parent sequence as defined herein.

In still other particular embodiments, the variant is a peptide consisting of 15-25 amino acids and comprises an amino acid sequence having at least 80% identity or similarity over at least 11-13 or 14-15 contiguous amino acids with the sequence of a parent peptide as defined herein.

In still other particular embodiments, the variant is a peptide consisting of 15-25 amino acids and comprises an amino acid sequence having at least 80%, such as at least 85%, or at least 90%, or at least 95%, or at least 98% identity or similarity over at least 11-13 or 14-15 contiguous amino acids of the parent peptide sequence as defined herein.

In still other particular embodiments, the variant is a peptide consisting of 16-25 amino acids and comprises an amino acid sequence having at least 80% identity or similarity over at least 11-13 or 14-15 contiguous amino acids with the sequence of a parent as defined herein.

In further embodiments, the at least 80% identity or similarity is over at least 16, 17, 18 or 19 contiguous amino acids with the sequence of a parent peptide as defined herein and the percent identity or similarity may be at least is 80%, such as at least 85%, 90% or 95% over at least 16, 17, 18 or 19 contiguous amino acids with the sequence of a parent peptide.

The term "identity" and "identical" and grammatical variations thereof, as used herein, mean that two or more referenced entities are the same (e.g., amino acid sequences). Thus, where two peptides are identical, they have the same amino acid sequence. The identity can be over a defined area, e.g. over at least 12, 13, 14, 15 or 16 contiguous amino acids with the sequence of a parent peptide as defined herein, optionally wherein the alignment is the best fit with gaps permitted.

For example, to determine whether a variant peptide has at least 80% similarity or identity over at least 15 contiguous amino acid residues of the sequence of a parent peptide as defined herein, the variant peptide may be aligned with the parent peptide as defined herein and the percent identity calculated with respect to the identical amino acid residues found within the amino acid sequence of the variant peptide that overlaps with the 15 contiguous amino acids with the sequence of a parent peptide as defined herein.

Identity can be determined by comparing each position in aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the Clustal Omega program available at the website located at www.ebi.ac.uk/Tools/msa/clustalo/, the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information (through the internet at the website located at www.ncbi.nlm.nih.gov/). Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981). Programs for quantitating protein structural similarity using Delaunay-based topological mapping have also been developed (Bostick et al., Biochem Biophys Res Commun. 304: 320 (2003)).

The term "similarity" and "similar" and grammatical variations thereof, as used herein, mean that an amino acid sequence contains a limited number of conservative amino acid substitutions compared to a peptide reference sequence, e.g. the variant peptide versus the parent peptide as defined herein. A variety of criteria can be used to indicate whether amino acids at a particular position in a peptide are similar. In making changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Substitutions may be conservative or non-conservative amino acid substitutions. A "conservative substitution" is the replacement of one amino acid by a biologically, chemically or structurally similar residue. Biological similarity means that the substitution does not destroy a biological activity, e.g. T cell reactivity or HLA coverage. Structural similarity means that the amino acids have side chains with similar length, such as alanine, glycine and serine, or a similar size. Chemical similarity means that the residues have the same charge, or are both either hydrophilic or hydrophobic. For example, a conservative amino acid substitution is one in which an amino acid residue is replaced with an amino acid residue having a similar side chain, for example amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); non-polar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Particular examples include the substitution of one hydrophobic residue, such as isoleucine, valine, leucine or methionine, for another, or the substitution of one polar residue for another, such as the substitution of arginine for lysine, glutamic acid for aspartic acid, or glutamine for asparagine, serine for threonine, and the like. Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively.

As mentioned, a variant of a parent peptide as defined herein disclosed herein may comprise one or more additional amino acid residues at the N- and/or C-terminal end than the parent peptide as defined herein. Such amino acid residues may be naturally occurring amino acids or non-naturally occurring amino acids. In some embodiments, the one or more additional amino acids are the same amino acid or amino acid sequence flanking the N- and/or C-terminal ends of the parent peptide as defined herein, when aligned with the amino acid sequence of the allergen isoform it is present in, based upon or derived from or is aligned with another isoform of the same allergen. Thus, additional amino acids may be the amino acids flanking the N- and/or C-terminal ends of the parent peptide as defined herein when aligned to the respective allergen (Phl p 1, Phl p 2, Phl p 3, Phl p 4, Phl p 5). Alternatively the parent peptide as defined herein may be aligned to an allergen of a different species from the same allergen group when changing amino acids.

A variant peptide may include a number of variations compared to the parent peptide as defined herein, for example to increase or decrease physical or chemical properties of the parent peptide as defined herein, for example to decrease its ability to resist oxidation, to improve or increase solubility in aqueous solution, to decrease aggregation, to decrease synthesis problems, etc.

Accordingly, in some embodiments of the invention, a variant of a parent peptide as defined herein comprises:
a) one or more (e.g. 1, 2, or 3) amino acid substitutions in the sequence of the parent peptide as defined herein, for example a glutamate residue at the N-terminus of the parent peptide as defined herein may be replaced with pyroglutamate and/or one or more cysteine residues in the parent peptide as defined herein may be replaced with serine or 2-aminobutyric acid; and/or
b) one or more amino acid additions (e.g. 1, 2, 3, 5, 4, 6, 7, 8) to the sequence of a parent peptide as defined herein, for example wherein the variant comprises one or more (e.g. 1, 2, 3, or 4) lysine residue(s) and/or one or more (e.g. 1, 2, 3, or 4) arginine residue(s) and/or one or more positively charged residues added at the N- and/or C-terminus of the parent peptide as defined herein or to a fragment of the parent peptide as defined herein consisting of at least 14 contiguous amino acids of the parent peptide as defined herein (such as at least 15 contiguous amino acids); and/or
c) one or more amino acid deletions from the parent peptide as defined herein, for example wherein a hydrophobic residue up to three amino acids from the N- or C-terminus of the parent peptide as defined herein are deleted; and/or any two consecutive amino acids comprising the sequence Asp-Gly up to four amino acids from the N- or C-terminus of the parent peptide as defined herein are deleted.

Furthermore, in some embodiments, a variant of a parent peptide as defined herein may comprise one, two, three or more lysine or arginine amino acid residue(s) added to the N- and/or C-terminus of the parent peptide as defined herein that have been extended with one or more, e.g. 1, 2, 3, 4, or 5 amino acid residues, optionally of the wild type sequence the peptide is based upon or another wild type isoform.

Example 14 herein discloses a number of variant derivatives of parent of the present invention.

Variants or variant peptides suitable for the compositions of the invention include one or more T cell epitopes. The T cell epitopes should preferably be recognized by the immune system of a high number of individuals. Such peptides will contribute to the donor response valency of the compositions of the invention. Examples of peptides which have been shown by the present inventors or in the art to fulfil these criteria have been divided into peptide groups, each group representing a parent peptide and variants thereof having at least 80% identity or similarity over at least 11-13 contiguous amino acids of the parent peptide. Exemplary peptide groups of parent peptides and corresponding variants of the invention are:

Group 1: Variants of parent peptide with the amino acid sequence SEQ ID NO: 64 (231) are WO2010/089554-0057;

Group 2: Variants of parent peptide with the amino acid sequence SEQ ID NO: 73 (240) are SEQ ID NO: 207 (249), SEQ ID NO: 208 (250), SEQ ID NO: 209 (251), SEQ ID NO: 210 (252), SEQ ID NO: 211 (253), SEQ ID NO: 185 (352), SEQ ID NO: 198 (365), WO2010/089554-0031 (Bio04A), WO2010/089554-0032, WO2010/089554-0045, WO2010/089554-0046 (Rye09B), WO2010/089554-0047, WO2010/089554-0053 (Tim10B), WO2010/089554-0054, WO2010/089554-0055, WO2010/089554-0061, WO2010/089554-0066, WO2010/089554-0073, WO2010/089554-0087, WO2010/089554-0088, WO2010/089554-0104, WO2010/089554-00, WO2010/089554-0110, WO2010/089554-0111, WO2010/089554-0135, WO2010/089554-0136, WO2010/089554-0137, WO2010/089554-0138, WO2010/089554-0139, WO2010/089554-0140 or US7112333-0024;

Group 3: Variants of parent peptide with the amino acid sequence SEQ ID NO: 68 (235) are SEQ ID NO: 129 (129), SEQ ID NO: 233 (286), SEQ ID NO: 69 (236), SEQ ID NO: 113 (241), SEQ ID NO: 222 (264), SEQ ID NO: 223 (265), SEQ ID NO: 228 (270), SEQ ID NO: 229 (271), SEQ ID NO: 233 (286), SEQ ID NO: 180 (347), SEQ ID NO: 181 (348), SEQ ID NO: 186 (353), SEQ ID NO: 193 (360), SEQ ID NO: 194 (361), SEQ ID NO: 195 (362), SEQ ID NO: 199 (366), WO2010/089554-0038, WO2010/089554-0040, WO2010/089554-0041, WO2010/089554-0059, WO2010/089554-0064, WO2010/089554-0070 (Tim07G), WO2010/089554-0108, WO2010/089554-0124, WO2010/089554-0125, WO2010/089554-0126, WO2010/089554-0127, WO2010/089554-0128, WO2010/089554-0129, WO2010/089554-0130, WO2010/089554-0131, WO2010/089554-0132, US7112333-0018, US7112333-0019 or US7112333-0020;

Group 4: Variants of parent peptide with the amino acid sequence SEQ ID NO: 232 (285), SEQ ID NO: 71 (238) are SEQ ID NO: 72 (239), Rye08A, SEQ ID NO: 218 (260), B090261, SEQ ID NO: 224 (266), SEQ ID NO: 225 (267), SEQ ID NO: 226 (268), SEQ ID NO: 227 (269), SEQ ID NO: 220 (262), SEQ ID NO: 197 (364), SEQ ID NO: 183 (350), SEQ ID NO: 184 (351), SEQ ID NO: 196 (363), WO2010/089554-0029 (Bio03A), WO2010/089554-0030, WO2010/089554-0042, WO2010/089554-0043, WO2010/089554-0044, WO2010/089554-0060, WO2010/089554-0065, WO2010/089554-0071, WO2010/089554-0072, WO2010/089554-0082, WO2010/089554-0083, WO2010/089554-0103, WO2010/089554-0109, WO2010/089554-0133, WO2010/089554-0134, US7112333-0021, US7112333-0022, US7112333-0023 or WO2011/106645-0005;

Group 5: Variants of parent peptide with the amino acid sequence SEQ ID NO: 66 (233) are SEQ ID NO: 128

(128), SEQ ID NO: 178 (345), SEQ ID NO: 179 (346), SEQ ID NO: 205 (247), SEQ ID NO: 206 (248), WO2010/089554-0028 (Bio02A), WO2010/089554-0051, WO2010/089554-0063, WO2010/089554-0078, WO2010/089554-0079, WO2010/089554-0102, WO2010/089554-0122, US7112333-0013, US7112333-0014, US7112333-0015, WO2011/106645-0025 or WO2011/106645-0026;

Group 6: Variants of parent peptide with the amino acid sequence SEQ ID NO: 61 (228) are US7112333-0030 or US7112333-0031;

Group 7: Variants of parent peptide with the amino acid sequence SEQ ID NO: 62 (229) are WO2010/089554-0035, WO2010/089554-0056, WO2010/089554-0062, WO2010/089554-0106, WO2010/089554-0112, WO2010/089554-0119, WO2010/089554-0120, WO2010/089554-0121, US7112333-0006, US7112333-0007 or WO2011/106645-0023;

Group 8: Variants of parent peptide with the amino acid sequence SEQ ID NO: 63 (230) are SEQ ID NO: 124 (124), SEQ ID NO: 131 (131), SEQ ID NO: 133 (133), SEQ ID NO: 114 (242), 800276, SEQ ID NO: 1174 (341), SEQ ID NO: 175 (342), SEQ ID NO: 187 (354), SEQ ID NO: 189 (356), WO2010/089554-0035, WO2010/089554-0056, WO2010/089554-0062, WO2010/089554-0106, WO2010/089554-0112, WO2010/089554-0119, WO2010/089554-0120, WO2010/089554-0121, US7112333-0006, US7112333-0007 or WO2011/106645-0023;

Group 9: Variants of parent peptide with the amino acid sequence SEQ ID NO: 65 (232) are SEQ ID NO: 177 (344), WO2010/089554-0037, WO2010/089554-0058, WO2010/089554-0107, WO2010/089554-0123, US7112333-0012 or WO2011/106645-0004;

Group 10: Variants of parent peptide with the amino acid sequence SEQ ID NO: 67 (234) are SEQ ID NO: 128 (128), SEQ ID NO: 178 (345), SEQ ID NO: 179 (346), SEQ ID NO: 205 (247), SEQ ID NO: 206 (248), WO2010/089554-0028 (Bio02A), WO2010/089554-0051, WO2010/089554-0063, WO2010/089554-0078, WO2010/089554-0079, WO2010/089554-0102, WO2010/089554-0122, US7112333-0013, US7112333-0014, US7112333-0015, WO2011/106645-0025 or WO2011/106645-0026;

Group 11: Variants of parent peptide with the amino acid sequence SEQ ID NO: 70 (237) are WO2010/089554-0033, WO2010/089554-0052, WO2010/089554-0105, US7112333-0019 or US7112333-0020;

Group 12: Variants of parent peptide with the amino acid sequence SEQ ID NO: 7 (207) are SEQ ID NO: 150 (317), SEQ ID NO: 151 (318), SEQ ID NO: 6 (206), SEQ ID NO: 212 (254), SEQ ID NO: 213 (255), SEQ ID NO: 214 (256), B00275, SEQ ID NO: 137 (304), SEQ ID NO: 138 (305), SEQ ID NO: 118 (117), WO2010/089554-0020, US7112333-0042, US7112333-0043 or US7112333-0044;

Group 13: Variants of parent peptide with the amino acid sequence SEQ ID NO: 8 (208) are SEQ ID NO: 9 (209), SEQ ID NO: 201 (243), SEQ ID NO: 202 (244), SEQ ID NO: 231 (273), B00274, SEQ ID NO: 139 (306), SEQ ID NO: 140 (307), SEQ ID NO: 152 (319), SEQ ID NO: 121 (121), WO2010/089554-0015, WO2010/089554-0021, WO2010/089554-0026, WO2010/089554-0100, WO2010/089554-0114, US7112333-0045, US7112333-0046, US7112333-0047, US7112333-0048, US7112333-0049, WO94/21675-0031, WO94/21675-0032, WO94/21675-0033, WO94/21675-0034, WO94/21675-0035, WO94/21675-0036, WO94/21675-0037, WO94/21675-0038, WO94/21675-0039, WO94/21675-0040, WO94/21675-0041, WO94/21675-0042, WO94/21675-0061, WO94/21675-0062, WO94/21675-0063, WO94/21675-0064, US6008340-0020, WO2011/106645-0022 or WO2011/106645-0024;

Group 14: Variants of parent peptide with the amino acid sequence SEQ ID NO: 11 (211) are SEQ ID NO: 215 (257), SEQ ID NO: 216 (258), SEQ ID NO: 217 (259), SEQ ID NO: 221 (263), SEQ ID NO: 142 (309), WO2010/089554-0003, WO2010/089554-0006, WO2010/089554-0007, WO2010/089554-0016, WO2010/089554-0017, WO2010/089554-0018, WO2010/089554-0022, WO2010/089554-0027, WO2010/089554-0089, WO2010/089554-0096, WO2010/089554-0101, WO2010/089554-0115, WO2010/089554-0116, 7112333-0051, US7112333-0056, WO94/21675-0043, WO94/21675-0044, WO94/21675-0045, WO94/21675-0046, WO94/21675-0047, WO94/21675-0065 or WO94/21675-0066;

Group 15: Variants of parent peptide with the amino acid sequence SEQ ID NO: 1 (201) are SEQ ID NO: 119 (118), WO2010/089554-0011, WO2010/089554-0012, WO2010/089554-0098, US7112333-0032, US7112333-0034 or US7112333-0055;

Group 16: Variants of parent peptide with the amino acid sequence SEQ ID NO: 2 (202) are SEQ ID NO: 3 (203), US7112333-0037, US7112333-0038 or US7112333-0039;

Group 17: Variants of parent peptide with the amino acid sequence SEQ ID NO: 4 (204) are SEQ ID NO: 132 (132), SEQ ID NO: 148 (315), US7112333-0039, 7112333-0040, WO2011/106645-0001, 6008340-0005, US6008340-0007, US6008340-0009, US6008340-0014, US6008340-0015, US6008340-0016, US6008340-0017, US6008340-0018 or US6008340-0019;

Group 18: Variants of parent peptide with the amino acid sequence SEQ ID NO: 5 (205) are SEQ ID NO: 117 (116), SEQ ID NO: 136 (303), SEQ ID NO: 149 (316), WO2010/089554-0001 (Ber01), WO2010/089554-0010, WO2010/089554-0013, WO2010/089554-0019, WO2010/089554-0024, WO2010/089554-0025, WO2010/089554-0074, WO2010/089554-0075, WO2010/089554-0076, WO2010/089554-0077, WO2010/089554-0095, WO2010/089554-0099, WO2010/089554-0113, US7112333-0041, US7112333-0061 or US7112333-0062;

Group 19: Variants of parent peptide with the amino acid sequence SEQ ID NO: 8 (208) are SEQ ID NO: 9 (209), SEQ ID NO: 201 (243), SEQ ID NO: 202 (244), SEQ ID NO: 231 (273), 600274, SEQ ID NO: 139 (306), SEQ ID NO: 140 (307), SEQ ID NO: 152 (319), SEQ ID NO: 121 (121), WO2010/089554-0015, WO2010/089554-0021, WO2010/089554-0026, WO2010/089554-0100, WO2010/089554-0114, US7112333-0045, US7112333-0046, US7112333-0047, US7112333-0048, US7112333-0049, WO94/21675-0031, WO94/21675-0032, WO94/21675-0033, WO94/21675-0034, WO94/21675-0035, WO94/21675-0036, WO94/21675-0037, WO94/21675-0038, WO94/21675-0039, WO94/21675-0040, WO94/21675-0041, WO94/21675-0042, WO94/21675-0061, WO94/21675-0062, WO94/21675-0063, WO94/21675-0064, US6008340-0020, WO2011/106645-0022 or WO2011/106645-0024;

Group 20: Variants of parent peptide with the amino acid sequence SEQ ID NO: 10 (210) are SEQ ID NO: 203 (245), SEQ ID NO: 204 (246), SEQ ID NO: 154 (321), SEQ ID NO: 155 (322), WO2010/089554-0004 (Ber02B), WO2010/089554-0005 (Ber02C) or US7112333-0050;

Group 21: Variants of parent peptide with the amino acid sequence SEQ ID NO: 12 (212) are SEQ ID NO: 143 (310), SEQ ID NO: 144 (311), WO2010/089554-0023, WO2010/089554-0118, US7112333-0052, US7112333-0053, WO94/21675-0048, WO94/21675-0049, WO94/21675-0050, WO94/21675-0067, WO94/21675-0068, WO94/21675-0069, WO94/21675-0070, WO2011/106645-0002, US6008340-0021, US6008340-0022, US6008340-0023, US6008340-0024, US6008340-0025, US6008340-0026, US6008340-0027 or US6008340-0028;

Group 22: Variants of parent peptide with the amino acid sequence SEQ ID NO: 13 (213) are SEQ ID NO: 143 (310), SEQ ID NO: 144 (311), WO2010/089554-0023, WO2010/089554-0118, US7112333-0052, US7112333-0053, WO94/21675-0048, WO94/21675-0049, WO94/21675-0050, WO94/21675-0067, WO94/21675-0068, WO94/21675-0069, WO94/21675-0070, WO2011/106645-0002, US6008340-0021, US6008340-0022, US6008340-0023, US6008340-0024, US6008340-0025, US6008340-0026, US6008340-0027 or US6008340-0028;

Group 23: A variant of parent peptide with the amino acid sequence SEQ ID NO: 28 (215) is SEQ ID NO: 27 (214);

The groups may be divided into subgroups representing a parent peptide and variants thereof having at least 80% identity or similarity over at least 14-15 or 16-17 contiguous amino acids of the parent peptide. Exemplary parent peptides of subgroups are:

For peptide group 3: Subgroup 3a with parent peptide with the amino acid sequence SEQ ID NO: 68 (235) and Subgroup 3b with parent peptide with the amino acid sequence SEQ ID NO: 69 (236);

A further subgroup of peptide group 3 could be the subgroup 3c with the parent peptide of the amino acid sequence SEQ ID NO. 113 (241) and variants thereof;

For peptide group 4: Subgroup 4a with parent peptide with the amino acid sequence SEQ ID NO: 71 (238) and Subgroup 4b with parent peptide with the amino acid sequence SEQ ID NO: 72 (239);

For peptide group 14: Subgroup 14a with parent peptide with the amino acid sequence SEQ ID NO: 10 (210) and Subgroup 14b with parent peptide with the amino acid sequence SEQ ID NO: 11 (211);

For peptide group 12: Subgroup 12a with parent peptide with the amino acid sequence SEQ ID NO: 7 (207) and Subgroup 12b with parent peptide with the amino acid sequence SEQ ID NO: 6 (206);

For peptide group 13: Subgroup 13a with parent peptide with the amino acid sequence SEQ ID NO: 8 (208) and Subgroup 13b with parent peptide with the amino acid sequence SEQ ID NO: 9 (209);

For peptide group 16: Subgroup 16a with parent peptide with the amino acid sequence SEQ ID NO: 2 (202) and Subgroup 16b with parent peptide with the amino acid sequence SEQ ID NO: 3 (203);

For peptide group 19: Subgroup 19a with parent peptide with the amino acid sequence SEQ ID NO: 8 (208) and Subgroup 19b with parent peptide with the amino acid sequence SEQ ID NO: 9 (209);

For peptide group 12: Subgroup 12a with parent peptide with the amino acid sequence SEQ ID NO: 7 (207) and Subgroup 12b with parent peptide with the amino acid sequence SEQ ID NO: 6 (206);

As is obvious even more narrow sequence identity around a parent peptide could be envisaged in which case the groups and subgroups could be divided in even further different groups.

Derivatives

A parent peptide as defined herein may be modified to contain "non-natural" modifications. Such peptides are referred to as variants herein and more specifically they are referred to as derivative peptides or derivatives. The term derivative refers to a chemically modified form of a peptide disclosed herein. Typically, a derivative is formed by reacting a functional side group of an amino acid (e.g. amino, sulfhydryl or carboxy-group) with another molecule to form a covalent or non-covalent attachment of any type of molecule (naturally occurring or designed), such as a sugar moiety. Specific examples of derivatives of a peptide include glycosylation, acylation (e.g. acetylation), phosphorylation, amidation, formylation, ubiquitination and derivatization by protecting/blocking groups and any of numerous chemical modifications. Additional specific non-limiting examples are tagged peptides, fusion peptides, chimeric peptides including peptides having one or more non-amino acyl groups (q.v., sugar, lipid, etc.) covalently linked to the peptide. Typically, a derivative comprises one or more modifications, for example selected from any of: (a) N-terminal acylation (e.g. acetylation or formylation); (b) C-terminal amidation (e.g. reaction with ammonia or an amine); (c) one or more hydrogens on the side chain amines of arginine and/or lysine replaced with a methylene group; (d) glycosylation and/or (e) phosphorylation.

In a particular embodiment, the peptides are amidated at the C-terminal end. Examples of variants or derivatives of selected parent peptides as defined herein are found in Example 14, which describes modifications of parent peptides which were made in order to increase the aqueous solubility. Particular examples of derivative variants of the present invention are the derivative variants of the peptides of SEQ ID NOs: 4, 5, 6, 7, 11, 36, 45, 69, 71, 72, 113 and 232. Other examples of selected derivative variants of the present invention include the example including derivative variants of the parent peptides of SEQ ID NOs: 4, 7, 45, 71, 72 and 113, or the example including derivative variants of the parent peptides of SEQ ID NOs: 7, 71, 72 and 113. Yet another example of selected derivative variants of the present invention is the the example including the derivative variants of the parent peptides of SEQ ID NOs: 5, 6, 36, 69, 232. Still another example of selected derivatives include the derivatives of SEQ ID NOs: 212 to 229, such as derivatives of the first peptide of SEQ ID NO: 7 selected from the group consisting of SEQ ID NOs: 212, 213 and 214, or such as derivatives of the second peptide of SEQ ID NO: 71 selected from the group consisting of SEQ ID NOs: 218, 219, 220, or such as derivatives of the third peptide of SEQ ID NO: 72 selected from the group consisting of SEQ ID NOs: 226, 227, or such as derivatives of the fourth peptide of SEQ ID NO: 113 selected from the group consisting of SEQ ID NOs: 228 and 229, or such as derivatives of a variant of the fourth peptide selected from the group consisting of SEQ ID NOs. 222 and 223, or such as derivatives of SEQ ID NO: 11 selected from the group consisting of SEQ ID NOs 215, 216, 217 and 221.

Fusion Products

In particular embodiments, a derivative comprises a fusion (chimeric) sequence of peptides, which optionally may contain an amino acid sequence having one or more molecules not normally present in a reference (wild type) sequence covalently attached to the peptide amino acid sequence. The term "chimeric" and grammatical variations thereof, when used in reference to a sequence, means that the sequence contains one or more portions that are derived from, obtained or isolated from, or based upon other physical or chemical entities.

Another particular example of a derivative is one in which a second heterologous sequence, i.e. a heterologous functional domain, is attached to a peptide disclosed herein, (covalent or non-covalent binding) that may confer a distinct or complementary function to a peptide disclosed herein. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), or a radioisotope.

Linkers, such as amino acid or peptidomimetic sequences, may be inserted between the peptide sequence and the addition (e.g., heterologous functional domain) so that the two entities maintain, at least in part, a distinct function or activity. Linkers may have one or more properties that may include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence.

In a particular aspect of the invention, the peptides of the peptide combination are not provided as individual peptides, but the peptides may be fused together or to a carrier molecule to form an isolated molecule. For example, the peptides may be fused to the N- and C-terminus of a surface polypeptide of a virus, e.g. a virus of the hepadnaviridae family as disclosed in international patent application WO12168487 A1.

A variant peptide may share the same functionality or activity as the parent peptide as defined herein or may have improved functionality or activity. For example, a variant of a parent peptide as defined herein may bind to at least 70% of the group of Class HLA II alleles that the parent peptide as defined herein binds to. Thus, in some embodiments, the variant peptide binds to the same, substantially the same or at least 75%, 80%, such as at least 82%, 85%, 88%, 90%, 92%, 95%, 98% or more, of the group of HLA Class II alleles that binds to the parent peptide as defined herein, optionally wherein this is determined under same test conditions, either using prediction tools or in-vitro binding assay. Optionally, the Class HLA II binding is determined with respect to a particular group of Class HLA II alleles, for example one or more or all of the following alleles: DPA1*02:01-DPB1*01:01, DPA1*01:03-DPB1*02:01, DPA1*01:03-DPB1*03:01, DPA1*01:03-DPB1*04:01, DPA1*01:03-DPB1*04:02, DPA1*02:02-DPB1*05:01, DPA1*02:01-DPB1*14:01, DQA1*05:01-DQB1*02:01, DQA1*05:01-DQB1*03:01, DQA1*03:01-DQB1*03:02, DQA1*04:01-DQB1*04:02, DQA1*01:01-DQB1*05:01, DQA1*01:02-DQB1*06:02, DRB1*01:01, DRB1*03:01, DRB1*04:01, DRB1*04:05, DRB1*07:01, DRB1*09:01, DRB1*11:01, DRB1*12:01, DRB1*13:02, DRB1*15:01, DRB3*01:01, DRB3*02:02, DRB4*01:01 and DRB5*01:01, or the alleles disclosed in Table 10 or in Table 28a-c. Assays for measuring Class HLA II binding invitro is well known in the art and some are described herein in Example 11.

Furthermore, a variant peptide may comprise one or more of the same T cell epitopes as the parent peptide as defined herein. This may be determined by the ability of the variant peptide to induce or stimulate in-vitro T cell proliferation using cultured PBMCs (peripheral blood monocytes) compared to the parent peptide as defined herein, optionally using same test conditions, or by the ability of the variant peptide to induce or stimulate production of cytokines, (e.g. cytokines, IL-5, IL-13 and/or IL-10) from T cells (obtained from cultured PBMC's) compared to the parent peptide as defined herein, as described herein in Example 3. Therefore, in one particular embodiment, a variant of a parent peptide as defined herein may include an overlap of at least 9 amino acid residues, preferably identical residues, when aligned with a parent peptide as defined herein. The overlap is preferably more than 9 amino acid residues, e.g. 10, 11 or 12 amino acid residues or more, such as 13, 14 or 15 amino acid residues. The core binding sequence of MHC II molecules is known to be approximately 9 amino acids long, although MHC II molecules can accommodate longer peptides of 10-30 residues (Murugan and Dai, 2005). Therefore, in certain embodiments, an overlap of 9 amino acids or more with a parent sequence is sufficient for a variant to be able to share a T cell epitope with the parent peptide.

Salts of Peptides

Peptides are typically provided in the form of a salt, for example as a pharmaceutically acceptable and/or a physiologically acceptable salt. For example, the salt may be an acid addition salt with an inorganic acid, an acid addition salt with an organic acid, a salt with a basic inorganic acid, a salt with a basic organic acid, a salt with an acidic or basic amino acid or a mixture thereof. Typical examples of an acid addition salts with an inorganic acid are selected from any of the salts with hydrochloric acid, hydrobromic acid, nitric acid, sulfuric acid, phosphoric acid, or the like. An acid salt with an organic acid may be selected from any of the salts with formic acid, acetic acid, trifluoroacetic acid, fumaric acid, oxalic acid, tartaric acid, maleic acid, succinic acid, malic acid, methanesulfonic acid, benzenesulfonic acid, p-toluenesulfonic acid, or the like. Salts with an inorganic base may be selected from a salt of an alkali metal salts such as sodium salts and potassium salts; alkali earth metal salts such as calcium salts and magnesium salts; and aluminum salts and ammonium salts. Salts with a basic organic base may be selected from any salt with trimethylamine, triethylamine, pyridine, picoline, ethanolamine, diethanolamine, triethanolamine, dicyclohexylamine, N,N-dibenzylethylenediamine, caffeine, piperidine, and pyridine. Salts with a basic amino acid may be selected from any salt with arginine, lysine, ornithine, or the like. Salts with an acidic amino acid may be selected from any salt with aspartic acid, glutamic acid, or the like.

In particular embodiments of the invention a salt, such as a pharmaceutically acceptable salt, is an acetate salt.

Pharmaceutical Compositions

The invention also features a pharmaceutical composition comprising a composition, e.g. a peptide combination, defined herein. The pharmaceutical composition may be a vaccine, e.g. a product for use in conducting immunotherapy, including but not limited to a vaccine for treating an allergic immune response to a grass allergen.

A pharmaceutical composition comprises in addition to the peptide combination, therapeutically inactive ingredients, such as a pharmaceutically acceptable or physiologically acceptable excipient, carrier and/or adjuvants, which are well-known to the person skilled in the art and may include, but are not limited to, solvents, emulsifiers, wetting agents, plasticizers, solubilizers (e.g. solubility enhancing agents) coloring substances, fillers, preservatives, anti-oxidants, anti-microbial agents, viscosity adjusting agents, buffering agents, pH adjusting agents, isotonicity adjusting agents, mucoadhesive substances, and the like. Examples of formulation strategies are well-known to the person skilled in the art.

In some embodiments, the peptide may be formulated (e.g. mixed together) with immune-modifying agents like adjuvants. The adjuvant may be any conventional adjuvant, including but not limited to oxygen-containing metal salts, e.g. aluminium hydroxide, chitosan, heat-labile enterotoxin (LT), cholera toxin (CT), cholera toxin B subunit (CTB), polymerized liposomes, mutant toxins, e.g. LTK63 and LTR72, microcapsules, interleukins (e.g. IL-1 BETA, IL-2, IL-7, IL-12, INFGAMMA), GM-CSF, MDF derivatives, CpG oligonucleotides, LPS, MPL, MPL-derivatives, phosphophazenes, Adju-Phos(R), glucan, antigen formulation, liposomes, DDE, DHEA, DMPC, DMPG, DOC/Alum Complex, Freund's incomplete adjuvant, ISCOMs(R), LT Oral Adjuvant, muramyl dipeptide, monophosphoryl lipid A, muramyl peptide, and phospatidylethanolamine. Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

In some embodiments, the pharmaceutical composition may be formulated for parenteral administration, such as formulated for injection, e.g. subcutaneous and/or intradermal injection. Therefore, in some embodiments, the pharmaceutical composition may be a liquid (i.e. formulated as a liquid), including a solution, a suspension, a dispersion, and a gelled liquid. For example, a liquid pharmaceutical composition may be formed by dissolving a powder, granulate or lyophilizate of a peptide combination described herein in a suitable solvent and then administering to a subject. Suitable solvents may be any solvent having physiologically acceptable properties and able to dissolve the peptide combination in desired concentrations. A desired concentration may depend on the aliquot to be administered (i.e. to be injected) and the desired single dose. It is emphasized that for the purposes of injection the aliquot is in the range of about 10 to 500 microliters, e.g. 50 to 300 microliters or less and a desired single dose is within range of 1 to 1000 nanomole. Therefore, a suitable solvent should be able to dissolve any peptide of the combination to achieve a final concentration of about 1 to 1000 µM for each of the peptides. Thus, in one embodiment, a liquid composition comprises each of the peptides of the combination in a concentration of 10 to 800 µM, for Example 20 to 500 µM or 20 to 300 µM. Typically, the concentration of each peptide is the same, such as in an equimolar concentration, but each peptide of the composition may be present in different concentrations. Typically, the solvent is an aqueous solution, optionally mixed with other solvents. Thus, a solvent may comprise at least 60% w/w of water, e.g. at least 65% w/w, 70% w/w, 75% w/w, 80% w/w, 85% w/w, 90% w/w or 95% w/w, 99% w/w of water, such as distilled water, such as sterile water. In some embodiments, the solvent is sterile distilled water, e.g. water for injection. An aqueous solution may comprise other solvents than water, for example DMSO (dimethylsulfoxide), glycerol, ethanol, acetonitrile, vegetable or synthetic oils. The pH of the aqueous phase of the solvent may be in a physiological acceptable range, typically in the range of 3 to 9, such as in the range of pH 3 to 8, such as in the range of pH 4 to 8, such as in the range of 5 to 8, such as in the range of 6 to 8. Thus, the liquid formulation may comprise a pH controlling agent or buffering agent (e.g. citrate buffer, phosphate buffer, acetate buffer), optionally the pH may be adjusted with dilutions of strong base (e.g. sodium hydroxide or the like) and/or dilutions of strong acids (e.g. hydrochloric acid).

Typically, the liquid formulation is isotonic, and optionally sterile. Therefore, in some embodiments, the formulation comprises saline, such as isotonic saline. The liquid may contain additional excipients, such as another solvent, a solubilizing enhancing agent (e.g. polyoxyethylene (20) sorbitan monolaurate (Tween® 20), ionic and non-ionic emulsifiers (e.g. poloxamers (Kolliphor®)), a dispersant, a thickener, a preservative, an anti-microbial agent, and/or an antioxidant. Non-limiting illustrative examples of solvents include water, saline, DMSO, glycerol, ethanol, acetonitrile, vegetable or synthetic oils.

Some peptides are known to be prone to oxidation or being unstable when exposed to water for a long period. Therefore, to achieve storage stable compositions, a pharmaceutical composition may be formulated to contain only a limited amount of water or aqueous solution, e.g. containing less than 10% w/w of water or aqueous solution, such as less than 9, 8, 7, 6, 5, 4, 3, 2, 1, 0.5% w/w of water or aqueous solution. Examples of pharmaceutical compositions with limited levels of water may include granulates, powders, for example lyophilizates, i.e. freeze-dried powders. Typically, the freeze-dried composition may be dissolved before use, for example dissolved in an aqueous, optionally sterile, solution, for example a solution having a pH in the range of 3-9, such as pH in the range of 3 to 8, such as pH in the range of 4 to 8. A lyophilizate may contain additional ingredients, e.g. bulking agents and lyoprotectants (e.g. sucrose, lactose, trehalose, mannose, mannitol, sorbitol, glucose, raffinose, glycine, histidine or mixtures thereof), buffering agents (e.g. sodium citrate, sodium phosphate, disodium phosphate, sodium hydroxide, Tris base, Tris acetate, Tris HCl or mixtures thereof), antioxidants, antimicrobial agents, solubilizers (e.g. polyoxyethylene (20) sorbitan monolaurate (Tween® 20)).

A freeze-dried composition may also be formulated into a solid dosage form that is administered for example by the oral route such as by oral mucosa. Thus, in some embodiments, the pharmaceutical composition may be formulated for oral administration, for example for sublingual administration. Therefore, the pharmaceutical composition may be a solid dosage form, such as a freeze-dried solid dosage form, typically a tablet, a capsule or sachet, which optionally may be formulated for fast disintegration. Pharmaceutical formulations and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel ad Soklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

As mentioned, pharmaceutical compositions can be formulated to be compatible with a particular route of administration, such as by intradermal or by sublingual administration. Thus, pharmaceutical compositions may include carriers, diluents, or excipients suitable for administration by various routes. Exemplary routes of administration for contact or in vivo delivery for which a composition can optionally be formulated include inhalation, intranasal, oral, buccal, sublingual, subcutaneous, intradermal, epicutaneous, rectal, transdermal, or intralymphatic administration routes.

For oral, buccal or sublingual administration, a composition may take the form of, for example, tablets or capsules, optionally formulated as fast-disintegrating tablets/capsules or slow-release tablets/capsules. In some embodiments, the tablet is freeze-dried, optionally a fast-disintegrating tablet or capsule suitable for being administered under the tongue.

The pharmaceutical composition may also be formulated into a "unit dosage form", which used herein refers to physically discrete units, wherein each unit contains a predetermined quantity of a peptide or peptide combination, optionally in association with a pharmaceutical carrier (excipient, diluent, vehicle or filling agent) which, when administered in one or more doses, may produce a desired effect. Unit dosage forms also include, for example, ampules and vials, which may include a composition in a freeze-dried or lyophilized state (a lyophilizate) or a sterile liquid carrier, for example that can be added prior to administration or delivery in vivo. Unit dosage forms additionally include, for example, ampules and vials with liquid compositions disposed therein. A unit dose form may be for single, sequential or simultaneous administration.

Peptides may be prone to degradation when exposed to oxygen, for example when exposed to air or solvents containing air. Therefore, in some embodiments, the pharmaceutical composition comprises an inert gas, e.g. argon or nitrogen.

Another aspect of the invention relates to a kit comprising a compartment and instructions, wherein the compartment comprises a pharmaceutical composition as described herein for single, sequential or simultaneous administration, and wherein the instructions are for use in treating allergy to grass, such as grass. A kit may further comprise packaging material comprising corrugated fiber, glass, plastic, foil, ampules, vials, blister pack, preloaded syringes or tubes, optionally that maintain sterility of the components. A kit may further comprise labels or inserts comprising printed matter or computer readable medium optionally including identifying components, dose amounts, clinical pharmacology and instructions for the clinician or for a subject using one or more of the kit components, prophylactic or therapeutic benefits, adverse side effects or manufacturer information.

In one embodiment, the kit additionally comprises a container comprising a solvent for dissolving the composition before use. Examples of suitable solvents are described supra. Optionally, the kit may also comprise a device for use in parenteral injection, e.g. for injecting the composition (e.g. dissolved composition) to a subcutaneous or intradermal tissue. A device may be any suitable device for that purpose, such as a needle or microneedle adapted for intradermal or subcutaneous delivery of the composition. For example, the device may be a microneedle or a device comprising a plurality of microneedles designed for intradermal delivery of liquids, e.g. as described in international patent applications WO14064543 A1, WO05049107 A2, WO06054280 A2, WO07066341 A3 and WO14188429 A1.

Therapy

Compositions (e.g. peptide combinations) described herein may be used for the treatment of an immune response or allergy to a grass allergen, in a subject in need thereof. Allergy to a grass allergen may be clinically presented in the subject as atopic dermatitis, urticaria, contact dermatitis, allergic conjunctivitis, allergic rhinitis, allergic asthma, anaphylaxis, and/or hay fever. Therefore, in some aspects of the present invention, the method comprises decreasing, reducing, suppressing or inhibiting atopic dermatitis, urticaria, contact dermatitis, allergic conjunctivitis, allergic rhinitis, allergic asthma, anaphylaxis, and/or hay fever.

The phrase "treatment of an immune response" or "treating an immune response" may encompass preventing, relieving, alleviating, reducing, inhibiting, decreasing, or suppressing an immune response, for example an allergic immune response, such as an immune response against an allergen of a grass species. The treatment of an immune response may also include the decrease, inhibition, suppression or reduction of a T cell response, which may include, but is not limited to, a Th2 cell response or a memory T cell response. Furthermore, the treatment of an immune response described herein may also comprise inducing, promoting, increasing or enhancing proliferation of regulatory T cells while optionally decreasing, reducing, inhibiting, suppressing or reducing production of pro-inflammatory lymphokines/cytokines.

Therefore, in some aspects, the invention relates to a method for relieving an immune response to an allergen of a grass species in a subject in need thereof, comprising administering to said subject a therapeutically effective amount of a composition described herein (e.g. a peptide combination described herein).

In other aspects, the administration of a composition described herein may induce immunological tolerance against the allergen(s) of grass species.

Thus, compositions disclosed herein may produce a therapeutic or beneficial effect, which optionally may be objectively or subjectively measurable. A therapeutic or beneficial effect can, but need not, be complete ablation of all or any immune response, or one or more symptoms caused by or associated with an allergen. Thus, a satisfactory clinical result is achieved when there is an incremental improvement or a partial reduction in an immune response or one or more symptoms caused by or associated with an allergen, or there is an inhibition, decrease, reduction, suppression, prevention, limit or control of worsening or progression of an immune response or one or more symptoms caused by or associated with an allergen over a short or long duration (hours, days, weeks, months, etc.).

Therefore, in still other aspects, the subject's administration of a therapeutically effective amount of a composition described herein may relieve one or more symptoms of the immune response. For example, the method may comprise relieving one or more symptoms associated with allergic rhinitis, allergic conjunctivitis, allergic asthma and/or allergic eczema (e.g. atopic dermatitis).

In some embodiments, the one or more symptoms may be associated with allergic rhinitis. For example, the method may comprise reducing one or more of the following symptoms: intensity of itchy nose; number of sneezes within a given period (e.g. daily, weekly, monthly); intensity of blocked nose (e.g. congestion); amount of nasal secretions; eosinophilic count in nasal secretions; specific IgE antibody level (titer) in nasal secretions or in serum; and basophil histamine release of blood.

In other embodiments, the one or more symptoms may be associated with allergic conjunctivitis. For example, the method may comprise reducing one or more of the following symptoms: intensity of itchy eyes, redness in the white of the eyes and/or watery eyes; eosinophilic count in conjunctival tissue scrapings; specific IgE antibody level (titer) in conjunctival tissue scrapings or in serum; and basophil histamine release in blood.

In some embodiments, the one or more symptoms may be associated with allergic asthma. For example, the method may comprise reducing one or more of the following symptoms: number of or frequency of asthma exacerbations (optionally that require hospitalization), intensity and/or number of coughs within a given period (e.g. daily, weekly, monthly); intensity of wheezes; intensity of shortness of breath or congestion (e.g. improvement of being short of breath); reducing Forced Expiratory Volume (FEV1); reducing specific IgE antibody level (titer) in lung fluid or in serum and basophil histamine release in blood; or the method may comprise improving lung function.

In some embodiments, the one or more symptoms may be symptoms associated with atopic dermatitis. For example, the method may comprise reducing one or more of the following symptoms: itch intensity of the skin; eczema score, and number of (peripheral) blood eosinophils.

A therapeutic or beneficial effect also includes reducing or eliminating the need, dosage frequency or amount of a second therapeutic method or therapeutically active drug (e.g. anti-inflammatory, decongestants or anti-allergic agent) used for treating a subject having an immune response or one or more symptoms caused by or associated with an allergen. For example, administration of a peptide combination described herein may reduce the amount of an adjunct therapy administered to a subject, such as reducing the subject's need for concomitant treatment with fast or long-acting β2-agonists, leukotriene modifiers, theophylline corticosteroids or H1 antihistamines (e.g. inhaled or oral) to reduce, relieve, or suppress one or more symptoms of the immune response.

As used herein, the term "immune response" includes T cell (cellular) mediated and/or B cell (humoral) mediated immune responses, or both cellular and humoral responses. In particular, the term "immune response" may include an IgE-mediated immune response (i.e. an allergic immune response). Exemplary immune responses include T cell responses, such as Th2 responses resulting in cytokine production and/or cellular cytotoxicity. In addition, the term "immune response" includes responses that are indirectly affected by T cell activation, e.g., antibody production (humoral responses) and activation of cytokine responsive cells, e.g., eosinophils, macrophages. Immune cells involved in the immune response include lymphocytes, such as T cells (CD4+, CD8+, Th1 and Th2 cells, memory T cells) and B cells; antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer (NK) cells; and myeloid cells, such as macrophages, eosinophils, mast cells, basophils, and granulocytes. A particular immune response is production of immunoglobulin (Ig) isotypes antibodies or decreasing IgE antibodies.

Therefore, in some embodiments, the method comprises inducing or increasing an IgG antibody (e.g. specific IgG) response in a subject to an allergen of a grass species. In still some embodiments, the method comprises decreasing an IgE antibody (e.g. specific IgE) response in a subject to an allergen of a grass species. In still some embodiments, the method comprises decreasing a T cell response in a subject to an allergen of a grass species, for example decreasing the production of Th-2 associated cytokines, like IL-5, IL-4, IL-13 in response to said allergen.

The term "modulating an immune response" or "modulate an immune response" may include to stimulate, induce, promote, increase or enhance an immune response, e.g. a T cell regulatory response, or may include inhibiting, decreasing, suppressing or reducing a T cell response, which may include, but is not limited to a Th2 cell response.

Without being limited to a particular mechanism of action, a peptide combination of the invention may modulate, such as suppress a T cell or an antibody response. For example, a T cell response and/or antibody response triggered by a grass allergen may be suppressed or inhibited by a peptide combination described herein. Typically, a T cell response is associated with a cytokine response, e.g. IL-2, IL-3, IL-4, IL-5, IL-6, IL-9, IL-10, IL-12, IL-13, IL-17, IL-22, IL-31 or IFN-g response. In particular embodiments, the T cell response against a grass allergen may result in decreased production in a subset of the cytokines, for example cytokines associated with a Th2-mediated response (e.g. IL-4, IL-5 and/or IL-13), and may optionally also result in increased production of cytokines associated with a Tregs (e.g. IL-10).

As mentioned, peptide combinations described herein may provide a beneficial effect on an immune response against a grass allergen. Exemplary grasses are Timothy grass, Bermuda grass, Rye grass, Johnson grass, Canary grass.

A grass allergen may be a group 1 allergen, a group 2 allergen, a group 3 allergen, a group 4 allergen or a group 5 allergen.

Typically, the grass allergen is a major grass allergen, for example a grass group 1 allergen such as Phl p 1, Lol p 1, Pha a 1, Cyn d 1, Poa p 1; or a grass group 5 allergen such as Phl p 5, Lol p 5, Pha a 5, Cyn d 5, Poa p 5.

Typically, the treatment comprises repeated administration of the composition with weekly, bi-weekly, monthly or quarterly intervals. Thus, in a particular embodiment, the treatment comprises immunotherapy with single doses repeatedly administered until a persistent effect is achieved. Immunotherapy is thought to produce immunological tolerance in the subject undergoing therapy. Thus, in still other embodiments, the compositions, such as peptide combinations, may be used to induce immunological tolerance in a subject in need thereof.

As used herein, the term "immunological tolerance" refers to a) a decreased or reduced level of a specific immunological response (thought to be mediated at least in part by antigen-specific effector T lymphocytes, B lymphocytes, antibodies, or a combination thereof); b) a delay in the onset or progression of a specific immunological response; or c) a reduced risk of the onset or progression of a specific immunological response (e.g. to a grass allergen). An increase, improvement, enhancement or induction of "tolerance" may refer to a decrease, reduction, inhibition, suppression, or limiting or controlling or clearing of specific immunological reactivity to an allergen as compared to reactivity to the allergen in a previous exposure to the same allergen. Thus, in certain embodiments, the method comprises inducing immunological tolerance in a subject to an allergen (e.g. grass allergen) to suppress an allergic immune response to the allergen. Immunological tolerance in a subject to an allergen can also be reflected by reducing the occurrence, frequency, severity, progression, or duration of an allergic response of the subject to the allergen. Induction of immune tolerance (also referred to as desensitization), and the relative amount of immune tolerance, can be measured by methods disclosed herein or known to the skilled artisan. For example, induction of immune tolerance can be measured by the modulated lymphokine and/or cytokine level in a subject or animal before versus after administering a peptide combination described herein for the first time. A modulated cytokine level can be an increase of a cytokine level, for instance an increase of a lymphokine and/or cytokine level of at least 1.5, 2, 3, 4, 5, 6, 7, 8, 10, 20, 50 times or more relative to before administering the peptide combination for the first time. Alternatively, modulation can be a decrease of the level of a particular cytokine level, for instance a decrease of the lymphokine and/or cytokine level of at least 1.5, 2, 3, 4, 5, 6, 7, 8, 10, 20, 50 times or more relative to before administering the peptide combination for the first time. The lymphokines/cytokines chosen to measure can be from any relevant lymphokines/cytokines, such as IL-2, IL-5, IL-4, IL-6, IL-10, IL-12, IL-13, IL-17, TNF-alfa, IFN-gamma, TGF-beta, MCP-1, RANK-L and Flt3L. Accordingly, the term "inducing immunological tolerance" may include eliciting, stimulating, promoting, increasing or enhancing immunological tolerance. Immunological tolerance may involve modulation of T cell activity, including but not limited to CD4+ T cells, CD8+ T cells, Th1 cells, Th2 cells and regulatory T cells (Tregs), and memory T cells, including inflammatory lymphokines/cytokines produced by T cells.

Administration

A peptide combination is typically administered by injection, such as by subcutaneous or intradermal administration, but may also include other routes of administration, such as epicutaneous, rectal, sublingual, oral, buccal, intranasal, respiratory and intralymphatic route of administration.

The peptide combination may be administered to any subject in need thereof, for example a human, a pet such as a dog or a cat, a domestic animal such as a horse, or a laboratory animal like a mouse, a guinea pig or a rabbit. The subject may be sensitized to an allergen of a grass allergen (e.g. having specific IgE antibodies against an allergen of a grass species and/or having a T cell response against a grass species). Therefore, a subject in need thereof may produce specific IgE antibodies or a T cell response against grass allergens, and optionally other grass allergens as described supra including an aqueous extract of one or more grass species.

The peptide combination may be administered in clinically relevant doses, such as therapeutically sufficient doses. For example, a single dose of each peptide of the composition may be in the range of 1 to 1000 nanomole, for example 1 to 500 nanomole, for example 1 to 250 nanomole, for example 5 to 250 nanomole, which single dose may be repeated once daily, weekly, biweekly or monthly or quarterly. Typically, the peptide combination is a liquid administered in a volume of about 50 to 150 microliter, such as by intradermal administration.

The compositions described herein may be dosed in a dosage regimen usually applied in the field of allergy immunotherapy, such as peptide allergy immunotherapy. For example, compositions may be administered as a single dose (e.g. one injection) with daily, weekly, bi-weekly, monthly or quarterly intervals over a period of at least 2-6 months or even longer until a more persistent effect is achieved. The term "persistent effect" means that one or more clinically relevant symptoms of the immune response is reduced in the subject when exposed to an allergen of a grass species compared to before the subject is administered the first dose. A persistent effect may be evaluated at least two months after the subject has stopped treatment, such as after at least three, four, five, six, nine or twelve months. It is also envisaged that the treatment is initiated by an up-dosing phase with the peptide combination being administered in increasing doses within one day or with daily, weekly or bi-weekly intervals until the target maintenance dose is achieved.

The subject administered a peptide combination described herein may optionally also be administered another therapeutic agent used for treating an immune response against a grass allergen. However, in some embodiments, the subject is not co-administered the peptide combination of another immunogen, e.g. an allergen extract or allergen, e.g. allergen extract or allergen of a grass species. Thus, in certain embodiments, a composition described herein may not comprise an allergen extract.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

A another aspect of the invention relates to an in vitro method of determining whether T cells of a subject in need of treatment recognize a composition as described herein, comprising contacting T cells obtained from the subject with said composition or a single peptide thereof and detecting whether the T cells are stimulated by said composition or single peptide. The in vitro method may be used to determine whether the subject has, or is at risk of developing, an allergy to a grass allergen.

FURTHER EMBODIMENTS OF THE INVENTION

In another aspect the present invention relates to a composition comprising at least three peptides, wherein two of the at least three peptides are selected from any two of the peptide groups 1-11; and wherein the third of the at least three peptides is selected from any one of the peptide groups 1-34 and wherein the third peptide is selected from a peptide group different from either of the peptide groups of the at least two peptides, the peptide groups being:

Group 1: a parent peptide with the amino acid sequence SEQ ID NO: 64 (peptide 231); or a variant thereof;
Group 2: a parent peptide with the amino acid sequence SEQ ID NO: 73 (peptide 240); or a variant thereof;
Group 3: a parent peptide with the amino acid sequence SEQ ID NO: 233 (peptide 286); or a variant thereof;
Group 4: a parent peptide with the amino acid sequence SEQ ID NO: 232 (peptide 285); or a variant thereof;
Group 5: a parent peptide with the amino acid sequence SEQ ID NO: 66 (peptide 233); or a variant thereof;
Group 6: a parent peptide with the amino acid sequence SEQ ID NO: 61 (peptide 228); or a variant thereof;
Group 7: a parent peptide with the amino acid sequence SEQ ID NO: 62 (peptide 229); or a variant thereof;
Group 8: a parent peptide with the amino acid sequence SEQ ID NO: 63 (peptide 230); or a variant thereof;
Group 9: a parent peptide with the amino acid sequence SEQ ID NO: 65 (peptide 232); or a variant thereof;
Group 10: a parent peptide with the amino acid sequence SEQ ID NO: 67 (peptide 234); or a variant thereof;
Group 11: a parent peptide with the amino acid sequence SEQ ID NO: 70 (peptide 237); or a variant thereof;
Group 12: a parent peptide with the amino acid sequence SEQ ID NO: 7 (peptide 207); or a variant thereof;
Group 13: a parent peptide with the amino acid sequence SEQ ID NO: 8 (peptide 208); or a variant thereof;

Group 14: a parent peptide with the amino acid sequence SEQ ID NO: 11 (peptide 211); or a variant thereof;
Group 15: a parent peptide with the amino acid sequence SEQ ID NO: 1 (peptide 201); or a variant thereof;
Group 16: a parent peptide with the amino acid sequence SEQ ID NO: 3 (peptide 203); or a variant thereof;
Group 17: a parent peptide with the amino acid sequence SEQ ID NO: 4 (peptide 204); or a variant thereof;
Group 18: a parent peptide with the amino acid sequence SEQ ID NO: 5 (peptide 205); or a variant thereof;
Group 19: a parent peptide with the amino acid sequence SEQ ID NO: 9 (peptide 209); or a variant thereof;
Group 20: a parent peptide with the amino acid sequence SEQ ID NO: 10 (peptide 210); or a variant thereof;
Group 21: a parent peptide with the amino acid sequence SEQ ID NO: 12 (peptide 212); or a variant thereof;
Group 22: a parent peptide with the amino acid sequence SEQ ID NO: 13 (peptide 213); or a variant thereof;
Group 23: a parent peptide with the amino acid sequence SEQ ID NO: 28 (peptide 215); or a variant thereof;
Group 24: a parent peptide with the amino acid sequence SEQ ID NO: 29 (peptide 216); or a variant thereof;
Group 25: a parent peptide with the amino acid sequence SEQ ID NO: 36 (peptide 217); or a variant thereof;
Group 26: a parent peptide with the amino acid sequence SEQ ID NO: 38 (peptide 219); or a variant thereof;
Group 27 a parent peptide with the amino acid sequence SEQ ID NO: 39 (peptide 220); or a variant thereof;
Group 28: a parent peptide with the amino acid sequence SEQ ID NO: 40 (peptide 221); or a variant thereof;
Group 29: a parent peptide with the amino acid sequence SEQ ID NO: 45 (peptide 222); or a variant thereof;
Group 30: a parent peptide with the amino acid sequence SEQ ID NO: 46 (peptide 223); or a variant thereof;
Group 31: a parent peptide with the amino acid sequence SEQ ID NO: 47 (peptide 224); or a variant thereof;
Group 32: a parent peptide with the amino acid sequence SEQ ID NO: 48 (peptide 225); or a variant thereof;
Group 33: a parent peptide with the amino acid sequence SEQ ID NO: 49 (peptide 226); or a variant thereof;
Group 34: a parent peptide with the amino acid sequence SEQ ID NO: 50 (peptide 227); or a variant thereof.

Peptides from peptide groups 1-11 correspond to a region of the grass allergens group 5, peptides from peptide groups 12-22 correspond to a region of the grass allergens group 1, peptides from peptide groups 23-24 correspond to a region of the group 2 grass allergens, peptides from peptide groups 25-28 correspond to a region of the grass allergens group 3, and peptides from peptide groups 29-34 correspond to a region of the group 4 grass allergens.

Compositions according to the invention will have a high donor coverage and/or high HLA Class II coverage and/or high predicted peptide binding valency and/or a high donor response valency, in particular, when compared to the number of peptides included in the composition (relative valency or contribution to valency per peptide in the composition). Accordingly, in one embodiment the composition will comprise at least two peptides from grass allergen group 5 and a third peptide from a grass allergen group 1 or a grass allergen group 5 allergen. The present inventors have found that especially the selected grass allergen group 5 peptides are very potent in inducing a significant T cell response in PBMCs from a large fraction of donors (cytokine response and/or proliferation). Accordingly, in one embodiment a peptide combination comprising only selected peptides derived from grass allergen group 5 may be potent enough to induce a T cell response in the PBMC's of more than 90% of the donor cohort tested. Other peptide combinations comprising selected peptides derived from both grass allergen group 1 and 5 are potent enough to induce a T cell response in the PBMC's of 90-100% of the donor cohort tested.

In one embodiment, a composition as disclosed herein comprises at least three peptides, wherein one of the at least three peptides is selected from peptide group 1; and wherein two of the at least three peptides are selected from any two of the peptide groups 2-34, the peptide groups being as defined above. Peptides from peptide group 1 of the invention have not previously been recognized as comprising important T cell epitopes. However, the present inventors have now found that such a peptide (e.g. peptide 231) comprises T cell epitopes recognized by a great fraction of the population. Accordingly peptide 231 produced a T cell response in ~40% of the donors tested and it has a predicted HLA coverage of 99%. Such a peptide will have a high contribution to the valency of the compositions as disclosed herein (both donor response and predicted peptide binding).

In another embodiment, a composition as disclosed herein comprises at least three peptides, wherein one of the at least three peptides is selected from peptide group 2; and wherein two of the at least three peptides are selected from any of the peptide groups 1 and 3-34, the peptide groups being as defined above. Various peptides from peptide group 2 of the invention have previously been recognized as comprising important T cell epitopes. Accordingly peptide 240 produced a T cell response in >50% of the donors tested and it has a predicted HLA coverage of ~100%. Such a peptide will have a high contribution to the valency of the composition (both donor response and predicted peptide binding). The present inventors have further found that a peptide from peptide group 2 (e.g. peptide 240) even though it comprises T cell epitopes recognized by a great fraction of the population seems to have some solubility issues in aqueous solutions.

In another embodiment a composition as disclosed herein comprises at least three peptides, wherein one of the at least three peptides is selected from peptide group 3; and wherein two of the at least three peptides are selected from any two of the peptide groups 1-2 and 4-34, the peptide groups being as defined above. Various peptides from peptide group 3 of the invention have previously been recognized as comprising important T cell epitopes. Accordingly peptides 235, 241 and 286 produced a T cell response in >60% of the donors tested and it has a predicted HLA coverage of ~93%, ~71% and ~93%, respectively. Such a peptide will have a high contribution to the valency of the composition (both donor response and predicted peptide binding). The present inventors have further found that a peptide from peptide group 3 (e.g. peptides 286, 235 and 241) in addition to comprising T cell epitopes recognized by a great fraction of the population have a surprisingly good solubility in aqueous solutions.

In another embodiment, a composition as disclosed herein comprises at least three peptides, wherein one of the at least three peptides is selected from peptide group 4; and wherein two of the at least three peptides are selected from any two of the peptide groups 1-3 and 5-34, the peptide groups being as defined above. Various peptides from peptide group 4 of the invention, have previously been recognized as comprising important T cell epitopes. Accordingly peptides 238, 239 and 285 produce a T cell response in ~50% of the donors tested and have a predicted HLA coverage of ~99%, ~76% and ~99%, respectively. Such a peptide will have a high contribution to the valency of the composition (both donor response and predicted peptide binding). The present inventors have further found that a peptide from peptide group 4

(e.g. peptide 285, 238 and 239) in addition to comprising T cell epitopes recognized by a great fraction of the population have surprisingly good solubility in aqueous solutions.

In another embodiment, a composition as disclosed herein comprises at least three peptides, wherein one of the at least three peptides is selected from peptide group 12; and wherein two of the at least three peptides are selected from any two of the peptide groups 1-11 and 13-34, the peptide groups being as defined above. A peptide from peptide group 12 of the invention has not previously been recognized as comprising important T cell epitopes. However, the present inventors have now found that such a peptide (e.g. peptide 207) comprises T cell epitopes recognized by a great fraction of the population. Also, the present inventors have now found that such a peptide in addition to comprising T cell epitopes recognized by a great fraction of the population has a surprisingly good solubility in aqueous solutions. Accordingly peptide 207 produced a T cell response in ~40% of the donors tested and it has a predicted HLA coverage of 80%. Such a peptide will have a high contribution to the valency of the composition (both donor response and predicted peptide binding).

In another embodiment, a composition as disclosed herein comprises at least three peptides, wherein one of the at least three peptides is selected from peptide group 13; and wherein two of the at least three peptides are selected from any two of the peptide groups 1-12 and 14-34, the peptide groups being as defined above. A peptide from group 13 of the invention has not previously been recognized as comprising important T cell epitopes. The present inventors have now found that such a peptide (e.g. peptide 208) comprises T cell epitopes recognized by a great fraction of the population. Accordingly peptide 208 produced a T cell response in <70% of the donors tested and it has a predicted HLA coverage of 68%. Such a peptide will have a high contribution to the valency of the composition (both donor response and predicted peptide binding). However, the present inventors have also found that a peptide from peptide group 13 (e.g. peptide 208) even though it comprises T cell epitopes recognized by a great fraction of the population seems to have some solubility issues in aqueous solutions.

In another embodiment, a composition as disclosed herein comprises at least three peptides, wherein one of the at least three peptides is selected from peptide group 14; and wherein two of the at least three peptides are selected from any two of the peptide groups 1-13 and 15-34, the peptide groups being as defined above. A peptide from group 14 of the invention has previously been recognized as comprising important T cell epitopes. However, the present inventors have now found that such a peptide (e.g. peptide 211) is predicted to bind to a DRB1 allele which is present in the world wide population at a high frequency and which is predicted to bind to very few grass allergen derived peptides. Also, the present inventors have now found that such a peptide in addition to comprising T cell epitopes recognized by a great fraction of the population has surprisingly good solubility in aqueous solutions. Accordingly peptide 211 produced a T cell response in ~40% of the donors tested and it has a predicted HLA coverage of 45%. Such a peptide will have a high contribution to the valency of the composition (both donor response and predicted peptide binding).

In another embodiment, a composition as disclosed herein comprises at least three peptides, wherein one of the at least three peptides is selected from peptide group 17; and wherein two of the at least three peptides are selected from any two of the peptide groups 1-16 and 18-34, the peptide groups being as defined above. A peptide from group 17 of the invention has previously been recognized as comprising important T cell epitopes. However, the present inventors have now found that such a peptide (e.g. peptide 204) is predicted to bind to a DRB1 allele which is present in the world wide population at a high frequency and which is predicted to bind to very few grass allergen derived peptides. Also, the present inventors have now found that such a peptide in addition to comprising T cell epitopes recognized by a great fraction of the population has surprisingly good solubility in aqueous solutions. Accordingly peptide 204 produced a T cell response in ~40% of the donors tested and it has a predicted HLA coverage of 26%. Such a peptide will have a high contribution to the valency of the composition (both donor response and predicted peptide binding).

In another embodiment a composition as disclosed herein comprises at least three peptides, wherein the at least three peptides are selected from at least three of the peptide groups 1-34 as defined above; and wherein the composition has a predicted peptide binding valency above 0.5.

Such a composition will be particularly suitable to be included in a pharmaceutical composition for use in immunotherapy. The present inventors have surprisingly found that compositions having a predicted peptide binding valency above 0.5 tend to produce a higher donor coverage and a higher strength of response in the donors tested than a composition having a lower predicted peptide binding valency even though the number of peptides are the same. The present inventors have surprisingly found that an advantage of such compositions is that the peptide dose can be lowered significantly with only little effect on the donor coverage and response strength. When the peptide dose can be lowered, the formulation of the active ingredients into a pharmaceutical product is in general easier.

In another embodiment a composition as disclosed herein comprises at least three peptides, wherein the at least three peptides are selected from at least three of the peptide groups 1-34 as defined above;
and wherein the composition has a donor response valency above 0.3.

Such a composition will be suitable for including in a pharmaceutical composition for use in immunotherapy. The present inventors have surprisingly found that compositions having a donor response valency above 0.3 tend to produce a higher donor coverage and a higher strength of response in the donors tested than a composition having a lower predicted peptide binding valency even though the number of peptides are the same. The present inventors have surprisingly found that an advantage of such compositions is that the peptide dose can be lowered without affecting the donor coverage and response strength much. When the peptide dose can be lowered, the formulation of the active ingredients into a pharmaceutical product is in general easier.

In another embodiment, a composition as disclosed herein comprises at least three peptides, wherein the at least three peptides are selected from at least three of the peptide groups 1-34 as defined above;
and wherein the pI of the peptides of the composition are within a range of 3 pI units.

The present inventors have surprisingly found that by limiting the span of the pIs of each peptide to be within a range of 3, the formulation of the composition into a pharmaceutical product becomes easier in that the solubility properties of the peptides are more similar thus having similar pH requirements. Examples of such ranges are: $2 \leq pI \leq 5$, $3 \leq pI \leq 6$, $4 \leq pI \leq 7$, $5 \leq pI \leq 8$, $6 \leq pI \leq 9$, $7 \leq pI \leq 10$, 8≤pI≤11 or 9≤pI≤12. It is even more advantageous if the pI range is even more narrow such as within a range of 2.5, 2, 1.5 or 1.

In another embodiment, a composition as disclosed herein comprises at least three peptides, wherein two of the at least three peptides are selected from any two of the peptide groups 1-5, and wherein the third of the at least three peptides is selected from any one of the peptide groups 12-14 and 17; and wherein the composition comprises a fourth peptide selected from any one of the peptide groups 1-5, 12-14 and 17, and wherein the fourth peptide is selected from a peptide group different from the peptide groups of the three other peptides of the at least three peptides;
and wherein the four peptides selected have been selected such that two peptides have been selected from any of the peptide groups 3, 4, 13 and 14, and two peptides have been selected from any of the peptide groups 1, 2, 4, 5 and 12; the peptide groups being as defined in claim 1.

The present inventors have surprisingly found, that peptides selected from any one of peptide groups 3, 4, 13 or 14 supplement peptides selected from any one of peptide groups 1, 2, 3, 5 or 12 particularly well with regard to HLA coverage in a worldwide population. Therefore compositions comprising two peptides from each of these two groups result in superior peptide combinations which due to the high donor coverage and high predicted HLA coverage of each of the peptides will have very high peptide valency (both the predicted peptide binding valency and the donor response valency as well as relative valencies). In certain embodiments the peptides of the compositions are selected such that the compositions comprise at least two peptides from a grass allergen of group 5 and at least one peptide from a grass allergen of group 1, whereas the fourth peptide may be selected from a grass allergen of group 1 or group 5. In certain embodiments the compositions comprise no other grass peptides eliciting a T cell response in an allergic individual. In other embodiments, the compositions comprise further, such as 1, 2 or 3 further grass peptides eliciting a T cell response in an allergic individual. In certain embodiments, such mixes will be efficient for use in immunotherapy and may be formulated at lower doses and with fewer peptides than compositions according to prior art.

ITEMS

The following items 1 to 124 further describe the present invention:

Item

1. A composition comprising at least three peptides, wherein two of the at least three peptides are selected from any two of the peptide groups 1-11; and wherein the third of the at least three peptides is selected from any one of the peptide groups 1-34 and wherein the third peptide is selected from a peptide group different from either of the peptide groups of the at least two peptides, the peptide groups being:

Group 1: a parent peptide with the amino acid sequence SEQ ID NO: 64 (peptide 231); or a variant thereof;
Group 2: a parent peptide with the amino acid sequence SEQ ID NO: 73 (peptide 240); or a variant thereof;
Group 3: a parent peptide with the amino acid sequence SEQ ID NO: 233 (peptide 286); or a variant thereof;
Group 4: a parent peptide with the amino acid sequence SEQ ID NO: 232 (peptide 285); or a variant thereof;
Group 5: a parent peptide with the amino acid sequence SEQ ID NO: 66 (peptide 233); or a variant thereof;
Group 6: a parent peptide with the amino acid sequence SEQ ID NO: 61 (peptide 228); or a variant thereof;
Group 7: a parent peptide with the amino acid sequence SEQ ID NO: 62 (peptide 229); or a variant thereof;
Group 8: a parent peptide with the amino acid sequence SEQ ID NO: 63 (peptide 230); or a variant thereof;
Group 9: a parent peptide with the amino acid sequence SEQ ID NO: 65 (peptide 232); or a variant thereof;
Group 10: a parent peptide with the amino acid sequence SEQ ID NO: 67 (peptide 234); or a variant thereof;
Group 11: a parent peptide with the amino acid sequence SEQ ID NO: 70 (peptide 237); or a variant thereof;
Group 12: a parent peptide with the amino acid sequence SEQ ID NO: 7 (peptide 207); or a variant thereof;
Group 13: a parent peptide with the amino acid sequence SEQ ID NO: 8 (peptide 208); or a variant thereof;
Group 14: a parent peptide with the amino acid sequence SEQ ID NO: 11 (peptide 211); or a variant thereof;
Group 15: a parent peptide with the amino acid sequence SEQ ID NO: 1 (peptide 201); or a variant thereof;
Group 16: a parent peptide with the amino acid sequence SEQ ID NO: 3 (peptide 203); or a variant thereof;
Group 17: a parent peptide with the amino acid sequence SEQ ID NO: 4 (peptide 204); or a variant thereof;
Group 18: a parent peptide with the amino acid sequence SEQ ID NO: 5 (peptide 205); or a variant thereof;
Group 19: a parent peptide with the amino acid sequence SEQ ID NO: 9 (peptide 209); or a variant thereof;
Group 20: a parent peptide with the amino acid sequence SEQ ID NO: 10 (peptide 210); or a variant thereof;
Group 21: a parent peptide with the amino acid sequence SEQ ID NO: 12 (peptide 212); or a variant thereof;
Group 22: a parent peptide with the amino acid sequence SEQ ID NO: 13 (peptide 213); or a variant thereof;
Group 23: a parent peptide with the amino acid sequence SEQ ID NO: 28 (peptide 215); or a variant thereof;
Group 24: a parent peptide with the amino acid sequence SEQ ID NO: 29 (peptide 216); or a variant thereof;
Group 25: a parent peptide with the amino acid sequence SEQ ID NO: 36 (peptide 217); or a variant thereof;
Group 26: a parent peptide with the amino acid sequence SEQ ID NO: 38 (peptide 219); or a variant thereof;
Group 27 a parent peptide with the amino acid sequence SEQ ID NO: 39 (peptide 220); or a variant thereof;
Group 28: a parent peptide with the amino acid sequence SEQ ID NO: 40 (peptide 221); or a variant thereof;
Group 29: a parent peptide with the amino acid sequence SEQ ID NO: 45 (peptide 222); or a variant thereof;
Group 30: a parent peptide with the amino acid sequence SEQ ID NO: 46 (peptide 223); or a variant thereof;
Group 31: a parent peptide with the amino acid sequence SEQ ID NO: 47 (peptide 224); or a variant thereof;
Group 32: a parent peptide with the amino acid sequence SEQ ID NO: 48 (peptide 225); or a variant thereof;
Group 33: a parent peptide with the amino acid sequence SEQ ID NO: 49 (peptide 226); or a variant thereof;
Group 34: a parent peptide with the amino acid sequence SEQ ID NO: 50 (peptide 227); or a variant thereof.

2. A composition comprising at least three peptides, wherein one of the at least three peptides is selected from peptide group 1; and wherein two of the at least three peptides are selected from any two of the peptide groups 2-34, the peptide groups being as defined in item 1.

3. A composition comprising at least three peptides, wherein one of the at least three peptides is selected from peptide group 2; and wherein two of the at least three peptides are selected from any two of the peptide groups 1 and 3-34, the peptide groups being as defined in item 1.

4. A composition comprising at least three peptides, wherein one of the at least three peptides is selected from peptide group 3; and wherein two of the at least three peptides are selected from any two of the peptide groups 1-2 and 4-34, the peptide groups being as defined in item 1.

5. A composition comprising at least three peptides, wherein one of the at least three peptides is selected from peptide group 4; and wherein two of the at least three peptides are selected from any two of the peptide groups 1-3 and 5-34, the peptide groups being as defined in item 1.

6. A composition comprising at least three peptides, wherein one of the at least three peptides is selected from peptide group 12; and wherein two of the at least three peptides are selected from any two of the peptide groups 1-11 and 13-34, the peptide groups being as defined in item 1.

7. A composition comprising at least three peptides, wherein one of the at least three peptides is selected from peptide group 13; and wherein two of the at least three peptides are selected from any two of the peptide groups 1-12 and 14-34, the peptide groups being as defined in item 1.

8. A composition comprising at least three peptides, wherein one of the at least three peptides is selected from peptide group 14; and wherein two of the at least three peptides are selected from any two of the peptide groups 1-13 and 15-34, the peptide groups being as defined in item 1.

9. A composition comprising at least three peptides, wherein one of the at least three peptides is selected from peptide group 17; and wherein two of the at least three peptides are selected from any of the peptide groups 1-16 and 18-34, the peptide groups being as defined in item 1.

10. A composition comprising at least three peptides, wherein the at least three peptides are selected from at least three of the peptide groups 1-34 as defined in item 1; and wherein the composition has a predicted peptide binding valency above 0.5.

11. A composition comprising at least three peptides, wherein the at least three peptides are selected from at least three of the peptide groups 1-34 as defined in item 1; and wherein the composition has a donor response valence above 0.3.

12. A composition comprising at least three peptides, wherein the at least three peptides are selected from at least three of the peptide groups 1-34 as defined in item 1; and wherein the pI of the peptides of the composition are within a range of 3.

13. A composition comprising at least three peptides, wherein two of the at least three peptides are selected from any two of the peptide groups 1-11; and wherein the third of the at least three peptides is selected from any one of the peptide groups 1-34 and wherein the third peptide is selected from a peptide group different from the peptide groups of the at least two peptides, the peptide groups being:

Group 1: a parent peptide with the amino acid sequence SEQ ID NO: 64 (231) or WO2010/089554-0057; or a variant thereof;

Group 2: a parent peptide with the amino acid sequence SEQ ID NO: 73 (240), SEQ ID NO: 207 (249), SEQ ID NO: 208 (250), SEQ ID NO: 209 (251), SEQ ID NO: 210 (252), SEQ ID NO: 211 (253), SEQ ID NO: 185 (352), SEQ ID NO: 198 (365), WO2010/089554-0031 (Bio04A), WO2010/089554-0032, WO2010/089554-0045, WO2010/089554-0046 (Rye09B), WO2010/089554-0047, WO2010/089554-0053 (Tim10B), WO2010/089554-0054, WO2010/089554-0055, WO2010/089554-0061, WO2010/089554-0066, WO2010/089554-0073, WO2010/089554-0087, WO2010/089554-0088, WO2010/089554-0104, WO2010/089554-00, WO2010/089554-0110, WO2010/089554-0111, WO2010/089554-0135, WO2010/089554-0136, WO2010/089554-0137, WO2010/089554-0138, WO2010/089554-0139, WO2010/089554-0140 or US7112333-0024; or a variant thereof;

Group 3: a parent peptide with the amino acid sequence SEQ ID NO: 68 (235), SEQ ID NO: 129 (129), SEQ ID NO: 233 (286), SEQ ID NO: 69 (236), SEQ ID NO: 113 (241), SEQ ID NO: 222 (264), SEQ ID NO: 223 (265), SEQ ID NO: 228 (270), SEQ ID NO: 229 (271), SEQ ID NO: 233 (286), SEQ ID NO: 180 (347), SEQ ID NO: 181 (348), SEQ ID NO: 186 (353), SEQ ID NO: 193 (360), SEQ ID NO: 194 (361), SEQ ID NO: 195 (362), SEQ ID NO: 199 (366), WO2010/089554-0038, WO2010/089554-0040, WO2010/089554-0041, WO2010/089554-0059, WO2010/089554-0064, WO2010/089554-0070 (Tim07G), WO2010/089554-0108, WO2010/089554-0124, WO2010/089554-0125, WO2010/089554-0126, WO2010/089554-0127, WO2010/089554-0128, WO2010/089554-0129, WO2010/089554-0130, WO2010/089554-0131, WO2010/089554-0132, US7112333-0018, US7112333-0019 or US7112333-0020; or a variant thereof;

Group 4: a parent peptide with the amino acid sequence SEQ ID NO: 232 (285), SEQ ID NO: 71 (238), SEQ ID NO: 72 (239), Rye08A, SEQ ID NO: 218 (260), B090261, SEQ ID NO: 224 (266), SEQ ID NO: 225 (267), SEQ ID NO: 226 (268), SEQ ID NO: 227 (269), SEQ ID NO: 220 (262), SEQ ID NO: 197 (364), SEQ ID NO: 183 (350), SEQ ID NO: 184 (351), SEQ ID NO: 196 (363), WO2010/089554-0029 (Bio03A), WO2010/089554-0030, WO2010/089554-0042, WO2010/089554-0043, WO2010/089554-0044, WO2010/089554-0060, WO2010/089554-0065, WO2010/089554-0071, WO2010/089554-0072, WO2010/089554-0082, WO2010/089554-0083, WO2010/089554-0103, WO2010/089554-0109, WO2010/089554-0133, WO2010/089554-0134, US7112333-0021, US7112333-0022, US7112333-0023 or WO2011/106645-0005; or a variant thereof;

Group 5: a parent peptide with the amino acid sequence SEQ ID NO: 66 (233), SEQ ID NO: 128 (128), SEQ ID NO: 178 (345), SEQ ID NO: 179 (346), SEQ ID NO: 205 (247), SEQ ID NO: 206 (248), WO2010/089554-0028 (Bio02A), WO2010/089554-0051, WO2010/089554-0063, WO2010/089554-0078, WO2010/089554-0079, WO2010/089554-0102, WO2010/089554-0122, US7112333-0013, US7112333-0014, US7112333-0015, WO2011/106645-0025 or WO2011/106645-0026; or a variant thereof;

Group 6: a parent peptide with the amino acid sequence SEQ ID NO: 61 (228), US7112333-0030 or US7112333-0031; or a variant thereof;

Group 7: a parent peptide with the amino acid sequence SEQ ID NO: 62 (229), WO2010/089554-0035, WO2010/089554-0056, WO2010/089554-0062, WO2010/089554-0106, WO2010/089554-0112, WO2010/089554-0119, WO2010/089554-0120, WO2010/089554-0121, US7112333-0006, US7112333-0007 or WO2011/106645-0023; or a variant thereof;

Group 8: a parent peptide with the amino acid sequence SEQ ID NO: 63 (230), SEQ ID NO: 124 (124), SEQ ID NO: 131 (131), SEQ ID NO: 133 (133), SEQ ID NO: 114 (242), 800276, SEQ ID NO: 1174 (341), SEQ ID NO: 175 (342), SEQ ID NO: 187 (354), SEQ ID NO: 189 (356), WO2010/089554-0035, WO2010/089554-0056, WO2010/089554-0062, WO2010/089554-0106, WO2010/089554-0112, WO2010/089554-0119, WO2010/089554-0120, WO2010/089554-0121, US7112333-0006, US7112333-0007 or WO2011/106645-0023; or a variant thereof;

Group 9: a parent peptide with the amino acid sequence SEQ ID NO: 65 (232), SEQ ID NO: 177 (344), WO2010/089554-0037, WO2010/089554-0058, WO2010/089554-0107, WO2010/089554-0123, US7112333-0012 or WO2011/106645-0004; or a variant thereof;

Group 10: a parent peptide with the amino acid sequence SEQ ID NO: 67 (234), SEQ ID NO: 128 (128), SEQ ID NO: 178 (345), SEQ ID NO: 179 (346), SEQ ID NO: 205 (247), SEQ ID NO: 206 (248), WO2010/089554-0028 (Bio02A), WO2010/089554-0051, WO2010/089554-0063, WO2010/089554-0078, WO2010/089554-0079, WO2010/089554-0102, WO2010/089554-0122, US7112333-0013, US7112333-0014, US7112333-0015, WO2011/106645-0025 or WO2011/106645-0026; or a variant thereof;

Group 11: a parent peptide with the amino acid sequence SEQ ID NO: 70 (237), WO2010/089554-0033, WO2010/089554-0052, WO2010/089554-0105, US7112333-0019 or US7112333-0020; or a variant thereof;

Group 12: a parent peptide with the amino acid sequence SEQ ID NO: 7 (207), SEQ ID NO: 150 (317), SEQ ID NO: 151 (318), SEQ ID NO: 6 (206), SEQ ID NO: 212 (254), SEQ ID NO: 213 (255), SEQ ID NO: 214 (256), B00275, SEQ ID NO: 137 (304), SEQ ID NO: 138 (305), SEQ ID NO: 118 (117), WO2010/089554-0020, US7112333-0042, US7112333-0043 or US7112333-0044; or a variant thereof;

Group 13: a parent peptide with the amino acid sequence SEQ ID NO: 8 (208), SEQ ID NO: 9 (209), SEQ ID NO: 201 (243), SEQ ID NO: 202 (244), SEQ ID NO: 231 (273), B00274, SEQ ID NO: 139 (306), SEQ ID NO: 140 (307), SEQ ID NO: 152 (319), SEQ ID NO: 121 (121), WO2010/089554-0015, WO2010/089554-0021, WO2010/089554-0026, WO2010/089554-0100, WO2010/089554-0114, US7112333-0045, US7112333-0046, US7112333-0047, US7112333-0048, US7112333-0049, WO94/21675-0031, WO94/21675-0032, WO94/21675-0033, WO94/21675-0034, WO94/21675-0035, WO94/21675-0036, WO94/21675-0037, WO94/21675-0038, WO94/21675-0039, WO94/21675-0040, WO94/21675-0041, WO94/21675-0042, WO94/21675-0061, WO94/21675-0062, WO94/21675-0063, WO94/21675-0064, US6008340-0020, WO2011/106645-0022 or WO2011/106645-0024; or a variant thereof;

Group 14: a parent peptide with the amino acid sequence SEQ ID NO: 11 (211), SEQ ID NO: 215 (257), SEQ ID NO: 216 (258), SEQ ID NO: 217 (259), SEQ ID NO: 221 (263), SEQ ID NO: 142 (309), WO2010/089554-0003, WO2010/089554-0006, WO2010/089554-0007, WO2010/089554-0016, WO2010/089554-0017, WO2010/089554-0018, WO2010/089554-0022, WO2010/089554-0027, WO2010/089554-0089, WO2010/089554-0096, WO2010/089554-0101, WO2010/089554-0115, WO2010/089554-0116, US7112333-0051, US7112333-0056, WO94/21675-0043, WO94/21675-0044, WO94/21675-0045, WO94/21675-0046, WO94/21675-0047, WO94/21675-0065 or WO94/21675-0066; or a variant thereof;

Group 15: a parent peptide with the amino acid sequence SEQ ID NO: 1 (201), SEQ ID NO: 119 (118), WO2010/089554-0011, WO2010/089554-0012, WO2010/089554-0098, US7112333-0032, US7112333-0034 or US7112333-0055; or a variant thereof;

Group 16: a parent peptide with the amino acid sequence SEQ ID NO: 2 (202), SEQ ID NO: 3 (203), US7112333-0037, US7112333-0038 or US7112333-0039; or a variant thereof;

Group 17: a parent peptide with the amino acid sequence SEQ ID NO: 4 (204), SEQ ID NO: 132 (132), SEQ ID NO: 148 (315), US7112333-0039, US7112333-0040, WO2011/106645-0001, US6008340-0005, US6008340-0007, US6008340-0009, US6008340-0014, US6008340-0015, US6008340-0016, US6008340-0017, US6008340-0018 or US6008340-0019; or a variant thereof;

Group 18: a parent peptide with the amino acid sequence SEQ ID NO: 5 (205), SEQ ID NO: 117 (116), SEQ ID NO: 136 (303), SEQ ID NO: 149 (316), WO2010/089554-0001 (Ber01), WO2010/089554-0010, WO2010/089554-0013, WO2010/089554-0019, WO2010/089554-0024, WO2010/089554-0025, WO2010/089554-0074, WO2010/089554-0075, WO2010/089554-0076, WO2010/089554-0077, WO2010/089554-0095, WO2010/089554-0099, WO2010/089554-0113, US7112333-0041, US7112333-0061 or US7112333-0062; or a variant thereof;

Group 19: a parent peptide with the amino acid sequence SEQ ID NO: 8 (208), SEQ ID NO: 9 (209), SEQ ID NO: 201 (243), SEQ ID NO: 202 (244), SEQ ID NO: 231 (273), B00274, SEQ ID NO: 139 (306), SEQ ID NO: 140 (307), SEQ ID NO: 152 (319), SEQ ID NO: 121 (121), WO2010/089554-0015, WO2010/089554-0021, WO2010/089554-0026, WO2010/089554-0100, WO2010/089554-0114, US7112333-0045, US7112333-0046, US7112333-0047, US7112333-0048, US7112333-0049, WO94/21675-0031, WO94/21675-0032, WO94/21675-0033, WO94/21675-0034, WO94/21675-0035, WO94/21675-0036, WO94/21675-0037, WO94/21675-0038, WO94/21675-0039, WO94/21675-0040, WO94/21675-0041, WO94/21675-0042, WO94/21675-0061, WO94/21675-0062, WO94/21675-0063, WO94/21675-0064, US6008340-0020, WO2011/106645-0022 or WO2011/106645-0024; or a variant thereof;

Group 20: a parent peptide with the amino acid sequence SEQ ID NO: 10 (210), SEQ ID NO: 203 (245), SEQ ID NO: 204 (246), SEQ ID NO: 154 (321), SEQ ID NO: 155 (322), WO2010/089554-0004 (Ber02B), WO2010/089554-0005 (Ber02C) or US7112333-0050; or a variant thereof;

Group 21: a parent peptide with the amino acid sequence SEQ ID NO: 12 (212), SEQ ID NO: 143 (310), SEQ ID NO: 144 (311), WO2010/089554-0023, WO2010/089554-0118, US7112333-0052, US7112333-0053, WO94/21675-0048, WO94/21675-0049, WO94/21675-0050, WO94/21675-0067, WO94/21675-0068, WO94/21675-0069, WO94/21675-0070, WO2011/106645-0002, US6008340-0021, US6008340-0022, US6008340-0023, US6008340-0024, US6008340-0025, US6008340-0026, US6008340-0027 or US6008340-0028; or a variant thereof;

Group 22: a parent peptide with the amino acid sequence SEQ ID NO: 13 (213), SEQ ID NO: 143 (310), SEQ ID NO: 144 (311), WO2010/089554-0023, WO2010/089554-0118, US7112333-0052, US7112333-0053, WO94/21675-0048, WO94/21675-0049, WO94/21675-0050, WO94/21675-0067, WO94/21675-0068, WO94/21675-0069, WO94/21675-0070, WO2011/106645-0002, US6008340-0021, US6008340-0022, US6008340-0023, US6008340-0024, US6008340-0025, US6008340-0026, US6008340-0027 or US6008340-0028; or a variant thereof;

Group 23: a parent peptide with the amino acid sequence SEQ ID NO: 27 (214) or SEQ ID NO: 28 (215); or a variant thereof;

Group 24: a parent peptide with the amino acid sequence SEQ ID NO: 29 (216); or a variant thereof;

Group 25: a parent peptide with the amino acid sequence SEQ ID NO: 36 (217); or a variant thereof;

Group 26: a parent peptide with the amino acid sequence SEQ ID NO: 37 (218) or SEQ ID NO: 38 (219); or a variant thereof;

Group 27 a parent peptide with the amino acid sequence SEQ ID NO: 39 (220); or a variant thereof;

Group 28: a parent peptide with the amino acid sequence SEQ ID NO: 40 (221); or a variant thereof;

Group 29: a parent peptide with the amino acid sequence SEQ ID NO: 45 (222); or a variant thereof;

Group 30: a parent peptide with the amino acid sequence SEQ ID NO: 46 (223); or a variant thereof;

Group 31: a parent peptide with the amino acid sequence SEQ ID NO: 47 (224); or a variant thereof;

Group 32: a parent peptide with the amino acid sequence SEQ ID NO: 48 (225); or a variant thereof;

Group 33: a parent peptide with the amino acid sequence SEQ ID NO: 49 (226); or a variant thereof;

Group 34: a parent peptide with the amino acid sequence SEQ ID NO: 50 (227); or a variant thereof, 14. The composition according to item 1.
wherein one or both of the two peptides selected from any two of the peptide groups 1-11 are selected from group 1 and/or group 2 and/or group 3 and/or group 4; and/or
wherein the third peptide selected from any one of the peptide groups 1-34 is selected from group 12 or group 13 or group 14 or group 17; and/or
wherein the composition has a predicted peptide binding valence above 0.4; and/or
wherein the composition has a donor response valence above 0.3; and/or
wherein the pI of the peptides of the composition are within a range of 3.

15. The composition according to item 2,
wherein at least one of the two peptides selected from any two of the peptide groups 2-34 is selected from any of the peptide groups 2-11; and/or
wherein at least one of the two peptides selected from any two of the peptide groups 2-34 is selected from group 2 or group 3 or group 4; and/or
wherein at least one of the two peptides selected from any two of the peptide groups 2-34 is selected from group 12 or group 13 or group 14 or group 17; and/or
wherein the composition has a predicted peptide binding valence above 0.4; and/or
wherein the composition has a donor response valence above 0.3 and/or
wherein the pI of the peptides of the composition are within a range of 3.

16. The composition according to item 3,
wherein at least one of the two peptides selected from any two of the peptide groups 1 and 3-34 is selected from any one of the peptide groups 1 and 3-11; and/or
wherein at least one of the two peptides selected from any two of the peptide groups 1 and 3-34 is selected from group 1 or group 3 or group 4; and/or
wherein at least one of the two peptides selected from any two of the peptide groups 1 and 3-34 is selected from group 12 or group 13 or group 14 or group 17; and/or
wherein the composition has a predicted peptide binding valence above 0.4; and/or wherein the composition has a donor response valence above 0.3 and/or
wherein the pI of the peptides of the composition are within a range of 3.

17. The composition according to item 4,
wherein at least one of the two peptides selected from any two of the peptide groups 1-2 and 4-34 is selected from any one of the peptide groups 1-2 and 4-11; and/or
wherein at least one of the two peptides selected from any two of the peptide groups 1-2 and 4-34 is selected from group 1 or group 2 or group 4; and/or
wherein at least one of the two peptides selected from any two of the peptide groups 1-2 and 4-34 is selected from group 12 or group 13 or group 14 or group 17; and/or
wherein the composition has a predicted peptide binding valence above 0.4; and/or
wherein the composition has a donor response valence above 0.3 and/or
wherein the pI of the peptides of the composition are within a range of 3.

18. The composition according to item 5,
wherein at least one of the two peptides selected from any two of the peptide groups 1-3 and 5-34 is selected from any one of the peptide groups 1-3 and 5-11; and/or
wherein at least one of the two peptides selected from any two of the peptide groups 1-3 and 5-34 is selected from group 1 or group 2 or group 3; and/or
wherein at least one of the two peptides selected from any two of the peptide groups 1-3 and 5-34 is selected from group 12 or group 13 or group 14 or group 17; and/or
wherein the composition has a predicted peptide binding valence above 0.4; and/or
wherein the composition has a donor response valence above 0.3 and/or
wherein the pI of the peptides of the composition are within a range of 3.

19. The composition according to item 6,
wherein the two peptides selected from any two of the peptide groups 1-11 and 13-34 are selected from any two of the peptide groups 1-11; and/or
wherein at least one of the two peptides selected from any two of the peptide groups 1-11 and 13-34 is selected from group 1 or group 2 or group 3 or group 4; and/or
wherein at least one of the two peptides selected from any two of the peptide groups 1-11 and 13-34 is selected from group 13 or group 14 or group 17; and/or
wherein the composition has a predicted peptide binding valence above 0.4; and/or
wherein the composition has a donor response valence above 0.3 and/or
wherein the pI of the peptides of the composition are within a range of 3.

20. The composition according to item 7,
wherein the two peptides selected from any two of the peptide groups 1-12 and 14-34 are selected from any two of the peptide groups 1-11; and/or
wherein at least one of the two peptides selected from any two of the peptide groups 1-12 and 14-34 is selected from group 1 or group 2 or group 3 or group 4; and/or
wherein at least one of the two peptides selected from any two of the peptide groups 1-12 and 14-34 is selected from group 12 or group 14 or group 17; and/or
wherein the composition has a predicted peptide binding valence above 0.4; and/or
wherein the composition has a donor response valence above 0.3 and/or
wherein the pI of the peptides of the composition are within a range of 3.

21. The composition according to item 8,
wherein the two peptides selected from any two of the peptide groups 1-13 and 15-34 are selected from any two of the peptide groups 1-11; and/or
wherein at least one of the two peptides selected from any two of the peptide groups 1-13 and 15-34 is selected from group 1 or group 2 or group 3 or group 4; and/or
wherein at least one of the two further peptides selected from any two of the peptide groups 1-13 and 15-34 is selected from group 12 or group 13 or group 17; and/or
wherein the composition has a predicted peptide binding valence above 0.4; and/or
wherein the composition has a donor response valence above 0.3 and/or
wherein the pI of the peptides of the composition are within a range of 3.

22. The composition according to item 9,
wherein the two peptides selected from any two of the peptide groups 1-16 and 18-34 are selected from any two of the peptide groups 1-11; and/or
wherein at least one of the two peptides selected from any two of the peptide groups 1-16 and 18-34 is selected from group 1 or group 2 or group 3 or group 4; and/or
wherein at least one of the two peptides selected from any two of the peptide groups 1-16 and 18-34 is selected from group 12 or group 13 or group 14; and/or
wherein the composition has a predicted peptide binding valence above 0.4; and/or
wherein the composition has a donor response valence above 0.3 and/or
wherein the pI of the peptides of the composition are within a range of 3.

23. The composition according to item 10,
wherein at least two of the at least three peptides selected from any three of the peptide groups 1-34 are selected from any two of the peptide groups 1-11; and/or
wherein at least one of the at least three peptides selected from any three of the peptide groups 1-34 is selected from group 1 or group 2 or group 3 or group 4; and/or
wherein at least one of the at least three peptides selected from any three of the peptide groups 1-34 is selected from group 12 or group 13 or group 14 or group 17; and/or
wherein the composition has a donor response valence above 0.3 and/or
wherein the pI of the peptides of the composition are within a range of 3.

24. The composition according to item 11,
wherein at least two of the at least three peptides selected from any three of the peptide groups 1-34 are selected from any two of the peptide groups 1-11; and/or
wherein at least one of the at least three peptides selected from any three of the peptide groups 1-34 is selected from group 1 or group 2 or group 3 or group 4; and/or
wherein at least one of the at least three peptides selected from any three of the peptide groups 1-34 is selected from group 12 or group 13 or group 14 or group 17; and/or
wherein the composition has a predicted peptide binding valence above 0.4 and/or
wherein the pI of the peptides of the composition are within a range of 3.

25. The composition according to item 12,
wherein at least two of the at least three peptides selected from any three of the peptide groups 1-34 are selected from any two of the peptide groups 1-11; and/or
wherein at least one of the at least three peptides selected from any three of the peptide groups 1-34 is selected from group 1 or group 2 or group 3 or group 4; and/or
wherein at least one of the at least three peptides selected from any three of the peptide groups 1-34 is selected from group 12 or group 13 or group 14 or group 17; and/or
wherein the composition has a predicted peptide binding valence above 0.4; and/or
wherein the composition has a donor response valence above 0.3.

26. A composition comprising at least three peptides, wherein two of the at least three peptides are selected from any two of the peptide groups 1-5, and wherein the third of the at least three peptides is selected from any one of the peptide groups 12-14 and 17; and wherein the composition comprises a fourth peptide selected from any one of the peptide groups 1-5, 12-14 and 17, and wherein the fourth peptide is selected from a peptide group different from the peptide groups of the at least three peptides;
and wherein the four peptides selected have been selected such that two peptides have been selected from any of the peptide groups 3, 4, 13 and 14, and two peptides have been selected from any of the peptide groups 1, 2, 4, 5 and 12; the peptide groups being as defined in item 1.

27. The composition according to item 26,
wherein the composition has a predicted peptide binding valence above 0.4; and/or
wherein the composition has a donor response valence above 0.3; and/or
wherein the pI of the peptides of the composition are within a range of 3.

28. The composition according to any one of the preceding items, wherein the at least three peptides are selected from any three of the peptide groups 1-6, 11-26, 28-29 and 31-34.

29. The composition according to any one of the preceding items, comprising a maximum of two peptides selected from any one of the peptide groups 1-34.

30. The composition according to any one of the preceding items provided the composition does not contain a peptide from peptide group 18.

31. The composition according to any one of the preceding items provided the composition does not contain a peptide corresponding to SEQ ID NO: 241 (peptide 141); or a variant thereof.

32. The composition according to any one of the preceding items comprising at least 4 peptides selected from any four of the peptide groups 1-34.

33. The composition according to any one of the preceding items, wherein two peptides have been selected from any two of peptide groups 1-5 and two peptides have been selected from any two of peptide groups 12-14 and group 17.

34. The composition according to any one of the preceding items, wherein the composition comprises a peptide selected from peptide group 13 and a peptide selected from any one of peptide groups 12 or 14.

35. The composition according to any one of the preceding items, wherein the composition comprises a peptide from peptide group 4 and a peptide selected from any one of peptide groups 2 or 3.

36. The composition according to any one of the preceding items comprising 4 peptides, wherein the composition comprises peptides selected from at least three of the peptide groups 13, 14, 2 and 4.

37. The composition according to any one of the preceding items comprising 4 peptides, wherein the composition comprises peptides selected from at least three of the peptide groups 12, 13, 2 and 4.

38. The composition according to any one of the preceding items comprising 5 peptides, wherein the composition comprises peptides selected from at least three of the peptide groups 12, 13, 14, 2 and 4.

39. The composition according to any one of the preceding items comprising 5 peptides, wherein the composition comprises peptides selected from at least three of the peptide groups 13, 14, 24, 2 and 4.

40. The composition according to any one of the preceding items comprising 5 peptides, wherein the composition comprises peptides selected from at least three of the peptide groups 12, 13, 2, 4 and 5.

41. The composition according to any one of the preceding items comprising 5 peptides, wherein the composition comprises peptides selected from at least three of the peptide groups 12, 13, 3, 4 and 5.

42. The composition according to any one of the preceding items comprising 5 peptides, wherein the composition comprises peptides selected from at least three of the peptide groups 13, 14, 3, 4 and 5.

43. The composition according to any one of the preceding items, wherein the at least three peptides are selected from three of the peptide groups 1, 3-4, 11-12, 14-15, 17-18, 21, 24-25, 29 and 33.

44. The composition according to any one of the preceding items, wherein the at least three peptides are selected from three of the peptide groups 1, 3-4, 12, 14, 17-18, 24-25 and 29.

45. The composition according to any one of the preceding items, wherein the composition comprises a peptide from peptide group 12 and a peptide from peptide group 14.

46. The composition according to any one of the preceding items, wherein the composition comprises a peptide from peptide group 4 and a peptide from peptide group 3.

47. The composition according to any one of the preceding items comprising 4 peptides, wherein the composition comprises peptides from each of the peptide groups 12, 3 and 4.

48. The composition according to any one of the preceding items comprising 5 peptides, wherein the composition comprises peptides from each of the peptide groups 12, 3 and 4.

49. The composition according to any one of the preceding items comprising 5 peptides, wherein the composition comprises peptides from each of the peptide groups 12, 14, 3 and 4.

50. The composition according to any one of the preceding items comprising 5 peptides, wherein the composition comprises peptides from each of the peptide groups 12, 14, 1, 3 and 4.

51. The composition according to any one of the preceding items comprising 5 peptides, wherein the composition comprises peptides from each of the peptide groups 12, 14, 28, 3 and 4.

52. The composition according to any one of the preceding items comprising 6 peptides, wherein the composition comprises peptides from each of the peptide groups 12, 14, 28, 1, 3 and 4.

53. The composition according to any one of the preceding items, wherein the peptides have a length of between 13 and 30 amino acid residues.

54. The composition according to any one of the preceding items, wherein the composition comprises a maximum of 4, 5, 6, 7, 8 or 9 peptides selected from peptide groups 1-34.

55. The composition according to any one of the preceding items, wherein the composition comprises a minimum of 4, 5, 6, 7 or 8 peptides selected from peptide groups 1-34.

56. The composition according to any one of the preceding items, wherein the composition comprises no more than two peptides from any one of peptide groups 1-34

57. The composition according to any one of the preceding items, wherein the peptides in the composition are each selected from different peptide groups, for example a maximum of 3 peptides selected from 3 different peptide groups, for example a maximum of 4 peptides selected from 4 different peptide groups, for example a maximum of 5 peptides selected from 5 different peptide groups, for example a maximum of 6 peptides selected from 6 different peptide groups, or for example a maximum of 7 peptides selected from 7 different peptide groups.

58. The composition according to any one of the preceding items, wherein the variant is a peptide comprising one or more additional amino acids than the parent peptide and comprises up to 30 amino acid residues in length, optionally wherein the variant peptide comprises an amino acid sequence having at least 80%, such as at least 85%, 90% 95%, 97%, 98% or 99% sequence identity over at least 13 contiguous amino acids of the parent peptide.

59. The composition according to any one of the preceding items, wherein the variant is a peptide comprising fewer amino acids than the parent peptide and wherein the amino acid sequence has at least 80%, such as at least 85%, 90%, 95%, 97%, 98% or 99% sequence identity over at least 13 contiguous amino acids of the parent peptide.

60. The composition according to any one of items 58-59, wherein the variant consists of 13 to 30 amino acid residues and comprises an amino acid sequence having at least 80%, such as at least 85%, 90%, 95%, 97%, 98% or 99% sequence identity over at least 15 contiguous amino acids of the parent peptide.

61. The composition according to any one of items 58-59, wherein the variant consists of 13-30 amino acid residues and comprises an amino acid sequence having at least 80%, such as at least 85%, 90%, 95%, 97%, 98% or 99% sequence identity over at least 12 contiguous amino acids of the parent peptide.

62. The composition according to any one of items 58-59, wherein the variant consists of 15-25 amino acid residues and comprises an amino acid sequence having at least 80%, such as at least 85%, 90%, 95%, 97%, 98% or 99% sequence identity over at least 15 contiguous amino acids of the parent peptide.

63. The composition according to any one of 58-59, wherein the variant consists of 13-30 amino acid residues and comprises an amino acid sequence having 100% sequence identity over at least 9 contiguous amino acids of the parent peptide.

64. The composition according to any one of the preceding items, wherein the variant comprises one or more (e.g. 1, 2, 3 or 4) arginine residue(s) (R), one or more lysine residue(s) (K), one or more glutamic residues (E), and/or one or more aspartic acid residues (D) added to the N- or C-terminus of the parent peptide or to a fragment of the parent peptide consisting of at least 13 contiguous amino acids of the parent peptide.

65. The composition according to any one of the preceding items, wherein the variant comprises one or more additional amino acid residues added at the N- and/or C-terminal ends of the parent peptide, wherein the one or more additional amino acid residues are the same amino acid or amino acid sequence flanking the N- and/or C-terminal ends of the parent peptide when it is aligned with the native allergen sequence it is derived from or with another grass allergen from the same allergen group.

66. The composition according to any one of the preceding items, wherein the variant comprises a deletion of a hydrophobic residue up to three amino acids from the N- or C-terminus of the parent peptide; and/or deletion of any two consecutive amino acids comprising the sequence Asp-Gly that are up to four amino acids from the N- or C-terminus of the parent peptide.

67. The composition according to any one of the preceding items, wherein a peptide of the composition contains at least one T cell epitope, optionally a Th-2 cell epitope.

68. The composition according to any one of the preceding items, wherein the variant binds to at least 70%, such as at least 80%, 85%, 90% or 95%, of the group of HLA Class II alleles that the parent peptide binds to.

69. The composition according to any one of the preceding items, wherein the variant is predicted to bind to at least 70%, such as at least 80%, 85%, 90% or 95%, of the group of HLA Class II alleles that the parent peptide is predicted to bind to.

70. The composition according to any one of the preceding items, wherein the variant thereof is a peptide derivative.

71. The composition according to item 70, wherein the peptide derivative is amidated at the C-terminal end.

72. The composition according to item 70, wherein the derivative comprises (a) N-terminal acetylation; (b) C-terminal amidation (c) one or more hydrogens on the side chain amines of arginine and/or lysine replaced with a methylene group; (d) glycosylation and/or (e) phosphorylation.

73. The composition according to any one of the preceding items, wherein the parent peptide or the variant thereof is a salt.

74. The composition according to item 73, wherein the salt is an acetate salt.

75. The composition according to any one of the preceding items, wherein the peptides are obtained synthetically or recombinantly.

76. The composition according to any one of the preceding items, wherein the peptides are freeze-dried.

77. The composition according to any one of the preceding items, wherein each peptide in the composition is present in a molar concentration of 1 to 1000 µM, preferably 1-100 µM and more preferred in 1-10 µM.

78. The composition according to any one of the preceding items, wherein each peptide in the composition is present in a soluble form in a molar concentration of 1 to 1000 µM preferably 1-100 µM and more preferred in 1-10 µM.

79. The composition according to any one of the preceding items, wherein each peptide in the composition is present in equimolar concentrations or in substantially equimolar concentrations.

80. The composition according to any one of items 1 to 79, wherein the composition is a pharmaceutical composition.

81. The pharmaceutical composition according to item 80, further comprising a pharmaceutically acceptable carrier, excipient and/or adjuvant, optionally sterile.

82. The pharmaceutical composition according to any one of items 80-81 formulated as a vaccine for parenteral administration.

83. The pharmaceutical composition according to any one of items 80-81, wherein the pharmaceutical composition is a powder.

84. The pharmaceutical composition according to any one of items 80-83, wherein the composition is formulated to be re-dissolved before use 85. The pharmaceutical composition according to any one of items 80-84, wherein the composition is isotonic.

86. A kit comprising a compartment and instructions, wherein the compartment comprises the composition according to any one of items 1-85 and wherein the instructions are for use in treating allergy to grass.

87. The kit according to item 86, wherein the kit further comprises packaging material comprising corrugated fiber, glass, plastic, foil, ampules, vials, blister pack, preloaded syringes or tubes, optionally that maintains sterility of the components.

88. The kit according to any one of items 86-87, wherein the kit further comprises labels or inserts comprising printed matter or computer readable medium optionally including identifying components, dose amounts, clinical pharmacology, instructions for the clinician or for a subject using one or more of the kit components, prophylactic or therapeutic benefits, adverse side effects or manufacturer information.

89. A method for relieving or reducing (e.g. treating) an immune response triggered by an allergen of a grass species in a subject in need thereof, comprising administering to the subject a therapeutically effective amount of the composition according to any one of items 1 to 85.

90. A method for relieving one or more symptoms of an immune response triggered by an allergen of a grass species in a subject in need thereof, comprising administering to the subject a therapeutically effective amount of the composition according to any one of items 1 to 85.

91. A method for inducing (developing) immunological tolerance against an allergen of a grass species, comprising administering to a subject a therapeutically effective amount of the composition according to any one of items 1 to 85.

92. The method according to any one of items 89-91, wherein the method comprises relieving one or more symptom(s) associated with allergic rhinitis, allergic conjunctivitis, allergic asthma and/or allergic eczema (e.g. atopic dermatitis).

93. The method according to item 92, wherein the one or more symptom(s) are symptoms associated with allergic rhinitis.

94. The method according to item 93, wherein the method comprises reducing the intensity of itchy nose; reducing the number of sneezes within a given period (e.g. daily, weekly, monthly); reducing the intensity of blocked nose (congestion); reducing the amount of nasal fluid; reducing the eosinophilic count in nasal fluid; reducing specific IgE antibody level (titer) in nasal fluid or in serum and/or reducing basophil histamine release of blood.

95. The method according to item 92, wherein the one or more symptom(s) are symptoms associated with allergic conjunctivitis.

96. The method according to item 95, wherein the method comprises reducing the intensity of itchy eyes, redness in the white of the eyes and/or watery eyes; reducing the eosinophilic count in conjunctival tissue scrapings; reducing specific IgE antibody level (titer) in conjunctival tissue scrapings or in serum and/or reducing basophil histamine release of blood.

97. The method according to item 92, wherein the one or more symptom(s) are symptoms associated with allergic asthma.

98. The method according to item 97, wherein the method comprises reducing the intensity and/or number of coughs within a given period (e.g. daily, weekly, monthly); reducing the intensity of wheezes; improving being short of breath; improving lung function; reducing specific IgE antibody level (titer) in lung fluid or in serum and/or reducing basophil histamine release of blood.

99. The method according to item 92, wherein the one or more symptom(s) are symptoms associated with atopic dermatitis.

100. The method according to item 99, wherein the method comprises reducing itch intensity of the skin; reducing eczema score and/or reducing number of (peripheral) blood eosinophils.

101. The method according to any one of items 89 to 100, wherein the method comprises reducing the subject's need for concomitant treatment with corticosteroids or H1 antihistamines to reduce, relieve or suppress one or more symptoms of the immune response.

102. The method according to any one of items 89 to 101, wherein the grass allergy is clinically presented as atopic dermatitis, urticaria, contact dermatitis, allergic conjunctivitis, allergic rhinitis, allergic asthma, anapylaxis, and/or hay fever.

103. The method according to any one of items 89 to 102, wherein the method decreases, reduces, suppresses or inhibits atopic dermatitis, urticaria, contact dermatitis, allergic conjunctivitis, allergic rhinitis, allergic asthma, anaphylaxis, and/or hay fever.

104. The method according to any one of items 89 to 103, wherein the method comprises inducing or increasing an IgG antibody response in the subject to an allergen of a grass species.

105. The method according to any one of items 89 to 104, wherein the method comprises decreasing an IgE antibody response in the subject to an allergen of a grass species.

106. The method according to any one of items 89 to 105, wherein the method comprises decreasing a T cell response in the subject to an allergen of a grass species.

107. The method according to any one of items 89 to 106, wherein the method comprises increasing the level of the regulatory transcription factor Foxp3 in the subject.

108. The method according to any one of items 89 to 107, wherein the subject is sensitized to an allergen of a grass species (e.g. has specific IgE antibodies against an allergen of a grass species and/or has a T cell response against an allergen of a grass species).

109. The method according to any one of items 89 to 108, wherein the grass species is Timothy grass, Bermuda grass, Rye grass, Johnson grass or Canary grass.

110. The method according to any one of items 89 to 109, wherein the allergen of a grass species is a group 1 allergen, a group 2 allergen, a group 3 allergen, a group 4 allergen or a group 5 allergen.

111. The method according to any one of items 89 to 110, wherein the treatment comprises repeated administration of the composition in weekly, bi-weekly, monthly or quarterly intervals.

112. The method according to any one of items 89 to 111, wherein the treatment is by immunotherapy.

113. The method according to any one of items 89 to 112, wherein a single dose of each single peptide of the composition is in the range of 1 to 1000 nanomoles.

114. The method according to any one of items 89 to 113, wherein the administration comprises administering a volume of about 50 to 150 microliters of the composition (e.g. by intradermal administration).

115. The method according to any one of items 89 to 114, wherein the administration is by a route of administration selected from any one of subcutaneous, intradermal, epicutaneous, rectal, topical, sublingual, oral, buccal, intranasal, respiratory and intralymphatic route.

116. The method according to any one of items 89 to 115, wherein the subject is a human, a pet such as a dog or a cat or a domestic animal such as a horse.

117. A composition according to any one of items 1-85 for use in a method according to any one of items 89-116.

118. Use of a composition according to any one of items 1-85 for the preparation of a medicament for use in a method according to any one of items 89-117.

119. An in-vitro method of determining whether T cells of a subject in need of treatment recognize a composition as defined in any of items 1 to 85, comprising contacting T cells obtained from the subject with the composition or a single peptide thereof and detecting whether the T cells are stimulated by the composition or single peptide.

120. The method of item 119 carried out to determine whether a subject has, or is at risk of developing, an allergy to a grass allergen.

121. A diagnostic kit comprising a composition according to any one of items 1-85.

122. The composition according to any one of items 1-85 comprising any one of the combinations of peptides as identified under the heading of "Peptide combination name" set forth in tables 23, 24a or 24b in Example 6.

123. The composition according to any one of items 1-85 containing any one of the combinations of peptides as identified under the heading of "Peptide combination name" set forth in tables 23, 24a or 24b in Example 6 and containing no other grass peptides eliciting a T cell response in an allergic individual.

124. The composition according to any one of items 1-85 containing no other grass peptides eliciting a T cell response in an allergic individual.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. The invention is further exemplified by way of the following non-limited examples.

EXAMPLES

Overview of Examples Described Herein:

Example 1 relates to peptide libraries used for testing.

Example 2 relates to genotyping and selection of grass pollen allergic donor cohorts used to test T cell reactivity.

Example 3 relates to testing of T cell reactivity in PBMCs obtained from grass pollen allergic donors.

Example 4 relates to in silico predictions of HLA class II binding and predicted HLA class II coverage of selected peptides.

Example 5 describes an initial test of solubility and stability. Example 18 summarizes results obtained from more extensive tests of solubility and stability on selected peptides.

Example 6 relates to initial assemblage of peptide combinations and includes Tables 23, 24a and 24b which comprise a number of peptide combinations. Example 17, Table 37 further discloses a number of peptide combinations including modified peptides. Example 24 further discloses selected peptide combinations and includes Tables 54, 55, 56 and 57 which provide an overview of these selected peptide combinations.

Example 7 relates to testing of T cell reactivity of peptide combinations listed in Tables 23 and 24a. Examples 10 and 24 further relates to testing of T cell reactivity of peptide combinations.

Example 8 relates to testing of T cell reactivity of homologue peptides selected on the basis of sequence homology to selected peptide fragments of *Phleum pratense* isoforms.

Example 9 relates to initial testing of cross-reactivity of homologue peptides derived from other grass species. Example 21 relates to further testing of cross-reactivity and summarizes results obtained from an extended study of homologues of selected peptides.

Example 10 relates to dose response analysis of selected peptides and combinations of peptides. Example 23 further relates to dose response analysis of selected peptides and combinations of peptides.

Example 11 relates to in vitro HLA class II binding analysis of selected peptides on a selected repertoire of 25 different HLA Class II alleles, which cover the majority of a world-wide population.

Example 12 relates to comparison of peptide mixes based on valency. The valency is calculated based on the results for each individual peptide of a mix using three alternatives a) in silico predictions of HLA class II binding, b) in vitro HLA class II binding studies or c) donor response in PBMCs from grass pollen allergic donors. Example 24 further relates to comparisons of selected peptide combinations.

Example 13 relates to selected peptides and combinations of selected peptides. Example 23 relates to further selected peptides and combinations of these.

Example 14 relates to a number of modified peptides. Example 15 relates to measurements of T cell reactivity of modified peptides. Example 16 relates to solubility of modified peptides. Example 17 relates to T cell reactivity of selected mixes comprising modified peptides.

Example 19 relates to synthesis and purification of selected peptides.

Example 20 relates to the testing of the bio-stability of selected peptides in comparison to prior art peptides.

Example 22 relates to testing of selected peptides for capability of basophil activation.

Example 24 relates to the evaluation of combinations of selected peptides and comparisons thereof using in silico prediction methods, HLA binding data and T cell donor response data.

Example 1

Peptide Libraries for Screening

This example describes the peptide library set out to screen for immunogenicity.

In grass pollen allergies it appears that the majority of grass pollen allergic individuals are sensitized to either group 1 and group 5 grass pollen allergens, or more commonly, they are sensitized to both groups of these allergens. However, some grass pollen allergic individuals may also, or exclusively, be sensitized to group 2, 3 and/or 4 grass pollen allergens. Therefore, the present screening includes peptides designed from allergen groups 1, 2, 3, 4 and 5 of grass pollen.

Initially, allergens of Timothy grass pollen (*Phleum pratense*) and Bermuda grass pollen (*Cynodon dactylon*) were selected as templates for the peptide libraries (for sequences see Table 1). A set of 20mer peptides, having 10 amino acid residues in overlap, were designed from the allergens Phl p 1 (isoform 1.0102), Phl p 2 (isoform 2.0101), Phl p 3 (isoform 3.0102), Phl p 4 (isoform varQ2I6V7), Phl p 5 (isoform 5.0109) and Cyn d 1 (isoform 1.0101). These isoforms were confirmed to be abundant isoforms in the various grass pollen, but alternatively other isoforms of these allergens could have been used. For example, the isoforms reported on the website located at www.allergen.org).

Some additional 15mer peptides were designed from allergens of *Phleum pratense* as well as corresponding allergens of grass pollen of the following species:

*Cynodon dactylon* (Cyn d 4 (SEQ ID NO: 334)

*Dactylis glomerate* (Dac g 1 (SEQ ID NO: 335), Dac g 3 (SEQ ID NO: 336), and Dac g 5 (SEQ ID NO: 335),

*Festuca pratensis* (Fes p 7. (SEQ ID NO: 338)

*Phleum pratense* (same as above)

*Lolium Perenne* (Lol p 1 (SEQ ID NO: 339), Lol p 2 (SEQ ID NO: 340), Lol p 3 (SEQ ID NO: 341), Lol p 5a (SEQ ID NO: 342) and Lol p 5b (SEQ ID NO: 343))

*Poa pratensis* (Poa p 1 (SEQ ID NO: 347) and Poa p 5 (SEQ ID NO: 348))

*Paspalum notatum* (Pha n 1 (SEQ ID NO: 344)) and

*Phalaris aquatica* (Pha a 1 (SEQ ID NO: 345) and Pha a 5 (SEQ ID NO: 346))

*Sorghum halepense* (Sor h 1 (SEQ ID NO: 349).

To avoid dimerization and polymerization of peptides by intra- and intermolecular disulfide bond formation between cysteine residues, this amino acid was consistently substituted by a serine residue in the peptides for screening.

The resulting libraries of peptides for screening are shown in Tables 2 to 8. In addition some reference peptides were tested, which had previously been included in peptide combinations for treating grass pollen allergy (International application WO2010/089554). These are shown in Table 9.

TABLE 1

Sequences used as templates to design the peptide library for T cell epitope screening

| SEQ ID NO: | Sequences of allergens of Phleum pratense and Cynodon dactylon |
|---|---|
| 328 | Phl p 1.0102<br>IPKVPPGPNITATYGDKWLDAKSTWYGKPTGAGPKDNGGACGYKDVDKPPFSGMTGCGNT<br>PIFKSGRGCGSCFEIKCTKPEACSGEPVVVHITDDNEEPIAPYHFDLSGHAFGAMAKKGDEQ<br>KLRSAGELELQFRRVKCKYPEGTKVTFHVEKGSNPNYLALLVKYVNGDGDVVAVDIKEKGKD<br>KWIELKESWGAIWRIDTPDKLTGPFTVRYTTEGGTKTEAEDVIPEGWKADTSYESK |
| 329 | Phl p 2.0101<br>VPKVTFTVEKGSNEKHLAVLVKYEGDTMAEVELREHGSDEWVAMTKGEGGVWTFDSEEPL<br>QGPFNFRFLTEKGMKNVFDDVVPEKYTIGATYAPEE |
| 330 | Phl p 3.0102<br>AVQVTFTVQKGSDPKKLVLNIKYTRPGDSLAEVELRQHGSEEWEPLTKKGNVWEVKSSKPL<br>VGPFNFRFMSKGGMRNVFDEVIPTAFKIGKTYTPEE |
| 331 | Phl p 4.varQ2I6V7<br>YFPPPAAKEDFLGCLVKEIPPRLLYAKSSPAYPSVLGQTIRNSRWSSPDNVKPLYIITPTNVSH<br>IQSAVVCGRRHSVRIRVRSGGHDYEGLSYRSLQPETFAVVDLNKMRAVWVDGKARTAWVD<br>SGAQLGELYYAIYKASPTLAFPAGVCPTIGVGGNFAGGGFGMLLRKYGIAAENVIDVKLVDA<br>NGKLHDKKSMGDDHFWAVRGGGGESFGIVVAWQVKLLPVPPTVTIFKISKTVSEGAVDIIN<br>KWQVVAPQLPADLMIRIIAQGPKATFEAMYLGTCKTLTPLMSSKFPELGMNPSHCNEMSWI<br>QSIPFVHLGHRDALEDDLLNRNNSFKPPAEYKSDYVYQPFPKTVWEQILNTWLVKPGAGIMI<br>FDPYGATISATPESATPFPHRKGVLFNIQYVNYWFAPGAAAAPLSWSKDIYNYMEPYVSKNP<br>RQAYANYRDIDLGRNEVVNDVSTYASGKVWGQKYFKGNFERLAITKGKVDPTDYFRNEQSI<br>PPLIKKY |
| 332 | Phl p 5.0109<br>AGYTPAAPAGAEPAGKATTEEQKLIEKINAGFKAALAAAAGVPPADKYRTFVATFGAASNKAF<br>AEGLSGEPKGAAESSSKAALTSKLDAAYKLAYKTAEGATPEAKYDAYVATLSEALRIIAGTLE<br>VHAVKPAAEEVKVIPAGELQVIEKVDAAFKVAATAANAAPANDKFTVFEAAFNNAIKASTGG<br>AYESYKFIPALEAAVKQAYAATVATAPEVKYTVFETALKKAITAMSEAQKAAKPAAAATATAT<br>SAVGAATGAATAATGGYKV |
| 333 | Cyn d 1.0101<br>AIGDKPGPNITATYGSKWLEARATFYGSNPRGAAPDDHGGACGYKDVDKPPFDGMTACGN<br>EPIFKDGLGCRACYEIKCKEPVECSGEPVLVKITDKNYEHIAAYHFDLSGKAFGAMAKKGQE<br>DKLRKAGELTLQFRRVKCKYPSGTKITFHIEKGSNDHYLALLVKYAAGDGNIVAVDIKPRDS<br>DEFIPMKSSWGAIWRIDPKKPLKGPFSIRLTSEGGAHLVQDDVIPANWKPDTVYTSKLQFGA |

Table 2—Peptide Library of Phl p 1 Derived 20mer Peptides for Screening

TABLE 2

| SEQ ID NO: | Sequence (derived from Phl p 1) | Start position | Peptide name | Peptide group |
|---|---|---|---|---|
| 1 | WLDAKSTWYGKPTGAGPKDN | 18 | 201 | 15 |
| 2 | GRGSGSSFEIKSTKPEASSG | 66 | 202 | 16 |
| 3 | EIKSTKPEASSGEPVVVHIT | 74 | 203 | 16 |
| 4 | TDDNEEPIAPYHFDLSGHAF | 93 | 204 | 17 |
| 5 | YHFDLSGHAFGAMAKKGDEQ | 103 | 205 | 18 |
| 6 | GDEQKLRSAGELELQFRRVK | 119 | 206 | 12 |
| 7 | AGELELQFRRVKSKYPEGTK | 127 | 207 | 12 |
| 8 | KGSNPNYLALLVKYVNGDGD | 153 | 208 | 13 |
| 9 | LVKYVNGDGDVVAVDIKEKG | 163 | 209 | 19 |
| 10 | KDKWIELKESWGAIWRIDTP | 183 | 210 | 20 |
| 11 | WGAIWRIDTPDKLTGPFTVR | 193 | 211 | 14 |
| 12 | VRYTTEGGTKTEAEDVIPEG | 211 | 212 | 21 |
| 13 | TEAEDVIPEGWKADTSYESK | 221 | 213 | 22 |

TABLE 2-continued

| SEQ ID NO: | Sequence (derived from Phl p 1) | Start position | Peptide name | Peptide group |
|---|---|---|---|---|
| 14 | IPKVPPGPNITATYGDKWLD | 1 | 001 | |
| 15 | KVPPGPNITATYGDKWLDAK | 3 | 002 | |
| 16 | ITATYGDKWLDAKSTWYGKP | 10 | 003 | |
| 17 | KPTGAGPKDNGGASGYKDVD | 28 | 005 | |
| 18 | GGASGYKDVDKPPFSGMTGS | 38 | 006 | |
| 19 | KPPFSGMTGSGNTPIFKSGR | 48 | 007 | |
| 20 | GNTPIFKSGRGSGSSFEIKS | 58 | 008 | |
| 21 | SGEPVVVHITDDNEEPIAPY | 84 | 011 | |
| 22 | AFGAMAKKGDEQKLRSAGEL | 111 | 014 | |
| 23 | FRRVKSKYPEGTKVTFHVEK | 134 | 017 | |
| 24 | EGTKVTFHVEKGSNPNYLAL | 143 | 018 | |
| 25 | VVAVDIKEKGKDKWIELKES | 173 | 021 | |
| 26 | TPDKLTGPFTVRYTTEGGTK | 201 | 024 | |

Table 3—Peptide Library of Phl p 2 Derived 20mer Peptides for Screening

TABLE 3

| SEQ ID NO: | Sequence (derived from Phl p 2) | Start position | Peptide name | Peptide group |
|---|---|---|---|---|
| 27 | EWVAMTKGEGGVWTFDSEEP | 40 | 214 | 23 |
| 28 | EGGVWTFDSEEPLQGPFNFR | 48 | 215 | 23 |
| 29 | EPLQGPFNFRFLTEKGMKNV | 58 | 216 | 24 |
| 30 | VPKVTFTVEKGSNEKHLAVL | 1 | 051 | |
| 31 | GSNEKHLAVLVKYEGDTMAE | 11 | 052 | |
| 32 | VKYEGDTMAEVELREHGSDE | 21 | 053 | |
| 33 | EVELREHGSDEWVAMTKGEG | 30 | 054 | |
| 34 | RFLTEKGMKNVFDDVVPEKY | 67 | 058 | |
| 35 | VFDDVVPEKYTIGATYAPEE | 77 | 059 | |

Table 4—Peptide Library of Phl p 3 Derived 20mer Peptides for Screening

TABLE 4

| SEQ ID NO: | Sequence (derived from Phl p 3) | Start position | Peptide name | Peptide group |
|---|---|---|---|---|
| 36 | GSDPKKLVLNIKYTRPGDSL | 11 | 217 | 25 |
| 37 | HGSEEWEPLTKKGNVWEVKS | 38 | 218 | 26 |
| 38 | TKKGNVWEVKSSKPLVGPFN | 47 | 219 | 27 |
| 39 | KSSKPLVGPFNFRFMSKGGM | 56 | 220 | 28 |
| 40 | NFRFMSKGGMRNVFDEVIPT | 66 | 221 | |
| 41 | AVQVTFTVQKGSDPKKLVLN | 1 | 060 | |

TABLE 4-continued

| SEQ ID NO: | Sequence (derived from Phl p 3) | Start position | Peptide name | Peptide group |
|---|---|---|---|---|
| 42 | IKYTRPGDSLAEVELRQHGS | 21 | 062 | |
| 43 | AEVELRQHGSEEWEPLTKKG | 31 | 063 | |
| 44 | RNVFDEVIPTAFKIGKTYTP | 76 | 068 | |

Table 5—Peptide Library of Phl p 4 Derived 20mer Peptides for Screening

TABLE 5

| SEQ ID NO: | Sequence (derived from Phl p 4) | Start position | Peptide name | Peptide group |
|---|---|---|---|---|
| 45 | KEDFLGSLVKEIPPRLLYAK | 8 | 222 | 29 |
| 46 | YIITPTNVSHIQSAVVSGRR | 55 | 223 | 30 |
| 47 | FAVVDLNKMRAVWVDGKART | 101 | 224 | 31 |
| 48 | GFGMLLRKYGIAAENVIDVK | 163 | 225 | 32 |
| 49 | SMGDDHFWAVRGGGGESFGI | 195 | 226 | 33 |
| 50 | TPFPHRKGVLFNIQYVNYWF | 386 | 227 | 34 |
| 51 | GRRHSVRIRVRSGGHDYEGL | 72 | 071 | |
| 52 | VRSGGHDYEGLSYRSLQPET | 81 | 072 | |
| 53 | LSYRSLQPETFAVVDLNKMR | 91 | 073 | |
| 54 | DGKARTAWVDSGAQLGELYY | 115 | 075 | |
| 55 | WSKDIYNYMEPYVSKNPRQA | 416 | 079 | |
| 56 | PYVSKNPRQAYANYRDIDLG | 426 | 080 | |
| 57 | RNEVVNDVSTYASGKVWGQK | 446 | 081 | |
| 58 | YASGKVWGQKYFKGNFERLA | 456 | 082 | |
| 59 | YFKGNFERLAITKGKVDPTD | 466 | 083 | |
| 60 | TKGKVDPTDYFRNEQSIPPL | 477 | 084 | |

Table 6—Peptide Library of Phl p 5 Derived 20mer Peptides for Screening

TABLE 6

| SEQ ID NO: | Sequence (derived from Phl p 5) | Start position | Peptide name | Peptide group |
|---|---|---|---|---|
| 61 | AGYTPAAPAGAEPAGKATTE | 1 | 228 | 6 |
| 62 | EQKLIEKINAGFKAALAAAA | 21 | 229 | 7 |
| 63 | GFKAALAAAAGVPPADKYRT | 31 | 230 | 8 |
| 64 | DKYRTFVATFGAASNKAFAE | 46 | 231 | 1 |
| 65 | TSKLDAAYKLAYKTAEGATP | 84 | 232 | 9 |
| 66 | EAKYDAYVATLSEALRIIAG | 104 | 233 | 5 |
| 67 | VATLSEALRIIAGTLEVHAV | 111 | 234 | 10 |
| 68 | IEKVDAAFKVAATAANAAPA | 148 | 235 | 3 |
| 69 | KVAATAANAAPANDKFTVFE | 156 | 236 | 3 |

TABLE 6-continued

| SEQ ID NO: | Sequence (derived from Phl p 5) | Start position | Peptide name | Peptide group |
|---|---|---|---|---|
| 70 | PANDKFTVFEAAFNNAIKAS | 166 | 237 | 11 |
| 71 | STGGAYESYKFIPALEAAVK | 185 | 238 | 4 |
| 72 | KFIPALEAAVKQAYAATVAT | 194 | 239 | 4 |
| 73 | APEVKYTVFETALKKAITAM | 214 | 240 | 2 |
| 74 | AEPAGKATTEEQKLIEKINA | 11 | 086 | |
| 75 | AAGVPPADKYRTFVATFGAA | 39 | 089 | |
| 76 | GAASNKAFAEGLSGEPKGAA | 56 | 091 | |
| 77 | AEGLSGEPKGAAESSSKAAL | 64 | 092 | |
| 78 | AAESSSKAALTSKLDAAYKL | 74 | 093 | |
| 79 | AYKTAEGATPEAKYDAYVAT | 94 | 095 | |
| 80 | RIIAGTLEVHAVKPAAEEVK | 119 | 098 | |
| 81 | AVKPAAEEVKVIPAGELQVI | 129 | 099 | |
| 82 | VIPAGELQVIEKVDAAFKVA | 139 | 100 | |
| 83 | EAAFNNAIKASTGGAYESYK | 175 | 104 | |
| 84 | KQAYAATVATAPEVKYTVFE | 204 | 107 | |
| 85 | TALKKAITAMSEAQKAAKPA | 224 | 109 | |
| 86 | AMSEAQKAAKPAAAATATAT | 232 | 110 | |
| 87 | KPAAAATATATSAVGAATGA | 241 | 111 | |
| 88 | TSAVGAATGAATAATGGYKV | 251 | 112 | |
| 232 | AYESYKFIPALEAAVKQAYA | 189 | 285 | |
| 233 | IEKVDAAFKVAATAANAAPAN | 148 | 286 | |

Table 7—Peptide Library of Cyn d 1 Derived 20mer Peptides for Screening

TABLE 7

| SEQ ID NO: | Sequence (derived from Cyn d 1) | Start position | Peptide name | Peptide group |
|---|---|---|---|---|
| 89 | AIGDKPGPNITATYGSKWLE | 1 | 027 | |
| 90 | TATYGSKWLEARATFYGSNP | 11 | 028 | |
| 91 | ARATFYGSNPRGAAPDDHGG | 21 | 029 | |
| 92 | RGAAPDDHGGASGYKDVDKP | 31 | 030 | |
| 93 | ASGYKDVDKPPFDGMTASGN | 41 | 031 | |
| 94 | PFDGMTASGNEPIFKDGLGS | 51 | 032 | |
| 95 | EPIFKDGLGSRASYEIKSKE | 61 | 033 | |
| 96 | RASYEIKSKEPVESSGEPVL | 71 | 034 | |
| 97 | PVESSGEPVLVKITDKNYEH | 81 | 035 | |
| 98 | VKITDKNYEHIAAYHFDLSG | 91 | 036 | |
| 99 | IAAYHFDLSGKAFGAMAKKG | 101 | 037 | |
| 100 | GKAFGAMAKKGQEDKLRKAG | 110 | 038 | |

TABLE 7-continued

| SEQ ID NO: | Sequence (derived from Cyn d 1) | Start position | Peptide name | Peptide group |
|---|---|---|---|---|
| 101 | GQEDKLRKAGELTLQFRRVK | 120 | 039 | |
| 102 | ELTLQFRRVKSKYPSGTKIT | 130 | 040 | |
| 103 | SKYPSGTKITFHIEKGSNDH | 140 | 041 | |
| 104 | FHIEKGSNDHYLALLVKYAA | 150 | 042 | |
| 105 | YLALLVKYAAGDGNIVAVDI | 160 | 043 | |
| 106 | GDGNIVAVDIKPRDSDEFIP | 170 | 044 | |
| 107 | KPRDSDEFIPMKSSWGAIWR | 180 | 045 | |
| 108 | PMKSSWGAIWRIDPKKPLKG | 189 | 046 | |
| 109 | WRIDPKKPLKGPFSIRLTSE | 198 | 047 | |
| 110 | GPFSIRLTSEGGAHLVQDDV | 208 | 048 | |
| 111 | EGGAHLVQDDVIPANWKPDT | 217 | 049 | |
| 112 | DDVIPANWKPDTVYTSKLQF | 225 | 050 | |

Table 8—Additional 15mer and 20mer Peptides for Screening

Table 8 shows additional peptides suggested for screening, which are also derived from other grass pollen allergens than Phl p 1 and Phl p 5 as described above.

TABLE 8

| SEQ ID NO: | Sequence | Derived from: | Peptide name | Peptide group |
|---|---|---|---|---|
| 113 | AFKVAATAANAAPAN | Phl p 5 | 241 (LJI 1) | |
| 114 | INVGFKAAVAAAAGV | Phl p 5 | 242 (LJI 8) | |
| 115 | NVWEVKSSKPLVGPF | Phl p 3 | 114 (LJI 2) | |
| 116 | NFRFMSKGGMRNVFD | Phl p 3 | 115 (LJI 3) | |
| 117 | SGIAFGSMAKKGDEQ | Phl p 1 | 116 (LJI 4) | |
| 118 | GELELQFRRVKSKYP | Phl p 1 | 117 (LJI 5) | |
| 119 | STWYGKPTGAGPKDN | Phl p 1 | 118 (LJI 6) | |
| 120 | EEWEPLTKKGNVWEV | Phl p 3 | 119 (LJI 7) | |
| 121 | NYLALLVKYVNGDGD | Phl p 1 | 121 (LJI 9) | |
| 122 | KPPFSGMTGSGNTPI | Phl p 1 | 122 (LJI 10) | |
| 123 | LIEKINAGFKAAVAA | Lol p 5a | 123 (LJI 11) | |
| 124 | NAGFKAAVAAAAVVP | Lol p 5a | 124 (LJI 12) | |
| 125 | SDAKTLVLNIKYTRP | Lol p 3 | 125 (LJI 13) | |
| 126 | MRNVFDDVVPADFKV | Lol p 2 | 126 (LJI 14) | |
| 127 | NVFDEVIPTAFTVGK | Lol p 3 | 127 (LJI 15) | |
| 128 | DAYVATLTEALRVIA | Lol p 5a | 128 (LJI 16) | |
| 129 | AFKIAATAANAAPTN | Lol p 5b | 129 (LJI 17) | |
| 130 | DGVWEIKSDKPLKGP | Lol p 2 | 130 (LJI 18) | |
| 131 | DINVGFKAAVAAAAG | Poa p 5 | 131 (LJI 19) | |

TABLE 8-continued

| SEQ ID NO: | Sequence | Derived from: | Peptide name | Peptide group |
|---|---|---|---|---|
| 132 | EPIAAYHFDLSGKAF | Poa p 1 | 132 (LJI 20) | |
| 133 | FKAAVAAAAGAPPAD | Poa p 5 | 133 (LJI 21) | |
| 134 | GRGSGSSFEIKSTKPESSSG | Lol p 1 | 301 | |
| 135 | EIKSTKPESSSGEAVTVTIT | Lol p 1 | 302 | |
| 136 | YHFDLSGHAFGSMAKKGEEQ | Lol p 1 | 303 | |
| 137 | GEEQNVRSAGELELQFRRVK | Lol p 1 | 304 | |
| 138 | AGELELQFRRVKSKYPDDTK | Lol p 1 | 305 | |
| 139 | KASNPNYLAILVKYVDGDGD | Lol p 1 | 306 | |
| 140 | LVKYVDGDGDVVAVDIKEKG | Lol p 1 | 307 | |
| 141 | KDKWIELKESWGAVWRIDTP | Lol p 1 | 308 | |
| 142 | WGAVWRIDTPDKLTGPFTVR | Lol p 1 | 309 | |
| 143 | VRYTTEGGTKSEFEDVIPEG | Lol p 1 | 310 | |
| 144 | SEFEDVIPEGWKADTSYSAK | Lol p 1 | 311 | |
| 145 | WLEARATFYGSNPRGAAPDD | Cyn d 1 | 312 | |
| 146 | GLGSRASYEIKSKEPVESSG | Cyn d 1 | 313 | |
| 147 | EIKSKEPVESSGEPVLVKIT | Cyn d 1 | 314 | |
| 148 | TDKNYEHIAAYHFDLSGKAF | Cyn d 1 | 315 | |
| 149 | YHFDLSGKAFGAMAKKGQED | Cyn d 1 | 316 | |
| 150 | GQEDKLRKAGELTLQFRRVK | Cyn d 1 | 317 | |
| 151 | AGELTLQFRRVKSKYPSGTK | Cyn d 1 | 318 | |
| 152 | KGSNDHYLALLVKYAAGDGN | Cyn d 1 | 319 | |
| 153 | LVKYAAGDGNIVAVDIKPRD | Cyn d 1 | 320 | |
| 154 | SDEFIPMKSSWGAIWRIDPK | Cyn d 1 | 321 | |
| 155 | WGAIWRIDPKKPLKGPFSIR | Cyn d 1 | 322 | |
| 156 | IRLTSEGGAHLVQDDVIPAN | Cyn d 1 | 323 | |
| 157 | LVQDDVIPANWKPDTVYTSK | Cyn d 1 | 324 | |
| 158 | EWLALKKNGDGVWEIKSDKP | Lol p 2 | 325 | |
| 159 | GDGVWEIKSDKPLKGPFNFR | Lol p 2 | 326 | |
| 160 | KPLKGPFNFRFVSEKGMRNV | Lol p 2 | 327 | |
| 161 | GSDAKTLVLNIKYTRPGDTL | Lol p 3 | 328 | |
| 162 | HGSEEWEPMTKKGNLWEVKS | Lol p 3 | 329 | |
| 163 | TKKGNLWEVKSAKPLTGPMN | Lol p 3 | 330 | |
| 164 | KSAKPLTGPMNFRFLSKGGM | Lol p 3 | 331 | |
| 165 | NFRFLSKGGMKNVFDEVIPT | Lol p 3 | 332 | |
| 166 | FAVVDLNQMRAVLVDGKART | Phl p4, 101 | 333 | |
| 167 | QVERDFLTSLTKDIPPRQLY | Cyn d 4 | 334 | |
| 168 | YIITPTNASHIQAAVVSGRR | Cyn d 4 | 335 | |
| 169 | FAVVDMNKMRAVSIDGKAAT | Cyn d 4 | 336 | |
| 170 | GFGMLLRKYGTAADNVIDAK | Cyn d 4 | 337 | |

TABLE 8-continued

| SEQ ID NO: | Sequence | Derived from: | Peptide name | Peptide group |
|---|---|---|---|---|
| 171 | AMGEDHFWAIRGGGGESFGI | Cyn d 4 | 338 | |
| 172 | TPFPRRSGVLFNIQYVVYWF | Cyn d 4 | 339 | |
| 173 | TAATPATPATPATPAAVPSG | Lol p 5 | 340 | |
| 174 | EQKLIEKINAGFKAAVAAAA | Lol p 5 | 341 | |
| 175 | GFKAAVAAAAVVPPADKYKT | Lol p 5 | 342 | |
| 176 | DKYKTFVETFGTATNKAFVE | Lol p 5 | 343 | |
| 177 | TSKLDAALKLAYEAAQGATP | Lol p 5 | 344 | |
| 178 | EAKYDAYVATLTEALRVIAG | Lol p 5 | 345 | |
| 179 | VATLTEALRVIAGTLEVHAV | Lol p 5 | 346 | |
| 180 | IDKVDAAYRTAATAANAAPA | Lol p 5 | 347 | |
| 181 | RTAATAANAAPANDKFTVFE | Lol p 5 | 348 | |
| 182 | PANDKFTVFENTFNNAIKVS | Lol p 5 | 349 | |
| 183 | SLGAAYDSYKFIPTLVAAVK | Lol p 5 | 350 | |
| 184 | KFIPTLVAAVKQAYAAKQAT | Lol p 5 | 351 | |
| 185 | APEVKYTVSETALKKAVTAM | Lol p 5 | 352 | |
| 186 | AYRTAATAANAAPAN | Lol p 5 | 353 | |
| 187 | INAGFKAALAAAAGV | Lol p 5 | 354 | |
| 188 | PTPRTPPLLPPPRARDKATL | Pha a 5 | 355 | |
| 189 | ASRRPWWASVPPADKFKTFA | Pha a 5 | 356 | |
| 190 | KAKLDAAYRVAYEAAEGSTP | Pha a 5 | 357 | |
| 191 | EAKYDAFIAALTEALRVIAG | Pha a 5 | 358 | |
| 192 | IAALTEALRVIAGAFEVHAV | Pha a 5 | 359 | |
| 193 | VDKIDAAFKIAATAANSAPA | Pha a 5 | 360 | |
| 194 | KIAATAANSAPANDKFTVFE | Pha a 5 | 361 | |
| 195 | PANDKFTVFEGAFNKAIKES | Pha a 5 | 362 | |
| 196 | STAGAYETYKFIPSLEAAVK | Pha a 5 | 363 | |
| 197 | KFIPSLEAAVKQAYGATVAR | Pha a 5 | 364 | |
| 198 | APEVKYAVFEAGLTKAITAM | Pha a 5 | 365 | |
| 199 | AFKIAATAANSAPAN | Pha a 5 | 366 | |
| 200 | INAASRRPWWASVPP | Pha a 5 | 367 | |
| 246 | TDKNYEHIAAYHFDLSGKAF | Cyn_d_1 | 315 | |
| 247 | TDMNYEPIAPYHFDLSGKAF | Pas_n_1 | 368 | |
| 248 | TDDNEEPIAAYHFDLSGKAF | Poa_p_1 | 369 | |
| 249 | TDMNYEQIAAYHFDLAGTAF | Sor_h_1 | 370 | |
| 250 | YHFDLSGKAFGAMAKKGEED | Cyn_d_1 | 371 | |
| 251 | YHFDLSGHAFGSMAKKGEEQ | Dac_g_1 | 372 | |
| 252 | YHFDLSGHAFGSMAKKGEEE | Pha_a_1 | 373 | |
| 253 | YHFDLSGKAFGAMAKKGEEQ | Poa_p_1 | 374 | |

TABLE 8-continued

| SEQ ID NO: | Sequence | Derived from: | Peptide name | Peptide group |
|---|---|---|---|---|
| 254 | YHFDLAGTAFGAMAKKGEEE | Sor_h_1 | 375 | |
| 255 | GEEDKLRKAGELMLQFRRVK | Cyn_d_1 | 376 | |
| 256 | GEEQKLRSAGELELQFRRVK | Dac_g_1 | 377 | |
| 257 | GLNDKLRHYGIFDLEFRRVR | Pas_n_1 | 378 | |
| 258 | GEEENVRGAGELELQFRRVK | Pha_a_1 | 379 | |
| 259 | GEEQKLRSAGELELKFRRVK | Poa_p_1 | 380 | |
| 260 | GEEEKLRKAGIIDMKFRRVK | Sor_h_1 | 381 | |
| 261 | AGELTLQFRRVKSKYPSGTK | Cyn_d_1 | 318 | |
| 262 | AGELELQFRRVKSKYPEGTK | Dac_g_1 | 382 | |
| 263 | AGELELQFRRVKSKYPDGTK | Fes_p_1 | 383 | |
| 264 | YGIFDLEFRRVRSKYQGGQK | Pas_n_1 | 384 | |
| 265 | AGELELKFRRVKSEYPEGTK | Poa_p_1 | 385 | |
| 266 | KGSNPNYLALLVKYAAGDGN | Cyn_d_1 | 386 | |
| 267 | KGSNPNYLALLVKYVDGDGD | Dac_g_1 | 387 | |
| 268 | KGSNPNYLAILVKYVDGDGD | Fes_p_1 | 388 | |
| 269 | KASNPNYLAILVKYVDGDGD | Lol_p_1 | 306 | |
| 270 | KGSNPNYLAMLVKFVADDGD | Pas_n_1 | 389 | |
| 271 | KGSNPNYLALLVKYVTGDGD | Poa_p_1 | 390 | |
| 272 | WGAIWRIDPPKPLKGPFTIR | Cyn_d_1 | 391 | |
| 273 | WGAIWRVDTPDKLTGPFTVR | Dac_g_1 | 392 | |
| 274 | WGAVWRIDTPDKLTGPFTVR | Fes_p_1 | 393 | |
| 275 | WGAIWRMDTPKALVPPFSIR | Pas_n_1 | 394 | |
| 276 | WGSIWRVDTPDKLTGPFTVR | Poa_p_1 | 395 | |
| 277 | WGAIWRKDSDKPIKFPVTVQ | Sor_h_1 | 396 | |
| 278 | GSDPKKLVLDIKYTRPGDTL | Dac_g_3 | 397 | |
| 279 | GSDAKTLVLNIKYTRPGDTL | Lol_p_3 | 328 | |
| 280 | ERDFLTSLTKDIPPRQLYAK | Cyn_d_4 | 398 | |
| 281 | VDKIDAAYKIAATAANAAPA | Dac_g_5 | 399 | |
| 282 | VDKIDAAFKIAATAANAAPT | Lol_p_5 | 400 | |
| 283 | VDKIDAAFKIAATAANSAPA | Pha_a_5 | 360 | |
| 284 | IDKVDAAFKVAATAANAAPA | Poa_p_5 | 401 | |
| 285 | KIAATAANAAPANDKFTVFE | Dac_g_5 | 402 | |
| 286 | KIAATAANAAPTNDKFTVFE | Lol_p_5 | 403 | |
| 287 | KIAATAANSAPANDKFTVFE | Pha_a_5 | 361 | |
| 288 | STGGAYESYKFIPTLEAAVK | Dac_g_5 | 404 | |
| 289 | STGGAYETYKFIPSLEAAVK | Lol_p_5 | 405 | |
| 290 | STAGAYETYKFIPSLEAAVK | Pha_a_5 | 363 | |
| 291 | STGGAYQSYKFIPALEAAVK | Poa_p_5 | 406 | |
| 292 | KFIPTLEAAVKQAYAATVAA | Dac_g_5 | 407 | |

TABLE 8-continued

| SEQ ID NO: | Sequence | Derived from: | Peptide name | Peptide group |
|---|---|---|---|---|
| 293 | KFIPSLEAAVKQAYAATVAA | Lol_p_5 | 408 | |
| 294 | KFIPSLEAAVKQAYGATVAR | Pha_a_5 | 364 | |
| 295 | KFIPALEAAVKQSYAATVAT | Poa_p_5 | 409 | |
| 296 | APEVKYAVFEAALTKAITAM | Dac_g_5 | 410 | |
| 297 | APEVKYTVSETALKKAVTAM | Lol_p_5 | 352 | |
| 247 | APEVKYAVFETALKKAISAM | Pha_a_5 | 411 | |
| 248 | APAVKYTVFETALKKAITAM | Poa_p_5 | 412 | |
| 249 | AYESYKFIPTLEAAVKQAYA | Dac_g_5 | 413 | |
| 250 | AYETYKFIPSLEAAVKQAYA | Lol_p_5 | 414 | |
| 251 | AYETYKFIPSLEAAVKQAYG | Pha_a_5 | 415 | |
| 252 | AYQSYKFIPALEAAVKQSYA | Poa_p_5 | 416 | |
| 253 | VDKIDAAYKIAATAANAAPAN | Dac_g_5 | 417 | |
| 254 | VDKIDAAFKIAATAANAAPTN | Lol_p_5 | 418 | |
| 255 | VDKIDAAFKIAATAANSAPAN | Pha_a_5 | 419 | |
| 256 | IDKVDAAFKVAATAANAAPAN | Poa_p_5 | 420 | |

Table 9—Peptide Library of Some Reference Peptides Disclosed in WO2010/089554

TABLE 9

| SEQ ID NO: | Sequence | Name used in WO2010/089554 | Peptide name |
|---|---|---|---|
| 234 | SGKAFGAMAKKGQED | Cyn d 1 (Ber01) | 134 |
| 235 | FIPMKSSWGA | Cyn d 1 (Ber02) | 135 |
| 236 | KSSWGAIWRIDPKKPLK | Cyn d 1 (Ber02C) | 136 |
| 237 | KYDAYVATLTEALR | Lol p 5b (Bio02A) | 137 |
| 238 | KFIPTLVAAVKQAYAAKQ | Lol p 5b (Bio03A) | 138 |
| 239 | LKKAVTAMSEAEK | Lol p 5b (Bio04A) | 139 |
| 240 | PEVKYAVFEAALTKAIT | Lol p 5a (Rye09B) | 140 |
| 241 | KIPAGELQIIDKIDA | phl p 5 (Tim07B) | 141 |
| 242 | KPEVKYAVFEAALTKAIT | Lol p 5a (Rye09B1) | 142 |
| 243 | KKPEVKYAVFEAALTKAIT | Lol p 5a (Rye09B2) | 143 |
| 244 | KKIPAGELQIIDKIDA | Phl p 5 (Tim07B1) | 144 |
| 245 | KKIPAGELQIIDKIDAK | Phl p 5 (Tim07B2) | 145 |

All peptides of Tables 2-9 except SEQ ID NOs: 134-200 were initially synthesized as Trifluoroacetic acid (TFA) salts in an approximately 10 mg scale of manufacturing and purchased from Innovagen. The other peptides were synthesized as acetic acid salts in various scales of manufacturing. These were also purchased from Innovagen.

The 42 selected high responder peptides which were further investigated and SEQ ID NOs: 134-200 were subsequently produced as acetate salts at a >10 mg scale of manufacturing and purchased from Innovagen.

Example 2

HLA Genotyping of Donor Cohorts

This example includes an overview of the genotypes present in the donor cohorts used in the testing of the peptides disclosed herein. Since the aim is to design peptide mixes providing high worldwide HLA Class II coverage, it was important to select a donor cohort that is representative of a worldwide population with respect to the HLA Class II allele repertoire.

For the purpose of estimate the worldwide HLA Class II coverage, a set of 77 HLA Class II alleles presented in Tables 10 and 11 were used, as sufficient knowledge about the HLA frequency data were available in public databases and articles. Allele frequencies were calculated in order to represent an average frequency across several population groups, which overall are estimated to represent the general worldwide distribution of alleles. In particular, the average allele frequencies for individual HLA-DRB1 alleles displayed in table 10 are based on MHC data available at The Allele Frequency Net Database (AFND), at the website located at www.allelefrequencies.net. As an estimated worldwide allele distribution were used frequencies from the four major ethnical groups in North America, Hispanics, Caucasians, African Americans, and Asians (database population IDs, 1514, 1513, 2419, and 2420, respectively). The frequencies were calculated as the simple mean of the frequencies of the ethnical groups. Each ethnical group consists of data from more than 1000 individuals. Average haplotype frequencies for the alleles displayed in Table 11 were based on published data (Paul, Sinu, Cecilia S Lindestam Arlehamn, Thomas J Scriba, Myles B C Dillon, Carla Oseroff, Denise Hinz, Denise M McKinney, and others. "Development and Validation of a Broad Scheme for Prediction of HLA Class II Restricted T Cell Epitopes." Journal of immunological methods (2015). This information may be incomplete regarding the loci DRB3, DRB4, DRB5, DQ and DP. However, using this information provides a valuable supplement to the information on DRB1 from the database.

Donors (n=54) from the Copenhagen area were recruited in two cohorts (DK1, n=30 and DK2, n=24) based on immunological reactivity to grass pollen allergen extract (grass specific IgE in blood sample) and by confirming that their clinical history was consistent with grass pollen allergy. Donors with detectable specific IgE levels towards grass extract in the blood sample were considered to have immunological reactivity.

Each donor was genotyped with respect to their HLA loci DRB1, DRB3, DRB4, DRB5, DP, and DQ by the vendor, ProImmune Ltd, using PCR amplification by the Tier 1 method. In short, PCR-sequence specific oligonucleotides (PCR-SSOP) were used to resolve major allele groups to 4 digits, with a certain degree of degeneracy between highly related alleles. PCR-SSOP: The genomic DNA was amplified using PCR and then incubated with a panel of different oligo-nucleotide probes, which had distinctive reactivity with different HLA-types.

The HLA Class II alleles found experimentally in donor cohorts DK1 and DK2 are shown in Table 12. The calculated fraction of a worldwide population expressing one or more of these alleles can be calculated for each locus by the Hardy Weinberg equation and the allele frequencies are given in Tables 10 and 11. The calculated WW coverage of the donor alleles are shown for each locus in Table 13.

Table 10. HLA Allele Frequencies in Locus DRB1 of a Worldwide Population.

These allele frequencies were used for estimation of worldwide coverage of the HLAs of the donor cohorts—(this table is also used in Example 12 regarding predicted peptide coverage).

TABLE 10

| Allele (n = 62) | Frequency |
|---|---|
| DRB1_0101 | 0.04275 |
| DRB1_0102 | 0.02325 |
| DRB1_0103 | 0.00475 |
| DRB1_0301 | 0.07725 |
| DRB1_0302 | 0.0175 |
| DRB1_0307 | 0.00025 |
| DRB1_0401 | 0.03375 |
| DRB1_0402 | 0.00775 |
| DRB1_0403 | 0.01575 |
| DRB1_0404 | 0.0275 |
| DRB1_0405 | 0.02325 |
| DRB1_0406 | 0.00625 |
| DRB1_0407 | 0.0245 |
| DRB1_0408 | 0.0025 |
| DRB1_0410 | 0.0025 |
| DRB1_0411 | 0.0035 |
| DRB1_0417 | 0.00025 |
| DRB1_0701 | 0.1015 |
| DRB1_0801 | 0.01125 |
| DRB1_0802 | 0.02725 |
| DRB1_0803 | 0.014 |
| DRB1_0804 | 0.01625 |
| DRB1_0806 | 0.0015 |
| DRB1_0809 | 0.0005 |
| DRB1_0811 | 0.0005 |
| DRB1_0901 | 0.0395 |
| DRB1_1001 | 0.017 |
| DRB1_1101 | 0.057 |
| DRB1_1102 | 0.01325 |
| DRB1_1103 | 0.00275 |
| DRB1_1104 | 0.0185 |
| DRB1_1106 | 0.00075 |
| DRB1_1110 | 0.00075 |
| DRB1_1111 | 0.00025 |
| DRB1_1201 | 0.02325 |
| DRB1_1202 | 0.0195 |
| DRB1_1301 | 0.04575 |
| DRB1_1302 | 0.0445 |
| DRB1_1303 | 0.01525 |
| DRB1_1304 | 0.004 |
| DRB1_1305 | 0.002 |
| DRB1_1311 | 0.00025 |
| DRB1_1312 | 0.001 |
| DRB1_1323 | 0.00025 |
| DRB1_1331 | 0.00025 |
| DRB1_1401 | 0.02275 |
| DRB1_1402 | 0.00925 |
| DRB1_1403 | 0.00125 |
| DRB1_1404 | 0.00525 |
| DRB1_1405 | 0.0045 |
| DRB1_1406 | 0.01 |
| DRB1_1407 | 0.001 |
| DRB1_1418 | 0.00025 |
| DRB1_1419 | 0.00025 |
| DRB1_1424 | 0.00025 |
| DRB1_1501 | 0.074 |
| DRB1_1502 | 0.02575 |
| DRB1_1503 | 0.03125 |
| DRB1_1504 | 0.00025 |
| DRB1_1506 | 0.001 |
| DRB1_1601 | 0.00425 |
| DRB1_1607 | 0.00025 |

Table 11. Frequencies of HLA Alleles Present on Loci, HLA-DRB3, HLA-DRB4, HLA-DRB5, HLA-DP, and HLA-DQ, in a Worldwide Population.

These allele frequencies were used for estimation of worldwide coverage of the HLAs of the donor cohorts—(this table is also used in Examples 4 and 12 regarding predicted peptide coverage).

TABLE 11

| Allele (n = 15) | Frequency |
|---|---|
| DPA10201-DPB10101 | 0.084 |
| DPA10103-DPB10201 | 0.092 |
| DPA10103-DPB10401 | 0.201 |
| DPA10103-DPB10402 | 0.236 |
| DPA10202-DPB10501 | 0.115 |
| DQA10501-DQB10201 | 0.058 |
| DQA10501-DQB10301 | 0.195 |
| DQA10301-DQB10302 | 0.1 |
| DQA10401-DQB10402 | 0.066 |
| DQA10101-DQB10501 | 0.076 |
| DQA10102-DQB10602 | 0.076 |
| DRB3_0101 | 0.14 |
| DRB3_0202 | 0.189 |
| DRB4_0101 | 0.237 |
| DRB5_0101 | 0.083 |

Table 12. HLA Class II Alleles Identified in Donor Cohorts DK1 and DK2

TABLE 12

| Allele | DK1 | DK2 |
|---|---|---|
| DRB1_0101 | X | X |
| DRB1_0103 | X |  |
| DRB1_0301 | X | X |
| DRB1_0401 | X | X |
| DRB1_0402 |  | X |
| DRB1_0405 | X |  |
| DRB1_0406 | X |  |
| DRB1_0407 | X |  |
| DRB1_0701 | X | X |
| DRB1_0801 | X | X |
| DRB1_0803 | X |  |
| DRB1_0804 | X |  |
| DRB1_0901 | X |  |
| DRB1_1101 | X | X |
| DRB1_1103 | X |  |
| DRB1_1104 | X |  |
| DRB1_1109 | X |  |
| DRB1_1201 | X | X |
| DRB1_1301 | X | X |
| DRB1_1302 | X | X |
| DRB1_1303 | X | X |
| DRB1_1501 | X | X |
| DRB1_1502 |  | X |
| DRB3_0101 | X | X |
| DRB3_0202 | X | X |
| DRB3_0301 | X | X |
| DRB4_0101 | X | X |
| DRB4_0103 | X | X |
| DRB5_0101 | X | X |
| DRB5_0102 |  | X |
| HLA-DPA10103-DPB10101 | X | X |
| HLA-DPA10103-DPB10201 | X | X |
| HLA-DPA10103-DPB10301 | X | X |
| HLA-DPA10103-DPB10401 | X | X |
| HLA-DPA10103-DPB10402 | X | X |
| HLA-DPA10103-DPB10501 | X | X |
| HLA-DPA10103-DPB10601 |  | X |
| HLA-DPA10103-DPB11001 | X |  |
| HLA-DPA10103-DPB110401 | X |  |
| HLA-DPA10103-DPB110501 | X | X |
| HLA-DPA10103-DPB11101 | X |  |
| HLA-DPA10103-DPB111101 | X |  |
| HLA-DPA10103-DPB11501 | X | X |
| HLA-DPA10103-DPB11601 |  | X |
| HLA-DPA10103-DPB11701 | X |  |
| HLA-DPA10103-DPB11901 | X |  |
| HLA-DPA10201-DPB10101 | X | X |
| HLA-DPA10201-DPB10201 | X |  |
| HLA-DPA10201-DPB10301 |  | X |
| HLA-DPA10201-DPB10401 | X | X |
| HLA-DPA10201-DPB10402 | X |  |
| HLA-DPA10201-DPB10501 | X |  |
| HLA-DPA10201-DPB10901 | X |  |
| HLA-DPA10201-DPB11001 | X |  |
| HLA-DPA10201-DPB11101 | X |  |
| HLA-DPA10201-DPB11301 | X | X |
| HLA-DPA10201-DPB11701 | X | X |
| HLA-DPA10202-DPB10201 | X | X |
| HLA-DPA10202-DPB10401 | X | X |
| HLA-DPA10202-DPB10501 | X | X |
| HLA-DPA10202-DPB11901 | X |  |
| HLA-DQA10101-DQB10201 | X |  |
| HLA-DQA10101-DQB10202 | X |  |
| HLA-DQA10101-DQB10301 | X | X |
| HLA-DQA10101-DQB10302 |  | X |
| HLA-DQA10101-DQB10402 |  | X |
| HLA-DQA10101-DQB10501 | X | X |
| HLA-DQA10101-DQB10602 |  | X |
| HLA-DQA10101-DQB10604 |  | X |
| HLA-DQA10102-DQB10201 |  | X |
| HLA-DQA10102-DQB10202 | X |  |
| HLA-DQA10102-DQB10301 | X | X |
| HLA-DQA10102-DQB10302 |  | X |
| HLA-DQA10102-DQB10303 | X | X |
| HLA-DQA10102-DQB10402 |  | X |
| HLA-DQA10102-DQB10501 |  | X |
| HLA-DQA10102-DQB10602 | X | X |
| HLA-DQA10102-DQB10603 | X | X |
| HLA-DQA10102-DQB10604 | X | X |
| HLA-DQA10102-DQB10609 | X |  |
| HLA-DQA10103-DQB10201 |  | X |
| HLA-DQA10103-DQB10202 | X | X |
| HLA-DQA10103-DQB10301 | X | X |
| HLA-DQA10103-DQB10302 | X |  |
| HLA-DQA10103-DQB10601 | X | X |
| HLA-DQA10103-DQB10602 | X |  |
| HLA-DQA10103-DQB10603 |  | X |
| HLA-DQA10103-DQB10604 |  | X |
| HLA-DQA10201-DQB10201 | X |  |
| HLA-DQA10201-DQB10202 | X | X |
| HLA-DQA10201-DQB10301 | X |  |
| HLA-DQA10201-DQB10303 | X | X |
| HLA-DQA10201-DQB10402 | X |  |
| HLA-DQA10201-DQB10501 | X |  |
| HLA-DQA10201-DQB10602 |  | X |
| HLA-DQA10201-DQB10603 | X | X |
| HLA-DQA10201-DQB10604 | X |  |
| HLA-DQA10201-DQB10609 | X |  |
| HLA-DQA10301-DQB10201 | X | X |
| HLA-DQA10301-DQB10202 | X |  |
| HLA-DQA10301-DQB10301 | X | X |
| HLA-DQA10301-DQB10302 | X | X |
| HLA-DQA10301-DQB10303 | X |  |
| HLA-DQA10301-DQB10402 | X |  |
| HLA-DQA10301-DQB10501 | X | X |
| HLA-DQA10301-DQB10601 | X |  |
| HLA-DQA10301-DQB10602 | X | X |
| HLA-DQA10301-DQB10603 |  | X |
| HLA-DQA10401-DQB10202 | X |  |
| HLA-DQA10401-DQB10301 | X |  |
| HLA-DQA10401-DQB10302 | X |  |
| HLA-DQA10401-DQB10402 | X | X |
| HLA-DQA10401-DQB10501 |  | X |
| HLA-DQA10401-DQB10602 |  | X |
| HLA-DQA10501-DQB10201 | X | X |
| HLA-DQA10501-DQB10202 | X |  |
| HLA-DQA10501-DQB10301 | X |  |
| HLA-DQA10501-DQB10302 | X | X |
| HLA-DQA10501-DQB10501 | X | X |
| HLA-DQA10501-DQB10601 |  | X |
| HLA-DQA10501-DQB10602 | X | X |
| HLA-DQA10501-DQB10603 | X |  |

Table 13. Calculated Worldwide (WW) Population Fraction Expressing One or More of the HLA Alleles Found in DK1 and DK2

TABLE 13

| Locus | DK1 | DK2 |
|---|---|---|
| DRB1 | 89 | 81 |
| DRB3 | 55 | 55 |
| DRB4 | 42 | 42 |
| DRB5 | 16 | 16 |
| DQ | 82 | 82 |
| DP | 96 | 96 |
| Cumulated | 100 | 100 |

Example 3

Screening for T Cell Reactivity

This example includes a description of the methods used to screen peptides and mixes for T cell reactivity as well as results of the single peptide screening.

The T cell reactivity of the peptides disclosed herein was assessed by measuring T cell proliferation of T cell lines specific to the allergens investigated and/or by measuring the cytokine production of allergen-specific T cells obtained from cultured PBMCs obtained from the donor cohorts of Example 2.

Establishing cultured PBMCs and T cell lines (TCL): Isolated PBMCs (peripheral blood mononuclear cells) obtained from the donors described in Example 2 were CD8 depleted and the T cell lines were established by stimulating the cultures with nPhl p1, mix of nPhl p 2 and nPhl p 3, nPhl p 4, nPhl p 5 and nCyn d 1. TCLs were established for each of the donors tested by stimulating with the mixture of above listed allergens.

Grass allergic donors were recruited (cohort DK1 including 30 grass allergic individuals, DK2 including 24 grass allergic individuals and US1 including 15 grass allergic individuals). PBMCs were isolated from freshly drawn heparinized blood by gradient centrifugation on lymphoprep (Nycomed, Norway), washed twice and re-suspended in RPMI 1640 medium with HEPES and ultraglutamine (Cambrex, Belgium) supplemented with 5% v/v human AB-serum (Cambrex, Belgium), 100 units/ml penicillin, and 0.1 mg/ml streptomycin (Sigma, St Louis, USA) (referred to as 5% AB-medium). Aliquots of the isolated PBMCs were frozen and were thawed later to stimulate the T cell lines. Additionally either fresh or thawed PBMCs were used as antigen presenting cells (APCs) in the proliferation assay as described later. In some cases the PBMCs were freezed at this stage and thawed later on to continue the experiment as described in the following. The isolated PBMCs (fresh or thawed) were CD8 depleted by MACS magnetic depletion according to the manufacturer's instructions (Miltenyi Biotec, Bergisch Gladbach, Germany). On day 0 the CD8-depleted PBMCs ($2\times10^6$/ml) were stimulated in 1 ml bulk cultures in AB medium in 24 well plates (Nunc, Denmark) with the mixture of natural allergens: nPhl p 1 (0.5 µg/ml), mix of nPhl p 2/nPhl p 3 (1.0 µg/ml), nPhl p 4 (0.5 µg/ml), nPhl p 5 (0.5 µg/ml) and nCyn d 1 (0.5 µg/ml). Amount of 65 U, 30 U, and 30 U recombinant IL-2 (Chiron, USA) were added per well at days 5, 6 and 7, respectively. On day 14 cells were harvested to obtain T cell line generation 01 (referred to as TCL01).

To measure the immunogenicity of the peptides, ELISpot/Fluorospot (day 14) and/or proliferation (day 24) experiments were carried out.

On day 14 the T cells of TCL01 were isolated, washed and counted. The isolated T cells of TCL01 generation were used to perform either ELISpot or Fluorospot assay. TCL01 were further re-stimulated as described in the next paragraph for use in T cell proliferation. The aliquot for use in T cell proliferation was re-stimulated on day 14 to carry out proliferation experiment at day 24.

Restimulation of T cell lines were performed in AB-medium with the thawed autologous PBMCs ($10^6$/well, irradiated 2500 Rad), the above mixture of natural allergens (concentration as mentioned above), and PHA-P (0.5 µg/ml, Difco, Detroit, Mich., USA). rIL-2 was added at day 17, 18 and 19. On day 24 cells were harvested to obtain T cell line generation 02 (referred as TCL02). T cells were isolated, washed, counted and used for T cell proliferation assay as described later.

Remaining cells were frozen for later thawing and re-stimulations. The T cell line generation 2 (TCL02) were thawed and were re-stimulated with allogeneic Epstein Bar Virus transformed lymphoblastoid cell lines (EBV) B cells (JY cells, $10^5$/well, irradiated 3500 Rad), allogeneic PBMCs ($10^6$/well, irradiated 2500 Rad), and 0.5 µg/ml PHA-P and subsequent addition of rIL-2 at days 3-5 to generate T cell line generation 03 (referred to as TCL03). T cell proliferation was carried out on $10^{th}$ day after re-stimulation.

To summarize ELISpot experiments were carried out at day 14 (with TCL01) and proliferation assay on either day 24 (with TCL02) or at day 34 (with TCL03).

ELISpot Assay

In the ELISpot assay the release of IL-5 from the cultured donor derived PBMCs described above (DK2-TCL01) in response to stimulation with a peptide or a peptide-mix described herein was measured with ELISpot PLUS kit (MABTECH) as described in Oseroff C et al, 2010. Briefly, mAb TRFK5 (anti IL-5) pre-coated flat-bottom 96-well were obtained and blocked with 10% AB Serum. The plates were washed thoroughly and the isolated T cells were plated and incubated with either single peptides (2 µg/ml) or a peptide pools (2 µg/ml), or allergens nPhl p1, nPhl p 2, nPhl p 3, nPhl p 4, nPhl p 5, nCyn d 1 at 2 µg/ml or 18 hrs/37° C./5% $CO_2$. There-after the plates were removed, cells were thrown away, plates were washed and detection antibody 5A10-biotin (1 µg/ml) in PBS-0.5% FCS was added. After 2 hrs incubation at room temperature plates were washed and Streptavidin-HRP (1:1000) in PBS-0.5% FCS was added and plates were incubated for 1 hr at room temperature. Subsequently the plates were washed and TMB substrate solution was added and plates were developed until distinct spots appear. Color development was quenched by washing with deionized water. Soft plastic under drain was removed and the plates were left in the dark to dry. The counts were inspected in a fluorospot reader. Hit criteria for peptide were 20 SFCs/$10^6$ PBMCs, p≤0.05 and poissons 0.05 stimulated cells compared to background, and a stimulation index (SI) 2.

Fluorospot Assays

In the Fluorospot assays, release of IL-5 and IFN-γ upon T cell activation (of donor derived lines DK1-TCL01, and US1-TCL01) with a peptide or a peptide-mix described herein was measured by Fluorospot assay kit (Mabtech AB) and procedures were followed as per manufacturer's instructions. Briefly anti-human IL-5 and anti-human IFN-γ coated 96 well plates were obtained and blocked with 10% AB serum in RPMI. The plates were washed thoroughly and the isolated T cells were plated and incubated with either single peptides (2 µg/ml) or peptide mixes (2 µg/ml), or allergens nPhl p1, nPhl p 2, nPhl p 3, nPhl p 4, nPhl p 5, Cyn d 1 at 2 µg/ml for 20 hrs/37° C./5% $CO_2$. After the incubation time the cells were removed by emptying the plate. Detection antibodies 7-B6-1-FS-FITC (1:200) and 5A10-biotin (2

μg/ml) were diluted in PBS-0.1% BSA and were added to the plate and incubated for 2 hours/room temperature (RT). There-after the plates were washed and anti-FITC-green (1:200) and SA-Red (1:200) diluted in PBS+0.1% BSA were added and incubated for 1 hour/RT/dark. After the incubation period the plates were washed, emptied and fluorescence enhancer solution was added for 15 minutes/RT. Plates were emptied, fluorescence enhancer solution was firmly tapped out against a clean paper, soft plastic under drain was removed and the plates were left in the dark to dry. The counts were inspected in a fluorospot reader. Hit criteria for peptide were 20 SFCs/$10^6$ PBMCs, p≤0.05 and poissons 0.05 stimulated cells compared to background, and a stimulation index (SI) 2.

T cell proliferation assay: The capacity of the different peptides, peptide mixes and native allergens to stimulate allergen specific T cells was analyzed in a standard 72 h T cell proliferation assay, as described in Henmar H et al., *Clin Exp Immunol* 2008; 153(3):316-23.

To ensure that all T cell epitopes regions from the major and intermediate grass allergens of the grass were identified T cell screening was carried out with either overlapping peptides or selected peptides. T cell reactivity of the peptide libraries described in Example 1, were tested according to these methods. These were overlapping 20-mer peptides spanning the entire full length amino acid sequence of Phl p 1, Cyn d 1, Phl p 2, Phl p 3, Phl p 5a and selected high binder peptides from Phl p 4 were tested. Additionally 21, 15 mer peptides were tested which were derived from various group 1 and 5 allergens. Also, 67 peptides from homologous grass allergens were tested. Finally some reference peptides and mixes thereof were also tested.

The 15-mer peptides were selected on the basis of predicted and measured promiscuous HLA binding and of sequence homology between known proteins sequences from the relevant pooideae grasses and the Bermuda grass. A previous study by the present inventors demonstrated comparable results between Fluorospot/Elispot and proliferation. It has been observed previously that the optimal responses are obtained with some patients (on day 14) while other patients might need an additional re-stimulation with relevant allergens (on day 24). To get comprehensive data from all the donors the peptides were tested in both Fluorospot/Elispot (day 14, TCL01) and proliferation (day 24, TCL02). Newly established 03 T cell lines (as described previously) were used and the peptides were tested at 2 μg/ml in triplicates in a 96 well assay format. Relevant allergens and media controls were used as reference. For the initial screening the peptides used were in TFA (Tri-fluoro acetic acid) counter ion. Peptides selected for further testing were in acetate counter ion. The IL-5 and proliferation data was analysed to select high responder peptides.

Selection Criteria for Peptides Tested

The peptides were identified as hits if they fulfilled the criteria as mentioned below where stimulation index (SI) value of 2 or above, Poisson value=<0.05 and P value=<0.05, SFC>=20 (IL-5/IFN-g)/$10^6$ cells and CPM>=1000 (proliferation) SI can be defined as [colony forming cells (cfc)/medium control] in a Fluorospot assay and [counts per minute (cpm)/medium control] in a proliferation assay. In some donors the background values were considered to be high if the medium control >100 in a Fluorospot assay or cpm >10,000 in a proliferation assay. In high background donors the SI cut-off was reduced to 1.5.

Selection of peptides was based on frequency and strength of the T cell responses (IL-5 and proliferation) as well as the level of predicted HLA binding of the peptides.

Briefly most of the peptides that have been selected for mix design showed good T cell reactivity in both Fluorospot and proliferation assays. The majority of the peptides selected showed a good predicted HLA coverage. A few peptides only showing response in the proliferation assay were selected, especially if they showed good predicted HLA coverage. Likewise, a few peptides without good predicted HLA-binding were selected if the experimental T cell response were high.

Some of the peptides having good T cell data were left out because the sequence was covered by the flanking regions of the selected peptides.

Figure 2A:
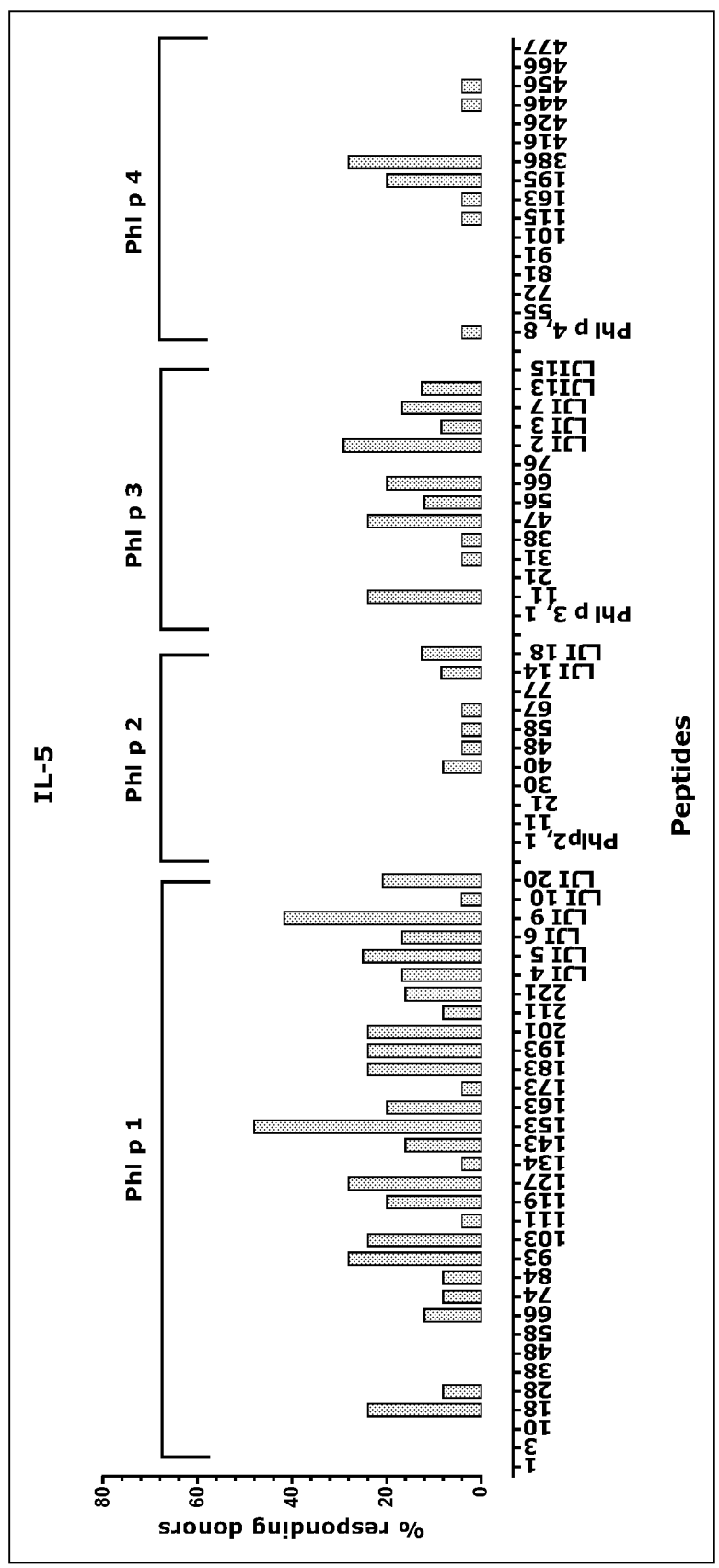
Figure 2B:
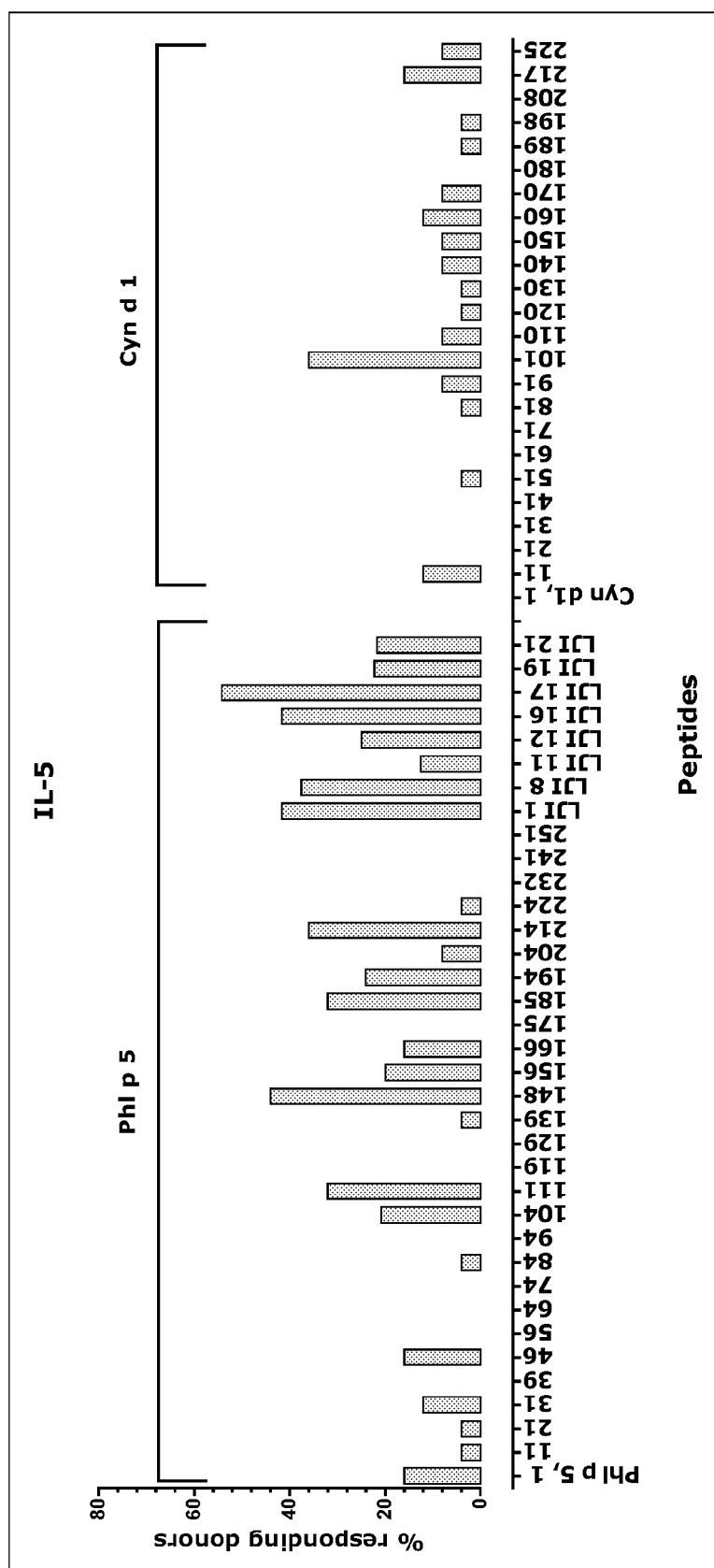
Figure 3A:
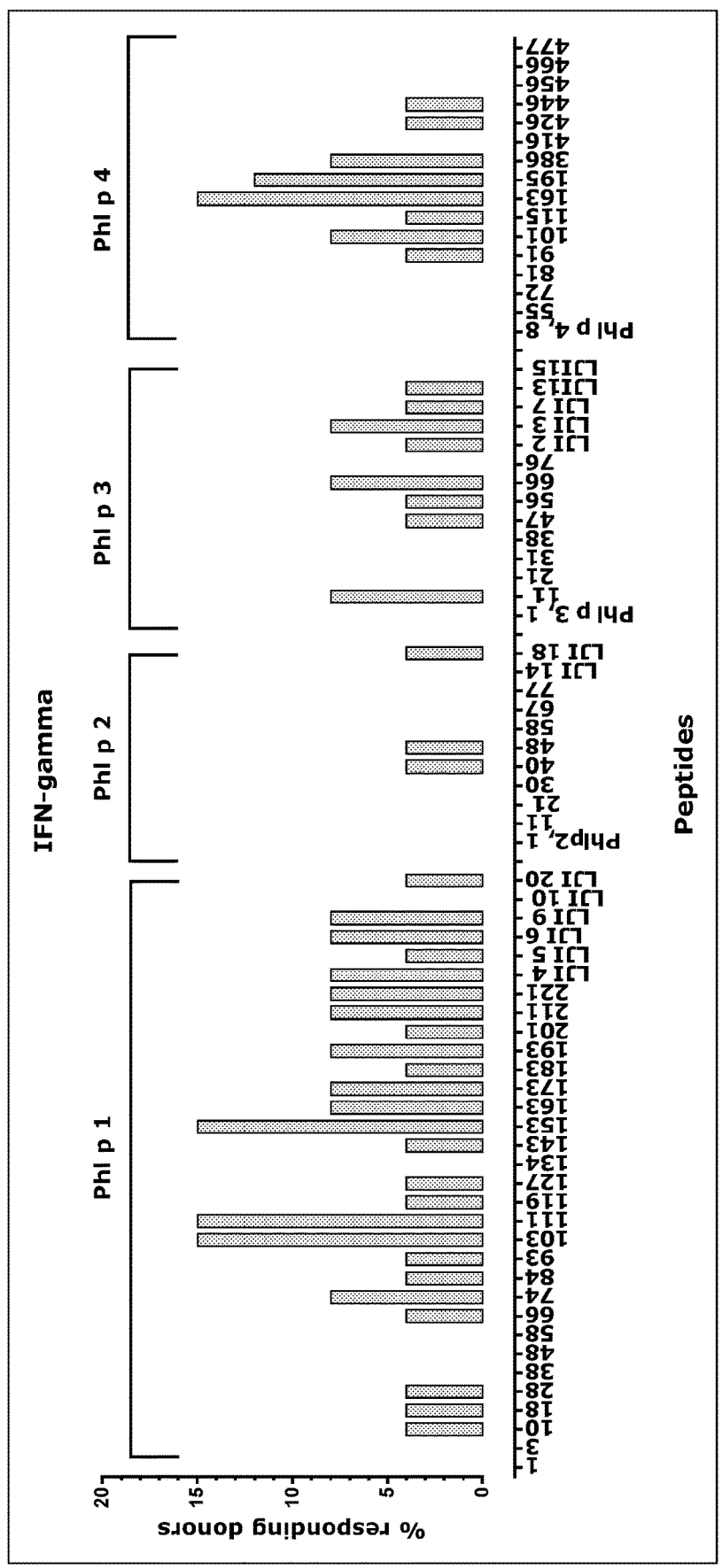
Figure 3B:
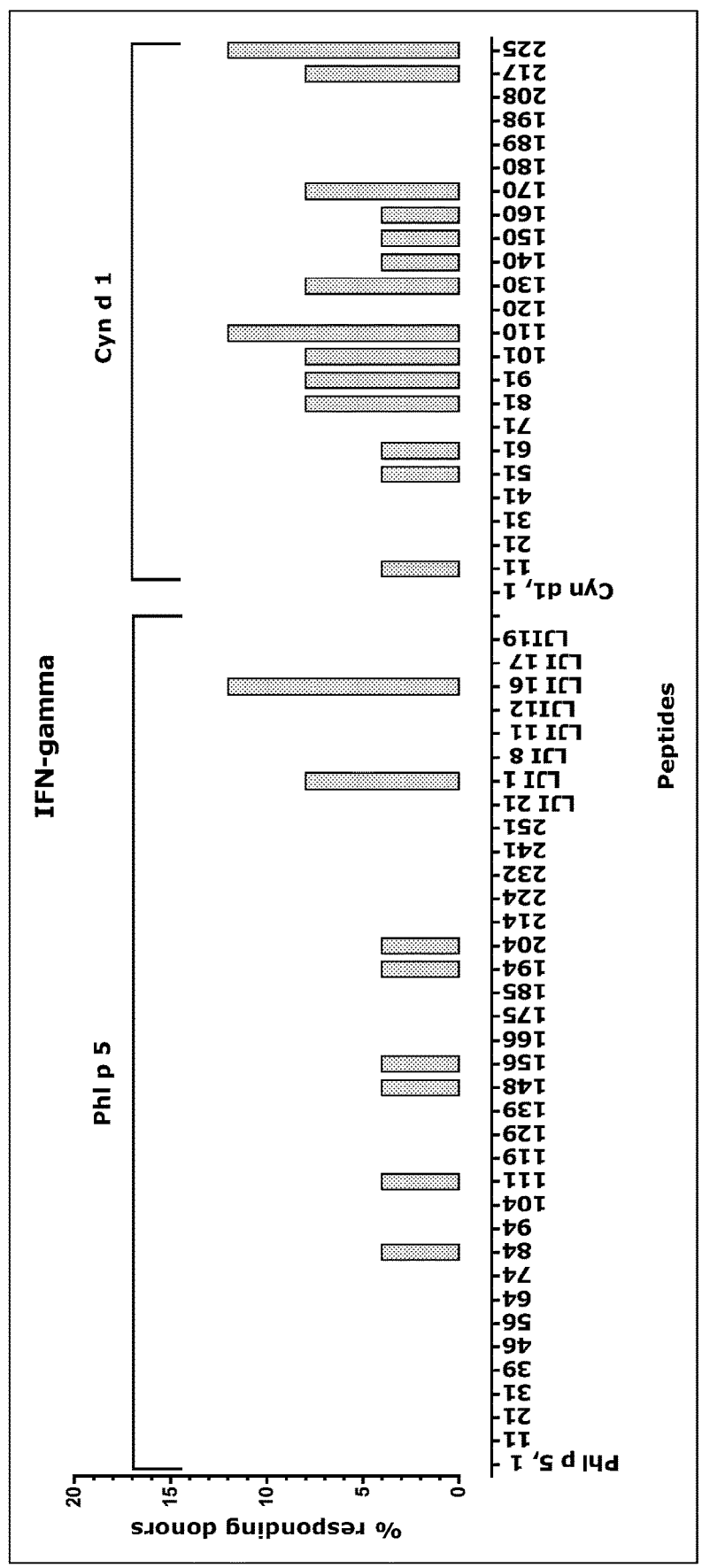
Figure 4A:
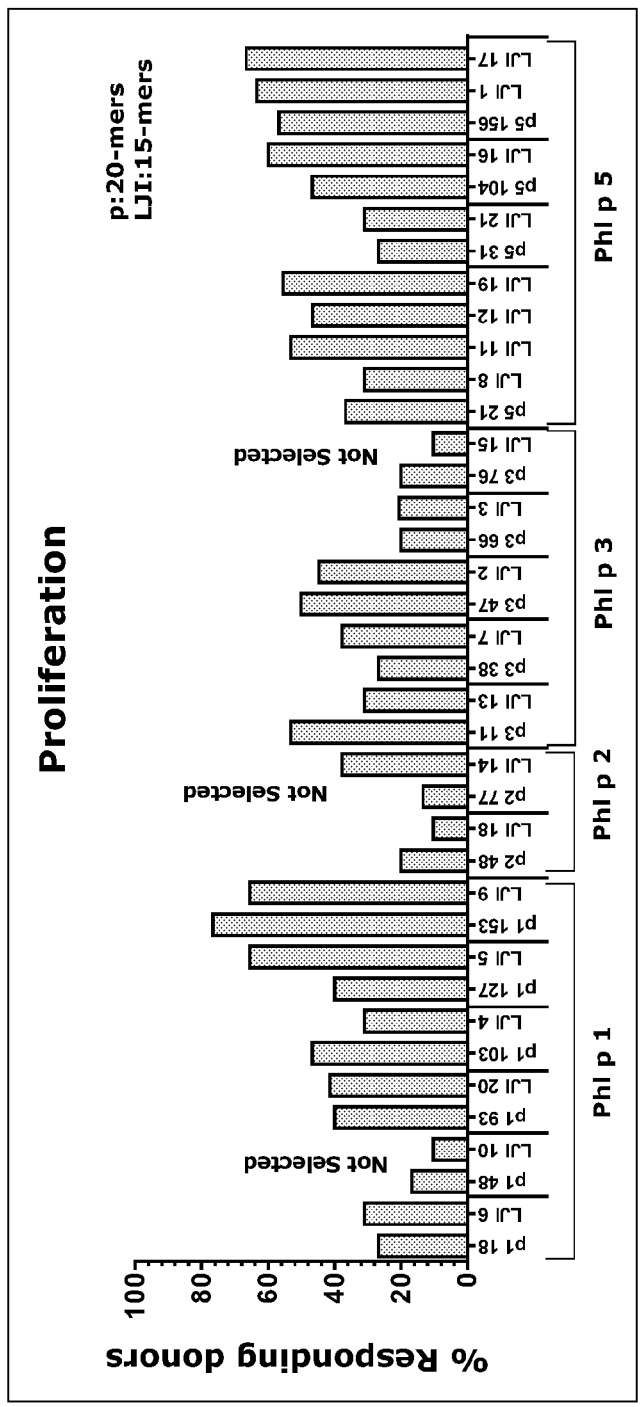
Figure 4B:
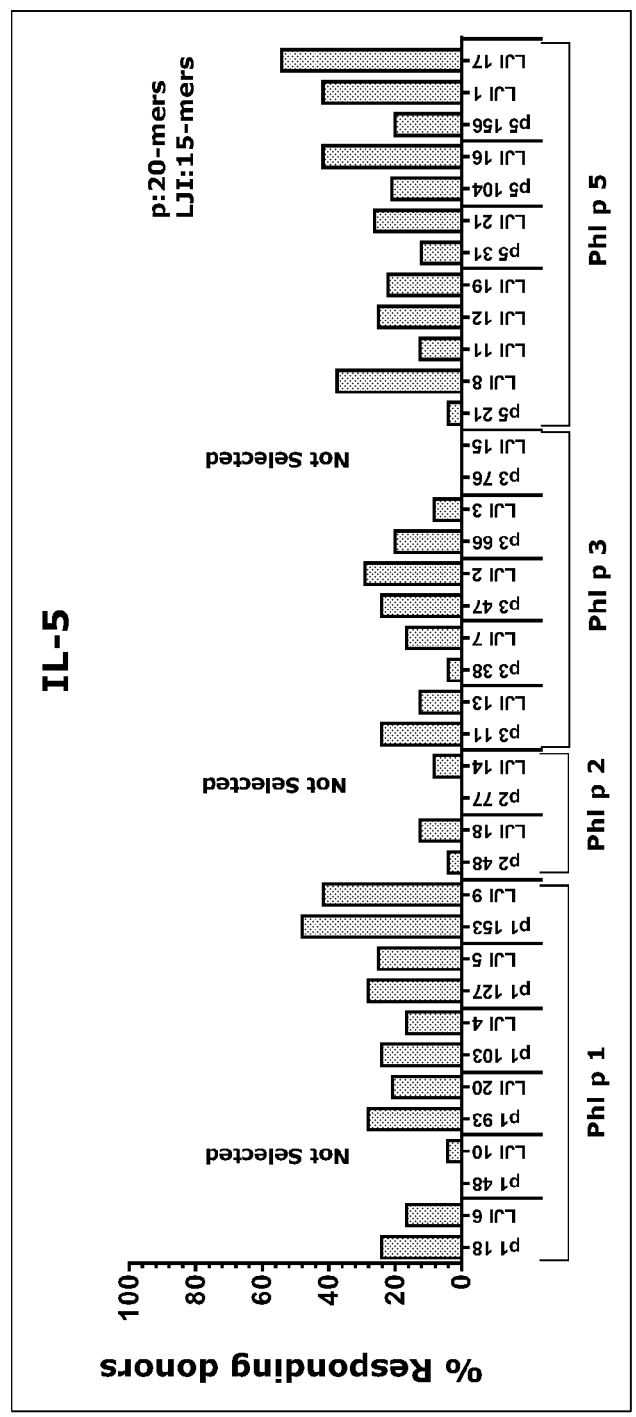

IL-5 data was obtained from 25 TCL-01 DK1, proliferation from 30 TCL-02 DK1 and IFN-g from 17 TCL-01 DK1 and has been summarized in the FIG. 1a & FIG. 1b (Proliferation), FIGS. 2a & 2b (IL-5) and FIGS. 3a & 3b (IFN-gamma). Donor coverage & strength of response with respect to proliferation, IL-5, IFN-gamma has been summarized in Table 1. Further comparison of the 15-mer peptides to corresponding 20-mer peptides with respect to peptide sequence and location has been summarised in FIG. 4a (Proliferation) and FIG. 4b (IL-5).

A total of 42 peptides derived from *Phleum pratense* allergen groups 1, 2, 3, 4 and 5 were selected for further testing based on proliferation and IL-5 production as well as predicted binding to various MHC molecules.

The peptides which had been included in mixes (12 peptides) disclosed in WO2010/089554 were tested in proliferation only.

Out of the 12 peptides tested only a few of them had a good T cell reactivity although comparatively low as compared to the 20-mer peptides of the present invention. Accordingly, Rye09B, Rye 09B1 and Rye 09B2 demonstrated good T cell activity with donor coverage of 50-60%, and average relative magnitude around 8. The T cell reactivity of the remaining peptides was ranging in between 15%-30% donor coverage with low average rel. magnitudes.

In total, screening of the 20-mers overlapping peptides (112 peptides) and 15-mers (21 peptides) on established T cell lines led to positive T cell responses. In particular, nearly all the group 5 peptides showed high T cell reactivity.

Table 14—T Cell Data of 133 Peptides

Table 14 shows the T cell data of the first 133 peptides tested (SEQ ID NOs: 1-133) and of the reference peptides (SEQ ID NOs: 234-245). Selected high responding 42 peptides for mix-design are in bold (see table 15).

| SEQ ID NO: | Peptide Name (position in full length) | Proliferation % donor coverage (TCL-02 DK1) | Proliferation strength (TCL-02 DK1) | IL-5-Fluorospotr % donor coverage (TCL-02 DK1) | IFN-gamma % donor coverage (TCL-02 DK1) |
|---|---|---|---|---|---|
| | Phl p 1 | | | | |
| 14 | 1 | 3.33 | 0.40 | 0.00 | 0.00 |
| 15 | 3 | 3.33 | 0.50 | 0.00 | 0.00 |
| 16 | 10 | 10.00 | 0.70 | 0.00 | 4.00 |

| SEQ ID NO: | Peptide Name (position in full length) | Proliferation % donor coverage (TCL-02 DK1) | Proliferation strength (TCL-02 DK1) | IL-5-Fluorospotr % donor coverage (TCL-02 DK1) | IFN-gamma % donor coverage (TCL-02 DK1) |
|---|---|---|---|---|---|
| 1 | 18 | 26.67 | 4.70 | 24.00 | 4.00 |
| 17 | 28 | 23.33 | 2.80 | 8.00 | 4.00 |
| 18 | 38 | 16.67 | 2.30 | 0.00 | 0.00 |
| 19 | 48 | 16.67 | 1.10 | 0.00 | 0.00 |
| 20 | 58 | 13.33 | 1.40 | 0.00 | 0.00 |
| 2 | 66 | 26.67 | 3.10 | 12.00 | 4.00 |
| 3 | 74 | 36.67 | 3.40 | 8.00 | 8.00 |
| 21 | 84 | 40.00 | 4.90 | 8.00 | 4.00 |
| 4 | 93 | 40.00 | 6.40 | 28.00 | 4.00 |
| 5 | 103 | 46.67 | 7.80 | 24.00 | 15.00 |
| 22 | 111 | 26.67 | 2.10 | 4.00 | 15.00 |
| 6 | 119 | 46.67 | 7.10 | 20.00 | 4.00 |
| 7 | 127 | 40.00 | 8.10 | 28.00 | 4.00 |
| 23 | 134 | 20.00 | 1.60 | 4.00 | 0.00 |
| 24 | 143 | 36.67 | 7.40 | 16.00 | 4.00 |
| 8 | 153 | 76.67 | 18.70 | 48.00 | 15.00 |
| 9 | 163 | 26.67 | 1.60 | 20.00 | 8.00 |
| 25 | 173 | 20.00 | 1.10 | 4.00 | 8.00 |
| 10 | 183 | 60.00 | 9.80 | 24.00 | 4.00 |
| 11 | 193 | 46.67 | 4.80 | 24.00 | 8.00 |
| 26 | 201 | 13.33 | 2.00 | 24.00 | 4.00 |
| 12 | 211 | 23.33 | 7.00 | 8.00 | 8.00 |
| 13 | 221 | 43.33 | 8.10 | 16.00 | 8.00 |
| 117 | LJI 4 | 31.03 | 6.20 | 16.67 | 8.00 |
| 118 | LJI 5 | 65.52 | 11.50 | 25.00 | 4.00 |
| 119 | LJI 6 | 31.03 | 4.20 | 16.67 | 8.00 |
| 121 | LJI 9 | 65.52 | 11.90 | 41.67 | 8.00 |
| 122 | LJI 10 | 10.34 | 0.60 | 4.17 | 0.00 |
| 132 | LJI 20 | 41.38 | 4.90 | 20.83 | 4.00 |
| Phl p 2 | | | | | |
| 30 | 1 | 3.33 | 0.40 | 0.00 | 0.00 |
| 31 | 11 | 10.00 | 1.40 | 0.00 | 0.00 |
| 32 | 21 | 6.67 | 0.20 | 0.00 | 0.00 |
| 33 | 30 | 0.00 | 0.00 | 0.00 | 0.00 |
| 27 | 40 | 13.33 | 2.30 | 8.00 | 4.00 |
| 28 | 48 | 20.00 | 2.80 | 4.00 | 4.00 |
| 29 | 58 | 13.33 | 1.70 | 4.00 | 0.00 |
| 34 | 67 | 6.67 | 0.60 | 4.00 | 0.00 |
| 35 | 77 | 13.33 | 0.70 | 0.00 | 0.00 |
| 126 | LJI 14 | 37.93 | 0.40 | 8.33 | 0.00 |
| 130 | LJI 18 | 10.34 | 1.80 | 12.50 | 4.00 |
| Phl p 3 | | | | | |
| 41 | 1 | 16.67 | 1.50 | 0.00 | 0.00 |
| 36 | 11 | 53.33 | 11.90 | 24.00 | 8.00 |
| 42 | 21 | 16.67 | 0.80 | 0.00 | 0.00 |
| 43 | 31 | 3.33 | 0.70 | 4.00 | 0.00 |
| 37 | 38 | 26.67 | 3.20 | 4.00 | 0.00 |
| 38 | 47 | 50.00 | 6.60 | 24.00 | 4.00 |
| 39 | 56 | 13.33 | 1.10 | 12.00 | 4.00 |
| 40 | 66 | 20.00 | 2.40 | 20.00 | 8.00 |
| 44 | 76 | 20.00 | 1.40 | 0.00 | 0.00 |
| 115 | LJI 2 | 44.83 | 6.10 | 29.17 | 4.00 |
| 116 | LJI 3 | 20.69 | 1.10 | 8.33 | 8.00 |
| 120 | LJI 7 | 37.93 | 5.00 | 16.67 | 4.00 |
| 125 | LJI 13 | 31.03 | 6.30 | 12.50 | 4.00 |
| 127 | LJI 15 | 10.34 | 2.80 | 0.00 | 0.00 |
| Phl p 4 | | | | | |
| 45 | 8 | 20.00 | 4.00 | 4.00 | 0.00 |
| 46 | 55 | 27.00 | 1.00 | 0.00 | 0.00 |
| 51 | 72 | 10.00 | 0.40 | 0.00 | 0.00 |
| 52 | 81 | 3.33 | 0.20 | 0.00 | 0.00 |
| 53 | 91 | 10.00 | 1.20 | 0.00 | 4.00 |
| 47 | 101 | 40.00 | 6.20 | 0.00 | 8.00 |
| 54 | 115 | 26.67 | 4.20 | 4.00 | 4.00 |
| 48 | 163 | 30.00 | 4.70 | 4.00 | 15.00 |
| 49 | 195 | 40.00 | 5.60 | 20.00 | 12.00 |
| 50 | 386 | 43.33 | 6.70 | 28.00 | 8.00 |
| 55 | 416 | 26.67 | 3.00 | 0.00 | 0.00 |
| 56 | 426 | 20.00 | 3.10 | 0.00 | 4.00 |
| 57 | 446 | 16.67 | 2.00 | 4.00 | 4.00 |
| 58 | 456 | 20.00 | 2.40 | 4.00 | 0.00 |

-continued

| SEQ ID NO: | Peptide Name (position in full length) | Proliferation % donor coverage (TCL-02 DK1) | Proliferation strength (TCL-02 DK1) | IL-5-Fluorospotr % donor coverage (TCL-02 DK1) | IFN-gamma % donor coverage (TCL-02 DK1) |
|---|---|---|---|---|---|
| 59 | 466 | 30.00 | 3.20 | 0.00 | 0.00 |
| 60 | 477 | 13.33 | 2.60 | 0.00 | 0.00 |
| | Phl p 5 | | | | |
| 61 | 1 | 26.67 | 3.40 | 16.00 | 0.00 |
| 74 | 11 | 10.00 | 1.50 | 4.00 | 0.00 |
| 62 | 21 | 36.67 | 6.20 | 4.00 | 0.00 |
| 63 | 31 | 26.67 | 4.10 | 12.00 | 0.00 |
| 75 | 39 | 10.00 | 1.10 | 0.00 | 0.00 |
| 64 | 46 | 36.67 | 6.00 | 16.00 | 0.00 |
| 76 | 56 | 16.67 | 1.60 | 0.00 | 0.00 |
| 77 | 64 | 3.33 | 0.40 | 0.00 | 0.00 |
| 78 | 74 | 16.67 | 3.00 | 0.00 | 0.00 |
| 65 | 84 | 30.00 | 5.70 | 4.00 | 4.00 |
| 79 | 94 | 26.67 | 3.30 | 0.00 | 0.00 |
| 66 | 104 | 46.67 | 11.20 | 20.83 | 0.00 |
| 67 | 111 | 43.33 | 7.30 | 32.00 | 4.00 |
| 80 | 119 | 30.00 | 4.40 | 0.00 | 0.00 |
| 81 | 129 | 20.00 | 2.60 | 0.00 | 0.00 |
| 82 | 139 | 20.00 | 2.60 | 4.00 | 0.00 |
| 68 | 148 | 63.33 | 15.30 | 44.00 | 4.00 |
| 69 | 156 | 56.67 | 9.40 | 20.00 | 4.00 |
| 70 | 166 | 46.67 | 8.10 | 16.00 | 0.00 |
| 83 | 175 | 10.00 | 0.90 | 0.00 | 0.00 |
| 71 | 185 | 46.67 | 8.20 | 32.00 | 0.00 |
| 72 | 194 | 53.33 | 10.30 | 24.00 | 4.00 |
| 84 | 204 | 20.00 | 2.80 | 8.00 | 4.00 |
| 73 | 214 | 57.00 | 11.30 | 36.00 | 0.00 |
| 85 | 224 | 20.00 | 2.80 | 4.00 | 0.00 |
| 86 | 232 | 10.00 | 1.40 | 0.00 | 0.00 |
| 87 | 241 | 10.00 | 0.70 | 0.00 | 0.00 |
| 88 | 251 | 0.00 | 0.00 | 0.00 | 0.00 |
| 133 | LJI 21 | 31.03 | 4.70 | 21.74 | 0.00 |
| 113 | LJI 1 (154) | 63.33 | 14.70 | 41.67 | 8.00 |
| 114 | LJI 8 | 56.67 | 11.10 | 37.50 | 0.00 |
| 123 | LJI 11 | 53.33 | 7.90 | 12.50 | 0.00 |
| 124 | LJI 12 | 46.67 | 9.50 | 25.00 | 0.00 |
| 128 | LJI 16 | 60.00 | 13.50 | 41.67 | 12.00 |
| 129 | LJI 17 | 66.67 | 14.30 | 54.17 | 0.00 |
| 131 | LJI 19 | 55.55 | 6.50 | 22.22 | 0.00 |
| | Cyn d1 | | | | |
| 89 | 1 | 6.67 | 1.10 | 0.00 | 0.00 |
| 90 | 11 | 26.67 | 3.50 | 12.00 | 4.00 |
| 91 | 21 | 10.00 | 2.90 | 0.00 | 0.00 |
| 92 | 31 | 3.33 | 0.60 | 0.00 | 0.00 |
| 93 | 41 | 16.67 | 2.40 | 0.00 | 0.00 |
| 94 | 51 | 16.67 | 2.90 | 4.00 | 4.00 |
| 95 | 61 | 20.00 | 2.20 | 0.00 | 4.00 |
| 96 | 71 | 6.67 | 0.60 | 0.00 | 0.00 |
| 97 | 81 | 10.00 | 0.70 | 4.00 | 8.00 |
| 98 | 91 | 53.33 | 9.70 | 8.00 | 8.00 |
| 99 | 101 | 70.00 | 16.70 | 36.00 | 8.00 |
| 100 | 110 | 26.67 | 3.00 | 8.00 | 12.00 |
| 101 | 120 | 13.33 | 1.20 | 4.00 | 0.00 |
| 102 | 130 | 33.33 | 4.70 | 4.00 | 8.00 |
| 103 | 140 | 36.67 | 6.50 | 8.00 | 4.00 |
| 104 | 150 | 46.67 | 5.60 | 8.00 | 4.00 |
| 105 | 160 | 16.67 | 1.90 | 12.00 | 4.00 |
| 106 | 170 | 40.00 | 5.20 | 8.00 | 8.00 |
| 107 | 180 | 36.67 | 4.90 | 0.00 | 0.00 |
| 108 | 189 | 33.33 | 4.10 | 4.00 | 0.00 |
| 109 | 198 | 6.67 | 0.40 | 4.00 | 0.00 |
| 110 | 208 | 20.00 | 2.90 | 0.00 | 0.00 |
| 111 | 217 | 43.33 | 7.70 | 16.00 | 8.00 |
| 112 | 225 | 26.67 | 2.60 | 8.00 | 12.00 |
| | Reference Peptides | | | | |
| 234 | Ber01 | 27.59 | 4.00 | X | X |
| 235 | Ber02 | 13.79 | 1.50 | X | X |
| 236 | Ber02C | 17.24 | 1.90 | X | X |
| 237 | Bio02A | 27.59 | 6.30 | X | X |
| 238 | Bio03A | 31.03 | 4.20 | X | X |
| 239 | Bio04A | 20.69 | 2.80 | X | X |

| SEQ ID NO: | Peptide Name (position in full length) | Proliferation % donor coverage (TCL-02 DK1) | Proliferation strength (TCL-02 DK1) | IL-5-Fluorospotr % donor coverage (TCL-02 DK1) | IFN-gamma % donor coverage (TCL-02 DK1) |
|---|---|---|---|---|---|
| 240 | Rye09B | 55.17 | 8.20 | X | X |
| 241 | Tim07B | 10.34 | 1.10 | X | X |
| 242 | Rye09B1 | 48.28 | 7.20 | X | X |
| 243 | Rye09B2 | 48.28 | 7.50 | X | X |
| 244 | Tim07B1 | 31.03 | 3.60 | X | X |
| 245 | Tim07B2 | 20.69 | 1.70 | X | X |

Evaluating the T cell data, HLA and species coverage, 40 20-mer peptides and 2 15-mer peptides were selected for designing the peptide mixes (Table 12).

Table 15—Selected 42 Peptides

Table 15 shows 42 high responding peptides selected for mix-design. For the peptide having the amino acid SEQ ID NO: 114, the table refers—not to the position in the allergen it is derived from—but instead to the position of a corresponding peptide derived from an allergen of *Phleum pratense* of Table 1 to which the peptide in question would align. SEQ ID NO: 114 is derived from *Lolium perenne*. In the table, reference is given to the corresponding start position in *Phleum pratense*, when the peptide is aligned to that.

TABLE 15

| SEQ ID NO: | Sequence | Allergen, position | Peptide name |
|---|---|---|---|
| 1 | WLDAKSTWYGKPTGAGPKDN | Phl p 1, 18 | 201 |
| 2 | GRGSGSSFEIKSTKPEASSG | Phl p 1, 66 | 202 |
| 3 | EIKSTKPEASSGEPVVVHIT | Phl p 1, 74 | 203 |
| 4 | TDDNEEPIAPYHFDLSGHAF | Phl p 1, 93 | 204 |
| 5 | YHFDLSGHAFGAMAKKGDEQ | Phl p 1, 103 | 205 |
| 6 | GDEQKLRSAGELELQFRRVK | Phl p 1, 119 | 206 |
| 7 | AGELELQFRRVKSKYPEGTK | Phl p 1, 127 | 207 |
| 8 | KGSNPNYLALLVKYVNGDGD | Phl p 1, 153 | 208 |
| 9 | LVKYVNGDGDVVAVDIKEKG | Phl p 1, 163 | 209 |
| 10 | KDKWIELKESWGAIWRIDTP | Phl p 1, 183 | 210 |
| 11 | WGAIWRIDTPDKLTGPFTVR | Phl p 1, 193 | 211 |
| 12 | VRYTTEGGTKTEAEDVIPEG | Phl p 1, 211 | 212 |
| 13 | TEAEDVIPEGWKADTSYESK | Phl p 1, 221 | 213 |
| 27 | EWVAMTKGEGGVWTFDSEEP | Phl p 2, 40 | 214 |
| 28 | EGGVWTFDSEEPLQGPFNFR | Phl p 2, 48 | 215 |
| 29 | EPLQGPFNFRFLTEKGMKNV | Phl p 2, 58 | 216 |
| 36 | GSDPKKLVLNIKYTRPGDSL | Phl p 3, 11 | 217 |
| 37 | HGSEEWEPLTKKGNVWEVKS | Phl p 3, 38 | 218 |
| 38 | TKKGNVWEVKSSKPLVGPFN | Phl p 3, 47 | 219 |
| 39 | KSSKPLVGPFNFRFMSKGGM | Phl p 3, 56 | 220 |
| 40 | NFRFMSKGGMRNVFDEVIPT | Phl p 3, 66 | 221 |
| 45 | KEDFLGSLVKEIPPRLLYAK | Phl p 4, 8 | 222 |
| 46 | YIITPTNVSHIQSAVVSGRR | Phl p 4, 55 | 223 |
| 47 | FAVVDLNKMRAVWVDGKART | Phl p 4, 101 | 224 |
| 48 | GFGMLLRKYGIAAENVIDVK | Phl p 4, 163 | 225 |
| 49 | SMGDDHFWAVRGGGGESFGI | Phl p 4, 195 | 226 |
| 50 | TPFPHRKGVLFNIQYVNYWF | Phl p 4, 386 | 227 |
| 61 | AGYTPAAPAGAEPAGKATTE | Phl p 5, 1 | 228 |
| 62 | EQKLIEKINAGFKAALAAAA | Phl p 5, 21 | 229 |
| 63 | GFKAALAAAAGVPPADKYRT | Phl p 5, 31 | 230 |
| 64 | DKYRTFVATFGAASNKAFAE | Phl p 5, 46 | 231 |
| 65 | TSKLDAAYKLAYKTAEGATP | Phl p 5, 84 | 232 |
| 66 | EAKYDAYVATLSEALRIIAG | Phl p 5, 104 | 233 |
| 67 | VATLSEALRIIAGTLEVHAV | Phl p 5, 111 | 234 |
| 68 | IEKVDAAFKVAATAANAAPA | Phl p 5, 148 | 235 |
| 69 | KVAATAANAAPANDKFTVFE | Phl p 5, 156 | 236 |
| 70 | PANDKFTVFEAAFNNAIKAS | Phl p 5, 166 | 237 |
| 71 | STGGAYESYKFIPALEAAVK | Phl p 5, 185 | 238 |
| 72 | KFIPALEAAVKQAYAATVAT | Phl p 5, 194 | 239 |
| 73 | APEVKYTVFETALKKAITAM | Phl p 5, 214 | 240 |
| 113 | AFKVAATAANAAPAN | Phl p 5, 154 | 241 (LJI 1) |
| 114 | INVGFKAAVAAAAGV | ~Phl p 5, 26 | 242 (LJI 8) |

Example 4

Predicted HLA Coverage of Selected Peptides

This example describes how HLA Class II allele coverage can be determined for individual peptides and peptide combinations disclosed herein, In order to elicit a T cell response a given peptide must be able to bind to at least one HLA class II molecule in a given individual. Each individual express several HLA molecules, and globally (worldwide), thousands of different alleles exist. Each HLA molecule can bind a limited number of different peptides and not all HLAs bind the same peptides. In order to estimate the potential coverage of a peptide in a given population, the frequency of the different HLA class II molecules present in the population, and the binding affinity of the peptide towards each of these molecules must be available. The peptide binding to a specific HLA molecule can be measured, for example as described in Example 11, or predicted using in silico algorithms such as e.g. NetMHCIIpan-3.0 (Karosiene, Edita, Michael Rasmussen, Thomas Blicher, Ole Lund, Soren Buus, and Morten Nielsen. "NetMHCIIpan-3.0, a Common Pan-specific MHC Class II Prediction Method Including All Three Human MHC Class II Isotypes, HLA-DR, HLA-DP and HLA-DQ." *Immunogenetics*) available at the internet site Located at www.cbs.dtu.dk/services/NetMHCIIpan-3.0.

The exact affinity necessary for an immune response is not known, but it is generally assumed to be below 1000 nM. For predicting the affinities of the peptides disclosed herein we used the NetMHCIIpan-3.0 algorithm. To assign a given peptide as a binder for a given HLA we used a binding threshold of 300 nM together with the percentile rank score reported in this algorithm of at least 30.

Assuming that alleles at different loci are independently distributed in the worldwide population (which is not entirely true, but is a reasonable approximation), the phenotypic coverage of the binding alleles were calculated using standard methods known in the art. For example, for each HLA locus (DRB1, DRB3, DRB4, DRB5) or locus combination (DQA1-DQB1, DPA1-DPB1), the HLA allele frequencies of all the alleles from the given locus found to bind the given peptide is summed ($f_{sum,locus}$). The total phenotypic coverage for each locus, n ($C_n$) is calculated as $(2 \times f_{sum,locus}) - (f_{sum,locus})^2$, assuming that the population is in Hardy-Weinberg equilibrium. This formula accounts for the fact that every individual has two alleles of each locus (i.e. $2 \times f_{sum,locus}$), while correcting for those individuals who are homozygous at a given locus (i.e.) $-(f_{sum,locus})^2$.

The total phenotypic coverage of all binding alleles from n loci can be calculated using Formula 1:

$$K_n = \sum_{i=1}^{n} (1 - K_{(i-1)}) \times C_i,$$ Formula 1 where $K_0 = 0$ and $C_1$ the coverage for locus i. For each locus i, the fraction of the population is added that is not already covered by the previous loci (1 through i-1).

A peptide is a good candidate for peptide combinations of the invention if it meets a criterion of having high WW HLA coverage, preferably of above 0.4 (40% of WW population). In general the likelihood that a peptide contributes to the overall peptide valency of a peptide combination is higher, the Higher the HLA Coverage is.

Table 16a—Predicted HLA coverage of selected Peptides

Table 16a shows the predicted worldwide (WW) HLA coverage of 41 of the 42 selected peptides suggested for peptide combinations of the invention for treating grass allergic individuals. The predicted WW HLA coverage was determined using the alleles and allele frequencies shown in Tables 10 and 11 of Example 2.

TABLE 16a

| SEQ ID NO: | Peptide | Peptide sequence | Predicted World Wide HLA coverage 77 alleles |
|---|---|---|---|
| 1 | 201 | WLDAKSTWYGKPTGAGPKDN | 35% |
| 2 | 202 | GRGSGSSFEIKSTKPEASSG | 0% |
| 3 | 203 | EIKSTKPEASSGEPVVVHIT | 35% |
| 4 | 204 | TDDNEEPIAPYHFDLSGHAF | 26% |
| 5 | 205 | YHFDLSGHAFGAMAKKGDEQ | 40% |
| 6 | 206 | GDEQKLRSAGELELQFRRVK | 0% |
| 7 | 207 | AGELELQFRRVKSKYPEGTK | 80% |
| 8 | 208 | KGSNPNYLALLVKYVNGDGD | 68% |
| 9 | 209 | LVKYVNGDGDVVAVDIKEKG | 35% |
| 10 | 210 | KDKWIELKESWGAIWRIDTP | 0% |
| 11 | 211 | WGAIWRIDTPDKLTGPFTVR | 45% |
| 12 | 212 | VRYTTEGGTKTEAEDVIPEG | 0% |
| 13 | 213 | TEAEDVIPEGWKADTSYESK | 0% |
| 27 | 214 | EWVAMTKGEGGVWTFDSEEP | 0% |
| 28 | 215 | EGGVWTFDSEEPLQGPFNFR | 34% |
| 29 | 216 | EPLQGPFNFRFLTEKGMKNV | 70% |
| 36 | 217 | GSDPKKLVLNIKYTRPGDSL | 61% |
| 37 | 218 | HGSEEWEPLTKKGNVWEVKS | 0% |
| 38 | 219 | TKKGNVWEVKSSKPLVGPFN | 35% |
| 39 | 220 | KSSKPLVGPFNFRFMSKGGM | 28% |
| 40 | 221 | NFRFMSKGGMRNVFDEVIPT | 33% |
| 45 | 222 | KEDFLGSLVKEIPPRLLYAK | 100% |
| 46 | 223 | YIITPTNVSHIQSAVVSGRR | 88% |
| 47 | 224 | FAVVDLNKMRAVWVDGKART | 89% |
| 48 | 225 | GFGMLLRKYGIAAENVIDVK | 87% |
| 49 | 226 | SMGDDHFWAVRGGGGESFGI | 35% |
| 50 | 227 | TPFPHRKGVLFNIQYVNYWF | 88% |
| 61 | 228 | AGYTPAAPAGAEPAGKATTE | 40% |
| 62 | 229 | EQKLIEKINAGFKAALAAAA | 99% |
| 63 | 230 | GFKAALAAAAGVPPADKYRT | 86% |
| 64 | 231 | DKYRTFVATFGAASNKAFAE | 99% |
| 65 | 232 | TSKLDAAYKLAYKTAEGATP | 79% |
| 66 | 233 | EAKYDAYVATLSEALRIIAG | 100% |
| 67 | 234 | VATLSEALRIIAGTLEVHAV | 90% |
| 68 | 235 | IEKVDAAFKVAATAANAAPA | 93% |
| 69 | 236 | KVAATAANAAPANDKFTVFE | 47% |
| 70 | 237 | PANDKFTVFEAAFNNAIKAS | 97% |
| 71 | 238 | STGGAYESYKFIPALEAAVK | 99% |
| 72 | 239 | KFIPALEAAVKQAYAATVAT | 76% |

TABLE 16a-continued

| SEQ ID NO: | Peptide | Peptide sequence | Predicted World Wide HLA coverage 77 alleles |
|---|---|---|---|
| 73 | 240 | APEVKYTVFETALKKAITAM | 100% |
| 113 | 241 (LJI 1) | AFKVAATAANAAPAN | 71% |

Table 16b—Predicted HLA Coverage of Selected Peptides

Table 16b (1-6) shows the predicted worldwide (WW) HLA coverage of 41 of the 42 selected peptides suggested for peptide combinations of the invention for treating grass allergic individuals. The predicted WW HLA coverage was determined using the alleles and allele frequencies shown in Tables 10 and 11 of Example 2.

TABLE 16b1

| Peptide name | DRB1_0101 | DRB1_0102 | DRB1_0103 | DRB1_0301 | DRB1_0302 | DRB1_0307 | DRB1_0401 | DRB1_0402 | DRB1_0403 |
|---|---|---|---|---|---|---|---|---|---|
| 201 | — | — | — | — | — | — | — | — | — |
| 202 | — | — | — | — | — | — | — | — | — |
| 203 | — | — | — | — | — | — | — | — | — |
| 204 | — | — | — | — | — | — | — | — | — |
| 205 | — | — | — | — | — | — | — | — | — |
| 206 | — | — | — | — | — | — | — | — | — |
| 207 | — | — | — | — | — | — | — | — | — |
| 208 | X | X | — | — | — | — | — | — | — |
| 209 | — | — | — | — | — | — | — | — | — |
| 210 | — | — | — | — | — | — | — | — | — |
| 211 | — | — | — | X | — | X | — | — | — |
| 212 | — | — | — | — | — | — | — | — | — |
| 213 | — | — | — | — | — | — | — | — | — |
| 215 | — | — | — | — | — | — | — | — | — |
| 216 | X | X | — | — | — | — | X | — | — |
| 217 | — | — | — | X | — | X | — | — | — |
| 218 | — | — | — | — | — | — | — | — | — |
| 220 | — | — | — | — | — | — | — | — | — |
| 222 | X | X | X | X | X | X | — | — | — |
| 223 | X | X | X | — | — | — | X | — | — |
| 225 | — | X | X | — | — | — | — | — | — |
| 226 | — | — | — | — | — | — | — | — | — |
| 227 | — | — | — | — | — | — | — | — | — |
| 228 | — | — | — | — | — | — | — | — | — |
| 231 | X | X | X | — | — | — | X | — | X |
| 233 | X | X | X | — | — | — | X | — | X |
| 235 | X | X | X | — | — | — | X | — | X |
| 236 | — | — | X | — | — | — | — | — | — |
| 238 | X | X | X | — | — | — | X | — | X |
| 239 | X | X | X | — | — | — | — | — | — |
| 240 | X | X | — | — | X | X | X | — | X |
| 241 | X | — | X | — | — | — | X | — | — |

| Peptide name | DRB1_0404 | DRB1_0405 | DRB1_0406 | DRB1_0407 | DRB1_0408 |
|---|---|---|---|---|---|
| 201 | — | — | — | — | — |
| 202 | — | — | — | — | — |
| 203 | — | — | — | — | — |
| 204 | — | — | — | — | — |
| 205 | — | — | — | — | — |
| 206 | — | — | — | — | — |
| 207 | — | — | — | — | — |
| 208 | X | X | — | — | — |
| 209 | — | — | — | — | — |
| 210 | — | — | — | — | — |
| 211 | — | — | — | — | — |
| 212 | — | — | — | — | — |
| 213 | — | — | — | — | — |
| 215 | — | — | — | — | — |
| 216 | — | X | — | — | X |
| 217 | — | — | — | — | — |
| 218 | — | — | — | — | — |
| 220 | — | — | — | — | — |
| 222 | — | — | — | — | — |
| 223 | — | — | — | — | — |
| 225 | — | — | — | — | — |
| 226 | — | — | — | — | — |
| 227 | — | — | — | — | — |
| 228 | — | — | — | — | — |

TABLE 16b1-continued

| | | | | | |
|---|---|---|---|---|---|
| 231 | X | X | X | X | X |
| 233 | X | X | X | X | X |
| 235 | X | X | X | X | X |
| 236 | — | — | — | — | — |
| 238 | X | X | X | X | X |
| 239 | — | — | — | — | — |
| 240 | X | X | X | X | X |
| 241 | X | X | — | X | X |

TABLE 16b2

| Peptide name | DRB1_0410 | DRB1_0411 | DRB1_0417 | DRB1_0701 | DRB1_0801 | DRB1_0802 | DRB1_0803 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | — | — | — |
| 206 | — | — | — | — | — | — | — |
| 207 | — | — | — | X | X | X | X |
| 208 | X | — | — | — | — | — | — |
| 209 | — | — | — | — | — | — | — |
| 210 | — | — | — | — | — | — | — |
| 211 | — | — | — | — | — | — | — |
| 212 | — | — | — | — | — | — | — |
| 213 | — | — | — | — | — | — | — |
| 215 | — | — | — | — | — | — | — |
| 216 | — | — | — | — | — | — | — |
| 217 | — | — | — | — | X | — | X |
| 218 | — | — | — | — | — | — | — |
| 220 | — | — | — | — | — | — | — |
| 222 | X | X | — | X | X | — | X |
| 223 | — | — | — | X | X | — | — |
| 225 | — | — | — | X | X | — | X |
| 226 | — | — | — | — | — | — | — |
| 227 | — | — | — | — | — | — | — |
| 228 | — | — | — | — | — | — | — |
| 231 | X | X | X | X | X | X | X |
| 233 | X | X | X | X | — | — | — |
| 235 | — | — | X | X | X | X | X |
| 236 | — | — | — | — | — | — | — |
| 238 | X | X | X | X | X | X | X |
| 239 | — | — | — | X | — | — | — |
| 240 | X | X | X | X | X | — | X |
| 241 | — | — | X | — | X | X | — |

| Peptide name | DRB1_0804 | DRB1_0806 | DRB1_0809 | DRB1_0811 | DRB1_0901 | DRB1_1001 | DRB1_1101 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | X | — | — |
| 206 | — | — | — | — | — | — | — |
| 207 | X | X | X | X | X | — | X |
| 208 | — | — | — | — | X | X | X |
| 209 | — | — | — | — | — | — | — |
| 210 | — | — | — | — | — | — | — |
| 211 | — | — | — | — | — | — | — |
| 212 | — | — | — | — | — | — | — |
| 213 | — | — | — | — | — | — | — |
| 215 | — | — | — | — | — | — | — |
| 216 | — | — | — | — | X | X | X |
| 217 | X | X | — | — | — | — | X |
| 218 | — | — | — | — | — | — | — |
| 220 | — | — | — | — | — | — | X |
| 222 | X | X | — | — | X | X | X |
| 223 | — | — | — | — | X | X | — |
| 225 | X | X | — | X | X | — | X |
| 226 | — | — | — | — | — | — | — |
| 227 | — | — | — | — | — | — | — |
| 228 | — | — | — | — | X | — | — |
| 231 | — | — | X | X | X | X | X |
| 233 | X | X | — | — | X | X | — |
| 235 | X | — | X | X | X | X | X |

TABLE 16b2-continued

| | | | | | | | |
|---|---|---|---|---|---|---|---|
| 236 | — | — | — | — | — | — | — |
| 238 | X | — | X | X | X | X | X |
| 239 | — | — | — | — | X | X | — |
| 240 | X | X | — | X | X | X | X |
| 241 | — | — | X | — | X | X | — |

TABLE 16b3

| Peptide name | DRB1_1102 | DRB1_1103 | DRB1_1104 | DRB1_1106 | DRB1_1110 | DRB1_1111 | DRB1_1201 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | — | — | — |
| 206 | — | — | — | — | — | — | — |
| 207 | — | — | X | X | X | — | X |
| 208 | — | — | X | X | X | — | X |
| 209 | — | — | — | — | — | — | — |
| 210 | — | — | — | — | — | — | — |
| 211 | — | — | — | — | — | X | — |
| 212 | — | — | — | — | — | — | — |
| 213 | — | — | — | — | — | — | — |
| 215 | — | — | — | — | — | — | — |
| 216 | — | — | — | — | X | — | — |
| 217 | X | X | X | X | X | — | X |
| 218 | — | — | — | — | — | — | — |
| 220 | — | — | — | — | X | — | — |
| 222 | X | X | X | X | X | X | X |
| 223 | X | X | — | — | — | X | — |
| 225 | — | — | X | X | X | — | X |
| 226 | — | — | — | — | — | — | — |
| 227 | — | — | — | — | — | — | — |
| 228 | — | — | — | — | — | — | — |
| 231 | — | — | — | — | X | — | — |
| 233 | X | X | X | X | — | X | — |
| 235 | — | — | — | — | X | — | — |
| 236 | — | — | — | — | — | — | — |
| 238 | — | — | X | X | X | — | — |
| 239 | — | — | — | — | — | — | — |
| 240 | — | — | X | X | X | — | X |
| 241 | — | — | — | — | — | — | — |

| Peptide name | DRB1_1202 | DRB1_1301 | DRB1_1302 | DRB1_1303 | DRB1_1304 | DRB1_1305 | DRB1_1311 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | — | — | — |
| 206 | — | — | — | — | — | — | — |
| 207 | X | — | — | X | — | X | X |
| 208 | X | — | — | — | — | X | X |
| 209 | — | — | — | — | — | — | — |
| 210 | — | — | — | — | — | — | — |
| 211 | — | — | X | X | — | — | — |
| 212 | — | — | — | — | — | — | — |
| 213 | — | — | — | — | — | — | — |
| 215 | — | — | — | — | — | — | — |
| 216 | — | — | — | — | — | X | — |
| 217 | X | X | — | X | X | X | X |
| 218 | — | — | — | — | — | — | — |
| 220 | — | — | — | — | — | X | — |
| 222 | X | X | X | X | X | X | X |
| 223 | — | X | X | X | X | — | — |
| 225 | X | — | — | — | — | X | X |
| 226 | — | — | — | — | — | — | — |
| 227 | — | — | — | — | — | — | — |
| 228 | — | — | — | — | — | — | — |
| 231 | — | — | — | — | — | X | — |
| 233 | — | X | X | X | X | — | X |
| 235 | — | — | — | — | — | X | — |
| 236 | — | — | — | — | — | — | — |
| 238 | — | — | — | X | — | X | X |

TABLE 16b3-continued

| | | | | | | | |
|---|---|---|---|---|---|---|---|
| 239 | — | — | X | — | — | — | — |
| 240 | X | — | — | X | — | X | X |
| 241 | — | — | — | — | — | — | — |

TABLE 16b4

| Peptide name | DRB1_1305 | DRB1_1311 | DRB1_1312 | DRB1_1323 | DRB1_1331 | DRB1_1401 | DRB1_1402 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | — | — | — |
| 206 | — | — | — | — | — | — | — |
| 207 | X | X | X | — | — | X | X |
| 208 | X | X | — | — | — | — | — |
| 209 | — | — | — | — | — | — | — |
| 210 | — | — | — | — | — | — | — |
| 211 | — | — | — | X | — | — | — |
| 212 | — | — | — | — | — | — | — |
| 213 | — | — | — | — | — | — | — |
| 215 | — | — | — | — | — | — | — |
| 216 | X | — | — | — | — | — | X |
| 217 | X | X | X | — | — | X | X |
| 218 | — | — | — | — | — | — | — |
| 220 | X | — | — | — | — | — | X |
| 222 | X | X | X | X | X | X | X |
| 223 | — | — | X | X | — | — | X |
| 225 | X | X | — | — | — | — | X |
| 226 | — | — | — | — | — | — | — |
| 227 | — | — | — | — | — | — | — |
| 228 | — | — | — | — | — | — | — |
| 231 | X | — | X | — | — | — | X |
| 233 | — | X | X | X | X | — | X |
| 235 | X | — | — | — | — | — | X |
| 236 | — | — | — | — | — | — | — |
| 238 | X | X | X | — | — | — | X |
| 239 | — | — | — | X | — | — | — |
| 240 | X | X | X | — | — | X | X |
| 241 | — | — | — | — | — | — | — |

| Peptide name | DRB1_1403 | DRB1_1404 | DRB1_1405 | DRB1_1406 | DRB1_1407 | DRB1_1418 | DRB1_1419 |
|---|---|---|---|---|---|---|---|
| 201 | — | — | — | — | — | — | — |
| 202 | — | — | — | — | — | — | — |
| 203 | — | — | — | — | — | — | — |
| 204 | — | — | — | — | — | — | — |
| 205 | — | — | — | — | — | — | — |
| 206 | — | — | — | — | — | — | — |
| 207 | X | X | X | X | — | X | X |
| 208 | — | — | — | — | — | — | — |
| 209 | — | — | — | — | — | — | — |
| 210 | — | — | — | — | — | — | — |
| 211 | — | — | — | — | — | — | — |
| 212 | — | — | — | — | — | — | — |
| 213 | — | — | — | — | — | — | — |
| 215 | — | — | — | — | — | — | — |
| 216 | — | — | — | X | — | — | X |
| 217 | X | X | X | X | — | X | X |
| 218 | — | — | — | — | — | — | — |
| 220 | — | — | — | — | — | — | — |
| 222 | X | X | X | X | — | — | — |
| 223 | — | — | — | — | — | — | X |
| 225 | X | X | — | X | — | — | — |
| 226 | — | — | — | — | — | — | — |
| 227 | — | — | — | — | — | — | — |
| 228 | — | — | — | — | — | — | — |
| 231 | — | — | — | — | — | — | X |
| 233 | — | — | — | X | — | — | X |
| 235 | — | — | — | — | — | — | X |
| 236 | — | — | — | — | — | — | — |
| 238 | X | X | X | X | X | — | X |
| 239 | — | — | — | — | — | — | — |

TABLE 16b4-continued

| | | | | | | | |
|---|---|---|---|---|---|---|---|
| 240 | X | X | X | X | X | X | X |
| 241 | — | — | — | — | — | — | X |

TABLE 16b5

| Peptide name | DRB1_1424 | DRB1_1501 | DRB1_1502 | DRB1_1503 | DRB1_1504 | DRB1_1506 |
|---|---|---|---|---|---|---|
| 201 | — | — | — | — | — | — |
| 202 | — | — | — | — | — | — |
| 203 | — | — | — | — | — | — |
| 204 | — | — | — | — | — | — |
| 205 | — | — | — | — | — | — |
| 206 | — | — | — | — | — | — |
| 207 | X | X | — | X | X | X |
| 208 | — | X | X | X | X | X |
| 209 | — | — | — | — | — | — |
| 210 | — | — | — | — | — | — |
| 211 | X | — | — | — | — | — |
| 212 | — | — | — | — | — | — |
| 213 | — | — | — | — | — | — |
| 215 | — | — | — | — | — | — |
| 216 | — | — | — | — | — | — |
| 217 | — | — | — | — | — | — |
| 218 | — | — | — | — | — | — |
| 220 | — | — | — | — | — | — |
| 222 | X | X | — | X | X | X |
| 223 | X | — | — | — | — | — |
| 225 | — | X | — | X | X | X |
| 226 | — | — | — | — | — | — |
| 227 | — | X | — | X | X | X |
| 228 | — | — | — | — | — | — |
| 231 | X | X | X | X | X | X |
| 233 | X | — | X | — | — | — |
| 235 | X | — | — | — | — | — |
| 236 | — | — | — | — | — | — |
| 238 | X | X | X | X | X | X |
| 239 | X | — | — | — | — | — |
| 240 | X | X | X | X | X | X |
| 241 | X | — | — | — | — | — |

| Peptide name | DRB1_1601 | DRB1_1607 | DRB3_0101 | DRB3_0202 | DRB4_0101 | DRB5_0101 |
|---|---|---|---|---|---|---|
| 201 | — | — | — | — | — | — |
| 202 | — | — | — | — | — | — |
| 203 | — | — | — | — | — | — |
| 204 | — | — | X | — | — | — |
| 205 | — | — | — | — | — | — |
| 206 | — | — | — | — | — | — |
| 207 | X | X | — | — | — | X |
| 208 | X | X | — | — | — | — |
| 209 | — | — | — | — | — | — |
| 210 | — | — | — | — | — | — |
| 211 | — | — | X | — | — | — |
| 212 | — | — | — | — | — | — |
| 213 | — | — | — | — | — | — |
| 215 | — | — | X | — | — | — |
| 216 | X | X | — | X | — | X |
| 217 | — | — | — | — | — | — |
| 218 | — | — | — | — | — | — |
| 220 | X | X | — | — | — | X |
| 222 | — | — | — | X | X | X |
| 223 | — | — | — | X | — | — |
| 225 | X | X | — | — | — | — |
| 226 | — | — | — | — | — | — |
| 227 | — | — | — | — | — | — |
| 228 | — | — | — | — | — | — |
| 231 | X | X | — | X | — | X |
| 233 | — | — | — | X | — | X |
| 235 | — | — | — | X | — | X |
| 236 | — | — | — | — | — | — |
| 238 | X | X | — | X | — | X |
| 239 | — | — | — | — | — | X |
| 240 | X | X | — | X | X | X |
| 241 | — | — | — | — | — | — |

TABLE 16b6

| Peptide name | HLA-DQA10501-DQB10201 | HLA-DQA10501-DQB10301 | HLA-DQA10301-DQB10302 | HLA-DQA10401-DQB10402 | HLA-DQA10101-DQB10501 | HLA-DQA10102-DQB10602 | HLA-DPA10201-DPB10101 |
|---|---|---|---|---|---|---|---|
| 201 | — | X | — | — | — | — | — |
| 202 | — | — | — | — | — | — | — |
| 203 | — | X | — | — | — | — | — |
| 204 | — | — | — | — | — | — | — |
| 205 | — | X | — | — | — | — | — |
| 206 | — | — | — | — | — | — | — |
| 207 | — | — | — | — | — | — | — |
| 208 | — | — | — | — | — | — | — |
| 209 | — | X | — | — | — | — | — |
| 210 | — | — | — | — | — | — | — |
| 211 | — | — | — | — | — | — | — |
| 212 | — | — | — | — | — | — | — |
| 213 | — | — | — | — | — | — | — |
| 215 | X | — | — | — | — | — | — |
| 216 | — | — | — | — | — | — | — |
| 217 | — | — | — | — | — | — | — |
| 218 | — | — | — | — | — | — | — |
| 220 | — | — | — | — | — | — | — |
| 222 | — | — | — | — | — | — | X |
| 223 | — | X | — | — | — | X | — |
| 225 | X | X | — | — | — | X | — |
| 226 | — | X | — | — | — | — | — |
| 227 | — | — | — | — | — | — | X |
| 228 | — | X | — | — | — | — | — |
| 231 | — | X | — | — | — | X | — |
| 233 | X | X | X | X | — | X | X |
| 235 | — | X | — | — | — | X | — |
| 236 | — | X | — | — | — | X | — |
| 238 | X | X | — | — | — | X | X |
| 239 | — | X | — | — | — | X | — |
| 240 | — | — | — | — | — | X | X |
| 241 | — | X | — | — | — | X | — |

| Peptide name | HLA-DPA10103-DPB10201 | HLA-DPA10103-DPB10301 | HLA-DPA10103-DPB10401 | HLA-DPA10202-DPB10501 | HLA-DPA10201-DPB11401 | HLA-DPA10103-DPB10402 |
|---|---|---|---|---|---|---|
| 201 | — | — | — | — | — | — |
| 202 | — | — | — | — | — | — |
| 203 | — | — | — | — | — | — |
| 204 | — | — | — | — | — | — |
| 205 | — | — | — | — | — | — |
| 206 | — | — | — | — | — | — |
| 207 | — | — | — | — | — | — |
| 208 | — | X | — | — | X | — |
| 209 | — | — | — | — | — | — |
| 210 | — | — | — | — | — | — |
| 211 | — | — | — | — | — | — |
| 212 | — | — | — | — | — | — |
| 213 | — | — | — | — | — | — |
| 215 | — | — | — | — | — | — |
| 216 | — | X | — | — | X | — |
| 217 | — | — | — | — | — | — |
| 218 | — | — | — | — | — | — |
| 220 | — | — | — | — | — | — |
| 222 | X | X | X | — | X | X |
| 223 | — | — | — | — | — | — |
| 225 | — | — | — | — | — | — |
| 226 | — | — | — | — | — | — |
| 227 | X | X | X | — | — | X |
| 228 | — | — | — | — | — | — |
| 231 | X | X | X | — | X | X |
| 233 | X | X | X | — | X | X |
| 235 | — | — | — | — | — | — |
| 236 | — | — | — | — | — | — |
| 238 | X | X | — | — | X | X |
| 239 | — | — | — | — | — | — |
| 240 | X | X | X | X | X | X |
| 241 | — | — | — | — | — | — |

Table 17—List of peptides included in Peptide combinations in International Patent Application WO2010/089554

TABLE 17

| SEQ ID NO: | Peptide name | Sequence | Predicted world wide HLA coverage |
|---|---|---|---|
| 234 | Ber01 | SGKAFGAMAKKGQED | 35% |
| 235 | Ber02 | FIPMKSSWGA | 0% |
| 236 | Ber02C | KSSWGAIWRIDPKKPLK | 63% |
| 237 | Bio02A | KYDAYVATLTEALR | 74% |
| 238 | Bio03A | KFIPTLVAAVKQAYAAKQ | 97% |
| 239 | Bio04A | LKKAVTAMSEAEK | 47% |
| 240 | Rye09B | PEVKYAVFEAALTKAIT | 100% |
| 241 | Tim07B | KIPAGELQIIDKIDA | 0% |
| 242 | Rye09B1 | KPEVKYAVFEAALTKAIT | 100% |
| 243 | Rye09B2 | KKPEVKYAVFEAALTKAIT | 100% |
| 244 | Tim07B1 | KKIPAGELQIIDKIDA | 0% |
| 245 | Tim07B2 | KKIPAGELQIIDKIDAK | 42% |

Example 5

Peptide Solubility and Stability

All peptides with SEQ ID NOs: 1-133 were initially synthesized as Trifluoroacetic acid (TFA) salts in an approximately 10 mg scale of manufacturing and supplied by. These preparations were made as 1-7 mg/mL solutions in DMSO for the 1$^{st}$ round of solubility screening. In a few cases the peptide had to be dissolved in water instead of DMSO. The selected peptides used for making peptide combinations were all produced by Innovagen as acetate salts at a >10 mg scale of manufacturing. All peptides manufactured as acetate salts were solubility tested at 0.5 mg/mL (dry matter) using the following conditions:
1. Water (pH 3-5)
2. 250 mM D-Mannitol and 25 mM sodium acetate, pH 4.5
3. 250 mM D-Mannitol and 25 mM sodium phosphate, pH 7.0
4. 250 mM D-Mannitol and 25 mM glycine, pH 8.5

Additionally, 1.0 mg/mL samples were solubility tested applying the following conditions:
1. Water (pH 3-5)
2. 250 mM D-Mannitol and 25 mM sodium acetate, pH 4.5
3. 250 mM D-Mannitol and 25 mM sodium phosphate, pH 7.0
4. 250 mM D-Mannitol and 25 mM glycine, pH 9.0

The results of the 1$^{st}$ round of solubility screening are found in Table 18. Accordingly, a subset of soluble peptides was identified. The peptides 201, 204, 205, 206, 207, 211, 212, 216, 217, 222, 226, 231, 235, 236, 237, 238, 239 and 240 are considered soluble and suitable for formulation into a pharmaceutical product as they are. In Example 7 peptide combinations are suggested which are assembled from this list of soluble peptides.

Table 18. Shows the First Screening Data for the 133 Peptides Dissolved in DMSO as Described Above.

Table scoring code: ok: clear solution; +: very small precipitation only visible with a magnifier; ++: precipitation/turbid solution; +++: more precipitation/turbid solution.

TABLE 18

| SEQ ID NO: | Sequence (derived from Phl p 1) | Start position | Peptide name | Visual inspection |
|---|---|---|---|---|
| 1 | WLDAKSTWYGKPTGAGPKDN | 18 | 201 | OK |
| 2 | GRGSGSSFEIKSTKPEASSG | 66 | 202 | + |
| 3 | EIKSTKPEASSGEPVVVHIT | 74 | 203 | OK |
| 4 | TDDNEEPIAPYHFDLSGHAF | 93 | 204 | OK |
| 5 | YHFDLSGHAFGAMAKKGDEQ | 103 | 205 | OK |
| 6 | GDEQKLRSAGELELQFRRVK | 119 | 206 | + |
| 7 | AGELELQFRRVKSKYPEGTK | 127 | 207 | ++ |
| 8 | KGSNPNYLALLVKYVNGDGD | 153 | 208 * | +++ |
| 9 | LVKYVNGDGDVVAVDIKEKG | 163 | 209 | + |
| 10 | KDKWIELKESWGAIWRIDTP | 183 | 210 | OK |
| 11 | WGAIWRIDTPDKLTGPFTVR | 193 | 211 | OK |
| 12 | VRYTTEGGTKTEAEDVIPEG | 211 | 212 | OK |
| 13 | TEAEDVIPEGWKADTSYESK | 221 | 213 | OK |
| 14 | IPKVPPGPNITATYGDKWLD | 1 | 001 | OK |
| 15 | KVPPGPNITATYGDKWLDAK | 3 | 002 | OK |
| 16 | ITATYGDKWLDAKSTWYGKP | 10 | 003 | OK |

TABLE 18-continued

| SEQ ID NO: | Sequence (derived from Phl p 1) | Start position | Peptide name | Visual inspection |
|---|---|---|---|---|
| 17 | KPTGAGPKDNGGASGYKDVD | 28 | 005 | OK |
| 18 | GGASGYKDVDKPPFSGMTGS | 38 | 006 | + |
| 19 | KPPFSGMTGSGNTPIFKSGR | 48 | 007 | OK |
| 20 | GNTPIFKSGRGSGSSFEIKS | 58 | 008 | OK |
| 21 | SGEPVVVHITDDNEEPIAPY | 84 | 011 | OK |
| 22 | AFGAMAKKGDEQKLRSAGEL | 111 | 014 | OK |
| 23 | FRRVKSKYPEGTKVTFHVEK | 134 | 017 | OK |
| 24 | EGTKVTFHVEKGSNPNYLAL | 143 | 018 | OK |
| 25 | VVAVDIKEKGKDKWIELKES | 173 | 021 | ++ |
| 26 | TPDKLTGPFTVRYTTEGGTK | 201 | 024 | ++ |
| 27 | EWVAMTKGEGGVWTFDSEEP | 40 | 214 | + |
| 28 | EGGVWTFDSEEPLQGPFNFR | 48 | 215 | OK |
| 29 | EPLQGPFNFRFLTEKGMKNV | 58 | 216 | OK |
| 30 | VPKVTFTVEKGSNEKHLAVL | 1 | 051 | OK |
| 31 | GSNEKHLAVLVKYEGDTMAE | 11 | 052 | OK |
| 32 | VKYEGDTMAEVELREHGSDE | 21 | 053 | OK |
| 33 | EVELREHGSDEWVAMTKGEG | 30 | 054 | OK |
| 34 | RFLTEKGMKNVFDDVVPEKY | 67 | 058 | OK |
| 35 | VFDDVVPEKYTIGATYAPEE | 77 | 059 | + |
| 36 | GSDPKKLVLNIKYTRPGDSL | 11 | 217 | OK |
| 37 | HGSEEWEPLTKKGNVWEVKS | 38 | 218 | OK |
| 38 | TKKGNVWEVKSSKPLVGPFN | 47 | 219 | OK |
| 39 | KSSKPLVGPFNFRFMSKGGM | 56 | 220 | OK |
| 40 | NFRFMSKGGMRNVFDEVIPT | 66 | 221 | OK |
| 41 | AVQVTFTVQKGSDPKKLVLN | 1 | 060 | OK |
| 42 | IKYTRPGDSLAEVELRQHGS | 21 | 062 | OK |
| 43 | AEVELRQHGSEEWEPLTKKG | 31 | 063 | + |
| 44 | RNVFDEVIPTAFKIGKTYTP | 76 | 068 | OK |
| 45 | KEDFLGSLVKEIPPRLLYAK | 8 | 222 | OK |
| 46 | YIITPTNVSHIQSAVVSGRR | 55 | 223 | OK |
| 47 | FAVVDLNKMRAVWVDGKART | 101 | 224 | + |
| 48 | GFGMLLRKYGIAAENVIDVK | 163 | 225 | OK |
| 49 | SMGDDHFWAVRGGGGESFGI | 195 | 226 | OK |
| 50 | TPFPHRKGVLFNIQYVNYWF | 386 | 227 | OK |
| 51 | GRRHSVRIRVRSGGHDYEGL | 72 | 071 | OK |
| 52 | VRSGGHDYEGLSYRSLQPET | 81 | 072 | OK |
| 53 | LSYRSLQPETFAVVDLNKMR | 91 | 073 | OK |
| 54 | DGKARTAWVDSGAQLGELYY | 115 | 075 | OK |
| 55 | WSKDIYNYMEPYVSKNPRQA | 416 | 079 | OK |

TABLE 18-continued

| SEQ ID NO: | Sequence (derived from Phl p 1) | Start position | Peptide name | Visual inspection |
|---|---|---|---|---|
| 56 | PYVSKNPRQAYANYRDIDLG | 426 | 080 | OK |
| 57 | RNEVVNDVSTYASGKVWGQK | 446 | 081 | OK |
| 58 | YASGKVWGQKYFKGNFERLA | 456 | 082 | OK |
| 59 | YFKGNFERLAITKGKVDPTD | 466 | 083 | OK |
| 60 | TKGKVDPTDYFRNEQSIPPL | 477 | 084 | OK |
| 61 | AGYTPAAPAGAEPAGKATTE | 1 | 228 | OK |
| 62 | EQKLIEKINAGFKAALAAAA | 21 | 229 | OK |
| 63 | GFKAALAAAAGVPPADKYRT | 31 | 230 | OK |
| 64 | DKYRTFVATFGAASNKAFAE | 46 | 231 | ++ |
| 65 | TSKLDAAYKLAYKTAEGATP | 84 | 232 | OK |
| 66 | EAKYDAYVATLSEALRIIAG | 104 | 233 | OK |
| 67 | VATLSEALRIIAGTLEVHAV | 111 | 234 | OK |
| 68 | IEKVDAAFKVAATAANAAPA | 148 | 235 | ++ |
| 69 | KVAATAANAAPANDKFTVFE | 156 | 236 | OK |
| 70 | PANDKFTVFEAAFNNAIKAS | 166 | 237 | OK |
| 71 | STGGAYESYKFIPALEAAVK | 185 | 238 | OK |
| 72 | KFIPALEAAVKQAYAATVAT | 194 | 239 | OK |
| 73 | APEVKYTVFETALKKAITAM | 214 | 240 | +++ |
| 74 | AEPAGKATTEEQKLIEKINA | 11 | 086 | OK |
| 75 | AAGVPPADKYRTFVATFGAA | 39 | 089 | OK |
| 76 | GAASNKAFAEGLSGEPKGAA | 56 | 091 | OK |
| 77 | AEGLSGEPKGAAESSSKAAL | 64 | 092 | OK |
| 78 | AAESSSKAALTSKLDAAYKL | 74 | 093 | OK |
| 79 | AYKTAEGATPEAKYDAYVAT | 94 | 095 | OK |
| 80 | RIIAGTLEVHAVKPAAEEVK | 119 | 098 | OK |
| 81 | AVKPAAEEVKVIPAGELQVI | 129 | 099 | OK |
| 82 | VIPAGELQVIEKVDAAFKVA | 139 | 100 | + |
| 83 | EAAFNNAIKASTGGAYESYK | 175 | 104 | OK |
| 84 | KQAYAATVATAPEVKYTVFE | 204 | 107 | OK |
| 85 | TALKKAITAMSEAQKAAKPA | 224 | 109 | OK |
| 86 | AMSEAQKAAKPAAAATATAT | 232 | 110 | OK |
| 87 | KPAAAATATATSAVGAATGA | 241 | 111 | OK |
| 88 | TSAVGAATGAATAATGGYKV | 251 | 112 | OK |
| 113 | AFKVAATAANAAPAN | Phl p 5 241 (L1) | | OK |
| 114 | INVGFKAAVAAAAGV | Phl p 5 242 (L8) | | OK |
| 115 | NVWEVKSSKPLVGPF | Phl p 3 114 (L2) | | OK |
| 116 | NFRFMSKGGMRNVFD | Phl p 3 115 (L3) | | OK |
| 117 | SGIAFGSMAKKGDEQ | Phl p 1 116 (L4) | | OK |

TABLE 18-continued

| SEQ ID NO: | Sequence (derived from Phl p 1) | Start position | Peptide name | Visual inspection |
|---|---|---|---|---|
| 118 | GELELQFRRVKSKYP | Phl p 1 117 | (L5) | OK |
| 119 | STWYGKPTGAGPKDN | Phl p 1 118 | (L6) | OK |
| 120 | EEWEPLTKKGNVWEV | Phl p 3 119 | (L7) | OK |
| 121 | NYLALLVKYVNGDGD | Phl p 1 121 | (L9) | OK |
| 122 | KPPFSGMTGSGNTPI | Phl p 1 122 | (L10) | OK |
| 123 | LIEKINAGFKAAVAA | Lol p 5a 123 | (L11) | ++ |
| 124 | NAGFKAAVAAAAVVP | Lol p 5a 124 | (L12) | OK |
| 125 | SDAKTLVLNIKYTRP | Lol p 3 125 | (L13) | OK |
| 126 | MRNVFDDVVPADFKV | Lol p 2 126 | (L14) | OK |
| 127 | NVFDEVIPTAFTVGK | Lol p 3 127 | (L15) | OK |
| 128 | DAYVATLTEALRVIA | Lol p 5a 128 | (L16) | + |
| 129 | AFKIAATAANAAPTN | Lol p 5b 129 | (L17) | OK |
| 130 | DGVWEIKSDKPLKGP | Lol p 2 130 | (L18) | OK |
| 131 | DINVGFKAAVAAAAG | Poa p 5 131 | (L19) | OK |
| 132 | EPIAAYHFDLSGKAF | Poa p 1 132 | (L20) | OK |
| 133 | FKAAVAAAAGAPPAD | Poa p 5 133 | (L21) | ++ |
| 89 | AIGDKPGPNITATYGSKWLE | 1 | 027 | |
| 90 | TATYGSKWLEARATFYGSNP | 11 | 028 | |
| 91 | ARATFYGSNPRGAAPDDHGG | 21 | 029 | |
| 92 | RGAAPDDHGGASGYKDVDKP | 31 | 030 | |
| 93 | ASGYKDVDKPPFDGMTASGN | 41 | 031 | |
| 94 | PFDGMTASGNEPIFKDGLGS | 51 | 032 | |
| 95 | EPIFKDGLGSRASYEIKSKE | 61 | 033 | |
| 96 | RASYEIKSKEPVESSGEPVL | 71 | 034 | |
| 97 | PVESSGEPVLVKITDKNYEH | 81 | 035 | |
| 98 | VKITDKNYEHIAAYHFDLSG | 91 | 036 | |
| 99 | IAAYHFDLSGKAFGAMAKKG | 101 | 037 | |
| 100 | GKAFGAMAKKGQEDKLRKAG | 110 | 038 | |
| 101 | GQEDKLRKAGELTLQFRRVK | 120 | 039 | |
| 102 | ELTLQFRRVKSKYPSGTKIT | 130 | 040 | |
| 103 | SKYPSGTKITFHIEKGSNDH | 140 | 041 | |
| 104 | FHIEKGSNDHYLALLVKYAA | 150 | 042 | |
| 105 | YLALLVKYAAGDGNIVAVDI | 160 | 043 | |
| 106 | GDGNIVAVDIKPRDSDEFIP | 170 | 044 | |
| 107 | KPRDSDEFIPMKSSWGAIWR | 180 | 045 | |
| 108 | PMKSSWGAIWRIDPKKPLKG | 189 | 046 | |
| 109 | WRIDPKKPLKGPFSIRLTSE | 198 | 047 | |
| 110 | GPFSIRLTSEGGAHLVQDDV | 208 | 048 | |

TABLE 18-continued

| SEQ ID NO: | Sequence (derived from Phl p 1) | Start position | Peptide name | Visual inspection |
|---|---|---|---|---|
| 111 | EGGAHLVQDDVIPANWKPDT | 217 | 049 | |
| 112 | DDVIPANWKPDTVYTSKLQF | 225 | 050 | |

A subset of the peptides was selected as candidate peptides for a final peptide mixture. The selected peptides were synthesized as acetate salts and further tested individually for solubility at 3 mg/mL (dry matter) in aqueous solutions comprising either 250 mM D-Mannitol and 25 mM sodium acetate, pH 4.5; 250 mM D-Mannitol and 25 mM sodium phosphate, pH 7.0; or 250 mM D-Mannitol and 25 mM glycine, pH 9.25.

Table 19. Solubility of a Subset of Peptides at 3 mg/mL Evaluated by Visual Inspection This table shows the solubility test results for the subset of peptides for non-filtered peptide preparations with and without centrifugation at 3 mg/mL.

Table scoring code; ok: clear solution; +: very small precipitation only visible with a magnifier; ++: precipitation/turbid solution; +++: more precipitation/turbid solution.

TABLE 19

| Peptide name | Visual inspection after 60 min pH 7 | Visual inspection after centrifugation pH 7 | Visual inspection after 60 min pH 4.5 | Visual inspection after centrifugation pH 4.5 |
|---|---|---|---|---|
| 207 | Clear with particles, tread + | + | OK | OK |
| 211 | Slightly turbid with particles + | +++ | + particles, hair | ++ |
| 216 | Gel-like surface ++ | OK | Hair | Ok |
| 217 | Clear with particles + | ++ | + particles | Ok |
| 222 | Clear with particles, tread + | ++ | + particles, hair | ++ |
| 235 | Clear with particles, tread + | + | + particles, turbid | ++ |
| 238 | Clear with particles, tread + | OK | OK | OK |
| 239 | Clear with particles + | + | OK | + |
| 241 | OK | OK | OK | OK |

Visual Inspection

During the solubility studies the peptide-containing solutions were inspected visually before and after filtration for turbidity, and presence of particles/aggregates. In addition, presence of turbidity/particles/aggregates was also detected by optical density (OD) or absorbance of filtered material, but might also be detected by size-exclusion chromatography. Furthermore, Sub-visual particles may also be detected by dynamic light scattering (DLS) analysis on filtered and non-filtered peptide containing solutions. Samples were furthermore subjected to centrifugation to allow for the possible visual inspection of pelleted material. Table 9 illustrates and example of the scoring performed under visual inspection of a multitude of peptides tested at two conditions with or without centrifugation. As represented in Table 9, some peptides are scored as ok (meaning soluble) where as others show the formation of apparent particles, turbidity, and/or a gel like appearance.

Subsequent to visual inspection, the peptide containing solutions were filtered using syringe based filters at a 0.2 μm pore size containing a polyethersulfone (PES) membrane chemistry. The membrane chemistry was selected to provide a potential for low peptide binding and low filter based extractables. As described below, the filtered peptide containing solutions was used to evaluate the loss of material associated with lack of dissolution and/or formation of higher aggregates retained by the filter (aggregate size >0.2 μm). The method analyze the filtered material compared to a non-filtered standard using reverse phase high pressure liquid chromatography (RP-HPLC), but might also be detected by other types of chromatography, to assess the relative mass balance between samples representing specific peptides.

Stability

The stability of the solubility was evaluated by optical density by addressing the apparent change in optical density measured at time zero and after 24 hours for samples stored at room temperature by UV-VIS spectroscopy (ultraviolet-visible). The UV-VIS spectroscopy method entailed the acquisition of a sample scan in the range of 200-800 nm and a reporting of the measured values at 220 nm, 280 nm, and 320 nm, but sample properties might also be detected by other wavelengths. The filtered aqueous peptide solution with and without excipients and buffer components was evaluated and the peptide containing solution was assessed as soluble or not by the method. More specifically, the specific peptide solution was evaluated as stabile at the specified condition, if the change in optical density during 24 hours did not constitute a change equal or more than 0.2 absorbance units at the above specified wavelengths.

HPLC Investigation

The solubility of each aqueous peptide solution with and without excipients and buffer components was also investigated using HPLC, e.g. RP-HPLC. In more details, each of the filtered aqueous peptide solutions, as described above, was injected onto the HPLC system using a reverse phase separation method. The resulting peptide chromatogram and subsequent manual integration derived a main peak height and/or a main peak area of each of the specific peptides (see Formula 2, aqueous). These results were compared to the chromatogram of corresponding peptide preparation dissolved in acetonitrile or DMSO. The non-filtered acetonitrile or DMSO based peptide preparations was integrated analogously to the peptide chromatogram based on filtered aqueous peptide solutions, giving a main peak height or main peak area (see Formula 2, non-aqueous). The peptide preparations dissolved in acetonitrile or DMSO was assumed to be fully dissolved and stable in the non-aqueous solvents. The resulting chromatograms from each specific peptide were compared and the % recovery was calculated using Formula 2. The recovery result corresponding to 80% or above was considered as an indication of an acceptable solubility profile in terms of filter associated peptide loss.

Tables 20, 21 and 22 demonstrate examples of filter recovery studies showing the percent (%) recovery performed on an multitude of peptide preparations and concentrations corresponding to 0.5, 1.0, and 3.0 mg/mL in various conditions (see table legend for details). As Tables 20, 21 and 22 illustrate, specific peptides display a range of recovery results for each peptide concentration and condition tested. For example, peptide identity 241 displayed apparent percent recoveries that were above 80% for all concentrations and conditions tested. In contrast, peptide identity 240 demonstrated acceptable solubility properties at 0.5 and 1.0 mg/mL in water, but failed to demonstrate an acceptable solubility profile under all other tested conditions.

$$\% \text{ recovery} = 100\% \times \frac{[\text{peak Height or peak Area}]^{aqueous}}{[\text{peak Height or peak Area}]^{non\text{-}aqueous}}. \quad \text{Formula 2}$$

The stability of the individual peptides was evaluated as the relative peak area of the main peak component at time zero compared to the 24 hours' time point for samples stored at room temperature. The main peak evaluation was followed by a qualitative evaluation of the entire chromatograms to assess the presence of apparent degradation product identified as the formation of significant new chromatographic peaks during stability.

Table 20. Examples of Peptide Recovery of Preparations Having a Peptide Concentration of 0.5 Mg/mL Conditions correspond to: Water, pH 3-5; pH 4.5: 250 mM D-Mannitol and 25 mM sodium acetate; pH 7.0: 250 mM D-Mannitol and 25 mM sodium phosphate; pH 8.5: 250 mM D-Mannitol and 25 mM glycine. % recovery was calculated according to Formula 2. as described above.

TABLE 20

| Peptide name | Predicted pI-value | % recovery | | | |
|---|---|---|---|---|---|
| | | water | pH 4.5 | pH 7.0 | pH 8.5 |
| 238 | 6.94 | 110.63 | 101.66 | 106.21 | 109.90 |
| 240 | 9.56 | 91.12 | 59.45 | 23.10 | 12.96 |
| 208 | 6.75 | 70.70 | 7.15 | 4.77 | 7.67 |
| 211 | 10.08 | 96.49 | 52.70 | 97.70 | 88.58 |
| 207 | 10.04 | 132.19 | 105.88 | 110.58 | 99.12 |
| 217 | 10.04 | 107.05 | 100.99 | 49.91 | 100.62 |
| 233 | 4.44 | 0.00 | 0.00 | 5.84 | 108.94 |
| 235 | 6.99 | 100.56 | 129.84 | 101.27 | 86.48 |
| 216 | 9.88 | 105.12 | 101.67 | 83.44 | 94.62 |
| 201 | 9.56 | 110.91 | 94.38 | 88.09 | 90.19 |
| 204 | 3.84 | 99.22 | 90.57 | 94.14 | 101.78 |
| 241 | 10.10 | 99.29 | 109.91 | 106.07 | 110.19 |
| 210 | 7.11 | 72.45 | 18.65 | 9.68 | 14.27 |
| 206 | 9.88 | 87.56 | 96.41 | 89.45 | 89.64 |
| 226 | 4.30 | 78.33 | 70.78 | 95.20 | 96.42 |
| 227 | 10.04 | 88.48 | 49.23 | 0.00 | 0.00 |
| 231 | 9.63 | 93.88 | 88.82 | 82.36 | 90.98 |
| 236 | 6.99 | 100.44 | 96.63 | 103.45 | 108.44 |
| 239 | 9.63 | 89.66 | 90.55 | 0.00 | 90.38 |
| 212 | 4.00 | 113.87 | 112.69 | 108.34 | 151.86 |
| 222 | 9.56 | 96.10 | 95.56 | 89.90 | 86.20 |
| 228 | 4.26 | 106.48 | 101.15 | 97.46 | 101.79 |
| 237 | 6.99 | 48.22 | 0.00 | 10.83 | 57.23 |

Table 21. Examples of Peptide Recovery of Preparations Having a Peptide Concentration of 1.0 Mg/mL Conditions correspond to: Water, pH 3-5; pH 4.5: 250 mM D-Mannitol and 25 mM sodium acetate; pH 7.0: 250 mM D-Mannitol and 25 mM sodium phosphate; pH 9.0: 250 mM D-Mannitol and 25 mM glycine. % recovery was calculated according to Equation 1 as described above.

TABLE 21

| Peptide Name | Predicted pI-value | % recovery | | | |
|---|---|---|---|---|---|
| | | water | pH 4.5 | pH 7.0 | pH 9.0 |
| 238 | 6.94 | 93.45 | 96.17 | 102.74 | 112.74 |
| 240 | 9.56 | 101.66 | 48.35 | 3.35 | 3.35 |
| 208 | 6.75 | 84.25 | 0.60 | 87.72 | 96.12 |
| 211 | 10.08 | 92.66 | 95.63 | 88.98 | 95.30 |
| 207 | 10.04 | 92.39 | 80.31 | 93.92 | 98.56 |
| 217 | 10.04 | 84.12 | 79.56 | 73.30 | 86.21 |
| 233 | 4.44 | 92.66 | 2.83 | 114.24 | 123.76 |
| 235 | 6.99 | 110.81 | 41.19 | 131.16 | 137.94 |
| 216 | 9.88 | 41.83 | 42.12 | 42.89 | 47.48 |
| 201 | 9.56 | 88.66 | 84.36 | 85.04 | 89.67 |
| 204 | 3.84 | 85.43 | 85.00 | 86.16 | 90.02 |
| 241 | 10.10 | 116.58 | 102.04 | 104.99 | 117.97 |
| 210 | 7.11 | 83.27 | 62.12 | 74.16 | 90.04 |
| 206 | 9.88 | 78.57 | 79.89 | 67.74 | 75.04 |
| 226 | 4.30 | 85.66 | 50.05 | 93.89 | 99.37 |
| 227 | 10.04 | 96.23 | 8.54 | 0.00 | 0.00 |
| 231 | 9.63 | 90.27 | 84.67 | 87.09 | 96.09 |
| 236 | 6.99 | 103.99 | 80.92 | 109.19 | 115.22 |
| 239 | 9.63 | 88.86 | 84.43 | 84.56 | 93.27 |
| 212 | 4.00 | 90.58 | 83.97 | 87.17 | 115.61 |
| 222 | 9.56 | 84.02 | 80.93 | 81.32 | 98.60 |
| 228 | 4.26 | 84.46 | 86.64 | 88.93 | 100.38 |
| 237 | 6.99 | 67.63 | 31.68 | 42.27 | 52.00 |

Table 22. Examples of Peptide Recovery of Preparations Having a Peptide Concentration of 3.0 mg/mL Conditions correspond to: Water, pH 3-5; pH 4.5: 250 mM D-Mannitol and 25 mM sodium acetate; pH 7.0: 250 mM D-Mannitol and 25 mM sodium phosphate; pH 8.5: 250 mM D-Mannitol and 25 mM glycine. % recovery was calculated according to Equation 1 as described above.

TABLE 22

| Peptide Name | Predicted pI-value | % recovery | | | |
|---|---|---|---|---|---|
| | | Water | pH 4.5 | pH 7.0 | pH 8.5 |
| 238 | 6.94 | ND | 109.47 | 125.40 | 108.06 |
| 211 | 10.08 | ND | 100.34 | 115.70 | 94.83 |
| 207 | 10.04 | ND | 85.07 | 105.14 | 94.98 |
| 217 | 10.04 | ND | 108.49 | 101.01 | 99.65 |
| 235 | 6.99 | ND | 126.68 | 129.62 | 112.13 |
| 216 | 9.88 | ND | 44.62 | 48.76 | 46.77 |
| 241 | 10.10 | ND | 122.50 | 131.14 | 108.38 |
| 239 | 9.63 | ND | 99.01 | 111.17 | 96.89 |
| 222 | 9.56 | ND | 76.35 | 89.86 | 79.41 |

Example 6

Assembling Peptide Combinations

This example describes how the best peptide combinations were found and shows the peptide combinations selected for testing.

The 42 peptides of Table 9 were selected mainly based on T cell reactivity, but also with a view to predicted cross reactivity and to the predicted HLA Class II repertoires of the high responder peptides.

The present inventors set out to produce the best peptide combinations both with regard to species coverage (both intra-species (isoforms) and inter-species (different species)), donor coverage, T cell reactivity, worldwide HLA Class II coverage, and peptide valency. Testing peptide combinations and estimating these characteristics by trial and error is possible. However, this would require the testing of a very high number of peptide combinations, and the outcome would rely entirely of the donor cohort selected both with regard to the number of donors, sensitations of the donors and HLA repertoire of the donors/cohort. However the peptide valency of the peptide combinations (i.e. the average number of peptides to which a donor responds), loci coverage and worldwide HLA coverage would not be directly measurable.

The present inventors used a rating system to rate each peptide according to species coverage, donor coverage, T cell reactivity, worldwide HLA Class II coverage, and peptide valency.

According to this method, several peptide combinations (Table 23) with predicted high species coverage, T cell reactivity, worldwide HLA Class II coverage and peptide valency of the peptide combinations, were assembled from the 42 selected high responder peptides. Similar peptide combinations can be assembled using another peptide (substitute peptide) from the same peptide group.

Table 23. Immunologically Optimized Peptide Combinations Tested

Table 23 shows examples of peptide combinations ("1" indicates that the peptide is present in the peptide combination) with high predicted species coverage, T cell reactivity, worldwide HLA Class II coverage and peptide valency.

TABLE 23

| Peptide number: | Peptide combination name | | | | | | | | | | |
|---|---|---|---|---|---|---|---|---|---|---|---|
| | 014 | 034 | 204 | 005 | 015 | 025 | 035 | 085 | 205 | 215 | 225 |
| 201 | | | | | | | | | | | |
| 204 | | | | | | | | 1 | | | |
| 205 | | 1 | | | | 1 | 1 | | | | |
| 207 | | | 1 | 1 | | | | | | 1 | 1 |
| 208 | 1 | | 1 | 1 | 1 | | | | 1 | 1 | 1 |
| 209 | | | | | | | | | | | |
| 210 | | | | | | | | | | | |
| 211 | 1 | | | 1 | 1 | 1 | | | | | 1 |
| 216 | | | | | 1 | 1 | 1 | | | | |
| 217 | | 1 | | | | | 1 | | | | |
| 218 | | | | | | | | | | | |
| 219 | | | | | | | | | | | |
| 222 | | | | | | | | | | | |
| 225 | | | | | | | | | | | |
| 226 | | | | | | | | | | | |
| 227 | | | | | | | | | 1 | | |
| 233 | | | | | | | | | 1 | 1 | 1 | 1 |
| 235 | | | | | | | | | 1 | | 1 | 1 |
| 238 | 1 | 1 | 1 | 1 | 1 | 1 | 1 | 1 | 1 | 1 | 1 |
| 239 | | | | | | | | | | | |
| 240 | 1 | 1 | 1 | 1 | 1 | 1 | 1 | | 1 | | |
| 241 (L1) | | | | | | | | | | | |
| # of peptides | 4 | 4 | 4 | 5 | 5 | 5 | 5 | 5 | 5 | 5 | 5 |

| Peptide number: | Peptide combination name | | | | | | | | | |
|---|---|---|---|---|---|---|---|---|---|---|
| | 207 | 007 | 037 | 097 | LJI mix 4 (735) | LJI mix 5 (745) | LJI Mix 6 (755) | LJI Mix 7 (765) | LJI Mix 8 (775) | LJI Mix 9 (785) |
| 201 | | | | | | 1 | | 1 | 1 | |
| 204 | | | | | 1 | | | | | 1 |
| 205 | | | 1 | | | | | | | 1 |
| 207 | 1 | 1 | | | | | 1 | | | |
| 208 | 1 | 1 | | | | | 1 | | | |
| 209 | | | | 1 | | | | | | |
| 210 | | | | 1 | | | | | | |
| 211 | 1 | 1 | | | | | | | | |
| 216 | | 1 | 1 | 1 | | | | | | |
| 217 | | 1 | 1 | 1 | 1 | 1 | | | | |
| 218 | | | | | | | | 1 | | |
| 219 | | | | | | | 1 | 1 | | |
| 222 | | | 1 | | | | | | | |
| 225 | | | | 1 | | | | | | |
| 226 | | | | | | | | | 1 | |
| 227 | | | | | | | | | 1 | |
| 233 | 1 | | 1 | | | 1 | 1 | | | 1 |
| 235 | 1 | | 1 | 1 | | | | | | |
| 238 | 1 | 1 | 1 | 1 | 1 | 1 | | | | |
| 239 | | | | | | 1 | | | | 1 |
| 240 | 1 | 1 | 1 | | | | | | 1 | 1 |
| 241 (L1) | | | | | 1 | 1 | 1 | 1 | 1 | |
| # of peptides | 7 | 7 | 7 | 7 | 5 | 5 | 5 | 5 | 5 | 5 |

Another aspect which is important for developing a pharmaceutical product is the manufacturing of the product. Factors such as solubility and manufacturability of the active ingredients (the peptides) as well as administration of the drug product may be of great importance.

Accordingly peptide combinations were assembled using the above method but including only the sub group of selected peptides which had shown good solubility in Example 5. These peptides and the peptide combinations assembled using the above method can be found in Table 24a below.

Table 24a. Solubility-Optimized Peptide Combinations Tested

Table 24a shows examples of peptide combinations ("1" indicates that the peptide is present in the peptide combination) assembled from soluble peptides with high predicted species coverage, T cell reactivity, worldwide HLA Class II coverage and peptide valency.

TABLE 24a

| Peptide ID | Peptide combination name | | | | | | | | | | | | | | | |
|---|---|---|---|---|---|---|---|---|---|---|---|---|---|---|---|---|
| | 2401 | 2402 | 2403 | 2404 | 2505 | 2506 | 2507 | 2508 | 2609 | 2610 | 2611 | 2612 | 2713 | 2714 | 2715 | 2716 |
| 207 | 1 | 1 | 1 | 1 | 1 | 1 | 1 | 1 | 1 | 1 | 1 | 1 | 1 | 1 | 1 | 1 |
| 211 | | | | | | 1 | 1 | 1 | 1 | 1 | 1 | 1 | 1 | 1 | 1 | 1 |
| 216 | | | | | | | | | | | | | 1 | 1 | 1 | 1 |
| 217 | | | | | | | | | | | | | | | | 1 |
| 222 | | | | 1 | | | | 1 | | 1 | 1 | 1 | | 1 | 1 | 1 |
| 231 | | 1 | | | | | 1 | | | | 1 | | | | 1 | |
| 235 | 1 | | | | 1 | | | 1 | | | | | 1 | | | |
| 238 | 1 | 1 | | | 1 | 1 | | | 1 | 1 | | | 1 | 1 | | |
| 239 | 1 | 1 | 1 | 1 | 1 | 1 | 1 | 1 | 1 | 1 | 1 | 1 | 1 | 1 | 1 | 1 |
| 241 | | 1 | 1 | 1 | 1 | 1 | 1 | 1 | 1 | 1 | 1 | 1 | 1 | 1 | 1 | 1 |
| # of peptides | 4 | 4 | 4 | 4 | 5 | 5 | 5 | 5 | 6 | 6 | 6 | 6 | 7 | 7 | 7 | 7 |

In addition some peptide combinations were assembled which included only peptides of similar pI in order to obtain peptide combinations which would have optimal solubility in the same pH interval. This was done by grouping the peptides of the 42 selected high responder peptides into groups having similar pI. Within each group the above method was used but including only the respective pI sub groups of selected peptides. The peptide combinations assembled using the above method can be found in Table 24b below.

Table 24b. pI-Optimized Peptide Combinations Tested

Table 24b shows examples of peptide combinations ("1" indicates that the peptide is present in the peptide combination) assembled from peptides of similar pI with high predicted species coverage, T cell reactivity, worldwide HLA Class II coverage and peptide valency.

TABLE 24b

| Peptide | Peptide combination name | | | | |
|---|---|---|---|---|---|
| | 1005 | 1015 | 1025 | 1055 | 1065 |
| 204 | | | | 1 | |
| 205 | | 1 | | | |
| 206 | 1 | | | | 1 |
| 207 | | | | | 1 |
| 208 | | 1 | 1 | | |
| 211 | | | | | 1 |
| 212 | | | | 1 | |
| 217 | 1 | | | | |
| 222 | 1 | | | | |
| 226 | | | | 1 | |

TABLE 24b-continued

| Peptide | Peptide combination name | | | | |
|---|---|---|---|---|---|
| | 1005 | 1015 | 1025 | 1055 | 1065 |
| 228 | | | | 1 | |
| 231 | 1 | | | | 1 |
| 233 | | | | 1 | |
| 235 | | 1 | 1 | | |
| 236 | | 1 | 1 | | |
| 237 | | | 1 | | |
| 238 | | 1 | 1 | | |
| 240 | 1 | | | | 1 |
| # of peptides | 5 | 5 | 5 | 5 | 5 |

Finally some reference peptide combinations were assembled. Accordingly, peptide combination 405 was assembled from the group of peptides tested in the first round of screening, which were not included in the selected high responder peptide group of Example 3. Peptide combination 505 was assembled within the 42 selected high responder peptide group of Example 3 and was designed to provide the best donor coverage possible. It contained the 5 peptides of SEQ ID NOs: 8, 10, 23, 46 and 68. Peptide combination 605 was assembled within the 42 selected high responder peptide group of Example 3 but with the purpose of obtaining the lowest possible valency (so reversing the score for HLA coverage in the method described above). Finally peptide combinations 807, 814 and 825 contained 7, 4 and 5 reference peptides of WO2010/089554 and represented three of the different peptide combinations suggested.

Table 25. Peptide Combinations of WO2010/089554 Tested

Table 25 shows three peptide combinations suggested in WO2010/089554 which have been tested.

TABLE 25

| | | Peptide combination name | | |
|---|---|---|---|---|
| Peptide name | Peptide number | 825 | RP35Mix807 (807) | RP35Mix814 (814) |
| Ber01 | 134 | 1 | 1 | 1 |
| Ber02 | 135 | | 1 | |
| Ber02C | 136 | 1 | 1 | 1 |
| Bio02A | 137 | | 1 | |
| Bio03A | 138 | | | |
| Bio04A | 139 | 1 | 1 | |
| Rye09B | 140 | 1 | | 1 |
| Tim07B | 141 | 1 | | 1 |
| Rye09B1 | 142 | | 1 | |

TABLE 25-continued

| | | Peptide combination name | | |
|---|---|---|---|---|
| Peptide name | Peptide number | 825 | RP35Mix807 (807) | RP35Mix814 (814) |
| Rye09B2 | 143 | | | |
| Tim07B1 | 144 | | | 1 |
| Tim07B2 | 145 | | | |

Example 7

T Cell Reactivity of Peptide Combinations

This example includes a description of the testing of T cell reactivity of the peptide combinations suggested in Example 6 and corresponding test results.

The peptide combinations 0014-1065 of Example 6 were tested at 2 µg/ml (of each peptide) in ELISpot on TCL01-DK2 (21 donors) on day 14 as described in Example 3 and in proliferation on TCL02-DK1 and on TCL02-DK2 (21 donors) on day 24 as described in Example 3. Data are presented in Table 26 below. Peptide combinations 807, 814 and 825 correspond to some of the peptide combinations tested in WO 2010/089554.

In addition 41 of the selected peptides of Example 6 were re-tested in ELISpot on TCL01-DK2 (21 donors) on day 14 as described in Example 3 and in proliferation on TCL02-DK1 and on TCL02-DK2 (21 donors) on day 24 as described in Example 3. The 15-mer peptide with SEQ ID NO: 114 was not re-tested. The results obtained for the individual peptides were comparable to the data obtained in Example 3 confirming the solidity of the data set (data not shown).

Figure 5A:
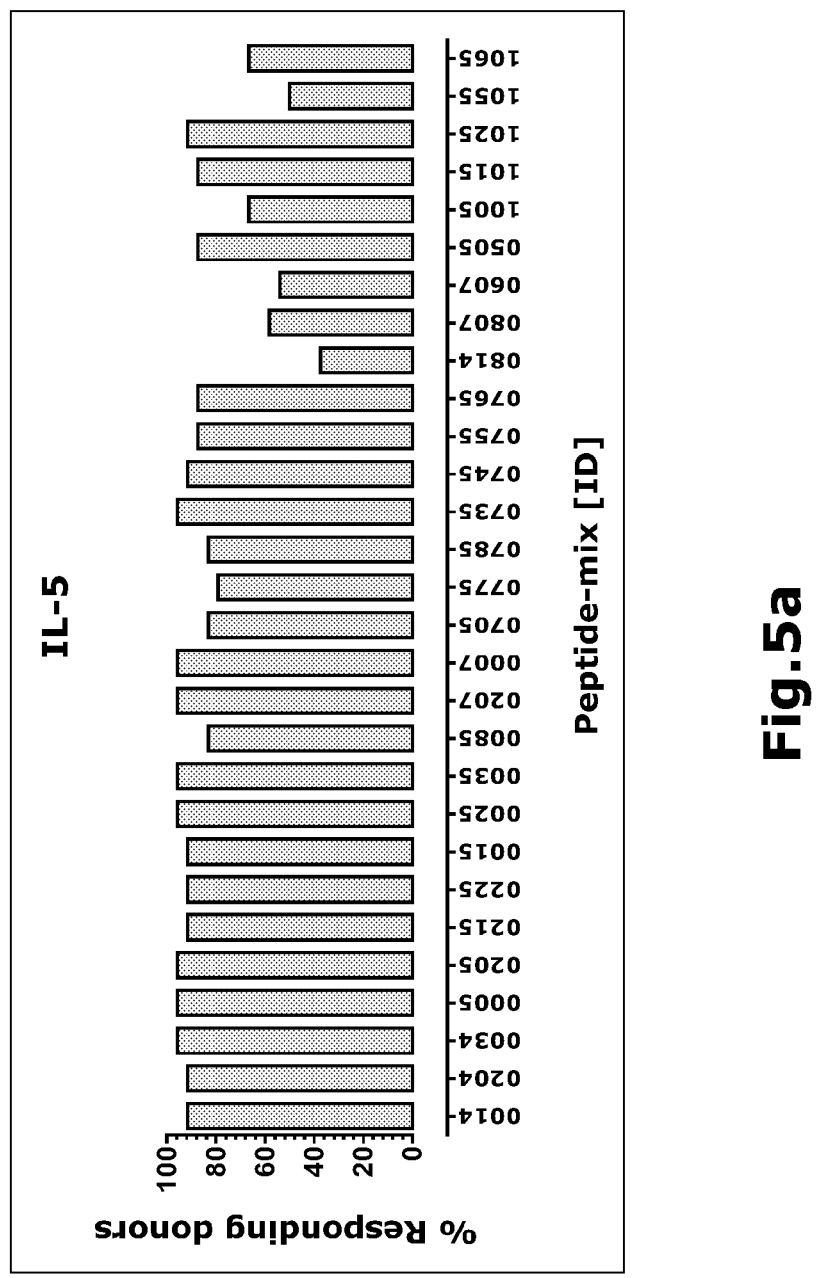
Figure 5B:
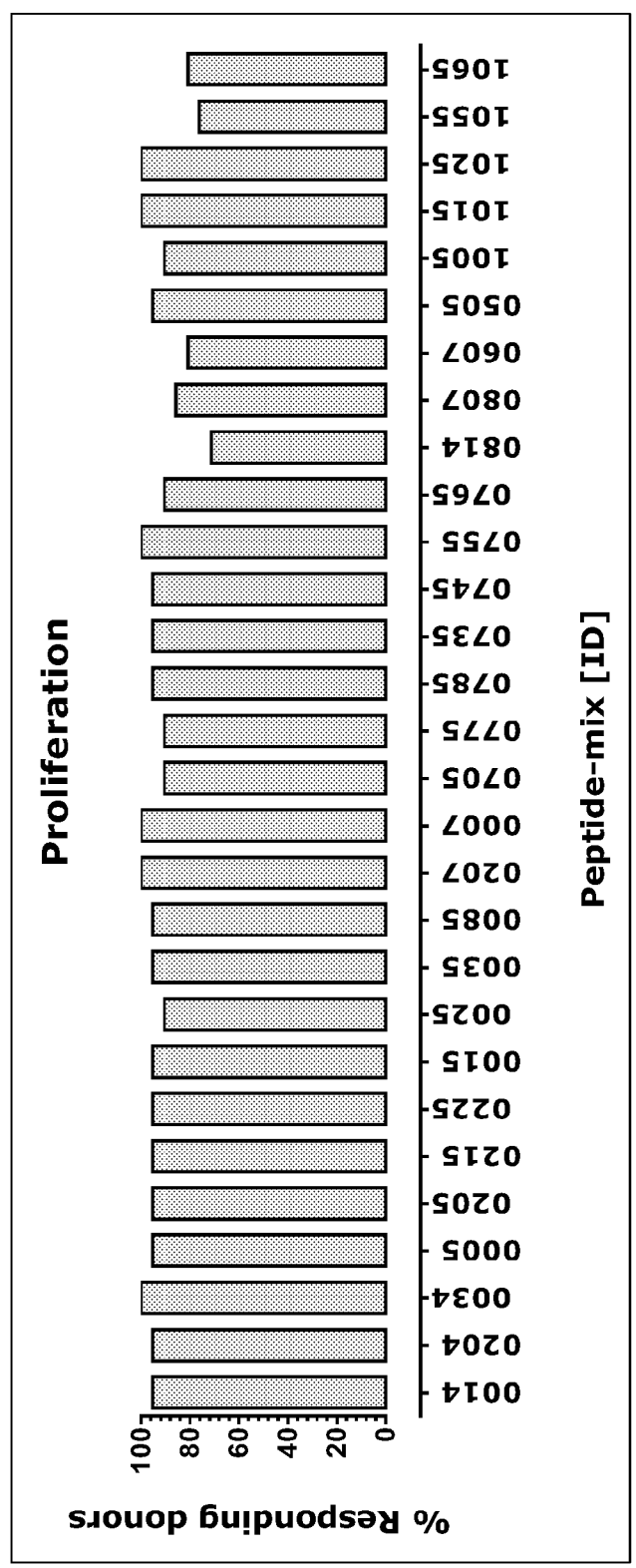
Figure 6:
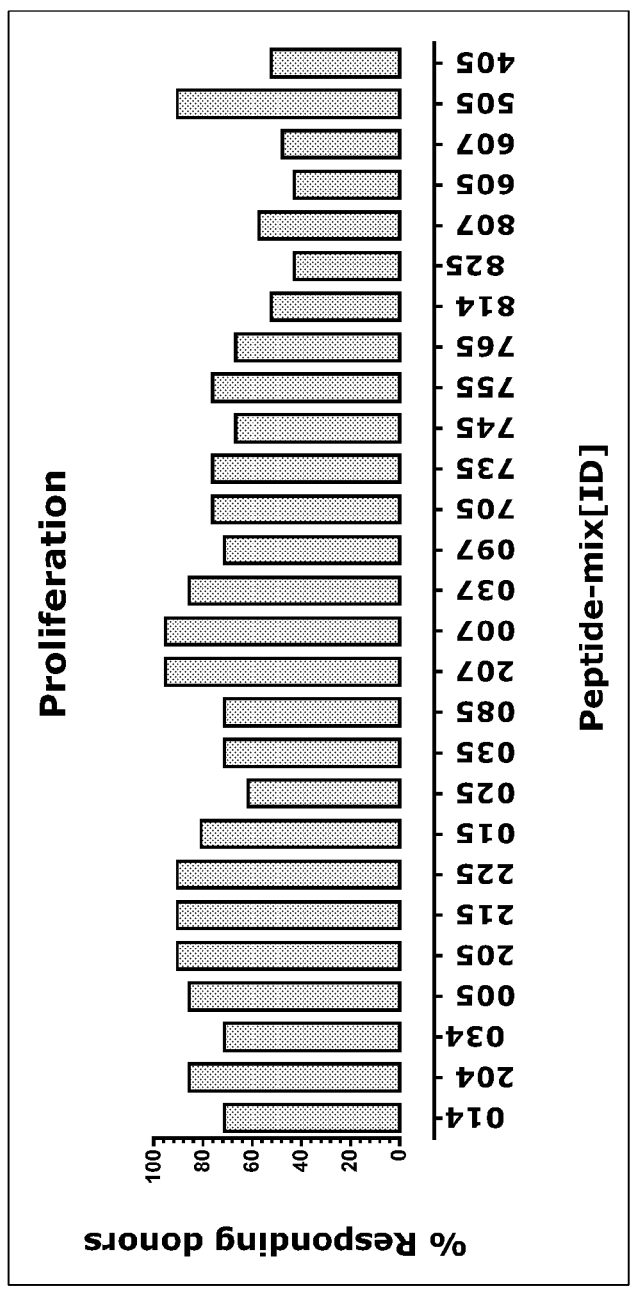

The data obtained from testing the peptide combinations 0014-1065 are presented in Table 26 below and are depicted in FIG. 5a (bar chart showing IL-5 donor coverage, TCL01-DK2) and FIG. 5b (bar chart showing the proliferation donor coverage, TCL02-DK2).

Table 26—T Cell Reactivity of Combinations 0014-1065

Table 26 shows T cell reactivity of combinations 0014 to 1065, where "*" means that the strength has been defined in form of "Average relative magnitude" calculated by averaging the relative magnitudes of response for a peptide from all donors. Relative magnitude value for a peptide was calculated as percentage of highest response to an allergen or a mix by the same donor. In this way, highest response for a peptide combination or allergen was given a value of 100 and subsequently responses for other combinations where calculated.

x: the response to the combinations were not measured.

TABLE 26

| | TCL01-DK2 24 Donors IL-5/ELIspot | | TCL02-DK2 21 donors Proliferation | | TCL03-DK1 21 Donors Proliferation | |
|---|---|---|---|---|---|---|
| Peptide Combination Name | % Donor Coverage | Strength of T cell response* | % Donor Coverage | Strength of T cell response* | % Donor Coverage | Strength of T cell response* |
| 0014 | 91.67 | 55.06 | 95.24 | 50.79 | 71.43 | 33.99 |
| 0204 | 91.67 | 58.90 | 95.24 | 52.90 | 85.71 | 47.04 |
| 0034 | 95.83 | 57.69 | 100 | 57.36 | 71.43 | 39.21 |
| 0005 | 95.83 | 57.56 | 95.24 | 50.91 | 85.71 | 50.47 |
| 0205 | 95.83 | 57.46 | 95.24 | 55.17 | 90.48 | 52.44 |
| 0215 | 91.67 | 63.86 | 95.24 | 58.20 | 90.48 | 51.62 |
| 0225 | 91.67 | 62.70 | 95.24 | 57.84 | 90.48 | 54.78 |
| 0015 | 91.67 | 56.53 | 95.24 | 52.82 | 80.95 | 45.07 |
| 0025 | 95.83 | 49.85 | 90.48 | 48.16 | 61.90 | 27.56 |
| 0035 | 95.83 | 58.94 | 95.24 | 55.76 | 71.43 | 36.94 |
| 0085 | 83.33 | 62.17 | 95.24 | 61.99 | 71.43 | 40.36 |
| 0207 | 95.83 | 75.60 | 100 | 72.27 | 95.24 | 70.53 |
| 0007 | 95.83 | 59.49 | 100 | 61.91 | 95.24 | 55.98 |
| 0037 | x | x | X | x | 85.71 | 57.28 |
| 0097 | x | x | X | x | 71.43 | 52.21 |
| 0705 | 83.33 | 48.12 | 90.48 | 50.92 | 76.19 | 43.66 |
| 0735 | 95.83 | 59.76 | 95.24 | 62.72 | 76.19 | 42.20 |
| 0745 | 91.67 | 67.79 | 95.24 | 60.57 | 66.67 | 39.64 |
| 0755 | 87.50 | 52.76 | 100 | 51.07 | 76.19 | 39.88 |
| 0765 | 87.50 | 49.76 | 90.48 | 51.95 | 66.67 | 31.44 |
| 0814 | 37.50 | 12.55 | 71.43 | 22.86 | 52.38 | 16.45 |
| 0825 | x | x | X | x | 42.86 | 14.36 |
| 0807 | 58.33 | 23.04 | 85.71 | 30.48 | 57.14 | 18.08 |
| 0605 | X | x | X | x | 42.86 | 20.41 |
| 0607 | 54.17 | 19.29 | 80.95 | 32.70 | 47.62 | 25.18 |
| 0505 | 87.50 | 45.15 | 95.24 | 52.46 | 90.48 | 54.52 |
| 0405 | X | x | X | x | 52.38 | 19.08 |
| 0775 | 79.17 | 58.06 | 90.48 | 50.40 | x | x |
| 0785 | 83.33 | 49.00 | 95.24 | 58.68 | x | x |
| 1005 | 66.67 | 29.75 | 90.48 | 45.60 | x | x |
| 1015 | 87.50 | 58.56 | 100 | 60.44 | x | x |
| 1025 | 91.67 | 60.44 | 100 | 58.67 | x | x |
| 1055 | 50.00 | 28.68 | 76.19 | 33.79 | x | x |
| 1065 | 66.67 | 26.83 | 80.95 | 33.51 | x | x |

Summary of the T cell responses (IL-5, ELispot) obtained from 24 donors-DK2 (FIG. 5a) have been shown below:

a. Peptide combinations with 4 peptides (0014 and 0204) showed donor coverage more that 90%, where peptide combination 34 showed coverage of 95%. The average relative magnitude was between 50-60.

b. Peptide-combinations with 5 peptides (0005, 0205, 0215, 0225, 0015, 0035) had donor coverage was between 90-95% and the avg. rel. mag. around 50-60. However peptide combination 0085 was a bit low (80%) on donor coverage. Similarly mix 0025 was good in donor coverage (96%) but low in avg. rel. mag. (around 50).

c. Peptide-combinations (007 & 207) with 7 peptides had donor coverage of 96%, avg. rel. mag. was between 80-96.

d. 7 LJI combinations had % donor coverage between 80-96%, where mix 735 was the best in the donor coverage (96%). The average relative magnitude was between 48-65.

e. Combinations 825 was used as control in the study. The donor coverage (around 15%-60%) and avg. rel. mag. (around 15-30) were relatively low in comparison to the combinations containing 20-mers or 15-mers.

f. Negative peptide combination 0607 which was supposed to be low in coverage and was observed to have low coverage around 60% donor population with avg. rel. mag. around 45.

g. Best donor coverage peptide combination 505 had a very good T cell activity with donor coverage around 90% and avg. rel. mag. around 60.

h. PI optimised combinations were also very good in T cell reactivity. Combinations 1015 and 1025 showed frequency of donor coverage above 90% with avg. rel. mag. around 60. While combinations with PI around basic pH (combinations 1005 and 1065) or acidic pH (mix 1055) had comparatively low donor coverage (between 50-70%) and avg. rel mag. around 30.

Summary of the T cell responses (Proliferation) obtained from 21 donors-DK2 (FIG. 5b) are shown below:

a. Peptide combinations with 4 peptides showed donor coverage more that 95%, where mix 0034 showed coverage of 100%. The average relative magnitude was between 30-50.

b. Peptide combinations with 5 peptides had donor coverage around 95%. Mix 005, 205, 215, 225 had donor coverage around 90% with average rel. magnitude around 50.

c. Peptide combinations (0007 and 0207) with 7 peptides had donor coverage of 100% and avg. rel. mag. was between 60-70.

d. 7 LJI combinations had donor coverage between 90-95% and the average relative magnitude between 50-60.

e. Combination 0825 also called 825 were used as control in the study. The donor coverage (around 70%-80%) and avg. rel. mag. (around 20-30) were relatively low in comparison to the peptide combinations of the invention.

f. Negative mix (0607) which was supposed to be low in coverage was low covering 80% donor population with avg. rel. mag. around 30.

g. Best donor coverage mix 0505 was had a very good T cell activity with donor coverage around 95% and avg. rel. mag. around 60.

h. PI optimised combinations were also very good in T cell reactivity. Combinations 1015 and 1025 showed frequency of donor coverage touching 96% with avg. rel. mag. around 60. While combinations with PI around basic pH (combinations 1005 and 1065) or acidic pH (mix 1055) had comparatively low donor coverage (between 70-90%) and avg. rel magnitude (between 30-40)

The combinations were also tested in previously established T cell lines from donor cohort DK-1. This was done in-order to confirm the immunogenicity of the combinations on a population DK-1 from where the 42 single peptides were selected. T cell lines generation 03 were used for the testing the combinations. The data has been summarized in FIG. 6 (bar chart showing donor coverage).

Summary of the T cell responses obtained from 21 donors have been listed below:

a. Peptide combinations with 4 peptides showed donor coverage more that 70%, where mix 204 showed coverage 85%. The average relative magnitudes were more than 30. Mix 204 had an average relative magnitude around 50.

b. Peptide combinations with 5 peptides coverage was between 70-90%. Mix 5, 205, 215, 225 had donor coverage 90% with avg. rel. magnitude around 50 while mix 25, 35 and 85 had donor coverage around 70% with average relative magnitude around 40.

c. Peptide combinations with 7 peptides had donor coverage between 90%-70%, where mix 207 & 007 had coverage of more than 90%, avg. rel. mag. between 60-70. While mix 037 and mix 097 had a donor coverage of 80% & 70% with avg. rel. mag. around 50.

d. 7 LJI combinations showed a good coverage of more than 90% and the average relative magnitude was above or around 40.

e. Reference combinations were used as control in the study. The donor coverage (around 50) and avg. rel. mag. (around 20) were relatively low in comparison to the combinations with 20-mers or 15-mers.

f. Negative combinations (0605, 0607) were very low in donor coverage (around 50%) and avg. rel. mag. (around 20).

g. Best of bad 5 peptide combination 0405 had a coverage around 50% with avg. rel. mag. around 20.

h. Best donor coverage peptide combination 0505 was had a very good T cell activity with donor coverage around 90% and avg. rel. mag. around 60.

In a second round of testing the combinations 2401-2716 of Example 6 (a total of 16 combinations) were tested for T cell reactivity using the same procedures as above. These peptide combinations were designed based on the peptides having good solubility profile as described in Example 6 with the purpose of avoiding any late stage formulation complications. In brief, the designed combinations were tested in a proliferation based T cell assay. Pre-established T cell line generation 03 (TCL03) were used for testing the combinations where 25 donors were selected from Danish cohort DK-1 and DK-2 to obtain a HLA profiles in the cohort to represent the worldwide HLA profiles. The combinations were tested at a concentration of 2 µg/ml.

The data obtained from testing the peptide combinations 2401-2716 are presented in table 27.

Figure 7A:
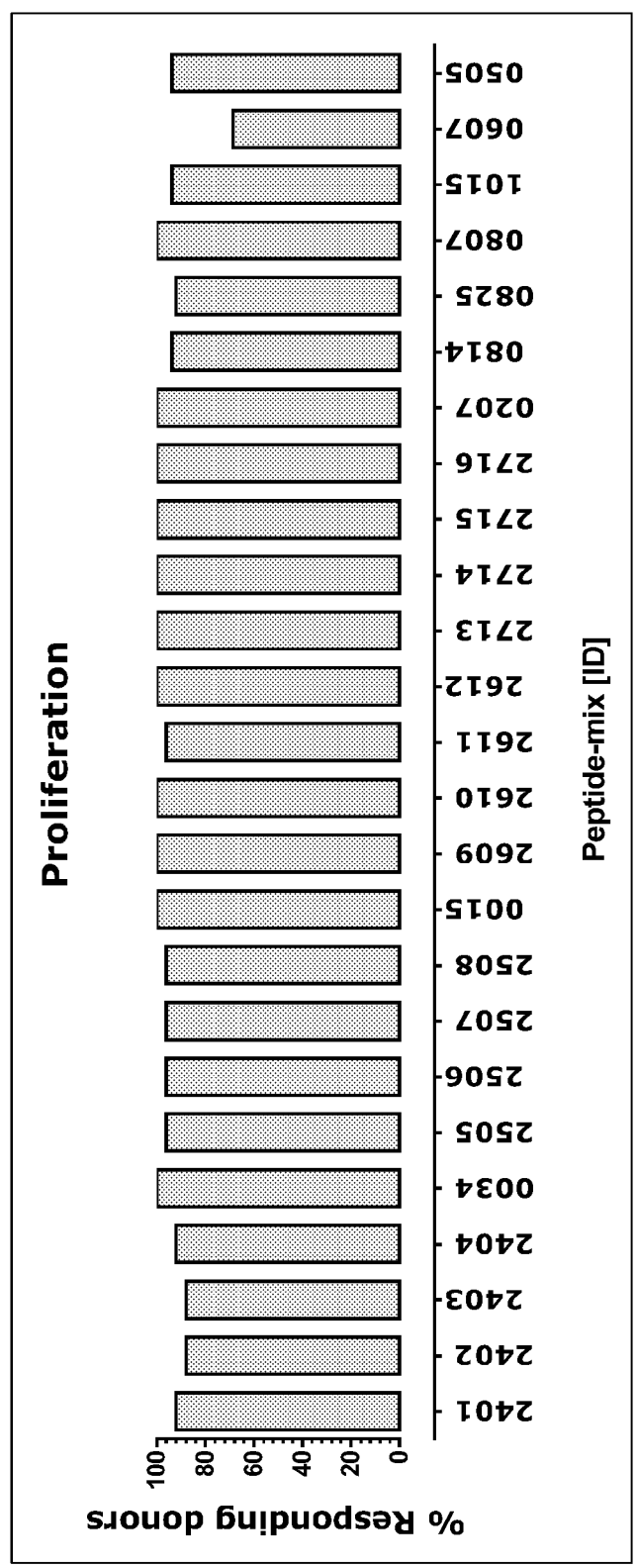
Figure 7B:
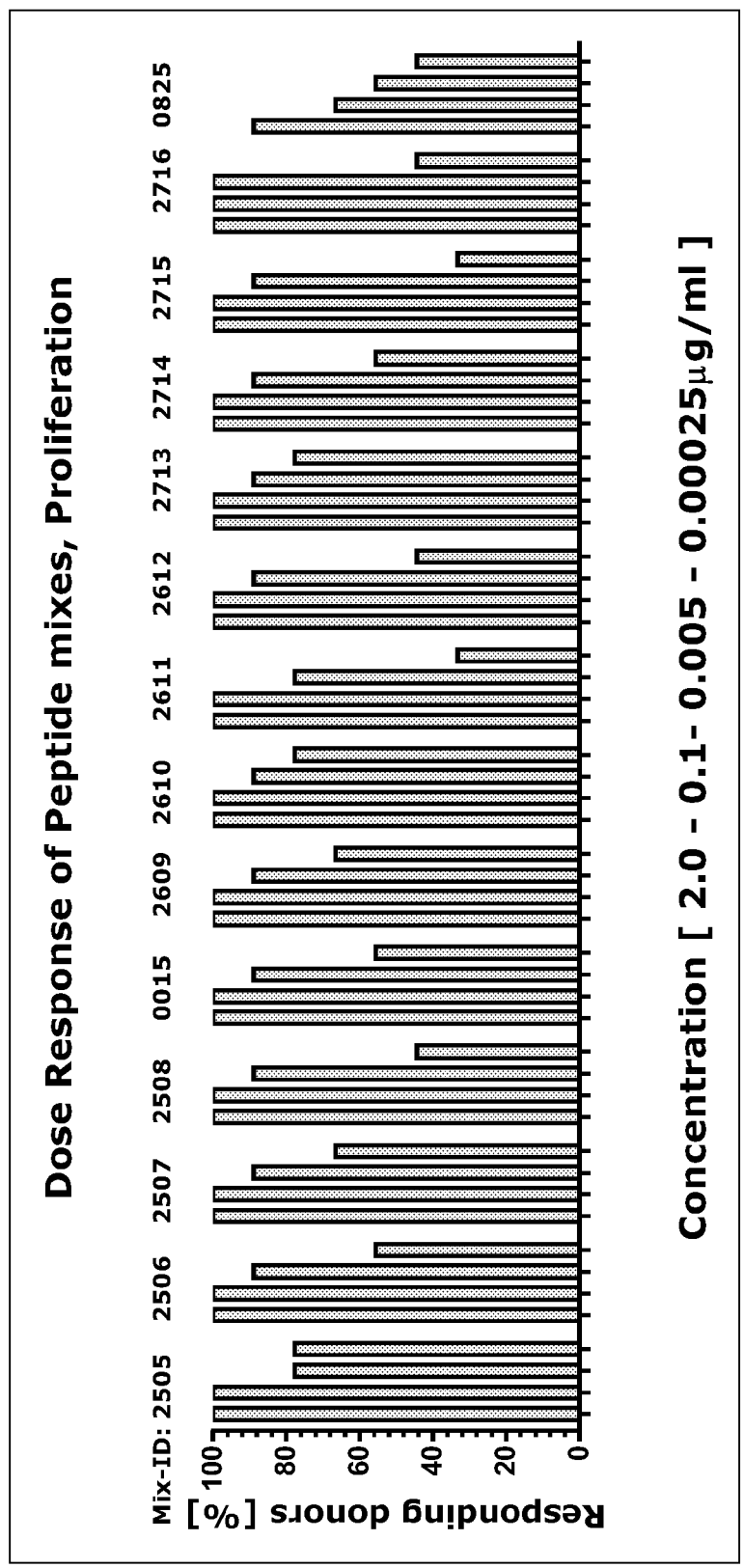

As shown in FIG. 7a nearly all the combinations tested had a donor coverage of more than 90% when tested at a single concentration 2 µg/ml. Some of the combinations (2609, 2610, 2613, 2714, 2715, 2716) had a donor coverage of 100%. The data was obtained from 25 donor derived TCLs.

Table 27—T Cell Reactivity of Combinations 2401-2716

Table 27 shows T cell reactivity of combinations 2401 to 2716. Strength of T cell response has been calculated as described before, except here it has been calculated on the basis of major allergens either Phl p 1 or Phl p 5.

TABLE 27

| Peptide Combination name | TCL03-DK1 + DK 2 Proliferation | |
|---|---|---|
| | % Donor Coverage | Strength of T cell response* |
| 2401 | 92.0 | 103.67 |
| 2402 | 88.0 | 106.30 |
| 2403 | 88.0 | 100.80 |
| 2404 | 92.0 | 106.78 |
| 0034 | 100.0 | 55.55 |
| 2505 | 96.0 | 115.69 |
| 2506 | 96.0 | 113.73 |
| 2507 | 96.0 | 104.12 |
| 2508 | 96.0 | 108.54 |
| 0015 | 100.0 | 108.29 |
| 2609 | 100.0 | 116.07 |
| 2610 | 100.0 | 121.08 |
| 2611 | 96.0 | 112.77 |
| 2612 | 100.0 | 116.90 |
| 2713 | 100.0 | 122.43 |
| 2714 | 100.0 | 125.67 |
| 2715 | 100.0 | 115.73 |
| 2716 | 100.0 | 127.08 |
| 0207 | 100.0 | 91.37 |
| 0814 | 93.8 | 53.37 |
| 0825 | 92.0 | 75.63 |
| 0807 | 100.0 | 74.38 |
| 1015 | 93.8 | 86.88 |
| 0607 | 68.8 | 42.49 |
| 0505 | 93.8 | 93.69 |

The individual data of each peptide (of Example 3) can be used to calculate the theoretical percentage of donors responding to the peptide combinations if there is a response to at least one peptide in the combination. Thus the percentage of responders recognizing a peptide combination can be calculated using information about the individual peptides that produce an in vitro T cell response in each of the donors tested.

This allows for calculating a theoretical percentage responders to other peptide combinations than the ones tested in this example.

The number of peptides that a donor of the donor population in average responds to may also be calculated using the information about how many of the peptides in the peptide combination a donor is able to respond to.

Example 8

T Cell Reactivity of Homologue Peptides

This example describes how the homologous peptides were tested and compared to its homologous counterpart peptides.

Homologue peptides were selected on the basis of sequence homology to the native *Phleum pratense* peptides. Homologue peptides were selected on the basis of sequence homology to the native *Phleum pratense* peptides (for sequences, see Example 1, SEQ ID NOs: 134-200). Cross-reactivity to *Phleum pratense* peptides with either close (*Lolium Perenne* (Lol p)) or distant (*Phalaris aquatica* (Pha a), *Cynodon dactylon* (Cyn d)) species was experimentally investigated. In this study 67 homologue peptides were investigated together with 41 phleum peptides at a concentration of 2 µg/ml. The sequences of the homologous peptides tested are listed as SEQ ID NOs: 134-200 in Table 8 of Example 1.

To test the activity of the predicted homologue peptides T cell proliferation assays were carried out on 21 grass allergic donor derived line (TCL-02 DK-2) as described in Example 3. Here in this study 67 homologue peptides (SEQ ID NOs: 134-200) corresponding to 41 native *Phleum pratense* derived peptides were investigated at a concentration of 2 µg/ml. The data has been summarized in the FIG. 8a and FIG. 8b. Summary of the T cell responses can be found below:

Phl p 1: Some of the homologue peptides had a donor coverage comparable to the native peptides. For example the following peptides #18 of Cyn d 1 (SEQ ID NO: 145), #66 of Lol p 1 (SEQ ID NO: 134), #93 of Cyn d 1 (SEQ ID NO: 148), #103 of Lol p 1 (SEQ ID NO: 136), #103 of Cyn d 1 (SEQ ID NO: 149), #183 of Lol p 1 (SEQ ID NO: 141) #183 of Cyn d 1 (SEQ ID NO: 154). However in some cases the homologues were low in donor coverage. For example #66 of Cyn d 1 (SEQ ID NO: 146), #193 of Lol p 1 (SEQ ID NO: 142), #211 of Lol p 1 (SEQ ID NO: 143), #211 of Cyn d 1 (SEQ ID NO: 156), #221 of Lol p1 (SEQ ID NO: 144) and #221 of Cyn d 1 (SEQ ID NO: 157). Homologue peptide #193 of Cyn dl (SEQ ID NO: 155) was not recognized by the T cell lines.

Phl p 2, Phl p3 & Phl p 4: In most cases the homologue peptides were recognized by the T cell lines, either with low or comparable donor coverage to the native peptides.

Phl p 5: Homologue peptides sharing resemblance to the *Phleum* p 5 peptides were found to be highly immunogenic in the T cell assay. Most of the homologues had comparable donor coverage when compared with the native *Phleum* peptides, for example #104 of Lol p 5 (SEQ ID NO: 178), #104 of Pha a 5 (SEQ ID NO: 191), #111 of Lol p 5 (SEQ ID NO: 179), #111 of Pha 5 (SEQ ID NO: 192), #148 of Lol p 5 (SEQ ID NO: 180) #148 of Pha a 5 (SEQ ID NO: 193), #156 of Lol p 5 (SEQ ID NO: 181). Some of the homologues had a better donor coverage than the native peptides, for example #1 of Lol p 5 (SEQ ID NO: 173) #1 of Pha a 5 (SEQ ID NO: 188), #21 of Lol p 5 (SEQ ID NO: 174), #31 of Lol p 5 (SEQ ID NO: 175), #46 of Lol p 5 (SEQ ID NO: 175). However some homologues did loose some of the donor coverage when compared to the parent peptides. For ex. #31 of Pha a5 (SEQ ID NO: 155), #156 of Pha a 5 (SEQ ID NO: 194), #185 of Lol p 5 (SEQ ID NO: 183), #194 of Lol p 5 (SEQ ID NO: 184) #194 of Pha 5 (SEQ ID NO: 197), #214 of Pha a5 (SEQ ID NO: 198).

Overall the homologue T cell data confirms the fact that the homologues showing comparable or better T cell activity may be used to replace the parent peptides as defined herein in case any problem arises due to solubility/pre-formulation issues with the parent peptides as defined herein.

Example 9

Cross Reactivity

This example includes a description of the procedure for testing cross reactivity between a selection of peptides derived from allergens of *Phleum pratense* and corresponding peptides (homologous peptides) derived from other grass pollen species, such as the species Bermuda grass, Canary grass and Rye grass.

Measured Cross-Reactivity:

To measure the experimental cross-reactivity the proliferation assay of Example 3 was carried out on 21 grass allergic donors (TCL02-DK2). Homologue peptides were selected on the basis of sequence homology to the native *Phleum pratense* peptides (for sequences, see Example 1, SEQ ID NOs: 134-200). Cross-reactivity to *Phleum pratense* peptides with either close (*Lolium perenne* (Lol p)) or distant (*Phalaris aquatica* (Pha a), *Cynodon dactylon* (Cyn d)) species was experimentally investigated. In this study 67 homologue peptides were investigated together with 41 phleum peptides at a concentration of 2 µg/ml.

The 67 peptides of homologue species were derived from the following species:

Table 8 shows additional peptides suggested for screening, which derive from pollen allergens of the following species:

*Cynodon dactylon* (Cyn d 1 (SEQ ID NO: 333) and Cyn d 4 (SEQ ID NO: 334))

*Lolium Perenne* (Lol p 1 (SEQ ID NO: 339), Lol p 2 (SEQ ID NO: 340), Lol p 3 (SEQ ID NO: 341), Lol p 5a (SEQ ID NO: 342) and Lol p 5b (SEQ ID NO: 343)) and

*Phalaris aquatica* (Pha a 1 (SEQ ID NO: 345) and Pha a 5 (SEQ ID NO: 346))

For analysing the cross-reactivity data, it was investigated if a donor responds to both native and homologue peptide, XY correlation plots were made where the donor responses to native peptides were plotted versus the donor responses to homologues. Cross-reactivity was considered to be present if this comparison revealed a correlation between native peptides and homologues in a group of donors where minimum of two or more donors were cross-reactive (same donor responds to both native and homolog peptide) and were labelled as 'Yes' else they were labelled as 'No'. If less than five donors were responding to the parent peptides, then the data was considered to be in-conclusive, and were thus labelled with "-". For some of the peptides the analysis was further supported by performing a Spearman r-Non Parametric test (data not shown).

The results of the measured cross-reactivity has been summarized in the Table 28 where all the homologues showing a positive cross-reactive responses were labelled as 'Yes', those where no cross-reactivity was observed were labelled as 'No'. With some of the homologues no conclusive results were obtained, which were marked with "-".

Table 28: Experimental Cross-Reactivity of the Homologue Peptides Measured by Donor Derived T Cell Lines (TCL-02 DK-2) has been Summarized

TABLE 28

| Native Peptide | Peptide naming | Homologue allergen | Peptide homologue naming | Measured Cross-reactivity (Yes/No/—) |
|---|---|---|---|---|
| Phl p 1, 18 | 201 | Cyn d 1 | 312 | No |
| 1Phl p 1, 66 | 202 | Lol p 1 | 301 | Yes |
|  |  | Cyn d 1 | 313 | No |
| Phl p 1, 74 | 203 | Lol p 1 | 302 | — |
|  |  | Cyn d 1 | 314 | — |
| Phl p 1, 93 | 204 | Cyn d 1 | 315 | Yes |
| Phl p 1, 103 | 205 | Lol p 1 | 303 | Yes |
|  |  | Cyn d 1 | 316 | Yes |
| Phl p 1, 119 | 206 | Lol p 1 | 304 | — |
|  |  | Cyn d 1 | 317 | — |
| Phl p 1, 127 | 207 | Cyn d 1 | 318 | — |
| Phl p 1, 153 | 208 | Lol p 1 | 306 | Yes |
|  |  | Cyn d 1 | 319 | Yes |
| Phl p 1, 163 | 209 | Lol p 1 | 307 | — |
|  |  | Cyn d 1 | 320 | — |
| Phl p 1, 183 | 210 | Lol p 1 | 308 | Yes |
|  |  | Cyn d 1 | 321 | Yes |
| Phl p 1, 193 | 211 | Lol p 1 | 309 | — |
|  |  | Cyn d 1 | 322 | — |
| Phl p 1, 211 | 212 | Lol p 1 | 310 | Yes |
|  |  | Cyn d 1 | 323 | Yes |
| Phl p 1, 221 | 213 | Lol p 1 | 311 | Yes |
|  |  | Cyn d 1 | 324 | Yes |
| Phl p 2, 40 | 214 | Lol p 2 | 325 | Yes |
| Phl p 2, 48 | 215 | Lol p 2 | 326 | — |
| Phl p 2, 58 | 216 | Lol p 2 | 327 | — |
| Phl p 3, 11 | 217 | Lol p 3 | 328 | Yes |
| Phl p 3, 38 | 218 | Lol p 3 | 329 | Yes |
| Phl p 3, 47 | 219 | Lol p 3 | 330 | Yes |
| Phl p 3, 56 | 220 | Lol p 3 | 331 | — |
| Phl p 3, 66 | 221 | Lol p 3 | 332 | Yes |
| Phl p 4, 8 | 222 | Lol p 4 | 333 | Yes |
|  |  | Cyn d 4 | 334 | No |
| Phl p 4, 55 | 223 | Cyn d 4 | 335 | — |
| Phl p4, 101 | 224 | Cyn d 4 | 336 | No |
| Phl p 4, 163 | 225 | Cyn d 4 | 337 | Yes |
| Phl p 4, 195 | 226 | Cyn d 4 | 338 | — |
| Phl p 4, 386 | 227 | Cyn d 4 | 339 | Yes |
| Phl p 5, 1 | 228 | Lol p 5 | 340 | — |
|  |  | Pha a 5 | 355 | — |
| Phl p 5, 21 | 229 | Lol p 5 | 341 | Yes |
| Phl p 5, 31 | 230 | Lol p 5 | 342 | Yes |
|  |  | Pha a 5 | 356 | Yes |
| Phl p 5, 46 | 231 | Lol p 5 | 342 | Yes |
| Phl p 5, 84 | 232 | Lol p 5 | 344 | — |
|  |  | Pha a 5 | 357 | — |
| Phl p 5, 104 | 233 | Lol p 5 | 345 | Yes |
|  |  | Pha a 5 | 358 | Yes |
| Phl p 5, 111 | 234 | Lol p 5 | 346 | Yes |
|  |  | Pha a 5 | 359 | Yes |
| Phl p 5, 148 | 235 | Lol p 5 | 347 | Yes |
|  |  | Pha a 5 | 360 | Yes |
| Phl p 5, 156 | 236 | Lol p 5 | 348 | Yes |
|  |  | Pha a 5 | 361 | Yes |
| Phl p 5, 166 | 237 | Lol p 5 | 349 | Yes |
|  |  | Pha a 5 | 362 | Yes |
| Phl p 5, 185 | 238 | Lol p 5 | 350 | Yes |
|  |  | Pha a 5 | 363 | Yes |
| Phl p 5, 194 | 239 | Lol p 5 | 351 | Yes |
|  |  | Pha a 5 | 364 | Yes |
| Phl p5, 214 | 240 | Lol p 5 | 352 | Yes |
|  |  | Pha a 5 | 365 | Yes |
| LJI 1 (Phl p5, 154) | 241 | Lol p 5 | 353 | Yes |
|  |  | Pha a 5 | 366 | Yes |

When it comes to experimental testing of cross-reactivity, some individuals may show cross-reactivity to a certain peptide whereas others may not show cross-reactivity.

The majority of the peptides tested showed experimental cross-reactivity as seen in T cell assay. Homologue peptides derived from group 2 and group 4 were not found to be cross-reactive. The peptides derived from group 1 and group 3 did show moderate cross-reactivity. Accordingly, at least peptides 202, 204, 205, 208, 210, 213, 216, 217, 218, 219, 221, 230, 231, 233, 234, 235, 236, 237, 238, 239, 240 and 241 showed cross-reactivity in the experiment conducted.

For example peptides 204 and 208 showed good cross-reactivity as depicted in FIGS. 11 and 12. Group 5 allergen derived peptides were highly cross-reactive and were the best in the experimental cross-reactivity assays. For example peptides 235, 238 and 241 showed very good cross-reactivity as depicted in FIGS. 13 and 14. Also 233, 236, 237, 239 and 240 showed good cross reactivity.

Further the magnitude of T cell response from a parent peptide as defined herein and homologue response were plotted in a XY plot by using GraphPad Prism 6. The magnitude of response obtained by the parent peptides as defined herein have been connected by a straight line. The homologue peptides indicating the presence of cross-reactivity have their responses scattered around the response to native peptide/straight line.

Example 10

Dose Response Analysis of Selected Mixes and Individual Peptides

This example includes a description of how the dose-response relationship was tested for selected mixes and the results thereof.

Further to get an overview of the immunogenicity of the mixes and peptides and the concentration dependency, a dose response titration was carried out for selected single peptides and combinations of peptides. The peptides used for dose response were the most frequent peptides of the peptide combinations tested (both soluble and poorly soluble).

The dose-response relationship was tested by measuring the percentage of donor response (i.e. the percentage of donor coverage) in concentrations of 2.0, 0.1, 0.005 and 0.00025 µg/ml for the peptide combinations and in concentrations of 2.0, 0.2, 0.02 and 0.002 µg/ml for single peptides. The donor response was determined using T cell proliferation data as described in Example 3.

Relative magnitude value for a peptide or a peptide combination was calculated as percentage of highest T cell response to an allergen or a mix, by the same donor. In this way, allergen or peptide combination with highest magnitude of T cell response gets a value of 100 and T cell response magnitude of remaining peptides/peptide combinations are normalized or calculated relative to 100, for example Relative magnitude=100*(T cell response magnitude of peptide or combination/Highest T cell response in a donor). Relative magnitude were calculated mainly on Phl p 1. For donors non reactive to Phl p 1, Phl p 5 was used as reference Peptide combinations 2505, 2506, 2507, 2508, 0015, 2609, 2610, 2611, 2612, 2713, 2714, 2715, 2716 and 0825 were titrated to get a broad picture of immunogenicity at low concentration. This was done on 9 grass pollen allergic donor derived T cell lines. See FIG. 7b for a demonstration of the results. Most of the peptide mixes had a donor coverage of 85% or above even at very low concentrations (0.005 µg/ml). Peptide mixes 2505, 2506, 2507, 2508, 2609, 2610, 2611, 2612, 2713, 2714, 2715 and 2716 had a donor coverage of 100% even at a concentration of 0.1 µg/ml which is 20 fold less to the highest concentration tested.

The single peptides were titrated to produce dose-response plots. As shown in FIG. 9, the dose response titration done on the peptides showed a detailed picture of the concentration dependent immunogenicity of the peptides on T cell lines. The data presented in FIG. 9 are based on dosage response measured on 25 donor derived T cell lines, except for peptide 205, which was tested on 16 donors. In FIG. 9, most of the single peptides tested had a donor coverage of 60% or above at 0.2 µg/ml. Some of the peptides retained their immunogenicity at very low concentrations. For example peptide 208 (SEQ ID NO: 8), peptide 217 (SEQ ID NO: 36), peptide 233 (SEQ ID NO: 66), peptide 235 (SEQ ID NO: 68), peptide 241 (SEQ ID NO: 113), peptide 238 (SEQ ID NO: 71), peptide 239 (SEQ ID NO: 72), peptide 236 (SEQ ID NO: 69) and peptide 240 (SEQ ID NO: 73)) had a donor coverage of more than 35% even at a concentration of 0.002 µg/ml.

In comparison, FIG. 9 additionally shows that only one of the reference peptide 142 (SEQ ID NO: 242) had a donor coverage comparable to 35% at a concentration of 0.002 µg/ml.

FIG. 21 demonstrates the relative magnitude of the T cell response for individual donors corresponding to the data presented in FIG. 9. FIG. 21 illustrates that the relative magnitude of the T cell proliferation response. It is seen from FIG. 21 that a number of peptides had a high relative magnitude in some donors of above 100, in particular peptides 241, 238, 239. The average relative magnitude calculated over all donors was high for peptides 241, 238 and 239, and only peptide 142 of the reference peptides had average relative magnitude in the same range.

Example 11

In Vitro HLA Class II Binding Analysis of Peptides

This example describes how to determine the HLA class II binding of peptides of the invention.

The assay employed is a competitive MHC class II binding assay, wherein each peptide is analyzed for its ability to displace a known control binder from each of the human MHC class II allotypes shown in Tables 10 and 11. Due to the nature of the competitive assay, the data for each peptide is determined as a ratio of its own $IC_{50}$ to that of the control peptide. Thus, a peptide that has an $IC_{50}$ value that is parity to the control peptide has an identical binding affinity, while peptides with a ratio less than one have a higher affinity and those with a ratio greater than one have a lower affinity. The ratio of $IC_{50}$ may be determined at different cutoff concentrations such as 300-1000 nM. In this example a cutoff of 300 nM was employed.

Assays to quantitatively measure peptide binding to purified class II MHC molecules are based on the inhibition of binding of a high affinity radiolabeled peptide to purified MHC molecules, and were performed essentially as detailed elsewhere (Sidney et al. 2008; Sidney et al. 2010b. a; Greenbaum et al. 2011; Sidney et al. 2001. Sidney et al 2013. McKinney et al 2013). Briefly, 0.1-1 nM of radiolabeled peptide was co-incubated at room temperature or 37° C. with purified MHC in the presence of a cocktail of protease inhibitors. Following a two- to four-day incubation, MHC bound radioactivity was determined by capturing MHC/peptide complexes on monoclonal Ab coated Lumitrac 600 plates (Greiner Bio-one, Frickenhausen, Germany) and measuring bound cpm using the TopCount (Packard Instrument Co., Meriden, Conn.) microscintillation counter. In the case of competitive assays, the concentration of peptide yielding 50% inhibition of the binding of the radiolabeled peptide was calculated. Under the conditions utilized, where [label] <[MHC] and $IC_{50}$ [MHC], the measured $IC_{50}$ values are reasonable approximations of the true $K_d$ values (Cheng and Prusoff 1973; Gulukota et al. 1997). Each peptide was tested at six different concentrations covering a 100,000-fold dose range in three or more independent experiments. As a positive control, the unlabeled version of the radiolabeled probe was also tested in each experiment.

Table 28 shows the HLA Class II alleles and the measured HLA binding affinity of the selected peptides of Example 3, Table 15. The $IC_{50}$ value of each peptide towards each of 25 alleles was determined by the above described method and is shown in Table 28 below. Peptides with an $IC_{50}$ value below 300 nM measured against a given HLA were considered as binding towards this HLA, and the $IC_{50}$ value is shaded in Table 28. The same measurements were performed on the peptides of Example 1, Table 9. The results are presented in Table 29 below.

Table 30 shows the Class II HLA phenotypic coverage in a worldwide population based on the alleles found to bind each peptide and calculated using allele frequencies from Tables 10 and 11 as described in Example 2.

Table 28a—Binding of the First 14 of 41 Selected Peptides of the Invention to 25 Representative HLA Class II Molecules TABLE 28a

| Peptide name | SEQ ID NO: | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 27 |
| | 201 | 202 | 203 | 204 | 205 | 206 | 207 | 208 | 209 | 210 | 211 | 212 | 213 | 214 |
| DPB1*02:01 | 100000 | 1281 | 10080 | 8299 | 578 | 124 | 364 | 389 | 10978 | 102 | 871 | 21963 | 9996 | 8719 |
| DPB1*04:01 | 100000 | 100000 | 100000 | 100000 | 3083 | 967 | 500 | 2852 | 100000 | 535 | 100000 | 100000 | 100000 | 22567 |
| DPB1*04:02 | 100000 | 1345 | 14838 | 3071 | 1448 | 232 | 411 | 66 | 1525 | 563 | 4768 | 29260 | 100000 | 11038 |
| DPB1*05:01 | 25934 | 100000 | 15774 | 22233 | 669 | 538 | 339 | 49 | 454 | 1292 | 1043 | 10817 | 8833 | 13786 |
| DQB1*02:01 | 71 | 371 | 5736 | 6121 | 22911 | 515 | 100000 | 6138 | 242 | 529 | 43 | 55 | 447 | 43 |
| DQB1*03:01 | 7.9 | 8,4 | 12 | 59 | 15 | 842 | 6988 | 368 | 15 | 121 | 767 | 2086 | 1237 | 369 |
| DQB1*03:02 | 17180 | 6054 | 23711 | 3272 | 5195 | 4073 | 100000 | 5035 | 286 | 3858 | 2361 | 123 | 104 | 103 |
| DQB1*04:02 | 25407 | 4735 | 27879 | 4469 | 8299 | 5488 | 100000 | 5734 | 610 | 5429 | 10507 | 464 | 391 | 796 |
| DQB1*05:01 | 26455 | 100000 | 100000 | 613 | 11989 | 14907 | 100000 | 2556 | 1126 | 290 | 772 | 2350 | 324 | 341 |
| DQB1*06:02 | 4101 | 20 | 52 | 770 | 14 | 111 | 100000 | 201 | 4517 | 302 | 875 | 4472 | 20189 | 638 |
| DRB1*01:01 | 2919 | 195 | 2003 | 170 | 33 | 431 | 1192 | 3.4 | 130 | 352 | 226 | 4853 | 18234 | 643 |
| DRB1*03:01 | 14923 | 125 | 2824 | 8978 | 100000 | 3336 | 533 | 100000 | 12 | 168 | 104 | 7479 | 11346 | 100000 |
| DRB1*04:01 | 4415 | 256 | 498 | 1093 | 50 | 452 | 763 | 173 | 140 | 138 | 32 | 4361 | 130 | 2376 |
| DRB1*04:05 | 16446 | 829 | 11639 | 19051 | 8337 | 10243 | 874 | 12 | 265 | 58 | 24 | 1188 | 243 | 292 |
| DRB1*07:01 | 6276 | 299 | 5045 | 1121 | 1160 | 1724 | 113 | 49 | 275 | 418 | 1688 | 100000 | 100000 | 253 |
| DRB1*08:02 | 11 | 7 | 253 | 98 | 201 | 359 | 29 | 18 | 176 | 100 | 922 | 5876 | 3524 | 197 |
| DRB1*09:01 | 1555 | 603 | 3962 | 47 | 53 | 168 | 211 | 4.2 | 169 | 31 | 151 | 1792 | 7851 | 390 |
| DRB1*11:01 | 19006 | 470 | 9869 | 8996 | 149 | 4455 | 105 | 5 | 330 | 268 | 1344 | 100000 | 100000 | 120 |
| DRB1*12:01 | 100000 | 100000 | 100000 | 632 | 1774 | 2783 | 484 | 8 | 659 | 1614 | 3815 | 100000 | 100000 | 100000 |
| DRB1*13:02 | 100000 | 801 | 4819 | 19499 | 17630 | 1184 | 13065 | 409 | 321 | 708 | 333 | 9682 | 26314 | 17778 |
| DRB1*15:01 | 4338 | 3015 | 1180 | 607 | 885 | 570 | 730 | 4789 | 882 | 44 | 129 | 4634 | 7298 | 7408 |
| DRB3*01:01 | 100000 | 100000 | 100000 | 13 | 271 | 6070 | 10621 | 439 | 344 | 11 | 7.1 | 869 | 759 | 240 |
| DRB3*02:02 | 21990 | 3505 | 100000 | 471 | 5049 | 100000 | 23884 | 648 | 3845 | 1132 | 79 | 7434 | 3982 | 29731 |
| DRB4*01:01 | 100000 | 0.81 | 33 | 1.2 | 173 | 373 | 32 | 228 | 1245 | 296 | 15 | 1487 | 56 | 90 |
| DRB5*01:01 | 412 | 311 | 4357 | 385 | 14 | 64 | 7.6 | 29 | 230 | 4275 | 6.4 | 227 | 1795 | 1154 |

Table 28b—Binding of the Next 14 of 41 Selected Peptides of the Invention to 25 Representative HLA Class II Molecules TABLE 28b

| Peptide name | SEQ ID NO: | | | | | | | | | | | | | |
|---|---|---|---|---|---|---|---|---|---|---|---|---|---|---|
| | 28 | 29 | 36 | 37 | 38 | 39 | 40 | 45 | 46 | 47 | 48 | 49 | 50 | 61 |
| | 215 | 216 | 217 | 218 | 219 | 220 | 221 | 222 | 223 | 224 | 225 | 226 | 227 | 228 |
| DPB1*02:01 | 395 | 42 | 241 | 3846 | 1028 | 201 | 156 | 2.3 | 52 | 438 | 431 | 3494 | 55 | 13420 |
| DPB1*04:01 | 2619 | 683 | 1238 | 15139 | 3425 | 1642 | 1342 | 5.1 | 62 | 245 | 725 | 1527 | 179 | 7718 |
| DPB1*04:02 | 103 | 59 | 142 | 1084 | 810 | 101 | 705 | 3.2 | 10 | 56 | 29 | 331 | 152 | 2062 |
| DPB1*05:01 | 290 | 8.8 | 40 | 4922 | 2605 | 93 | 951 | 4.3 | 124 | 122 | 6.3 | 1146 | 580 | 100000 |
| DQB1*02:01 | 7 | 239 | 1119 | 15336 | 231 | 11821 | 5.9 | 79 | 435 | 95 | 46 | 1314 | 564 | 7289 |
| DQB1*03:01 | 1077 | 2379 | 17 | 21 | 7.8 | 997 | 959 | 25 | 18 | 251 | 56 | 27 | 1668 | 15 |
| DQB1*03:02 | 2595 | 26619 | 100000 | 100000 | 4576 | 100000 | 2462 | 281 | 5573 | 6859 | 1892 | 3581 | 100000 | 169 |
| DQB1*04:02 | 1356 | 100000 | 17393 | 100000 | 3808 | 100000 | 3104 | 795 | 14308 | 24359 | 2981 | 7281 | 100000 | 534 |
| DQB1*05:01 | 838 | 4061 | 100000 | 14766 | 100000 | 7545 | 6,6 | 232 | 1154 | 229 | 129 | 4396 | 85 | 100000 |
| DQB1*06:02 | 12026 | 743 | 89 | 6101 | 30 | 54 | 8.2 | 8.3 | 41 | 116 | 328 | 2941 | 241 | 2846 |
| DRB1*01:01 | 1114 | 11 | 207 | 1187 | 43 | 24 | 37 | 3.7 | 8.5 | 16 | 21 | 176 | 120 | 22 |
| DRB1*03:01 | 1781 | 4101 | 2.7 | 491 | 2379 | 3040 | 971 | 92 | 20 | 7.3 | 286 | 11457 | 5950 | 100000 |
| DRB1*04:01 | 170 | 2025 | 306 | 1918 | 174 | 312 | 605 | 477 | 7.3 | 236 | 149 | 2328 | 57 | 23 |
| DRB1*04:05 | 870 | 167 | 522 | 3903 | 4217 | 674 | 394 | 108 | 48 | 90 | 137 | 526 | 151 | 4636 |
| DRB1*07:01 | 5113 | 1537 | 44 | 1401 | 140 | 169 | 191 | 6.6 | 30 | 316 | 103 | 412 | 3525 | 4971 |
| DRB1*08:02 | 2228 | 15 | 1.4 | 34 | 7.7 | 33 | 19 | 145 | 65 | 30 | 23 | 234 | 1006 | 89 |
| DRB1*09:01 | 484 | 45 | 417 | 3271 | 62 | 36 | 67 | 2.8 | 13 | 85 | 18 | 111 | 635 | 8.8 |
| DRB1*11:01 | 100000 | 509 | 16 | 382 | 878 | 4.2 | 21 | 492 | 367 | 127 | 6.4 | 829 | 2219 | 12479 |
| DRB1*12:01 | 100000 | 134 | 239 | 4311 | 859 | 17 | 4387 | 35 | 82 | 27 | 254 | 5463 | 68 | 12584 |
| DRB1*13:02 | 15737 | 17187 | 86 | 5620 | 14 | 169 | 1279 | 35 | 69 | 51 | 350 | 11255 | 242 | 23973 |
| DRB1*15:01 | 2068 | 295 | 98 | 845 | 48 | 8.9 | 66 | 7.8 | 4758 | 54 | 58 | 443 | 54 | 4043 |
| DRB3*01:01 | 5 | 486 | 3038 | 8307 | 100000 | 23710 | 800 | 584 | 4474 | 611 | 1204 | 26292 | 487 | 100000 |
| DRB3*02:02 | 2981 | 469 | 339 | 28654 | 1138 | 2336 | 3652 | 188 | 47 | 148 | 742 | 29703 | 177 | 2668 |
| DRB4*01:01 | 9437 | 72 | 8.5 | 558 | 28 | 63 | 56 | 5.4 | 5 | 20 | 39 | 4771 | 7.6 | 3180 |
| DRB5*01:01 | 16508 | 3.6 | 38 | 510 | 50 | 7.5 | 3.8 | 11 | 9.5 | 44 | 163 | 266 | 571 | 59 |

Table 28c—Binding of the Last 134 of the 41 Selected Peptides of the Invention to 25 Representative HLA Class II Molecules TABLE 28c

| | SEQ ID NO: | | | | | | | | | | | | |
|---|---|---|---|---|---|---|---|---|---|---|---|---|---|
| | 62 | 63 | 64 | 65 | 66 | 67 | 68 | 69 | 70 | 71 | 72 | 73 | 113 |
| Peptide name | 229 | 230 | 231 | 232 | 233 | 234 | 235 | 236 | 237 | 238 | 239 | 240 | 241 (LJI) |
| DPB1*02:01 | 1166 | 1963 | 37 | 195 | 130 | 531 | 2213 | 2792 | 30 | 15 | 247 | 4.5 | 753 |
| DPB1*04:01 | 7608 | 9281 | 203 | 4023 | 1744 | 743 | 17658 | 11052 | 446 | 146 | 2358 | 325 | 2032 |
| DPB1*04:02 | 227 | 618 | 40 | 697 | 35 | 73 | 1035 | 7748 | 234 | 36 | 272 | 34 | 1136 |
| DPB1*05:01 | 16 | 773 | 8.2 | 82 | 125 | 452 | 14 | 1621 | 3.3 | 9.8 | 3.1 | 1.1 | 43 |
| DQB112:01 | 776 | 1067 | 1158 | 9130 | 17912 | 13382 | 354 | 551 | 476 | 89 | 139 | 3057 | 525 |
| DQ8113:01 | 1.1 | 2.3 | 3 | 7.9 | 44 | 31 | 4 | 8.9 | 33 | 44 | 7.4 | 205 | 6.2 |
| DQB113:02 | 1778 | 2620 | 264 | 9370 | 585 | 1157 | 945 | 188 | 705 | 130 | 274 | 4686 | 942 |
| DQB114:02 | 606 | 1457 | 206 | 9549 | 704 | 1936 | 155 | 595 | 3356 | 438 | 1618 | 25620 | 1607 |
| DQB1*05:01 | 42 | 1467 | 581 | 2623 | 1795 | 814 | 1305 | 12658 | 249 | 200 | 550 | 25025 | 100000 |
| DQB116:02 | 3.5 | 58 | 2.6 | 5.2 | 14 | 9.7 | 24 | 7.6 | 36 | 76 | 38 | 54 | 10 |
| DRB111:01 | 1.1 | 0.53 | 2.2 | 16 | 7.5 | 36 | 5.6 | 41 | 2.6 | 2 | 5.2 | 13 | 14 |
| DRB113:01 | 634 | 21892 | 10856 | 35 | 627 | 971 | 516 | 7461 | 2052 | 6159 | 47 | 238 | 6615 |
| DRB114:01 | 353 | 838 | 2178 | 5229 | 2505 | 703 | 499 | 9514 | 5910 | 6309 | 5187 | 878 | 4325 |
| DRB1*04:05 | 294 | 162 | 81 | 115 | 82 | 66 | 7.1 | 327 | 4.2 | 68 | 205 | 53 | 43 |
| DRB1*07:01 | 79 | 33 | 15 | 645 | 18 | 108 | 31 | 79 | 9.1 | 55 | 52 | 342 | 18 |
| DRB1*08:02 | 3.5 | 3.4 | 1.6 | 3.7 | 202 | 373 | 3.2 | 1959 | 36 | 4 | 24 | 3 | 15 |
| DRB1*09:01 | 4.6 | 1.6 | 2.3 | 23 | 8.9 | 66 | 11 | 216 | 1.5 | 4.9 | 5.8 | 31 | 7.6 |
| DRB1*11:01 | 292 | 378 | 7.6 | 45 | 96 | 360 | 42 | 7488 | 204 | 4.3 | 9.9 | 19 | 298 |
| DRB1*12:01 | 87 | 831 | 2958 | 380 | 66 | 231 | 3978 | 100000 | 4793 | 728 | 156 | 146 | 6564 |
| DRB1*13:02 | 136 | 1149 | 2764 | 18450 | 7.4 | 110 | 329 | 952 | 4 | 301 | 70 | 2572 | 344 |
| DRB11.5:01 | 2 | 134 | 458 | 12 | 31 | 47 | 29 | 5548 | 5188 | 76 | 22 | 17 | 158 |
| DRB311:01 | 8905 | 100000 | 207 | 3426 | 178 | 4980 | 2172 | 19114 | 201 | 3737 | 14090 | 100000 | 100000 |
| DRB312:02 | 273 | 192 | 13 | 833 | 71 | 3870 | 8.2 | 6.3 | 1 | 43 | 1002 | 13595 | 8.5 |
| DR8411:01 | 44 | 182 | 630 | 65 | 104 | 22 | 69 | 3013 | 9.9 | 458 | 47 | 5.1 | 80 |
| DRB511:01 | 5.7 | 1.8 | 2.1 | 19 | 27 | 209 | 6.2 | 18 | 1.8 | 3.3 | 16 | 4.7 | 31 |

Table 29—Binding of 12 Preferred Peptides of WO2010/089554 to 25 Representative HLA Class II Molecules

TABLE 29

| | SEQ ID NO: | | | | | | | | | | | |
|---|---|---|---|---|---|---|---|---|---|---|---|---|
| | 234 | 235 | 236 | 237 | 238 | 239 | 240 | 241 | 242 | 243 | 244 | 245 |
| Peptide name | 134 | 135 | 136 | 137 | 138 | 139 | 140 | 141 | 142 | 143 | 144 | 145 |
| DPB1*02:01 | 100000 | 100000 | 7260 | 14 | 173 | 1530 | 31 | 1538 | 5.4 | 5.4 | 189 | 632 |
| DPB1*04:01 | 100000 | 100000 | 100000 | 67 | 41 | 2042 | 21 | 916 | 3.6 | 2,3 | 60 | 659 |
| DPB1*04:02 | 100000 | 100000 | 100000 | 1.8 | 1 | 374 | 595 | 100000 | 14 | 11 | 555 | 2647 |
| DPB1*05:01 | 869 | 100000 | 356 | 1134 | 4.1 | 637 | 107 | 9269 | 63 | 77 | 2389 | 3644 |
| DQB1*02:01 | 24901 | 100000 | 26254 | 34 | 713 | 690 | 719 | 1575 | 905 | 893 | 3905 | 9247 |
| DQB1*03:01 | 7.4 | 1073 | 607 | 11 | 79 | 415 | 18 | 196 | 20 | 17 | 165 | 195 |
| DQB1*03:02 | 10057 | 100000 | 27234 | 199 | 1053 | 539 | 9620 | 100000 | 15082 | 5622 | 10339 | 100000 |
| DQB1*04:02 | 16502 | 100000 | 100000 | 62 | 1378 | 247 | 4848 | 100000 | 6596 | 10610 | 100000 | 100000 |
| DQB1*05:01 | 26748 | 100000 | 29500 | 16237 | 100000 | 100000 | 8027 | 5295 | 4517 | 4914 | 7463 | 8136 |
| DQB1*06:02 | 137 | 6478 | 11158 | 100000 | 34 | 2081 | 2697 | 100000 | 453 | 1375 | 29857 | 100000 |
| DRB1*01:01 | 1193 | 88 | 1329 | 11 | 55 | 5558 | 6.2 | 660 | 5.1 | 5.8 | 306 | 616 |
| DRB1*03:01 | 100000 | 100000 | 88 | 4996 | 2.5 | 282 | 229 | 21431 | 145 | 99 | 4380 | 100000 |
| DRB1*04:01 | 2601 | 90 | 589 | 16 | 26 | 77 | 7,8 | 2477 | 15 | 12 | 2358 | 4830 |
| DRB1*04:05 | 1831 | 12 | 235 | 25 | 386 | 1026 | 185 | 911 | 7.8 | 9.3 | 1661 | 3717 |
| DRB1*07:01 | 100000 | 100000 | 23849 | 94 | 99 | 8753 | 74 | 8681 | 25 | 31 | 4824 | 100000 |
| DRB1*08:02 | 16163 | 3212 | 221 | 4231 | 123 | 180 | 582 | 204 | 82 | 651 | 768 | 162 |
| DRB1*09:01 | 515 | 525 | 1282 | 6.4 | 7.9 | 367 | 5.5 | 171 | 2.9 | 1.7 | 122 | 348 |
| DRB1*11:01 | 793 | 18197 | 470 | 10100 | 364 | 5705 | 1199 | 20265 | 1163 | 2517 | 4883 | 406 |
| DRB1*12:01 | 100000 | 100000 | 100000 | 7091 | 56 | 1614 | 4374 | 1184 | 5488 | 7186 | 1301 | 627 |
| DRB1*13:02 | 100000 | 100000 | 2778 | 100000 | 576 | 19897 | 284 | 28034 | 247 | 255 | 14331 | 100000 |
| DRB1*15:01 | 100000 | 100000 | 36 | 2015 | 172 | 15809 | 16 | 2294 | 4.5 | 2.6 | 1090 | 3599 |
| DRB3*01:01 | 100000 | 100000 | 67 | 27 | 490 | 5438 | 38 | 1796 | 33 | 24 | 1971 | 11846 |
| DRB3*02:02 | 17803 | 100000 | 28 | 28 | 34 | 1388 | 368 | 5466 | 132 | 196 | 8142 | 100000 |
| DRB4*01:01 | 100000 | 24532 | 5270 | 17634 | 5.1 | 169 | 5.2 | 4.3 | 2 | 1.3 | 4 | 4.6 |
| DRB5*01:01 | 379 | 4816 | 118 | 79 | 31 | 1096 | 0.8 | 580 | 4.6 | 2.1 | 183 | 669 |

Table 30—Measured and Predicted Binding Coverage of 41 Selected Peptides of the Invention and of 12 Preferred Peptides of WO2010/089554

TABLE 30

| SEQ ID NO: | Peptide name | Predicted HLA coverage 25 alleles | Measured binding coverage 25 alleles | Predicted HLA coverage 77 alleles |
|---|---|---|---|---|
| 1 | 201 | 35% | 47% | 35% |
| 2 | 202 | 0% | 84% | 0% |
| 3 | 203 | 35% | 71% | 35% |
| 4 | 204 | 26% | 78% | 26% |
| 5 | 205 | 40% | 88% | 40% |
| 6 | 206 | 0% | 70% | 0% |
| 7 | 207 | 61% | 71% | 80% |
| 8 | 208 | 45% | 93% | 68% |
| 9 | 209 | 35% | 85% | 35% |
| 10 | 210 | 0% | 92% | 0% |
| 11 | 211 | 43% | 90% | 45% |
| 12 | 212 | 0% | 40% | 0% |
| 13 | 213 | 0% | 58% | 0% |
| 27 | 214 | 0% | 81% | 0% |
| 28 | 215 | 34% | 74% | 34% |
| 29 | 216 | 64% | 92% | 70% |
| 36 | 217 | 29% | 98% | 61% |
| 37 | 218 | 0% | 39% | 0% |
| 38 | 219 | 35% | 91% | 35% |
| 39 | 220 | 25% | 96% | 28% |
| 40 | 221 | 25% | 89% | 33% |
| 45 | 222 | 98% | 100% | 100% |
| 46 | 223 | 81% | 99% | 88% |
| 47 | 224 | 78% | 99% | 89% |
| 48 | 225 | 78% | 98% | 87% |
| 49 | 226 | 35% | 57% | 35% |
| 50 | 227 | 81% | 97% | 88% |
| 61 | 228 | 40% | 69% | 40% |
| 62 | 229 | 91% | 98% | 99% |
| 63 | 230 | 78% | 92% | 86% |
| 64 | 231 | 98% | 99% | 99% |
| 65 | 232 | 78% | 93% | 79% |
| 66 | 233 | 98% | 99% | 100% |
| 67 | 234 | 80% | 94% | 90% |
| 68 | 235 | 87% | 96% | 93% |
| 69 | 236 | 47% | 85% | 47% |
| 70 | 237 | 96% | 99% | 97% |
| 71 | 238 | 96% | 99% | 99% |
| 72 | 239 | 73% | 99% | 76% |
| 73 | 240 | 99% | 97% | 100% |
| 113 | 241 (LJI 1) | 63% | 95% | 71% |
| 234 | 134 | 35% | 47% | 35% |
| 235 | 135 | 0% | 19% | 0% |
| 236 | 136 | 53% | 76% | 63% |
| 237 | 137 | 69% | 98% | 74% |
| 238 | 138 | 90% | 99% | 97% |
| 239 | 139 | 47% | 62% | 47% |
| 240 | 140 | 99% | 99% | 100% |
| 241 | 141 | 0% | 67% | 0% |
| 242 | 142 | 99% | 100% | 100% |
| 243 | 143 | 99% | 99% | 100% |
| 244 | 144 | 0% | 85% | 0% |
| 245 | 145 | 42% | 64% | 42% |

Example 12

Description of Predicted Peptide Binding Valency and Donor Response Valency

This example describes how peptide combinations (peptide mixes) can be compared with respect to:

A. Predicted average number of binding peptides per individual in a population (also herein named "predicted Peptide binding valency"). The potential binding is based on in silico HLA class II binding predictions, in the present example performed as described in Example 4. However, other suitable methods for prediction of HLA Class II binding could also be used. The population in this example is simulated by generating virtual patients (VPs) using a selection of HLA Class II alleles and corresponding frequencies in a real human population. For the present example, the alleles and corresponding frequencies listed in Table 10 and/or Table 11 of Example 2 were used, and thus the population of virtual patients was an estimate of a world-wide population.

B. Actual average number of binding peptides per individual in a population (also herein named "actual peptide binding valency"). The binding is based on data from in vitro HLA class II binding assays using a selection of HLA class II alleles, in the present example performed as described in Example 11 and using the 25 alleles listed in Table 28a. However, other suitable methods for measuring HLA Class II binding and other sets of HLA class II alleles could also be used. The population in this example is simulated by generating VPs using the selection of HLA Class II alleles of Table 28a, and corresponding frequencies listed in Table 10 and/or Table 11 of Example 2 for generating VPs. The selection of alleles of Table 28a have previously been described as representing the majority (50-75%) of the HLA class II genes expressed worldwide for all four different HLA class II loci (Greenbaum et al. 2011), thus the population of virtual patients generated was a further estimate of a world-wide population.

C. Average number of peptides that gives a T cell response per individual in a donor cohort (also herein called "donor response valency"), which in the present example is determined by using data of measured in vitro T cell responses towards single peptides in a real cohort of blood donors. Other T cell response data could also be used to calculate the donor response valency. For each donor in the cohort, the number of peptides of a given mix which produced an in vitro T cell response is counted. These numbers are then used to calculate an average of the number of peptides that producing an in vitro T cell response per donor using all donors in the cohort.

D. The fraction of individuals in a population (% of VPs) having HLA Class II alleles potentially being able to bind a given number of peptides (0, 1, 2, 3, 4, 5 or 6 peptides) present in a peptide combination wherein the potential binding is based on in silico HLA class II binding predictions. The fraction of VPs predicted to bind at least one peptide of a given mix is called "Predicted HLA coverage" when used herein. A related parameter is the fraction of VPs which have at least one HLA-DRB1 allele predicted to bind a peptide if a given mix. The latter parameter is of relevance, since the DRB1 locus the most characterized of the loci.

E. The fraction of individuals in a donor cohort (% of patients) having a T cell response to a given number of peptides present in a peptide combination (such as 0, 1, 2, 3, 4, 5 or 6 peptides in a peptide mix comprising 6 peptides). Peptide mixes can further be described by calculating the fraction of donors having a T cell response to at least any given number of peptides in a combination (such as at least 1, 2, 3, 4, 5 or 6 peptides in a peptide mix comprising 6 peptides). "Donor response fraction" as used herein is the fraction of donors having a T cell response to at least 1 peptide in a mix. Another parameter which can be useful for evaluating peptide mixes, is the fraction of donors which did not respond to any peptides in a given mix (calculated by subtracting donor response fraction from 100%). It is envisaged that is favourable to decrease the fraction of non-responding donors, since it is favourable to use a peptide combination when used as a Predicted Peptide Binding Valency For the calculation of the predicted peptide binding valency of peptide combinations, a system was created that generated a theoretical in silico population of 10000 virtual patients (VP). Each individual VP was generated by using the 77 allele frequencies from Table 10 and 11 (see Example 2) as probabilities at each locus to have this particular allele. For the DRB1 locus, there was full knowledge of allele distribution in a world-wide population, and the allele frequencies therefore sum up to 1.0 (see Example 2). However, for the DRB 3, 4 and 5 loci, not all individuals in a world-wide population express an allele at the given locus, and for the DQ and DP loci only in-complete knowledge of the allele distributions exist, thus the used allele frequencies for these loci will not sum up to one. Consequently, some of the generated VPs lacked one or both alleles at these loci. As a result the calculated theoretical population coverage was under-estimated, but will serves as a good guidance.

The VPs generated as described above were used to calculate the fraction of VPs which had HLA alleles predicted to bind a given number of peptides (ranging from 0 to the total number of peptides in a peptide mix) using the prediction method and affinity thresholds (300 nM and 30% fractile) described in Example 2. Using such fractions, the predicted average number of peptides that a VP in the population would bind (i.e. the predicted peptide binding valency) was calculated as a weighted sum, wherein each peptide number was weighted by the fraction of VPs predicted to bind to the given peptide number.

Predicted peptide binding valency may be visualized in diagrams showing the fraction of the VPs which have HLAs predicted to bind to either 0, 1, 2, 3, 4, or up to the total number of peptides in the peptide mix. Such diagrams may further visualize the cumulative curve, which is generated by calculating the fraction of donors predicted to bind at least y, wherein y is the number of peptides, and y is decreased incrementally starting from the total number of peptides in a peptide mix. Thus, when generating a cumulative curve for a mix comprising 6 peptides, the fraction of donors predicted to bind at least 6 peptides is a first point in the curve, the fraction of donors predicted to bind at least 5 peptides is a second point in a curve, and so forth. The area under the cumulative curve in such a diagram may then further be used to describe the valency of a peptide combination, and is denoted "AUC".

It is envisaged that it is preferable to have a large fraction of VPs which are predicted to bind a high number of peptides. If 100% of the VPs are predicted to bind all peptides of a peptide combination, the AUC would be 1, which is the maximum. Similarly, if a large fraction of VPs are predicted to bind all peptides, (or a higher number of peptides), the AUC will be close to 1. Thus, an AUC of 0.98 reflects that a high number of the VPs bind a high number of peptides.

An example is shown in FIGS. 10a and 10b, which relates to Mix 2610 (consisting of peptides 207, 211, 238, 239 and 241). This distribution of the fractions of VPs predicted to bind to a given number of peptides is shown for Mix2610 in reverse order in FIG. 10a. In FIG. 10a is also visualized the cumulative curve, i.e. the fraction of donors predicted to bind all peptides of this combination (6 peptides), then at least 5 peptides (i.e. the fraction predicted to potentially react to 5 or 6 peptides), and so forth. It can be seen from FIG. 10a, that there are very few VPs (close to 0%) which are predicted to bind 0 or 1 peptide of mix 2610, and about 90% of the VPs are predicted to bind 4 or less peptides of the mix.

In order to be able to compare combinations of a different number of peptides only the part of the cumulative curve calculated using peptides numbers ranging between 4 to 1 peptides was used as predicted valence AUC. This method for calculation of AUC was further chosen in order to better reflect the donor coverage of a given mix. Using this method for calculating the predicted valence AUC for the cumulated curve shown in FIG. 10b, the predicted valence AUC peptide for mix 2610 was determined to 0.98.

Actual Peptide Binding Valency

For calculation of actual peptide binding valency, a population of peptide combinations, a theoretical in silico population of 10000 virtual patients (VP) were generated. Each individual VP was generated by using the 25 alleles of Table 28 and using the frequencies from Table 10 and 11 (see Example 2) as probabilities at each locus to have this particular allele. The VPs generated used to calculate the fraction of VPs which had HLA alleles measured to bind a given number of peptides (ranging from 0 to the total number of peptides in a peptide mix) using affinity thresholds of 300 nM for determining peptide binding.

The actual peptide binding valency may be visualized in similar diagrams as described above for predicted peptide binding valency. In this case, the fraction of the VP which has HLA alleles that are measured in vitro as binding to either 0, 1, 2, 3, 4, or up to the total number of peptides in the peptide combination is plotted for a combination of 4 or more peptides. Such fractions were further used for calculating the actual peptide binding valency using a weighted sum as described above. The cumulative curve was likewise calculated by using the fraction of VPs which have HLA alleles measured to bind to at least y peptides, wherein y is the number of peptides, and y is decreased incrementally starting from the total number of peptides in a mix. The area under such a curve may be called "actual peptide binding valency AUC". In the present example only the part of the cumulative curve calculated using peptides numbers ranging between 4 to 1 peptides was used to determine actual binding valency AUC.

Donor Response Valency

In addition, a donor response valency was calculated using the measured T cell responses from a number of individual donors. The donor response valency as used herein is calculated based on a measure of the fraction of individuals in a donor cohort that have a T cell response to a given number of peptides in a peptide combination as determined in Example 3. Similarly as described above, the donor response valency was calculated as a weighted sum wherein each peptide number was weighted by the fraction of donors having a T cell response to the given peptide number.

The donor response valency may similarly be visualized in diagrams as described above. In this case, the cumulative curve is calculated by determining the fraction of T cell donors responding to at least y peptides, wherein y is the number of peptides, and y is decreased incrementally starting from the total number of peptides in a mix. The area under the curve of such a cumulative curve is called "donor response valency AUC", however in the present example only the part of the cumulative curve calculated using peptides numbers ranging between 4 to 1 peptides was used to determine donor response valency AUC.

Table 31—Predicted Peptide Binding Valency and Donor Response Valency Including AUC for the Peptide Combinations Tested Table 31 shows AUC for the mixes tested including the reference mixes of WO2010/089554. In addition AUC for further peptide combinations of WO2010/089554 page 66, lines 9 to 18, which were not tested experimentally as peptide combinations.

TABLE 31

| Peptide combination name | Peptide combination size | Predicted HLA coverage | Donor response fraction | Predicted peptide binding Valency AUC | Donor Response Valency AUC |
|---|---|---|---|---|---|
| 005 | 5 | 1 | 0.933 | 0.949 | 0.641 |
| 007 | 7 | 1 | 0.967 | 0.988 | 0.693 |
| 014 | 4 | 1 | 0.933 | 0.847 | 0.569 |
| 015 | 5 | 1 | 0.933 | 0.937 | 0.586 |
| 025 | 5 | 1 | 0.9 | 0.9 | 0.497 |
| 034 | 4 | 1 | 0.967 | 0.811 | 0.502 |
| 035 | 5 | 1 | 0.967 | 0.919 | 0.511 |
| 037 | 7 | 1 | 0.967 | 0.996 | 0.683 |
| 085 | 5 | 1 | 0.933 | 0.976 | 0.633 |
| 097 | 7 | 1 | 0.867 | 0.989 | 0.626 |
| 204 | 4 | 1 | 0.933 | 0.907 | 0.55 |
| 205 | 5 | 1 | 0.933 | 0.983 | 0.65 |
| 207 | 7 | 1 | 0.933 | 0.998 | 0.786 |
| 215 | 5 | 1 | 0.9 | 0.978 | 0.681 |
| 225 | 5 | 1 | 0.9 | 0.969 | 0.674 |
| 405 | 5 | 0.782 | 0.733 | 0.359 | 0.361 |
| 505 | 5 | 0.999 | 1 | 0.829 | 0.602 |
| 605 | 5 | 0.352 | 0.6 | 0.049 | 0.319 |
| 607 | 7 | 0.352 | 0.733 | 0.303 | 0.387 |
| 705 | 5 | 1 | 0.793 | 1 | 0.42 |
| 715 | 5 | 0.994 | 0.9 | 0.685 | 0.552 |
| 725 | 5 | 1 | 0.967 | 0.922 | 0.564 |
| 735 | 5 | 1 | 0.933 | 0.683 | 0.624 |
| 745 | 5 | 1 | 0.9 | 0.833 | 0.595 |
| 755 | 5 | 1 | 0.867 | 1 | 0.677 |
| 765 | 5 | 1 | 0.828 | 1 | 0.587 |
| 775 | 5 | 0.999 | 0.867 | 0.773 | 0.595 |
| 785 | 5 | 1 | 0.933 | 0.865 | 0.622 |
| 807 | 7 | 0.999 | 0.727 | 0.757 | 0.438 |
| 814 | 4 | 0.999 | 0.682 | 0.491 | 0.242 |
| 825 | 5 | 0.999 | 0.682 | 0.609 | 0.331 |
| 1005 | 5 | 1 | 0.933 | 0.945 | 0.509 |
| 1015 | 5 | 0.994 | 0.933 | 0.838 | 0.681 |
| 1025 | 5 | 0.998 | 0.9 | 0.953 | 0.686 |
| 1055 | 5 | 0.997 | 0.867 | 0.485 | 0.438 |
| 1065 | 5 | 1 | 0.867 | 0.874 | 0.517 |
| 2401 | 4 | 0.997 | 0.8 | 0.901 | 0.551 |
| 2402 | 4 | 0.997 | 0.833 | 0.848 | 0.519 |
| 2403 | 4 | 0.998 | 0.833 | 0.849 | 0.443 |
| 2404 | 4 | 1 | 0.8 | 0.842 | 0.429 |
| 2505 | 5 | 0.997 | 0.833 | 0.937 | 0.66 |
| 2506 | 5 | 0.999 | 0.867 | 0.903 | 0.607 |
| 2507 | 5 | 0.999 | 0.833 | 0.905 | 0.553 |
| 2508 | 5 | 1 | 0.833 | 0.906 | 0.536 |
| 2609 | 6 | 0.999 | 0.867 | 0.961 | 0.695 |
| 2610 | 6 | 1 | 0.867 | 0.979 | 0.641 |
| 2611 | 6 | 1 | 0.833 | 0.979 | 0.594 |
| 2612 | 6 | 1 | 0.833 | 0.952 | 0.553 |
| 2713 | 7 | 0.999 | 0.867 | 0.973 | 0.7 |
| 2714 | 7 | 1 | 0.867 | 0.989 | 0.653 |
| 2715 | 7 | 1 | 0.833 | 0.989 | 0.606 |
| 2716 | 7 | 1 | 0.867 | 0.979 | 0.648 |
| 3502 | 5 | 1 | 0.933 | 0.993 | 0.689 |
| Ref 1 | 8 | 1 | 0.727 | 0.908 | 0.484 |
| Ref 2 | 7 | 1 | 0.727 | 0.901 | 0.458 |
| Ref 3 | 6 | 0.999 | 0.682 | 0.611 | 0.36 |
| Ref 4 | 5 | 0.999 | 0.682 | 0.49 | 0.298 |
| Ref 5 | 5 | 0.999 | 0.682 | 0.615 | 0.337 |
| Ref 6 | 4 | 0.999 | 0.682 | 0.496 | 0.265 |
| Ref 7 | 6 | 1 | 0.682 | 0.833 | 0.415 |
| Ref 8 | 4 | 0.999 | 0.682 | 0.496 | 0.242 |
| Ref 9 | 5 | 1 | 0.682 | 0.838 | 0.393 |
| Ref 10 | 4 | 1 | 0.682 | 0.795 | 0.324 |

In the table above, Ref 1 consists of the peptides of SEQ ID NOs: 234, 235, 236, 237, 238, 240, 241 and 239. Ref 2 consists of the peptides of SEQ ID NOs: 234, 235, 236, 237, 238, 240 and 241. Ref 3 consists of the peptides of SEQ ID NOs: 234, 235, 236, 240, 241 and 239. Ref 4 consists of the peptides of SEQ ID NOs: 234, 235, 236, 240 and 241. Ref 5 consists of the peptides of SEQ ID NOs: 234, 235, 236, 240 and 239. Ref 6 consists of the peptides of SEQ ID NOs: 234, 235, 236 and 240. Ref 7 consists of the peptides of SEQ ID NOs: 234, 236, 238, 240, 241 and 239. Ref 8 consists of the peptides of SEQ ID NOs: 234, 236, 240 and 241. Ref 9 consists of the peptides of SEQ ID NOs: 234, 236, 238, 240 and 239. Ref 10 consists of the peptides of SEQ ID NOs: 234, 236, 238 and 240. Other mixes of reference peptides include mix 807 consisting of SEQ ID NOs: 234, 235, 236, 237, 240, 241 and 239, mix 814 (identical to Ref 8 above), and mix 825 consisting of SEQ ID NOs: 234, 236, 239, 240, and 241.

The data show that indeed a much higher AUC is obtained for the mixes of the invention assembled by the method disclosed herein compared to the reference peptide combinations of WO2010/089554 if the number of peptides of the respective peptide combinations are taken into consideration. Accordingly the four peptide combinations 2401, 2402, 014, 034 and 204 are seen to show superior AUC compared to the reference peptide combinations Ref 6, Ref 8, Ref 10 and 814. The five peptide combinations 2505, 2506, 2507, 2508, 005, 015, 035, 085, 205, 215, 225, 505, 715, 725, 735, 745, 755, 765, 775, 785, 1005, 1015, 1025, 1055 and 1065 are seen to show superior AUC compared to the reference peptide combinations Ref 4, Ref 5, Ref 9 and 825. The six peptide combinations 2609, 2610, 2611 and 2612 are seen to show superior AUC compared to the reference peptide combination Ref 7. The seven peptide combinations 2713, 2714, 2715, 2716, 007, 037, 097 and 207 are seen to show superior AUC compared to the reference peptide combinations Ref 2 and 807.

In summary, the peptide combinations assembled according to the invention, show a consistently superior peptide valency (AUC) compared to the previously proposed reference peptide combinations for treating grass allergics. The effect of this is seen e.g. in Example 9, where the peptide combinations of the invention show significantly higher T cell reactivity at low concentrations compared to the reference peptide combination 825.

Example 13

First Choice Peptides and Combinations Thereof

This example lists the "first choice" peptides within the 42 selected high responder peptides. These peptides seem to be present in the best peptide combinations and appear to possess suitable pharmaceutical properties, such as satisfactory solubility in aqueous solution in the pH range of 4 to 9 and to be manufacturable and/or to possess superior immunological properties and or to be highly cross reactive to other relevant grass species as mentioned in example). In some cases they will need modification or solubility aid, such as special solubilisation procedure or chemical stabilisation to be useful in a pharmaceutical preparation.

Accordingly superior peptides of the invention can be found in Table 32 below. Variants of those peptides are also considered superior.

Table 32—List of First Choice Peptides

Table 32 contains a list of first choice peptides. Peptides marked with "*" are considered to have some solubility or manufacturability issues

TABLE 32

| SEQ ID NO: | Peptide Name | Allergen group | pI | Sequence shown in Table: |
|---|---|---|---|---|
| 4 | 204 | 1 | 3.84 | 2 |
| 7 | 207 | 1 | 10.04 | 2 |
| 8 | 208* | 1 | 6.75 | 2 |
| 11 | 211 | 1 | 10.08 | 2 |
| 45 | 222 | 4 | 9.56 | 5 |
| 64 | 231* | 5 | 9.63 | 6 |
| 66 | 233 | 5 | 4.44 | 6 |
| 68 | 235 | 5 | 6.99 | 6 |
| 71 | 238 | 5 | 6.94 | 6 |
| 72 | 239 | 5 | 9.63 | 6 |
| 73 | 240* | 5 | 9.56 | 6 |
| 113 | 241 | 5 | 10.10 | 6 |

Based on the first choice peptides, superior mixes with regard to T cell reactivity and peptide valency may be assembled even without the use of the computer implemented method. For instance peptide combinations fulfilling the following criteria will possess such superior properties:
Containing at least one of the peptides with SEQ ID NOs: 8, 11, 68, 72 or 113; or a variant thereof.
Containing at least one of the peptides with SEQ ID NOs: 7, 64, 66, 71 or 73; or a variant thereof.
Containing at least a total of three of the peptides of Table 32; or a variant thereof.
Containing at least one of the peptides with SEQ ID NOs: 1-13 (Table 2); or a variant thereof.
Containing at least one of the peptides with SEQ ID NOs: 61-73; or a variant thereof; and
Containing at least four peptides selected within the 42 selected peptides; or variants thereof.

The preferred superior peptide combinations preferably contains no more than 4, 5 or 6 peptides selected within the 42 selected peptides; or variants thereof. The 4, 5 or 6 peptides are preferably selected only within the first choice peptides. Preferably the peptide combinations contain no other peptides having T cell reactivity as determined by the experiments described in Example 3.

Examples of such first choice peptide combinations can be found in Table 33. Preferably the peptide combinations contain no other peptides having a T cell reactivity above the shreshold values in the experiments described in Example 3.

Table 33—List of First Choice Peptide Combinations

This table contains examples of first choice peptide combinations Peptides marked with "*" are considered to have some solubility or manufacturability issues.

TABLE 33

| SEQ ID NO | Peptide Name | 2506 | 2610 | 3502 | 4502 | 4504 |
|---|---|---|---|---|---|---|
| 4 | 204 | | | | | |
| 7 | 207 | 1 | 1 | | | |
| 8 | 208* | | | 1 | | 1 |
| 11 | 211 | 1 | 1 | | 1 | 1 |
| 45 | 222 | | 1 | 1 | | |
| 64 | 231* | | | | | |
| 66 | 233 | | | | | |
| 68 | 235 | | | 1 | 1 | |
| 71 | 238 | 1 | 1 | 1 | 1 | 1 |
| 72 | 239 | 1 | 1 | | 1 | 1 |
| 73 | 240* | | | 1 | 1 | 1 |
| 113 | 241 | 1 | 1 | | | |

Example 14

Modified Peptides

This example describes modifications of parent peptides as defined herein, or of any one of the first, second, third, fourth, fifth, sixth peptide or peptides a) through h) as defined herein to improve the aqueous solubility, in particular to increase the solubility in an aqueous solution having pH in a physiologically acceptable range, e.g. from 6 to 8. Solubility is closely related to the ratio between hydrophilic and hydrophobic amino acid residues and the net charge state of the peptide. Peptides have zero net charge at pH=pI, and would be expected to show the lowest solubility at this pH. Also peptide stability and manufacturability may be affected by modifying the peptide sequences.

The following peptide modifications are suggested:

Modifications of 238: Although this peptide has a reasonable number of hydrophilic AAs, it has zero charge at pH ~5-9 so is likely to benefit from an optimization.

Table 34a: Examples of Modifications of Peptide 238

TABLE 34a

| SEQ ID NO: | Peptide Name | Amino acid sequence | Modification | Peptide length | pI | Charge at pH 7 |
|---|---|---|---|---|---|---|
| 71 | 238 | STGGAYESYKFIPALEAAVK | Native peptide | 20-mer | 6.9 | 0 |
| 224 | 238_1 | KASTGGAYESYKFIPALEAAVK | Allergen-encoded KA added to N-terminus | 22-mer | 9.4 | +1 |
| 225 | 238_2 | KASTGGAYESYKFIPALEAAVK-amide | Allergen-encoded KA added to N-terminus + C-term amidation | 22-mer | 9.9 | +2 |
| 308 | 238_3 | RKASTGGAYESYKFIPALEAAVK | Non-encoded R + allergen-encoded KA added to N-terminus | 23-mer | 9.9 | +2 |

TABLE 34a-continued

| SEQ ID NO: | Peptide Name | Amino acid sequence | Modification | Peptide length | pI | Charge at pH 7 |
|---|---|---|---|---|---|---|
| 309 | 238_4 | RKASTGGAYESYKFIPALEAAVK-amide | Non-encoded R + allergen-encoded KA added to N-terminus + C-term amidation | 23-mer | 10.2 | +3 |

Modifications of 240: This peptide may not need to be engineered more hydrophilic. However, below in Table 34b are some suggestions.

Table 34b: Examples of Modifications of Peptide 240.

TABLE 34b

| SEQ ID NO: | Peptide Name | Amino acid sequence | Modification | Peptide length | pI | Charge at pH 7 |
|---|---|---|---|---|---|---|
| 73 | 240 | APEVKYTVFETALKKAITAM | Native peptide Methionines are very prone to oxidations | 20-mer | 9.6 | +1 |
| 207 | 240_1 | APEVKYTVFETALKKAITAM-amide | C-term amidation | 20-mer | 10.1 | +2 |
| 310 | 240_2 | RAPEVKYTVFETALKKAITAM | Non-encoded R added to N-terminus | 21-mer | 10.0 | +2 |
| 311 | 240_3 | RAPEVKYTVFETALKKAITAM-amide | Non-encoded R added to N-terminus + C-term amidation | 21-mer | 10.4 | +3 |
| 312 | 240_4 | RAPEVKYTVFETALKKAITAMR | Non-encoded R added to both N- and C-termini | 22-mer | 10.4 | +3 |
| 313 | 240_5 | RAPEVKYTVFETALKKAITAMR-amide | Non-encoded R added to both N- and C-termini + C-term amidation | 22-mer | 10.9 | +4 |

Modification of 208: Although this peptide has a reasonable number of hydrophilic AA, it has zero charge at pH ~5-9 so is likely to benefit from an optimization.

Table 34c: Examples of Modifications of Peptide 208

TABLE 34c

| SEQ ID NO: | Peptide Name | Amino acid sequence | Modification | Peptide length | pI | Charge at pH 7 |
|---|---|---|---|---|---|---|
| 8 | 208 | KGSNPNYLALLVKYVNGDGD | Native peptide (NB DG risk of isoAsp) (NB NG risk of isoAsp) | 20-mer | 6.8 | 0 |
| 201 | 208_1 | KGSNPNYLALLVKYVNGDGD-amide | C-term amidation | 20-mer | 9.5 | +1 |
| 314 | 208_2 | RKGSNPNYLALLVKYVNGDGD | Non-encoded R added to N-terminus | 21-mer | 9.5 | +1 |
| 202 | 208_3 | RKGSNPNYLALLVKYVNGDGR | Non-encoded R added to both N- and C-termini | 22-mer | 9.9 | +2 |

TABLE 34c-continued

| SEQ ID NO: | Peptide Name | Amino acid sequence | Modification | Peptide length | pI | Charge at pH 7 |
|---|---|---|---|---|---|---|
| 315 | 208_4 | RKGSNPNYLALLVKYVNGDGDR-amide | Non-encoded R added to both N- and C-termini + C-term amidation | 22-mer | 10.3 | +3 |
| 316 | 208_5 | Acetyl-EKGSNPNYLALLVKYVNGDGD | Allergen-encoded E added to the N-terminus + N-terminal acetylation | 21-mer | 3.7 | −2 |

Modification of 211: Although this peptide has a reasonable number of hydrophilic AA, it could potentially benefit for some additional charge at pH 5-8.

Table 34d: Examples of Modifications of Peptide 211.

TABLE 34d

| SEQ ID NO: | Peptide Name | Amino acid sequence | Modification | Peptide length | pI | Charge at pH 7 |
|---|---|---|---|---|---|---|
| 11 | 211 | WGAIWRIDTPDKLTGPFTVR | Native peptide | 20-mer | 10.1 | +1 |
| 216 | 211_1 | WGAIWRIDTPDKLTGPFTVR-amide | C-terminal amidation | 20-mer | 11.3 | +2 |
| 317 | 211_2 | RWGAIWRIDTPDKLTGPFTVR | Non-encoded R added to N-terminus | 21-mer | 11.2 | +2 |
| 221 | 211_3 | RWGAIWRIDTPDKLTGPFTVR-amide | Non-encoded R added to N-terminus + C-term amidation | 21-mer | 12.1 | +3 |
| 318 | 211_4 | RWGAIWRIDTPDKLTGPFTVRR | Non-encoded R added to both N- and C-termi | 22-mer | 12.0 | +3 |
| 319 | 211_5 | RWGAIWRIDTPDKLTGPFTVRR-amide | Non-encoded R added to both N- and C-termini + C-term amidation | 22-mer | 12.4 | +4 |

Modification of 207: This peptide already looks incredibly hydrophilic, no optimizations are deemed necessary except the serine for cysteine replacement introduced from the outset.

Table 34e: Sequence of Peptide 207, Wherein a Cysteine of the Sequence of Phl p 1 has been Replaced by Serine.

TABLE 34e

| SEQ ID NO: | Peptide Name | Amino acid sequence | Modification | Peptide length | pI | Charge at pH 7 |
|---|---|---|---|---|---|---|
| 7 | 207 | AGELELQFRRVKSKYPEGTK | Native peptide (C13S substitution) | 20-mer | 10.4 | +3 |

Modification of 217: This peptide does probably not need to be engineered more hydrophilic. However, below are some suggestions.

Table 34f: Examples of Modifications of Peptide 217

TABLE 34f

| SEQ ID NO: | Peptide Name | Amino acid sequence | Modification | Peptide length | pI | Charge at pH 7 |
|---|---|---|---|---|---|---|
| 36 | 217 | GSDPKKLVLNIKYTRPGDSL | Native peptide | 20-mer | 10.0 | +2 |
| 320 | 217_1 | KGSDPKKLVLNIKYTRPGDSL | Allergen-encoded K added to N-terminus | 21-mer | 10.3 | +3 |
| 321 | 217_2 | GSDPKKLVLNIKYTRPGDSL-amide | C-terminal amidation | 20-mer | 10.4 | +3 |
| 322 | 217_3 | KGSDPKKLVLNIKYTRPGDSL-amide | Allergen-encoded K added to N-terminus + C-term amidation | | 10.6 | +4 |

Modification of 233: Although this peptide has a reasonable number of hydrophilic AAs, it has a low pI and has low charge in both low pH and at physiological pH—so optimization would probably be beneficial.

Table 34a: Examples of Modifications of Peptide 233

TABLE 34g

| SEQ ID NO: | Peptide Name | Amino acid sequence | Modification | Peptide length | pI | Charge at pH 7 |
|---|---|---|---|---|---|---|
| 66 | 233 | EAKYDAYVATLSEALRIIAG | Native peptide (NB N-term E) | 20-mer | 4.4 | −1 |
| 205 | 233_1 | Acetyl-EAKYDAYVATLSEALRIIAG | N-terminal acetylation | 20-mer | 3.8 | −2 |
| 323 | 233_2 | REAKYDAYVATLSEALRIIAGR | Non-encoded R added to both N- and C-termini | 22-mer | 9.5 | +1 |
| 206 | 233_3 | REAKYDAYVATLSEALRIIAGR-amide | Non-encoded R added to both N- and C-termini + C-term amidation | 22-mer | 10.0 | +2 |

Modification of 235: Although this peptide does not contain many highly hydrophobic residues and has a reasonable number of hydrophilic AA, it has zero charge at pH ~5-9 so is likely to benefit from an optimization.

Table 34h: Examples of Modifications of Peptide 235

TABLE 34h

| SEQ ID NO: | Peptide Name | Amino acid sequence | Modification | Peptide length | pI | Charge at pH 7 |
|---|---|---|---|---|---|---|
| 68 | 235 | IEKVDAAFKVAATAANAAPA | Native peptide | 20-mer | 7.0 | 0 |
| 222 | 235_1 | IEKVDAAFKVAATAANAAPA-amide | C-terminal amidation | 20-mer | 9.9 | +1 |
| 324 | 235_2 | RIEKVDAAFKVAATAANAAPA | Non-encoded R added to N-terminus | 21-mer | 9.9 | +1 |

TABLE 34h-continued

| SEQ ID NO: | Peptide Name | Amino acid sequence | Modification | Peptide length | pI | Charge at pH 7 |
|---|---|---|---|---|---|---|
| 223 | 235_3 | IEKVDAAFKVAATAANAAPAR-amide | Non-encoded R added to C-terminus + C-term amidation | 21-mer | 10.6 | +2 |
| 325 | 235_4 | RIEKVDAAFKVAATAANAAPAR | Non-encoded R added to both N- and C-termini | 22-mer | 10.6 | +2 |
| 326 | 235_5 | RIEKVDAAFKVAATAANAAPAR-amide | Non-encoded R added to both N- and C-termini + C-term amidation | 22-mer | 11.5 | +3 |

Modification of 210: This peptide has a high number of charged/hydrophilic residues, so would be expected to show good aqueous solubility. However, it does also have quite a few highly hydrophobic residues, and initial solubility screening (surprisingly) indicates that this peptide may have solubility issues. It has zero charge at pH ~5-9 so it is likely to benefit from an optimization anyway.

TABLE 34i

Examples of modifications of peptide 210

| SEQ ID NO: | Peptide Name | Amino acid sequence | Modification | Peptide length | pI | Charge at pH 7 |
|---|---|---|---|---|---|---|
| | 210 | KDKWIELKESWGAIWRIDTP | Native peptide | 20-mer | 7.1 | 0 |
| 203 | 210_1 | KGKDKWIELKESWGAIWRIDTP | Allergen-encoded KG added to N-terminus | 22-mer | 9.7 | +1 |
| 327 | 210_2 | KDKWIELKESWGAIWRIDTP-amide | C-terminal amidation | 20-mer | 9.8 | +1 |
| 204 | 210_3 | KGKDKWIELKESWGAIWRIDTP-amide | Allergen-encoded KG added to N-terminus + C-terminal amidation | 22-mer | 10.2 | +2 |

In Table 34 below is a sequence listing of the sequences for testing:

TABLE 34 modified peptides tested

| SEQ ID NO | Modified Peptide sequence | Peptide name | pI | Parent sequence | (Parent) peptide name | pI | Comment |
|---|---|---|---|---|---|---|---|
| 201 | KGSNPNYLALIVKYVNGDGD-amide | 243 | 9.47 | KGSNPNYLALIVKYVNGDGD | 208 | 6.75 | C-term amidation (Increase solubility) |
| 202 | RKGSNPNYLALIVKYVNGDGDR | 244 | 9.94 | KGSNPNYLALIVKYVNGDGD | 208 | 6.75 | Non-encoded R added to both N- and C-termini (Increase solubility) |
| 203 | KGKDKWIELKESWGAIWRIDTP | 245 | | KDKWIELKESWGAIWRIDTP | 210 | | Encoded KG added to N-term + C-term amidation (Increase solubility) |
| 204 | KGKDKWIELKESWGAIWRIDTP-amide | 246 | | KDKWIELKESWGAIWRIDTP | 210 | | Encoded KG added to N-term + C-term amidation (Increase solubility) |
| 205 | Acetyl-EAKYDAYVATLSEALRIIAG | 247 | | EAKYDAYVATLSEALRIIAG | 233 | | |
| 206 | REAKYDAYVATLSEALRIIAGR-amide | 248 | | EAKYDAYVATLSEALRIIAG | 233 | | Non-encoded R added to both N- and C-termini (Increase solubility) |
| 207 | APEVKYTVFETALKKAITAM-amide | 249 | 10.05 | APEVKYTVFETALKKAITAM | 240 | 9.56 | C-term amidation (Increase solubility) |
| 208 | RAPEVKYTVFETALKKAITAMR | 250 | 10.44 | APEVKYTVFETALKKAITAM | 240 | 9.56 | |
| 209 | APEVKYTVFETALKKAITA | 251 | 9.56 | APEVKYTVFETALKKAITAM | 240 | 9.56 | Met in C-term removed (Avoid oxidation) |
| 210 | APEVKYTVFETALKKAITA-amide | 252 | 10.05 | APEVKYTVFETALKKAITAM | 240 | 9.56 | Met in C-term removed + C-term amidation (Avoid oxidation + increase solubility) |
| 211 | RAPEVKYTVFETALKKAITAR | 253 | 10.44 | APEVKYTVFETALKKAITAM | 240 | 9.56 | Met in C-term removed + non-encoded R added to both N- and C-termini (Avoid oxidation + increase solubility) |
| 212 | Acetyl-AGELELQFRRVKSKYPEGTK | 254 | | AGELELQFRRVKSKYPEGTK | 207 | | N-term acetylation (Decrease biological degradation) |
| 213 | AGELELQFRRVKSKYPEGTK-amide | 255 | | AGELELQFRRVKCKYPEGTK | 207 | | C-term amidation (Decrease biological degradation) |
| 214 | Acetyl-AGELELQFRRVKSKYPEGTK-amide | 256 | | AGELELQFRRVKCKYPEGTK | 207 | | N-term acetylation + C-term amidation (Decrease biological degradation) |
| 215 | Acetyl-WGAIWRIDTPDKLTGPFTVR | 257 | | WGAIWRIDTPDKLTGPFTVR | 211 | | N-term acetylation (Decrease biological degradation) |
| 216 | WGAIWRIDTPDKLIGPFIVR-amide | 258 | | WGAIWRIDTPDKLIGPFIVR | 211 | | C-term amidation (Decrease biological degradation and increase solubility) |
| 217 | Acetyl-WGAIWRIDTPDKLTGPFTVR-amide | 259 | | WGAIWRIDTPDKLTGPFTVR | 211 | | N-term acetylation + C-term amidation (Decrease biological degradation) |
| 218 | Acetyl-STGGAYESYKFIPALEAAVK | 260 | | STGGAYESYKFIPALEAAVK | 238 | | N-term acetylation (Decrease biological degradation) |

TABLE 34-continued modified peptides tested

| SEQ ID NO | Modified Peptide sequence | Peptide name | pI | Parent sequence | (Parent) peptide name | pI | Comment |
|---|---|---|---|---|---|---|---|
| 219 | STGGAYESYKFIPALEAAVK-amide | 261 | | STGGAYESYKFIPALEAAVK | 238 | | C-term amidation (Decrease biological degradation) |
| 220 | Acetyl-STGGAYESYKFIPALEAAVK-amide | 262 | | STGGAYESYKFIPALEAAVK | 238 | | N-term acetylation + C-term amidation (Decrease biological degradation) |
| 221 | RWGAIWRIDTPDKLTGPFTVR-amide | 263 | | WGAIWRIDTPDKLTGPFTVR | 211 | | Non-encoded R added to N-term + C-term amidation (Increase solubility) |
| 222 | IEKVDAAFKVAATAANAAPA-amide | 264 | | IEKVDAAFKVAATAANAAPA | 235 | | C-term amidation (Increase solubility) |
| 223 | IEKVDAAFKVAATAANAAPAR-amide | 265 | | IEKVDAAFKVAATAANAAPA | 235 | | Non-encoded R added to C-term + C-term amidation (Increase solubility) |
| 224 | KASTGGAYESYKFIPALEAAVK | 266 | | STGGAYESYKFIPALEAAVK | 238 | | Allergen encoded KA added to N-term (Increase solubility) |
| 225 | KASTGGAYESYKFIPALEAAVK-amide | 267 | | STGGAYESYKFIPALEAAVK | 238 | | Allergen encoded KA added to N-term + C-term amidation (Increase solubility) |
| 226 | KFIPALEAAVKQAYAATVAT-amide | 268 | | KFIPALEAAVKQAYAATVAT | 239 | | C-term amidation (Increase solubility) |
| 227 | KFIPALEAAVKQAYAATVATR-amide | 269 | | KFIPALEAAVKQAYAATVAT | 239 | | Non-encoded R added to C-term + C-term amidation (Increase solubility) |
| 228 | AFKVAATAANAAPAN-amide | 270 | | AFKVAATAANAAPAN | 241 | | C-term amidation (Increase solubility) |
| 229 | AFKVAATAANAAPANR | 271 | | AFKVAATAANAAPAN | 241 | | Non-encoded R added to C-term (Increase solubility) |
| 230 | PLQGPFNFRFLTEKGMKNV | 272 | | EPLQGPFNFRFLTEKGMKNV | 216 | | N-term glutamine (E) removed to prohibit cyclisation (potentially problematic sequence) |
| 231 | KGSNPNYLALLVKYVQGEGD | 273 | 6.87 | KGSNPNYLALLVKYVNGDGD | 208 | 6.75 | ND replaced with QG and DG with EG to prohibit is-Asp formation (potentially problematic sequence) |
| 232 | AYESYKFIPALEAAVKQAYA | 285 | | | 238/239 | | Phleum encoded variation of peptides 238c and 239 |
| 233 | IEKVDAAFKVAATAANAAPAN | 286 | | | 235 + N | | Phleum encoded variation of peptide 235 |

Some peptides have been modified to improve solubility, others for improving manufacturability (sequencing) and yet other have been modified to improve metabolic stability e.g. by capping the ends (acetylation and/or amidation). However there are no indications that the parent peptides should have a poor metabolic stability. In the latter case the metabolic stability is improved at the expense of a theoretically lower solubility. So in this case choosing a modified variant of the parent peptide is a balance.

In effect, not all effects of blocked ends are helpful. Blocking charged groups on the ends of a peptide tends to decrease the solubility of the peptide, maybe to the extent where solubility becomes a limitation on the effective concentration of that peptide which can be obtained in solution. It may even make the peptide so hard to dissolve that its usefulness is compromised. Thus, a decision may need to be made about what is more important: solubility, or the closeness of a peptide's structure to resembling the protein from which its sequence was derived.

Similar issues arise each time a new peptide study is devised. For example, in the study of cytotoxic T cell epitopes, it is appropriate to have short peptides made with free amine and free acid endings, because they are the natural endings of peptides which have been processed intracellularly from whole proteins. Natural helper T cell epitopes are longer than cytotoxic T cell epitopes, and even though in nature helper T cell epitopes have free ends, relatively short end-blocked synthetic peptides may function better in helper T cell assays than peptides with free ends. The reason may be related either to the synthetic peptide not being made with an ideal length, or it may be related to the amount of time the peptides persist in cultures before being broken down. The lengthened amount of time that end-blocked peptides have, to begin exerting a biological effect in a culture, may be more important than their ability to exactly mimic a natural epitope.

Example 15

T Cell Reactivity of Modified Peptides

This example describes the results of the testing of T cell reactivity towards modified versions of certain selected peptides.

The modified peptides (28 peptides) and their unmodified counterparts (11 parent peptides) are listed in Table 34, which also shows the specific modifications of the individual peptides. The modifications include acetylation, amidation, truncation, addition of arginines to N/C terminal, elongation with allergen encoded amino acids, and replacement of selected amino acids. The purpose of the modification was to make insoluble peptides soluble, to increase solubility of soluble peptides, to increase stability, or a combination of these as indicated in table 34 of Example 14

All peptides were tested at 2 μg/ml in proliferation assays with T cell lines selected from TCL03-DK1 and on TCL03-DK2 (27 lines/donors in total with diverse HLA profiles) on day 34 after initiation of the T cell cultures as described in Example 3 (T cell proliferation).

The data obtained from testing the modified peptides and their parent peptides in proliferation assays are presented in FIG. 15.

The figure depicts the % of donors responding to the individual modified peptides and their parent peptides. The data have been grouped according to allergen group and amino acid number of the parent peptide. The characteristics of the individual peptides are listed in Table 34 above.

In general all parent peptides induced T cell responses in a high percentage of the donors resulting in donor coverages from 33 to 89% in the donors tested and this confirms that these peptides contain important T cell epitopes recognized by grass allergic patients expressing various HLA molecules. Overall, only marginal increases or decreases in the number of responding donors were observed as a result of the modifications. In most cases, modified peptides with markedly increased T cell coverage are peptides modified (acetylation/amidation) to increase the stability of the peptide (ex. peptides 252, 254-256, 258, and 259). Some of the modifications that were done to increase the solubility also showed enhancement in the donor coverage (ex. peptides 253, 265, and 271). This further implies that these modifications are important for either stabilizing MHC/peptide complex or TCR recognition.

Markedly reduced T cell coverage of modified peptides compared to the parent peptide was only observed in two cases (peptides 243 and 272). The parent peptide 208 is recognized by the vast majority (89%) of the patients and the coverage is reduced to 70% by a C-terminal amidation. However, recognition in 70% of donors is still a very good coverage for a single peptide. Peptide 243 was amidated primarily to increase the solubility and additionally it may protect the peptide from from C-terminal cleavage which may enhance the stability in serum. However it seemed that for some donors modification of the peptide is unacceptable. For peptide 272 the T cell coverage is more than halved (18%) compared to the parent peptide (pep 216: 40%) and this is the result of a truncation of the peptide by removing the N-term glutamine (E) to avoid cyclisation. So this amino acid seems to be highly important for HLA binding or for T cell recognition in some donors.

Taken together, modification of peptides containing important T cell epitopes can be performed without loss of T cell reactivity and may even in some cases lead to increased coverage. However, some minor alterations may for some peptides lead to a clear reduction in T cell coverage.

Example 16

Solubility of Modified Peptides

This example includes a description of the solubility data for modified versions of certain selected peptides.

The modified peptides 243, 244, 273, 249, 250, 251 and 252 of Example 14 were tested for solubility as described in Example 5. The parent peptides 208 and 240 were tested at the same time for reference.

Table 35. Solubility of Some Modified Peptides at 3 mg/mL Evaluated by Visual Inspection This table shows solubility results for a subset of peptides for non-filtered peptide preparations with and without centrifugation at 3 mg/mL. The pH 7 preparation contains 250 mM D-Mannitol and 25 mM sodium phosphate (pH 7.0). and the pH 4.5 preparation contains 250 mM D-Mannitol and 25 mM sodium acetate (pH 4.5).

Table scoring code; ok: clear solution; +: very small precipitation only visible with a magnifier; ++: precipitation/turbid solution; +++: more precipitation/turbid solution.

TABLE 35

| SEQ ID NO: | Peptide name | Visual inspection after 60 min, pH 7 | Visual inspection after centrifugation, pH 7 | Visual inspection after 60 min, pH 4.5 | Visual inspection after centrifugation, pH 4.5 |
|---|---|---|---|---|---|
| 8 | 208 | +++ | +++ | ND | ND |
| 201 | 243 | +++ | +++ | OK | + |
| 202 | 244 | +++ | +++ | OK | + |
| 231 | 273 | +++ | +++ | +++ | +++ |
| 73 | 240 | ND | ND | ++ | + Very difficult to filter |
| 207 | 249 | OK | + | OK | + |
| 208 | 250 | OK | + | OK | + |
| 209 | 251 | +++ | +++ | OK | + |
| 210 | 252 | +++ | ++ | OK | OK |
| 211 | 253 | OK | + | OK | + |

For peptide 208 both the modified peptides 243 and 244 show improved solubility. At pH 4.5 there is no visible aggregation. At pH 7 solubility problems remain. For peptide 273 no solubility improvement was seen. Peptide 273 was modified only to increase stability, so therefore this is not surprising that solubility was not improved.

For peptide 240, the modified peptides 249, 250 and 253 show improved solubility both at pH 4.5 and 7. They show no visible aggregation. Peptides 251 and 252 show improved solubility both at pH 4.5 where they show no visible aggregation.

Table 36. Examples of Peptide Recovery of Preparations Having a Peptide Concentration of 3.0 Mg/mL.

Conditions correspond to: pH 3-5; pH 4.5: 250 mM D-Mannitol and 25 mM sodium acetate; pH 7.0: 250 mM D-Mannitol and 25 mM sodium phosphate. % recover was calculated according to Equation 1 of Example 5, based on RP-HPLC test sample analysis using the obtained integration peak area results.

TABLE 36

| Peptide name | Predicted pI value | % recovery, pH 7.0 | % recovery, pH 4.5 |
|---|---|---|---|
| 208 | 6.75 | No ref | No ref |
| 243 | 9.47 | 7.54 | 118.59 |
| 244 | 9.94 | 5.02 | 104.03 |
| 273 | 6.87 | 0 | 0 |
| 240 | 9.56 | No ref | No ref |
| 249 | 10.05 | 94.37 | 115.37 |
| 250 | 10.44 | 96.13 | 94.39 |
| 251 | 9.56 | 30.23 | 129.26 |
| 252 | 10.05 | 19.30 | 166.46 |
| 253 | 10.44 | 87.52 | 85.77 |

NB based on filtered sample. For some peptides it may have been higher when not filtered.

The recoveries confirm the results of the visual inspection shown in Table 35 above.

The stability of the modified peptides was tested as described in Example 5, and after 24 hours no degradation was observed for any of the modified peptides.

Example 17

T Cell Reactivity of Peptide Combinations Including Modified Peptides

This example describes the testing of T cell reactivity of the peptide combinations that include the modified peptides described in Examples 14-16 above.

The peptide combinations 005, 215, 735, and 745 were tested in the original composition and in versions with one or more peptides replaced by peptides with various modifications as specified in Table 37 below (a total of 24 mixes). The mixes were tested at 2 µg/ml (of each peptide) in proliferation on TCL03-DK1 and on TCL03-DK2 (27 donors in total with divers HLA profiles) on day 34 as described in Example 3 (T cell proliferation).

Peptides were modified as described in Example 14 above and included in the peptide combination replacing the unmodified parent peptide as listed in Table 37, which also include the specific modification of the individual peptides. The function of the modification was to make insoluble peptides soluble, to increase solubility of soluble peptides, to increase stability, or a combination of these as indicated in Table 37.

Table 37—Overview of Peptide Combinations Tested Including Modified Peptides

TABLE 37

| Peptide combination name | Original peptide combination name | Modified peptide in peptide combination | (Parent) peptide modified | Purpose of modification |
|---|---|---|---|---|
| 005-1 | 005 | 243 | 208 | Increase |
| 005-2 | 005 | 244 | 208 | Solubility |
| 005-3 | 005 | 249 | 240 | Increase |
| 005-4 | 005 | 252 | 240 | Solubility |
| 005-5 | 005 | 253 | 240 | |
| 215-6 | 215 | 248 | 233 | |
| 735-7 | 735 | 246 | 210 | |
| 005-8 | 005 | 263 | 211 | Increase |
| 215-9 | 215 | 264 | 235 | Solubility |
| 215-10 | 215 | 265 | 235 | of soluble |
| 215-11 | 215 | 266 | 238 | Peptides |
| 215-12 | 215 | 267 | 238 | |
| 745-13 | 745 | 268 | 239 | |
| 745-14 | 745 | 269 | 239 | |
| 745-15 | 745 | 270 | 241 | |
| 745-16 | 745 | 271 | 241 | |
| 215-17 | 215 | 260 | 238 | Resist |
| 215-18 | 215 | 261 | 238 | Degradation |
| 215-19 | 215 | 262 | 238 | |
| 215-20 | 215 | 244 | 208 | 2, 3 or 4 |
| | | 248 | 233 | modified |
| Mix 215-21 | Mix 215 | 244 | 208 | Peptides |
| | | 248 | 233 | |
| | | 265 | 235 | |
| Mix 215-22 | Mix 215 | 244 | 208 | |
| | | 248 | 233 | |
| | | 265 | 235 | |
| | | 267 | 238 | |
| Mix 005-42 | Mix 005 | 251 | 240 | Increase solubility |
| Mix 005-43 | Mix 005 | 273 | 208 | Potentially problematic sequence |

The data obtained from testing the peptide combinations 005 and 215 and their counterparts containing modified peptides in proliferation assays are presented in FIG. 16. Similar data were obtained for peptide combination 735 and 745 and their counterparts containing modified peptides supporting the interpretations and conclusions described in detail below.

FIG. 16 depicts the % of donors responding to the individual peptide combinations for original peptide combinations 005 and 215. The peptides of the peptide combinations including modified peptides are listed in Table 37 above and data for various modified peptide combinations are shown together with data for the original peptide combinations (205-23 and 215-24).

Modified peptide combinations of 005: All combinations induced T cell activation in 24 donors or more resulting in a donor coverage of more than 88%, and all combinations containing one or more modified peptides showed a donor coverage equal to or above the original combinations. The replacements represented amidations, acetylations, addition of arginines to N and/or C terminal end as well as removal of methionine or specific replacement of other problematic amino acid combinations and all of these where introduced without losing the response of any of the patients.

Modified peptide combinations of 215: All combinations induced T cell activation in 24 donors or more resulting in a donor coverage of more than 88%, and all mixes containing one or more modified peptides showed a donor coverage equal to or above the original peptide combination. The replacements represented amidations, acetylations, addition of arginines to N and/or C terminal end as well as N-terminal elongation of a peptide with allergen encoded amino acids and all of these modified peptides where introduced one by one without losing the response of any of the patients. Similarly, replacement of 2, 3 or 4 peptides with modified versions did not change the donor coverage markedly with 2 replacements leading to a slightly increased coverage, whereas replacement of 3 or 4 peptides resulted in a slight reduction in the coverage.

Taken together, various modifications that theoretically will lead to increased peptide solubility or stability do not alter the donor coverage of a peptide combination disclosed herein, containing 5 peptides each inducing high T cell responses in a large percentage of a donor cohort.

Example 18

Extended Study of Peptide Solubility and Stability of Selected Peptides and Summary The present example describes further extensive testing of selected peptides with respect to solubility and stability in a range of buffer solutions and further includes a summary of the results obtained in the testing of the present example as well as Example 5.

Peptides with satisfactorily solubility at in vivo conditions are more desirable for a number of reasons. For example insoluble peptides are more likely to produce undesirable inflammatory responses and insoluble peptides may also be difficult to manufacture and formulate in therapeutically sufficient amounts, in particular to formulate into pharmaceutical formulations for injection that are compatible with physiological conditions with respect to pH and osmolality.

Therefore, the immuno-dominant peptides detected during the "T cell response screening" were then tested for solubility in various aqueous solutions within a pH range of 4.5 to 8.5, preferably 4.5 to 7.

For that purpose, the peptides were provided as acetate salts (produced by Innovagen® at a >10 mg scale of manufacturing). To take into account batch-to-batch variations, some peptides were tested from other batches of the manufacturer Innovagen®, as well as from another manufacturer (Almac) and from in-house production. Solubility experiments were performed on peptide in solution in concentrations ranging from 0.5 mg/mL to 3 mg/mL (dry matter)—with the following solvents:

Water
Acetate buffer, pH 4.5 (25 mM sodium acetate containing 250 mM D-Mannitol)
Phosphate buffer, pH 7.0 (25 mM sodium phosphate containing 250 mM D-Mannitol)
Glycine buffer, pH 8.5 (25 mM glycine containing 250 mM D-Mannitol)

The solubility of the peptides was initially investigated by visual inspection and U-HPLC recovery. Visual inspection included assessment of turbidity and presence of particles/aggregates of each peptide solution before and after centrifugation as well as visual inspection of pelleted material. The visual inspection were reported as "clear solution", "very small precipitation only visible with a magnifier", "precipitation visible/turbid solution" or "more precipitation/turbid solution". Filtration of peptide solutions were conducted using syringe based filters containing a polyethersulfone (PES) membrane chemistry and a pore size of 0.2 μm. The amount of the peptide in the supernatant of a filtered sample was determined using U-HPLC with reverse phase chromatography and recovery were determined as described in Example 5.

Peptides tested in a concentration of 0.5 mg/mL and/or 1 mg/mL in the pH range of 4.5 to 8.5 and which showed visible precipitation/turbidity in combination with a decrease (>20%) in main peak Ultra-HPLC (U-HPLC) area compared to a reference in all of the tested solutions were discarded for further consideration in this initially solubility test.

It was found that peptides 201 (SEQ ID NO: 1), 204 (SEQ ID NO: 4), 205 (SEQ ID NO: 5), 206 (SEQ ID NO: 6), 207 (SEQ ID NO: 7), 211 (SEQ ID NO: 11), 212 (SEQ ID NO: 12), 217 (SEQ ID NO: 36), 222 (SEQ ID NO: 45), 226 (SEQ ID NO: 49), 228 (SEQ ID NO: 61), 231 (SEQ ID NO: 64), 235 (SEQ ID NO: 68), 236 (SEQ ID NO: 69), 238 (SEQ ID NO: 71), 239 (SEQ ID NO: 72) and 241 (SEQ ID NO: 113) had an acceptable solubility in the above test of peptide concentrations of 0.5 and 1 mg/mL.

Testing of 3 mg/mL Solutions

Selected peptides (204 (SEQ ID NO: 4), 205 (SEQ ID NO: 5), 206 (SEQ ID NO: 6), 207 (SEQ ID NO: 7), 211 (SEQ ID NO: 11), 217 (SEQ ID NO: 36), 222 (SEQ ID NO: 45), 235 (SEQ ID NO: 68), 236 (SEQ ID NO: 69), 238 (SEQ ID NO: 71), 239 (SEQ ID NO: 72), 241 (SEQ ID NO: 113), 285 (SEQ ID NO: 232), 286 (SEQ ID NO: 233), 260 (SEQ ID NO: 218), 261 (SEQ ID NO: 219) and 262 (SEQ ID NO: 220)) were further characterised with regard to solubility, filter recovery and short term stability in a higher concentration of 3 mg/mL in 3 or 4 solvents:

Acetate buffer, pH 4.5 (25 mM sodium acetate containing 250 mM D-Mannitol)
Phosphate buffer, pH 7.0 (25 mM sodium phosphate containing 250 mM D-Mannitol)
Glycine buffer, pH 8.5 (25 mM glycine containing 250 mM D-Mannitol)
Histidine buffer, pH 7.0 (25 mM Histidine)
(Peptides 204, 205, 206, 236, 285, 286, 260, 261 and 262 were not tested in the glycine buffer above).

Peptide solutions were investigated at a time point of 1 hour after production, but were also repeated at later time point (e.g. 24. 48 or 96 hours) to investigate the stability of the peptides.

Analysis

Peptide solutions were investigated to determine the presence of turbidity/particles/aggregates by use of optical density (OD) and change in UV-VIS absorbance at a wavelength of 320 nm, of the filtrate. The presence of sub-visual particles was detected using dynamic light scattering (DLS) analysis using the particle diameter calculated for the number distribution and 90° LS (90 degrees light scattering) at a wavelength of 400 nm. In addition or as an alternative, the amount of the peptide in the supernatant of a filtered sample was determined using U-HPLC as described above, with the exception that the recovery was determined by dividing the peak area of the filtered sample in relation to the peak area in the original solution prior to filtration. See also Example 5 for further details regarding UV-VIS, and recovery measured by U-HPLC.

Overall Determination of Solubility

The peptides were scored in relation to the outcome of the above mentioned tests: For each peptide in a given buffer and at a given concentration, a sum of test scores was calculated and the sum used to rank the peptides according to solubility:
1. Visual evaluation of the dissolved, centrifuged sample: No visual precipitation resulted in a score of 0, and in the case of visual precipitation the samples were given a score of 1 to 3 depending on the degree of visual precipitation.
2. U-HPLC recovery compared to reference: >90% gave a score of 1, 80%-90% a score of 2, 50%-80% a score of 3 and <50% a score of 4.
3. U-HPLC filter recovery compared to reference: >90% gave a score of 1, 80%-90% a score of 2, 50%-80% a score of 3 and <50% a score of 4.
4. DLS peak 1 number ≤3 nm gave a score of 1, 3-10 nm gave a score of 2, 10-100 nm gave a score of 3, >100 nm gave a score of 4.
5. 90LS at 400 nm: Intensity <450 gave a score of 1, <800 gave a score of 2, >800 gave a score of 3.
6. UV-VIS change in absorbance at 320 nm within 24 hours: ≤0.01 gave a score of 1, ≤0.05 gave a score of 2, ≤0.2 gave a score of 3 and >0.2 gave a score of 4.

Peptides having a sum of scores of 4-7 when calculated based on at least 5 of the tests point above were considered to have a good solubility in a given buffer and at a given concentration.

The following 23 peptides with ID NOs: 201, 204, 205, 206, 207, 211, 212, 217, 222, 226, 228, 231, 235, 236, 238, 239, 240, 241, 260, 261, 262, 285 and 286 passed the majority of the test parameters and were considered sufficiently soluble in aqueous solutions of pH in the range of 4.5 to 8.5 and with insignificant signs of short-term stability problems and thus suitable for being formulated into a pharmaceutical injection product. In more details it was found that the 9 peptides (204, 205, 206, 207, 217, 236, 238, 239, 241) showed good solubility in all the test samples (concentrations and pH tested) and using all the solubility tests. Additionally, peptides 260, 261, 262, 285 and 286, which were only tested in a concentration of 3 mg/ml showed good solubility in the buffers tested using the ranking scheme based on a sum of scores as mentioned above.

Example 19

Synthesis and Purification of Synthesized Peptides

The present example describes a manufacturing method for the synthesis of peptides to be used according to the present invention. The present example is not to be regarded as limiting for the invention.

Synthesis

The peptides as described in Example 1 above, were synthesised by SPPS (Solid-phase peptide synthesis) using a resin where peptides were built by chemically adding single amino acids attached with a Fmoc-group. The resin was first loaded with one Fmoc-amino acid as an ester binding. Thereafter all remaining amino acid additions were performed as amid-bindings. The SPPS chemical setup used the repetitive steps 306 below for adding each extra amino acid:
1) Starting setup and mixing chemicals
2) Resin swelling
3) Deprotection of resin AA by removing Fmoc
4) Activation of Fmoc Amino Acid (AA) using DIC and Oxyma in a separate container.
5) Coupling of activated Fmoc-AA to the amino acid on the resin.
6) Capping of unreacted resin sites using acetic anhydride.
7) Washing and drying of the resin After drying the peptide was be cleaved from resin using triflouric acid. The filtered liquid was then precipitated using ether, and the resulting crude peptide was dried and stored frozen until purification.

Purification

A 250 mm long column was regenerated and equilibrated in 8 column volumes prior to purification and crude peptide was dissolved and filtered using a 0.2 µm filter (Milex PES filter). The preparative chromatography started by loading large amount of the filtered peptide solution on the column (5 g per litre resin) which binds the peptide to the C18 column (Luna 10-15 µm). After loading, a gradient elution (½% increase per minute) was used to elute the peptide and its impurities into separated fractions. Each fraction was analysed using HPLC and selected pure fractions were pooled and used on the second chromatographic step—the ion exchange.

The diluted pool (1:1 in purified water) was reloaded on the same column as described above and washed with 5 column volumes of 0.5 M ammonia acetate followed by 5 column volumes 0.1% acetic acid solution (aqua). Thereafter the TFA-depleted peptide was eluted using an acetonitrile gradient (1% increase per minute) and selected pure fractions of peptide were pooled. This $2^{nd}$ pool contained acetonitrile which was subsequently removed by vacuum rotary evaporation, and the peptide solution was then 0.2 µm filtered and freeze dried. After freeze drying, the water content in the freeze dried peptide was standardized in controlled air humidity to obtain a less static electric product. Thereafter the peptide containers were closed and stored frozen at −20 degrees celsius.

Peptides were synthesised and purified using the protocols described above. It was found that all the peptides 204, 207, 222, 238, 239 and 241 gave high yields of approx. 500 mg pure peptide per 0.5 mM synthesis setup (approx. 1 gram crude). The synthesis yield of the crude peptide was close to 100%, and purification yield was approx. 50% of the weight of the crude.

Example 20

Bio-Stability Testing

The present example describes a study estimated bio-stability of selected peptides including peptides 207, 238, 239 and 241.

Peptides of the present invention are according to one embodiment intended for use in peptide immunotherapy with intra-dermal injection (optionally with other injection routes to the skin or within the skin). The skin is a highly metabolic organ with considerable proteolytic activity. This activity may include exo- and endo-peptidases as well as aminopeptidases and dipeptidylpeptidases, which could potentially degrade the peptides resulting in very low half-life of the peptide in the skin and thus possibly lower the effect on the immune system.

In order to provide an estimate of in vivo stability, the peptides of the present invention were incubated in human serum which contains a number of peptidases with different specificity and T½ determined as described below:

About 50 µg to 100 µg of each peptide was incubated with 25% human non-heat inactivated serum (from male AB plasma commercially available from Sigma) over 3 hours at 37° C. Samples were collected at different time points 0 h, 30 min, 60 min, 90 min, 120 min, 150 min and 180 min and serum proteins were hereafter precipitated with 6% cold trichloroacetic acid (TCA). The supernatant was analyzed by UHPLC-UV/VIS and the peak-height/peak-area of the original peptide was determined at each time point. T½ of the original peptide was estimated by plotting Ln (peak-area) as a function of time.

T½ estimates the half-life of the original peptide, but does not provide any information about the type of degradation. Therefore, the degradation pattern of each peptide was additionally studied. Extra peaks compared to the peak of the original peptide in the chromatogram were notified as potential degradation products. To assess the degradation pattern of each peptide and identify degradation products, the test samples were also investigated by mass spectroscopy (MS). Some peptides, for example, may be prone to cleavage by endopeptidases resulting in short peptide fragments unfit for binding to the HLA binding site, whereas other peptides may be more prone to cleavage by exopeptidases which may cleave one or more amino acid residues from the N or C-terminal end of the peptide resulting in a conserved HLA binding. It is therefore possible that an degradation product of an original peptide (even if the latter has a low T½) has a conserved HLA binding function and thus the cleavage would possibly not affect the efficacy in vivo. Therefore, it is important to look at both the MS data and functional data to estimate the extent and effect of the degradation.

A number of peptides of the invention were tested according to the above mentioned protocol. Selected prior art peptides disclosed in WO2010089554 were additionally tested for comparison.

Peptides tested: 204 (SEQ ID NO: 4), 207 (SEQ ID NO: 7), 211 (SEQ ID NO: 11), 222 (SEQ ID NO: 45), 238 (SEQ ID NO: 71), 239 (SEQ ID NO: 72), 241 (SEQ ID NO: 113), 285 (SEQ ID NO: 232) and 286 (SEQ ID NO: 233). Additionally modified peptides: 262 (SEQ ID NO: 220), 261 (SEQ ID NO: 219), 255 (SEQ ID NO: 213), 256 (SEQ ID NO: 214) 257 (SEQ ID NO: 215)) and 259 (SEQ ID NO: 217). (An overview of the sequences of modified peptides can be found in Table 34.)

Prior art: 278 (SEQ ID NO: 234), 279 (SEQ ID NO: 235), 280 (SEQ ID NO: 236), 281 (SEQ ID NO: 237), 282 (SEQ ID NO: 239), 283 (SEQ ID NO: 242) and 284 (SEQ ID NO: 244). (An overview of the sequences of modified peptides can be found in Table 9.)

Table 38. Degradation of Selected Peptides in Human Serum

TABLE 38

| SEQ ID NO: | Peptide | Peptide length | T½ (min) | Sum full length or −1aa to −3aa | Full length (%) | −1aa to −3aa (%) | <−3aa (%) |
|---|---|---|---|---|---|---|---|
| 4 | 204 | 20 | >500 | 100 | 99 | 1 | 0 |
| 7 | 207 | 20 | 49 | 98 | 48 | 50 | 2 |
| 45 | 222 | 20 | 7 | 100 | 1 | 99 | 0 |
| 71 | 238 | 20 | 340 | 99 | 82 | 17 | 1 |
| 72 | 239 | 20 | 202 | 98 | 53 | 45 | 2 |
| 113 | 241 | 15 | 157 | 100 | 83 | 17 | 0 |
| 233 | 286 | 21 | >500 | 100 | 100 | 0 | 0 |
| 232 | 285 | 20 | 82 | 100 | 66 | 34 | 0 |
| 234 | 278 (Ber01) | 15 | N/A | 99.5 | 89 | 10.5 | 0.5 |
| 235 | 279 (Ber02) | 10 | 13 | 100 | 20 | 80 | 0 |
| 236 | 280 (Ber02C) | 17 | 80 | 96 | 73 | 23 | 4 |
| 237 | 281 (Bio02A) | 14 | 21 | 97 | 2 | 95 | 3 |
| 239 | 282 (Bio04A) | 13 | 39 | 100 | 88 | 12 | 0 |
| 242 | 283 (Rye09B1) | 18 | 224 | 97.5 | 68 | 29.5 | 2.5 |
| 244 | 284 (Tim07B1) | 16 | 67 | 90 | 60 | 30 | 10 |

The results of the test showed that peptides 204, 238, 239, 241 and 286 all had a remarkably high T½ above 100 minutes, whereas peptides 207, 211, 222 and 285 had a shorter T½ of 49, 37, 7 and 82 minutes, respectively. In comparison, only peptide 283 of the peptides disclosed in the prior art had a T½ above 100 min.

In the columns of Table 38, which discloses the degradation details at time-point 60 minutes, it can be seen that many of the peptides are degraded by the cleavage of 1 to 3 amino acids in the terminus, since the fraction derived by adding full length peptide and degraded peptides resulting from a loss of 1 to 3 terminal amino acids is close to 100% for most peptides. Such a degradation pattern is preferable considered compared to endopeptidase cleavage, which may have a larger risk of disrupting the T cell reactivity of a peptide. However, the length of the peptide should also be taken into account. It is noteworthy that for the prior art peptide 279, which only consists of 10 amino acids, only 20% of the peptide had full length after 60 minutes, whereas 80% had been degraded by cleavage of 1-3 amino acids. The binding pocket of a MHC class II epitope typically comprises 9-10 amino acids, and it is therefore highly likely that the T cell reactivity is lost when 1 to 3 amino acids are cleaved of a peptide with the length of 10 amino acids. Since most of the peptides of the invention have a length of 15 or more amino acids, it is considered more likely that the T cell reactivity is conserved even if the peptide is degraded by cleavage of 1-3 terminal amino acids.

By comparing results for peptides 211, 257 and 259, (where 257 is a modified variant of 211 which has an additional N-terminal acetyl moiety added to 211, and 259 is a modified variant of 211 having an N-terminal acetyl moiety and a C-terminal amide moiety added to the sequence of 211) it was observed that the T½ is increased by the modifications from 37 to 61 and 78 minutes, respectively.

By comparing results for peptides 207, 255 and 256, (where 255 is a modified variant of 207 which has an additional C-terminal amid moiety added to 207, and 259 is a modified variant of 207 having an N-terminal acetyl moiety and a C-terminal amide moiety added to the sequence of 207) it was observed that the T½ was increased by the modifications from 49 to 146 and 347 minutes, respectively. Thus, these results indicate that modifications were useful for increasing the T½.

By comparing results for peptides 238, 261 and 262, (where 261 is a modified variant of 238 which has an additional C-terminal amid moiety added to the sequence of 238, and 262 is a modified variant of 238 having an N-terminal acetyl moiety and a C-terminal amide moiety added to the sequence of 238) it was observed that the T½ was increased by the modifications from 340 minutes to >500 for both modified variants.

Thus, the examples above indicate that modification by adding an N-terminal acetyl moiety and/or adding a C-terminal amide were useful for increasing the T½ for a number of peptides of the invention.

These results demonstrate that a number of peptides of the present invention has a higher T½ compared to peptides of the prior art which have been proposed for use in grass pollen allergy vaccines. Further, most of the tested peptides had a high fraction of full length peptide or degradation product lacking only 1 to 3 terminal amino acids, which indicates that the effects on the immune system are likely to be conserved for some time even after degradation.

Example 21

Extended Cross Reactivity Study and Summary of Cross-Reactivity Results for Selected Peptides This example includes an extended cross-reactivity study performed on selected peptides, including peptides 207, 238, 239 and 241, against eight different species (including the three species (*Lolium perenne* (Lol p), *Phalaris aquatica* (Pha a), *Cynodon dactylon* (Cyn d)) of Example 9 and five additional species namely *Poa pratensis* (Poa p), *Dactylis* glomerate (Dac g), *Festuca pratensis* (Fes p), *Paspalum notatum* (Pas n), *Sorghum halepense* (Sor h)). Homologue peptides were derived from allergens of the following species:

*Cynodon dactylon* (Cyn d 4 (SEQ ID NO: 334)

*Dactylis* glomerate (Dac g 1 (SEQ ID NO: 335), Dac g 3 (SEQ ID NO: 336), and Dac g 5 (SEQ ID NO: 335),

*Festuca pratensis* (Fes p 1 (SEQ ID NO: 338)

*Phleum pratense* (same as above)

*Lolium Perenne* (Lol p 1 (SEQ ID NO: 339), Lol p 2 (SEQ ID NO: 340), Lol p 3 (SEQ ID NO: 341), Lol p 5a (SEQ ID NO: 342) and Lol p 5b (SEQ ID NO: 343))

*Poa pratensis* (Poa p 1 (SEQ ID NO: 347) and Poa p 5 (SEQ ID NO: 348))

*Paspalum notatum* (Pha n 1 (SEQ ID NO: 344)) and

*Phalaris aquatica* (Pha a 1 (SEQ ID NO: 345) and Pha a 5 (SEQ ID NO: 346))

*Sorghum halepense* (Sor h 1 (SEQ ID NO: 349).

Measured Cross-Reactivity:

To measure the experimental cross-reactivity, the proliferation assay of Example 3 was carried out on 21 grass pollen allergic donors (TCL02-DK2, Study XR1) and 20 grass pollen allergic donors (TCL03-DK1+DK2, Study XR2). Homologue peptides were selected on the basis of sequence homology to the native *Phleum pratense* peptides (for sequences, see Example 1, SEQ ID NOs: 134-200). In Study XR1, Cross-reactivity to *Phleum pratense* peptides with either close (*Lolium perenne*-Lol p) or distant (*Phalaris Canariensis*-Pha a, *Cynodon dactylon*-Cyn d) species was experimentally investigated. In Study XR1, 67 homologue peptides corresponding to 41 native *Phleum pratense* peptides were investigated together with the 41 *Phleum pratense* peptides at a concentration of 2 μg/ml. Similarly, study XR2 was carried out on 20 grass pollen allergic donors where donor derived TCL-03 lines were used to investigate *Phleum pratense* cross-reactivity to *Poa pratensis* (Poa p), *Dactylis glomerata* (Dac g), *Festuca pratensis* (Fes p), *Paspalum notatum* (Pas n), *Sorghum halepense* (Sor h), *Lolium perenne* (Lol p), *Phalaris aquatica* (Pha a) and *Cynodon dactylon* (Cyn d). In Study XR2, 62 homologue peptides corresponding to 15 native *Phleum pratense* peptides (SEQ ID NO: 4 (204), SEQ ID NO: 7 (207), SEQ ID NO: 45 (222), SEQ ID NO: 71 (238), SEQ ID NO: 72 (239), SEQ ID NO: 5 (205), SEQ ID NO: 6 (206), SEQ ID NO: 11 (211), SEQ ID NO: 36 (217), SEQ ID NO: 68 (235), SEQ ID NO: 69 (236), SEQ ID NO:232 (285), SEQ ID NO:233 (286), SEQ ID NO: 8 (208) and SEQ ID NO: 73 (240) were tested at a concentration of 2 μg/ml.

Sequences of homologues of peptides can be found in Tables 40 to 53 below and Table 8 of Example 1. Further, the tested homologues of peptide 208 with SEQ ID NO: 8 were SEQ ID NO: 266 (peptide name 386), SEQ ID NO: 267 (peptide name 387), SEQ ID NO: 268 (peptide name 388), SEQ ID NO: 269 (peptide name 306), SEQ ID NO: 270 (peptide name 389) and SEQ ID NO: 271 (peptide name 390). The tested homologues of peptide 240 with SEQ ID NO: 73 were: SEQ ID NO: 296 (peptide name 410), SEQ ID NO: 297 (peptide name 352), SEQ ID NO: 298 (peptide name 411) and SEQ ID NO: 299 (peptide name 412).

See further description regarding the analysis of cross-reactivity data for Study XR1 in Example 9.

Cross-reactivity data from study XR2 was analysed in similar way to Study XR1, where the magnitude of T cell responses from native *Phleum pratense* peptides and the homologue were plotted in a XY plot. (See examples of XY plots in FIGS. 11 to 14). T cell response magnitude from *Phleum pratense* peptide were joined to form a straight diagonal line/identity line. Cross-reactivity was confirmed if the T cell responses from homologues were scattered around the diagonal identity line, representing similar magnitudes of T cell proliferation. When compared to the *Phleum pratense* peptide T cell responses, the homologue responses were found either higher, lower or comparable. Additionally the extent of cross-reactivity was scored as below:

a) If <6 donors were cross-reactive then the cross-reactivity was analysed both manually and statistically, else only statistical calculation/values were considered,
b) If 50% or more donors reacted to a homologue, provided same donor reacted to native peptide then 1 point was given. If it was between 30%-50% then 0.5 was given and <30% then 0 was given,
c) If >=9 donors were cross-reactive then additional 1 point was given.
d) Spearman r/ Non parametric analysis was done and P value summary was considered for analysis where each statistical * earns 1 point in rating, Maximum **** can earn 4 points,
e) If the Spearman rank correlation coefficient (r) >=0.9 then additional 1 point was given,
f) Scoring has been done at a level of 1 to 7, where 7 is the highest, 0.5 is the lowest score and 0 is no cross-reactivity. Depending on the above listed parameters a peptide can get a maximum score of 7 and minimum score of 0.5,
g) Final score for a peptide was calculated by adding up the scores earned by homologues and have been mentioned in Table 39 below.

The results of study XR2 has been summarized in the Table 39 below, where specific cross-reactivity scores for the given homologue has been listed. For *Phleum pratense* peptides which did not have an available corresponding sequence in the homologue grass specie, then it was mentioned as "-" and therefore was not tested. The homologues that have not been experimentally tested have been mentioned as "NT" (Not Tested). Some of the homologues were not tested experimentally because they were completely identical, either to the corresponding *Phleum pratense* peptide, or to another tested homologue peptide. Homologue sequences completely identical to a *Phleum pratense* peptide were given highest score (Score 7), while a homologue with identical sequence to another tested homologue was given same score as the tested homologue.

Additionally, homologues of peptide 241 (SEQ ID NO. 113) were measured only in the study XR1 where peptide 241 homologues got the highest score (Score 5) as measure of cross-reactivity. Since 241 was not tested in the study XR2, the cross-reactivity scores from XR1 were taken directly for XR2 study, except score 5 was upgraded to score 7 (highest possible score in XR2 study). All the data has been compiled in Table 39 below:

Table 39: Scoring Used to Rank the Experimental Cross-Reactivity for Selected Peptides Based on Data Obtained from Study XR1 (Peptide SEQ ID NO:113) and XR2 (Remaining Peptides)

TABLE 39

| Peptide name | Cyn d | Dac g | Fes p | Lol p | Pas n | Pha a | Poa p | Sor h | Species covered | Cross-reactivity sum | Cross-reactivity/ species |
|---|---|---|---|---|---|---|---|---|---|---|---|
| 204 | 1.5 | 7 | 7 | 7 | 1 | 7 | 1.5 | 2 | 8 | 34 | 4.25 |
| 207 | 0 | 3 | 6 | 6 | 0.5 | 6 | 1 | — | 5 | 22.5 | 3.2 |
| 211 | 0.5 | 5 | 4 | 4 | 1 | 7 | 3 | 0.5 | 8 | 25 | 3.12 |
| 222 | 1 | — | — | — | — | — | — | — | 1 | 1 | 1 |
| 235 | — | 5 | NT | 6 | — | 6 | 7 | — | 4 | 24 | 6 |
| 238 | — | 5 | 5 | 5 | — | 5 | 4 | — | 5 | 24 | 4.8 |
| 239 | — | 7 | 7 | 7 | — | 6 | 7 | — | 5 | 34 | 6.8 |
| 206 | 0 | 2 | 2 | 2 | 0 | 1 | 0.5 | 0.5 | 8 | 8 | 1 |
| 217 | — | 1 | — | 5 | — | — | NT | — | 2 | 6 | 3 |
| 236 | — | 3 | 3 | 4 | — | 2 | 7 | — | 5 | 19 | 3.8 |
| 285 | — | 6 | 6 | 6 | — | 6 | 7 | — | 5 | 31 | 6.2 |
| 286 | — | 7 | NT | 7 | — | 7 | 7 | — | 4 | 28 | 7 |
| 205 | 2 | 7 | 7 | 7 | — | 6 | 3 | 7 | 7 | 39 | 5 |
| 241 | — | NT | NT | 7 | — | 7 | 7 | — | 3 | 21 | 7 |

Cross-reactivity scores of the peptides were added and the sum was divided by the number of species measured. Peptides were grouped on the basis of degree of cross-reactivity using the scheme below:
0=No cross-reactivity, 0.5 to 2.99=Low cross-reactivity, 3.0 to 4.99=Medium cross-reactivity and 5.0 to 7.0=High cross-reactivity.

The grouping resulted in the following groups:
High cross-reactivity: 241, 239, 235, 285, 286, 205,
Medium cross-reactivity: 204, 207, 211, 238, 217, 236
Low cross-reactivity: 222, 206
Table 40. Peptide 204: Cross-Reactivity of the Tested Homologue

TABLE 40

| SEQ ID NO: | Sequences | Peptide number | Allergen source | Cross-reactivity score | Query % Id | No. diff | Align. length |
|---|---|---|---|---|---|---|---|
| 4 | TDDNEEPIAPYHFDLSGHAF | 204 | Phl p 1 | | | | |
| 246 | TDKNYEHIAAYHFDLSGKAF | 315 | Cyn d 1 | 1.5 | 75.00 | 5 | 20 |
| 247 | TDMNYEPIAPYHFDLSGKAF | 368 | Pas n 1 | 1 | 85.00 | 3 | 20 |
| 248 | TDDNEEPIAAYHFDLSGKAF | 369 | Poa p 1 | 1.5 | 90.00 | 2 | 20 |
| 249 | TDMNYEQIAAYHFDLAGTAF | 370 | Sor h 1 | 2 | 70.00 | 6 | 20 |

Thus, for 204, the homologues of SEQ ID NOs: 246-249 had cross-reactivity of or above 1 as measured using PBMCs from *Phleum pratense* grass pollen allergic donors.

Table 41. Peptide 205: Cross-Reactivity of the Tested Homologue Peptides

TABLE 41

| SEQ ID NO: | Sequences | Peptide number | Allergen source | Cross-reactivity score | Query % Id | No. diff | Align. length |
|---|---|---|---|---|---|---|---|
| 5 | YHFDLSGHAFGAMAKKGDEQ | 205 | Phl_p_1 | | | | |
| 250 | YHFDLSGKAFGAMAKKGEED | 371 | Cyn_d_1 | 2 | 85.00 | 3 | 20 |
| 251 | YHFDLSGHAFGSMAKKGEEQ | 372 | Dac_g_1 | 7 | 90.00 | 2 | 20 |
| 252 | YHFDLSGHAFGSMAKKGEEE | 373 | Pha_a_1 | 6 | 85.00 | 3 | 20 |
| 253 | YHFDLSGKAFGAMAKKGEEQ | 374 | Poa_p_1 | 3 | 90.00 | 2 | 20 |
| 254 | YHFDLAGTAFGAMAKKGEEE | 375 | Sor_h_1 | 7 | 80.00 | 4 | 20 |

Thus, for 205, the homologues of SEQ ID NOs: 250-254 had cross-reactivity above 1 as measured using PBMCs from *Phleum pratense* grass pollen allergic donors, and in particular SEQ ID NOs: 251, 252, 254 had very high reactivity.

Table 42. Peptide 206: Cross-Reactivity of the Tested Homologue Peptides

TABLE 42

| SEQ ID NO: | Sequences | Peptide number | Allergen source | Cross-reactivity score | Query % Id | No. diff | Align. length |
|---|---|---|---|---|---|---|---|
| 6 | GDEQKLRSAGELELQFRRVK | 206 | Phl_p_1 | | | | |
| 255 | GEEDKLRKAGELMLQFRRVK | 376 | Cyn_d_1 | 0 | 80.00 | 4 | 20 |
| 256 | GEEQKLRSAGELELQFRRVK | 377 | Dac_g_1 | 2 | 95.00 | 1 | 20 |
| 257 | GLNDKLRHYGIFDLEFRRVR | 378 | Pas_n_1 | 0 | 75.00 | 5 | 20 |
| 258 | GEEENVRGAGELELQFRRVK | 379 | Pha_a_1 | 1 | 75.00 | 5 | 20 |
| 259 | GEEQKLRSAGELELKFRRVK | 380 | Poa_p_1 | 0.5 | 90.00 | 2 | 20 |
| 260 | GEEEKLRKAGIIDMKFRRVK | 381 | Sor_h_1 | 0.5 | <65.00 | 8 | 20 |

Thus, for 206, the homologues of SEQ ID NOs: 256 and 258 had cross-reactivity of or above 1 as measured using PBMCs from *Phleum pratense* grass pollen allergic donors, and in particular SEQ ID NOs: 256 had cross-reactivity.

Table 43. Peptide 207: Cross-Reactivity of the Tested Homologue Peptides

TABLE 43

| SEQ ID NO: | Sequences | Peptide number | Allergen source | Cross-reactivity score | Query % Id | No. diff | Align. length |
|---|---|---|---|---|---|---|---|
| 7 | AGELELQFRRVKSKYPEGTK | 207 | Phl_p_1 | — | | | |
| 261 | AGELTLQFRRVKSKYPSGTK | 318 | Cyn_d_1 | 0 | 85.00 | 3 | 20 |
| 262 | AGELELQFRRVKSKYPEGTK | 382 | Dac_g_1 | 3 | 95.00 | 1 | 20 |
| 263 | AGELELQFRRVKSKYPDGTK | 383 | Fes_p_1 | 6 | 90.00 | 2 | 20 |

TABLE 43-continued

| SEQ ID NO: Sequences | Peptide number | Allergen source | Cross-reactivity score | Query % Id | No. diff | Align. length |
|---|---|---|---|---|---|---|
| 264 YGIFDLEFRRVRSKYQGGQK | 384 | Pas_n_1 | 0.5 | <65.00 | 9 | 20 |
| 265 AGELELKFRRVKSEYPEGTK | 385 | Poa_p_1 | 1 | 85.00 | 3 | 20 |

Thus, for 207, the homologues of SEQ ID NOs: 262-263 and 265 had cross-reactivity of or above 1 as measured using PBMCs from *Phleum pratense* grass pollen allergic donors, and in particular SEQ ID NOs: 262 and 263 had considerable cross-reactivity.

Table 44. Peptide 211: Cross-Reactivity of the Tested Homologue Peptides

TABLE 44

| SEQ ID NO: Sequences | Peptide number | Allergen source | Cross-reactivity score | Query % Id | No. diff | Align. length |
|---|---|---|---|---|---|---|
| 11 WGAIWRIDTPDKLTGPFTVR | 211 | Phl_p_1 | — | | | |
| 272 WGAIWRIDPPKPLKGPFTIR | 391 | Cyn_d_1 | 0.5 | 75.00 | 5 | 20 |
| 273 WGAIWRVDTPDKLTGPFTVR | 392 | Dac_g_1 | 5 | 95.00 | 1 | 20 |
| 274 WGAVWRIDTPDKLTGPFTVR | 393 | Fes_p_1 | 4 | 95.00 | 1 | 20 |
| 275 WGAIWRMDTPKALVPPFSIR | 394 | Pas_n_1 | 1 | 65.00 | 7 | 20 |
| 276 WGSIWRVDTPDKLTGPFTVR | 395 | Poa_p_1 | 3 | 90.00 | 2 | 20 |
| 277 WGAIWRKDSDKPIKFPVTVQ | 396 | Sor_h_1 | 0.5 | 78.00 | 2 | 9 |

Thus, for 211, the homologues of SEQ ID NOs: 273-276 had cross-reactivity of or above 1 as measured using PBMCs from *Phleum pratense* grass pollen allergic donors, and in particular SEQ ID NOs: 273, 274 and 276 had considerable cross-reactivity.

Table 45. Peptide 217: Cross-Reactivity of the Tested Homologue Peptides

TABLE 45

| SEQ ID NO: Sequences | Peptide number | Allergen source | Cross-reactivity score | Query % Id | No. diff | Align. length |
|---|---|---|---|---|---|---|
| 36 GSDPKKLVLNIKYTRPGDSL | 217 | Phl_p_3 | — | | | |
| 279 GSDAKTLVLNIKYTRPGDTL | 328 | Lol_p_3 | 5 | 0.85 | 3 | 20 |
| 278 GSDPKKLVLDIKYTRPGDTL | 397 | Dac_g_3 | 1 | 0.95 | 1 | 20 |

Thus, for 217, the homologues of SEQ ID NOs: 279 and 278 had cross-reactivity of or above 1 as measured using PBMCs from *Phleum pratense* grass pollen allergic donors, and in particular SEQ ID NOs: 279 had considerable cross-reactivity.

Table 46. Peptide 222: Cross-Reactivity of the Tested Homologue Peptides

TABLE 46

| SEQ ID NO: Sequences | Peptide number | Allergen source | Cross-reactivity score | Query % Id | No. diff | Align. length |
|---|---|---|---|---|---|---|
| 45 KEDFLGSLVKEIPPRLLYAK | 222 | Phl p 4 | — | | | |
| 280 ERDFLTSLTKDIPPRQLYAK | 398 | Cyn d 4 | 1 | 0.7 | 4 | 20 |

Thus, for 222, the homologues of SEQ ID NOs: 280 had cross-reactivity of 1 as measured using PBMCs from *Phleum pratense* grass pollen allergic donors.

Table 47. Peptide 236: Cross-Reactivity of the Tested Homologue Peptides

TABLE 47

| SEQ ID NO: Sequences | Peptide number | Allergen source | Cross-reactivity score | Query % Id | No. diff | Align. length |
|---|---|---|---|---|---|---|
| 69 KVAATAANAAPANDKFTVFE | 236 | Phl p 5 | — | | | |
| 285 KIAATAANAAPANDKFTVFE | 402 | Dac_g_5 | 3 | 95.00 | 1 | 20 |
| 286 KIAATAANAAPTNDKFTVFE | 403 | Lol_p_5 | 4 | 90.00 | 2 | 20 |
| 287 KIAATAANSAPANDKFTVFE | 361 | Pha_a_5 | 2 | 90.00 | 2 | 20 |

Thus, for 236, the homologues of SEQ ID NOs: 285-287 had cross-reactivity of or above 1 as measured using PBMCs from *Phleum pratense* grass pollen allergic donors, and in particular SEQ ID NOs: 285 and 287 had considerable cross-reactivity.

Table 48. Peptide 238: Cross-Reactivity of the Tested Homologue Peptides

TABLE 48

| SEQ ID NO: Sequences | Peptide number | Allergen source | Cross-reactivity score | Query % Id | No. diff | Align. length |
|---|---|---|---|---|---|---|
| 71 STGGAYESYKFIPALEAAVK | 238 | Phl p 5 | — | | | |
| 288 STGGAYESYKFIPTLEAAVK | 404 | Dac g 5 | 5 | 95.00 | 1 | 20 |
| 289 STGGAYETYKFIPSLEAAVK | 405 | Lol p 5 | 5 | 90.00 | 2 | 20 |
| 290 STAGAYETYKFIPSLEAAVK | 363 | Pha a 5 | 5 | 85.00 | 3 | 20 |
| 291 STGGAYQSYKFIPALEAAVK | 406 | Poa p 5 | 4 | 95.00 | 1 | 20 |

Thus, for 238, the homologues of SEQ ID NOs: 288-291 all had considerable cross-reactivity.

Table 49. Peptide 239: Cross-Reactivity of the Tested Homologue Peptides

TABLE 49

| SEQ ID NO: Sequences | Peptide number | Allergen source | Cross-reactivity score | Query % Id | No. diff | Align. length |
|---|---|---|---|---|---|---|
| 72 KFIPALEAAVKQAYAATVAT | 239 | Phl p 5 | — | | | |
| 292 KFIPTLEAAVKQAYAATVAA | 407 | Dac_g_5 | 7 | 90.00 | 2 | 20 |
| 293 KFIPSLEAAVKQAYAATVAA | 408 | Lol_p_5 | 7 | 90.00 | 2 | 20 |

TABLE 49-continued

| SEQ ID NO: Sequences | Peptide number | Allergen source | Cross-reactivity score | Query % Id | No. diff | Align. length |
|---|---|---|---|---|---|---|
| 294 KFIPSLEAAVKQAYGATVAR | 364 | Pha_a_5 | 6 | 85.00 | 3 | 20 |
| 295 KFIPALEAAVKQSYAATVAT | 409 | Poa_p_5 | 7 | 95.00 | 1 | 20 |

Thus, for 239, the homologues of SEQ ID NOs: 292-295 all had high cross-reactivity.

Table 50. Peptide 285: Cross-Reactivity of the Tested Homologue Peptides

TABLE 50

| SEQ ID NO: Sequences | Peptide number | Allergen source | Cross-reactivity score | Query % Id | No. diff | Align. length |
|---|---|---|---|---|---|---|
| 232 AYESYKFIPALEAAVKQAYA | 285 | Phl p 1 | — | | | |
| 300 AYESYKFIPTLEAAVKQAYA | 413 | Dac_g_5 | 6 | 95.00 | 1 | 20 |
| 301 AYETYKFIPSLEAAVKQAYA | 414 | Lol_p_5 | 6 | 90.00 | 2 | 20 |
| 302 AYETYKFIPSLEAAVKQAYG | 415 | Pha_a_5 | 6 | 85.00 | 3 | 20 |
| 303 AYQSYKFIPALEAAVKQSYA | 416 | Poa_p_5 | 1 | 90.00 | 2 | 20 |

Thus, for 285, the homologues of SEQ ID NOs: 300-302 all had high cross-reactivity, and SEQ ID NOs: 416 had cross-reactivity of 1.

Table 51. Peptide 241: Cross-Reactivity of the Tested Homologue Peptides Based on Results from Study XR1

TABLE 51

| SEQ ID NO: Sequences | Peptide number | Allergen source | Cross-reactivity score | Query % Id | No. diff | Align. length |
|---|---|---|---|---|---|---|
| 113 AFKVAATAANAAPAN | 241 | Phl p 5 | — | | | |
| 186 AYRTAATAANAAPAN | 353 | Lol p 5 | 7 | 80.00 | 3 | 15 |
| 199 AFKIAATAANSAPAN | 366 | Pha a 5 | 7 | 86.67 | 2 | 15 |

Thus, for 241, the homologues of SEQ ID NOs: 186 and 199 had very high cross-reactivity as measured using PBMCs from *Phleum pratense* grass pollen allergic donors.

Table 52. Peptide 286: Cross-Reactivity of the Tested Homologue

TABLE 52

| SEQ ID NO: Sequences | Peptide number | Allergen source | Cross-reactivity score | Query % Id | No. diff | Align. length |
|---|---|---|---|---|---|---|
| 233 IEKVDAAFKVAATAANAAPAN | 286 | Phl p 5 | | | | |
| 304 VDKIDAAYKIAATAANAAPAN | 417 | Dac_g_5 | 7 | 81.95 | 5 | 22 |
| 305 VDKIDAAFKIAATAANAAPTN | 418 | Lol_p_5 | 7 | 80.95 | 5 | 22 |
| 306 VDKIDAAFKIAATAANSAPAN | 419 | Pha_a_5 | 7 | 80.95 | 5 | 22 |
| 307 IDKVDAAFKVAATAANAAPAN | 420 | Poa p 5 | 7 | 95.24 | 1 | 21 |

Thus, for 286, the homologues of SEQ ID NOs: 304-307 had very high cross-reactivity as measured using PBMCs from *Phleum pratense* grass pollen allergic donors.

Table 53. Peptide 235: Cross-Reactivity of the Tested Homologue Peptides

TABLE 53

| SEQ ID NO: Sequences | Peptide number | Allergen source | Cross-reactivity score | Query % Id | No. diff | Align. length |
|---|---|---|---|---|---|---|
| 68 IEKVDAAFKVAATAANAAPA | 235 | Phl_p_5 | | | | |
| 281 VDKIDAAYKIAATAANAAPA | 399 | Dac_g_5 | 5 | 80.00 | 5 | 21 |
| 282 VDKIDAAFKIAATAANAAPT | 400 | Lol_p_5 | 6 | 80.00 | 5 | 21 |
| 283 VDKIDAAFKIAATAANSAPA | 360 | Pha_a_5 | 6 | 80.00 | 5 | 21 |
| 284 IDKVDAAFKVAATAANAAPA | 401 | Poa_p_5 | 7 | 95.00 | 1 | 20 |

Thus, for 235, the homologues of SEQ ID NOs: 281-384 had very high cross-reactivity as measured using PBMCs from *Phleum pratense* grass pollen allergic donors.

The results show that a number of the *Phleum pratense* peptides have homologues in other grass species which give rise to T cell responses in grass pollen allergic donors. Peptide 222 has a low score, since only one homolog sequence (from Cyn d) was found in sequence data banks which had 6 substitutions compared to the sequence of peptide 222. It is possible that other more similar homologues derived from other grass species, but which are not included in data banks exist.

The above results indicate that patients which are sensitized to other grass pollen species than *Phleum pratense* may also benefit from treatment with compositions including *Phleum* peptides, given that one or more of these *Phleum pratense* peptides have cross-reactivity.

Example 22

Basophil Activation Testing of Selected Peptide Combinations

It is an object of the present invention to provide compositions for peptide-based immunotherapy (PIT), which have a decreased risk of inducing adverse events potentially resulting in serious anaphylactic responses.

Initiation of such adverse events is characterized by histamine release from basophils and mast cells. Therefore BAT (Basophil activation test) assay is widely used as a predictive in vitro assay for indication of safety/immediate hypersensitivity reactions. Three mixes, a) consisting peptides of SEQ ID NO:4 (204), SEQ ID NO:7 (207), SEQ ID NO:45 (222), SEQ ID NO:71 (238), SEQ ID NO:72 (239) and SEQ ID NO:113 (241); b) consisting peptides of SEQ ID NO:5 (205), SEQ ID NO:36 (217) and SEQ ID NO:232 (285); and c) consisting peptides of SEQ ID NO:36 (217) and SEQ ID NO:232 (285) were tested to verify the inability to trigger histamine release from basophils. Each mix was incubated with the whole blood obtained from grass allergic donors for 1h. The mixes were tested at four different concentrations (60 μM, 24 μM, 6 μM, 0.000038 μM) in duplicates. *Phleum pratense* pollen extract was tested as a positive control for the BAT assay. Upon activation, basophils up-regulate the protein CD63 on their surface. The percentage of activated basophils was determined by measuring CD63 by flow cytometry (FACS). The BAT data obtained for mix a) and b) incubated with whole blood from 23 grass pollen allergic donors indicated that no basophil activation was triggered after incubation of both mixes. Similarly, for mix c), which was incubated with whole blood from 15 grass pollen allergic donors, no basophil activation was seen.

Example 23

Dosage Response of Selected Mixes and Individual Peptides

The present example further relates to dosage response of selected peptide combinations and individual peptides, in particular peptide mixes comprising the peptides 207, 238, 239 and 241.

Dose Response Analysis of Selected Mixes and Individual Peptides

This example includes a description of an additional study of the dose-response relationship for additionally selected single peptides and mixes.

Experimental setups were similar to the setup disclosed in Example 10 with minor differences:

The dose-response was tested by measuring the percentage of responding donors (i.e. the donor coverage) in concentrations of 2.0, 0.133, 0.0088 and 0.00059 μg/ml for single peptides on a set of T cell lines (TCL-03DK1+DK2) derived from 18 grass pollen allergic donors. The donors were selected by seeking to maximize the HLA class II diversity in the donor cohort.

For peptide combinations, two set-ups were used:
A) Concentrations of 2.0, 0.1, 0.005 and 0.00025 μg/ml were tested on a set of T cell lines derived from 9 grass pollen allergic donors (same experiment as the data shown in FIG. 7b). In this way, every single peptide present in the peptide combination had the same concentration as indicated above for that given dose.
B) Concentrations of 2.0, 0.066, 0.0022 and 0.00007 μg/ml were used on a set of T cell lines derived from 18 grass pollen allergic donors (same set as the donors used for testing of single peptides as described above). In this way, every single peptide present in the peptide combination had the same concentration as indicated above for that given dose.

Relative magnitude value for a peptide or a peptide combination was calculated as percentage of highest T cell response to an allergen or a mix, by the same donor. In this way, allergen or peptide combination with highest magnitude of T cell response gets a value of 100 and T cell response magnitude of remaining peptides/peptide combinations are normalized or calculated relative to 100, for example Relative magnitude=100*(T cell response magnitude of peptide or combination/Highest T cell response in a donor). For setup B) above, the highest magnitude of T cell response to *Phleum pratense* pollen extract in each donor was used as 100. For setup A) above, the highest magnitude of T cell response to purified Phl p 1 was used for donors reactive to Phl p 1, else the highest magnitude of the T cell response to purified Phl p 5 for each donor was used as reference.

FIG. 17 includes dosage response data measured on single peptides in an experimental setup using concentrations of 2.0, 0.133, 0.0088 and 0.00059 µg/ml on a set of 18 grass pollen allergic donor derived T cell lines. Due to the differences in the number and identity of donors it is not possible to directly compare the data between FIG. 9 and FIG. 17. Some variance is observed in the percentage of donor response measured for the same peptides (see for example the data on peptide 207 in FIG. 9a and FIG. 17). However, the data demonstrated in FIG. 17 confirmed that most of the peptides retained their immunogenicity at very low concentrations, for example it can be seen that peptide 241 (SEQ ID NO: 113), 235 (SEQ ID NO: 68), 286 (SEQ ID NO: 233), 238 (SEQ ID NO: 71), 239 (SEQ ID NO: 72) and 285 (SEQ ID NO: 232) have a donor response of more than 20% even in the lowest concentration of 0.00059 µg/ml, and that all the peptides included in FIG. 17, that is peptide 204 (SEQ ID NO: 4), peptide 207 (SEQ ID NO: 7), peptide 211 (SEQ ID NO: 11), peptide 222 (SEQ ID NO: 45), peptide 241 (SEQ ID NO: 113), 235 (SEQ ID NO: 68), 286 (SEQ ID NO: 233), 238 (SEQ ID NO: 71), 239 (SEQ ID NO: 72) and 285 (SEQ ID NO: 232) had a percentage of donor response of at least 20% in the low concentration of 0.0088 µg/ml.

FIG. 18, includes dosage response data measured on set-up A) above. The data are derived from the same experiment and cell culture plate as described in Example 10, and are therefore directly comparable to data presented in FIG. 7b. It can be seen that the three combinations 2401, 2402 and 2404 (wherein 2401 is consisting of peptides 207 (SEQ ID NO:7), 235 (SEQ ID NO:68), 238 (SEQ ID NO: 71), and 239 (SEQ ID NO: 72); 2402 is consisting of peptides 207 (SEQ ID NO:7), 241 (SEQ ID NO:113), 238 (SEQ ID NO: 71), and 239 (SEQ ID NO: 72) and 2404 is consisting of peptides 207 (SEQ ID NO:7), 222 (SEQ ID NO:45), 238 (SEQ ID NO: 71), and 239 (SEQ ID NO: 72) all had a donor response (or percentage of responding donors) of 89% even in a low concentration of 0.005 µg/ml, whereas the mix 825 which is a mix of 5 reference peptides has a % donor response of 56% and can only reach a donor response 89% in the highest concentration of 2.0 µg/ml.

FIG. 18 additionally shows that the mix 2610 consisting of peptides 207 (SEQ ID NO:7), 222 (SEQ ID NO:45), 238 (SEQ ID NO: 71), 239 (SEQ ID NO: 72), 241 (SEQ ID NO:113) and 211 (SEQ ID NO:11), had a high donor response in concentrations of 2.0 and 0.1 µg/ml of about 100%, and had a donor response (or percentage of responding donors) of at least 80% even in a low concentration of 0.005 µg/ml. By comparing the data points of each individual concentration of mix 2610 with the corresponding data of mix 825, it is seen that the donor response of mix 2610 is better than the mix 825 for each concentration tested.

FIG. 19 demonstrates the relative magnitude of the T cell response as measured by proliferation of T cell lines (TCL-03DK1+DK2) derived from PBMC5 of 9 grass pollen allergic donors. Relative magnitudes for the indicated mixes were calculated by comparing the magnitude of proliferation response of the mix, to the T cell response magnitude obtained by Phl p 1, from the same donor, as described earlier in detail.

It can be seen from FIG. 19 that the relative magnitude of the T cell response for some donors (see asterisks) was determined to be remarkably increased compared to Phl p 1 which was indexed as 100. The average relative magnitude taken over all 9 donors is shown in black horizontal bars. FIG. 19 demonstrates that in concentrations of 2 or 0.1 µg/ml, mixes 2401, 2402, 2404 and 2610 had an average relative magnitude above 100, whereas the peptide mix 825 (containing peptides of the prior art) did not have an average relative magnitude above 100 when tested in the same concentrations.

FIG. 20 includes dosage response data measured on set-up B) above, which included more donors compared to set-up A). (Due to the differences in the number and identity of donors it is not possible to directly compare the data between FIGS. 18 and 19). From FIG. 20 it can be seen that the peptide combination 5602 (consisting of peptides 207 (SEQ ID NO: 7), 238 (SEQ ID NO: 71), 239 (SEQ ID NO: 72), 241 (SEQ ID NO: 113), 222 (SEQ ID NO: 45) and 204 (SEQ ID NO: 4)), had an even higher donor response than peptide mix 2610 in all concentrations tested.

In summary, the present example and Example 10 above demonstrates that peptide mixes of the invention, for example such as mixes comprising, or consisting of, peptides 207, 238, 239 and 241 are very potent in relation to stimulating an immune response as measured in T cell lines derived from donors, even in low concentrations.

Example 24

Combinations of Selected Peptides and Comparisons Thereof

The present example relates to peptide mixes comprising the peptides 207 (SEQ ID NO:7), 238 (SEQ ID NO:71), 239 (SEQ ID NO:72) and 241 (SEQ ID NO:113) (such as Mix 2402, 2610 and 5602). Additionally, the present example relates to mixes wherein some of the peptides of peptide mixes 2402, 5602 and 2610 are replaced by a peptide selected from peptide 205 (SEQ ID NO:5), peptide 6 (SEQ ID NO:6), peptide 217 (SEQ ID NO:36), peptide 236 (SEQ ID NO:69) and peptide 285 (SEQ ID NO:232) (peptides a) to e) as defined herein).

The above peptide mixes are compared to peptide mixes of the prior art as defined in Table 25 and Example 12.

The peptide mixes were compared as described above in Examples 4 and 12, by calculating:
a) Predicted HLA coverage
b) Predicted HLA DRB1 coverage
c) Predicted peptide binding valency AUC
d) Predicted peptide binding valency
e) Actual peptide binding HLA coverage
f) Actual peptide binding valency
g) Actual peptide binding valency AUC
h) Donor response fraction
i) Donor response valency
j) Donor response valency AUC Wherein the parameters in a) to d) above were calculated by using the 77 alleles in Tables 10 and 11 of Example 2. Parameters in a) to d) were further calculated using 28 alleles which have previously been described as representing the majority (50-75%) of the HLA class II genes expressed worldwide for all four different HLA class II loci (Greenbaum et al. 2011), thus the population of virtual patients generated was a further estimate of a world-wide population. For parameters e) to g), virtual patients were generated by using the 28 alleles disclosed in Greenbaum et al. and parameters were calculated by using the actual binding data for each peptide obtained from in vitro HLA class II binding assays described in Example 11. For all calculations, the frequencies of Tables 10 and 11 of Example 2 were used to generate VPs.

The single peptides were tested in two different experimental set-ups using different donor cohorts (phase I and V, respectively). Therefore, the parameters i) to k) above were calculated on the basis of the results from both studies for peptide mix 2402, 5602 and 2610. The donors in both cohorts were selected by seeking to maximize the diversity of the genotyped HLA alleles in each donor cohort. For phase I, the donor cohort DK1 of 30 grass pollen allergic donors were used which covered a high number of the various HLA class II alleles (see Example 2, Table 12). For phase V, T cells from 18 grass pollen allergic donors from the donor cohort DK2 were used.

Table 54 demonstrates a comparison of the following mixes:

Four Peptide Mixes

Mix 2402 consisting of the four peptides 207 (SEQ ID NO: 7), 238 (SEQ ID NO: 71), 239 (SEQ ID NO: 72) and 241 (SEQ ID NO: 113)).

Six Peptide Mixes

Mix 5602 consisting of the peptides 207 (SEQ ID NO: 7), 238 (SEQ ID NO: 71), 239 (SEQ ID NO: 72), 241 (SEQ ID NO: 113), 204 (SEQ ID NO: 4) and 222 (SEQ ID NO: 45).

Mix 2610 consisting of the peptides 207 (SEQ ID NO: 7), 238 (SEQ ID NO: 71), 239 (SEQ ID NO: 72), 241 (SEQ ID NO: 113), 211 (SEQ ID NO: 11) and 222 (SEQ ID NO: 45).

Table 54 includes parameters calculated on the basis of T cell responses measured using single peptides on PBMCs derived from each patient in a donor cohort. T cell response data are important for evaluating peptide mixes, since a T cell response in a patient not only relies on HLA class II binding, but also on the binding and activation of a T cell receptor. Further, it is important to notice that predictions of peptide HLA class II binding are not always corresponding to what is found in actual HLA class II binding assays. Therefore, the parameters calculated on the basis of actual peptide binding as determined in HLA class II binding assays and ability of a given peptide to elicit a T cell response in a donor cohort may be more important.

In Table 54 below, peptide mixes of the present invention are compared to peptide mixes as mentioned in the prior art (see Table 25 and Example 12). It can be seen that peptide mixes 2402, 5602 and 2610 all had a very high donor fraction of at least 83%, which is considerably increased compared to the mixes comprising peptides of the prior art (see Mix807, Mix814, Mix825 and Ref_mix 1-10) which had a donor fraction ranging of 67-70%. A high fraction of responding donors is considered highly favourable, since it is preferable to use mixes which result in a T cell response in as many patients as possible. The mixes comprising or consisting of peptides 207, 238, 239 and 241 have a donor response fraction of 83-90% (mix 2402), 89-97% (mix 5602) and 93-94% (2610), which suggests that very few patients would not have a T cell reaction when treated with such mixes. In contrast, for the mixes comprising peptides of the prior art, the donor response fraction is not above 70%, which suggests that about 30% or more of grass pollen allergic patients will not have a T cell reaction towards these proposed mixes of the prior art.

The donor response valency AUC in Table 54 further reflects that a high fraction of donors have a T cell reaction towards at least one peptide of the peptide mixes comprising or consisting of peptides 207, 238, 239 and 241. For mix 2402, the donor response valency AUC is 0.51 and 0.49, for Study I and V, respectively. Mixes of the prior art (comprising up to 8 peptides) all have lower donor response valency AUC of 0.46-0.24.

The donor response valency of peptide mixes 2402, 5602 and 2610 (all comprising or consisting of peptides 207, 238, 239 and 241) have a relatively high donor response valency of 1.9 or higher, indicating that on average, an individual donor has T cell response to about two or more peptides of the mix (see Table 54). For mix 5602, the donor response valency was 2.6 and 2.7 (phase I and V, respectively), and for mix 2610 the the donor response valency was 2.7 for both phase I and V. By comparing with the mixes of the prior art it can be seen that only the peptide mix Ref_mix1 gave a donor response valency of 2.0, whereas the remaining prior art mixes had lower donor response valencies of 1.1-1.8. Thus, the results indicate that the fractions of donors which respond to 2, 3 and 4 peptides in a mix is higher for peptide mixes 2402, 5602 and 2610 than for peptide mixes of the prior art.

With respect to the predicted HLA coverage (as calculated based on different virtual populations of 10,000 individuals which are estimates of a real world-wide population), peptide mix 2402 as well as mixes 2610 and 5602 all had a very high HLA coverage of 98 to 100% when predicted on the basis of both 77 alleles and 28 alleles as mentioned above. Further, the peptide mixes 2402, 2610 and 5602 all had an actual peptide binding coverage of 98 to 100%. Thus, the fraction of VPs which were not predicted to bind at least one peptide was minuscule.

Table 54. Comparison of Peptide Mixes Comprising Four Peptides, Including Peptide Mix 2402 and Prior Art Mixes

TABLE 54

Comparison of peptide mixes 2402, 5602 and 2610 to mixes of the prior art

| Replaced | No of peptides | Predicted Valency AUC 77 alleles | Predicted Average Valency 77 alleles | Predicted Valency AUC 28 alleles | Predicted Average Valency 28 alleles | Actual Binding Valency AUC | Actual Binding Valency | Donor response fraction | Donor Response Valency AUC | Donor Response Valency | Phase |
|---|---|---|---|---|---|---|---|---|---|---|---|
| Mix2610 | 6 | 0.98 | 4.7 | 0.9 | 4.4 | 1.00 | 5.6 | 93% | 0.66 | 2.7 | I |
| Mix2610 | 6 | 0.98 | 4.7 | 0.9 | 4.4 | 1.00 | 5.6 | 94% | 0.63 | 2.7 | V |
| Mix5602 | 6 | 0.97 | 4.5 | 0.9 | 4.2 | 0.99 | 5.4 | 89% | 0.65 | 2.7 | V |
| Mix5602 | 6 | 0.97 | 4.5 | 0.9 | 4.2 | 0.99 | 5.4 | 97% | 0.63 | 2.6 | I |
| Mix2402 | 4 | 0.85 | 3.3 | 0.8 | 3.0 | 0.94 | 3.6 | 90% | 0.51 | 2.0 | I |
| Mix2402 | 4 | 0.85 | 3.3 | 0.8 | 3.0 | 0.94 | 3.7 | 83% | 0.49 | 1.9 | V |
| Ref_mix1 | 8 | 0.91 | 4.2 | 0.9 | 4.0 | 0.99 | 5.7 | 70% | 0.46 | 2.0 | I |
| Mix_807 | 7 | 0.75 | 3.2 | 0.7 | 3.1 | 0.97 | 4.9 | 70% | 0.42 | 1.8 | I |
| Ref_mix2 | 7 | 0.90 | 3.7 | 0.9 | 3.5 | 0.99 | 5.1 | 70% | 0.44 | 1.8 | I |
| Ref_mix7 | 6 | 0.84 | 3.4 | 0.8 | 3.3 | 0.95 | 4.5 | 67% | 0.38 | 1.6 | I |
| Ref_mix9 | 5 | 0.84 | 3.4 | 0.8 | 3.2 | 0.93 | 3.8 | 67% | 0.36 | 1.5 | I |

TABLE 54-continued

Comparison of peptide mixes 2402, 5602 and 2610 to mixes of the prior art

| Replaced | No of peptides | Predicted Valency AUC 77 alleles | Predicted Average Valency 77 alleles | Predicted Valency AUC 28 alleles | Predicted Average Valency 28 alleles | Actual Binding Valency AUC | Actual Binding Valency | Donor response fraction | Donor Response Valency AUC | Donor Response Valency | Phase |
|---|---|---|---|---|---|---|---|---|---|---|---|
| Ref_mix3 | 6 | 0.61 | 2.4 | 0.6 | 2.3 | 0.86 | 3.7 | 67% | 0.32 | 1.4 | I |
| Ref_mix5 | 5 | 0.61 | 2.4 | 0.6 | 2.3 | 0.79 | 3.0 | 67% | 0.29 | 1.3 | I |
| Ref_mix10 | 4 | 0.79 | 3.0 | 0.7 | 2.8 | 0.86 | 3.2 | 67% | 0.31 | 1.3 | I |
| Mix_825 | 5 | 0.61 | 2.4 | 0.6 | 2.3 | 0.85 | 3.5 | 67% | 0.30 | 1.3 | I |
| Ref_mix4 | 5 | 0.49 | 2.0 | 0.5 | 1.9 | 0.79 | 3.1 | 67% | 0.28 | 1.2 | I |
| Ref_mix6 | 4 | 0.49 | 2.0 | 0.5 | 1.9 | 0.63 | 2.4 | 67% | 0.24 | 1.1 | I |
| Ref_mix8 | 4 | 0.49 | 2.0 | 0.5 | 1.9 | 0.75 | 2.9 | 67% | 0.24 | 1.1 | I |
| Mix_814 | 4 | 0.49 | 2.0 | 0.5 | 1.9 | 0.75 | 2.9 | 67% | 0.24 | 1.1 | I |

Table 54 further includes parameters calculated on the basis of virtual patients generated by using the 28 HLA alleles mentioned in Greenbaum et al., used in combination with actual binding data from in vitro HLA class II binding assays. With respect to these parameters, it can be seen that mix 2402 consisting of 4 peptides had an actual binding valency of 3.6 and 3.7 (phase I and V, respectively), which demonstrates that an average virtual patient was able to bind 3 to 4 four peptides of the four peptide mix. In comparison, the prior art mixes Ref_mix10, Ref_mix 6, Ref_mix 8 and Mix814 (which also consist of four peptides) had actual binding valencies of 3.0, 2.9, 2.9 and 2.4, respectively.

Peptide mixes 5602 and 2610 both comprise 6 peptides. The actual binding valency for peptide mixes 5602 and 2610 were 5.4 and 5.6, respectively. This is considerably higher than most of the mixes of the prior art, except Ref_mix 1 which had an actual binding valency of 5.7.

Thus to conclude, peptide mixes comprising peptides 207, 238, 239 and 241 all had increased donor response fraction and donor response valency AUC as well as a comparable or increased donor response valency compared to peptide mixes of the prior art. These numbers illustrate that the fraction of donors not responding to any peptide in a mix was decreased, while at the same time, a larger fraction of donors responded to more than one peptide of a mix. At the same time, the actual binding valency and the predicted binding valency (based on 77 or 28 HLA class II alleles) were increased compared to mixes of the prior art which included the same amount of peptides.

Mixes Wherein One or More Peptides are Selected from Peptides a) to e)

Table 55 below demonstrates a comparison of peptide mixes with the basis in 2402 (see the top two rows, where the parameters for mix 2402 is calculated with donor responses from both phase I and V), and mixes with basis in 2402 wherein one of the peptides 207, 238, 239 or 241 is replaced by a peptide a) to e). (For example the third row denotes a mix wherein the peptide 207 is replaced by 236 and further comprising the peptides 238, 239 and 241). It can be seen that donor response valency calculated for each of these "replacement mixes" were the same as mix 2402 or higher, and higher than all reference mixes, except Ref_mix1. At the same time, the donor response fraction for all the mixes except the one wherein 207 was replaced by 285 were higher than the mixes of the prior art (in general above 80%, except for a few mixes). Similarly, with respect to the donor response valency AUC, the AUC is 0.49 or higher for most mixes, which is also the case for peptide mix 2402, while the donor response valency AUC for the prior art mixes is lower and ranges between 0.24 to 0.46.

Table 55. Comparison of Peptide Mix 2402 to Similar Mixes Comprising Peptides a) to e)

TABLE 55

Comparison of peptide mix 2402 to similar mixes comprising peptides a) to e)

| Replaced | Replacement | Number of peptides | Predicted peptide binding valency AUC 77 alleles | Predicted peptide binding valency 77 alleles | Predicted peptide binding valency AUC 28 alleles | Predicted peptide binding valency 28 alleles | Actual peptide binding valency AUC | Actual peptide binding valency | Donor response fraction | Donor response valency AUC | Donor response valency | Phase |
|---|---|---|---|---|---|---|---|---|---|---|---|---|
| Mix2402 | | 4 | 0.85 | 3.3 | 0.77 | 3.0 | 0.94 | 3.6 | 90% | 0.51 | 2.0 | I |
| Mix2402 | | 4 | 0.85 | 3.3 | 0.77 | 3.0 | 0.94 | 3.7 | 83% | 0.49 | 1.9 | V |
| 207 | 236 | 4 | 0.73 | 2.9 | 0.69 | 2.8 | 0.97 | 3.8 | 77% | 0.57 | 2.2 | I |
| 207 | 217 | 4 | 0.81 | 3.1 | 0.70 | 2.6 | 0.99 | 3.9 | 87% | 0.55 | 2.2 | I |
| 238 | 236 | 4 | 0.69 | 2.7 | 0.63 | 2.4 | 0.91 | 3.5 | 90% | 0.53 | 2.1 | I |
| 207 | 205 | 4 | 0.72 | 2.9 | 0.68 | 2.7 | 0.97 | 3.8 | 87% | 0.51 | 2.1 | I |
| 207 | 206 | 4 | 0.67 | 2.5 | 0.63 | 2.3 | 0.95 | 3.6 | 87% | 0.52 | 2.1 | I |
| 238 | 217 | 4 | 0.76 | 2.9 | 0.60 | 2.3 | 0.94 | 3.6 | 93% | 0.52 | 2.1 | I |
| 239 | 236 | 4 | 0.77 | 3.0 | 0.69 | 2.7 | 0.91 | 3.5 | 90% | 0.52 | 2.1 | I |
| 207 | 285 | 4 | 0.89 | 3.5 | 0.85 | 3.3 | N/A | N/A | 67% | 0.52 | 2.1 | V |
| 238 | 205 | 4 | 0.68 | 2.7 | 0.61 | 2.4 | 0.90 | 3.5 | 93% | 0.50 | 2.0 | I |
| 238 | 206 | 4 | 0.61 | 2.3 | 0.52 | 2.0 | 0.88 | 3.4 | 90% | 0.51 | 2.0 | I |
| 239 | 217 | 4 | 0.83 | 3.1 | 0.66 | 2.5 | 0.94 | 3.6 | 93% | 0.51 | 2.0 | I |
| 238 | 285 | 4 | 0.85 | 3.3 | 0.77 | 3.0 | N/A | N/A | 78% | 0.51 | 2.0 | V |
| 239 | 285 | 4 | 0.92 | 3.5 | 0.85 | 3.2 | N/A | N/A | 83% | 0.51 | 2.0 | V |
| 241 | 285 | 4 | 0.92 | 3.6 | 0.86 | 3.3 | N/A | N/A | 78% | 0.51 | 2.0 | V |
| 239 | 205 | 4 | 0.75 | 2.9 | 0.67 | 2.6 | 0.91 | 3.5 | 93% | 0.49 | 2.0 | I |

TABLE 55-continued

Comparison of peptide mix 2402 to similar mixes comprising peptides a) to e)

| Replaced | Replacement | Number of peptides | Predicted peptide binding valency AUC 77 alleles | Predicted peptide binding valency 77 alleles | Predicted peptide binding valency AUC 28 alleles | Predicted peptide binding valency 28 alleles | Actual peptide binding valency AUC | Actual peptide binding valency | Donor response fraction | Donor response valency AUC | Donor response valency | Phase |
|---|---|---|---|---|---|---|---|---|---|---|---|---|
| 239 | 206 | 4 | 0.68 | 2.5 | 0.59 | 2.2 | 0.88 | 3.4 | 90% | 0.50 | 2.0 | I |
| 241 | 236 | 4 | 0.79 | 3.0 | 0.73 | 2.8 | 0.92 | 3.6 | 80% | 0.51 | 2.0 | I |
| 241 | 217 | 4 | 0.84 | 3.2 | 0.69 | 2.6 | 0.95 | 3.7 | 80% | 0.51 | 1.9 | I |
| 241 | 205 | 4 | 0.78 | 3.0 | 0.71 | 2.7 | 0.92 | 3.6 | 83% | 0.47 | 1.9 | I |
| 241 | 206 | 4 | 0.70 | 2.6 | 0.62 | 2.3 | 0.89 | 3.4 | 77% | 0.50 | 1.9 | I |
| Ref_mix1 | | 8 | 0.91 | 4.2 | 0.87 | 4.0 | 0.99 | 5.7 | 70% | 0.46 | 2.0 | I |
| Mix_807 | | 7 | 0.75 | 3.2 | 0.74 | 3.1 | 0.97 | 4.9 | 70% | 0.42 | 1.8 | I |
| Ref_mix2 | | 7 | 0.90 | 3.7 | 0.87 | 3.5 | 0.99 | 5.1 | 70% | 0.44 | 1.8 | I |
| Ref_mix7 | | 6 | 0.84 | 3.4 | 0.79 | 3.3 | 0.95 | 4.5 | 67% | 0.38 | 1.6 | I |
| Ref_mix9 | | 5 | 0.84 | 3.4 | 0.79 | 3.2 | 0.93 | 3.8 | 67% | 0.36 | 1.5 | I |
| Ref_mix3 | | 6 | 0.61 | 2.4 | 0.59 | 2.3 | 0.86 | 3.7 | 67% | 0.32 | 1.4 | I |
| Ref_mix5 | | 5 | 0.61 | 2.4 | 0.58 | 2.3 | 0.79 | 3.0 | 67% | 0.29 | 1.3 | I |
| Ref_mix10 | | 4 | 0.79 | 3.0 | 0.74 | 2.8 | 0.86 | 3.2 | 67% | 0.31 | 1.3 | I |
| Mix_825 | | 5 | 0.61 | 2.4 | 0.59 | 2.3 | 0.85 | 3.5 | 67% | 0.30 | 1.3 | I |
| Ref_mix4 | | 5 | 0.49 | 2.0 | 0.46 | 1.9 | 0.79 | 3.1 | 67% | 0.28 | 1.2 | I |
| Ref_mix6 | | 4 | 0.49 | 2.0 | 0.46 | 1.9 | 0.63 | 2.4 | 67% | 0.24 | 1.1 | I |
| Ref_mix8 | | 4 | 0.49 | 2.0 | 0.46 | 1.9 | 0.75 | 2.9 | 67% | 0.24 | 1.1 | I |
| Mix_814 | | 4 | 0.49 | 2.0 | 0.46 | 1.9 | 0.75 | 2.9 | 67% | 0.24 | 1.1 | I |

With respect to the actual peptide binding valency, and actual peptide binding valency AUC it can be seen in Table 55 that the "replacement mixes" comprising peptides a) to e) had higher values than the peptide mixes of the prior art which consisted of four peptides.

Table 56 below demonstrates a comparison of peptide mixes with the basis of 5602 (see the two top rows, where the parameters for mix 2402 is calculated with donor responses from both phase I and V), and "replacement mixes" with basis in 5602 wherein one of the peptides 204, 207, 222, 238, 239 or 241 is replaced by a peptide a) to e). (For example the third row denotes a mix wherein the peptide 222 is replaced by 236 and further comprising the peptides 204, 207, 238, 239 and 241). It can be seen in Table 56 that the donor response fraction was 83% or above for all the mixes of the present invention which was increased compared to the reference mixes of the prior art which had donor response fraction of 67 or 70%. Similarly, with respect to the donor response valency AUC, the AUC is 0.59 or higher, which is increased compared to all the mixes of the prior art (ranging between 0.24 and 0.46). It can be further seen in Table 56, that the donor response valency is 2.5 or above for all mixes of the invention which is improved compared to reference mixes of the prior art, which had donor response valency of 1.1 to 2.0.

Table 56 further shows that the actual peptide binding valency of the mixes of the invention ranged between 5.1 and 5.7, whereas the mixes of the prior art ranged between 2.9 to 5.7. Further, actual peptide binding valency AUC of the mixes of the invention ranged between 0.98 and 1.00, whereas actual peptide binding valency AUC of peptide mixes of the prior art ranged between 0.75 and 0.99. By comparing the peptide mixes 5602 and mixes with the basis in 5602 with other prior art mixes consisting of 6 peptides (Ref_mix 7 and Ref mix3) it can be seen that the peptide mixes of the invention had increased actual peptide binding valency and actual peptide binding valency AUC.

Table 56. Comparison of Peptide Mix 5602 with Similar Mixes Comprising Peptides a) to e)

TABLE 56

Comparison of peptide mix 5602 to similar mixes comprising peptides a) to e)

| Replaced | Replacement | No of peptides | Predicted peptide binding valency AUC 77 alleles | Predicted peptide binding valency 77 alleles | Predicted peptide binding valency AUC 28 alleles | Predicted peptide binding valency 28 alleles | Actual peptide binding valency AUC | Actual peptide binding valency | Donor response fraction | Donor response valency AUC | Donor response valency | Phase |
|---|---|---|---|---|---|---|---|---|---|---|---|---|
| Mix5602 | | 6 | 0.97 | 4.5 | 0.93 | 4.2 | 0.99 | 5.4 | 89% | 0.65 | 2.7 | V |
| Mix5602 | | 6 | 0.97 | 4.5 | 0.93 | 4.2 | 0.99 | 5.4 | 97% | 0.63 | 2.6 | I |
| 222 | 236 | 6 | 0.89 | 4.0 | 0.82 | 3.7 | 0.98 | 5.3 | 97% | 0.68 | 3.0 | I |
| 222 | 217 | 6 | 0.94 | 4.1 | 0.85 | 3.5 | 0.99 | 5.4 | 97% | 0.70 | 3.0 | I |
| 222 | 285 | 6 | 0.97 | 4.5 | 0.92 | 4.2 | N/A | N/A | 89% | 0.65 | 2.9 | V |
| 222 | 205 | 6 | 0.88 | 3.9 | 0.82 | 3.6 | 0.98 | 5.3 | 97% | 0.66 | 2.9 | I |
| 222 | 206 | 6 | 0.88 | 3.5 | 0.80 | 3.2 | 0.98 | 5.1 | 97% | 0.67 | 2.9 | I |
| 204 | 236 | 6 | 0.96 | 4.7 | 0.91 | 4.4 | 0.99 | 5.5 | 90% | 0.67 | 2.8 | I |
| 207 | 236 | 6 | 0.91 | 4.2 | 0.88 | 4.1 | 1.00 | 5.6 | 90% | 0.65 | 2.8 | I |
| 204 | 285 | 6 | 0.99 | 5.3 | 0.97 | 4.9 | N/A | N/A | 83% | 0.62 | 2.8 | V |
| 207 | 285 | 6 | 0.98 | 4.7 | 0.96 | 4.6 | N/A | N/A | 89% | 0.62 | 2.8 | V |
| 204 | 217 | 6 | 0.99 | 4.9 | 0.93 | 4.2 | 1.00 | 5.6 | 93% | 0.67 | 2.8 | I |
| 207 | 217 | 6 | 0.97 | 4.3 | 0.92 | 3.9 | 1.00 | 5.7 | 97% | 0.65 | 2.8 | I |

TABLE 56-continued

Comparison of peptide mix 5602 to similar mixes comprising peptides a) to e)

| Replaced | Replacement | No of peptides | Predicted peptide binding valency AUC 77 alleles | Predicted peptide binding valency 77 alleles | Predicted peptide binding valency AUC 28 alleles | Predicted peptide binding valency 28 alleles | Actual peptide binding valency AUC | Actual peptide binding valency | Donor response fraction | Donor response valency AUC | Donor response valency | Phase |
|---|---|---|---|---|---|---|---|---|---|---|---|---|
| 238 | 236 | 6 | 0.89 | 4.0 | 0.83 | 3.7 | 0.98 | 5.3 | 97% | 0.66 | 2.7 | I |
| 238 | 285 | 6 | 0.97 | 4.5 | 0.93 | 4.2 | N/A | N/A | 89% | 0.65 | 2.7 | V |
| 239 | 285 | 6 | 0.99 | 4.7 | 0.97 | 4.5 | N/A | N/A | 89% | 0.67 | 2.7 | V |
| 241 | 285 | 6 | 0.99 | 4.8 | 0.97 | 4.6 | N/A | N/A | 83% | 0.65 | 2.7 | V |
| 204 | 205 | 6 | 0.96 | 4.7 | 0.91 | 4.4 | 0.99 | 5.5 | 93% | 0.63 | 2.7 | I |
| 207 | 205 | 6 | 0.91 | 4.1 | 0.88 | 4.0 | 0.99 | 5.6 | 90% | 0.61 | 2.7 | I |
| 204 | 206 | 6 | 0.96 | 4.3 | 0.91 | 4.0 | 1.00 | 5.3 | 90% | 0.66 | 2.7 | I |
| 207 | 206 | 6 | 0.91 | 3.7 | 0.88 | 3.6 | 1.00 | 5.4 | 97% | 0.63 | 2.7 | I |
| 238 | 217 | 6 | 0.94 | 4.1 | 0.85 | 3.5 | 0.99 | 5.4 | 97% | 0.67 | 2.7 | I |
| 239 | 236 | 6 | 0.95 | 4.2 | 0.90 | 3.9 | 0.98 | 5.3 | 97% | 0.65 | 2.7 | I |
| 238 | 205 | 6 | 0.89 | 3.9 | 0.82 | 3.6 | 0.98 | 5.3 | 97% | 0.61 | 2.6 | I |
| 238 | 206 | 6 | 0.88 | 3.5 | 0.81 | 3.2 | 0.98 | 5.1 | 97% | 0.65 | 2.6 | I |
| 239 | 217 | 6 | 0.97 | 4.4 | 0.91 | 3.8 | 0.99 | 5.4 | 97% | 0.65 | 2.6 | I |
| 239 | 205 | 6 | 0.95 | 4.2 | 0.90 | 3.9 | 0.98 | 5.3 | 97% | 0.60 | 2.6 | I |
| 239 | 206 | 6 | 0.94 | 3.8 | 0.88 | 3.5 | 0.99 | 5.1 | 97% | 0.64 | 2.6 | I |
| 241 | 236 | 6 | 0.95 | 4.3 | 0.91 | 4.1 | 0.99 | 5.3 | 93% | 0.62 | 2.6 | I |
| 241 | 217 | 6 | 0.97 | 4.4 | 0.92 | 3.9 | 1.00 | 5.5 | 90% | 0.63 | 2.5 | I |
| 241 | 205 | 6 | 0.95 | 4.2 | 0.91 | 4.0 | 0.98 | 5.3 | 90% | 0.59 | 2.5 | I |
| 241 | 206 | 6 | 0.94 | 3.8 | 0.89 | 3.6 | 0.99 | 5.2 | 90% | 0.62 | 2.5 | I |
| Ref_mix1 | | 8 | 0.91 | 4.2 | 0.87 | 4.0 | 0.99 | 5.7 | 70% | 0.46 | 2.0 | I |
| Mix_807 | | 7 | 0.75 | 3.2 | 0.74 | 3.1 | 0.97 | 4.9 | 70% | 0.42 | 1.8 | I |
| Ref_mix2 | | 7 | 0.90 | 3.7 | 0.87 | 3.5 | 0.99 | 5.1 | 70% | 0.44 | 1.8 | I |
| Ref_mix7 | | 6 | 0.84 | 3.4 | 0.79 | 3.3 | 0.95 | 4.5 | 67% | 0.38 | 1.6 | I |
| Ref_mix9 | | 5 | 0.84 | 3.4 | 0.79 | 3.2 | 0.93 | 3.8 | 67% | 0.36 | 1.5 | I |
| Ref_mix3 | | 6 | 0.61 | 2.4 | 0.59 | 2.3 | 0.86 | 3.7 | 67% | 0.32 | 1.4 | I |
| Ref_mix5 | | 5 | 0.61 | 2.4 | 0.58 | 2.3 | 0.79 | 3.0 | 67% | 0.29 | 1.3 | I |
| Ref_mix10 | | 4 | 0.79 | 3.0 | 0.74 | 2.8 | 0.86 | 3.2 | 67% | 0.31 | 1.3 | I |
| Mix_825 | | 5 | 0.61 | 2.4 | 0.59 | 2.3 | 0.85 | 3.5 | 67% | 0.30 | 1.3 | I |
| Ref_mix4 | | 5 | 0.49 | 2.0 | 0.46 | 1.9 | 0.79 | 3.1 | 67% | 0.28 | 1.2 | I |
| Ref_mix6 | | 4 | 0.49 | 2.0 | 0.46 | 1.9 | 0.63 | 2.4 | 67% | 0.24 | 1.1 | I |
| Ref_mix8 | | 4 | 0.49 | 2.0 | 0.46 | 1.9 | 0.75 | 2.9 | 67% | 0.24 | 1.1 | I |
| Mix_814 | | 4 | 0.49 | 2.0 | 0.46 | 1.9 | 0.75 | 2.9 | 67% | 0.24 | 1.1 | I |

Table 57 below demonstrates a comparison of peptide mixes with the basis of 2610 (see the two top rows, where the parameters for mix 2610 is calculated with donor responses from both phase I and V), and "replacement mixes" with basis in 2610 wherein one of the peptides 211, 207, 222, 238, 239 or 241 is replaced by a peptide a) to e). (For example the third row denotes a mix wherein the peptide 222 is replaced by 236 and further comprising the peptides 211, 207, 238, 239 and 241).

It can be seen in Table 57 that the donor response fraction was 83% or above for all the mixes of the present invention which was increased compared to the reference mixes of the prior art which had donor response fraction of 67 or 70%. Similarly, with respect to the donor response valency AUC, the AUC is 0.59 or higher, which is increased compared to all the mixes of the prior art (ranging between 0.24 and 0.46). It can be further seen in Table 57, that the donor response valency is 2.5 or above for all mixes of the invention which is improved compared to reference mixes of the prior art, which had donor response valency of 1.1 to 2.0.

Table 57 further shows that the actual peptide binding valency of the mixes of the invention ranged between 5.1 and 5.8, whereas the mixes of the prior art ranged between 2.9 to 5.7. Further, actual peptide binding valency AUC of the mixes of the invention were 0.99 or 1.00, whereas actual peptide binding valency AUC of peptide mixes of the prior art ranged between 0.75 and 0.99. By comparing the peptide mixes 2610 and "replacement mixes" with the basis in 2610 with other prior art mixes consisting of 6 peptides (Ref_mix 7 and Ref mix3) it can be seen that the peptide mixes of the invention had increased actual peptide binding valency and actual peptide binding valency AUC.

Thus to conclude, the results of the present example demonstrate that the mixes comprising the peptides 207, 238, 239 and 241, and further those wherein one of the peptides is replaced by one of the peptide a) to e) are highly potent in T cell donor response assays where an increased number of donors respond to the mixes compared to mixes of the prior art.

Table 57. Comparison of Peptide Mix 2610 to Similar Mixes Comprising Peptides a) to e)

TABLE 57

Comparison of peptide mix 2610 to similar mixes comprising peptides a) to e)

| Replaced | Replacement | No of peptides | Predicted peptide binding valency AUC 77 alleles | Predicted peptide binding valency 77 alleles | Predicted peptide binding valency AUC 28 alleles | Predicted peptide binding valency 28 alleles | Actual peptide binding valency AUC | Actual peptide binding valency | Donor response fraction | Donor response valency AUC | Donor response valency | Phase |
|---|---|---|---|---|---|---|---|---|---|---|---|---|
| Mix2610 |  | 6 | 0.98 | 4.7 | 0.94 | 4.4 | 1.00 | 5.6 | 93% | 0.66 | 2.7 | I |
| Mix2610 |  | 6 | 0.98 | 4.7 | 0.94 | 4.4 | 1.00 | 5.6 | 94% | 0.63 | 2.7 | V |
| 222 | 236 | 6 | 0.91 | 4.2 | 0.85 | 3.9 | 0.99 | 5.4 | 93% | 0.70 | 3.1 | I |
| 222 | 217 | 6 | 0.96 | 4.3 | 0.86 | 3.7 | 0.99 | 5.5 | 93% | 0.71 | 3.0 | I |
| 222 | 205 | 6 | 0.91 | 4.1 | 0.84 | 3.8 | 0.99 | 5.4 | 97% | 0.67 | 3.0 | I |
| 222 | 206 | 6 | 0.90 | 3.7 | 0.83 | 3.4 | 0.99 | 5.3 | 93% | 0.70 | 3.0 | I |
| 222 | 285 | 6 | 0.98 | 4.7 | 0.93 | 4.4 | N/A | N/A | 94% | 0.62 | 2.9 | V |
| 207 | 236 | 6 | 0.93 | 4.4 | 0.90 | 4.2 | 1.00 | 5.7 | 93% | 0.66 | 2.9 | I |
| 207 | 217 | 6 | 0.98 | 4.5 | 0.92 | 4.1 | 1.00 | 5.8 | 93% | 0.67 | 2.8 | I |
| 211 | 236 | 6 | 0.96 | 4.7 | 0.91 | 4.4 | 0.99 | 5.5 | 90% | 0.67 | 2.8 | I |
| 238 | 236 | 6 | 0.91 | 4.2 | 0.85 | 3.9 | 0.99 | 5.4 | 93% | 0.68 | 2.8 | I |
| 207 | 285 | 6 | 0.99 | 4.9 | 0.97 | 4.7 | N/A | N/A | 89% | 0.59 | 2.8 | V |
| 211 | 285 | 6 | 0.99 | 5.3 | 0.97 | 4.9 | N/A | N/A | 83% | 0.62 | 2.8 | V |
| 207 | 205 | 6 | 0.93 | 4.3 | 0.90 | 4.2 | 1.00 | 5.7 | 97% | 0.62 | 2.8 | I |
| 207 | 206 | 6 | 0.93 | 3.9 | 0.90 | 3.8 | 1.00 | 5.5 | 93% | 0.65 | 2.8 | I |
| 211 | 217 | 6 | 0.99 | 4.9 | 0.93 | 4.2 | 1.00 | 5.6 | 93% | 0.67 | 2.8 | I |
| 238 | 217 | 6 | 0.96 | 4.3 | 0.87 | 3.7 | 0.99 | 5.5 | 93% | 0.68 | 2.8 | I |
| 239 | 236 | 6 | 0.96 | 4.4 | 0.92 | 4.1 | 0.99 | 5.4 | 93% | 0.66 | 2.7 | I |
| 238 | 285 | 6 | 0.98 | 4.7 | 0.94 | 4.4 | N/A | N/A | 94% | 0.63 | 2.7 | V |
| 239 | 285 | 6 | 1.00 | 4.9 | 0.98 | 4.6 | N/A | N/A | 94% | 0.63 | 2.7 | V |
| 241 | 285 | 6 | 0.99 | 5.0 | 0.98 | 4.7 | N/A | N/A | 89% | 0.64 | 2.7 | V |
| 211 | 205 | 6 | 0.96 | 4.7 | 0.91 | 4.4 | 0.99 | 5.5 | 93% | 0.63 | 2.7 | I |
| 238 | 205 | 6 | 0.91 | 4.1 | 0.85 | 3.8 | 0.99 | 5.4 | 97% | 0.63 | 2.7 | I |
| 211 | 206 | 6 | 0.96 | 4.3 | 0.91 | 3.9 | 1.00 | 5.3 | 90% | 0.66 | 2.7 | I |
| 238 | 206 | 6 | 0.91 | 3.7 | 0.84 | 3.4 | 0.99 | 5.3 | 93% | 0.67 | 2.7 | I |
| 239 | 217 | 6 | 0.98 | 4.6 | 0.92 | 3.9 | 1.00 | 5.5 | 93% | 0.67 | 2.7 | I |
| 239 | 205 | 6 | 0.96 | 4.4 | 0.92 | 4.1 | 0.99 | 5.4 | 97% | 0.63 | 2.6 | I |
| 239 | 206 | 6 | 0.96 | 3.9 | 0.91 | 3.6 | 0.99 | 5.3 | 93% | 0.67 | 2.6 | I |
| 241 | 236 | 6 | 0.96 | 4.5 | 0.93 | 4.2 | 1.00 | 5.5 | 90% | 0.64 | 2.6 | I |
| 241 | 217 | 6 | 0.98 | 4.6 | 0.93 | 4.0 | 1.00 | 5.6 | 87% | 0.66 | 2.6 | I |
| 241 | 205 | 6 | 0.96 | 4.4 | 0.92 | 4.2 | 0.99 | 5.5 | 90% | 0.61 | 2.5 | I |
| 241 | 206 | 6 | 0.96 | 4.0 | 0.91 | 3.7 | 0.99 | 5.3 | 87% | 0.64 | 2.5 | I |
| Ref_mix1 |  | 8 | 0.91 | 4.2 | 0.87 | 4.0 | 0.99 | 5.7 | 70% | 0.46 | 2.0 | I |
| Mix_807 |  | 7 | 0.75 | 3.2 | 0.74 | 3.1 | 0.97 | 4.9 | 70% | 0.42 | 1.8 | I |
| Ref_mix2 |  | 7 | 0.90 | 3.7 | 0.87 | 3.5 | 0.99 | 5.1 | 70% | 0.44 | 1.8 | I |
| Ref_mix7 |  | 6 | 0.84 | 3.4 | 0.79 | 3.3 | 0.95 | 4.5 | 67% | 0.38 | 1.6 | I |
| Ref_mix9 |  | 5 | 0.84 | 3.4 | 0.79 | 3.2 | 0.93 | 3.8 | 67% | 0.36 | 1.5 | I |
| Ref_mix3 |  | 6 | 0.61 | 2.4 | 0.59 | 2.3 | 0.86 | 3.7 | 67% | 0.32 | 1.4 | I |
| Ref_mix5 |  | 5 | 0.61 | 2.4 | 0.58 | 2.3 | 0.79 | 3.0 | 67% | 0.29 | 1.3 | I |
| Ref_mix10 |  | 4 | 0.79 | 3.0 | 0.74 | 2.8 | 0.86 | 3.2 | 67% | 0.31 | 1.3 | I |
| Mix_825 |  | 5 | 0.61 | 2.4 | 0.59 | 2.3 | 0.85 | 3.5 | 67% | 0.30 | 1.3 | I |
| Ref_mix4 |  | 5 | 0.49 | 2.0 | 0.46 | 1.9 | 0.79 | 3.1 | 67% | 0.28 | 1.2 | I |
| Ref_mix6 |  | 4 | 0.49 | 2.0 | 0.46 | 1.9 | 0.63 | 2.4 | 67% | 0.24 | 1.1 | I |
| Ref_mix8 |  | 4 | 0.49 | 2.0 | 0.46 | 1.9 | 0.75 | 2.9 | 67% | 0.24 | 1.1 | I |
| Mix_814 |  | 4 | 0.49 | 2.0 | 0.46 | 1.9 | 0.75 | 2.9 | 67% | 0.24 | 1.1 | I |

REFERENCES

Altschul et al. Basic local alignment search tool. 1990, J. Mol. Biol. 215:403-10.
Ansel ad Soklosa, Pharmaceutical Calculations (2001) 11th ed., Lippincott Williams & Wilkins, Baltimore, Md.
Bostick et al. A new topological method to measure protein structure similarity. Biochem Biophys Res Commun. 2003 May 2; 304(2):320-5.
Cambell et al, Peptide immunotherapy in allergic asthma generates IL-10-dependent immunological tolerance associated with linked epitope suppression. Exp Med. 2009 Jul. 6; 206(7):1535-47. doi: 10.1084/jem.20082901. Epub 2009 Jun. 15.
Greenbaum J, Sidney 3, Chung J, Brander C, Peters B, Sette A. Functional classification of class II human leukocyte antigen (HLA) molecules reveals seven different supertypes and a surprising degree of repertoire sharing across supertypes. Immunogenetics. 2011 June; 63(6):325-35. doi: 10.1007/s00251-011-0513-0. Epub 2011 Feb. 9.
Henmar H et al., Allergenicity, immunogenicity and dose-relationship of three intact allergen vaccines and four allergoid vaccines for subcutaneous grass pollen immunotherapy. Clin Exp Immunol. 2008 September; 153(3): 316-23.
Karosiene E, Rasmussen M, Blicher T, Lund O, Buus S, Nielsen M. NetMHCIIpan-3.0, a common pan-specific MHC class II prediction method including all three human MHC class II isotypes, HLA-DR, HLA-DP and HLA-DQ. Immunogenetics. 2013 October; 65(10):711-24. doi: 10.1007/s00251-013-0720-y. Epub 2013 Jul. 31.
McKinney D M, Southwood 5, Hinz D, Oseroff C, Arlehamn C S, Schulten V, et al. A strategy to determine HLA class II restriction broadly covering the DR, DP, and DQ allelic variants most commonly expressed in the general population. Immunogenetics; 65:357-70, 2013.

Moldaver and Larche. Immunotherapy with peptides, Allergy. 2011 June; 66(6):784-91

Murugan N, Dai Y. Prediction of MHC class II binding peptides based on an iterative learning model. Immunome Res. 2005 Dec. 13; 1:6.

Needleman and Wunsch, 1970, *J. Mol. Biol.* 48:443.

Paul S, Lindestam Arlehamn C S, Scriba T J, Dillon M B, Oseroff C, Hinz D, McKinney D M, Carrasco Pro S, Sidney J, Peters B, Sette A. Development and validation of a broad scheme for prediction of HLA class II restricted T cell epitopes. 3 Immunol Methods. 2015 July; 422:28-34. doi: 10.1016/j.jim.2015.03.022. Epub 2015 Apr. 7.

Pearson and Lipman. Improved tools for biological sequence comparison. Proc Natl Acad Sci USA. 1988 April; 85(8):2444-8.

Pearson. Flexible sequence similarity searching with the FASTA3 program package. *Methods, Mol Biol.* 2000; 132:185-219.

Pharmaceutical Principles of Solid Dosage Forms (1993), Technonic Publishing Co., Inc., Lancaster, Pa.

Powell, M. F. and Newman M. "Vaccine Design—the subunit and adjuvant approach" (Edited by Powell, M. F. and Newman, M. 3; 1995, Pharmaceutical Biotechnology (Plenum Press, New York and London, ISBN 0-306-44867-X) entitled "Compendium of vaccine adjuvants and excipients".

Poznansky et al., Drug Delivery Systems (1980), R. L. Juliano, ed., Oxford, N.Y., pp. 253-315.

Remington: The Science and Practice of Pharmacy (2003) 20th ed., Mack Publishing Co., Easton, Pa.

Remington's Pharmaceutical Sciences (1990) 18th ed., Mack Publishing Co., Easton, Pa.

Sidney 3, Southwood S, Oseroff C, del Guercio M F, Sette A, Grey H M. Measurement of MHC/peptide interactions by gel filtration. Curr Protoc Immunol. Chapter 18(Unit 18):13. doi: 10.1002/0471142735.im1803s31, 2001.

Sidney 3, Assarsson E, Moore C, Ngo S, Pinilla C, Sette A, Peters B. Quantitative peptide binding motifs for 19 human and mouse MHC class I molecules derived using positional scanning combinatorial peptide libraries. Immunome Res. 4:2, doi: 10.1186/1745-7580-4-2, 2008.

Sidney J, Steen A, Moore C, Ngo S, Chung 3, Peters B, Sette A. Divergent motifs but overlapping binding repertoires of six HLA-DQ molecules frequently expressed in the worldwide human population. J Immunol, 185(7), 4189-4198, 2010a.

Sidney J, Steen A, Moore C, Ngo S, Chung J, Peters B, Sette A. Five HLA-DP molecules frequently expressed in the worldwide human population share a common HLA supertypic binding specificity. J Immunol, 184(5), 2492-2503, 2010b.

Sidney J, Southwood S, Grey H M, Moore C, Oseroff C, Pinilla C, Sette A. Measurement of MHC/peptide interactions by gel filtration or monoclonal antibody capture. Current protocols in immunology/edited by John E. Coligan et al, Chapter 18( ):Unit 18.3, 2013.

The Merck Index (1996) 12th ed., Merck Publishing Group, Whitehouse, N.J.

Smith et al., Identification of common molecular subsequences. J Mol Biol. 1981 Mar. 25; 147(1):195-7.

Smith and Waterman 1981: Smith and Waterman. Comparison of biosequences. Adv. Appl. Math 2: 482, 1981.

---

The invention claimed is:

1. A composition comprising:
   1) a first peptide consisting of the amino acid sequence selected from the group consisting of: SEQ ID NOs: 7, 212-214, 261, 262, 263 and 265;
   2) a second peptide consisting of the amino acid sequence selected from the group consisting of: SEQ ID NOs: 71, 218-220, 224, 225, 288-291, 308 and 309;
   3) a third peptide consisting of the amino acid sequence selected from the group consisting of: SEQ ID NOs: 72, 226, 227, 292-295; and
   4) a fourth peptide consisting of the amino acid sequence selected from the group consisting of: SEQ ID NOs: 113, 186, 199, 228 and 229.

2. A composition according to claim 1, further comprising a peptide consisting of the amino acid sequence of SEQ ID NO: 45.

3. A composition according to claim 2, further comprising a peptide consisting of the amino acid sequence selected from the group consisting of: SEQ ID NOs: 4, 247-248.

4. A composition according to claim 1 comprising:
   1) a first peptide consisting of the amino acid sequence of SEQ ID NO: 7;
   2) a second peptide consisting of the amino acid sequence of SEQ ID NO: 71;
   3) a third peptide consisting of the amino acid sequence of SEQ ID NO:72; and
   4) a fourth peptide consisting of the amino acid sequence of SEQ ID NO: 113.

5. A composition according to claim 1 comprising:
   1) a first peptide consisting of the amino acid sequence of SEQ ID NO: 7;
   2) a second peptide consisting of the amino acid sequence of SEQ ID NO: 71;
   3) a third peptide consisting of the amino acid sequence of SEQ ID NO:72;
   4) a fourth peptide consisting of the amino acid sequence of SEQ ID NO: 113;
   5) a fifth peptide consisting of the amino acid sequence of SEQ ID NO: 45; and
   6) a sixth peptide consisting of the amino acid sequence of SEQ ID NO: 4.

6. The composition according to claim 1, wherein the composition is a pharmaceutical composition.

7. A method for relieving or reducing an immune response being triggered by a grass pollen allergen of a grass species in a subject in need thereof, said method comprising administering to said subject a therapeutically effective amount of the composition according to claim 1.

8. The method according to claim 7, wherein the method comprises relieving one or more symptom(s) associated with allergic rhinitis, allergic conjunctivitis, allergic asthma and/or allergic eczema.

9. A kit comprising a composition according to claim 1 and instructions for using said composition in a method for relieving or reducing an immune response being triggered by a grass pollen allergen of a grass species.

* * * * *